United States Patent
Blencowe et al.

(10) Patent No.: US 12,358,886 B2
(45) Date of Patent: *Jul. 15, 2025

(54) HETEROCYCLIC COMPOUNDS FOR USE IN THE TREATMENT OF CANCER

(71) Applicant: Artios Pharma Limited, Cambridge (GB)

(72) Inventors: Peter Blencowe, Cambridge (GB); Mark Charles, Cambridge (GB); Tennyson Ekwuru, Cambridge (GB); Harry Finch, Cambridge (GB); Robert Heald, Cambridge (GB); Hollie McCarron, Cambridge (GB); Martin Stockley, Cambridge (GB)

(73) Assignee: Artios Pharma Limited, Cambridge (GB)

( * ) Notice: Subject to any disclaimer, the term of this patent is extended or adjusted under 35 U.S.C. 154(b) by 730 days.

This patent is subject to a terminal disclaimer.

(21) Appl. No.: 17/597,939

(22) PCT Filed: Aug. 9, 2019

(86) PCT No.: PCT/GB2019/052240
§ 371 (c)(1),
(2) Date: Jan. 29, 2022

(87) PCT Pub. No.: WO2021/028643
PCT Pub. Date: Feb. 18, 2021

(65) Prior Publication Data
US 2022/0298134 A1  Sep. 22, 2022
US 2023/0242503 A9  Aug. 3, 2023

(51) Int. Cl.
| | | |
|---|---|---|
| *C07D 413/14* | (2006.01) |
| *A61K 31/437* | (2006.01) |
| *A61K 31/4439* | (2006.01) |
| *A61K 31/496* | (2006.01) |
| *A61K 31/5377* | (2006.01) |
| *A61K 31/5383* | (2006.01) |
| *A61K 31/541* | (2006.01) |
| *A61K 45/06* | (2006.01) |
| *A61P 35/00* | (2006.01) |
| *C07D 401/04* | (2006.01) |
| *C07D 401/14* | (2006.01) |
| *C07D 405/14* | (2006.01) |
| *C07D 413/04* | (2006.01) |
| *C07D 417/14* | (2006.01) |
| *C07D 471/04* | (2006.01) |
| *C07D 491/04* | (2006.01) |
| *C07D 491/048* | (2006.01) |
| *C07D 491/056* | (2006.01) |
| *C07D 495/04* | (2006.01) |
| *C07D 498/04* | (2006.01) |

(52) U.S. Cl.
CPC ......... *C07D 401/04* (2013.01); *A61K 31/437* (2013.01); *A61K 31/4439* (2013.01); *A61K 31/496* (2013.01); *A61K 31/5377* (2013.01); *A61K 31/5383* (2013.01); *A61K 31/541* (2013.01); *A61K 45/06* (2013.01); *A61P 35/00* (2018.01); *C07D 401/14* (2013.01); *C07D 405/14* (2013.01); *C07D 413/04* (2013.01); *C07D 417/14* (2013.01); *C07D 471/04* (2013.01); *C07D 491/04* (2013.01); *C07D 498/04* (2013.01)

(58) Field of Classification Search
None
See application file for complete search history.

(56) References Cited

U.S. PATENT DOCUMENTS

2022/0259174 A1 * 8/2022 Blencowe ............ A61K 45/06
2024/0166623 A1 * 5/2024 Stockley ............. C07D 493/04

FOREIGN PATENT DOCUMENTS

| WO | WO-2010077836 A2 * | 7/2010 | ......... C07D 207/16 |
|---|---|---|---|
| WO | 2013/107291 A1 | 7/2013 | |
| WO | 2013/107405 A1 | 7/2013 | |
| WO | 2015/010297 A1 | 1/2015 | |

(Continued)

OTHER PUBLICATIONS

Golub et al., Science, vol. 286, Oct. 15, 1999, pp. 531-537 (Year: 1999).*

(Continued)

Primary Examiner — Kortney L. Klinkel
Assistant Examiner — Alison Azar Salamatian
(74) Attorney, Agent, or Firm — ALGM LLP; Harry J. Guttman

(57) ABSTRACT

The application relates to heterocyclic amide derivatives and their use in the treatment and prophylaxis of cancer, and to compositions containing said derivatives and processes for their preparation.

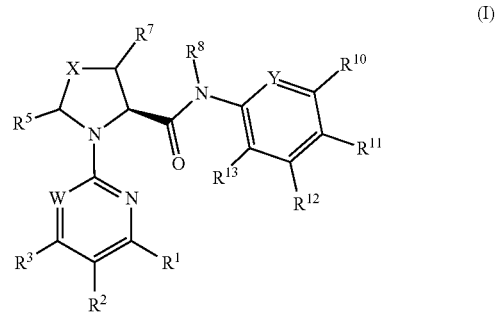

(I)

17 Claims, No Drawings
Specification includes a Sequence Listing.

(56) References Cited

FOREIGN PATENT DOCUMENTS

WO        2018/001332 A1     1/2018
WO        WO-2021028644 A1 *    2/2021    ....... A61K 31/4439

OTHER PUBLICATIONS

International Search Report from PCT/GB2019/052240, mailed Oct. 28, 2019, 8 pages.
Written Opinion from PCT/GB2019/052240, mailed Oct. 28, 2019, 7 pages.
Popovici-Muller et al. (2018) "Discovery of AG-120 (Ivosidenib): A First-in-Class Mutant IDH1 Inhibitor for the Treatment of IDH1 Mutant Cancers" ACS Med Chem Lett, vol. 9, No. 4, pp. 300-305.

* cited by examiner

SEQUENCE LISTING

```
<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: primer

<400> SEQUENCE: 1
gcggctgtca taag                                                    14

<210> SEQ ID NO 2
<211> LENGTH: 51
<212> TYPE: DNA
<213> ORGANISM: Artificial Sequence
<220> FEATURE:
<223> OTHER INFORMATION: template

<400> SEQUENCE: 2
gctacattga caatggcatc aaatctcaga ttgcgtctta tgacagccgc g            51
```

HETEROCYCLIC COMPOUNDS FOR USE IN THE TREATMENT OF CANCER

REFERENCE TO A SEQUENCE LISTING

The instant application contains a Sequence Listing that has been submitted in ASCII format via Patent Center and is hereby incorporated by reference in its entirety. Said ASCII copy, created on Apr. 7, 2025, is named 2025-04-02 36722 04009_ST25.txt and is 908 Bytes in size.

FIELD OF THE INVENTION

The invention relates to heterocyclic amide derivatives and their use in the treatment and prophylaxis of cancer, and to compositions containing said derivatives and processes for their preparation.

BACKGROUND OF THE INVENTION

Robust repair of DNA double-strand breaks (DSBs) is essential for the maintenance of genome stability and cell viability. DSBs can be repaired by one of three main pathways: homologous recombination (HR), non-homologous end-joining (NHEJ) and alternative NHEJ (alt-NHEJ). Microhomology-mediated end-joining (MMEJ) is the most well characterised alt-NHEJ mechanism. HR-mediated repair is a high-fidelity mechanism essential for accurate error-free repair, preventing cancer-predisposing genomic stability. Conversely, NHEJ and MMEJ are error-prone pathways that can leave mutational scars at the site of repair. MMEJ can function parallel to both HR and NHEJ pathways (Truong et al. PNAS 2013, 110 (19), 7720-7725).

The survival of cancer cells, unlike normal cells, is often dependent on the mis-regulation of DNA damage response (DDR) pathways. For example, an increased dependency on one pathway (often mutagenic) to cope with either the inactivation of another one, or the enhanced replication stress resulting from increased proliferation. An aberrant DDR can also sensitise cancer cells to specific types of DNA damage, thus, defective DDR can be exploited to develop targeted cancer therapies. Crucially, cancer cells with impairment or inactivation of HR and NHEJ become hyper-dependent on MMEJ-mediated DNA repair. Genetic, cell biological and biochemical data have identified Polθ (Uni-ProtKB—075417 (DPOLQ_HUMAN) as the key protein in MMEJ (Kent et al. Nature Structural & Molecular Biology (2015), 22(3), 230-237, Mateos-Gomez et al. Nature (2015), 518(7538), 254-257). Polθ is multifunctional enzyme, which comprises an N-terminal helicase domain (SF2 HEL308-type) and a C-terminal low-fidelity DNA polymerase domain (A-type) (Wood & Doublié DNA Repair (2016), 44, 22-32). Both domains have been shown to have concerted mechanistic functions in MMEJ. The helicase domain mediates the removal of RPA protein from ssDNA ends and stimulates annealing. The polymerase domain extends the ssDNA ends and fills the remaining gaps.

Therapeutic inactivation of Polθ would thus disable the ability of cells to perform MMEJ and provide a novel targeted strategy in an array of defined tumour contexts. Firstly, Polθ has been shown to be essential for the survival of HR-defective (HRD) cells (e.g. synthetic lethal with FA/BRCA-deficiency) and is up-regulated in HRD tumour cell lines (Ceccaldi et al. Nature (2015), 518(7538), 258-262). In vivo studies also show that Polθ is significantly over-expressed in subsets of HRD ovarian, uterine and breast cancers with associated poor prognosis (Higgins et al. Oncotarget (2010), 1, 175-184, Lemée et al. PNAS (2010), 107(30), 13390-13395, Ceccaldi et al. (2015), supra). Importantly, Polθ is largely repressed in normal tissues but has been shown to be upregulated in matched cancer samples thus correlating elevated expression with disease (Kawamura et al. International Journal of Cancer (2004), 109(1), 9-16). Secondly, its suppression or inhibition confers radio-sensitivity in tumour cells. Finally, Polθ inhibition could conceivably prevent the MMEJ-dependent functional reversion of BRCA2 mutations that underlies the emergence of cisplatin and PARPi resistance in tumours.

There is therefore a need to provide effective Polθ inhibitors for the treatment of cancer.

SUMMARY OF THE INVENTION

According to a first aspect of the invention, there is provided a compound of formula (I):

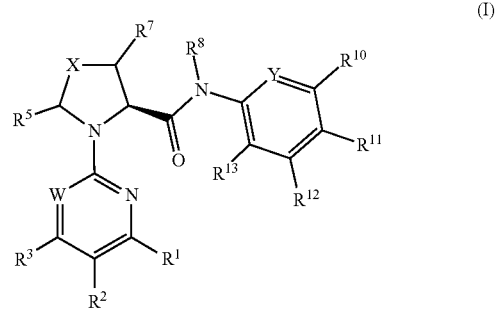

or a tautomeric or a stereochemically isomeric form, a pharmaceutically acceptable salt or a solvate thereof, wherein:

W represents =$C(R^4)$— or =N—;

$R^1$, $R^2$, $R^3$ and $R^4$ independently represent hydrogen, $C_{1-6}$ alkyl, $C_{2-6}$ alkenyl, $C_{1-6}$ alkoxy, halogen, halo$C_{1-6}$ alkyl, halo$C_{1-6}$ alkoxy, $C_{3-8}$ cycloalkyl, cyano or —$NR^xR^y$;

X represents —C(H)($R^6$)—, —N($R^{14}$)— or —O—;

$R^5$ represents hydrogen, —$CH_2$—$R^z$ or oxo, such that when X represents —N($R^{14}$)— or —O—, $R^5$ represents oxo;

$R^6$ represents hydrogen, —$OR^{15a}$, cyano, $C_{1-6}$ alkyl, halo$C_{1-6}$ alkyl, $C_{1-6}$ alkoxy, $C_{1-6}$ alkanol, $C_{3-8}$ cycloalkyl, halogen, —$NR^vR^w$, —$CH_2$—$NR^vR^w$, —Z-aryl or heterocyclyl, wherein said aryl or heterocyclyl groups may be optionally substituted by one or more oxo, hydroxy, $C_{1-6}$ alkanol, —$COC_{1-6}$ alkyl (such as —COMe) or —$COOC_{1-6}$ alkyl (such as —COOtBu) groups;

Z represents a bond or $C_{1-6}$ alkylenyl optionally substituted with an oxygen atom;

$R^7$ represents hydrogen, —$CH_2$—$R^z$ or —$OR^{15b}$, such that when X represents —N(H)— or —O—, $R^7$ represents hydrogen;

$R^8$ represents $C_{1-6}$ alkyl, halo$C_{1-6}$ alkyl or $C_{3-8}$ cycloalkyl;

Y represents —C($R^9$)= or —N=;

$R^9$, $R^{10}$, $R^{11}$, $R^{12}$ and $R^{13}$ independently represent hydrogen, $C_{1-6}$ alkyl, $C_{2-6}$ alkenyl, hydroxy, $C_{1-6}$ alkoxy, $C_{3-8}$ cycloalkyl, halogen, halo$C_{1-6}$ alkyl or —$NR^mR^n$ or two adjacent groups of said $R^9$, $R^{10}$, $R^{11}$, $R^{12}$ and $R^{13}$ groups may join to form a 5 to 7 membered saturated or unsaturated ring optionally containing one or more heteroatoms selected from O, N or S and said ring may optionally be substituted by one or more $C_{1-6}$ alkyl or halogen groups;

$R^{14}$ represents hydrogen, $C_{1-6}$ alkyl, $C_{1-6}$ alkanol, —V—CO—NR'''R'', —V—NR'''R'', —V—SO$_2$—$C_{1-6}$ alkyl, —V—O—SO$_2$—NR'''R'', —V—SO$_2$—NR'''R'', —V—S(=NH)(=O)($C_{1-6}$ alkyl), —V—NH—SO$_2$—$C_{1-6}$ alkyl, —V—N=S(=O)($C_{1-6}$ alkyl)$_2$, —V-heterocyclyl, wherein said heterocyclyl ring may be optionally substituted by one or more oxo, hydroxy, halogen, cyano, $C_{1-6}$ alkyl, —CO$C_{1-6}$ alkyl, —NR'''—CO$C_{1-6}$ alkyl or $C_{1-6}$ alkanol groups;

V represents a bond or a linker selected from —CH$_2$—, —(CH$_2$)$_2$—, —(CH$_2$)$_3$— and —CH$_2$—CH(OH)—CH$_2$—;

$R^{15a}$ and $R^{15b}$ independently represent hydrogen or $R^{15a}$ and $R^{15b}$ join together to form a 5 to 7 membered saturated ring system which may be optionally substituted by one or more $C_{1-6}$ alkyl groups;

$R'''$ and $R''$ independently represent hydrogen or $C_{1-6}$ alkyl;

$R^v$, $R^w$, $R^x$ and $R^y$ independently represent hydrogen, $C_{1-6}$ alkyl, halo$C_{1-6}$ alkyl, $C_{3-8}$ cycloalkyl, —CO$C_{1-6}$ alkyl or heterocyclyl, wherein said alkyl groups may be optionally substituted with or more hydroxy, amino or sulfone groups and said heterocyclyl ring may be optionally substituted by one or more oxo, hydroxy, $C_{1-6}$ alkanol or —CO$C_{1-6}$ alkyl groups; and $R^z$ represents hydrogen, $C_{1-6}$ alkyl, hydroxy, $C_{1-6}$ alkoxy or $C_{1-6}$ alkanol.

DETAILED DESCRIPTION OF THE INVENTION

Definitions

According to one aspect of the invention which may be mentioned, there is provided a compound of formula (I):

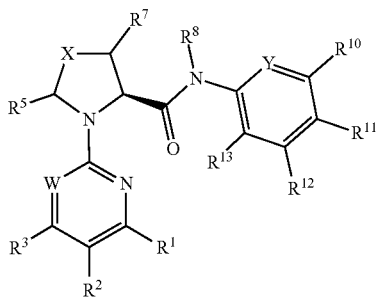

(I)

or a tautomeric or a stereochemically isomeric form, a pharmaceutically acceptable salt or a solvate thereof, wherein:

W represents =C($R^4$)— or =N—;

$R^1$, $R^2$, $R^3$ and $R^4$ independently represent hydrogen, $C_{1-6}$ alkyl, $C_{1-6}$ alkoxy, halogen, halo$C_{1-6}$ alkyl, $C_{3-8}$ cycloalkyl, cyano or —NR$^x$R$^y$;

X represents —C(H)($R^6$)—, —N(H)— or —O—;

$R^5$ represents hydrogen, —CH$_2$—$R^z$ or oxo, such that when X represents —N(H)— or —O—, $R^5$ represents oxo;

$R^6$ represents hydrogen, hydroxy, $C_{1-6}$ alkyl, halo$C_{1-6}$ alkyl, $C_{1-6}$ alkoxy, $C_{1-6}$ alkanol, $C_{3-8}$ cycloalkyl, halogen, —NR$^v$R$^w$ or heterocyclyl;

$R^7$ represents hydrogen, —CH$_2$—$R^z$ or hydroxy, such that when X represents —N(H)— or —O—, $R^7$ represents hydrogen;

$R^8$ represents $C_{1-6}$ alkyl, halo$C_{1-6}$ alkyl or $C_{3-8}$ cycloalkyl;

Y represents —C($R^9$)= or —N=;

$R^9$, $R^{10}$, $R^{11}$, $R^{12}$ and $R^{13}$ independently represent hydrogen, $C_{1-6}$ alkyl, $C_{1-6}$ alkoxy, $C_{3-8}$ cycloalkyl, halogen or halo$C_{1-6}$ alkyl;

$R^v$, $R^w$, $R^x$ and $R^y$ independently represent hydrogen, $C_{1-6}$ alkyl, halo$C_{1-6}$ alkyl, $C_{3-8}$ cycloalkyl, —CO$C_{1-6}$ alkyl or heterocyclyl, wherein said alkyl groups may be optionally substituted with or more hydroxy, amino or sulfone groups and said heterocyclyl ring may be optionally substituted by one or more oxo or —CO$C_{1-6}$ alkyl groups; and $R^z$ represents $C_{1-6}$ alkyl, hydroxy, $C_{1-6}$ alkoxy or $C_{1-6}$ alkanol.

According to a first aspect of the invention which may be mentioned, there is provided a compound of formula (I):

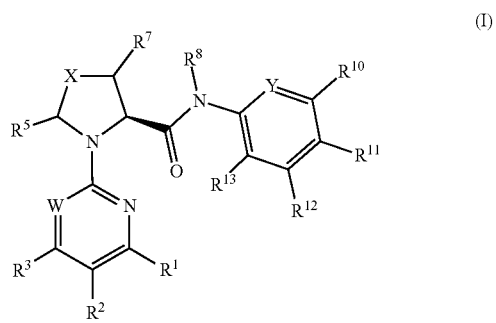

(I)

or a tautomeric or a stereochemically isomeric form, a pharmaceutically acceptable salt or a solvate thereof, wherein:

W represents =C($R^4$)— or =N—;

$R^1$, $R^2$, $R^3$ and $R^4$ independently represent hydrogen, $C_{1-6}$ alkyl, $C_{2-6}$ alkenyl, $C_{1-6}$ alkoxy, halogen, halo$C_{1-6}$ alkyl, halo$C_{1-6}$ alkoxy, $C_{3-8}$ cycloalkyl, cyano or —NR$^x$R$^y$;

X represents —C(H)($R^6$)—, —N($R^{14}$)— or —O—;

$R^5$ represents hydrogen, —CH$_2$—$R^z$ or oxo, such that when X represents —N($R^{14}$)— or —O—, $R^5$ represents oxo;

$R^6$ represents hydrogen, —OR$^{15a}$, cyano, $C_{1-6}$ alkyl, halo$C_{1-6}$ alkyl, $C_{1-6}$ alkoxy, $C_{1-6}$ alkanol, $C_{3-8}$ cycloalkyl, halogen, —NR$^v$R$^w$, —CH$_2$—NR$^v$R$^w$, —Z-aryl or heterocyclyl, wherein said aryl or heterocyclyl groups may be optionally substituted by one or more oxo, hydroxy, $C_{1-6}$ alkanol, —CO$C_{1-6}$ alkyl (such as —COMe) or —COO$C_{1-6}$ alkyl (such as —COOtBu) groups;

Z represents a bond or $C_{1-6}$ alkylenyl optionally substituted with an oxygen atom;

$R^7$ represents hydrogen, —CH$_2$—$R^z$ or —OR$^{15b}$, such that when X represents —N(H)— or —O—, $R^7$ represents hydrogen;

$R^8$ represents $C_{1-6}$ alkyl, halo$C_{1-6}$ alkyl or $C_{3-8}$ cycloalkyl;

Y represents —C($R^9$)= or —N=;

$R^9$, $R^{10}$, $R^{11}$, $R^{12}$ and $R^{13}$ independently represent hydrogen, $C_{1-6}$ alkyl, $C_{2-6}$ alkenyl, hydroxy, $C_{1-6}$ alkoxy, $C_{3-8}$ cycloalkyl, halogen or halo$C_{1-6}$ alkyl or two adjacent groups of said $R^9$, $R^{10}$, $R^{11}$, $R^{12}$ and $R^{13}$ groups may join to form a 5 to 7 membered saturated or unsaturated ring optionally containing one or more heteroatoms selected from O, N or S;

$R^{14}$ represents hydrogen, $C_{1-6}$ alkyl, $C_{1-6}$ alkanol or —$SO_2$—$C_{1-6}$ alkyl; $R^{15a}$ and $R^{15b}$ independently represent hydrogen or $R^{15a}$ and $R^{15b}$ join together to form a 5 to 7 membered saturated ring system which may be optionally substituted by one or more $C_{1-6}$ alkyl groups;

$R^v$, $R^w$, $R^x$ and $R^y$ independently represent hydrogen, $C_{1-6}$ alkyl, halo$C_{1-6}$ alkyl, $C_{3-8}$ cycloalkyl, —$COC_{1-6}$ alkyl or heterocyclyl, wherein said alkyl groups may be optionally substituted with or more hydroxy, amino or sulfone groups and said heterocyclyl ring may be optionally substituted by one or more oxo, hydroxy, $C_{1-6}$ alkanol or —$COC_{1-6}$ alkyl groups; and $R^z$ represents $C_{1-6}$ alkyl, hydroxy, $C_{1-6}$ alkoxy or $C_{1-6}$ alkanol.

The term 'halo' or 'halogen' as used herein refers to fluorine, chlorine, bromine or iodine.

The term 'cyano' as used herein refers to a group where a carbon atom is triple bonded to a nitrogen atom.

The term '$C_{1-6}$ alkyl' as used herein as a group or part of a group refers to a linear or branched saturated hydrocarbon group containing from 1 to 6 carbon atoms. Examples of such groups include methyl, ethyl, n-propyl, iso-propyl, butyl, iso-butyl, tert-butyl, pentyl, hexyl and the like.

The term '$C_{2-6}$ alkenyl' as used herein as a group or part of a group refers to a linear or branched unsaturated hydrocarbon group containing from 2 to 6 carbon atoms and at least one double bond. Examples of such groups include ethenyl, propenyl, butenyl, pentenyl, hexenyl and the like.

The term '$C_{1-6}$ alkoxy' as used herein as a group or part of a group refers to a $C_{1-6}$ alkyl group which contains an oxygen atom wherein $C_{1-6}$ alkyl is as defined herein. Examples of such groups include methoxy, ethoxy or propoxy.

The term '$C_{1-6}$ alkanol' as used herein as a group or part of a group refers to a $C_{1-6}$ alkyl group which contains an oxygen atom wherein $C_{1-6}$ alkyl is as defined herein.

The term 'halo$C_{1-6}$ alkyl' as used herein as a group or part of a group refers to a $C_{1-6}$ alkyl group as defined herein wherein one or more than one hydrogen atom is replaced with a halogen. The term 'halo$C_{1-6}$ alkyl' therefore includes monohalo$C_{1-6}$ alkyl and also polyhalo$C_{1-6}$ alkyl. There may be one, two, three or more hydrogen atoms replaced with a halogen, so the halo$C_{1-6}$ alkyl may have one, two, three or more halogens. Examples of such groups include fluoroethyl, fluoromethyl, trifluoromethyl or trifluoroethyl and the like.

The term "$C_{3-8}$ cycloalkyl" as used herein refers to a saturated monocyclic hydrocarbon ring of 3 to 8 carbon atoms. Examples of such groups include cyclopropyl, cyclobutyl, cyclopentyl, cyclohexyl, cycloheptyl, cyclooctyl and the like.

The term 'oxo' as used herein refers to the group =O.

The term 'amino' as used herein refers to the group —NR'R", wherein R' and R" independently represent a hydrogen or $C_{1-6}$ alkyl group.

The term 'heterocyclyl' as used herein refers to a monocyclic or bicyclic non-aromatic, partially saturated or fully saturated ring system containing for example 3 to 12 ring members. Each ring may contain up to five heteroatoms typically selected from nitrogen, sulfur and oxygen.

Particular examples of 'heterocyclyl' include morpholine, piperidine (e.g. piperidin-1-yl, piperidin-2-yl, piperidin-3-yl and piperidin-4-yl), piperidinone, pyrrolidine (e.g. pyrrolidin-1-yl, pyrrolidin-2-yl and pyrrolidin-3-yl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. tetrahydropyran-4-yl), imidazoline, imidazolidinone, oxazoline, thiazoline, pyrazolin-2-yl, pyrazolidine, piperazinone and piperazine.

It will be appreciated that the term 'heterocyclyl' includes reference to spiro and bridged heterocyclic derivatives. Examples of such spiro and bridged heterocyclic derivatives include: hexahydropyrrolo[2,3-c]pyrrolidinyl, diazaspiro[3.4]octanyl, diazaspiro[4.4]nonyl, oxa-azaspiro[3.4]octanyl, oxa-azaspiro[4.4]nonyl, tetrahydrofuro[3,4-c]pyrrolidinyl, oxa-azaspiro[3.3]heptyl, diazaspiro[4.5]decanyl, diazaspiro[3.4]octanyl, octahydro-naphthyridinyl, tetrahydropyrazino-oxazinyl, oxadiazospiro[5.5]undecanyl and oxabicyclo[2.2.1]heptanyl.

The term 'optionally substituted' as used herein refers to a group which may be substituted or unsubstituted by a substituent as herein defined.

Embodiments

In one embodiment, the compound of formula (I) is a compound of formula (I)$^a$:

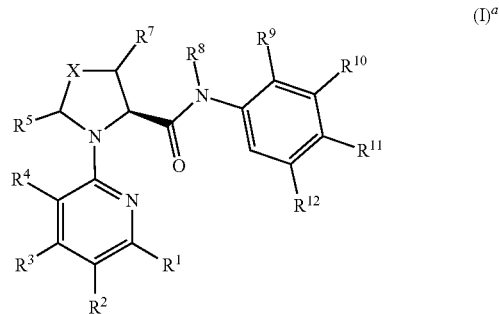

(I)$^a$ wherein $R^1$, $R^2$, $R^3$, $R^4$, $R^5$, X, $R^7$, $R^8$, $R^9$, $R^{10}$, $R^{11}$ and $R^{12}$ are as defined hereinbefore or as defined in any embodiments defined herein.

In a further embodiment, the compound of formula (I) is a compound of formula (I)$^b$:

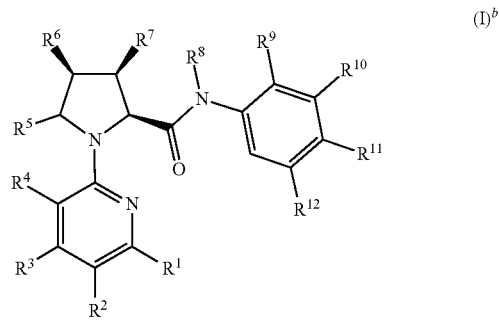

(I)$^b$ wherein $R^1$, $R^2$, $R^3$, $R^4$, $R^5$, $R^6$, $R^7$, $R^8$, $R^9$, $R^{10}$, $R^{11}$ and $R^{12}$ are as defined hereinbefore or as defined in any embodiments defined herein.

In one embodiment, W represents =C($R^4$)—. In an alternative embodiment, W represents =N—.

In one embodiment, W represents =C(H)—, =C(CN)— or =N—. In a further embodiment, W represents =C(H)— or =C(CN)—.

In one embodiment, $R^1$ represents:
hydrogen;
$C_{1-6}$ alkyl (such as methyl or ethyl);
$C_{2-6}$ alkenyl (such as ethenyl); $C_{1-6}$ alkoxy (such as methoxy);
halogen (such as chlorine); or
—$NR^xR^y$ (such as —$N(Me)_2$ or —$N(Me)(Et)$).

In one embodiment which may be mentioned, $R^1$ represents:
hydrogen;
$C_{1-6}$ alkyl (such as methyl);
$C_{1-6}$ alkoxy (such as methoxy); or
—$NR^xR^y$ (such as —$N(Me)_2$ or —$N(Me)(Et)$).

In a further embodiment, $R^1$ represents $C_{1-6}$ alkyl (such as methyl).

In one embodiment, $R^2$ represents:
hydrogen;
halogen (such as chlorine); or
$C_{1-6}$ alkyl (such as methyl).

In one embodiment, $R^2$ represents hydrogen.

In one embodiment, $R^3$ represents:
$C_{1-6}$ alkyl (such as methyl, ethyl or isopropyl);
$C_{2-6}$ alkenyl (such as —$C(=CH_2)(Me)$);
halogen (such as bromine);
haloC$_{1-6}$ alkyl (such as trifluoromethyl or —$C(H)(Me)$-$CF_3$); or
haloC$_{1-6}$ alkoxy (such as difluoromethoxy).

In one embodiment which may be mentioned, $R^3$ represents:
$C_{1-6}$ alkyl (such as methyl, ethyl or isopropyl); or
haloC$_{1-6}$ alkyl (such as trifluoromethyl).

In a further embodiment, $R^3$ represents haloC$_{1-6}$ alkyl (such as trifluoromethyl).

In one embodiment, $R^4$ represents:
hydrogen; or
cyano.

In a further embodiment, $R^4$ represents hydrogen.

In one embodiment, $R^x$ and $R^y$ represent $C_{1-6}$ alkyl (such as methyl or ethyl). In a further embodiment, $R^x$ and $R^y$ both represent $C_{1-6}$ alkyl (such as methyl or ethyl). In a yet further embodiment, $R^x$ and $R^y$ both represent methyl or one represents methyl and the other represents ethyl.

In one embodiment, W represents =$C(R^4)$— and:
$R^1$ represents $C_{1-6}$ alkyl (such as methyl), $R^2$ represents hydrogen, $R^3$ represents haloC$_{1-6}$ alkyl (such as trifluoromethyl) and $R^4$ represents cyano; or
$R^1$ represents $C_{1-6}$ alkyl (such as methyl), $R^2$ represents hydrogen, $R^3$ represents $C_{1-6}$ alkyl (such as methyl or isopropyl) and $R^4$ represents cyano; or
$R^1$ represents $C_{1-6}$ alkyl (such as methyl or ethyl), $R^2$ represents hydrogen, $R^3$ represents haloC$_{1-6}$ alkyl (such as trifluoromethyl or —CH(Me)-$CF_3$) and $R^4$ represents hydrogen; or
$R^1$ represents $C_{1-6}$ alkyl (such as methyl), $R^2$ represents hydrogen, $R^3$ represents $C_{1-6}$ alkyl (such as isopropyl) and $R^4$ represents hydrogen; or
$R^1$ represents $C_{1-6}$ alkyl (such as methyl), $R^2$ represents halogen (such as chlorine), $R^3$ represents $C_{1-6}$ alkyl (such as methyl) and $R^4$ represents hydrogen; or
$R^1$ represents $C_{1-6}$ alkoxy (such as methoxy), $R^2$ represents hydrogen, $R^3$ represents haloC$_{1-6}$ alkyl (such as trifluoromethyl) and $R^4$ represents cyano; or
$R^1$ represents —$NR^xR^y$ (such as —$N(Me)_2$ or —$N(Me)(Et)$), $R^2$ represents hydrogen, $R^3$ represents haloC$_{1-6}$ alkyl (such as trifluoromethyl) and $R^4$ represents cyano; or
$R^1$ represents hydrogen, $R^2$ represents hydrogen, $R^3$ represents haloC$_{1-6}$ alkyl (such as trifluoromethyl) and $R^4$ represents cyano; or
$R^1$ represents hydrogen, $R^2$ represents $C_{1-6}$ alkyl (such as methyl), $R^3$ represents $C_{1-6}$ alkyl (such as ethyl) and $R^4$ represents hydrogen; or
$R^1$ represents halogen (such as chlorine), $R^2$ represents hydrogen, $R^3$ represents haloC$_{1-6}$ alkyl (such as trifluoromethyl) and $R^4$ represents hydrogen; or
$R^1$ represents halogen (such as chlorine), $R^2$ represents hydrogen, $R^3$ represents haloC$_{1-6}$ alkoxy (such as difluoromethoxy) and $R^4$ represents hydrogen; or
$R^1$ represents $C_{2-6}$ alkenyl (such as ethenyl), $R^2$ represents hydrogen, $R^3$ represents haloC$_{1-6}$ alkyl (such as trifluoromethyl) and $R^4$ represents hydrogen; or
$R^1$ represents $C_{1-6}$ alkyl (such as methyl), $R^2$ represents hydrogen, $R^3$ represents haloC$_{1-6}$ alkoxy (such as difluoromethoxy) and $R^4$ represents hydrogen; or
$R^1$ represents $C_{1-6}$ alkyl (such as methyl), $R^2$ represents hydrogen, $R^3$ represents $C_{2-6}$ alkenyl (such as —$C(Me)(=CH_2)$) and $R^4$ represents hydrogen; or
$R^1$ represents $C_{1-6}$ alkyl (such as methyl), $R^2$ represents hydrogen, $R^3$ represents halogen (such as bromine) and $R^4$ represents hydrogen.

In one embodiment which may be mentioned, W represents =$C(R^4)$— and:
$R^1$ represents $C_{1-6}$ alkyl (such as methyl), $R^2$ represents hydrogen, $R^3$ represents haloC$_{1-6}$ alkyl (such as trifluoromethyl) and $R^4$ represents cyano; or
$R^1$ represents $C_{1-6}$ alkyl (such as methyl), $R^2$ represents hydrogen, $R^3$ represents $C_{1-6}$ alkyl (such as methyl or isopropyl) and $R^4$ represents cyano; or
$R^1$ represents $C_{1-6}$ alkyl (such as methyl), $R^2$ represents hydrogen, $R^3$ represents haloC$_{1-6}$ alkyl (such as trifluoromethyl) and $R^4$ represents hydrogen; or
$R^1$ represents $C_{1-6}$ alkyl (such as methyl), $R^2$ represents hydrogen, $R^3$ represents $C_{1-6}$ alkyl (such as isopropyl) and $R^4$ represents hydrogen; or
$R^1$ represents $C_{1-6}$ alkyl (such as methyl), $R^2$ represents halogen (such as chlorine), $R^3$ represents $C_{1-6}$ alkyl (such as methyl) and $R^4$ represents hydrogen; or
$R^1$ represents $C_{1-6}$ alkoxy (such as methoxy), $R^2$ represents hydrogen, $R^3$ represents haloC$_{1-6}$ alkyl (such as trifluoromethyl) and $R^4$ represents cyano; or
$R^1$ represents —$NR^xR^y$ (such as —$N(Me)_2$ or —$N(Me)(Et)$), $R^2$ represents hydrogen, $R^3$ represents haloC$_{1-6}$ alkyl (such as trifluoromethyl) and $R^4$ represents cyano; or
$R^1$ represents hydrogen, $R^2$ represents hydrogen, $R^3$ represents haloC$_{1-6}$ alkyl (such as trifluoromethyl) and $R^4$ represents cyano; or
$R^1$ represents hydrogen, $R^2$ represents $C_{1-6}$ alkyl (such as methyl), $R^3$ represents $C_{1-6}$ alkyl (such as ethyl) and $R^4$ represents hydrogen.

In a further embodiment, W represents =$C(R^4)$— and:
$R^1$ represents $C_{1-6}$ alkyl (such as methyl), $R^2$ represents hydrogen, $R^3$ represents haloC$_{1-6}$ alkyl (such as trifluoromethyl) and $R^4$ represents hydrogen $R^1$ represents hydrogen In an alternative embodiment, W represents =N— and:
$R^1$ represents $C_{1-6}$ alkyl (such as methyl), $R^2$ represents hydrogen and $R^3$ represents haloC$_{1-6}$ alkyl (such as trifluoromethyl) and $R^4$ represents hydrogen.

In one embodiment, X represents —$C(H)(R^6)$— or —O—. In a further embodiment, X represents —C(H)

($R^6$)—. In an alternative embodiment, X represents —O—. In a yet further alternative embodiment, X represents —N($R^{14}$)—.

In one embodiment, $R^5$ represents:
hydrogen; or
oxo.

In an alternative embodiment, $R^5$ represents hydrogen. In a yet further alternative embodiment, $R^5$ represents oxo. In a yet further alternative embodiment, $R^5$ represents —$CH_2$—$R^z$.

In one embodiment, $R^z$ represents hydrogen.

In one embodiment, $R^6$ represents:
hydrogen;
—$OR^{15a}$ (such as hydroxy);
halogen (such as fluorine);
$C_{1-6}$ alkanol (such as $CH_2OH$);
$C_{1-6}$ alkoxy (such as methoxy);
—$NR^vR^w$ (such as —$NH_2$, —$NMe_2$, —N(H)(Me), —N(H)(COMe), —N(H)(($CH_2$)$_2$OH), —N(H)(($CH_2$)$_2$SO$_2$Me), N(Me)(($CH_2$)$_2$SO$_2$Me), —N(H)(pyrrolidinyl), —N(Me)(pyrrolidinyl), —N(H)(azetidinyl), —N(H)(oxetanyl), —N(Me)(oxetanyl), —N(H)(cyclopentyl), —N(Me)(cyclopentyl), —N(H)(tetrahydropyranyl), —N(Me)(tetrahydropyranyl) or —N(H)(($CH_2$)$_2$NH$_2$), wherein said pyrrolidinyl, tetrahydropyranyl or cyclopentyl rings may be optionally substituted by one or more oxo, hydroxy, —$COC_{1-6}$ alkyl (such as —COMe) or —$COOC_{1-6}$ alkyl (such as —COOtBu) groups;
—$CH_2$—NRvRw (such as —$CH_2$—N(Me)$_2$);
—Z-aryl (such as —$CH_2$—O—$CH_2$-phenyl); or
heterocyclyl (such as azetidinyl, pyrrolidinyl, morpholinyl or piperazinyl) optionally substituted by one or more hydroxy or $C_{1-6}$ alkanol (such as $CH_2OH$) groups.

In one embodiment which may be mentioned, $R^6$ represents:
hydrogen;
hydroxy;
halogen (such as fluorine);
$C_{1-6}$ alkoxy (such as methoxy);
—$NR^vR^w$ (such as —$NH_2$, —$NMe_2$, —N(H)(Me), —N(H)(COMe), —N(H)(($CH_2$)$_2$OH), —N(H)(($CH_2$)$_2$SO$_2$Me), N(Me)(($CH_2$)$_2$SO$_2$Me), —N(H)(pyrrolidinyl), —N(Me)(pyrrolidinyl), —N(H)(azetidinyl), —N(H)(($CH_2$)$_2$NH$_2$), wherein said pyrrolidinyl ring may be optionally substituted by an oxo or —$COC_{1-6}$ alkyl (such as —COMe) group; or
heterocyclyl (such as morpholinyl or piperazinyl).

In a further embodiment, $R^6$ represents hydroxy.

In one embodiment, $R^7$ represents:
hydrogen; or
—$OR^{15b}$ (such as hydroxy).

In one embodiment which may be mentioned, $R^7$ represents:
hydrogen; or
hydroxy.

In a further embodiment, $R^7$ represents —$OR^{15b}$ (such as hydroxy).

In one embodiment, X represents —C(H)($R^6$)— and:
$R^5$, $R^6$ and $R^7$ each represent hydrogen; or
$R^5$ and $R^7$ both represent hydrogen and $R^6$ represents —$OR^{15a}$ (such as hydroxy); or
$R^5$ and $R^6$ both represent hydrogen and $R^7$ represents —$OR^{15b}$ (such as hydroxy); or
$R^5$ and $R^7$ both represent hydrogen and $R^6$ represents halogen (such as fluorine); or
$R^5$ and $R^7$ both represent hydrogen and $R^6$ represents $C_{1-6}$ alkoxy (such as methoxy); or
$R^5$ and $R^7$ both represent hydrogen and $R^6$ represents —$NR^vR^w$ (such as —$NH_2$, —$NMe_2$, —N(H)(Me), —N(H)(($CH_2$)$_2$OH), —N(H)(($CH_2$)$_2$SO$_2$Me), N(Me)(($CH_2$)$_2$SO$_2$Me), —N(H)(pyrrolidinyl), —N(Me)(pyrrolidinyl), —N(H)(azetidinyl), —N(H)(oxetanyl), —N(Me)(oxetanyl), —N(H)(cyclopentyl), —N(Me)(cyclopentyl), —N(H)(tetrahydropyranyl), —N(Me)(tetrahydropyranyl) or —N(H)(($CH_2$)$_2$NH$_2$), wherein said pyrrolidinyl, tetrahydropyranyl or cyclopentyl rings may be optionally substituted by one or more oxo, hydroxy, —$COC_{1-6}$ alkyl (such as —COMe) or —$COOC_{1-6}$ alkyl (such as —COOtBu) groups; or
$R^5$ and $R^7$ both represent hydrogen and $R^6$ represents heterocyclyl (such as azetidinyl, pyrrolidinyl, morpholinyl or piperazinyl optionally substituted by one or more hydroxy or $C_{1-6}$ alkanol (i.e. $CH_2OH$) groups); or
$R^5$ represents hydrogen, $R^6$ represents —$OR^{15a}$ (such as hydroxy) and $R^7$ represents —$OR^{15b}$ (such as hydroxy); or
$R^5$ represents oxo and $R^6$ and $R^7$ both represent hydrogen; or
$R^5$ represents oxo, $R^6$ represents —$NR^vR^w$ (such as —$NH_2$ or —N(H)(COMe)) and $R^7$ represent hydrogen; or
$R^5$ represents oxo, $R^6$ represents heterocyclyl (such as morpholinyl) and $R^7$ represents hydrogen; or
$R^5$ represents oxo, $R^6$ represents —$OR^{15a}$ (such as hydroxy) and $R^7$ represents —$OR^{15b}$ (such as hydroxy); or
$R^5$ represents oxo, $R^6$ represents —$OR^{15a}$ (such as hydroxy) and $R^7$ represents hydrogen; or
$R^5$ represents oxo, $R^6$ represents —Z-aryl (such as —$CH_2$—O—$CH_2$-phenyl) and $R^7$ represents hydrogen; or
$R^5$ represents oxo, $R^6$ represents $C_{1-6}$ alkanol (such as $CH_2OH$) and $R^7$ represents hydrogen; or
$R^5$ represents oxo, $R^6$ represents hydrogen and $R^7$ represents —$OR^{15b}$ (such as hydroxy); or
$R^5$ represents oxo, $R^6$ represents —$CH_2$—$NR^vR^w$ (such as —$CH_2$—N(Me)$_2$) and $R^7$ represents hydrogen; or
$R^5$ represents oxo, $R^6$ represents —$OR^{15a}$ and $R^7$ represents —$OR^{15b}$, wherein $R^{15a}$ and $R^{15b}$ join together to form a 5 to 7 (such as 5) membered saturated ring system (such as dioxolanyl) which may be optionally substituted by one or more $C_{1-6}$ alkyl groups (such as two methyl groups); or
$R^6$ and $R^7$ both represent hydrogen and $R^5$ represents —$CH_2$—$R^z$ (such as methyl).

In one embodiment which may be mentioned, X represents —C(H)($R^6$)— and:
$R^5$, $R^6$ and $R^7$ each represent hydrogen; or
$R^5$ and $R^7$ both represent hydrogen and $R^6$ represents —$OR^{15a}$ (such as hydroxy); or
$R^5$ and $R^6$ both represent hydrogen and $R^7$ represents —$OR^{15b}$ (such as hydroxy); or
$R^5$ and $R^7$ both represent hydrogen and $R^6$ represents halogen (such as fluorine); or
$R^5$ and $R^7$ both represent hydrogen and $R^6$ represents $C_{1-6}$ alkoxy (such as methoxy); or
$R^5$ and $R^7$ both represent hydrogen and $R^6$ represents —$NR^vR^w$ (such as —$NH_2$, —$NMe_2$, —N(H)(Me), —N(H)(($CH_2$)$_2$OH), —N(H)(($CH_2$)$_2$SO$_2$Me), N(Me)(($CH_2$)$_2$SO$_2$Me), —N(H)(pyrrolidinyl), —N(Me)(pyrrolidinyl), —N(H)(azetidinyl), —N(H)(oxetanyl), —N(Me)(oxetanyl), —N(H)(cyclopentyl), —N(Me)

(cyclopentyl), —N(H)(tetrahydropyranyl), —N(Me)(tetrahydropyranyl) or —N(H)((CH$_2$)$_2$NH$_2$), wherein said pyrrolidinyl, tetrahydropyranyl or cyclopentyl rings may be optionally substituted by one or more oxo, hydroxy, —COC$_{1-6}$ alkyl (such as —COMe) or —COOC$_{1-6}$ alkyl (such as —COOtBu) groups; or R$^5$ and R$^7$ both represent hydrogen and R$^s$ represents heterocyclyl (such as azetidinyl, pyrrolidinyl, morpholinyl or piperazinyl optionally substituted by one or more hydroxy or C$_{1-6}$ alkanol (i.e. CH$_2$OH) groups); or R$^5$ represents hydrogen, R$^6$ represents —OR$^{15a}$ (such as hydroxy) and R$^7$ represents —OR$^{15b}$ (such as hydroxy); or R$^5$ represents oxo and R$^6$ and R$^7$ both represent hydrogen; or R$^5$ represents oxo, R$^6$ represents —NR$^v$R$^w$ (such as —NH$_2$ or —N(H)(COMe)) and R$^7$ represent hydrogen; or R$^5$ represents oxo, R$^6$ represents heterocyclyl (such as morpholinyl) and R$^7$ represents hydrogen; or R$^5$ represents oxo, R$^6$ represents —OR$^{15a}$ (such as hydroxy) and R$^7$ represents —OR$^{15b}$ (such as hydroxy); or R$^5$ represents oxo, R$^6$ represents —OR$^{15a}$ (such as hydroxy) and R$^7$ represents hydrogen; or R$^5$ represents oxo, R$^6$ represents —Z-aryl (such as —CH$_2$—O—CH$_2$-phenyl) and R$^7$ represents hydrogen; or R$^5$ represents oxo, R$^6$ represents C$_{1-6}$ alkanol (such as CH$_2$OH) and R$^7$ represents hydrogen; or R$^5$ represents oxo, R$^6$ represents hydrogen and R$^7$ represents —OR$^{15b}$ (such as hydroxy); or R$^5$ represents oxo, R$^6$ represents —CH$_2$—NR$^v$R$^w$ (such as —CH$_2$—N(Me)$_2$) and R$^7$ represents hydrogen; or R$^5$ represents oxo, R$^6$ represents —OR$^{15a}$ and R$^7$ represents —OR$^{15b}$, wherein R$^{15a}$ and R$^{15b}$ join together to form a 5 to 7 (such as 5) membered saturated ring system (such as dioxolanyl) which may be optionally substituted by one or more C$_{1-6}$ alkyl groups (such as two methyl groups).

In one embodiment which may be mentioned, X represents —C(H)(R$^6$)— and:

R$^5$, R$^6$ and R$^7$ each represent hydrogen; or

R$^5$ and R$^7$ both represent hydrogen and R$^6$ represents hydroxy; or

R$^5$ and R$^6$ both represent hydrogen and R$^7$ represents hydroxy; or

R$^5$ and R$^7$ both represent hydrogen and R$^6$ represents halogen (such as fluorine); or R$^5$ and R$^7$ both represent hydrogen and R$^6$ represents C$_{1-6}$ alkoxy (such as methoxy); or R$^5$ and R$^7$ both represent hydrogen and R$^6$ represents —NR$^v$R$^w$ (such as —NH$_2$, —NMe$_2$, —N(H)(Me), —N(H)((CH$_2$)$_2$OH), —N(H)((CH$_2$)$_2$SO$_2$Me), N(Me)((CH$_2$)$_2$SO$_2$Me), —N(H)(pyrrolidinyl), —N(Me)(pyrrolidinyl), —N(H)(azetidinyl), —N(H)((CH$_2$)$_2$NH$_2$), wherein said pyrrolidinyl ring may be optionally substituted by an oxo or —COC$_{1-6}$ alkyl (such as —COMe) group; or R$^5$ and R$^7$ both represent hydrogen and R$^6$ represents heterocyclyl (such as morpholinyl or piperazinyl); or R$^5$ represents hydrogen and R$^6$ and R$^7$ both represent hydroxy; or R$^5$ represents oxo and R$^6$ and R$^7$ both represent hydrogen; or R$^5$ represents oxo, R$^6$ represents —NR$^v$R$^w$ (such as —NH$_2$ or —N(H)(COMe)) and R$^7$ represent hydrogen; or R$^5$ represents oxo, R$^6$ represents heterocyclyl (such as morpholinyl) and R$^7$ represent hydrogen; or R$^5$ represents oxo and R$^6$ and R$^7$ both represent hydroxy.

In a further embodiment, X represents —C(H)(R$^6$)— and:
R$^5$ represents oxo and R$^6$ and R$^7$ both represent hydroxy.

In one embodiment, X represents —O— and:
R$^5$ represents oxo and R$^7$ represent hydrogen.

In one embodiment, X represents —N(R$^{14}$)— and:
R$^5$ represents oxo and R$^7$ and R$^{14}$ both represent hydrogen; or R$^5$ represents oxo, R$^7$ represents hydrogen and R$^{14}$ represents:
C$_{1-6}$ alkanol (such as —CH$_2$—CH(OH)Me, —(CH$_2$)$_2$—OH, —CH$_2$—CHOH—CH$_2$OH or —(CH$_2$)$_2$—CHOH—CH$_2$OH);
—V—SO$_2$—C$_{1-6}$ alkyl (such as —SO$_2$-Me or —(CH$_2$)$_2$—SO$_2$-Me);
—V—SO$_2$—NR$^m$R$^n$ (such as —(CH$_2$)$_2$—SO$_2$—N(Me)$_2$);
—V—NR$^m$R$^n$ (such as —(CH$_2$)$_2$—N(Me)$_2$, —(CH$_2$)$_3$—N(Me)$_2$ or —CH$_2$—CHOH—CH$_2$—NMe$_2$);
—V—CO—NR$^m$R$^n$ (such as —CH$_2$—CONH$_2$, —CH$_2$—CON(Me)$_2$, —(CH$_2$)$_2$—CON(Me)$_2$ or —(CH$_2$)$_2$—CON(H)(Me));
—V—NH—SO$_2$—C$_{1-6}$ alkyl (such as —(CH$_2$)$_2$—NH—SO$_2$-Me);
—V—S(=NH)(=O)(C$_{1-6}$ alkyl) (such as —(CH$_2$)$_2$—S(=NH)(=O)(Me));
—V—O—SO$_2$—NR$^m$R$^n$ (such as —(CH$_2$)$_2$—O—SO$_2$—NH$_2$);
—V—N=S(=O)(C$_{1-6}$ alkyl)$_2$ (such as —(CH$_2$)$_2$—N=S(=O)(Me)$_2$); or
—V-heterocyclyl (such as —CH$_2$-oxetanyl, —CH$_2$-azetidinyl, —(CH$_2$)$_2$-azetidinyl, —CH$_2$—oxazolidinyl, —(CH$_2$)$_2$-piperidinyl, —(CH$_2$)$_2$-piperazinyl, —(CH$_2$)$_3$-piperazinyl, —CH$_2$-morpholinyl, —(CH$_2$)$_2$-morpholinyl, —CH$_2$—CHOH—CH$_2$-morpholinyl, —(CH$_2$)$_2$-thiomorpholinyl, —CH$_2$-pyrrolidinyl, —(CH$_2$)$_2$-pyrrolidinyl or —CH$_2$—CHOH—CH$_2$-pyrrolidinyl), wherein said heterocyclyl ring may be optionally substituted by one or more oxo, hydroxy, halogen (such as fluorine), cyano, C$_{1-6}$ alkyl (such as methyl), —COC$_{1-6}$ alkyl (such as —COMe), —NR$^m$—COC$_{1-6}$ alkyl (such as —NMe-COMe) or C$_{1-6}$ alkanol (such as —CH$_2$OH or —(CH$_2$)$_2$—OH) groups.

In one embodiment which may be mentioned, X represents —N(R$^{14}$)— and:
R$^5$ represents oxo and R$^7$ and R$^{14}$ both represent hydrogen; or R$^5$ represents oxo, R$^7$ represents hydrogen and R$^{14}$ represents C$_{1-6}$ alkanol (such as —CH$_2$—CH(OH)Me); or R$^5$ represents oxo, R$^7$ represents hydrogen and R$^{14}$ represents —SO$_2$—C$_{1-6}$ alkyl (such as —SO$_2$-Me).

In one embodiment, R$^v$ and R$^w$ represent hydrogen, C$_{1-6}$ alkyl (such as methyl), —COC$_{1-6}$ alkyl (such as —COMe), C$_{3-8}$ cycloalkyl (such as cyclopentyl) or heterocyclyl (such as oxetanyl, azetidinyl, tetrahydropyranyl or pyrrolidinyl), wherein said alkyl groups may be optionally substituted with or more hydroxy (such as (CH$_2$)$_2$OH), amino (such as (CH$_2$)$_2$NH$_2$) or sulfone (such as (CH$_2$)$_2$SO$_2$Me) groups and said heterocyclyl ring may be optionally substituted by one or more oxo or —COC$_{1-6}$ alkyl (such as —COMe) groups.

In one embodiment which may be mentioned, R$^v$ and R$^w$ represent hydrogen, $C_{1-6}$ alkyl (such as methyl), $-COC_{1-6}$ alkyl (such as —COMe) or heterocyclyl (such as azetidinyl or pyrrolidinyl), wherein said alkyl groups may be optionally substituted with or more hydroxy (such as $(CH_2)_2OH$), amino (such as $(CH_2)_2NH_2$) or sulfone (such as $(CH_2)_2SO_2Me$) groups and said heterocyclyl ring may be optionally substituted by one or more oxo or $-COC_{1-6}$ alkyl (such as —COMe) groups. In one embodiment, $R^v$ and $R^w$ both represent hydrogen or $C_{1-6}$ alkyl (such as methyl) or one represents hydrogen and the other represents $C_{1-6}$ alkyl (such as methyl) or one represents hydrogen or $C_{1-6}$ alkyl (such as methyl) and the other represents $-COC_{1-6}$ alkyl (such as —COMe), $C_{3-8}$ cycloalkyl (such as cyclopentyl) or heterocyclyl (such as azetidinyl, tetrahydropyranyl or pyrrolidinyl), wherein said alkyl groups may be optionally substituted with or more hydroxy (such as $(CH_2)_2OH$), amino (such as $(CH_2)_2NH_2$) or sulfone (such as $(CH_2)_2SO_2Me$) groups and said heterocyclyl ring may be optionally substituted by one or more oxo or $-COC_{1-6}$ alkyl (such as —COMe) groups. In one embodiment which may be mentioned, $R^v$ and $R^w$ both represent hydrogen or $C_{1-6}$ alkyl (such as methyl) or one represents hydrogen and the other represents $C_{1-6}$ alkyl (such as methyl) or one represents hydrogen or $C_{1-6}$ alkyl (such as methyl) and the other represents $-COC_{1-6}$ alkyl (such as —COMe) or heterocyclyl (such as azetidinyl or pyrrolidinyl), wherein said alkyl groups may be optionally substituted with or more hydroxy (such as $(CH_2)_2OH$), amino (such as $(CH_2)_2NH_2$) or sulfone (such as $(CH_2)_2SO_2Me$) groups and said heterocyclyl ring may be optionally substituted by one or more oxo or $-COC_{1-6}$ alkyl (such as —COMe) groups.

In one embodiment, $R^8$ represents $C_{1-6}$ alkyl (such as $CH_3$, $CD_3$, ethyl or isopropyl) or $C_{3-8}$ cycloalkyl (such as cyclopropyl). In one embodiment which may be mentioned, $R^8$ represents $C_{1-6}$ alkyl (such as methyl, ethyl or isopropyl). In a further embodiment, $R^8$ represents $C_{1-6}$ alkyl (such as $CH_3$, $CD_3$ or ethyl). In a further embodiment, $R^8$ represents $C_{1-6}$ alkyl (such as methyl or ethyl). In a yet further embodiment, $R^8$ represents $C_{1-6}$ alkyl (such as $CH_3$ or $CD_3$).

In one embodiment, Y represents $-C(R^9)=$. In an alternative embodiment, Y represents $-N=$.

In one embodiment, $R^9$ represents:
hydrogen;
halogen (such as fluorine or chlorine); or
$C_{1-6}$ alkoxy (such as methoxy).

In one embodiment which may be mentioned, $R^9$ represents:
hydrogen;
halogen (such as fluorine); or
$C_{1-6}$ alkoxy (such as methoxy).

In one embodiment which may be mentioned, $R^9$ represents:
hydrogen; or
halogen (such as fluorine).

In a further embodiment, $R^9$ represents hydrogen.

In one embodiment, $R^{10}$ represents:
hydrogen;
halogen (such as fluorine, bromine or chlorine);
$C_{1-6}$ alkyl (such as methyl or ethyl);
$C_{2-6}$ alkenyl (such as ethenyl);
hydroxy;
$C_{1-6}$ alkoxy (such as methoxy);
$-NR'''R''$ (such as $-NH_2$, —NHMe or $-NMe_2$); or
$R^{10}$ and $R^{11}$ join to form a 5 to 7 membered saturated or unsaturated ring optionally containing one or more heteroatoms selected from O, N or S (such as a pyrrolinyl, tetrahydropyranyl, pyrazolyl, morpholinyl, pyridyl, furanyl or thiophenyl ring optionally substituted by one or more methyl or fluorine groups).

In one embodiment which may be mentioned, $R^{10}$ represents:
hydrogen;
halogen (such as fluorine, bromine or chlorine);
$C_{1-6}$ alkyl (such as methyl or ethyl);
$C_{2-6}$ alkenyl (such as ethenyl);
hydroxy;
$C_{1-6}$ alkoxy (such as methoxy); or
$R^{10}$ and $R^{11}$ join to form a 5 to 7 membered saturated or unsaturated ring optionally containing one or more heteroatoms selected from O, N or S (such as a pyrrolinyl or tetrahydropyranyl ring).

In one embodiment which may be mentioned, $R^{10}$ represents:
hydrogen;
halogen (such as fluorine or chlorine); or
$C_{1-6}$ alkyl (such as methyl).

In a further embodiment, $R^{10}$ represents halogen (such as chlorine).

In one embodiment, $R'''$ and $R''$ independently represent hydrogen or methyl. In a further embodiment, both of $R'''$ and $R''$ represent hydrogen or both of $R'''$ and $R''$ represent methyl or one of $R'''$ and $R''$ represents hydrogen and the other represents methyl.

In one embodiment, $R^{11}$ represents:
hydrogen;
halogen (such as fluorine, bromine or chlorine);
$C_{1-6}$ alkyl (such as methyl or ethyl);
$C_{2-6}$ alkenyl (such as ethenyl);
$C_{3-8}$ cycloalkyl (such as cyclopropyl);
$haloC_{1-6}$ alkyl (such as trifluoromethyl); or
$R^{11}$ and $R^{10}$ join to form a 5 to 7 membered saturated or unsaturated ring optionally containing one or more heteroatoms selected from O, N or S (such as a pyrrolinyl, tetrahydropyranyl, pyrazolyl, morpholinyl, pyridyl, furanyl or thiophenyl ring optionally substituted by one or more methyl or fluorine groups).

In one embodiment which may be mentioned, $R^{11}$ represents:
hydrogen;
halogen (such as fluorine, bromine or chlorine);
$C_{1-6}$ alkyl (such as methyl or ethyl);
$C_{2-6}$ alkenyl (such as ethenyl);
$haloC_{1-6}$ alkyl (such as trifluoromethyl); or
$R^{11}$ and $R^{10}$ join to form a 5 to 7 membered saturated or unsaturated ring optionally containing one or more heteroatoms selected from O, N or S (such as a pyrrolinyl or tetrahydropyranyl ring).

In one embodiment which may be mentioned, $R^{11}$ represents:
hydrogen;
halogen (such as fluorine or chlorine); or
$haloC_{1-6}$ alkyl (such as trifluoromethyl).

In a further embodiment, $R^{11}$ represents halogen (such as fluorine).

In one embodiment, $R^{12}$ represents:
hydrogen;
halogen (such as fluorine or chlorine);
$C_{1-6}$ alkyl (such as methyl);
$haloC_{1-6}$ alkyl (such as fluoromethyl, difluoromethyl or trifluoromethyl); or
$C_{1-6}$ alkoxy (such as methoxy).

In a further embodiment, $R^{12}$ represents hydrogen.

In one embodiment, $R^{13}$ represents:
hydrogen; or
halogen (such as fluorine).

In one embodiment which may be mentioned, $R^{13}$ represents hydrogen.

In one embodiment, Y represents —C($R^9$)= and:
each of $R^9$, $R^{10}$, $R^{11}$, $R^{12}$ and $R^{13}$ represent hydrogen; or
each of $R^9$, $R^{10}$, $R^{11}$ and $R^{13}$ represent hydrogen and $R^{12}$ represents $C_{1-6}$ alkyl (such as methyl); or
each of $R^9$, $R^{10}$ and $R^{13}$ represent hydrogen and $R^{11}$ and $R^{12}$ both represents halogen (such as fluorine or chlorine); or
each of $R^9$, $R^{10}$ and $R^{13}$ represent hydrogen, $R^{11}$ represents halogen (such as fluorine) and $R^{12}$ represents $C_{1-6}$ alkyl (such as methyl); or
each of $R^9$, $R^{10}$ and $R^{13}$ represent hydrogen, $R^{11}$ represents halogen (such as fluorine) and $R^{12}$ represents haloC$_{1-6}$ alkyl (such as fluoromethyl or trifluoromethyl); or
each of $R^9$, $R^{10}$, $R^{11}$ and $R^{13}$ represent hydrogen and $R^{12}$ represents haloC$_{1-6}$ alkyl (such as fluoromethyl or difluoromethyl); or
each of $R^9$, $R^{10}$, $R^{11}$ and $R^{13}$ represent hydrogen and $R^{12}$ represents halogen (such as chlorine); or
each of $R^9$, $R^{10}$ and $R^{13}$ represent hydrogen, $R^{11}$ represents halogen (such as fluorine) and $R^{12}$ represents $C_{1-6}$ alkoxy (such as methoxy); or
each of $R^9$, $R^{11}$ and $R^{13}$ represent hydrogen and $R^{10}$ and $R^{12}$ both represent halogen (such as fluorine or chlorine); or
each of $R^9$, $R^{10}$ and $R^{13}$ represent hydrogen, $R^{11}$ represents haloC$_{1-6}$ alkyl (such as trifluoromethyl) and $R^{12}$ represents halogen (such as fluorine); or
each of $R^9$, $R^{11}$, $R^{12}$ and $R^{13}$ represent hydrogen and $R^{10}$ represents $C_{1-6}$ alkyl (such as methyl);
each of $R^9$, $R^{11}$, $R^{12}$ and $R^{13}$ represent hydrogen and $R^{10}$ represents halogen (such as chlorine);
each of $R^9$, $R^{12}$ and $R^{13}$ represent hydrogen and $R^{10}$ and $R^{11}$ both represent halogen (such as fluorine, bromine or chlorine);
each of $R^9$, $R^{10}$ and $R^{13}$ represent hydrogen, $R^{11}$ represents $C_{1-6}$ alkyl (such as methyl) and $R^{12}$ represents halogen (such as chlorine);
each of $R^9$, $R^{12}$ and $R^{13}$ represent hydrogen, $R^{10}$ represents $C_{1-6}$ alkyl (such as methyl or ethyl) and $R^{11}$ represents halogen (such as chlorine or fluorine);
each of $R^9$, $R^{12}$ and $R^{13}$ represent hydrogen, $R^{10}$ represents $C_{1-6}$ alkoxy (such as methoxy) and $R^{11}$ represents halogen (such as fluorine);
each of $R^9$, $R^{12}$ and $R^{13}$ represent hydrogen, $R^{10}$ represents $C_{1-6}$ alkoxy (such as methoxy) and $R^{11}$ represents $C_{1-6}$ alkyl (such as methyl);
each of $R^9$, $R^{12}$ and $R^{13}$ represent hydrogen, $R^{10}$ represents halogen (such as chlorine) and $R^{11}$ represents $C_{1-6}$ alkyl (such as methyl);
both of $R^{12}$ and $R^{13}$ represent hydrogen, both of $R^9$ and $R^{11}$ represent halogen (such as fluorine) and $R^{10}$ represents $C_{1-6}$ alkyl (such as methyl or ethyl);
each of $R^{10}$, $R^{12}$ and $R^{13}$ represent hydrogen and both of $R^9$ and $R^{11}$ represent halogen (such as chlorine, bromine or fluorine);
both of $R^9$ and $R^{12}$ represent hydrogen and each of $R^{10}$, $R^{11}$ and $R^{13}$ represent halogen (such as chlorine or fluorine);
each of $R^{11}$, $R^{12}$ and $R^{13}$ represent hydrogen and both of $R^9$ and $R^{10}$ represents halogen (such as chlorine or fluorine);
each of $R^9$, $R^{12}$ and $R^{13}$ represent hydrogen, $R^{10}$ represents hydroxy and $R^{11}$ represents halogen (such as fluorine);
each of $R^9$, $R^{12}$ and $R^{13}$ represent hydrogen, $R^{10}$ represents $C_{2-6}$ alkenyl (such as ethenyl) and $R^{11}$ represents halogen (such as fluorine)
each of $R^9$, $R^{12}$ and $R^{13}$ represent hydrogen, $R^{10}$ represents hydroxy and $R^{11}$ represents $C_{1-6}$ alkyl (such as methyl);
each of $R^{10}$, $R^{11}$ and $R^{13}$ represent hydrogen and both of $R^9$ and $R^{12}$ represent halogen (such as fluorine or chlorine);
both of $R^{10}$ and $R^{13}$ represent hydrogen, both of $R^{11}$ and $R^{12}$ represent halogen (such as fluorine or chlorine) and $R^9$ represents $C_{1-6}$ alkoxy (such as methoxy);
both of $R^{12}$ and $R^{13}$ represent hydrogen and each of $R^9$, $R^{10}$ and $R^{11}$ represent halogen (such as fluorine or chlorine);
both of $R^{12}$ and $R^{13}$ represent hydrogen, both of $R^9$ and $R^{11}$ represent halogen (such as fluorine) and $R^{10}$ represents $C_{2-6}$ alkenyl (such as ethenyl);
each of $R^9$, $R^{12}$ and $R^{13}$ represent hydrogen and $R^{10}$ and $R^{11}$ join to form a pyrrolinyl, tetrahydropyranyl, pyrazolyl or pyridyl ring optionally substituted by a methyl group;
both of $R^{10}$ and $R^{13}$ represent hydrogen and each of $R^9$, $R^{11}$ and $R^{12}$ represent halogen (such as chlorine or fluorine); or
each of $R^9$, $R^{12}$ and $R^{13}$ represent hydrogen, $R^{10}$ represents halogen (such as chlorine) and $R^{11}$ represents $C_{3-8}$ cycloalkyl (such as cyclopropyl).

In one embodiment which may be mentioned, Y represents —C($R^9$)= and:
each of $R^9$, $R^{10}$, $R^{11}$, $R^{12}$ and $R^{13}$ represent hydrogen; or
each of $R^9$, $R^{10}$, $R^{11}$ and $R^{13}$ represent hydrogen and $R^{12}$ represents $C_{1-6}$ alkyl (such as methyl); or
each of $R^9$, $R^{10}$ and $R^{13}$ represent hydrogen and $R^{11}$ and $R^{12}$ both represents halogen (such as fluorine or chlorine); or
each of $R^9$, $R^{10}$ and $R^{13}$ represent hydrogen, $R^{11}$ represents halogen (such as fluorine) and $R^{12}$ represents $C_{1-6}$ alkyl (such as methyl); or
each of $R^9$, $R^{10}$ and $R^{13}$ represent hydrogen, $R^{11}$ represents halogen (such as fluorine) and $R^{12}$ represents haloC$_{1-6}$ alkyl (such as fluoromethyl or trifluoromethyl); or
each of $R^9$, $R^{10}$, $R^{11}$ and $R^{13}$ represent hydrogen and $R^{12}$ represents haloC$_{1-6}$ alkyl (such as fluoromethyl or difluoromethyl); or
each of $R^9$, $R^{10}$, $R^{11}$ and $R^{13}$ represent hydrogen and $R^{12}$ represents halogen (such as chlorine); or
each of $R^9$, $R^{10}$ and $R^{13}$ represent hydrogen, $R^{11}$ represents halogen (such as fluorine) and $R^{12}$ represents $C_{1-6}$ alkoxy (such as methoxy); or
each of $R^9$, $R^{11}$ and $R^{13}$ represent hydrogen and $R^{10}$ and $R^{12}$ both represent halogen (such as fluorine or chlorine); or
each of $R^9$, $R^{10}$ and $R^{13}$ represent hydrogen, $R^{11}$ represents haloC$_{1-6}$ alkyl (such as trifluoromethyl) and $R^{12}$ represents halogen (such as fluorine); or
each of $R^9$, $R^{11}$, $R^{12}$ and $R^{13}$ represent hydrogen and $R^{10}$ represents $C_{1-6}$ alkyl (such as methyl);
each of $R^9$, $R^{11}$, $R^{12}$ and $R^{13}$ represent hydrogen and $R^{10}$ represents halogen (such as chlorine);
each of $R^9$, $R^{12}$ and $R^{13}$ represent hydrogen and $R^{10}$ and $R^{11}$ both represent halogen (such as fluorine, bromine or chlorine);

each of $R^9$, $R^{10}$ and $R^{13}$ represent hydrogen, $R^{11}$ represents $C_{1-6}$ alkyl (such as methyl) and $R^{12}$ represents halogen (such as chlorine);

each of $R^9$, $R^{12}$ and $R^{13}$ represent hydrogen, $R^{10}$ represents $C_{1-6}$ alkyl (such as methyl or ethyl) and $R^{11}$ represents halogen (such as chlorine or fluorine);

each of $R^9$, $R^{12}$ and $R^{13}$ represent hydrogen, $R^{10}$ represents $C_{1-6}$ alkoxy (such as methoxy) and $R^{11}$ represents halogen (such as fluorine);

each of $R^9$, $R^{12}$ and $R^{13}$ represent hydrogen, $R^{10}$ represents $C_{1-6}$ alkoxy (such as methoxy) and $R^{11}$ represents $C_{1-6}$ alkyl (such as methyl);

each of $R^9$, $R^{12}$ and $R^{13}$ represent hydrogen, $R^{10}$ represents halogen (such as chlorine) and $R^{11}$ represents $C_{1-6}$ alkyl (such as methyl);

both of $R^{12}$ and $R^{13}$ represent hydrogen, both of $R^9$ and $R^{11}$ represent halogen (such as fluorine) and $R^{10}$ represents $C_{1-6}$ alkyl (such as methyl or ethyl);

each of $R^{10}$, $R^{12}$ and $R^{13}$ represent hydrogen and both of $R^9$ and $R^{11}$ represent halogen (such as chlorine, bromine or fluorine);

both of $R^9$ and $R^{12}$ represent hydrogen and each of $R^{10}$, $R^{11}$ and $R^{13}$ represent halogen (such as chlorine or fluorine);

each of $R^{11}$, $R^{12}$ and $R^{13}$ represent hydrogen and both of $R^9$ and $R^{10}$ represents halogen (such as chlorine or fluorine);

each of $R^9$, $R^{12}$ and $R^{13}$ represent hydrogen, $R^{10}$ represents hydroxy and $R^{11}$ represents halogen (such as fluorine);

each of $R^9$, $R^{12}$ and $R^{13}$ represent hydrogen, $R^{10}$ represents $C_{2-6}$ alkenyl (such as ethenyl) and $R^{11}$ represents halogen (such as fluorine)

each of $R^9$, $R^{12}$ and $R^{13}$ represent hydrogen, $R^{10}$ represents hydroxy and $R^{11}$ represents $C_{1-6}$ alkyl (such as methyl);

each of $R^{10}$, $R^{11}$ and $R^{13}$ represent hydrogen and both of $R^9$ and $R^{12}$ represent halogen (such as fluorine or chlorine);

both of $R^{10}$ and $R^{13}$ represent hydrogen, both of $R^{11}$ and $R^{12}$ represent halogen (such as fluorine or chlorine) and $R^9$ represents $C_{1-6}$ alkoxy (such as methoxy);

both of $R^{12}$ and $R^{13}$ represent hydrogen and each of $R^9$, $R^{10}$ and $R^{11}$ represent halogen (such as fluorine or chlorine);

both of $R^{12}$ and $R^{13}$ represent hydrogen, both of $R^9$ and $R^{11}$ represent halogen (such as fluorine) and $R^{10}$ represents $C_{2-6}$ alkenyl (such as ethenyl);

each of $R^9$, $R^{12}$ and $R^{13}$ represent hydrogen and $R^{10}$ and $R^{11}$ join to form a pyrrolinyl or tetrahydropyranyl ring; or both of $R^{10}$ and $R^{13}$ represent hydrogen and each of $R^9$, $R^{11}$ and $R^{12}$ represent halogen (such as chlorine or fluorine).

In one embodiment which may be mentioned, Y represents —C($R^9$)= and:

each of $R^9$, $R^{10}$, $R^{11}$, $R^{12}$ and $R^{13}$ represent hydrogen; or each of $R^9$, $R^{10}$, $R^{11}$ and $R^{13}$ represent hydrogen and $R^{12}$ represents $C_{1-6}$ alkyl (such as methyl); or each of $R^9$, $R^{10}$ and $R^{13}$ represent hydrogen and $R^{11}$ and $R^{12}$ both represents halogen (such as fluorine or chlorine); or each of $R^9$, $R^{10}$ and $R^{13}$ represent hydrogen, $R^{11}$ represents halogen (such as fluorine) and $R^{12}$ represents $C_{1-6}$ alkyl (such as methyl); or each of $R^9$, $R^{10}$ and $R^{13}$ represent hydrogen, $R^{11}$ represents halogen (such as fluorine) and $R^{12}$ represents haloC$_{1-6}$ alkyl (such as fluoromethyl or trifluoromethyl); or each of $R^9$, $R^{10}$, $R^{11}$ and $R^{13}$ represent hydrogen and $R^{12}$ represents haloC$_{1-6}$ alkyl (such as fluoromethyl or difluoromethyl); or each of $R^9$, $R^{10}$, $R^{11}$ and $R^{13}$ represent hydrogen and $R^{12}$ represents halogen (such as chlorine); or each of $R^9$, $R^{10}$ and $R^{13}$ represent hydrogen, $R^{11}$ represents halogen (such as fluorine) and $R^{12}$ represents $C_{1-6}$ alkoxy (such as methoxy); or each of $R^9$, $R^{11}$ and $R^{13}$ represent hydrogen and $R^{10}$ and $R^{12}$ both represent halogen (such as fluorine); or each of $R^9$, $R^{10}$ and $R^{13}$ represent hydrogen, $R^{11}$ represents haloC$_{1-6}$ alkyl (such as trifluoromethyl) and $R^{12}$ represents halogen (such as fluorine); or each of $R^9$, $R^{11}$, $R^{12}$ and $R^{13}$ represent hydrogen and $R^{10}$ represents $C_{1-6}$ alkyl (such as methyl); or each of $R^9$, $R^{12}$ and $R^{13}$ represent hydrogen and $R^{10}$ and $R^{11}$ both represent halogen (such as fluorine or chlorine).

In a further embodiment, Y represents —C($R^9$)= and:

each of $R^9$, $R^{12}$ and $R^{13}$ represent hydrogen and $R^{10}$ and $R^{11}$ both represent halogen (such as fluorine or chlorine), such as each of $R^9$, $R^{12}$ and $R^{13}$ represent hydrogen, $R^{10}$ represents halogen (such as chlorine) and $R^{11}$ represents halogen (such as fluorine).

In an alternative embodiment, Y represents —N= and:

$R^{11}$ and $R^{13}$ both represent hydrogen, $R^{10}$ represents $C_{1-6}$ alkyl (such as methyl) and $R^{12}$ represents haloC$_{1-6}$ alkyl (such as trifluoromethyl);

$R^{10}$ and $R^{11}$ join to form a pyrrolinyl ring and $R^{12}$ and $R^{13}$ both represent hydrogen;

$R^{12}$ and $R^{13}$ both represent hydrogen, $R^{10}$ represents $C_{1-6}$ alkyl (such as methyl) and $R^{11}$ represents halogen (such as fluorine);

each of $R^{11}$, $R^{12}$ and $R^{13}$ represent hydrogen and $R^{10}$ represents —NR'''R'' (such as —NH$_2$, —NHMe or —NMe$_2$);

$R^{12}$ and $R^{13}$ both represent hydrogen and $R^{10}$ and $R^{11}$ join to form a pyrrolinyl, morpholinyl, furanyl or thiophenyl ring optionally substituted by a methyl, fluorine or chlorine group; or $R^{13}$ represents hydrogen, $R^{12}$ represents halogen (such as chlorine) and $R^{10}$ and $R^{11}$ join to form a pyrrolinyl ring optionally substituted by a methyl group.

In one embodiment which may be mentioned, Y represents —N= and:

$R^{11}$ and $R^{13}$ both represent hydrogen, $R^{10}$ represents $C_{1-6}$ alkyl (such as methyl) and $R^{12}$ represents haloC$_{1-6}$ alkyl (such as trifluoromethyl); or $R^{10}$ and $R^{11}$ join to form a pyrrolinyl ring and $R^{12}$ and $R^{13}$ both represent hydrogen.

In one embodiment which may be mentioned, Y represents —N= and:

$R^{11}$ and $R^{13}$ both represent hydrogen, $R^{10}$ represents $C_{1-6}$ alkyl (such as methyl) and $R^{12}$ represents haloC$_{1-6}$ alkyl (such as trifluoromethyl).

In one embodiment, the invention provides a compound of formula (I) which is the free base of a compound of Examples 1-245 or a pharmaceutically acceptable salt or solvate thereof.

In one embodiment which may be mentioned, the invention provides a compound of formula (I) which is the free base of a compound of Examples 1-163 or a pharmaceutically acceptable salt or solvate thereof.

In one embodiment which may be mentioned, the invention provides a compound of formula (I) which is the free base of a compound of Examples 1-67 or a pharmaceutically acceptable salt or solvate thereof.

In one embodiment, the compound of formula (I) is a compound which is other than a compound of Example 65.

In one embodiment, the compound of formula (I) is a compound which is other than a compound of Example 163.

In one embodiment, the compound of formula (I) is a compound which is other than a compound of Examples 65 and 163.

A reference to a compound of the formula (I) and subgroups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, prodrugs, isotopes and protected forms thereof as defined in any aspect of the invention (except intermediate compounds in chemical processes) are referred to as "compounds of the invention".

Salts

Certain compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the $pK_a$ of the acid from which the salt is formed.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge, Bighley and Monkhouse, *J. Pharm. Sci.* 1977, 66, pp. 1-19. Such pharmaceutically acceptable salts include acid addition salts formed with inorganic acids e.g. hydrochloric, hydrobromic, sulfuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates may be used, for example in the isolation of compounds of formula (I) and are included within the scope of this invention. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Certain of the compounds of formula (I) may form acid addition salts with one or more equivalents of the acid. The present invention includes within its scope all possible stoichiometric and non-stoichiometric forms.

Solvates

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention. In one embodiment, the pharmaceutically acceptable solvates of the compounds of the invention include the hydrate thereof.

In one embodiment, said crystalline form of the compounds of formula (I) is a cocrystal or coformer. Such a cocrystal or coformer may be prepared using water-soluble molecules such as saccharin, caffeine, nicotinamide or carboxylic acids. Coformers may be prepared as described in Emami S et al (2018) BioImpacts 8(4), 305-320, the techniques of which are herein incorporated by reference.

It will be understood that the invention includes pharmaceutically acceptable derivatives of compounds of formula (I) and that these are included within the scope of the invention.

As used herein "pharmaceutically acceptable derivative" includes any pharmaceutically acceptable ester or salt of such ester of a compound of formula (I) which, upon administration to the recipient is capable of providing (directly or indirectly) a compound of formula (I) or an active metabolite or residue thereof.

N-Oxides

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry, by Jerry March*, 4th Edition, Wiley Interscience. More particularly, N-oxides can be made by the procedure of L. W. Deady (*Syn. Commun.* 1977, 7, 509-514) in which the amine compound is reacted with m-chloroperoxybenzoic acid (mCPBA), for example, in an inert solvent such as dichloromethane.

Prodrugs

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in *Drugs of Today*, 19, 9, 1983, 499-538 and in *Topics in Chemistry*, Chapter 31, pp. 306-316 and in "*Design of Prodrugs*" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "*Design of Prodrugs*" (the disclosure in which document is incorporated herein by reference) may be placed on appropriate functionalities when such functionalities are present within compounds of the invention.

Also included within the scope of the compound and various salts of the invention are polymorphs thereof.

Enantiomers

Where chiral centres are present in compounds of formula (I), the present invention includes within its scope all possible enantiomers and diastereoisomers, including mixtures thereof. The different isomeric forms may be separated or resolved one from the other by conventional methods, or any given isomer may be obtained by conventional synthetic methods or by stereospecific or asymmetric syntheses. The invention also extends to any tautomeric forms or mixtures thereof.

Isotopes

The subject invention also includes all pharmaceutically acceptable isotopically-labelled compounds which are identical to those recited in formula (I) but for the fact that one or more atoms are replaced by an atom having an atomic mass or mass number different from the atomic mass or mass number most commonly found in nature.

Examples of isotopes suitable for inclusion in the compounds of the invention comprise isotopes of hydrogen, such as $^2$H (D) and $^3$H (T), carbon, such as $^{11}$C $^{13}$C and $^{14}$C, chlorine, such as $^{36}$C, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase) etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy. Isotopically-labelled compounds of formula (I) can generally be prepared by conventional techniques known to those skilled in the art or by processes analogous to those described in the accompanying Examples and Preparations using appropriate isotopically-labelled reagents in place of the non-labelled reagent previously employed.

Purity

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are given on a weight for weight basis). Impure preparations of the compounds may be used for preparing the more pure forms used in the pharmaceutical compositions.

Processes

According to a further aspect of the present invention there is provided a process for the preparation of compounds of formula (I) and derivatives thereof. The following schemes are examples of synthetic schemes that may be used to synthesise the compounds of the invention. In the following schemes reactive groups can be protected with protecting groups and de-protected according to well established techniques.

According to a further aspect of the invention there is provided a process for preparing a compound of formula (I) as herein defined which comprises:

(a) reacting a compound of formula (II):

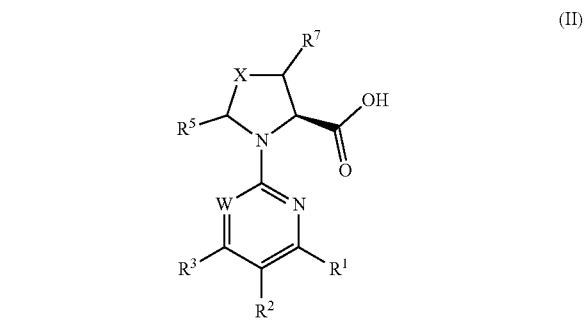

(II)

wherein $R^1$, $R^2$, $R^3$, W, $R^5$, X and $R^7$ are as defined herein, with a compound of formula (III):

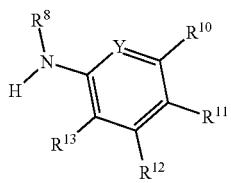

wherein $R^8$, Y, $R^{10}$, $R^{11}$, $R^{12}$ and $R^{13}$ are as defined herein;
(b) reacting a compound of formula (IV):

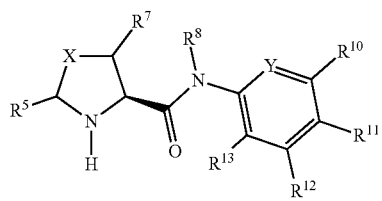

wherein $R^5$, X, $R^7$, $R^8$, Y, $R^{10}$, $R^{11}$, $R^{12}$ and $R^{13}$ are as defined herein, with a compound of formula (V):

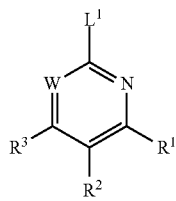

wherein $R^1$, $R^2$, $R^3$ and W are as defined herein and $L^1$ represents a suitable leaving group, such as a halogen atom (e.g. chlorine);
(c) deprotection of a protected derivative of a compound of formula (I);
(d) interconversion of a compound of formula (I) or protected derivative thereof to a further compound of formula (I) or protected derivative thereof; and
(e) optional formation of a pharmaceutically acceptable salt of a compound of formula (I).

Process (a) typically comprises reacting a compound of formula (II) with a compound of formula (III) in the presence of suitable reagents, such as EtOAc pyridine and T3P.

Process (b) typically comprises reacting a compound of formula (IV) with a compound of formula (V) in the presence of suitable reagents, such as DIPEA in NMP, under suitable conditions, such as heating to a suitable temperature (such as 100° C.).

Compounds of formula (II) and (IV) may be prepared in accordance with the procedures described herein. For example, compounds of formula (II) may be prepared in accordance with the experimental procedure described in Example 1 and compounds of formula (IV) may be prepared in accordance with the experimental procedure described in Example 2.

Compounds of formula (III) and (V) are either known or may be prepared in accordance with known procedures.

A wide range of well known functional group interconversions for process (d) are known by a person skilled in the art for converting a precursor compound to a compound of formula (I) and are described in Advanced Organic Chemistry by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions described herein are followed or preceded by one or more reactions known to the skilled of the art and are performed in an appropriate order to achieve the requisite substitutions on $R^1$, $R^2$, $R^3$, $R^4$, $R^5$, $R^6$, $R^7$, $R^8$, $R^9$, $R^{10}$, $R^{11}$, $R^{12}$ and $R^{13}$ defined herein to afford other compounds of formula (I). Non-limiting examples of such reactions whose conditions can be found in the literature include:
protection of reactive functions,
deprotection of reactive functions,
halogenation,
dehalogenation,
dealkylation,
alkylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of esters groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

It is recognised that the sequence of reactions involving aryl coupling and reduction may be varied. It is also recognised that a wide range of palladium based catalysts are suitable for conducting aryl coupling reactions.

It may also be recognised that isomer separation may occur at any suitable stage in the synthetic sequence. It should be stressed that such chiral separation forms a key aspect of the invention and that such separation may be conducted in accordance with the methodology described herein or may be conducted in accordance with known methodology.

It is also recognised that it may be beneficial to temporarily form a protected derivative of an intermediate in the synthesis, for example, a Boc-protected amine, or SEM-protected amide, in order to facilitate chromatographic separation, chiral resolution or to give improved solubility or yields in particular steps.

In many of the reactions described above, it may be necessary to protect one or more groups to prevent reaction from taking place at an undesirable location on the molecule. Examples of protecting groups, and methods of protecting and de-protecting functional groups, can be found in Protective Groups in Organic Synthesis (T. Green and P. Wuts; 4th Edition; John Wiley and Sons, 2007).

A hydroxy group may be protected, for example, as an ether (—OR) or an ester (—OC(=O)R), for example, as: a tert-butyl ether; a tetrahydropyranyl (THP) ether; a benzyl, benzhydryl (diphenylmethyl), or trityl (triphenylmethyl) ether; a trimethylsilyl or tert-butyldimethylsilyl ether; or an acetyl ester (—OC(=O)CH$_3$).

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a tert-butyl carbamate (—NHCOOC(CH$_3$)$_3$, NH-Boc); a 2-biphenyl-2-propyl carbamate (—NHCO—OC(CH$_3$)$_2$C$_6$H$_4$C$_6$H$_5$, NH-Boc), as a 9-fluorenylmethyl carbamate (—NH—Fmoc), as a 6-nitroveratryl carbamate (—NH—Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH—Psec).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g. a methyl ester; a tert-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester; para-methoxybenzyl ester.

It will be understood by those skilled in the art that certain compounds of the invention can be converted into other compounds of the invention according to standard chemical methods.

Pharmaceutically acceptable salts may be prepared conventionally by reaction with the appropriate acid or acid derivative.

Therapeutic Utility

The compounds of the invention, subgroups and examples thereof, are inhibitors of Polθ polymerase activity, and which may be useful in preventing or treating disease states or conditions described herein. In addition the compounds of the invention, and subgroups thereof, will be useful in preventing or treating diseases or condition mediated by Polθ.

References to the preventing or prophylaxis or treatment of a disease state or condition such as cancer include within their scope alleviating or reducing the incidence of cancer.

Thus, for example, it is envisaged that the compounds of the invention will be useful in alleviating or reducing the incidence of cancer.

The compounds of the present invention may be useful for the treatment of the adult population. The compounds of the present invention may be useful for the treatment of the pediatric population.

As a consequence of their inhibition of Polθ, the compounds will be useful in providing a means of disabling the ability of cells to perform MMEJ. It is therefore anticipated that the compounds may prove useful in treating or preventing proliferative disorders such as cancers. In addition, the compounds of the invention may be useful in the treatment of diseases in which there is a disorder associated with cell accumulation.

Without being bound by theory it is expected that the Polθ inhibitors of the present invention will demonstrate certain properties for them to be of particular utility in the therapeutic treatment of certain cancers. For example, in one embodiment, the Polθ inhibitors of the present invention are suitably lethal in BRCA1 and BRCA2 deficient primary and secondary solid tumours, including breast, ovarian, prostate and pancreas.

In a further embodiment, the Polθ inhibitors of the present invention are suitably lethal in a variety of primary and secondary solid tumours which are HRD by mechanisms other than BRCA deficiency, such as those with promoter hypermethylation. In these tumours where no DSB repair pathway may be fully down regulated the Polθi may be given along with another DDR modulator such as a PARP inhibitor, a DNA-PK inhibitor, an ATR inhibitor, an ATM inhibitor, a wee1 inhibitor or a CHK1 inhibitor.

In a further embodiment, the Polθ inhibitors of the present invention are suitably lethal in primary and secondary breast, ovarian, prostate and pancreatic tumours retaining BRCA1 deficiency but which, following or not following exposure to PARPi medication, are resistant to PARPi treatment.

In a further embodiment, the Polθ inhibitors of the present invention suitably increase the ORR including CRR, will delay the onset of PARPi resistance, will increase the time to relapse and DFS, and will increase the OS of HRD (BRCA1/2 deficient and other HRD mechanisms) primary and secondary tumours (breast, ovarian, prostate and pancreas) when given with PARPi treatment programmes.

In a further embodiment, the Polθ inhibitors of the present invention suitably show synthetic sickness and/or synthetic lethality in a variety of tumours with loss of ATM activity (ATM$^{-/-}$) particularly in the context of WT p53. Tumour types will include around 10% of all solid tumours including gastric, lung, breast, and CRC, along with CLL. Co-medicating with another DDR modifier, such as a DNA-PK inhibitor, PARP inhibitor or ATR inhibitor, may further enhance such activity. Polθ inhibitors will resensitise CLL to classical chemotherapy and chemo-immunotherapy where drug resistance has emerged. Thus, according to a further embodiment, the pharmaceutical composition of the present invention additionally comprises a DNA-PK inhibitor, PARP inhibitor, or ATR inhibitor.

In a further embodiment, the Polθ inhibitors of the present invention suitably show synthetic sickness and/or synthetic lethality in a variety of tumours deficient in the DNA double strand break repair process of non-homologous end-joining (NHEJ-D). Tumour types will include approximately 2-10% of all solid tumours including prostate, pancreatic, cervical, breast, lung, bladder and oesophageal. Co-medicating with another DDR modifier, such as a PARP inhibitor, ATM inhibitor, wee1 inhibitor, CHK inhibitor, or ATR inhibitor, may further enhance such activity. Polθ inhibitors will further sensitise NHEJD cancer cells to DNA DSB inducing chemotherapies and to ionising radiation based therapies. Thus, according to a further embodiment, the pharmaceutical composition of the present invention additionally comprises a PARP inhibitor, ATM inhibitor, wee1 inhibitor, CHK inhibitor, or ATR inhibitor.

In a further embodiment, the Polθ inhibitors of the present invention suitably reduce the DNA replication stress response during the chemotherapy of HR proficient tumours such as ovarian, NSCL and breast tumours over expressing Polθ. This will increase the ORR to treatment and increase OS. Such effects are particularly likely with cytarabine (Ara-C) and hydroxyurea used in a wide variety of leukemias including CML, and the management of squamous cell carcinomas.

In a further embodiment, the Polθ inhibitors of the present invention suitably selectively sensitise solid tumours to radiotherapy, including EBRT and brachytherapy, with little or no sensitisation of normal tissues. In a fractionated curative-intent setting this will increase loco-regional control driving increased survival. This will be particularly evident in the management of NSCLC, SCCH&N, rectal cancer, prostate cancer and pancreatic cancer.

In a further embodiment, the Polθ inhibitors of the present invention suitably show synthetic sickness and/or synthetic lethality in PTEN deleted tumours such as CaP, with or without comedication with a PARPi. Furthermore, such tumours will exhibit exquisite sensitivity to radiotherapy both by dint of the PTEN deletion as well as the Polθ inhibitor induced radiosensitivity.

In a further embodiment, the Polθ inhibitors of the present invention suitably suppress TLS polymerase activity, sensitising primary and secondary solid tumours (e.g. breast, lung, ovarian, CRC) to drugs (e.g. cisplatin, mitomycin and cyclophosphamide) as well as reducing the acquisition of drug-induced mutations implicated in tumour resistance leading to prolongation of remission and increased TTR.

In a further embodiment, the Polθ inhibitors of the present invention suitably resensitise BCR-ABL-positive CML which is has developed imatinib resistance, as well as other solid tumours with elevated ligase IIIα levels, reduced ligase IV levels and increased dependence upon altEJ DSB repair.

In a further embodiment, the Polθ inhibitors of the present invention suitably show synthetic sickness and/or synthetic lethality in aromatase inhibitor resistant ER⁻ primary and secondary breast cancers, again showing elevated ligase IIIα levels, reduced ligase IV levels and increased dependence upon altEJ DSB repair.

According to a further aspect of the invention there is a provided a compound of formula (I) as defined herein for use in the treatment of tumours characterised by a deficiency in homologous recombination (HRD).

It will be appreciated that references herein to "deficiency in homologous recombination (HRD)" refer to any genetic variation which results in a deficiency or loss of function of the resultant homologous recombination gene. Examples of said genetic variation include mutations (e.g. point mutations), substitutions, deletions, single nucleotide polymorphisms (SNPs), haplotypes, chromosome abnormalities, Copy Number Variation (CNV), epigenetics, DNA inversions, reduction in expression and mis-localisation.

In one embodiment, said homologous recombination genes are selected from any of: ATM, ATR, BRCA1, BRCA2, BARD1, RAD51C, RAD50, CHEK1, CHEK2, FANCA, FANCB, FANCC, FANCD2, FANCE, FANCF, FANCG, FANCI, FANCL, FANCM, PALB2 (FANCN), FANCP (BTBD12), ERCC4 (FANCQ), PTEN, CDK12, MRE11, NBS1, NBN, CLASPIN, BLM, WRN, SMARCA2, SMARCA4, LIG1, RPA1, RPA2, BRIP1 and PTEN.

It will be appreciated that references herein to "non-homologous end-joining deficiency (NHEJD)" refer to any genetic variation which results in a deficiency or loss of function of the resultant homologous recombination gene. Examples of said genetic variation include mutations (e.g. point mutations), substitutions, deletions, single nucleotide polymorphisms (SNPs), haplotypes, chromosome abnormalities, Copy Number Variation (CNV), epigenetics, DNA inversions, reduction in expression and mis-localisation.

In one embodiment, said non-homologous end-joining genes are selected from any one or more of: LIG4, NHEJ1, POLL, POLM, PRKDC, XRCC4, XRCC5, XRCC6, and DCLRE1C.

According to a further aspect of the invention there is a provided a compound of formula (I) as defined herein for use in the treatment of tumours which overexpress Polθ.

According to a further aspect of the invention there is a provided a compound of formula (I) as defined herein for use in the treatment of tumours which have elevated ligase IIIα levels, reduced ligase IV levels and increased dependence upon altEJ DSB repair.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and pre-malignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, MALT lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis. In particular, the compounds of the invention may be useful in the treatment of metastasis and metastatic cancers.

Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body.

Particular cancers include hepatocellular carcinoma, melanoma, oesophageal, renal, colon, colorectal, lung e.g. mesothelioma or lung adenocarcinoma, breast, bladder, gastrointestinal, ovarian and prostate cancers.

A further aspect provides the use of a compound for the manufacture of a medicament for the treatment of a disease or condition as described herein, in particular cancer.

The compounds may also be useful in the treatment of tumour growth, pathogenesis, resistance to chemo- and radio-therapy by sensitising cells to chemotherapy and as an anti-metastatic agent.

The potency of the compounds of the invention as inhibitors of Polθ can be measured using the biological and biophysical assays set forth in the examples herein and the level of affinity exhibited by a given compound can be defined in terms of the $IC_{50}$ value. Particular compounds of the present invention are compounds having an $IC_{50}$ value of less than 1 µM, more particularly less than 0.1 µM.

A role for the loss of Polθ enhancing the efficacy of CRISPR mediated gene editing has been described in WO 2017/062754. Thus, Polθ inhibitory compounds are likely to be useful in enhancing the efficiency of CRISPR based editing methodologies and/or CRISPR based editing therapeutics. Furthermore, compound mediated Polθ inhibition is likely to reduce the frequency of random integration events and thus provide a route to ameliorate any safety concerns of CRISPR mediated technology. Thus, according to a further aspect of the invention, there is provided the use of a compound of formula (I) as defined herein in a CRISPR based editing methodology and/or CRISPR based editing therapeutics, such as the enhancement of efficiency of CRISPR based editing methodology and/or CRISPR based editing therapeutics.

Pharmaceutical Compositions

While it is possible for the active compound to be administered alone, it is preferable to present it as a pharmaceutical composition (e.g. formulation). In one embodiment this is a sterile pharmaceutical composition.

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, interalia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of formula (I), or sub-groups thereof.

Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one particular embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another particular embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13$^{th}$ March 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Particularly, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, particularly from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g. solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by Polθ. Thus, according to a further aspect of the invention there is provided a method of treating a disease state or condition mediated by Polθ (e.g. cancer) which comprises administering to a subject in need thereof a compound of formula (I) as described herein. Examples of such disease states and conditions are set out above, and in particular include cancer.

The compounds are generally administered to a subject in need of such administration, for example a human or animal patient, particularly a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

In another particular dosing schedule, a patient is given the compound orally once a week.

In another particular dosing schedule, a patient is given the compound orally once-daily for between 7 and 28 days such as 7, 14 or 28 days.

In another particular dosing schedule, a patient is given the compound orally once-daily for 1 day, 2 days, 3 days, 5 days or 1 week followed by the required amount of days off to complete a one or two week cycle.

In another particular dosing schedule, a patient is given the compound orally once-daily for 2 weeks followed by 2 weeks off.

In another particular dosing schedule, a patient is given the compound orally once-daily for 2 weeks followed by 1 week off.

In another particular dosing schedule, a patient is given the compound orally once-daily for 1 week followed by 1 week off.

Ultimately, however, the quantity of compound administered and the type of composition used will be commensurate with the nature of the disease or physiological condition being treated and will be at the discretion of the physician.

It will be appreciated that Polθ inhibitors can be used as a single agent or in combination with other anticancer agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (I) include but are not limited to:

Topoisomerase I inhibitors;
Antimetabolites;
Tubulin targeting agents;
DNA binder and topoisomerase II inhibitors;
Alkylating Agents;
Monoclonal Antibodies;
Anti-Hormones;
Signal Transduction Inhibitors;
Proteasome Inhibitors;
DNA methyl transferase inhibitors;
Cytokines and retinoids;
Chromatin targeted therapies;
Radiotherapy; and
Other therapeutic or prophylactic agents.

Particular examples of anti-cancer agents or adjuvants (or salts thereof), include but are not limited to any of the agents selected from groups (i)-(xlvi), and optionally group (xlvii), below:

(i) Platinum compounds, for example cisplatin (optionally combined with amifostine), carboplatin or oxaliplatin;
(ii) Taxane compounds, for example paclitaxel, paclitaxel protein bound particles (Abraxane™), docetaxel, cabazitaxel or larotaxel;
(iii) Topoisomerase I inhibitors, for example camptothecin compounds, for example camptothecin, irinotecan (CPT11), SN-38, or topotecan;
(iv) Topoisomerase II inhibitors, for example anti-tumour epipodophyllotoxins or podophyllotoxin derivatives for example etoposide, or teniposide;
(v) Vinca alkaloids, for example vinblastine, vincristine, liposomal vincristine (Onco-TCS), vinorelbine, vindesine, vinflunine or vinvesir;
(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;
(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);

(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine or decitabine, or SGI-110;

(xii) Antifolates, for example methotrexate, pemetrexed disodium, or raltitrexed;

(xiii) Cytotoxic antibiotics, for example antinomycin D, bleomycin, mitomycin C, dactinomycin, carminomycin, daunomycin, levamisole, plicamycin, or mithramycin;

(xiv) Tubulin-binding agents, for example combrestatin, colchicines or nocodazole;

(xv) Signal Transduction inhibitors such as Kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032/RG7204), dabrafenib, encorafenib or an IκB kinase inhibitor such as SAR-113945, bardoxolone, BMS-066, BMS-345541, IMD-0354, IMD-2560, or IMD-1041, or MEK inhibitors such as Selumetinib (AZD6244) and Trametinib (GSK121120212);

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;

(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, PD332991, ZK-304709, or AZD-5438;

(xviii) PKA/B inhibitors and PKB (akt) pathway inhibitors for example AKT inhibitors such as KRX-0401 (perifosine/NSC 639966), ipatasertib (GDC-0068; RG-7440), afuresertib (GSK-2110183; 2110183), MK-2206, MK-8156, AT13148, AZD-5363, triciribine phosphate (VQD-002; triciribine phosphate monohydrate (API-2; TCN-P; TCN-PM; VD-0002), RX-0201, NL-71-101, SR-13668, PX-316, AT13148, AZ-5363, Semaphore, SF1126, or Enzastaurin HCl (LY317615) or MTOR inhibitors such as rapamycin analogues such as RAD 001 (everolimus), CCI 779 (temsirolemus), AP23573 and ridaforolimus, sirolimus (originally known as rapamycin), AP23841 and AP23573, calmodulin inhibitors e.g. CBP-501 (forkhead translocation inhibitors), enzastaurin HCl (LY317615) or PI3K Inhibitors such as dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, or sonolisib (PX-866);

(xix) Hsp90 inhibitors for example AT13387, herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;

(xx) Monoclonal Antibodies (unconjugated or conjugated to radioisotopes, toxins or other agents), antibody derivatives and related agents, such as anti-CD, anti-VEGFR, anti-HER2, anti-CTLA4, anti-PD-1 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxomab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), siltuximab (IL6), or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (anti-PD-1), BMS-936559 (anti-PD-L1), MPDL320A, AMP-514 or MEDI4736 (anti-PD-L1), or tremelimumab (formerly ticilimumab, CP-675,206, anti-CTLA-4);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17,20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example panobinostat, resminostat, abexinostat, vorinostat, romidepsin, belinostat, entinostat, quisinostat, pracinostat, tefinostat, mocetinostat, givinostat, CUDC-907, CUDC-101, ACY-1215, MGCD-290, EVP-0334, RG-2833, 4SC-202, romidepsin, AR-42 (Ohio State University), CG-200745, valproic acid, CKD-581, sodium butyrate, suberoylanilide hydroxamide acid (SAHA), depsipeptide (FR 901228), dacinostat (NVP-LAQ824), R306465/JNJ-16241199, JNJ-26481585, trichostatin A, chlamydocin, A-173, JNJ-MGCD-0103, PXD-101, or apicidin;

(xxxii) Proteasome Inhibitors for example bortezomib, carfilzomib, delanzomib (CEP-18770), ixazomib (MLN-9708), oprozomib (ONX-0912) or marizomib;

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, rucaparib (AG-014699 or PF-01367338), talazoparib or AG-014699;

(xlvi) DNA damage response inhibitors such as ATM inhibitors AZD0156 MS3541, ATR inhibitors AZD6738, M4344, M6620 wee1 inhibitor AZD1775;

(xlvii) Agonists of Death receptor (e.g. TNF-related apoptosis inducing ligand (TRAIL) receptor), such as mapatumumab (formerly HGS-ETR1), conatumumab (formerly AMG 655), PR095780, lexatumumab, dulanermin, CS-1008, apomab or recombinant TRAIL ligands such as recombinant Human TRAIL/Apo2 Ligand;

(xlviii) Prophylactic agents (adjuncts); i.e. agents that reduce or alleviate some of the side effects associated with chemotherapy agents, for example
anti-emetic agents,
agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim),
agents that inhibit bone resorption such as denosumab or bisphosphonates e.g. zoledronate, zoledronic acid, pamidronate and ibandronate,
agents that suppress inflammatory responses such as dexamethasone, prednisone, and prednisolone,
agents used to reduce blood levels of growth hormone and IGF-I (and other hormones) in patients with acromegaly or other rare hormone-producing tumours, such as synthetic forms of the hormone somatostatin e.g. octreotide acetate,
antidote to drugs that decrease levels of folic acid such as leucovorin, or folinic acid,
agents for pain e.g. opiates such as morphine, diamorphine and fentanyl,
non-steroidal anti-inflammatory drugs (NSAID) such as COX-2 inhibitors for example celecoxib, etoricoxib and lumiracoxib,
agents for mucositis e.g. palifermin,
agents for the treatment of side-effects including anorexia, cachexia, oedema or thromoembolic episodes, such as megestrol acetate.

In one embodiment the anticancer is selected from recombinant interferons (such as interferon-γ and interferon α) and interleukins (e.g. interleukin 2), for example aldesleukin, denileukin diftitox, interferon alfa 2a, interferon alfa 2b, or peginterferon alfa 2b; interferon-α2 (500μ/ml) in particular interferon-β; and signal transduction inhibitors such as kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032/RG7204), dabrafenib, encorafenib or an IκB kinase inhibitor such as SAR-113945, bardoxolone, BMS-066, BMS-345541, IMD-0354, IMD-2560, or IMD-1041, or MEK inhibitors such as Selumetinib (AZD6244) and Trametinib (GSK121120212), in particular Raf inhibitors (e.g. vemurafenib) or MEK inhibitors (e.g. trametinib).

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m2 per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m2, and for vinorelbine in dosage of about 10 to 30 mg/m2 per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m2 per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, particularly 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

Where the compound of the formula (I) is administered in combination therapy with one, two, three, four or more other therapeutic agents (particularly one or two, more particularly one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

In one embodiment is provided a compound of formula (I) for the manufacture of a medicament for use in therapy wherein said compound is used in combination with one, two, three, or four other therapeutic agents. In another embodiment is provided a medicament for treating cancer which comprises a compound of formula (I) wherein said medicament is used in combination with one, two, three, or four other therapeutic agents. The invention further provides use of a compound of formula (I) for the manufacture of a medicament for enhancing or potentiating the response rate in a patient suffering from a cancer where the patient is being treated with one, two, three, or four other therapeutic agents.

It will be appreciated that the particular method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

In one embodiment the compound of the invention is administered with a "radiosensitizer" and/or "chemosensitizer". In one embodiment the compound of the invention is administered with an "immune sensitizer".

The term "immune sensitizer" is defined as a molecule administered to patients in therapeutically effective amounts to increase the sensitivity of cells to a Polθ inhibitor.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds of the invention; compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds of the invention; compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

Examples of immune sensitizers include the following, but are not limited to: immunomodulating agents, for example monoclonal antibodies such as immune checkpoint antibodies [e.g. CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (anti-PD-1), BMS-936559 (anti-PD-L1), MPDL320A, AMP-514 or MED14736 (anti-PD-L1), or tremelimumab (formerly ticilimumab, CP-675,206, anti-CTLA-4)]; or Signal Transduction inhibitors; or cytokines (such as recombinant interferons); or oncolytic viruses; or immune adjuvants (e.g. BCG).

Immune sensitizers may be administered in conjunction with a therapeutically effective amount of one or more other compounds, including but not limited to: compounds of the invention; compounds which promote the incorporation of immune sensitizers to the target cells; compounds which control the flow of therapeutics, nutrients, and/or oxygen to the target cells; therapeutic agents which act on the tumour or other therapeutically effective compounds for treating cancer or other disease.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all agents. In an alternative embodiment, the individual therapeutic agents may be formulated separately and presented together in the form of a kit, optionally with instructions for their use.

In one embodiment is provided a combination of a compound of formula (I) with one or more (e.g. 1 or 2) other therapeutic agents (e.g. anticancer agents as described above). In a further embodiment is provided a combination of a Polθ inhibitor as described herein and a PI3K/AKT pathway inhibitor selected from: apitolisib, buparlisib, Copanlisib, pictilisib, ZSTK-474, CUDC-907, GSK-2636771, LY-3023414, ipatasertib, afuresertib, MK-2206, MK-8156, Idelalisib, BEZ235 (dactolisib), BYL719, GDC-0980, GDC-0941, GDC-0032 and GDC-0068.

In another embodiment is provided a compound of formula (I) in combination with one or more (e.g. 1 or 2) other therapeutic agents (e.g. anticancer agents) for use in therapy, such as in the prophylaxis or treatment of cancer.

In one embodiment the pharmaceutical composition comprises a compound of formula (I) together with a pharmaceutically acceptable carrier and optionally one or more therapeutic agent(s).

In another embodiment the invention relates to the use of a combination according to the invention in the manufacture of a pharmaceutical composition for inhibiting the growth of tumour cells.

In a further embodiment the invention relates to a product containing a compound of formula (I) and one or more anticancer agent, as a combined preparation for simultaneous, separate or sequential use in the treatment of patients suffering from cancer.

EXAMPLES

The invention will now be illustrated, but not limited, by reference to the specific embodiments described in the following examples.

Abbreviations
   aq. Aqueous
   BOC tert-Butyloxycarbonyl
   (Boc)$_2$O Di-tert-butyl dicarbonate
   dba Dibenzylideneacetone
   dppf 1,1'-Bis(diphenylphosphino)ferrocene
   DCM Dichloromethane
   DIPEA N,N-Diisopropylethylamine
   DMAP 4-Dimethylaminopyridine
   DMF Dimethylformamide
   DMSO Dimethylsulfoxide
   EEDQ N-Ethoxycarbonyl-2-ethoxy-1,2-dihydroquinoline
   EtOH Ethanol
   EtOAc Ethyl acetate
   h hour(s)
   HPLC High-performance liquid chromatography
   MeCN Acetonitrile
   MeOH Methanol
   min minutes
   NMO 4-Methylmorpholine 4-oxide
   NMP N-Methylpyrrolidinone
   NMR Nuclear magnetic resonance
   PE Petroleum ether
   rt Room temperature or ambient temperature
   sat. Saturated solution
   SCX-2 Propylsulfonic acid (non-endcapped) functionalized silica column
   SFC Supercritical Fluid Chromatography
   T3P 1-Propanephosphonic anhydride solution
   TBAB Tetrabutylammonium bromide
   TBAF Tetra-n-butylammonium fluoride
   TEA Triethylamine
   TFA Trifluoroacetic acid
   THF Tetrahydrofuran
   TLC Thin layer chromatography
Typical Preparative HPLC Method For purification of samples by HPLC the following columns were typically used; SunFire C18, Xtimate C18, Phenomenex Gemini, Phenomenex Synergi C18, Phenomenex Luna, Waters Xbridge C18, Boston Prime C18 and Shim-pack C18. Typical mobile phases used were water and MeCN, with either acidic or basic additives, such as formic acid (0.1% v/v) or ammonium hydroxide (0.05% v/v). A typical method started with 95% water:5% MeCN and decreasingly polar ratios of water and MeCN over a period of 5 to 12 min, with a typical flow rate of 25 mL/min. For mass-directed HPLC the typical mass spectrometer used was a Waters 3100 which detected masses between 100 and 700 g/mol.

Intermediate 1: 2-Chloro-6-methyl-4-(trifluoromethyl)nicotinonitrile

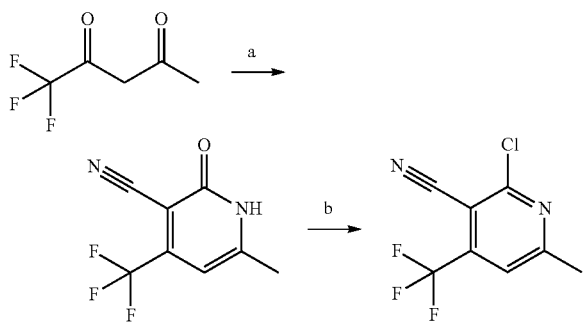

Step a. To a solution of 1,1,1-trifluoropentane-2,4-dione (25 g, 162 mmol) and 2-cyano-acetamide (15 g, 178 mmol) in EtOH (200 mL) was added diethylamine (5.93 g, 81.1 mmol). The mixture was stirred at 70° C. for 12 h. On completion, white solid was precipitated from EtOH. The reaction mixture was filtered and solid was collected, further dried under vacuum to afford 2-hydroxy-6-methyl-4-(trifluoromethyl)pyridine-3-carbonitrile (24.5 g, 121 mmol, crude) as a white solid.

m/z ES+[M+H]$^+$ 203.0; $^1$H NMR (400 MHz, DMSO-d6) δ ppm 6.51 (s, 1H), 2.33 (s, 3H).

Step b. 2-Hydroxy-6-methyl-4-(trifluoromethyl)pyridine-3-carbonitrile (24.5 g, 121 mmol) was carefully added to POCl$_3$ (400 mL) at rt and the resultant solution was stirred at 110° C. for 12 h. On completion, POCl$_3$ was carefully removed by distillation to afford a residue. The residue was purified by column chromatography (0-20% EtOAc in PE) to afford 2-chloro-6-methyl-4-(trifluoromethyl)pyridine-3-carbonitrile (24.5 g, 111 mmol, 91.6% yield) as a light yellow oil.

$^1$H NMR (400 MHz, CDCl$_3$) δ ppm 7.50 (s, 1H), 2.73 (s, 3H).

Intermediate 2: (2S,4S)-1-(tert-Butoxycarbonyl)-4-((tert-butyldimethylsilyl)oxy)-pyrrolidine-2-carboxylic acid

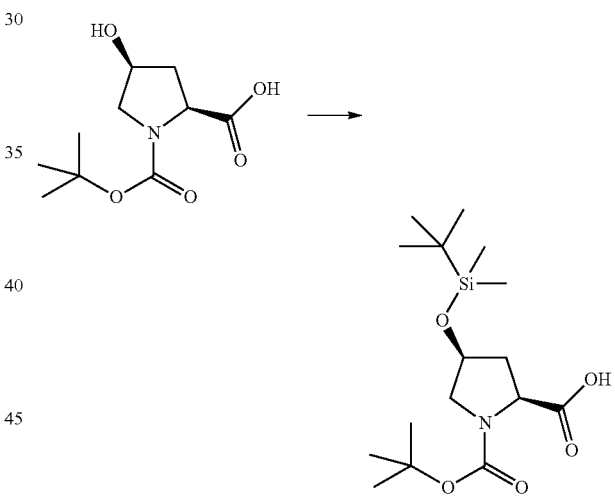

A mixture of (2S,4S)-1-tert-butoxycarbonyl-4-hydroxy-pyrrolidine-2-carboxylic acid (CAS Number 87691-27-8; 5 g, 21.6 mmol), tert-butylchlorodimethylsilane (3.91 g, 25.9 mmol), imidazole (2.21 g, 32.4 mmol) in DCM (3 mL) was degassed and purged 3 times with N$_2$ and then the mixture was stirred at rt for 12 h under N$_2$ atmosphere. The reaction mixture was quenched by addition of aq. NH$_4$Cl (60 mL), diluted with water (100 mL) and extracted with DCM (200 mL×3). The combined organic layers were washed with brine (100 mL×3), dried over anhydrous sodium sulfate, filtered and evaporated to afford (2S,4S)-1-tert-butoxycarbonyl-4-[tert-butyl(dimethyl)silyl]oxy-pyrrolidine-2-carboxylic acid (7.2 g, 20.8 mmol, 96% yield) as an off-white oil.

$^1$H NMR (400 MHz, DMSO-d6) δ ppm 4.42-4.20 (m, 1H), 4.26-4.07 (m, 1H), 3.64-3.44 (m, 1H), 3.14-2.99 (m, 1H), 2.43-2.31 (m, 1H), 1.91-1.76 (m, 1H), 1.40-1.33 (m, 9H), 0.85-0.76 (m, 9H), 0.23-0.16 (m, 6H).

Intermediate 3: (2S,4S)-4-Hydroxy-N-methyl-N-(m-tolyl)pyrrolidine-2-carboxamide hydrochloride

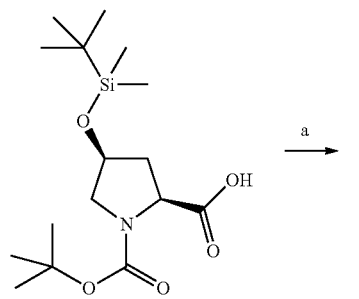

Step a. A solution of Intermediate 2 (2 g, 5.79 mmol), N-methyl-3-methyl-aniline (468 mg, 3.86 mmol) and T3P (7.37 g, 11.6 mmol, 50% wt. % in DMF) in pyridine (20 mL) was stirred at rt for 16 h. Upon completion, the reaction mixture was quenched by addition of water (50 mL) and extracted with EtOAc (50 mL×3). The combined organic extracts were washed with brine (50 mL×3), dried over sodium sulphate and evaporated. The residue was purified by silica gel column chromatography (5-25% EtOAc in PE) to obtain tert-butyl (2S,4S)-4-[tert-butyl(dimethyl)silyl]oxy-2-[methyl(m-tolyl)carbamoyl]pyrrolidine-1-carboxylate (1.23 g, 71% yield) as a yellow oil.

m/z ES+[M+H]$^+$ 449.7

Step b. Tert-butyl (2S,4S)-4-[tert-butyl(dimethyl)silyl]oxy-2-[methyl(m-tolyl)carbamoyl]-pyrrolidine-1-carboxylate (1.2 g, 2.67 mmol) was dissolved in HCl in 1,4-dioxane (4 M, 2 mL) and stirred at rt for 2 h. The solution was evaporated to give (2S,4S)-4-hydroxy-N-methyl-N-(m-tolyl)pyrrolidine-2-carboxamide (0.9 g, crude, HCl salt) as a yellow solid.

m/z ES+[M+H]$^+$ 235.3

Intermediate 4: (2S,4S)-4-(Benzyloxy)-1-(tert-butoxycarbonyl)pyrrolidine-2-carboxylic acid

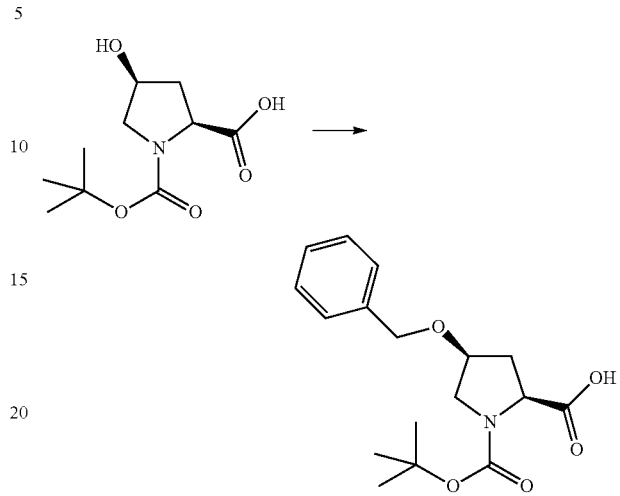

To a solution of (2S,4S)-1-tert-butoxycarbonyl-4-hydroxy-pyrrolidine-2-carboxylic acid (30 g, 123 mmol) in THF (400 mL) was added NaH (11.42 g, 285 mmol, 60% dispersion in mineral oil) and benzyl bromide (26.63 g, 155.7 mmol). The mixture was stirred at rt for 16 h. The mixture was slowly poured into water (200 mL) and adjusted to pH=2 by slow addition of HCl (2 M) and then extracted with EtOAc (400 mL×3). The combined organic extracts were dried over Na$_2$SO$_4$, filtered and evaporated to give the crude product. The crude product was triturated with PE/EtOAc=10/1 at rt for 30 min and the solid collected by filtration. Residual solvent was removed by drying under vacuum to give (2S,4S)-4-(benzyloxy)-1-(tert-butoxycarbonyl)pyrrolidine-2-carboxylic acid (36 g, 112 mmol, 86% yield) as a white solid.

$^1$H NMR (400 MHz, DMSO-d6) δ ppm 7.55-7.25 (m, 5H), 4.55-4.40 (m, 2H), 4.25-4.10 (m, 2H), 3.60-3.50 (m, 1H), 2.40-2.30 (m, 1H), 2.18-2.08 (m, 2H), 1.50-1.26 (m, 9H).

Intermediate 5: (3aS,4S,6aS)-2,2-Dimethyl-6-oxo-tetrahydro-4H-[1,3]dioxolo[4,5-c]pyrrole-4-carboxylic acid

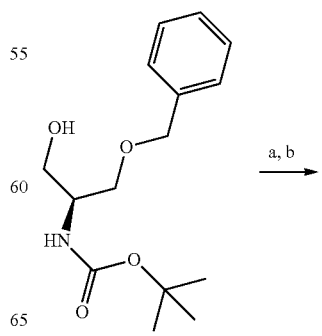

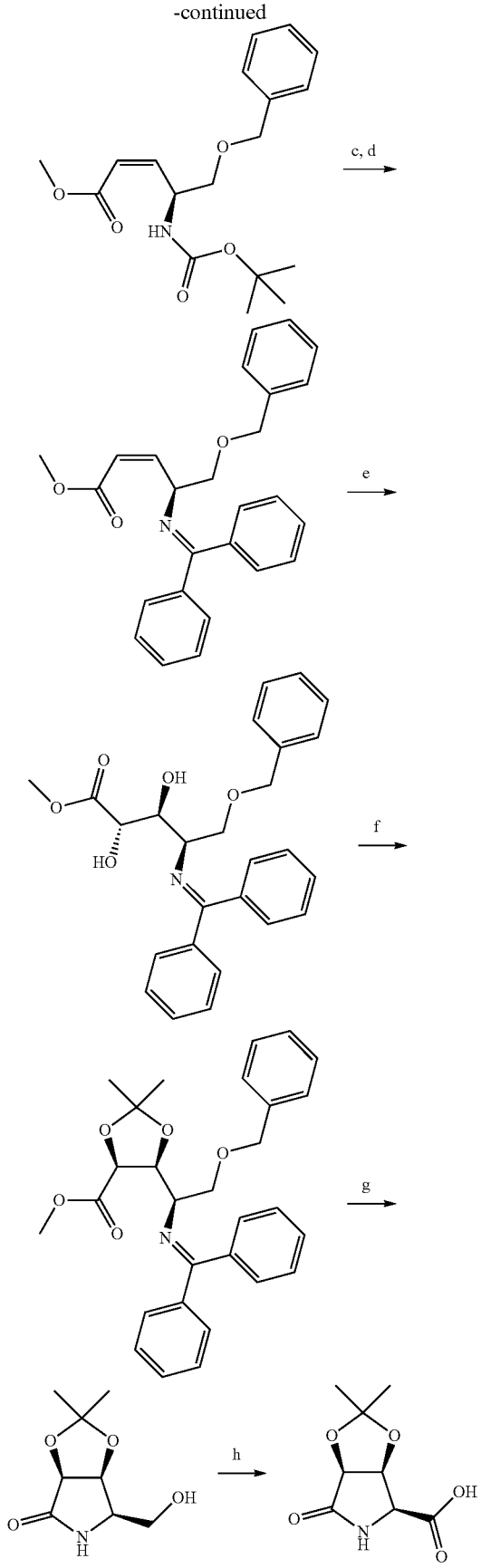

Step a. To a solution of tert-butyl (S)-(1-(benzyloxy)-3-hydroxypropan-2-yl)carbamate (4.68 g, 16.6 mmol) in DCM (15 mL) was added Dess Martin reagent (68 g, 50 mL, 24.2 mmol, 15 wt. % in DCM). An exotherm was observed and the temperature increased to 30° C. The mixture was stirred at rt for 1.5 h. The reaction was quenched by addition of a sat. aq. NaHCO$_3$ solution (100 mL) and stirred vigorously for 1.5 h until all Dess-Martin reagent was fully quenched. The biphasic mixture was filtered over Celite. The phases were separated and the aqueous phase was extracted into DCM (2×50 mL), dried over Na$_2$SO$_4$ and evaporated. The resulting material was co-evaporated with toluene (25 mL) to afford tert-butyl (R)-(1-(benzyloxy)-3-oxopropan-2-yl)carbamate (4.65 g) as a slightly turbid light yellow oil. This crude aldehyde was used without any further purification in the next step.

$^1$H NMR (300 MHz, CDCl$_3$) δ ppm 9.61 (s, 1H), 7.51-7.08 (m, 5H), 5.47 (s, 1H), 4.55 (m, 2H), 4.30 (m, 1H), 3.96 (m, 1H), 3.71 (m, 1H), 1.42 (s, 9H).

Step b. A solution of methyl 2-(bis(2,2,2-trifluoroethoxy)phosphoryl)acetate (6.607 g, 20.77 mmol) and 18-crown-6 (21.96 g, 83.08 mmol; dried by co-evaporation with toluene prior to use) in dry THF (30 mL) was cooled to −78° C. and a solution of KHMDS in toluene (0.7 M, 4.15 g, 29.7 mL, 20.8 mmol) was added within 10 min. The mixture was stirred for 15 min at −78° C. and a solution of tert-butyl (R)-(1-(benzyloxy)-3-oxopropan-2-yl)carbamate (4.65 g, 16.6 mmol) in anhydrous THF (20 mL) was added dropwise within 15 min. The mixture was stirred for 2.5 h at −78° C. A sat. aq. NH$_4$Cl (100 mL) was added and the biphasic mixture was warmed to rt. The phases were separated and the aqueous phase was extracted into EtOAc (2×50 mL). The combined organic phases were washed with brine, dried over Na$_2$SO$_4$ and evaporated to afford 11.6 g of a yellow oil. Purification by column chromatography (0-10% EtOAc in heptanes) afforded methyl (S,Z)-5-(benzyloxy)-4-((tert-butoxycarbonyl)amino)pent-2-enoate (3.70 g, 66.3%) as a colorless oil.

Step c. To a solution of methyl (S,Z)-5-(benzyloxy)-4-((tert-butoxycarbonyl)amino)pent-2-enoate (3.70 g, 11.0 mmol) in MeOH (25 mL) was added acetyl chloride (8.66 g, 7.87 mL, 110 mmol) dropwise at 0° C. The solution was stirred at rt for 3 h and evaporated. The crude product methyl (S,Z)-5-(benzyloxy)-4-(chloro-l5-azaneyl)pent-2-enoate hydrochloride (3.00 g, 100%) was used as such in the next step.

Step d. To a solution of methyl (S,Z)-4-amino-5-(benzyloxy)pent-2-enoate hydrochloride (3.00 g, 11.0 mmol) in DCM (30 mL), was added diphenylmethanimine (1.994 g, 11.00 mmol) at rt. A precipitate was formed within 5 min and the mixture was stirred at rt overnight.

A sat. aq. NaHCO$_3$ solution (30 mL) was added and the phases were separated. The aqueous phase was extracted with DCM (2×20 mL). The combined organic phases were dried over Na$_2$SO$_4$ and evaporated to afford 4.34 g of a yellow oil. Purification by column chromatography (0-10% EtOAc in heptanes) afforded methyl (S,Z)-5-(benzyloxy)-4-((diphenylmethylene)amino)pent-2-enoate (3.30 g, 75.1%) as a colorless oil.

Step e. To a solution of methyl (S,Z)-5-(benzyloxy)-4-((diphenylmethylene)amino)pent-2-enoate (3.30 g, 8.26 mmol) in a mixture of water (30 mL) and THF (30 mL) was added NMO (2.42 g, 20.7 mmol) at rt, followed by the addition of osmium tetroxide 4% in water (1.0 g, 1.0 mL, 0.2 mmol). The mixture was stirred at rt for 24 h. Sat. aq. Na$_2$SO$_3$ was added and the aqueous phase was extracted with EtOAc (2×40 mL). The combined organic phases were washed with brine, dried over Na₂SO₄ and concentrated under vacuum to afford 4.12 g of a crude material. Purification by chromatography (0-20% EtOAc in Heptanes) afforded 2.90 g of a pure product as a mixture of syn and anti isomers (predominantly syn). Methyl (2S,3S,4R)-5-(benzyloxy)-4-((diphenylmethylene)-amino)-2,3-dihydroxypentanoate (2.90 g, 81.0%) was isolated as an equilibrium mixture of the acyclic diol and the cyclic oxazolidine. The ratio of syn and anti isomers was not determined.

Step f. To a solution of methyl (2S,3S,4R)-5-(benzyloxy)-4-((diphenylmethylene)amino)-2,3-dihydroxypentanoate (2.90 g, 6.69 mmol) and 2,2-dimethoxypropane (12.3 g, 14.65 mL, 118 mmol) in benzene (220 mL), was added pyridinium p-toluenesulfonate (505 mg, 2.01 mmol). The mixture was heated at reflux with a Dean-Stark trap for 3 h. The volatiles were removed under vacuum and the residue was dissolved in EtOAc (75 mL). The solution was washed with sat. aq. NaHCO₃ solution (2×75 mL), dried over Na₂SO₄ and concentrated under vacuum to afford 3.14 g of a light brown oil. The diastereomeric ratio of syn and anti isomers was 91.5:8.5, by HPLC. Purification by column chromatography (10-15% EtOAc in heptanes) afforded the syn isomer methyl (4S,5S)-5-((R)-2-(benzyloxy)-1-((diphenyl-methylene)amino)ethyl)-2,2-dimethyl-1,3-dioxolane-4-carboxylate (2.77 g, 87.4%) as a colourless oil.

m/z ES+[M+H]⁺ 474.3; ¹H NMR (300 MHz, CDCl₃) δ ppm 7.71 (m, 2H), 7.48 (m, 13H), 4.71 (m, 2H), 4.50 (s, 2H), 3.92 (m, 1H), 3.73 (m, 2H), 3.40 (s, 3H), 1.76 (s, 3H), 1.45 (s, 3H).

Step g. To a solution of methyl (4S,5S)-5-((R)-2-(benzyloxy)-1-((diphenylmethylene)-amino)ethyl)-2,2-dimethyl-1,3-dioxolane-4-carboxylate (2.77 g, 5.85 mmol) in MeOH (180 mL) palladium hydroxide on carbon (277 mg, 0.39 mmol) was added. The mixture was stirred under a hydrogen atmosphere (balloon) for 40 h. Pd/C (10 wt %, 100 mg) was added to the mixture and the stirring under hydrogen atmosphere was continued for 72 h. The mixture was filtered over Celite and concentrated under vacuum. Purification by column chromatography (10% MeOH in DCM) afforded (3aS,6R,6aS)-6-(hydroxymethyl)-2,2-dimethyltetrahydro-4H-[1,3]dioxolo[4,5-c]pyrrol-4-one 8 (0.874 g, 79.8%) as a white solid.

Step h. To a solution of (3aS,6R,6aS)-6-(hydroxymethyl)-2,2-dimethyltetrahydro-4H-[1,3]dioxolo[4,5-c]pyrrol-4-one 8 (875 mg, 4.67 mmol) in a mixture of water (12 mL), MeCN (8 mL) and carbon tetrachloride (8 mL), was added sodium periodate (3.00 g, 14.0 mmol) and ruthenium(III) chloride hydrate (105 mg, 0.467 mmol). The mixture was stirred at rt overnight. EtOAc (50 mL) was added and the phases were separated. The aqueous phase was extracted with EtOAc (2×20 mL). The combined organic phases were washed with brine (5 mL), dried over Na₂SO₄ and concentrated under vacuum to afford 250 mg of an off-white solid. The aqueous phase was extracted again with THF (2×50 mL). The organic phases were washed with brine (5 mL), dried over Na₂SO₄ and added to the EtOAc extract. In total 760 mg of an off-white solid was isolated. Trituration in DCM afforded (3aS,4S,6aS)-2,2-dimethyl-6-oxotetrahydro-4H-[1,3]dioxolo[4,5-c]pyrrole-4-carboxylic acid (600 mg, 63.8%) as an off-white solid.

m/z ES+[M+H]⁺ 202.0; ¹H NMR (300 MHz, D₂O) δ ppm 5.07 (dd, J=5.3, 5.3 Hz, 1H), 4.79 (d, J=5.3 Hz, 1H), 4.53 (d, J=5.3 Hz, 1H), 1.31 (s, 3H, 1.30 (s, 3H).

Example 1

(S)-1-(3-Cyano-6-methyl-4-(trifluoromethyl)pyridin-2-yl)-N-methyl-N-phenylpyrrolidine-2-carboxamide

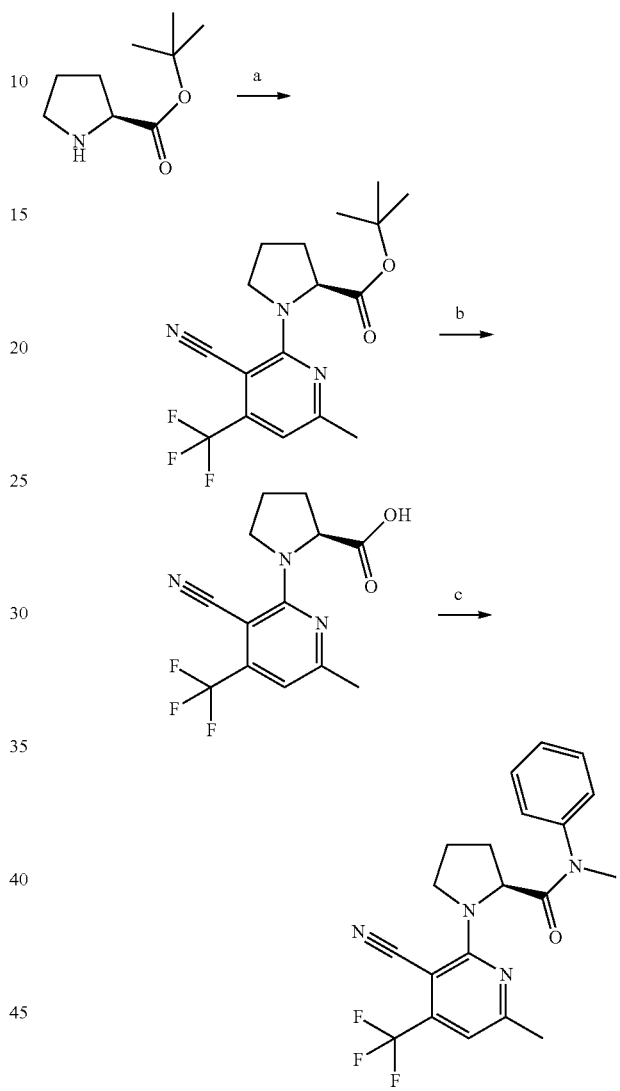

Step a. A mixture of (S)-2-(tert-butoxycarbonyl)pyrrolidine (0.88 g, 5.0 mmol), 2-chloro-6-methyl-4-(trifluoromethyl)nicotinonitrile (1.1 g, 5.0 mmol) and DIPEA (2.79 mL, 15.0 mmol) in NMP (10 mL) was heated at 80° C. for 45 min using microwave irradiation. Further (S)-2-(tert-butoxy-carbonyl)pyrrolidine (0.26 g, 1.5 mmol) was added and the mixture heated using microwave irradiation at 80° C. for 30 min. The reaction mixture was partitioned between EtOAc (20 mL) and sat. aq. NaHCO₃. The aqueous was extracted with EtOAc (20 mL) and the combined organic layers were washed with brine (2×20 mL), dried and evaporated. The crude material was purified by column chromatography eluting with DCM. Product fractions were combined and evaporated to give tert-butyl (2S)-1-[3-cyano-6-methyl-4-(trifluoromethyl)-2-pyridyl]pyrrolidine-2-carboxylate (1.59 g, 89%) as a yellow solid.

m/z ES+[M+H]⁺ 300.38; ¹H NMR (400 MHz, DMSO-d6) δ ppm 7.09 (s, 1H), 4.56 (dd, J=8.1, 5.0 Hz, 1H), 3.99-3.84

(m, 2H), 2.42 (s, 3H), 2.25 (dt, J=12.1, 7.7 Hz, 1H), 2.02 (p, J=6.7 Hz, 2H), 1.96-1.87 (m, 1H), 1.39 (s, 9H).

Step b. To a solution of tert-butyl (2S)-1-[3-cyano-6-methyl-4-(trifluoromethyl)-2-pyridyl]-pyrrolidine-2-carboxylate (700 mg, 1.97 mmol) in DCM (5 mL) was added TFA (2.0 mL, 26 mmol) and the mixture stirred at rt for 2 h. Further TFA (4.0 mL, 52 mmol) was added and the mixture stirred at rt for 3 h. The reaction mixture was evaporated and the residue treated with toluene and evaporated three times to help remove residual TFA. The residue was further treated with IPA and evaporated, treated with MeOH and evaporated and finally treated with EtOAc and evaporated to give (2S)-1-[3-cyano-6-methyl-4-(trifluoromethyl)-2-pyridyl]pyrrolidine-2-carboxylic acid, (715 mg). This material was used in the next step without further purification.

m/z ES+[M+H]$^+$ 300.39; $^1$H NMR (400 MHz, DMSO-d6) δ ppm 12.59 (s, 1H), 7.08 (s, 1H), 4.66 (dd, J=8.3, 4.8 Hz, 1H), 3.92 (t, J=6.6 Hz, 2H), 2.42 (s, 3H), 2.32-2.23 (m, 1H), 2.07-1.92 (m, 3H).

Step c. To a solution of (2S)-1-[3-cyano-6-methyl-4-(trifluoromethyl)-2-pyridyl]pyrrolidine-2-carboxylic acid (70 mg, 0.234 mmol) in EtOAc (2 mL) was added N-methylaniline (0.03 mL, 0.234 mmol), pyridine (0.08 mL, 0.936 mmol) and T3P (0.28 mL, 0.468 mmol, 50 wt. % in EtOAc) and the mixture stirred at rt for 16 h. The reaction mixture was partitioned between EtOAc and sat. aq. NaHCO$_3$. The aqueous layer was extracted with EtOAc and the combined organics were washed with brine, dried and evaporated. The crude mixture was purified by mass-directed preparative HPLC to provide the title compound, (25 mg, 27%).

m/z ES+[M+H]$^+$ 389.50; $^1$H NMR (400 MHz, DMSO-d6) δ ppm 7.58-7.47 (m, 4H), 7.45-7.39 (m, 1H), 7.06 (s, 1H), 4.60-4.48 (m, 1H), 3.97-3.83 (m, 2H), 3.17 (s, 3H), 2.53 (s, 3H), 2.12-2.02 (m, 1H), 1.95-1.80 (m, 3H).

Example 2

(S)-1-(3-Cyano-6-methyl-4-(trifluoromethyl)pyridin-2-yl)-N-isopropyl-N-(m-tolyl)pyrrolidine-2-carboxamide

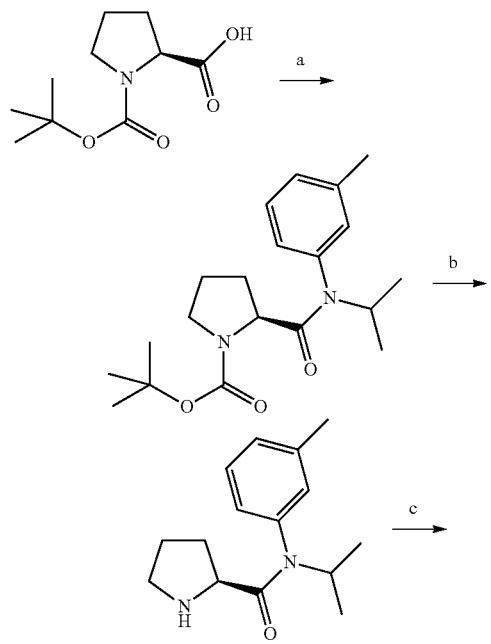

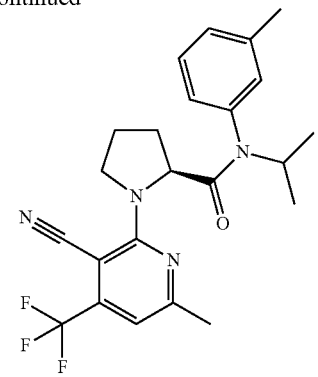

Step a. To a solution of N-isopropyl-3-methyl-aniline (0.164 g, 1.1 mmol), (S)-1-(tert-butoxycarbonyl)pyrrolidine-2-carboxylic acid (0.22 g, 1.0 mmol) and pyridine (0.32 mL, 4.0 mmol) in EtOAc (1 mL) at 0° C., was added T3P (1.19 mL, 2.0 mmol, 50 wt. % in EtOAc) and the mixture stirred for 1 h. The mixture was warmed to rt and stirred for 21 h. Further T3P (1.19 mL, 2.0 mmol, 50 wt. % in EtOAc) was added and the mixture stirred for 24 h. The mixture was cooled to 0° C., quenched by addition of aq HCl (0.5 M) and extracted into EtOAc. The organic extract was washed with aq HCl (0.5 M) and then brine, dried and evaporated to give tert-butyl (2S)-2-[isopropyl(m-tolyl)carbamoyl]pyrrolidine-1-carboxylate (338 mg, 97%) as a gum.

m/z ES+[M+H]$^+$ 347.61; $^1$H NMR (400 MHz, DMSO-d6) δ ppm 7.43-7.31 (m, 1H), 7.30-7.22 (m, 1H), 7.12-6.94 (m, 2H), 4.74 (h, J=6.7 Hz, 1H), 4.10-4.00 (m, 1H), 3.34-3.29 (m, 2H), 2.36 (s, 3H), 1.87-1.73 (m, 4H), 1.43-1.38 (m, 9H), 0.98-0.92 (m, 6H).

Step b. A solution of tert-butyl (2S)-2-[isopropyl(m-tolyl)carbamoyl]pyrrolidine-1-carboxylate (320 mg, 0.924 mmol) in DCM (8 mL) was treated with TFA (0.07 mL, 0.924 mmol) and stirred for 2 h. The reaction mixture was evaporated, re-dissolved in MeOH, adsorbed onto SCX-2, washed with MeOH and eluted with methanolic ammonia (2 M). The basic fractions were combined and solvent was evaporated to give (2S)—N-isopropyl-N-(m-tolyl)pyrrolidine-2-carboxamide (134 mg, 59%).

m/z ES+[M+H]$^+$ 247.54; $^1$H NMR (400 MHz, DMSO-d6) δ ppm 7.40-7.31 (m, 1H), 7.31-7.20 (m, 1H), 7.08-7.00 (m, 2H), 4.79 (hept, J=6.8 Hz, 1H), 3.25-3.17 (m, 1H), 3.10-3.03 (m, 1H), 3.00-2.94 (m, 1H), 2.45-2.39 (m, 1H), 2.38-2.32 (m, 3H), 1.57-1.34 (m, 4H), 1.01-0.88 (m, 6H).

Step c. A mixture of (2S)—N-isopropyl-N-(m-tolyl)pyrrolidine-2-carboxamide (50 mg, 0.20 mmol), 2-chloro-6-methyl-4-(trifluoromethyl)nicotinonitrile (45 mg, 0.20 mmol) and DIPEA (0.11 mL, 0.61 mmol) in NMP (2 mL) was heated at 100° C., using microwave irradiation, for 1 h. The reaction mixture was partitioned between EtOAc and sat. aq. NaHCO$_3$ and the layers separated. The organics were washed with brine (×2), dried and evaporated. The residue was purified by column chromatography (5-30% EtOAc in cyclohexane). Product fractions were combined and evaporated to provide the title compound (33 mg, 38%).

m/z ES+[M+H]$^+$ 431.59; $^1$H NMR (400 MHz, DMSO-d6) δ ppm 7.50-7.42 (m, 1H), 7.42-7.29 (m, 2H), 7.21-7.14 (m, 1H), 7.12-7.04 (m, 1H), 4.78 (hept, J=6.7 Hz, 1H), 4.38-4.28 (m, 1H), 3.98-3.86 (m, 2H), 2.64-2.57 (m, 3H), 2.43 (s, 3H), 2.13-2.02 (m, 1H), 1.98-1.80 (m, 3H), 1.10-0.98 (m, 6H).

Example 3

(2S,4S)-1-(3-Cyano-6-methyl-4-(trifluoromethyl)pyridin-2-yl)-4-hydroxy-N-methyl-N-(m-tolyl)pyrrolidine-2-carboxamide

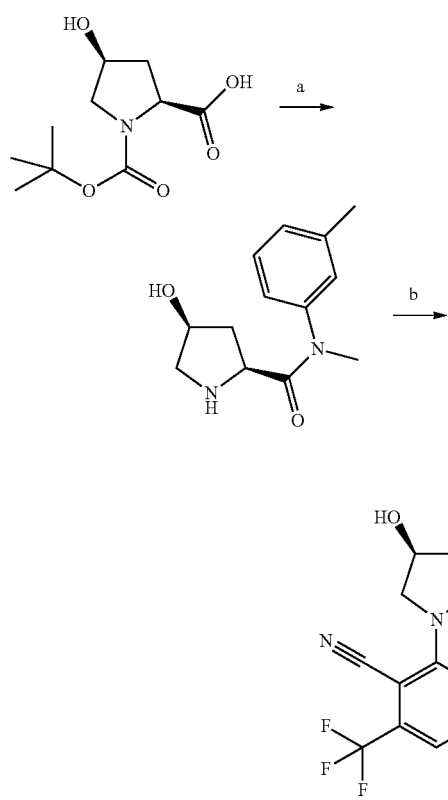

Step a. To a solution of (2S,4S)-1-(tert-butoxycarbonyl)-4-hydroxypyrrolidine-2-carboxylic acid (CAS Number 87691-27-8; 0.75 g, 3.15 mmol) in DCM (15 mL) was added N-methyl-3-methyl-aniline (0.8 mL, 6.292 mmol) and EEDQ (1.57 g, 6.29 mmol) and the mixture was stirred at rt overnight. The reaction mixture was washed with 2 M aq. HCl (2×25 mL), the organic layer was dried and evaporated. The resultant residue was dissolved in DCM (6 mL), treated with TFA (3.0 mL, 6.0 mmol) and the mixture stirred at rt overnight. The reaction mixture was absorbed onto SCX-2, washed with MeOH, and eluted with methanolic ammonia (7 M), and solvent was removed under vacuum. The crude material was purified by flash column chromatography (0-10% methanolic ammonia (7 M) in DCM) to provide (2S,4S)-4-hydroxy-N-methyl-N-(m-tolyl)pyrrolidine-2-carboxamide, (0.368 g, 50%).

$^1$H NMR (400 MHz, DMSO-d6) δ ppm 7.35 (t, J=7.7 Hz, 1H), 7.24-6.92 (m, 3H), 4.60 (d, J=4.3 Hz, 1H), 4.18-3.91 (m, 1H), 3.17 (d, J=4.7 Hz, 3H), 2.76 (d, J=11.6 Hz, 1H), 2.45-2.37 (m, 1H), 2.33 (s, 3H), 1.74-1.55 (m, 1H), 1.51-1.30 (m, 1H).

Step b. To a solution of (2S,4S)-4-hydroxy-N-methyl-N-(m-tolyl)pyrrolidine-2-carboxamide (200 mg, 0.854 mmol) in NMP (4 mL) was added Intermediate 1 (218 mg, 0.939 mmol) and DIPEA (0.45 mL, 2.56 mmol) and the mixture was stirred at 100° C. for 1 h. The cooled mixture was diluted with EtOAc (20 mL), washed with sat. aq. NaHCO$_3$ (20 mL) and then brine (20 mL), dried and evaporated. The crude material was purified by mass-directed preparative HPLC. Product fractions were combined and evaporated. The resulting material was further dried under vacuum for 24 h to provide the title compound (0.290 g, 81%) as a white solid.

m/z ES+[M+H]$^+$ 419.45; $^1$H NMR (400 MHz, DMSO-d6) δ ppm 7.41 (t, J=7.7 Hz, 1H), 7.34-7.19 (m, 3H), 7.09 (s, 1H), 5.34 (d, J=6.3 Hz, 1H), 4.50 (t, J=8.2 Hz, 1H), 4.14 (q, J=6.9 Hz, 1H), 4.03 (dd, J=9.7, 6.8 Hz, 1H), 3.62 (dd, J=9.7, 7.2 Hz, 1H), 3.16 (s, 3H), 2.53 (s, H), 2.37 (s, 3H), 2.23-2.04 (m, 1H), 1.89-1.61 (m, 1H).

Example 4

(2S,4S)-1-(3-Cyano-4,6-dimethylpyridin-2-yl)-N-(3,4-difluorophenyl)-4-hydroxy-N-methylpyrrolidine-2-carboxamide

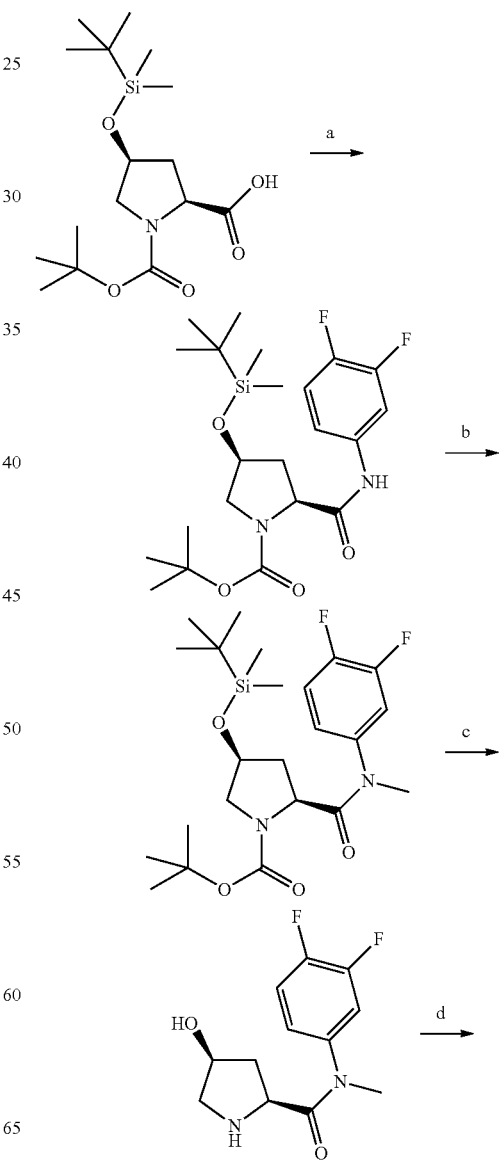

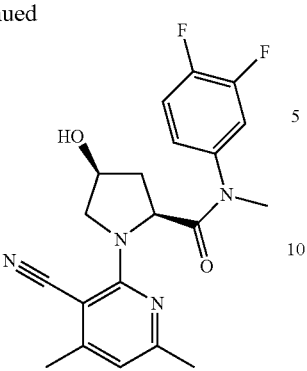

Step a. To a solution of Intermediate 2 (400 mg, 1.16 mmol) and 3,4-difluoroaniline (299 mg, 2.32 mmol) in pyridine (4 mL) was added T3P (2.22 g, 3.48 mmol, 50% wt. % in DMF) and stirred at rt for 12 h. Upon completion, the reaction mixture was quenched by addition of water (40 mL), diluted with aq. NH₄Cl solution (40 mL) and extracted with EtOAc (80 mL). The organic extract was washed with aq. NH₄Cl solution (80 mL), dried over Na₂SO₄ and evaporated. The crude residue was purified by column chromatography (10% EtOAc in PE) to give (2S,4S)-tert-butyl 4-((tert-butyldimethylsilyl)oxy)-2-((3,4-difluorophenyl)carbamoyl)-pyrrolidine-1-carboxylate (230 mg, 40% yield) as a yellow oil.

m/z ES+[M+H]⁺ 457.3

Step b. To a solution of (2S,4S)-tert-butyl 4-((tert-butyldimethylsilyl)oxy)-2-((3,4-difluoro-phenyl)carbamoyl)pyrrolidine-1-carboxylate (230 mg, 0.50 mmol) in DMF (1 mL) was added NaH (22 mg, 0.55 mmol, 60% dispersion in mineral oil) at 0° C. and the mixture was stirred at 0° C. for 30 min. Methyl iodide (86 mg, 0.60 mmol) was added dropwise to the mixture at 0° C. and stirred for 2 h. The reaction mixture was evaporated to give (2S,4S)-tert-butyl 4-((tert-butyldimethylsilyl)oxy)-2-((3,4-difluorophenyl)(methyl)carbamoyl)-pyrrolidine-1-carboxylate (237 mg, crude) as a yellow oil.

m/z ES+[M+H]⁺ 471.3

Step c. To a solution of (2S,4S)-tert-butyl 4-((tert-butyldimethylsilyl)oxy)-2-((3,4-difluoro-phenyl)(methyl)carbamoyl)pyrrolidine-1-carboxylate (237 mg, crude) in 1,4-dioxane (0.5 mL) was added HCl in 1,4-dioxane (4 M, 2 mL). The mixture was stirred at rt for 12 h. Upon completion, the mixture was concentrated under vacuum to give (2S,4S)—N-(3,4-difluoro-phenyl)-4-hydroxy-N-methylpyrrolidine-2-carboxamide (140 mg, crude) as a yellow solid.

m/z ES+[M+H]⁺ 257.2

Step d. To a solution of (2S,4S)—N-(3,4-difluorophenyl)-4-hydroxy-N-methylpyrrolidine-2-carboxamide (129 mg, crude) and 2-chloro-4,6-dimethylnicotinonitrile (84 mg, 0.53 mmol) in NMP (1 mL) was added DIPEA (325 mg, 2.52 mmol, 0.44 mL). The mixture was stirred at 60° C. for 12 h. Upon completion, the mixture was diluted with water (20 mL) and extracted with EtOAc (30 mL×3). The combined organic extracts were washed with brine (20 mL), dried and evaporated. The residue was purified by preparative HPLC to provide the title compound (27 mg, 14% yield) as a white solid.

m/z ES+[M+H]⁺ 387.0; ¹H NMR (400 MHz, DMSO-d6) δ ppm 7.43 (s, 1H), 7.26 (d, J=9.2 Hz, 2H), 6.46 (s, 1H), 4.99 (d, J=12.0 Hz, 1H), 4.62 (d, J=9.2 Hz, 1H), 4.53-4.44 (m, 1H), 4.33-4.27 (m, 1H), 4.23-4.18 (m, 1H), 3.33 (s, 3H), 2.50-2.30 (m, 6H), 2.17-2.05 (m, 2H).

Example 5

(2S,4S)—N-(3-Chloro-4-fluorophenyl)-1-(3-cyano-6-methyl-4-(trifluoro-methyl)pyridin-2-yl)-4-hydroxy-N-methylpyrrolidine-2-carboxamide

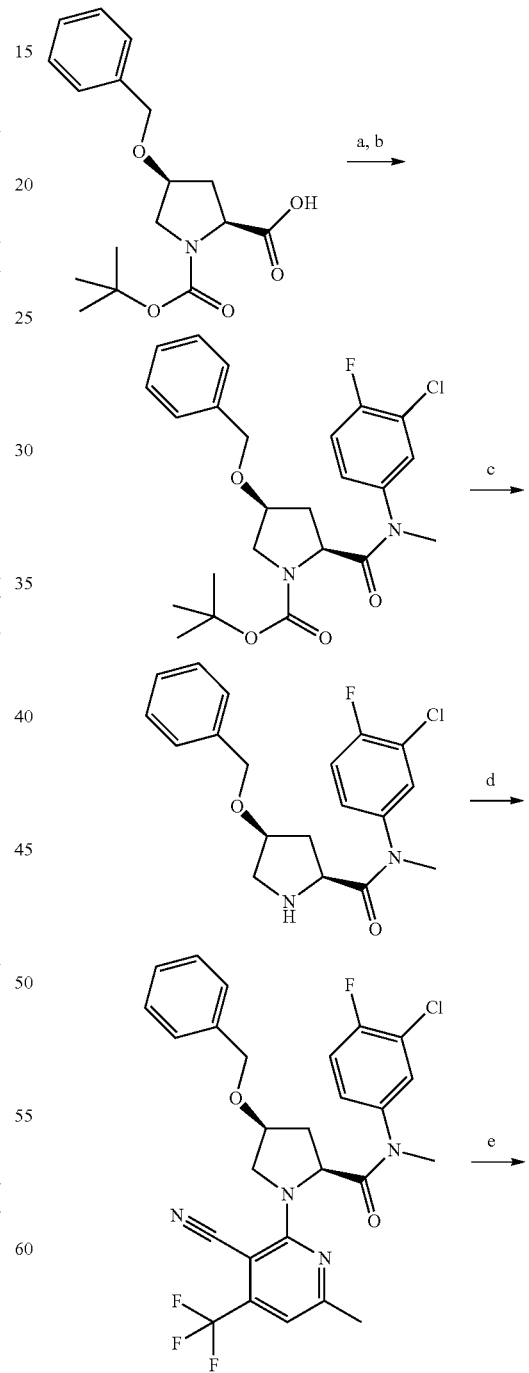

-continued

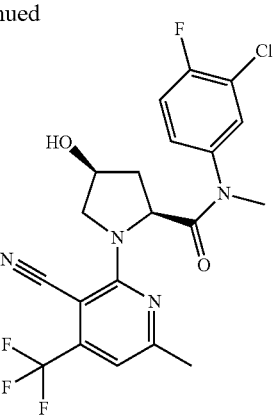

Step a. A solution of Intermediate 4 (0.5 g, 1.56 mmol), 3-chloro-4-fluoro-aniline (226 mg, 1.56 mmol) and T3P (1.49 g, 4.67 mmol, 50 wt. % in EtOAc) in pyridine (10 mL) was stirred at rt for 3 h. The mixture was evaporated, treated with water (20 mL) and extracted with EtOAc (20 mL×3). The combined organic extracts were washed with brine (20 mL), dried over sodium sulfate, filtered and evaporated. The crude residue was purified by column chromatography (5-25% EtOAc in PE) to give tert-butyl (2S,4S)-4-benzyloxy-2-[(3-chloro-4-fluoro-phenyl)-carbamoyl]pyrrolidine-1-carboxylate (0.46 g) as a yellow oil.

m/z ES+[M+H]+ 449.9

Step b. To a solution of tert-butyl (2S,4S)-4-benzyloxy-2-[(3-chloro-4-fluoro-phenyl)-carbamoyl]pyrrolidine-1-carboxylate (0.36 g, 0.80 mmol) in DMF (5 mL) was added NaH (48 mg, 1.20 mmol, 60% dispersion in mineral oil) and the mixture was stirred at 0° C. for 30 min. Methyl iodide (137 mg, 0.96 mmol) was added dropwise into the mixture at 0° C. and then stirred at rt for 2 h. On completion, the reaction mixture was quenched by addition of water (10 mL) and extracted with EtOAc (20 mL×3). The combined organic extracts were washed with brine (10 mL), dried over sodium sulfate, filtered and evaporated to give tert-butyl (2S,4S)-4-benzyloxy-2-[(3-chloro-4-fluoro-phenyl)-methyl-carbamoyl]pyrrolidine-1-carboxylate (0.3 g, crude) as a yellow oil.

m/z ES+[M+H]+ 463.9

Step c. A solution of tert-butyl (2S,4S)-4-benzyloxy-2-[(3-chloro-4-fluoro-phenyl)-methyl-carbamoyl]pyrrolidine-1-carboxylate (0.25 g, 0.54 mmol) in HCl in 1,4-dioxane (4M, 2 mL) was stirred at rt for 2 h. On completion, the mixture was evaporated to give (2S,4S)-4-benzyloxy-N-(3-chloro-4-fluoro-phenyl)-N-methyl-pyrrolidine-2-carboxamide (0.25 g, crude, HCl salt) as a yellow oil.

m/z ES+[M+H]+ 363.8

Step d. A solution of crude (2S,4S)-4-benzyloxy-N-(3-chloro-4-fluoro-phenyl)-N-methyl-pyrrolidine-2-carboxamide (0.24 g, 0.60 mmol, HCl salt), Intermediate 1 (146 mg, 0.66 mmol) and DIPEA (233 mg, 1.80 mmol) in NMP (5 mL) was stirred at 60° C. for 16 h. The reaction mixture was quenched by addition of water (10 mL) and extracted with EtOAc (20 mL×3). The combined organic layers were washed with brine (10 mL×3), dried over sodium sulfate, filtered and evaporated. The crude residue was purified by column chromatography (5-25% EtOAc in PE) to afford (2S,4S)-4-benzyloxy-N-(3-chloro-4-fluoro-phenyl)-1-[3-cyano-6-methyl-4-(trifluoromethyl)-2-pyridyl]-N-methyl pyrrolidine-2-carboxamide (0.11 g, 0.036 mmol) as a yellow solid.

m/z ES+[M+H]+ 547.9

Step e. To a solution of (2S,4S)-4-benzyloxy-N-(3-chloro-4-fluoro-phenyl)-1-[3-cyano-6-methyl-4-(trifluoromethyl)-2-pyridyl]-N-methyl-pyrrolidine-2-carboxamide (0.1 g, 0.18 mmol) in DCM (5 mL) was added BCl$_3$ (1 M, 3.66 mL) at 0° C. The mixture was stirred at 0° C. for 20 min. On completion, the reaction mixture was quenched by addition of cold water (10 mL) and adjusted to pH 8-9 with sat. aq. NaHCO$_3$. The mixture was extracted into EtOAc (10 mL×3) and the combined organic extracts washed with brine (10 mL), dried over sodium sulfate, filtered and evaporated. The residue was purified by preparative HPLC and dried by lyophilization to provide the title compound (44 mg, 0.095 mmol) as an off-white solid.

m/z ES+[M+H]+ 457.8; $^1$H NMR (400 MHz, CDCls) 6 ppm 7.61-7.60 (m, 1H), 7.31 (m, 1H), 7.25-7.23 (m, 1H), 6.83 (s, 1H), 4.70-4.66 (m, 2H), 4.50 (m, 1H), 4.32-4.25 (m, 2H), 3.33 (s, 3H), 2.55 (s, 3H), 2.17-2.05 (m, 2H).

Example 6

(2S,4S)-1-(3-Cyano-6-methyl-4-(trifluoromethyl) pyridin-2-yl)-N-(4-fluoro-3-methylphenyl)-4-hydroxy-N-methylpyrrolidine-2-carboxamide

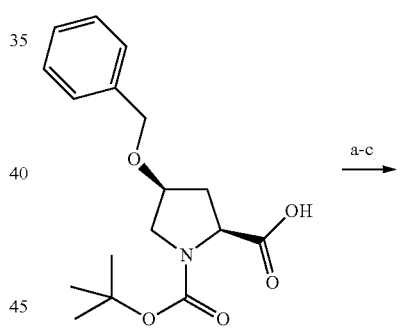

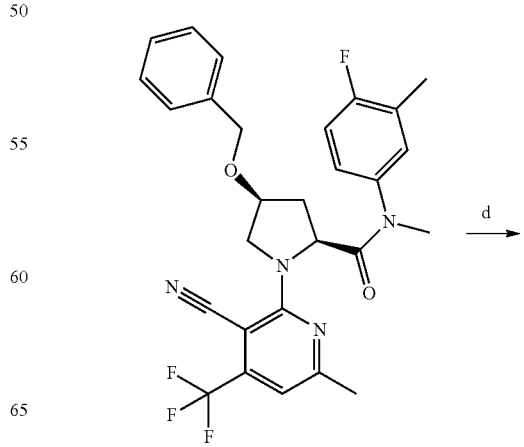

-continued

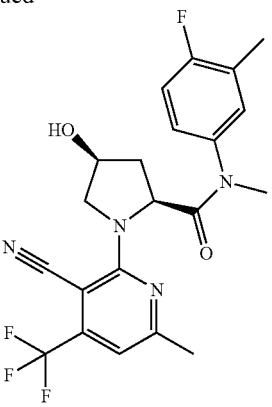

Step a. A mixture of Intermediate 4 (0.5 g, 1.56 mmol, 1 eq), 4-fluoro-3-methyl-aniline (234 mg, 1.87 mmol, 1.2 eq) and T3P (2.98 g, 4.68 mmol, 50 wt. % in EtOAc) in pyridine (2 mL) was stirred at rt for 12 h. The reaction mixture was evaporated and the residue was purified by column chromatography (5-25% EtOAc in PE) to give tert-butyl (2S,4S)-4-benzyloxy-2-[(4-fluoro-3-methyl-phenyl)carbamoyl]pyrrolidine-1-carboxylate (662 mg, 91% yield) as a colourless oil.

m/z ES+[M+H]+ 429.3; $^1$H NMR (400 MHz, DMSO-d6) δ ppm 9.78-9.60 (m, 1H), 7.47-7.35 (m, 2H), 7.34-7.21 (m, 5H), 7.13-7.00 (m, 1H), 4.52-4.42 (m, 2H), 4.32-4.12 (m, 2H), 3.64 (dd, J=5.9, 11.0 Hz, 1H), 3.44-3.35 (m, 1H), 2.43 (br s, 1H), 2.19 (s, 3H), 2.11-2.00 (m, 1H), 1.49-1.24 (m, 9H)

Steps b-c. Conducted as described in the synthesis of Example 5 steps c-d to provide (2S,4S)-4-benzyloxy-1-[3-cyano-6-methyl-4-(trifluoromethyl)-2-pyridyl]-N-(4-fluoro-3-methyl-phenyl)-N-methyl-pyrrolidine-2-carboxamide.

m/z ES+[M+H]+ 527.2

Step d. A mixture of (2S,4S)-4-benzyloxy-1-[3-cyano-6-methyl-4-(trifluoromethyl)-2-pyridyl]-N-(4-fluoro-3-methyl-phenyl)-N-methyl-pyrrolidine-2-carboxamide (150 mg, 0.28 mmol) and Pd/C (30 mg, 10 wt. % loading) in EtOH (10 mL) was stirred at rt for 12 h under hydrogen atmosphere (balloon). On completion, the reaction mixture was filtered and evaporated. The crude residue was purified by preparative HPLC to provide the title compound (58 mg, 47% yield) as a white solid.

m/z ES+[M+H]+ 437.1; $^1$H NMR (400 MHz, DMSO-d6) δ ppm 7.45-7.40 (m, 1H), 7.40-7.25 (m, 2H), 7.08 (s, 1H), 5.32 (d, J=6.0 Hz, 1H), 4.49 (t, J=8.4 Hz, 1H), 4.25-4.10 (m, 1H), 4.09-3.98 (m, 1H), 3.67-3.58 (m, 1H), 3.14 (s, 3H), 2.53 (s, 3H), 2.28 (s, 3H), 2.19-2.03 (m, 1H), 1.83-1.69 (m, 1H)

The Examples in Table 1 were prepared using methods similar to those described in the synthesis of Examples 4-6.

TABLE 1

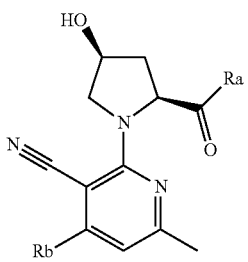

| Example Number | Ra | Rb | Name | Amine CAS No. | $^1$H NMR (400 MHz) δ ppm | MI |
|---|---|---|---|---|---|---|
| 7 | ![N-methyl-N-phenyl] | CH₃ | (2S,4S)-1-(3-Cyano-4,6-dimethylpyridin-2-yl)-4-hydroxy-N-methyl-N-phenyl-pyrrolidine-2-carboxamide | 100-61-8 | (DMSO-d6) 7.59-7.48 (m, 4H), 7.47-7.38 (m, 1H), 6.59 (s, 1H), 5.30 (d, J = 6.6 Hz, 1H), 4.43 (t, J = 7.7 Hz, 1H), 4.20-4.07 (m, 1H), 3.98 (t, J = 8.2 Hz, 1H), 3.63 (dd, J = 9.7, 6.7 Hz, 1H), 3.17 (s, 3H), 2.37 (s, 3H), 2.32 (s, 3H), 2.18-2.02 (m, 1H), 1.75 (m, 1H). | 351.47 |
| 8 | ![N-methyl-N-phenyl] | CF₃ | (2S,4S)-1-(3-Cyano-6-methyl-4-(trifluoromethyl)pyridin-2-yl)-4-hydroxy-N-methyl-N-phenylpyrrolidine-2-carboxamide | 100-61-8 | (DMSO-d6) 7.57-7.48 (m, 4H), 7.46-7.38 (m, 1H), 7.09 (s, 1H), 5.34 (d, J = 6.4 Hz, 1H), 4.48 (m, 1H), 4.13 (m, 1H), 4.03 (m, 1H), 3.63 (m, 1H), 3.18 (s, 3H), 2.53 (s, 3H), 2.13 (m, 1H), 1.77 (m, 1H). | 405.45 |
| 9 | ![N-methyl-N-(m-tolyl)] | CH₃ | (2S,4S)-1-(3-Cyano-4,6-dimethylpyridin-2-yl)-4-hydroxy-N-methyl-N-(m-tolyl)pyrrolidine-2-carboxamide | 696-44-6 | (DMSO-d6) 7.44-7.26 (m, 3H), 7.23 (d, J = 7.6 Hz, 1H), 6.59 (s, 1H), 5.28 (s, 1H), 4.45 (t, J = 8.0 Hz, 1H), 4.13 (s, 1H), 3.97 (t, J = 8.2 Hz, 1H), 3.62 (m, 1H), 3.15 (s, 3H), 2.37 (d, J = 4.9 Hz, 6H), 2.32 (s, 3H), 2.17-2.02 (m, 1H), 1.80-1.64 (m, 1H). | 365.47 |

TABLE 1-continued

| Example Number | Ra | Rb | Name | Amine CAS No. | 1H NMR (400 MHz) δ ppm | MI |
|---|---|---|---|---|---|---|
| 10 | N-methyl, N-(4-fluoro-3-(trifluoromethyl)phenyl) | CH₃ | (2S,4S)-1-(3-Cyano-4,6-dimethylpyridin-2-yl)-N-(4-fluoro-3-(trifluoromethyl)phenyl)-4-hydroxy-N-methyl-pyrrolidine-2-carboxamide | 2357-47-3 | (DMSO-d6) 8.01-7.78 (m, 2H), 7.76-7.46 (m, 1H), 6.59 (s, 1H), 5.26 (d, J = 6.0 Hz, 1H), 4.51-4.31 (m, 1H), 4.28-4.06 (m, 1H), 4.05-3.88 (m, 1H), 3.68-3.54 (m, 1H), 3.18 (s, 3H), 2.35-2.29 (m, 6H), 2.18-2.00 (m, 1H), 1.77 (s, 1H) | 437.2 |
| 11 | N-methyl, N-(3-(fluoromethyl)phenyl) | CH₃ | (2S,4S)-1-(3-Cyano-4,6-dimethylpyridin-2-yl)-N-(3-(fluoromethyl)phenyl)-4-hydroxy-N-methylpyrrolidine-2-carboxamide | 456-46-2 | (CDCl₃) 7.59-7.47 (m, 2H), 7.46-7.40 (m, 1H), 7.39-7.32 (m, 1H), 6.42 (s, 1H), 5.49 (s, 1H), 5.37 (s, 1H), 5.12 (d, J = 12.0 Hz, 1H), 4.59 (t, J = 5.2 Hz, 1H), 4.45 (d, J = 10.4 Hz, 1H), 4.31-4.25 (m, 1H), 4.21-4.14 (m, 1H), 3.36 (s, 3H), 2.45-2.35 (m, 6H), 2.12-2.04 (m, 2H) | 383.0 |
| 12 | N-methyl, N-(3-(difluoromethyl)phenyl) | CH₃ | (2S,4S)-1-(3-Cyano-4,6-dimethylpyridin-2-yl)-N-(3-(difluoromethyl)phenyl)-4-hydroxy-N-methylpyrrolidine-2-carboxamide | 368-99-0 | (DMSO-d6) 7.73-7.61 (m, 4 H), 7.25-6.95 (t, J = 55.6 Hz, 1 H), 6.59 (s, 1 H), 5.27-5.25 (m, 1 H), 4.45-4.30 (m, 1 H), 4.20-4.10 (m, 1 H), 4.05-3.95 (m, 1 H), 3.64-3.60 (m, 1 H), 3.19 (s, 3 H), 2.36 (s, 3 H), 2.32 (s, 3 H), 2.18-2.00 (m, 1 H), 1.80-1.75 (m, 1 H). | 401.2 |
| 13 | N-methyl, N-(3-chlorophenyl) | CH₃ | (2S,4S)-N-(3-Chlorophenyl)-1-(3-cyano-4,6-dimethyl-pyridin-2-yl)-4-hydroxy-N-methylpyrrolidine-2-carboxamide | 108-42-9 | (CDCl₃) 7.58 (s, 1H), 7.42-7.33 (m, 3H), 6.43 (s, 1H), 5.04 (d, 1H), 4.62 (d, 1H), 4.51-4.43 (m, 1H), 4.29 (d, J = 11.2 Hz, 1H), 4.22-4.15 (m, 1H), 3.34 (s, 3H), 2.43 (s, 3H), 2.39 (s, 3H), 2.12-2.05 (m, 2H). | 384.9 |
| 14 | N-methyl, N-(4-fluoro-3-(fluoromethyl)phenyl) | CH₃ | (2S,4S)-1-(3-Cyano-4,6-dimethylpyridin-2-yl)-N-(4-fluoro-3-(fluoromethyl)phenyl)-4-hydroxy-N-methyl-pyrrolidine-2-carboxamide | 1445796-35-9 | (DMSO-d6) 7.69-7.60 (m, 2H), 7.46-7.44 (m, 1H), 6.59 (s, 1H), 5.54 (d, J = 47.2 Hz, 2H), 5.34-5.21 (m, 1H), 4.43-4.40 (m, 1H), 4.17-4.10 (m, 1H), 4.01-3.96 (m, 1H), 3.64-3.60 (m, 1H), 3.16 (s, 3H), 2.37 (s, 3H), 2.35 (s, 3H), 2.15-2.09 (m, 1H), 1.80-1.73 (m, 1H). | 401.0 |
| 15 | N-methyl, N-(4-fluoro-3-(fluoromethyl)phenyl) | CF₃ | (2S,4S)-1-(3-Cyano-6-methyl-4-(trifluoromethyl)pyridin-2-yl)-N-(4-fluoro-3-(fluoromethyl)-phenyl)-4-hydroxy-N-methyl-pyrrolidine-2-carboxamide | 1445796-35-9 | (DMSO-d6) 7.67-7.60 (m, 2H), 7.47-7.43 (m, 1H), 7.08 (s, 1H), 5.54 (d, J = 47.2 Hz, 2H), 5.32 (s, 1H), 4.48-4.43 (m, 1H), 4.16-4.02 (m, 2H), 3.64-3.60 (m, 1H), 3.17-3.16 (m, 3H), 2.52 (s, 3H), 2.15-2.12 (m, 1H), 1.80-1.72 (m, 1H). | 455.0 |
| 16 | N-methyl, N-(4-fluoro-3-methoxyphenyl) | CF₃ | (2S,4S)-1-(3-Cyano-6-methyl-4-(trifluoromethyl)pyridin-2-yl)-N-(4-fluoro-3-methoxy-phenyl)-4-hydroxy-N-methyl-pyrrolidine-2-carboxamide | 64465-53-8 | (DMSO-d6) 7.40-7.32 (m, 1H), 7.28 (d, J = 6.0 Hz, 1H), 7.08 (s, 2H), 5.30 (d, J = 6.0 Hz, 1H), 4.56 (t, J = 8.0 Hz, 1H), 4.25-4.15 (m, 1H), 4.09-3.98 (m, 1H), 3.88 (s, 3H), 3.70-3.59 (m, 1H), 3.17 (s, 3H), 2.53 (s, 3H), 2.21-2.10 (m, 1H), 1.90-1.71 (m, 1H). | 453.1 |

TABLE 1-continued

| Example Number | Ra | Rb | Name | Amine CAS No. | $^1$H NMR (400 MHz) δ ppm | MI |
|---|---|---|---|---|---|---|
| 17 | N-methyl-(3,5-difluorophenyl) | CF$_3$ | (2S,4S)-1-(3-Cyano-6-methyl-4-(trifluoromethyl)pyridin-2-yl)-N-(3,5-difluorophenyl)-4-hydroxy-N-methylpyrrolidine-2-carboxamide | 372-39-4 | (CDCl$_3$) 7.04-7.01 (m, 2H), 6.92-6.88 (m, 1H), 6.83 (s, 1H), 4.81-4.78 (m, 1H), 4.72-4.70 (m, 1H), 4.53-4.49 (m, 1H), 4.32-4.26 (m, 2H), 3.35 (s, 3H), 2.54 (s, 3H), 2.23-2.17 (m, 1H), 2.10-2.07 (m, 1H). | 440.9 |
| 18 | N-methyl-(4-chloro-3-fluorophenyl) | CF$_3$ | (2S,4S)-N-(4-Chloro-3-fluorophenyl)-1-(3-cyano-6-methyl-4-(trifluoromethyl)pyridin-2-yl)-4-hydroxy-N-methyl-pyrrolidine-2-carboxamide | 367-22-6 | (CD$_3$OD) 7.72-7.35 (m, 3H), 6.98 (s, 1H), 4.80-4.70 (m, 1H), 4.40-4.15 (m, 2H), 4.00-3.90 (m, 1H), 3.30-3.25 (m, 3H), 2.56 (s, 3H), 2.30-2.20 (m, 1H), 2.02-1.93 (m, 1H). | 457.1 |
| 19 | N-methyl-(3-fluoro-4-trifluoromethylphenyl) | CF$_3$ | (2S,4S)-1-(3-Cyano-6-methyl-4-(trifluoromethyl)pyridin-2-yl)-N-(3-fluoro-4-(trifluoromethyl)-phenyl)-4-hydroxy-N-methyl-pyrrolidine-2-carboxamide | 69411-68-3 | (CDCl$_3$) 7.78-7.70 (m, 1H), 7.45-7.30 (m, 2H), 6.84 (s, 1H), 4.84-4.65 (m, 2H), 4.60-4.46 (m, 1H), 4.35-4.25 (m, 2H), 3.38 (s, 3H), 2.53 (s, 3H), 2.25-2.05 (m, 2H). | 491.1 |
| 20 | N-methyl-(2,4,5-trifluorophenyl) | CF$_3$ | (2S,4S)-1-(3-Cyano-6-methyl-4-(trifluoromethyl)pyridin-2-yl)-4-hydroxy-N-methyl-N-(2,4,5-trifluorophenyl)pyrrolidine-2-carboxamide | 367-34-0 | (DMSO-d6) 7.67 (s, 2H), 7.03 (s, 1H), 4.76 (s, 1H), 4.35-4.10 (m, 2H), 3.69 (dd, J = 10, 6.8 Hz, 2H), 3.21 (s, 3H), 2.50 (s, 3H), 2.30-2.10 (m, 1H), 1.90-1.75 (m, 1H). | 459.1 |
| 21 | N-ethyl-(m-tolyl) | CH$_3$ | (2S,4S)-1-(3-Cyano-4,6-dimethylpyridin-2-yl)-N-ethyl-4-hydroxy-N-(m-tolyl)pyrrolidine-2-carboxamide | 102-27-2 | (DMSO-d6) 7.41 (m, 1H), 7.36-7.19 (m, 3H), 6.59 (s, 1H), 5.26 (d, 1H), 4.38 (m, 1H), 4.10 (m, 1H), 3.98 (m, 1H), 3.81-3.70 (m, 1H), 3.60 (m, 1H), 3.50-3.39 (m, 1H), 2.39 (s, 3H), 2.37 (s, 3H), 2.33 (s, 3H), 2.09-2.00 (m, 1H), 1.76-1.64 (m, 1H), 1.01 (t, J = 7.1 Hz, 3H). | 379.50 |
| 22 | N-ethyl-(m-tolyl) | CF$_3$ | (2S,4S)-1-(3-Cyano-6-methyl-4-(trifluoromethyl)pyridin-2-yl)-N-ethyl-4-hydroxy-N-(m-tolyl)-pyrrolidine-2-carboxamide | 102-27-2 | (DMSO-d6) 7.47-7.37 (m, 1H), 7.32-7.21 (m, 3H), 7.09 (s, 1H), 5.32 (d, 1H), 4.48-4.37 (m, 1H), 4.16-4.08 (m, 1H), 4.07-3.99 (m, 1H), 3.82-3.72 (m, 1H), 3.60 (dd, J = 9.6, 7.2 Hz, 1H), 3.51-3.41 (m, 1H), 2.55 (s, 3H), 2.37 (s, 3H), 2.12-2.02 (m, 1H), 1.72 (dt, J = 12.2, 8.8 Hz, 1H), 1.02 (t, J = 7.1 Hz, 3H). | 433.47 |

Example 23

(2S,4R)-1-(3-Cyano-6-methyl-4-(trifluoromethyl)pyridin-2-yl)-4-hydroxy-N-methyl-N-(m-tolyl)pyrrolidine-2-carboxamide

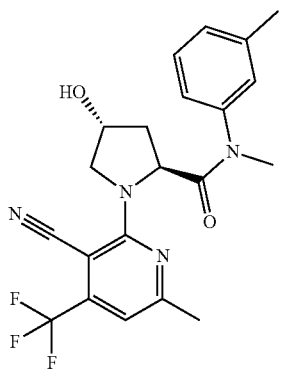 [SMILES: Cc1cccc(N(C)C(=O)[C@@H]2C[C@@H](O)CN2c2nc(C)cc(C(F)(F)F)c2C#N)c1]

The title compound was prepared in a similar manner to Example 3, using (2S,4R)-1-(tert-butoxycarbonyl)-4-hydroxypyrrolidine-2-carboxylic acid (CAS Number 13726-69-7) in step a.

m/z ES+[M+H]+ 419.38; $^1$H NMR (400 MHz, DMSO-d6) δ ppm 7.42 (t, J=7.7 Hz, 1H), 7.36-7.29 (m, 2H), 7.25 (d, J=7.7 Hz, 1H), 7.10 (s, 1H), 5.02 (d, J=3.3 Hz, 1H), 4.66 (t, J=8.2 Hz, 1H), 4.38 (br s, 1H), 4.00 (m, 1H), 3.67 (d, J=10.9 Hz, 1H), 3.15 (s, 3H), 2.55 (s, 3H), 2.38 (s, 3H), 1.95 (m, 1H), 1.86 (t, J=10.2 Hz, 1H).

Example 24

(2S,3R)-1-(3-Cyano-6-methyl-4-(trifluoromethyl)pyridin-2-yl)-3-hydroxy-N-methyl-N-(m-tolyl)pyrrolidine-2-carboxamide

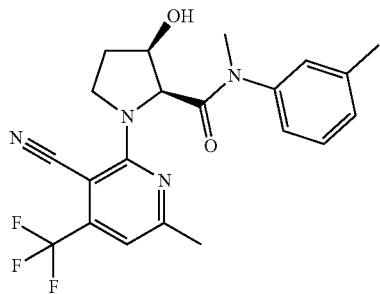 [SMILES: Cc1cccc(N(C)C(=O)[C@@H]2[C@H](O)CCN2c2nc(C)cc(C(F)(F)F)c2C#N)c1]

The title compound was prepared in a similar manner to Example 3, using (2S,3R)-1-(tert-butoxycarbonyl)-3-hydroxypyrrolidine-2-carboxylic acid (CAS Number 186132-96-7) in step a.

m/z ES+[M+H]+ 419.51; $^1$H NMR (400 MHz, CD$_3$OD) δ ppm 7.47-7.36 (m, 3H), 7.32-7.22 (m, 1H), 6.96 (s, 1H), 4.87 (d, J=5.7 Hz, 1H), 4.26-4.17 (m, 2H), 4.02-3.88 (m, 1H), 3.28 (s, 3H), 2.58 (s, 3H), 2.43 (s, 3H), 2.12-1.92 (m, 2H).

Example 25

(2S,3R)-1-(3-Cyano-4,6-dimethylpyridin-2-yl)-3-hydroxy-N-methyl-N-(m-tolyl)pyrrolidine-2-carboxamide

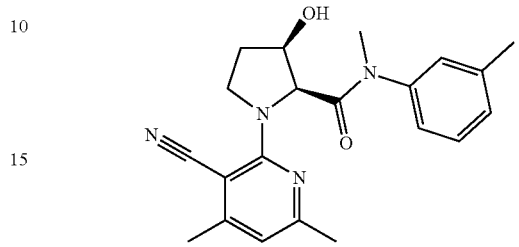

The title compound was prepared in a similar manner to Example 3, using (2S,3R)-1-(tert-butoxycarbonyl)-3-hydroxypyrrolidine-2-carboxylic acid (CAS Number 186132-96-7) in step a and 2-chloro-3-cyano-4,6-dimethylpyridine (CAS Number 14237-71-9) in step b.

m/z ES+[M+H]+ 365.47; $^1$H NMR (400 MHz, DMSO-d6) δ ppm 7.45-7.28 (m, 3H), 7.18 (d, J=6.8 Hz, 1H), 6.56 (s, 1H), 5.34 (d, J=5.6 Hz, 1H), 4.69 (d, J=6.3 Hz, 1H), 4.17-4.03 (m, 1H), 4.00-3.87 (m, 1H), 3.82-3.67 (m, 1H), 3.13 (s, 3H), 2.34 (d, J=4.6 Hz, 6H), 2.32 (s, 3H), 2.06-1.89 (m, 2H).

Example 26

(2S,3S)-1-(3-Cyano-6-methyl-4-(trifluoromethyl)pyridin-2-yl)-3-hydroxy-N-methyl-N-(m-tolyl)pyrrolidine-2-carboxamide

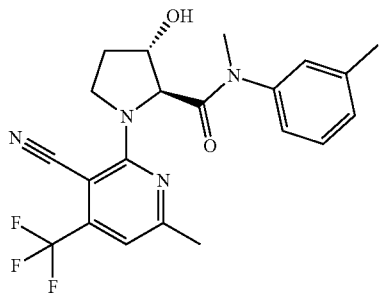 [SMILES: Cc1cccc(N(C)C(=O)[C@@H]2[C@@H](O)CCN2c2nc(C)cc(C(F)(F)F)c2C#N)c1]

The title compound was prepared in a similar manner to Example 3, using (2S,3S)-1-(tert-butoxycarbonyl)-3-hydroxypyrrolidine-2-carboxylic acid (CAS Number 187039-57-2) in step a.

m/z ES+[M+H]+ 419.47; $^1$H NMR (400 MHz, CD$_3$OD) δ ppm 7.47-7.34 (m, 3H), 7.31-7.25 (m, 1H), 6.95 (s, 1H), 4.72 (s, 1H), 4.44 (dt, J=4.2, 1.3 Hz, 1H), 4.23-4.14 (m, 2H), 3.28 (s, 3H), 2.58 (s, 3H), 2.44 (s, 3H), 2.37-2.28 (m, 1H), 2.11-1.99 (m, 1H).

Example 27

(2S,4S)-4-Hydroxy-N-methyl-1-(6-methyl-4-(trifluoromethyl)pyridin-2-yl)-N-(m-tolyl)pyrrolidine-2-carboxamide

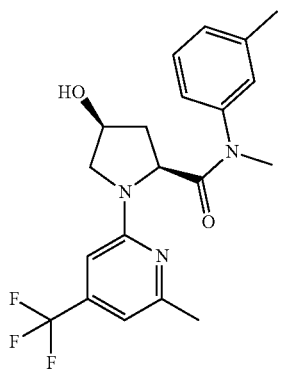 [SMILES: Cc1cccc(N(C)C(=O)[C@@H]2C[C@H](O)CN2c2cc(C(F)(F)F)cc(C)n2)c1]

The title compound was prepared in a similar manner to Example 3, using 2-chloro-6-methyl-4-(trifluoromethyl)pyridine (CAS Number 22123-14-4) in step b.

m/z ES+[M+H]$^+$ 394.2; $^1$H NMR (400 MHz, CDCl$_3$) δ ppm 7.50-7.40 (m, 1H), 7.35-7.25 (m, 1H), 7.22-7.05 (m, 2H), 6.73 (s, 1H), 6.52 (s, 1H), 4.80-4.20 (m, 5H), 3.36 (s, 3H), 2.96 (s, 3H), 2.52-2.25 (m, 5H).

Example 28

(2S,4S)-4-Hydroxy-1-(4-isopropyl-6-methylpyridin-2-yl)-N-methyl-N-(m-tolyl)pyrrolidine-2-carboxamide

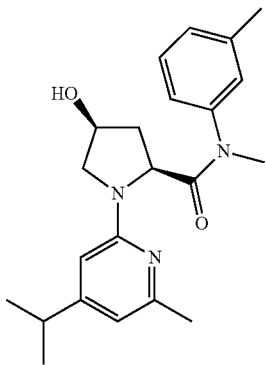 [SMILES: Cc1cccc(N(C)C(=O)[C@@H]2C[C@H](O)CN2c2cc(C(C)C)cc(C)n2)c1]

The title compound was prepared in a similar manner to Example 3, using 2-chloro-4-isopropyl-6-methylpyridine (CAS Number 1427502-12-2) in step b.

m/z ES+[M+H]$^+$ 368.2; $^1$H NMR (400 MHz, CD$_3$OD) δ ppm 7.50-7.46 (m, 1H), 7.34-7.27 (m, 3H), 6.81 (s, 1H), 6.27 (s, 1H), 4.67-4.62 (m, 1H), 4.45-4.37 (m, 1H), 3.92-3.83 (m, 1H), 3.67-3.59 (m, 1H), 3.31 (m, 3H), 3.02-2.95 (m, 1H), 2.56 (s, 3H), 2.44 (s, 3H), 2.37-2.30 (m, 1H), 2.18-2.10 (m, 1H), 1.33-1.28 (m, 6H).

Example 29

(2S,4S)-1-(5-Chloro-4,6-dimethylpyridin-2-yl)-4-hydroxy-N-methyl-N-(m-tolyl)pyrrolidine-2-carboxamide

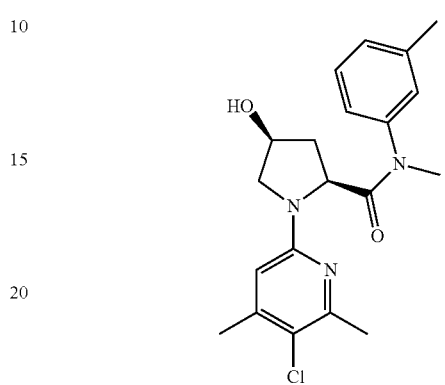

The title compound was prepared in a similar manner to Example 3, using 3,6-dichloro-2,4-dimethylpyridine (CAS Number 1639373-35-5) in step b.

m/z ES+[M+H]$^+$ 374.2; $^1$H NMR (400 MHz, CDCl$_3$) δ ppm 7.35 (t, J=7.6 Hz, 2H), 7.22-7.16 (m, 1H), 6.10 (s, 1H), 5.28 (d, J=12.4 Hz, 1H), 4.58-4.55 (m, 1H), 4.44-4.41 (m, 1H), 3.69-3.66 (m, 1H), 3.51-3.47 (m, 1H), 3.33 (s, 3H), 2.52 (s, 3H), 2.42 (s, 3H), 2.27 (s, 3H), 2.12-2.10 (m, 2H).

Example 30

(2S,4S)-1-(3-Cyano-6-methoxy-4-(trifluoromethyl)pyridin-2-yl)-4-hydroxy-N-methyl-N-(m-tolyl)pyrrolidine-2-carboxamide

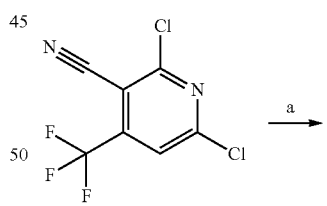

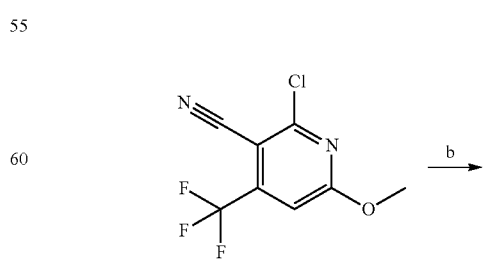

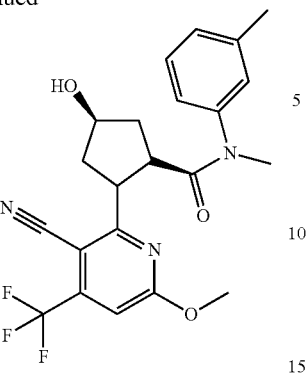

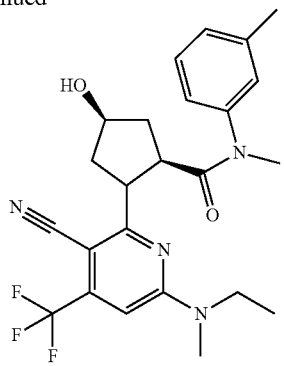

Step a. A solution of 2,6-dichloro-4-(trifluoromethyl)pyridine-3-carbonitrile (CAS Number 13600-42-5; 0.5 g, 2.07 mmol) and sodium methoxide (106 mg, 1.97 mmol) in MeOH (2 mL) was stirred at −10° C. for 2 h. Upon completion, the mixture was filtered and evaporated. The resultant residue was purified by preparative TLC (25% EtOAc in PE) to give 2-chloro-6-methoxy-4-(trifluoromethyl)pyridine-3-carbonitrile (0.1 g, 20% yield) as a yellow solid.

$^1$H NMR (400 MHz, DMSO-d6) δ ppm 7.57 (d, J=4.0 Hz, 1H), 4.03 (d, J=3.6 Hz, 3H).

Step b. A solution of Intermediate 3 (0.1 g, 0.37 mmol, HCl salt), 2-chloro-6-methoxy-4-(trifluoromethyl)pyridine-3-carbonitrile (87 mg, 0.37 mmol) and DIPEA (143 mg, 1.11 mmol) in NMP (2 mL) was stirred at 60° C. for 16 h. Upon completion, the reaction mixture was quenched by addition of water (10 mL) and extracted with EtOAc (10 mL×3). The combined organic layer was washed with brine (10 mL×3), dried and evaporated. The residue was purified by prep-HPLC to provide the title compound (47 mg, 29% yield) as a white solid.

m/z ES+[M+H]$^+$ 435.4; $^1$H NMR (400 MHz, CDCl$_3$) δ ppm 7.37-7.33 (m, 1H), 7.22-7.09 (m, 3H), 6.45 (s, 1H), 4.86 (d, J=7.2 Hz, 1H), 4.43-4.18 (m, 4H), 4.00 (s, 3H), 3.34 (s, 3H), 2.41 (s, 3H), 2.18-2.05 (m, 2H).

Step a. A solution of 2,6-dichloro-4-(trifluoromethyl)pyridine-3-carbonitrile (CAS Number 13600-42-5; 0.5 g, 2.07 mmol), N-methylethanamine (147 mg, 2.49 mmol) and NaHCO$_3$ (523 mg, 6.22 mmol) in EtOH (10 mL) was stirred at rt for 16 h. Upon completion, the reaction mixture was filtered and concentrated via evaporation. The residue was purified by column chromatography (5-25% EtOAc in PE) to provide 2-chloro-6-[ethyl(methyl)-amino]-4-(trifluoromethyl)pyridine-3-carbonitrile (0.3 g, 49% yield) as a white solid.

m/z ES+[M+H]$^+$ 264.0

Step b. A solution of 2-chloro-6-[ethyl(methyl)amino]-4-(trifluoromethyl)pyridine-3-carbonitrile (60 mg, 0.23 mmol), Intermediate 3 (53 mg, 0.23 mmol, HCl salt) and DIPEA (88 mg, 0.68 mmol) in NMP (2 mL) was stirred at 60° C. for 16 h. Upon completion, the reaction mixture was quenched by addition of water (10 mL) and extracted with EtOAc (10 mL×3). The combined organic layers were washed with brine (10 mL), dried over sodium sulphate and evaporated. The residue was purified by preparative HPLC to provide the title compound (23 mg, 22% yield) as a yellow solid.

m/z ES+[M+H]$^+$ 462.2; $^1$H NMR (400 MHz, CDCl$_3$) δ ppm 7.35-7.31 (m, 1H), 7.19-7.16 (m, 3H), 6.23 (s, 1H), 4.86-4.83 (m, 1H), 4.36-4.32 (m, 1H), 4.24-4.20 (m, 1H), 4.11-4.08 (m, 1H), 3.75-3.53 (m, 3H), 3.31 (s, 3H), 3.12 (s, 3H), 2.39 (s, 3H), 2.08-1.97 (m, 2H), 1.19 (t, J=3.6 Hz, 3H).

Example 31

(2S,4S)-1-(3-Cyano-6-(ethyl(methyl)amino)-4-(trifluoromethyl)pyridin-2-yl)-4-hydroxy-N-methyl-N-(m-tolyl)pyrrolidine-2-carboxamide Example 32

(2S,4S)-1-(3-Cyano-6-(dimethylamino)-4-(trifluoromethyl)pyridin-2-yl)-4-hydroxy-N-methyl-N-(m-tolyl)pyrrolidine-2-carboxamide

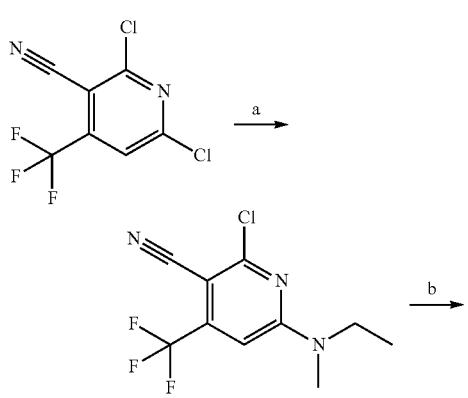

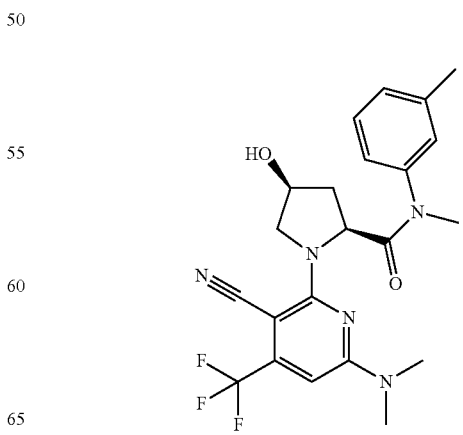

The title compound was prepared in a similar manner to Example 31, using dimethylamine in step a.

m/z ES+[M+H]$^+$ 448.2; $^1$H NMR (400 MHz, CDCl$_3$) δ ppm 7.33 (t, J=7.6 Hz, 1H), 7.22-7.11 (m, 3H), 6.25 (s, 1H), 4.81 (dd, J=8.0, 2.4 Hz, 1H), 4.40-4.35 (m, 1H), 4.26-4.20 (m, 1H), 4.15-4.08 (m, 1H), 3.31 (s, 3H), 3.18 (s, 6H), 2.39 (s, 3H), 2.10-2.00 (m, 2H).

Example 33

(2S,4S)-1-(3-Cyano-4-isopropyl-6-methylpyridin-2-yl)-4-hydroxy-N-methyl-N-(m-tolyl)pyrrolidine-2-carboxamide

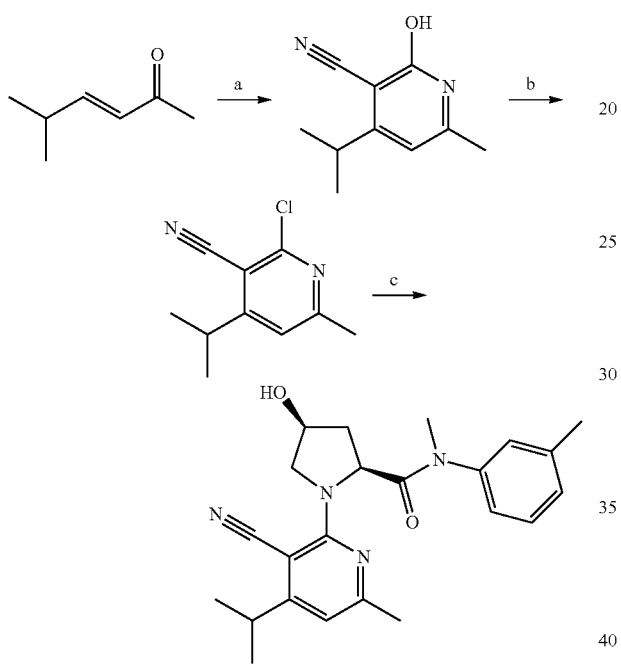

Step a. To a solution of (E)-5-methylhex-3-en-2-one (5 g, 44.6 mmol) in EtOH (50 mL) was added 2-cyanoacetamide (4.12 g, 49.0 mmol) and diethylamine (1.63 g, 22.3 mmol). The mixture was stirred at 70° C. for 24 h. Upon completion, the mixture was evaporated and the residue was purified by column chromatography (30% EtOAc in PE) to give 2-hydroxy-4-isopropyl-6-methylnicotinonitrile (3.69 g, 45% yield) as a yellow solid.

m/z ES+[M+H]$^+$ 177.2

Step b. 2-Hydroxy-4-isopropyl-6-methylnicotinonitrile (3.69 g, 20.9 mmol) was slowly added to phosphorus oxychloride (61 g, 397 mmol). The mixture was stirred at 100° C. for 3 h. Upon completion, the mixture was slowly poured into ice water (200 mL). The aqueous phase was extracted with EtOAc (200 mL×3). The combined organic extracts were dried over Na$_2$SO$_4$ and evaporated. The residue was purified by column chromatography (2-5% EtOAc in PE) to give 2-chloro-4-isopropyl-6-methylnicotinonitrile (1.13 g, 28% yield) as a light yellow solid.

m/z ES+[M+H]$^+$ 195.1; $^1$H NMR (400 MHz, CDCl$_3$) δ ppm 7.10 (s, 1H), 3.40-3.25 (m, 1H), 2.60 (s, 3H), 1.32 (d, J=6.8 Hz, 6H).

Step c. A mixture of 2-chloro-4-isopropyl-6-methylnicotinonitrile (100 mg, 0.51 mmol), Intermediate 3 (120 mg, 0.51 mmol, HCl salt), DIPEA (199 mg, 1.54 mmol) in NMP (1 mL) was stirred at 60° C. for 16 h. Upon completion, EtOAc (10 mL) and water (10 mL) were added to the reaction mixture and then separated. The aqueous phase was extracted with EtOAc (10 mL×2). The combined organic extracts were dried and evaporated. The residue was purified by preparative HPLC to provide the title compound (16.7 mg, 8% yield) as a yellow solid.

m/z ES+[M+H]$^+$ 393.1; $^1$H NMR (400 MHz, DMSO-d6) δ ppm 7.42-7.19 (m, 4H), 6.65 (s, 1H), 5.25 (d, J=6.4 Hz, 1H), 4.44 (t, J=8.0 Hz, 1H), 4.09 (s, 1H), 4.00-3.92 (m, 1H), 3.62 (dd, J=9.6, 7.2 Hz, 1H), 3.14 (s, 3H), 3.12-3.06 (m, 1H), 2.40 (s, 3H), 2.36 (s, 3H), 2.15-2.05 (m, 1H), 1.78-1.68 (m, 1H), 1.25-1.15 (m, 6H).

Example 34

(2S,4S)-1-(3-Cyano-4-(trifluoromethyl)pyridin-2-yl)-4-hydroxy-N-methyl-N-(m-tolyl)pyrrolidine-2-carboxamide Step a. To a solution of 4-(trifluoromethyl)nicotinonitrile (500 mg, 2.91 mmol) in DCM (40 mL) was added H$_2$O$_2$ (659 mg, 5.81 mmol, 30% aqueous solution), and then TFA (663 mg, 5.81 mmol) was added dropwise at 0° C. The reaction mixture was stirred at 40° C. for 16 h under N$_2$ atmosphere. Upon completion, the mixture was quenched with sat. aq. NH$_4$Cl (40 mL) and extracted with DCM (30 mL×3). The combined organic layer was washed with brine (50 mL×3), dried and evaporated to give 3-cyano-4-(trifluoromethyl)pyridine 1-oxide (500 mg, crude) as a white solid.

m/z ES+[M+H]$^+$ 189.2

Step b. 3-Cyano-4-(trifluoromethyl)pyridine 1-oxide (500 mg, 2.66 mmol) in POCl$_3$ (4.08 g, 26.6 mmol) was stirred at 110° C. for 12 h. Upon completion, the mixture was quenched by addition of ice water (10 mL) and extracted with EtOAc (10 mL×3). The combined organic layer was washed with brine (10 mL×3), dried and evaporated. The residue was purified by preparative TLC (25% EtOAc in PE) to give 2-chloro-4-(trifluoromethyl)nicotinonitrile (100 mg, 18% yield over two steps) as a colourless oil.

m/z ES+[M+H]$^+$ 207.2

Step c. To a solution of 2-chloro-4-(trifluoromethyl)nicotinonitrile (50 mg, 0.24 mmol) in NMP (1 mL) was added DIPEA (78 mg, 0.61 mmol) and Intermediate 3 (55 mg, 0.20 mmol, HCl salt). The reaction mixture was stirred at 80° C.

for 16 h. Upon completion, the mixture was concentrated under vacuum. The residue was purified by prep-HPLC to provide the title compound (31 mg, 37% yield) as a brown solid.

m/z ES+[M+H]$^+$ 405.2; $^1$H NMR (400 MHz, DMSO-d6) δ ppm 8.63 (d, J=4.4 Hz, 1H), 7.43-7.19 (m, 4H), 7.14 (d, J=4.8 Hz, 1H), 5.35 (d, J=6.0 Hz, 1H), 4.51-4.43 (m, 1H), 4.20-4.10 (m, 1H), 4.09-4.00 (m, 1H), 3.65-3.60 (m, 1H), 3.14 (s, 3H), 2.36 (s, 3H), 2.17-2.08 (m, 1H), 1.83-1.70 (m, 1H).

Example 35

(2S,4S)-1-(4-Ethyl-5-methylpyridin-2-yl)-4-hydroxy-N-methyl-N-(m-tolyl)pyrrolidine-2-carboxamide

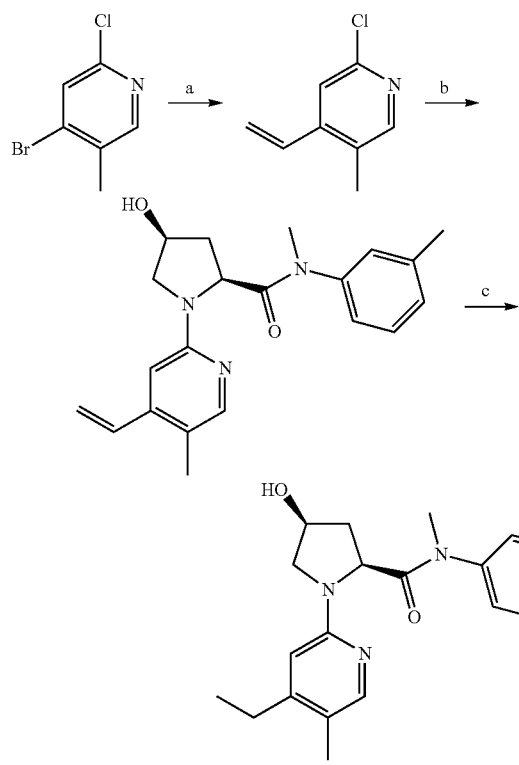

Step a. To a solution of potassium trifluoro(vinyl)borate (CAS Number 13682-77-4; 649 mg, 4.84 mmol), 4-bromo-2-chloro-5-methyl-pyridine (CAS Number 867279-13-8; 500 mg, 2.42 mmol), K$_2$CO$_3$ (1.67 g, 12.1 mmol) in 1,4-dioxane (20 mL) and water (2 mL) was added Pd(dppf)Cl$_2$-DCM (198 mg, 0.24 mmol). The reaction mixture was purged with N$_2$ three times and then stirred at 80° C. for 16 h under N$_2$ atmosphere. Upon completion, the reaction mixture was quenched by addition of water (50 mL) and extracted with EtOAc (50 mL×3). The combined organic layer was washed with brine (50 mL×3), dried and evaporated. The residue was purified by column chromatography (5-10% EtOAc in PE) to provide 2-chloro-5-methyl-4-vinyl-pyridine (0.11 g, 27% yield) as a colourless oil.

m/z ES+[M+H]$^+$ 154.2

Step b. A solution of 2-chloro-5-methyl-4-vinyl-pyridine (55 mg, 0.36 mmol), Intermediate 3 (97 mg, 0.36 mmol, HCl salt), Cs$_2$CO$_3$ (350 mg, 1.07 mmol) and RuPhos-Pd-G2 (28 mg, 0.036 mmol) in 1,4-dioxane (10 mL) was stirred at 80° C. for 4 h. Upon completion, the reaction mixture was quenched by addition of water (5 mL) and extracted with EtOAc (5 mL×3). The combined organic layer was washed with brine (5 mL×3), dried over sodium sulphate and evaporated. The residue was purified by preparative TLC (30% EtOAc in PE) to provide (2S,4S)-4-hydroxy-N-methyl-1-(5-methyl-4-vinyl-2-pyridyl)-N-(m-tolyl)pyrrolidine-2-carboxamide (0.12 g, 91% yield) as a white solid.

m/z ES+[M+H]$^+$ 352.4

Step c. A suspension of (2S,4S)-4-hydroxy-N-methyl-1-(5-methyl-4-vinyl-2-pyridyl)-N-(m-tolyl)pyrrolidine-2-carboxamide (0.12 g, 0.34 mmol) and Pd/C (12 mg, 10 wt. % loading) in MeOH (2 mL) was stirred at rt for 3 h under H$_2$ balloon (1 atm). The mixture was filtered and the filtrate was evaporated to provide the title compound (35 mg, 28% yield) as a grey solid. m/z ES+[M+H]$^+$ 354.2; $^1$H NMR (400 MHz, CDCl$_3$) δ ppm 7.86 (s, 1H), 7.34 (t, J=7.6 Hz, 2H), 7.18 (d, J=7.6 Hz, 1H), 6.15 (s, 1H), 5.58 (d, J=11.6 Hz, 1H), 4.52-4.42 (m, 2H), 3.76-3.71 (m, 1H), 3.51-3.48 (m, 1H), 3.32 (s, 3H), 2.52 (dd, J=15.2, 7.6 Hz, 2H), 2.42 (s, 3H), 2.13 (s, 3H), 2.11-2.08 (m, 2H), 1.18 (t, J=7.6 Hz, 3H).

Example 36

(2S,4S)-1-(3-Cyano-6-methyl-4-(trifluoromethyl)pyridin-2-yl)-4-methoxy-N-methyl-N-(m-tolyl)pyrrolidine-2-carboxamide

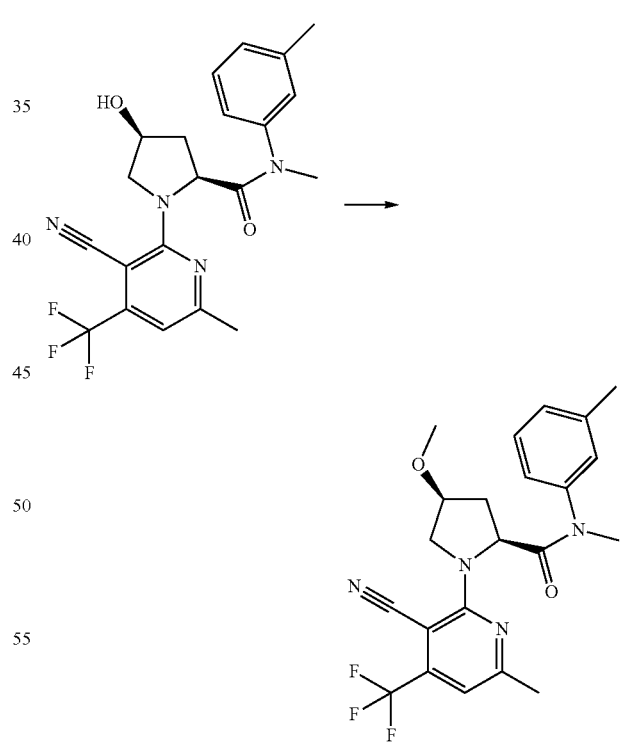

A suspension of Example 3 (15 mg, 0.036 mmol) in MeCN (1 mL) was slowly treated with silver(I)oxide (25 mg, 0.108 mmol). The reaction mixture was cooled to 0° C. and methyl iodide (0.011 mL, 0.179 mmol) was added dropwise. The reaction was stirred at rt for 18 h. Further portions of methyl iodide (3×0.022 mL, 0.352 mmol) were added over a further 5 days. The reaction mixture was diluted with EtOAc (10 mL) and filtered through celite. The filtrate was washed with water (15 mL), sat. aq. NaHCO₃ (15 mL) and brine (15 mL), dried and evaporated. The residue was purified by prep-HPLC to provide the title compound, (5.8 mg, 38%).

m/z ES+[M+H]⁺ 433.47; ¹H NMR (400 MHz, DMSO-d6) δ ppm 7.41 (t, J=7.7 Hz, 1H), 7.36-7.19 (m, 3H), 7.11 (s, 1H), 4.58 (t, J=8.3 Hz, 1H), 4.22-4.12 (m, 1H), 3.91 (m, 1H), 3.63 (m, 1H), 3.25 (s, 3H), 3.14 (s, 3H), 2.54 (s, 3H), 2.37 (s, 3H), 2.31-2.22 (m, 1H), 1.80-1.69 (m, 1H).

Example 37

(2S,4S)-1-(3-Cyano-4,6-dimethylpyridin-2-yl)-N-(3,4-difluorophenyl)-N-ethyl-4-fluoropyrrolidine-2-carboxamide

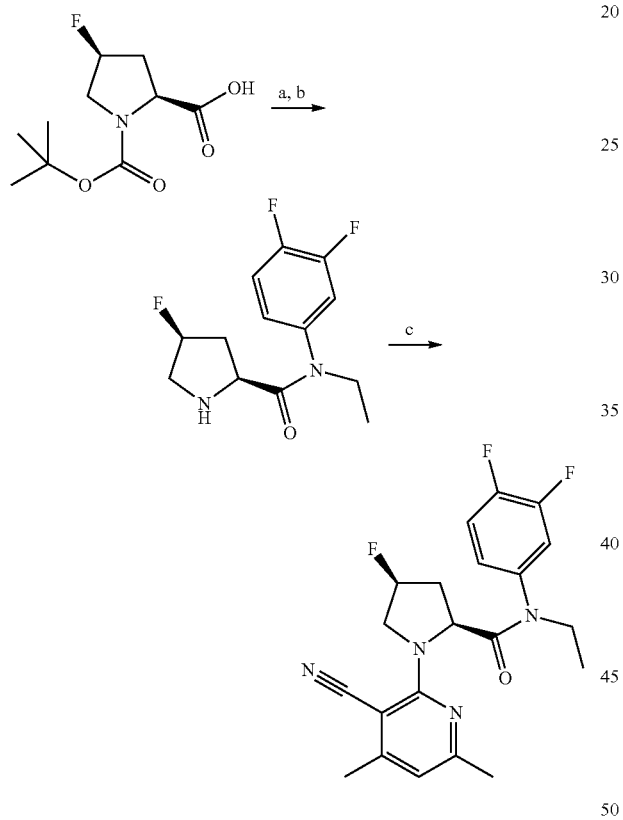

Step a. A solution of N-ethyl-3,4-difluoroaniline (0.07 mL, 0.44 mmol), (2S,4S)-1-(tert-butoxycarbonyl)-4-fluoropyrrolidine-2-carboxylic acid (CAS Number 203866-13-1; 0.25 g, 1.07 mmol) and pyridine (0.35 mL, 4.29 mmol) in EtOAc (1 mL) was treated with T3P (1.28 mL, 2.14 mmol, 50 wt. % in EtOAc) at 0° C. The mixture was stirred for 3 days at rt. The reaction mixture was quenched with 0.5 M aq. HCl and extracted into EtOAc. The organic extract was washed with brine, dried and evaporated. The residue was purified by column chromatography (10-50% EtOAc in cyclohexane) to provide tert-butyl (2S,4S)-2-[(3,4-difluorophenyl)-ethyl-carbamoyl]-4-fluoro-pyrrolidine-1-carboxylate, (0.170 g, 42%) as a clear gum.

m/z ES+[M+H]⁺ 373

Step b. A solution of tert-butyl (2S,4S)-2-[(3,4-difluorophenyl)-ethyl-carbamoyl]-4-fluoro-pyrrolidine-1-carboxylate (0.17 g, 0.457 mmol) in DCM (5 mL) and treated with TFA (1 mL) and stirred for 3 days at rt. The reaction mixture was evaporated, re-dissolved in MeOH and loaded onto SCX-2. The cartridge was washed with MeOH and then eluted with methanolic ammonia (7 M). Evaporation of the basic fractions provided (2S,4S)—N-(3,4-difluorophenyl)-N-ethyl-4-fluoro-pyrrolidine-2-carboxamide, (0.072 g, 58%) as a white solid which was used directly in the next step.

m/z ES+[M+H]⁺ 273

Step c. A solution of (2S,4S)—N-(3,4-difluorophenyl)-N-ethyl-4-fluoro-pyrrolidine-2-carboxamide (50 mg, 0.18 mmol), 2-chloro-4,6-dimethylnicotinonitrile (30 mg, 0.198 mmol) and DIPEA (0.09 mL, 0.54 mmol) in NMP (2 mL) was heated at 90° C. for 2 h then at 130° C. for 4 h. The reaction mixture was cooled and purified by prep-HPLC to provide the title compound (5.2 mg, 7%) as a pale brown solid.

m/z ES+[M+H]⁺ 403; ¹H NMR (400 MHz, CD₃OD) δ ppm 7.64-7.55 (m, 1H), 7.53-7.37 (m, 2H), 6.61 (s, 1H), 5.29 (d, J=55.3 Hz, 1H), 4.88-4.80 (m, 1H), 4.45-4.15 (m, 2H), 4.02-3.89 (m, 1H), 3.60-3.48 (m, 1H), 2.45 (s, 3H), 2.41 (s, 3H), 2.32-2.14 (m, 2H), 1.16 (t, J=7.1 Hz, 3H).

Example 38

(2S,4S)-4-Amino-1-(3-cyano-4,6-dimethylpyridin-2-yl)-N-ethyl-N-(m-tolyl)pyrrolidine-2-carboxamide

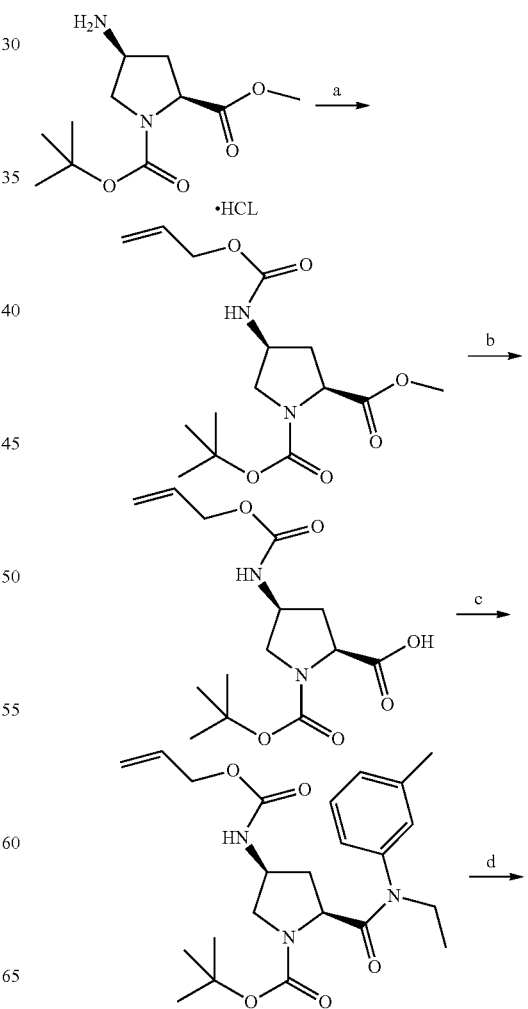

-continued

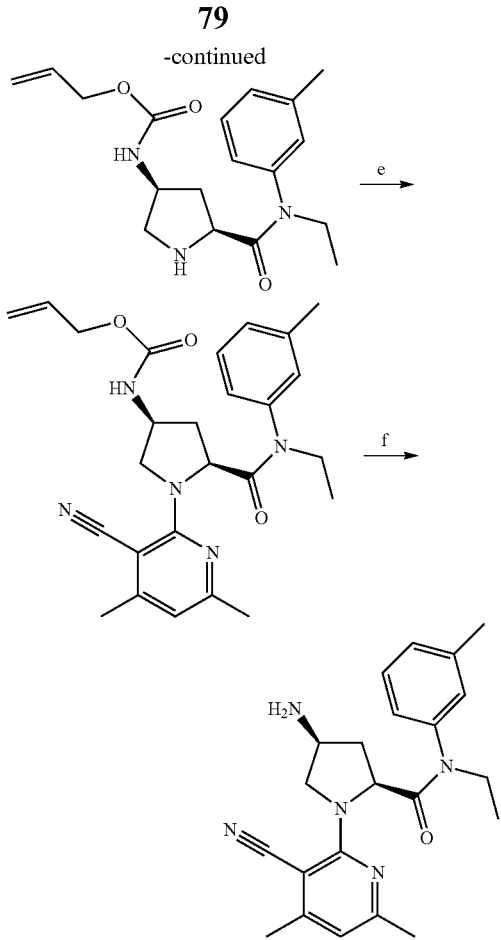

Step a. A solution of 1-tert-butyl 2-methyl (2S,4S)-4-aminopyrrolidine-1,2-dicarboxylate hydrochloride, (CAS Number 171110-72-8; 1.0 g, 3.46 mmol) and DIPEA (1.81 mL, 10.4 mmol) in DCM (8 mL) was treated with allyl chloroformate (0.44 mL, 4.15 mmol) at 0O0 and then stirred at rt for 3 h. The mixture was partitioned between sat. aq. NH₄Cl and DCM and the layers separated. The organic layer was washed with brine, dried and evaporated to give 1-tert-butyl 2-methyl (2S,4S)-4-(allyloxycarbonylamino)-pyrrolidine-1,2-dicarboxylate (1.2 g) used without further purification.

m/z ES+[M+H]⁺ 329.43; ¹H NMR (400 MHz, DMSO-d6) δ ppm 7.46-7.43 (m, 1H), 5.98-5.85 (m, 1H), 5.33-5.24 (m, 1H), 5.22-5.13 (m, 1H), 4.55-4.42 (m, 2H), 4.19 (t, J=8.1 Hz, 1H), 4.11-3.97 (m, 1H), 3.71-3.61 (m, 4H), 3.11-3.03 (m, 1H), 2.50-2.39 (m, 1H), 1.86-1.70 (m, 1H), 1.43-1.28 (m, 9H).

Step b. At 0° C. 2 M aq. NaOH (3.6 mL, 7.25 mmol) was added to 1-tert-butyl 2-methyl (2S,4S)-4-(allyloxycarbonylamino)pyrrolidine-1,2-dicarboxylate (1.2 g, 3.62 mmol) in MeOH (4 mL) and the mixture allowed to warm to rt and stirred for 4 h. The mixture was evaporated and then partitioned between sat. aq. NaHCO₃ and EtOAc. The layers were separated and the organics discarded. The aqueous was acidified with 3 M aq. HCl and extracted with EtOAc (×2). The organics extracts were washed with brine, dried and evaporated to give (2S,4S)-4-(allyloxycarbonylamino)-1-tert-butoxycarbonyl-pyrrolidine-2-carboxylic acid (1.24 g) used without further purification.

m/z ES+[M+H]⁺ 315.43; ¹H NMR (400 MHz, DMSO-d6) δ ppm 12.25 (s, 1H), 7.41 (d, J=7.4 Hz, 1H), 5.99-5.81 (m, 1H), 5.34-5.22 (m, 1H), 5.22-5.13 (m, 1H), 4.58-4.42 (m, 2H), 4.08-3.94 (m, 2H), 3.74-3.58 (m, 1H), 3.09-2.97 (m, 1H), 2.49-2.41 (m, 1H), 1.83-1.68 (m, 1H), 1.43-1.33 (m, 9H).

Step c. A solution of N-ethyl-3-methylaniline (0.17 mL, 1.15 mmol), (2S,4S)-4-(allyloxy-carbonylamino)-1-tert-butoxycarbonyl-pyrrolidine-2-carboxylic acid (0.28 g, 0.884 mmol) and pyridine (0.29 mL, 3.54 mmol) in EtOAc (0.9 mL) was treated with T3P (1.04 mL, 1.77 mmol, 50 wt. % in EtOAc) and stirred for 18 h. The mixture was diluted with EtOAc and washed twice with 1 M aq. HCl, brine, dried and evaporated to give a crude oil (400 mg). The crude product was purified by column chromatography (0-35% EtOAc in cyclohexane) to give tert-butyl (2S,4S)-4-(allyloxycarbonylamino)-2-[ethyl(m-tolyl)-carbamoyl]pyrrolidine-1-carboxylate (205 mg, 54%)

m/z ES+[M+H]⁺ 432.24; ¹H NMR (400 MHz, DMSO-d6) δ ppm 7.46-7.32 (m, 2H), 7.28-7.19 (m, 1H), 7.16-7.02 (m, 2H), 5.89 (ddt, J=17.3, 10.6, 5.4 Hz, 1H), 5.26 (dt, J=17.2, 1.7 Hz, 1H), 5.18 (dq, J=10.5, 1.5 Hz, 1H), 4.46 (d, J=5.4 Hz, 2H), 3.99-3.90 (m, 1H), 3.90-3.81 (m, 1H), 3.75-3.63 (m, 1H), 3.63-3.52 (m, 2H), 3.12-3.00 (m, 1H), 2.35 (s, 3H), 2.13-2.03 (m, 1H), 1.75-1.62 (m, 1H), 1.40 (s, 9H), 1.08-0.97 (m, 3H).

Step d. A solution of tert-butyl (2S,4S)-4-(allyloxycarbonylamino)-2-[ethyl(m-tolyl)-carbamoyl]pyrrolidine-1-carboxylate (184 mg, 0.426 mmol) in MeOH (4 mL) was treated with 4 M HCl in 1,4-dioxane (0.11 mL, 0.44 mmol) and stirred for 2 h. The mixture was evaporated and then loaded onto SCX-2 in MeOH, washed with MeOH and eluted with methanolic ammonia (2 M). The basic fractions were evaporated to give allyl N-[(3S,5S)-5-[ethyl(m-tolyl)carbamoyl]-pyrrolidin-3-yl]carbamate (99 mg, 70%).

m/z ES+[M+H]⁺ 332.48; ¹H NMR (400 MHz, DMSO-d6) δ ppm 7.36 (t, J=7.7 Hz, 1H), 7.27 (d, J=7.0 Hz, 1H), 7.22 (d, J=7.7 Hz, 1H), 7.10 (s, 1H), 7.06 (d, J=7.9 Hz, 1H), 5.90 (ddt, J=17.4, 10.6, 5.4 Hz, 1H), 5.27 (dq, J=17.2, 1.7 Hz, 1H), 5.17 (dq, J=10.5, 1.6 Hz, 1H), 4.44 (dt, J=5.3, 1.6 Hz, 2H), 3.81-3.70 (m, 1H), 3.68 (dq, J=14.7, 7.2 Hz, 1H), 3.59 (dq, J=13.9, 7.3 Hz, 1H), 3.31 (d, J=9.2 Hz, 1H), 2.78 (dd, J=11.3, 4.1 Hz, 1H), 2.62 (dd, J=11.3, 6.0 Hz, 1H), 2.35 (s, 3H), 1.77 (dt, J=13.0, 7.8 Hz, 1H), 1.50 (dt, J=12.9, 6.5 Hz, 1H), 1.01 (t, J=7.1 Hz, 3H).

Step e. A mixture of allyl N-[(3S,5S)-5-[ethyl(m-tolyl)carbamoyl]pyrrolidin-3-yl]carbamate (97 mg, 0.293 mmol), 2-chloro-4,6-dimethylnicotinonitrile (0.05 g, 0.293 mmol) and DIPEA (0.2 mL, 1.17 mmol) in NMP (1.6 mL) were heated at 130° C. for 3 h. The mixture was partitioned between EtOAc and sat. aq. NaHCO₃ and layers separated. The aqueous was extracted with EtOAc and the combined organic extracts were washed with brine, dried and evaporated to give allyl N-[(3S,5S)-1-(3-cyano-4,6-dimethyl-2-pyridyl)-5-[ethyl(m-tolyl)carbamoyl]pyrrolidin-3-yl]carbamate (70 mg, 52%).

m/z ES+[M+H]⁺ 462.54; ¹H NMR (400 MHz, DMSO-d6) δ ppm 7.55 (d, J=7.3 Hz, 1H), 7.41 (t, J=7.7 Hz, 1H), 7.38-7.21 (m, 3H), 6.61 (s, 1H), 5.90 (ddt, J=16.2, 10.6, 5.4 Hz, 1H), 5.28 (d, J=17.2 Hz, 1H), 5.18 (d, J=10.5 Hz, 1H), 4.47 (d, J=5.7 Hz, 2H), 4.42 (dd, J=9.1, 7.4 Hz, 1H), 4.06-3.94 (m, 2H), 3.77 (dq, J=14.1, 7.1 Hz, 1H), 3.70-3.59 (m, 1H), 3.43 (dq, J=14.4, 7.1 Hz, 1H), 2.40 (s, 3H), 2.37 (s, 3H), 2.33 (s, 3H), 2.13-2.02 (m, 1H), 1.81-1.67 (m, 1H), 1.01 (t, J=7.1 Hz, 3H)

Step f. Tetrakis(triphenylphosphine)palladium (0.02 g, 0.015 mmol) was added to allyl N-[(3S,5S)-1-(3-cyano-4, 6-dimethyl-2-pyridyl)-5-[ethyl(m-tolyl)carbamoyl]pyrrolidin-3-yl]-carbamate (70 mg, 0.152 mmol) and 1,4-diazabicyclo[2.2.2]octane (0.09 g, 0.758 mmol) in DCM (4 mL) and the mixture stirred for 5 h. The mixture was partitioned between EtOAc and sat. aq. NaHCO$_3$. The layers were separated and the aqueous extracted with EtOAc. The combined organic extracts were washed with brine, dried and evaporated. The residue was purified by mass-directed preparative HPLC to give the title compound (25 mg, 44%).

m/z ES+[M+H]$^+$ 378.48; $^1$H NMR (400 MHz, DMSO-d6) δ ppm 7.40 (t, J=7.6 Hz, 1H), 7.36-7.19 (m, 3H), 6.57 (s, 1H), 4.37 (t, J=8.3 Hz, 1H), 3.90 (dd, J=9.5, 7.0 Hz, 1H), 3.76 (dt, J=14.1, 7.0 Hz, 1H), 3.49 (t, J=8.9 Hz, 1H), 3.45-3.39 (m, 1H), 3.24-3.12 (m, 1H), 2.38 (s, 3H), 2.37 (s, 3H), 2.32 (s, 3H), 1.96 (dt, J=13.0, 6.9 Hz, 1H), 1.55 (dt, J=12.1, 9.4 Hz, 1H), 1.01 (t, J=7.0 Hz, 3H).

Example 39

(2R,4R)-1-(3-Cyano-4,6-dimethylpyridin-2-yl)-4-(dimethylamino)-N-ethyl-N-(m-tolyl)pyrrolidine-2-carboxamide

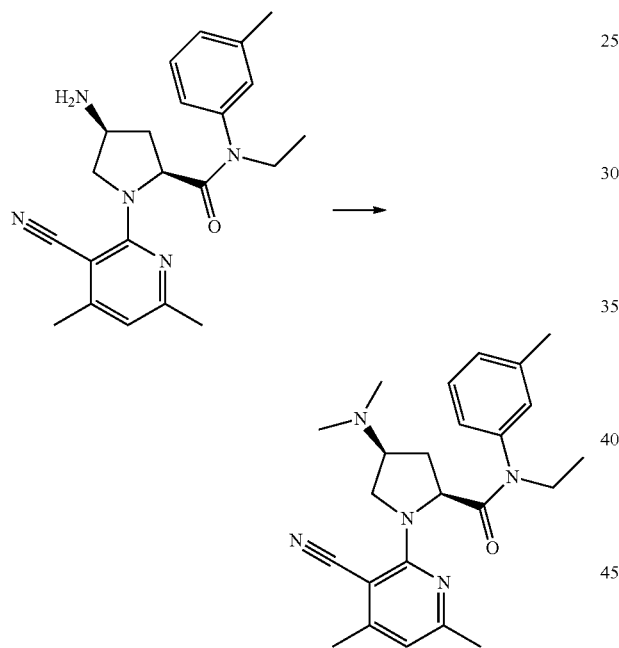

A solution of Example 38 (20 mg, 0.053 mmol) in THF (1.0 mL) was treated with formaldehyde (37% aq. solution; 0.11 mL, 1.325 mmol), followed by acetic acid (0.01 mL, 0.175 mmol) and the mixture stirred for 5 min. Sodium triacetoxyborohydride (20 mg, 0.106 mmol) was added and the mixture stirred for 2 h. The mixture was partitioned between sat. aq. NaHCO$_3$ and DCM. The layers were separated and the aqueous extracted with EtOAc. The combined organics were dried and evaporated to provide the title compound (16 mg, 74%).

m/z ES+[M+H]$^+$ 406.30; $^1$H NMR (400 MHz, Acetone-d6) δ ppm 7.42 (m, 3H), 7.27 (d, J=7.4 Hz, 1H), 6.54 (s, 1H), 4.60 (dd, J=10.4, 7.1 Hz, 1H), 4.13 (dd, J=9.3, 7.0 Hz, 1H), 3.85 (dq, J=14.2, 7.1 Hz, 1H), 3.74 (t, J=9.5 Hz, 1H), 3.51 (dq, J=14.0, 7.0 Hz, 1H), 2.55 (ddt, J=10.9, 9.4, 6.7 Hz, 1H), 2.45 (s, 3H), 2.42 (s, 3H), 2.37 (s, 3H), 2.20 (s, 6H), 2.09-2.08 (m, 1H), 1.74 (q, J=11.0 Hz, 1H), 1.07 (t, J=7.1 Hz, 3H).

Example 40

(2S,4R)-4-Amino-1-(3-cyano-4,6-dimethylpyridin-2-yl)-N-ethyl-N-(m-tolyl)pyrrolidine-2-carboxamide

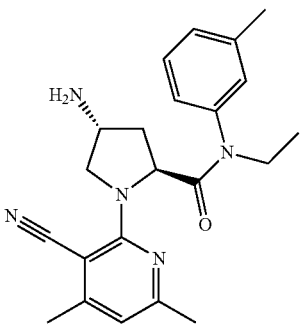 [SMILES: CCN(C(=O)[C@@H]1C[C@@H](N)CN1c1nc(C)cc(C)c1C#N)c1cccc(C)c1]

The title compound was prepared in a similar manner to Example 38, using 1-tert-butyl 2-methyl (2S,4R)-4-aminopyrrolidine-1,2-dicarboxylate hydrochloride, (CAS Number 334999-32-5) in step a.

m/z ES+[M+H]$^+$ 378.49; $^1$H NMR (400 MHz, DMSO-d6) δ ppm 7.40 (t, J=7.7 Hz, 1H), 7.37-7.25 (m, 2H), 7.23 (d, J=7.6 Hz, 1H), 6.56 (s, 1H), 4.54 (t, J=7.0 Hz, 1H), 3.96 (dd, J=10.0, 5.8 Hz, 1H), 3.77 (dq, J=14.0, 7.3 Hz, 1H), 3.68-3.59 (m, 1H), 3.46 (dd, J=9.9, 4.0 Hz, 1H), 3.44-3.39 (m, 1H), 2.39 (s, 3H), 2.37 (s, 3H), 2.32 (s, 3H), 1.88 (dt, J=12.0, 5.9 Hz, 1H), 1.63-1.52 (m, 2H), 1.00 (t, J=7.0 Hz, 3H).

Example 41

(2S,4R)-1-(3-Cyano-4,6-dimethylpyridin-2-yl)-4-(dimethylamino)-N-ethyl-N-(m-tolyl)pyrrolidine-2-carboxamide

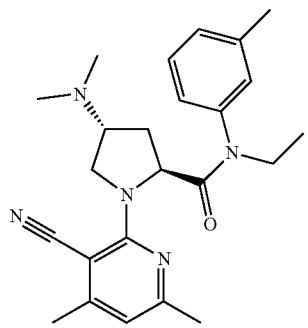 [SMILES: CCN(C(=O)[C@@H]1C[C@@H](N(C)C)CN1c1nc(C)cc(C)c1C#N)c1cccc(C)c1]

The title compound was prepared in a similar manner to Example 39.

m/z ES+[M+H]$^+$ 406.32; $^1$H NMR (400 MHz, DMSO-d6) δ ppm 7.46-7.30 (m, 3H), 7.30-7.18 (m, 1H), 6.59 (s, 1H), 4.52 (dd, J=8.4, 3.3 Hz, 1H), 4.03 (dd, J=9.7, 7.1 Hz, 1H), 3.80 (dq, J=14.1, 7.1 Hz, 1H), 3.67 (dd, J=9.7, 6.3 Hz, 1H), 3.48-3.36 (m, 1H), 3.01 (p, J=6.8 Hz, 1H), 2.39 (s, 3H), 2.36 (s, 3H), 2.33 (s, 3H), 2.07 (s, 6H), 2.03-1.92 (m, 1H), 1.75 (dt, J=12.6, 8.5 Hz, 1H), 1.01 (t, J=7.1 Hz, 3H).

Example 42

(2S,4S)-1-(3-Cyano-4,6-dimethylpyridin-2-yl)-N-ethyl-4-morpholino-N-(m-tolyl)pyrrolidine-2-carboxamide

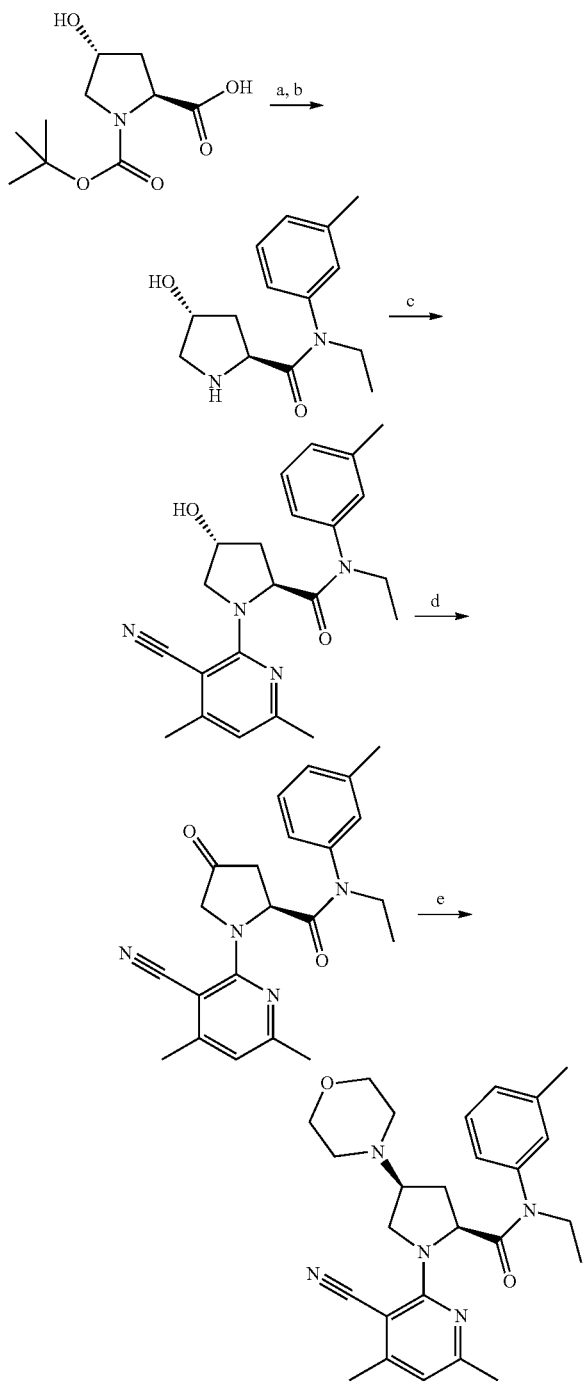

Step a. A solution of N-Boc-(2S,4R)-4-hydroxyproline (2.0 g, 8.48 mmol) and N-ethyl-3-methylaniline (2.44 mL, 16.95 mmol) in DCM (5 mL) was treated with EEDQ (4.23 g, 16.95 mmol) and stirred for 2 h. N-Ethyl-3-methylaniline (1.22 mL, 8.48 mmol) and EEDQ (2.12 g, 8.48 mmol) were added and the mixture stirred for another 2 h. A third portion of N-ethyl-3-methylaniline (1.22 mL, 8.48 mmol) and EEDQ (2.12 g, 8.48 mmol) were added and stirred for another 2 h. A final portion of EEDQ (2.12 g, 8.48 mmol) was added and the mixture stirred for 16 h. The mixture was diluted with DCM and washed sequentially, twice with 1 M aq. HCl, sat. aq. NH$_4$Cl, water and brine. The organic extract was dried and evaporated to give a yellow oil (7 g). The mixture was purified by column chromatography (0-5% MeOH in DCM) to give tert-butyl (2S,4R)-2-[ethyl(m-tolyl)carbamoyl]-4-hydroxy-pyrrolidine-1-carboxylate (1.5 g, 51%) as a colourless gum.

m/z ES+[M+H]$^+$ 349.47; $^1$H NMR (400 MHz, DMSO-d6) δ ppm 7.46-7.32 (m, 1H), 7.29-7.19 (m, 1H), 7.17-7.02 (m, 2H), 4.89-4.80 (m, 1H), 4.07-3.99 (m, 1H), 3.76-3.46 (m, 2H), 3.37-3.28 (m, 2H), 3.25-3.20 (m, 1H), 2.36 (s, 3H), 1.89-1.75 (m, 1H), 1.75-1.65 (m, 1H), 1.46-1.35 (m, 9H), 1.07-0.94 (m, 3H).

Step b. A solution of tert-butyl (2S,4R)-2-[ethyl(m-tolyl)carbamoyl]-4-hydroxy-pyrrolidine-1-carboxylate (1.0 g, 2.87 mmol) in MeOH (10 mL) was treated with 4 M HCl in 1,4-dioxane (0.72 mL, 2.87 mmol) and the mixture stirred for 3 h. The mixture was evaporated then loaded onto SCX-2 in MeOH, washed with MeOH and eluted with methanolic ammonia (2 M). The basic fractions were evaporated to give (2S,4R)—N-ethyl-4-hydroxy-N-(m-tolyl)-pyrrolidine-2-carboxamide (665 mg, 93%) as a colourless solid.

m/z ES+[M+H]$^+$ 249.36; $^1$H NMR (400 MHz, DMSO-d6) δ ppm 7.36 (t, J=7.7 Hz, 1H), 7.22 (d, J=7.6 Hz, 1H), 7.11 (s, 1H), 7.07 (d, J=7.8 Hz, 1H), 4.52 (d, J=4.0 Hz, 1H), 4.15-4.08 (m, 1H), 3.67 (dq, J=14.2, 7.1 Hz, 1H), 3.56 (dq, J=14.0, 7.0 Hz, 1H), 3.45 (t, J=7.9 Hz, 1H), 3.07 (dd, J=11.6, 5.2 Hz, 1H), 2.35 (s, 3H), 1.65 (ddd, J=13.0, 8.8, 6.2 Hz, 1H), 1.42 (ddd, J=12.9, 7.1, 2.2 Hz, 1H), 1.00 (t, J=7.1 Hz, 3H).

Step c. A mixture of (2S,4R)—N-ethyl-4-hydroxy-N-(m-tolyl)pyrrolidine-2-carboxamide (200 mg, 0.805 mmol), 2-chloro-4,6-dimethylnicotinonitrile (134 mg, 0.805 mmol) and DIPEA (1.12 mL, 6.4 mmol) in NMP (1.5 mL) was heated at 110° C. for 4 h. The temperature was increased to 130° C. and the reaction stirred for 1 h. The mixture was cooled and partitioned between EtOAc and sat. aq. NaHCO$_3$. The aqueous was extracted with EtOAc and the combined organics were washed with brine, dried and evaporated to give a brown oil (700 mg). The mixture was purified by column chromatography (30-80% EtOAc in cyclohexane) to give (2S,4R)-1-(3-cyano-4,6-dimethyl-2-pyridyl)-N-ethyl-4-hydroxy-N-(m-tolyl)pyrrolidine-2-carboxamide (245 mg, 80%) as a colourless gum.

m/z ES+[M+H]$^+$ 379.45; $^1$H NMR (400 MHz, DMSO-d6) δ ppm 7.46-7.20 (m, 4H), 6.59 (s, 1H), 4.97 (d, J=3.3 Hz, 1H), 4.54 (t, J=8.1 Hz, 1H), 4.37-4.30 (m, 1H), 3.95 (dd, J=10.6, 4.1 Hz, 1H), 3.77 (dq, J=14.1, 7.1 Hz, 1H), 3.63 (d, J=10.6 Hz, 1H), 3.47-3.38 (m, 1H), 2.40 (s, 3H), 2.37 (s, 3H), 2.33 (s, 3H), 1.91-1.81 (m, 1H), 1.81-1.71 (m, 1H), 1.00 (t, J=7.1 Hz, 3H).

Step d. A solution of oxalyl chloride (0.08 mL, 0.971 mmol) in DCM (2.5 mL) at −78° C. was treated dropwise with a mixture of DMSO (0.14 mL, 1.94 mmol) in DCM (2 ml) and stirred for 5 min. The reaction mixture was treated dropwise with a solution of (2S,4R)-1-(3-cyano-4,6-dimethyl-2-pyridyl)-N-ethyl-4-hydroxy-N-(m-tolyl)pyrrolidine-2-carboxamide (245 mg, 0.647 mmol) in DCM (3 mL) and stirred for 5 min. TEA (0.45 mL, 3.24 mmol) was then added dropwise and the mixture stirred for 15 min. The mixture was then allowed to warm to rt and stirred for 10 min. Sat. aq. NH$_4$Cl and DCM were added, and the layers separated. The aqueous was extracted with DCM and the combined organics were washed with brine, dried and evaporated to give a brown oil (300 mg). The crude product was purified by column chromatography (10-40% EtOAc in cyclohexane) to give (2S)-1-(3-cyano-4,6-dimethyl-2-pyridyl)-N-ethyl-N-(m-tolyl)-4-oxo-pyrrolidine-2-carboxamide (203 mg, 83%)

m/z ES+[M+H]$^+$ 377.42; $^1$H NMR (400 MHz, DMSO-d6) δ ppm 7.41 (t, J=7.7 Hz, 1H), 7.38-7.28 (m, 2H), 7.25 (d, J=7.6 Hz, 1H), 6.73 (s, 1H), 4.94 (dd, J=9.6, 2.5 Hz, 1H), 4.46 (d, J=17.0 Hz, 1H), 4.18 (d, J=17.0 Hz, 1H), 3.68 (dq, J=14.1, 7.1 Hz, 1H), 3.50 (dq, J=14.0, 7.1 Hz, 1H), 2.76 (dd, J=18.0, 9.6 Hz, 1H), 2.63 (dd, J=18.1, 2.5 Hz, 1H), 2.42 (s, 3H), 2.37 (s, 3H), 2.36 (s, 3H), 0.99 (t, J=7.1 Hz, 3H).

Step e. Sodium triacetoxyborohydride (180 mg, 0.85 mmol) was added to a mixture of (2S)-1-(3-cyano-4,6-dimethyl-2-pyridyl)-N-ethyl-N-(m-tolyl)-4-oxo-pyrrolidine-2-carboxamide (80 mg, 0.213 mmol), morpholine (0.04 mL, 0.425 mmol) and acetic acid (0.01 g, 0.213 mmol) in THF (5 mL) and stirred for 16 h. The mixture was partitioned between sat. aq. NaHCO$_3$ and EtOAc and the layers separated. The aqueous was extracted with EtOAc and the combined organics were evaporated. The residue was purified by mass-directed preparative HPLC to give the title compound (47 mg, 49%).

m/z ES+[M+H]$^+$ 448.57; $^1$H NMR (400 MHz, CD$_3$OD) δ ppm 7.57-7.11 (m, 4H), 6.57 (s, 1H), 4.57 (dd, J=10.6, 6.8 Hz, 1H), 4.16 (dd, J=9.4, 7.3 Hz, 1H), 3.89 (dq, J=13.6, 7.1 Hz, 1H), 3.82 (t, J=9.5 Hz, 1H), 3.76-3.62 (m, 4H), 3.53 (dq, J=14.2, 7.2 Hz, 1H), 2.73 (ddt, J=11.0, 9.5, 6.9 Hz, 1H) 2.61-2.51 (m, 2H), 2.49-2.43 (m, 5H), 2.41 (s, 3H), 2.38 (s, 3H), 2.18 (dt, J=12.6, 6.6 Hz, 1H), 1.78 (q, J=11.2 Hz, 1H), 1.12 (t, J=7.1 Hz, 3H).

Examples in Table 2 were prepared by a procedure similar to that described for the synthesis of Example 42.

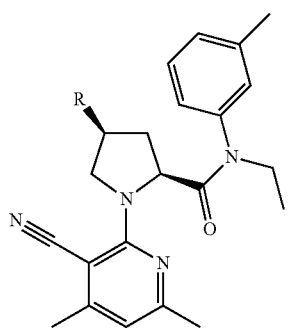

TABLE 2

| Example Number | R | Name | Amine CAS No. | $^1$H NMR (400 MHz) δ ppm | MI |
|---|---|---|---|---|---|
| 43 | —NH (methyl) | (2R,4R)-1-(3-Cyano-4,6-dimethylpyridin-2-yl)-N-ethyl-4-(methylamino)-N-(m-tolyl)-pyrrolidine-2-carboxamide | 74-89-5 | (Acetone-d6) 7.34-7.16 (m, 3H), 7.12 (d, J = 7.4 Hz, 1H), 6.39 (s, 1H), 4.43 (t, J = 7.7 Hz, 1H), 3.97 (dd, J = 9.9, 6.7 Hz, 1H), 3.76-3.64 (m, 2H), 3.41 (dq, J = 13.9, 7.1 Hz, 1H), 3.01 (p, J = 6.8 Hz, 1H), 2.31 (s, 3H), 2.28 (s, 3H), 2.22 (s, 3H), 2.21 (s, 3H), 2.03-1.97 (m, 1H), 1.61 (dt, J = 12.5, 7.3 Hz, 1H), 0.95 (t, J = 7.1 Hz, 3H). | 392.54 |
| 44 | HO—NH | (2R,4R)-1-(3-Cyano-4,6-dimethylpyridin-2-yl)-N-ethyl-4-((2-hydroxyethyl)amino)-N-(m-tolyl)pyrrolidine-2-carboxamide | 141-43-5 | (DMSO-d6) 7.41 (t, J = 7.7 Hz, 1H), 7.37-7.20 (m, 3H), 6.58 (s, 1H), 4.47 (t, J = 5.4 Hz, 1H), 4.40 (dd, J = 9.1, 7.4 Hz, 1H), 4.00 (dd, J = 9.6, 6.9 Hz, 1H), 3.76 (dq, J = 14.0, 7.1 Hz, 1H), 3.56 (t, J = 8.8 Hz, 1H), 3.47-3.38 (m, 3H), 3.20-3.07 (m, 1H), 2.59-2.55 (m, 2H), 2.39 (s, 3H), 2.37 (s, 3H), 2.32 (s, 3H), 2.10-2.01 (m, 1H), 1.63-1.54 (m, 1H), 1.01 (t, J = 7.1 Hz, 3H). | 422.54 |
| 45 | methylsulfonylethyl-NH | (2R,4R)-1-(3-Cyano-4,6-dimethylpyridin-2-yl)-N-ethyl-4-((2-(methylsulfonyl)ethyl)amino)-N-(m-tolyl)pyrrolidine-2-carboxamide | 49773-20-8 | (DMSO-d6) 7.46-7.17 (m, 4H), 6.59 (s, 1H), 4.45-4.38 (m, 1H), 4.05-3.97 (m, 1H), 3.81-3.70 (m, 1H), 3.54 (t, J = 8.9 Hz, 1H), 3.47-3.40 (m, 2H), 3.21-3.17 (m, 2H), 3.00 (s, 3H), 2.90-2.84 (m, 2H), 2.39 (s, 3H), 2.37 (s, 3H), 2.33 (s, 3H), 2.15-2.02 (m, 1H), 1.62-1.52 (m, 1H), 1.00 (t, J = 7.1 Hz, 3H). | 484.53 |
| 46 | methyl(methylsulfonylethyl)-N | (2S,4S)-1-(3-Cyano-4,6-dimethylpyridin-2-yl)-N-ethyl-4-(methyl(2-(methylsulfonyl)ethyl)amino)-N-(m-tolyl)-pyrrolidine-2-carboxamide | 202198-18-3 | (CD$_3$OD) 7.52-7.07 (m, 4H), 6.57 (s, 1H), 4.57 (dd, J = 10.6, 6.9 Hz, 1H), 4.14 (dd, J = 9.4, 7.3 Hz, 1H), 3.94-3.68 (m, 2H), 3.63-3.45 (m, 1H), 3.27-3.17 (m, 1H), 3.05 (s, 3H), 3.03-2.77 (m, 3H), 2.46 (s, 3H), 2.40 (d, J = 10.3 Hz, 6H), 2.30 (s, 3H), 2.25-2.08 (m, 1H), 1.83 (q, J = 11.1 Hz, 1H), 1.13 (t, J = 7.1 Hz, 3H). | 498.58 |
| 47 | 2-oxopyrrolidin-3-yl-NH | (2R,4R)-1-(3-Cyano-4,6-dimethylpyridin-2-yl)-N-ethyl-4-((2-oxopyrrolidin-3-yl)amino)-N-(m-tolyl)pyrrolidine-2-carboxamide | 2483-65-0 | (DMSO-d6) 7.36-7.18 (m, 3H), 6.58 (s, 1H), 4.40 (dd, J = 9.0, 7.4 Hz, 1H), 4.05 (dd, J = 9.5, 7.0 Hz, 1H), 3.75 (dq, J = 14.1, 7.0 Hz, 1H), 3.54 (t, J = 8.9 Hz, 1H), 3.48-3.39 (m, 1H), 3.29-3.22 (m, 1H), 3.20-3.13 (m, 2H), 3.12-3.04 (m, 1H), 2.39 (s, 3H), 2.37 (s, 3H), 2.32 (s, 3H), 2.28-2.21 (m, 1H), 2.17-2.07 (m, 1H), 1.69-1.57 (m, 2H), 1.01 (t, J = 7.1 Hz, 3H). | 461.56 |

Example 48

(2R,4R)-1-(3-Cyano-4,6-dimethylpyridin-2-yl)-N-ethyl-4-(methyl(pyrrolidin-3-yl)amino)-N-(m-tolyl)pyrrolidine-2-carboxamide

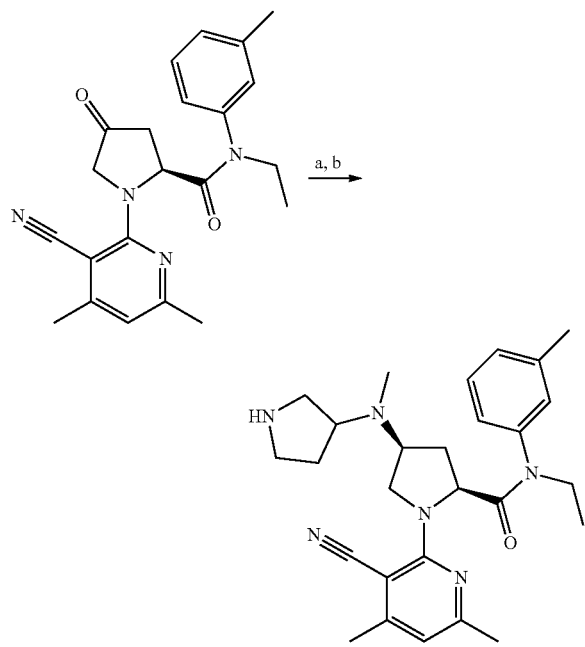

Step a. A solution of (2S)-1-(3-cyano-4,6-dimethyl-2-pyridyl)-N-ethyl-N-(m-tolyl)-4-oxo-pyrrolidine-2-carboxamide (60 mg, 0.159 mmol), 1-Boc-3-methylamino-pyrrolidine (0.02 mL, 0.32 mmol) and acetic acid (0.01 mL, 0.161 mmol) in THF (3.7 mL) was treated with sodium triacetoxyborohydride (0.07 g, 0.32 mmol) and the mixture stirred for 18 h. Further sodium triacetoxyborohydride (0.07 g, 0.32 mmol) was added and the mixture stirred for a further 6 h. The mixture was partitioned between sat. aq. NaHCO₃ and EtOAc and the layers separated. The aqueous was extracted with EtOAc and the combined organics were evaporated. The residue was purified by mass-directed preparative HPLC and the fractions evaporated to give a clear gum (45 mg).

Step b. A solution of the crude intermediate in MeOH (2 mL) was treated with 4M HCl in 1,4-dioxane (1.85 mL, 7.4 mmol) and stirred for 2 h. The reaction was evaporated and then loaded onto SCX-2 in MeOH, washed with MeOH and eluted with methanolic ammonia (2 M). The basic fractions were evaporated to provide the title compound (33 mg, 45%).

m/z ES+[M+H]⁺ 461.59; $^1$H NMR (400 MHz, DMSO-d6) δ ppm 7.41 (t, J=7.7 Hz, 1H), 7.38-7.25 (m, 2H), 7.24 (d, J=7.6 Hz, 1H), 6.59 (s, 1H), 4.46-4.34 (m, 1H), 3.88 (t, J=8.3 Hz, 1H), 3.77 (dq, J=14.0, 7.0 Hz, 1H), 3.70-3.58 (m, 1H), 3.47-3.38 (m, 2H), 3.12-3.03 (m, 2H), 2.86-2.68 (m, 3H), 2.39 (s, 3H), 2.37 (s, 3H), 2.33 (s, 3H), 2.13 (s, 3H), 1.98-1.87 (m, 1H), 1.76-1.61 (m, 2H), 1.56-1.47 (m, 1H), 1.00 (t, J=7.1 Hz, 3H).

Examples in Table 3 were prepared by a procedure similar to that described for the synthesis of Example 48

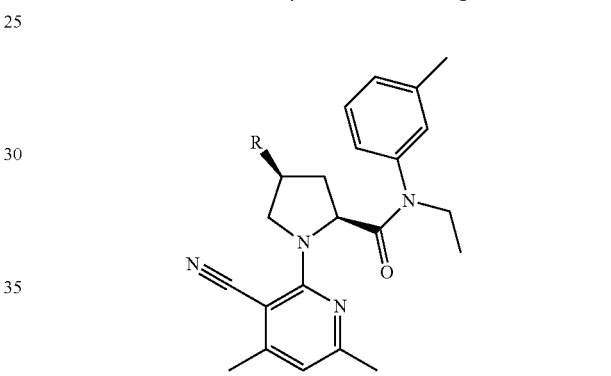

TABLE 3

| Example Number | R | Name | Amine CAS No. | $^1$H NMR (400 MHz) δ ppm | MI |
|---|---|---|---|---|---|
| 49 | H₂N-NH (2-Aminoethyl)amino | (2R,4R)-4-((2-Aminoethyl)amino)-1-(3-cyano-4,6-dimethylpyridin-2-yl)-N-ethyl-N-(m-tolyl)pyrrolidine-2-carboxamide | 57260-73-8 | (DMSO-d6) 7.45-7.18 (m, 4H), 6.58 (s, 1H), 4.40 (dd, J = 9.2, 7.4 Hz, 1H), 3.98 (dd, J = 9.6, 6.9 Hz, 1H), 3.76 (m, 1H), 3.56 (t, J = 8.9 Hz, 1H), 3.47-3.36 (m, 3H), 3.13-3.05 (m, 1H), 2.58-2.55 (m, 2H), 2.39 (s, 3H), 2.37 (s, 3H), 2.32 (s, 3H), 2.11-1.98 (m, 1H), 1.65-1.52 (m, 1H), 1.01 (t, J = 7.1 Hz, 3H). | 421.53 |
| 50 | HN piperazinyl | (2R,4R)-1-(3-Cyano-4,6-dimethylpyridin-2-yl)-N-ethyl-4-(piperazin-1-yl)-N-(m-tolyl)-pyrrolidine-2-carboxamide | 57260-71-6 | (DMSO-d6) 7.40 (t, J = 7.7 Hz, 1H), 7.37-7.26 (m, 2H), 7.24 (d, J = 7.6 Hz, 1H), 6.60 (s, 1H), 4.42 (dd, J = 10.3, 7.1 Hz, 1H), 4.02 (dd, J = 9.2, 7.1 Hz, 1H), 3.74 (dq, J = 14.0, 6.9 Hz, 1H), 3.56 (t, J = 9.4 Hz, 1H), 3.48-3.39 (m, 1H), 2.73-2.66 (m, 4H), 2.65-2.58 (m, 1H), 2.41-2.30 (m, 11H), 2.25-2.17 (m, 2H), 2.11-2.01 (m, 1H), 1.60 (q, J = 11.1 Hz, 1H), 0.99 (t, J = 7.1 Hz, 3H). | 447.58 |
| 51 | HN-azetidinyl-NH | (2S,4S)-4-(Azetidin-3-ylamino)-1-(3-cyano-4,6-dimethylpyridin-2-yl)-N-ethyl-N-(m-tolyl)pyrrolidine-2-carboxamide | 193269-78-2 | (CD₃OD) 8.55 (s, 1H), 7.54-7.10 (m, 4H), 6.57 (s, 1H), 4.62-4.43 (m, 1H), 4.26-4.02 (m, 3H), 3.97-3.80 (m, 4H), 3.78-3.69 (m, 1H), 3.62-3.45 (m, 1H), 3.27-3.13 (m, 1H), 2.46 (s, 3H), 2.39 (d, J = 11.6 Hz, 6H), 2.20-2.05 (m, 1H), 1.76-1.61 (m, 1H), 1.14 (t, J = 7.1 Hz, 3H). | 433.57 |

Example 52

(2R,4R)-4-((1-Acetylpyrrolidin-3-yl)(methyl)amino)-1-(3-cyano-4,6-dimethylpyridin-2-yl)-N-ethyl-N-(m-tolyl)pyrrolidine-2-carboxamide

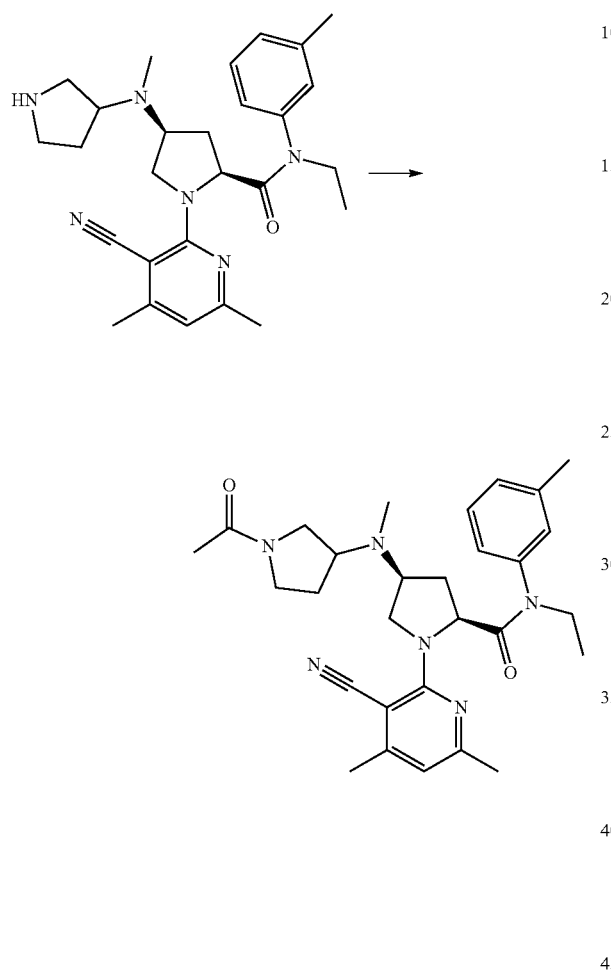

A solution of Example 48 (16.0 mg, 0.035 mmol) in DCM (1 mL) was treated with acetic anhydride (0.01 mL, 0.104 mmol) and TEA (0.05 mL, 0.347 mmol) and stirred at rt for 1 h. The mixture was partitioned between sat. aq. NaHCO$_3$ and DCM. The layers were separated, the organics were washed with further sat. aq. NaHCO$_3$ and brine, dried and evaporated. The crude product was purified by column chromatography (0-10% MeOH in DCM). Product fractions were combined and evaporated. The material was dissolved in DCM, washed with 1 M aq. NaOH and brine, dried and evaporated. The product was further dried under vacuum to provide the title compound, (11.1 mg, 63%).

m/z ES+[M+H]$^+$ 503.64; $^1$H NMR (400 MHz, DMSO-d6) δ ppm 7.46-7.18 (m, 4H), 6.60 (s, 1H), 4.42 (dt, J=9.3, 5.7 Hz, 1H), 3.96-3.82 (m, 1H), 3.81-3.71 (m, 1H), 3.68-3.55 (m, 2H), 3.51 (dd, J=10.6, 7.6 Hz, 1H), 3.48-3.36 (m, 2H), 3.24-3.03 (m, 3H), 2.39 (s, 3H), 2.37 (s, 3H), 2.33 (s, 3H), 2.21-2.15 (m, 3H), 2.07-1.90 (m, 2H), 1.91-1.88 (m, 3H), 1.84-1.58 (m, 2H), 1.00 (t, J=7.0 Hz, 3H).

Example 53

(2S,3R,4S)-1-(3-Cyano-6-methyl-4-(trifluoromethyl)pyridin-2-yl)-3,4-dihydroxy-N-methyl-N-(m-tolyl)pyrrolidine-2-carboxamide

Example 54

(2S,3S,4R)-1-(3-Cyano-6-methyl-4-(trifluoromethyl)pyridin-2-yl)-3,4-dihydroxy-N-methyl-N-(m-tolyl)pyrrolidine-2-carboxamide

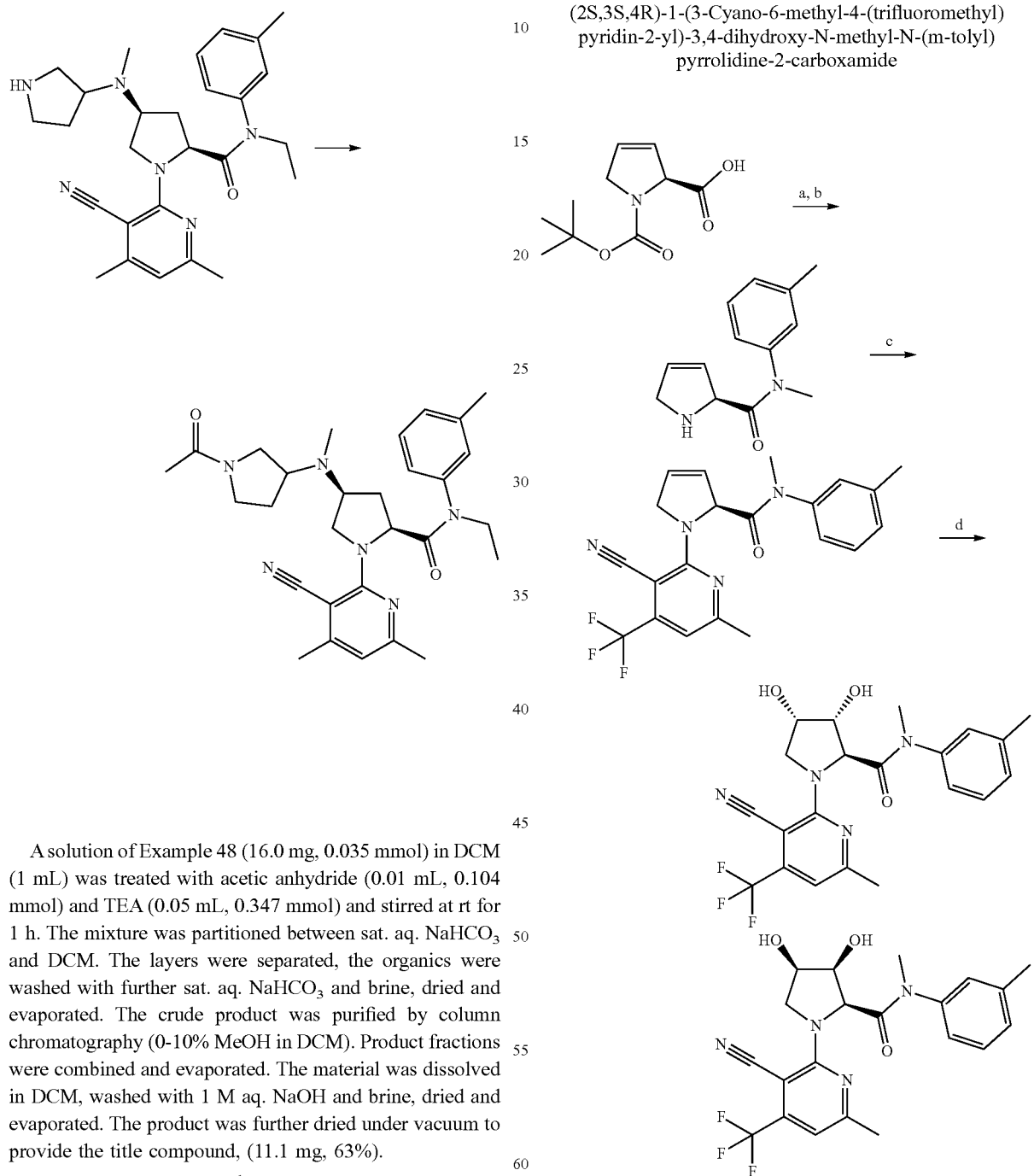

Step a. A solution of N-methyl-3-methylaniline (1.58 mL, 12.6 mmol), (S)-1-(tert-butoxycarbonyl)-2,5-dihydro-1H-pyrrole-2-carboxylic acid (CAS Number 51154-06-4; 2.5 g, 11.5 mmol) and pyridine (3.7 mL, 46 mmol) in EtOAc (12 mL) was treated with T3P (13.7 mL, 23.0 mmol, 50 wt. % in EtOAc) at 0° C. and stirred for 3 h at rt. Further T3P (6.8 mL, 11.5 mmol, 50 wt. % in EtOAc) was added and the mixture stirred for 1 h. The mixture was diluted with EtOAc and washed twice with 1 M aq. HCl, once with brine, dried and evaporated to give a brown oil (4.1 g). The mixture was purified by column chromatography (10-50% EtOAc in cyclohexane) to give tert-butyl (2S)-2-[methyl(m-tolyl)carbamoyl]-2,5-dihydropyrrole-1-carboxylate (3.64 g, 100%).

m/z ES+[M+H]$^+$ 317.48; $^1$H NMR (400 MHz, DMSO-d6) δ ppm 7.44-7.35 (m, 1H), 7.31-7.15 (m, 3H), 6.04-5.88 (m, 1H), 5.70-5.60 (m, 1H), 4.87-4.71 (m, 1H), 4.08-3.93 (m, 2H), 3.23-3.07 (m, 3H), 2.35 (s, 3H), 1.46-1.34 (m, 9H).

Step b. A solution of tert-butyl (2S)-2-[methyl(m-tolyl)carbamoyl]-2,5-dihydropyrrole-1-carboxylate (3.64 g, 11.5 mmol) in MeOH (15 mL) was treated with 4 M HCl in 1,4-dioxane (15 mL, 60 mmol) and stirred for 1 h. The reaction mixture was evaporated to give (2S)—N-methyl-N-(m-tolyl)-2,5-dihydro-1H-pyrrole-2-carboxamide hydrochloride (3.1 g) as a pale yellow hygroscopic solid used without further purification.

m/z ES+[M+H]$^+$ 217.37; $^1$H NMR (400 MHz, DMSO-d6) δ ppm 10.73 (s, 1H), 8.86 (s, 1H), 7.43 (t, J=7.7 Hz, 1H), 7.39-7.25 (m, 3H), 6.00 (dq, J=6.4, 2.1 Hz, 1H), 5.51 (dq, J=6.6, 2.3 Hz, 1H), 4.86 (s, 1H), 4.06 (d, J=15.9 Hz, 1H), 3.90 (d, J=14.9 Hz, 1H), 3.23 (s, 3H), 2.37 (s, 3H).

Step c. (2S)—N-methyl-N-(m-tolyl)-2,5-dihydro-1H-pyrrole-2-carboxamide hydrochloride (1.0 g, 3.957 mmol), Intermediate 1 (0.87 g, 3.957 mmol) and DIPEA (2.76 mL, 15.8 mmol) in NMP (4 mL) were heated at 100° C. for 2 h. The mixture was partitioned between EtOAc and sat. aq. NaHCO$_3$. The layers were separated and the aqueous was extracted with EtOAc and the combined organics were washed twice with brine, dried and evaporated. The mixture was purified by column chromatography (10-50% EtOAc in cyclohexane) to give (2S)-1-[3-cyano-6-methyl-4-(trifluoromethyl)-2-pyridyl]-N-methyl-N-(m-tolyl)-2,5-dihydropyrrole-2-carboxamide (1.284 g, 81%) as a pale yellow solid.

m/z ES+[M+H]$^+$ 401.45; $^1$H NMR (400 MHz, DMSO-d6) δ ppm 7.41 (t, J=7.6 Hz, 1H), 7.38-7.32 (m, 2H), 7.25 (d, J=7.5 Hz, 1H), 7.10 (s, 1H), 6.16-6.08 (m, 1H), 5.90-5.78 (m, 1H), 5.45-5.29 (m, 1H), 4.74-4.57 (m, 2H), 3.15 (s, 3H), 2.54 (s, 3H), 2.37 (s, 3H).

Step d. A mixture of (2S)-1-[3-cyano-6-methyl-4-(trifluoromethyl)-2-pyridyl]-N-methyl-N-(m-tolyl)-2,5-dihydropyrrole-2-carboxamide (0.60 g, 1.50 mmol), citric acid monohydrate (0.24 g, 1.124 mmol) and NMO (0.23 g, 1.99 mmol) in MeCN (6.8 mL) and water (1.7 mL) was treated with potassium osmate(VI) dihydrate (6 mg, 0.015 mmol) and stirred for 18 h. The mixture was evaporated and purified by column chromatography (30-70% EtOAc in cyclohexane) to provide (2S,3R,4S)-1-(3-cyano-6-methyl-4-(trifluoromethyl)-pyridin-2-yl)-3,4-dihydroxy-N-methyl-N-(m-tolyl)pyrrolidine-2-carboxamide (450 mg, 69%) as the major product.

Example 53 m/z ES+[M+H]$^+$ 435.45; $^1$H NMR (400 MHz, DMSO-d6) δ ppm 7.46-7.35 (m, 3H), 7.25-7.14 (m, 1H), 7.08 (s, 1H), 5.21 (d, J=5.6 Hz, 2H), 4.52 (d, J=2.9 Hz, 1H), 4.32-4.26 (m, 1H), 4.16-4.06 (m, 2H), 3.66 (dd, J=10.0, 6.2 Hz, 1H), 3.17 (s, 3H), 2.36 (s, 3H).

The fractions containing the minor product were further purified by prep-HPLC to give (2S,3S,4R)-1-(3-cyano-6-methyl-4-(trifluoromethyl)pyridin-2-yl)-3,4-dihydroxy-N-methyl-N-(m-tolyl)pyrrolidine-2-carboxamide (21 mg, 3%).

Example 54 m/z ES+[M+H]$^+$ 435.45; $^1$H NMR (400 MHz, DMSO-d6) δ ppm 7.44-7.37 (m, 1H), 7.36-7.27 (m, 2H), 7.26-7.20 (m, 1H), 7.08 (s, 1H), 5.38-5.27 (m, 1H), 5.26-5.15 (m, 1H), 4.75-4.66 (m, 1H), 3.98-3.82 (m, 2H), 3.82-3.69 (m, 2H), 3.19-3.11 (m, 3H), 2.36 (s, 3H)

Examples in Table 4 were prepared by a procedure similar to that described for the synthesis of Example 54:

TABLE 4

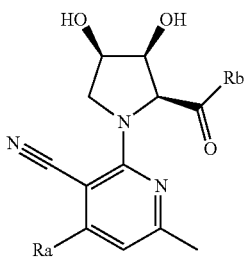

| Example Number | Ra | Rb | Name | Amine CAS No. | $^1$H NMR (400 MHz, DMSO-d6) δ ppm | MI |
|---|---|---|---|---|---|---|
| 55 | CH$_3$ | | (2S,3S,4R)-1-(3-Cyano-4,6-dimethyl-pyridin-2-yl)-3,4-dihydroxy-N-methyl-N-(m-tolyl)-pyrrolidine-2-carboxamide | 696-44-6 | 7.40-7.35 (m, 3H), 7.26-7.15 (m, 1H), 6.58 (s, 1H), 5.24 (d, J = 4.8 Hz, 1H), 5.18 (d, J = 8.3 Hz, 1H), 4.68 (d, J = 5.6 Hz, 1H), 3.95-3.79 (m, 3H), 3.73 (dd, J = 9.5, 6.9 Hz, 1H), 3.15 (s, 3H), 2.37-2.30 (m, 9H) | 381.47 |

TABLE 4-continued

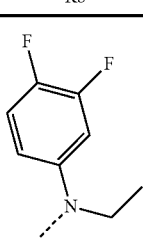

| Example Number | Ra | Rb | Name | Amine CAS No. | $^1$H NMR (400 MHz, DMSO-d6) δ ppm | MI |
|---|---|---|---|---|---|---|
| 56 | CF$_3$ | 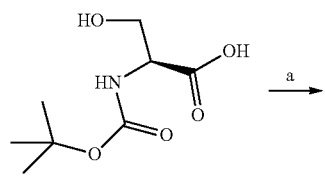 | (2S,3S,4R)-1-(3-Cyano-6-methyl-4-(trifluoromethyl)pyridin-2-yl)-N-(3,4-difluorophenyl)-N-ethyl-3,4-dihydroxypyrrolidine-2-carboxamide | 136491-15-1 | 7.61 (q, J = 9.4 Hz, 1H), 7.55-7.49 (m, 1H), 7.41-7.28 (m, 1H), 7.08 (s, 1H), 5.40 (s, 1H), 5.19 (s, 1H), 4.67 (d, J = 5.2 Hz, 1H), 3.98-3.73 (m, 4H), 3.67 (t, J = 8.8 Hz, 1H), 3.44-3.40 (m, 1H), 1.01 (t, J = 7.1 Hz, 3H). | 471.46 |
| 57 | CF$_3$ | 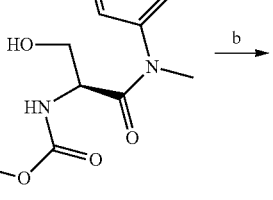 | (2S,3S,4R)-N-(3-Chloro-4-fluorophenyl)-1-(3-cyano-6-methyl-4-(trifluoromethyl)pyridin-2-yl)-N-ethyl-3,4-dihydroxypyrrolidine-2-carboxamide | 106847-36-3 | 7.74-7.66 (m, 1H), 7.66-7.53 (m, 1H), 7.53-7.42 (m, 1H), 7.08 (s, 1H), 5.32 (s, 1H), 5.11 (s, 1H), 4.67 (d, J = 5.2 Hz, 1H), 3.98-3.64 (m, 5H), 3.52-3.36 (m, 1H), 1.02 (t, J = 7.2 Hz, 3H). | 487.43 |

Example 58

(S)—N-Methyl-3-(6-methyl-4-(trifluoromethyl)pyridin-2-yl)-2-oxo-N-(m-tolyl)oxazolidine-4-carboxamide

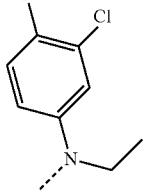

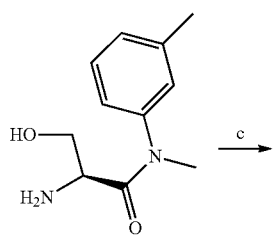

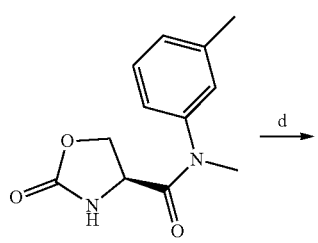

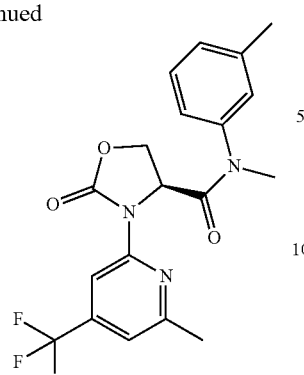

Step a. To a solution of (S)-2-((tert-butoxycarbonyl)amino)-3-hydroxypropanoic acid (800 mg, 3.90 mmol) in IPA (10 mL) at 0° C. was added DIPEA (1.01 g, 7.80 mmol, 1.36 mL). After 30 min, T3P (4.96 g, 7.80 mmol, 50 wt. % in DMF) and N-methyl-3-methyl-aniline (472 mg, 3.90 mmol) were added at 0° C. The reaction mixture was stirred at rt for 12 h. The reaction mixture was evaporated and the resultant residue diluted with water (20 mL) and extracted with EtOAc (30 mL×3). The combined organic layer was washed with brine, dried and evaporated. The residue was purified by column chromatography (50% EtOAc in PE) to give (S)-tert-butyl (3-hydroxy-1-(methyl(m-tolyl)amino)-1-oxopropan-2-yl)carbamate (456 mg, 87% yield) as a yellow oil.

m/z ES+[M+H]+ 309.4

Step b. To a solution of (S)-tert-butyl (3-hydroxy-1-(methyl(m-tolyl)amino)-1-oxopropan-2-yl)carbamate (456 mg, 1.48 mmol) in 1,4-dioxane (4 mL) was added 4 M HCl in 1,4-dioxane (4 mL). The mixture was stirred at rt for 2 h. Upon completion, the mixture was evaporated to give (S)-2-amino-3-hydroxy-N-methyl-N-(m-tolyl)propanamide (450 mg, crude) as a yellow solid.

Step c. A mixture of (S)-2-amino-3-hydroxy-N-methyl-N-(m-tolyl)propanamide (450 mg, 2.16 mmol), KHCO$_3$ (238 mg, 2.38 mmol) and K$_2$CO$_3$ (328 mg, 2.38 mmol) in water (5 mL) was cooled to 0° C. Then bis(trichloromethyl) carbonate (321 mg, 1.08 mmol) in toluene (5 mL) was added to the mixture and stirred for 2 h at 0° C. Upon completion, the mixture was separated, and the aqueous phase was extracted with EtOAc (30 mL). The combined organic layer was washed with brine (30 mL), dried and evaporated. The residue was purified by column chromatography (30% EtOAc in PE) to give (S)—N-methyl-2-oxo-N-(m-tolyl)oxazolidine-4-carboxamide (140 mg, 28% yield) as a yellow oil.

m/z ES+[M+H]+ 235.1

Step d. To a solution of (S)—N-methyl-2-oxo-N-(m-tolyl)oxazolidine-4-carboxamide (60 mg, 0.26 mmol), 2-chloro-6-methyl-4-(trifluoromethyl)pyridine (65 mg, 0.33 mmol), Pd$_2$(dba)$_3$ (23 mg, 0.026 mmol), Xantphos (22 mg, 0.038 mmol) in 1,4-dioxane (3 mL) was added Cs$_2$CO$_3$ (167 mg, 0.52 mmol). The mixture was degassed with N$_2$ 3 times and stirred at 120° C. for 2 h. Upon completion, the mixture was diluted with water (10 mL) and extracted into EtOAc (20 mL×2). The combined organic layer was washed with brine (20 mL), dried and evaporated. The residue was purified by prep-HPLC to provide the title compound (45 mg, 43% yield) as a yellow solid.

m/z ES+[M+H]+ 394.1; $^1$H NMR (400 MHz, DMSO-d6) δ ppm 8.14 (s, 1H), 7.50-7.40 (m, 2H), 7.36-7.25 (m, 3H), 4.97 (dd, J=9.2, 3.2 Hz, 1H), 4.57 (dd, J=8.4, 3.6 Hz, 1H), 4.35 (t, J=9.2 Hz, 1H), 3.20 (s, 3H), 2.59 (s, 3H), 2.39 (s, 3H).

Example 59

(S)—N-Methyl-1-(6-methyl-4-(trifluoromethyl)pyridin-2-yl)-5-oxo-N-(m-tolyl)pyrrolidine-2-carboxamide

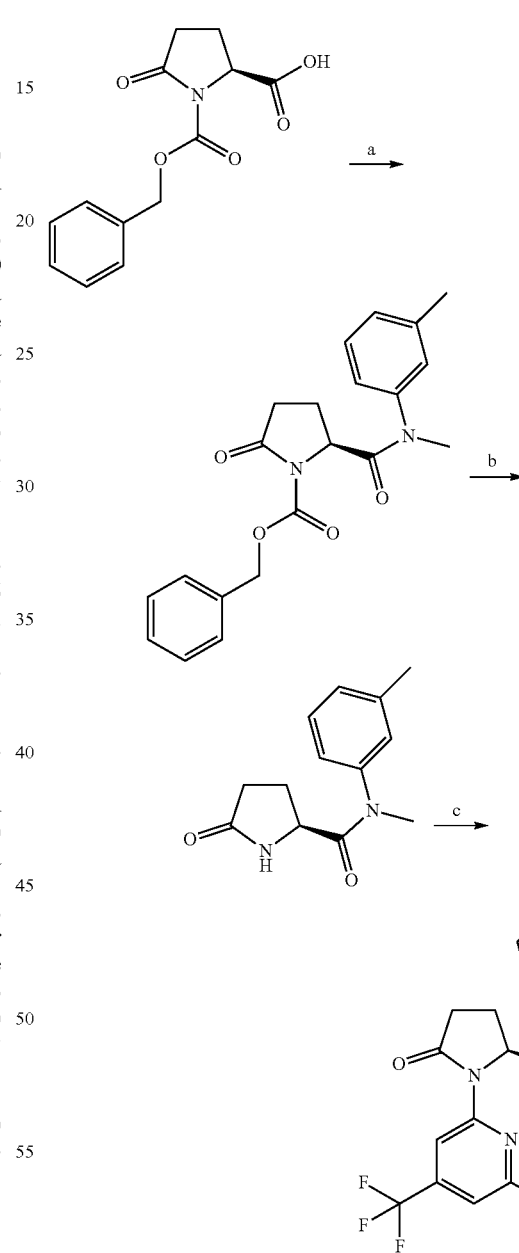

Step a. To a solution of (2S)-1-benzyloxycarbonyl-5-oxo-pyrrolidine-2-carboxylic acid (CAS Number 32159-21-0; 200 mg, 0.76 mmol) and N-methyl-3-methyl-aniline (119 mg, 0.99 mmol) in pyridine (8 mL) was added T3P (1.45 g, 2.28 mmol, 50 wt. % in EtOAc). The mixture was stirred at rt for 12 h. The reaction mixture was diluted with water (40 mL) and extracted with EtOAc (30 mL×3). The combined organic extracts were washed with brine (30 mL×2), dried over sodium sulfate, filtered and evaporated. The residue was purified by column chromatography (0-10% EtOAc in PE) to afford benzyl (2S)-2-[methyl(m-tolyl)-carbamoyl]-5-oxo-pyrrolidine-1-carboxylate (210 mg, 75% yield) as a white solid.

$^1$H NMR (400 MHz, CDCl$_3$) δ ppm 7.48-7.34 (m, 5H), 7.27-7.21 (m, 1H), 7.19-7.13 (m, 1H), 6.84-6.75 (m, 2H), 5.38-5.15 (m, 2H), 4.57 (dd, J=3.6, 8.8 Hz, 1H), 3.24 (s, 3H), 2.83-2.72 (m, 1H), 2.45-2.36 (m, 1H), 2.32 (s, 3H), 2.02-1.89 (m, 2H).

Step b. To a solution of benzyl (2S)-2-[methyl(m-tolyl) carbamoyl]-5-oxo-pyrrolidine-1-carboxylate (190 mg, 0.52 mmol) in THF (15 mL) was added Pd/C (20 mg, 10 wt. % loading) under N$_2$ atmosphere. The suspension was degassed under vacuum and purged with H$_2$ several times. The mixture was stirred under H$_2$ (15 psi) at rt for 1 h. The reaction mixture was filtered and concentrated under vacuum to afford (2S)—N-methyl-N-(m-tolyl)-5-oxo-pyrrolidine-2-carboxamide (120 mg, 99.6% yield) as a colourless oil.

Step c. To a solution of (2S)—N-methyl-N-(m-tolyl)-5-oxo-pyrrolidine-2-carboxamide (80 mg, 0.34 mmol) and 2-chloro-6-methyl-4-(trifluoromethyl)pyridine (74 mg, 0.38 mmol) in 1,4-dioxane (8 mL) was added Pd$_2$(dba)$_3$ (31.5 mg, 0.034 mmol), Xantphos (39.9 mg, 0.069 mmol) and Cs$_2$CO$_3$ (337 mg, 1.03 mmol). The mixture was stirred at 100° C. for 2 h under N$_2$ atmosphere. The reaction mixture was diluted with water (20 mL) and extracted with EtOAc (15 mL×3). The combined organic extracts were washed with brine (20 mL×2), dried over sodium sulfate, filtered and evaporated. The crude residue was purified by column chromatography (0-20% EtOAc in PE) and further purified by prep-HPLC to provide the title compound (121 mg, 88% yield) as a white solid.

m/z ES+[M+H]$^+$ 392.0; $^1$H NMR (400 MHz, DMSO-d6) δ ppm 8.42 (s, 1H), 7.47-7.42 (m, 1H), 7.40 (s, 2H), 7.38-7.34 (m, 1H), 7.29-7.24 (m, 1H), 4.91 (dd, J=3.2, 8.8 Hz, 1H), 3.18 (s, 3H), 2.71-2.63 (m, 1H), 2.60 (s, 3H), 2.49-2.46 (m, 1H), 2.39 (s, 3H), 2.14-1.99 (m, 2H).

Example 60

(S)—N-(5-Fluoro-6-methylpyridin-2-yl)-N-methyl-1-(6-methyl-4-(trifluoromethyl)pyridin-2-yl)-5-oxopyrrolidine-2-carboxamide

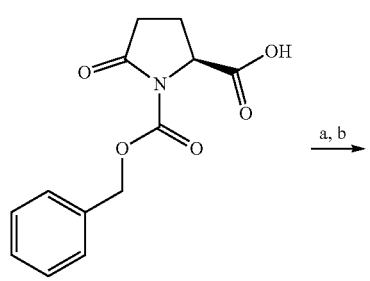

a, b

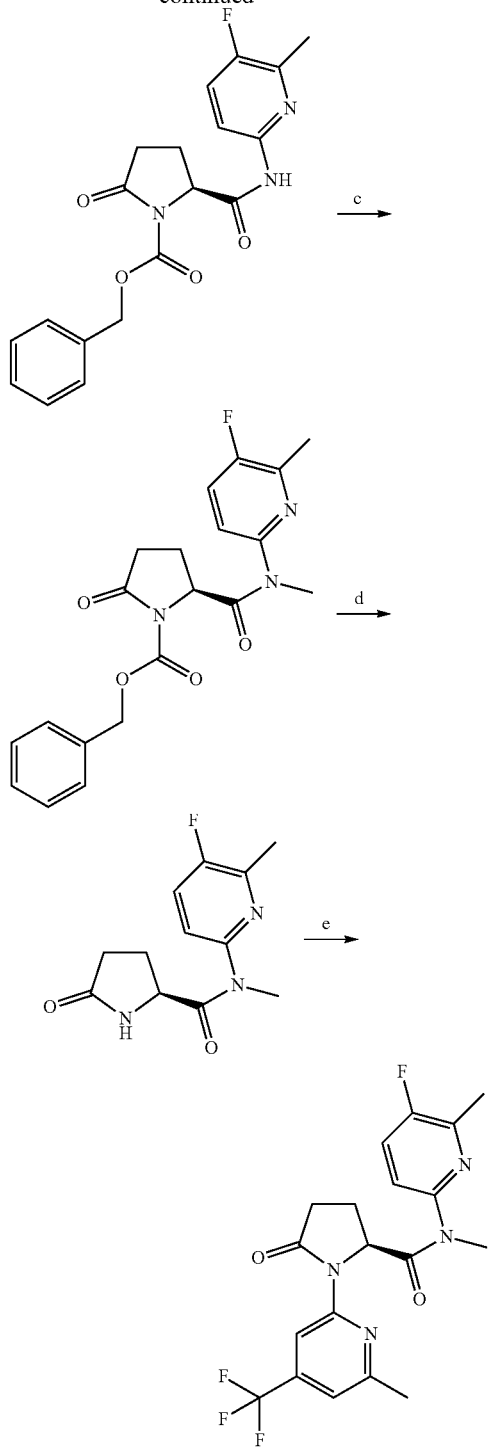

Steps a, b. To a solution of (S)-1-((benzyloxy)carbonyl)-5-oxopyrrolidine-2-carboxylic acid (CAS Number 32159-21-0; 2.00 g, 7.60 mmol) in DCM (40 mL) and DMF (2 mL) was added oxalyl chloride (1.45 g, 11.4 mmol). The mixture was stirred at 0° C. for 30 min. The reaction mixture was evaporated to give the acid chloride intermediate (2.3 g, crude) as a brown solid. A solution of the crude acid chloride (0.20 g, 1.59 mmol) in DCM (6 mL) was treated with TEA (0.48 g, 4.76 mmol), followed by portion-wise addition of 5-fluoro-6-methylpyridin-2-amine (0.67 g, 2.38 mmol). The resulting mixture was stirred at 0° C. for 30 min. Upon completion, the reaction mixture was evaporated to give a residue, which was purified by column chromatography (25% EtOAc in PE) to give (S)-benzyl 2-((5-fluoro-6-methylpyridin-2-yl)carbamoyl)-5-oxopyrrolidine-1-carboxylate (400 mg, 66% yield) as a yellow solid.

m/z ES+[M+H]+372.2

Step c. To a solution of (S)-benzyl 2-((5-fluoro-6-methylpyridin-2-yl)carbamoyl)-5-oxo-pyrrolidine-1-carboxylate (200 mg, 0.54 mmol) in DMF (2 mL) was added NaH (24 mg, 0.59 mmol, 60% dispersion in mineral oil) at 0° C. and the mixture was stirred at 0° C. for 30 min. Methyl iodide (92 mg, 0.65 mmol) was added dropwise into the mixture at 0° C. and then stirred at rt for 2 h. Upon completion, the mixture was quenched with water (5 mL) and evaporated. The crude residue was purified by column chromatography (50% EtOAc in PE) to give (S)-benzyl 2-((5-fluoro-6-methylpyridin-2-yl)(methyl)carbamoyl)-5-oxopyrrolidine-1-carboxylate (105 mg, 46% yield) as a white solid.

m/z ES+[M+H]+ 385.4

Step d. To a solution of (S)-benzyl 2-((5-fluoro-6-methylpyridin-2-yl)(methyl)carbamoyl)-5-oxopyrrolidine-1-carboxylate (105 mg, 0.27 mmol) in THF (2 mL) was added Pd on activated carbon (5 mg, 10 wt. % loading). The mixture was purged 3 times with H₂ and stirred at rt for 4 h (15 psi H₂). Upon completion, the mixture was filtered through celite. The filter cake was washed with 20 mL of EtOAc. The combined organic layer was evaporated to give a residue, which was purified by column chromatography (3% MeOH in EtOAc) to give (S)—N-(5-fluoro-6-methylpyridin-2-yl)-N-methyl-5-oxopyrrolidine-2-carboxamide (54 mg, 78% yield) as a white solid.

m/z ES+[M+H]+ 252.1

Step e. To a solution of (S)—N-(5-fluoro-6-methylpyridin-2-yl)-N-methyl-5-oxopyrrolidine-2-carboxamide (44 mg, 0.18 mmol), 2-chloro-6-methyl-4-(trifluoromethyl) pyridine (44 mg, 0.23 mmol), Xantphos (15.2 mg, 0.026 mmol) and Cs₂CO₃ (114 mg, 0.35 mmol) in 1,4-dioxane (5 mL) was added Pd₂(dba)₃ (16 mg, 0.018 mmol). The mixture was degassed 3 times with N₂ and stirred at 100° C. for 2 h. Upon completion, the mixture was diluted with water (20 mL) and extracted with EtOAc (40 mL×3). The combined organic extracts were washed with brine (20 mL×2), dried and evaporated. The crude residue was purified by prep-HPLC to give the title compound (27 mg, 14% yield) as a white solid.

m/z ES+[M+H]+ 411.0; ¹H NMR (400 MHz, CDCl₃) δ ppm 8.56 (s, 1H), 7.56-7.40 (m, 1H), 7.31-7.25 (m, 1H), 7.06 (s, 1H), 5.29-4.84 (m, 1H), 3.40 (br s, 3H), 3.05-2.90 (m, 1H), 2.70-2.60 (m, 1H), 2.55 (d, J=2.8 Hz, 3H), 2.48 (s, 3H), 2.47-2.40 (m, 1H), 2.39-2.25 (m, 1H).

Example 61

(2S,4S)-4-Amino-N-(3-chloro-4-fluorophenyl)-N-ethyl-1-(6-methyl-4-(trifluoromethyl)pyridin-2-yl)-5-oxopyrrolidine-2-carboxamide

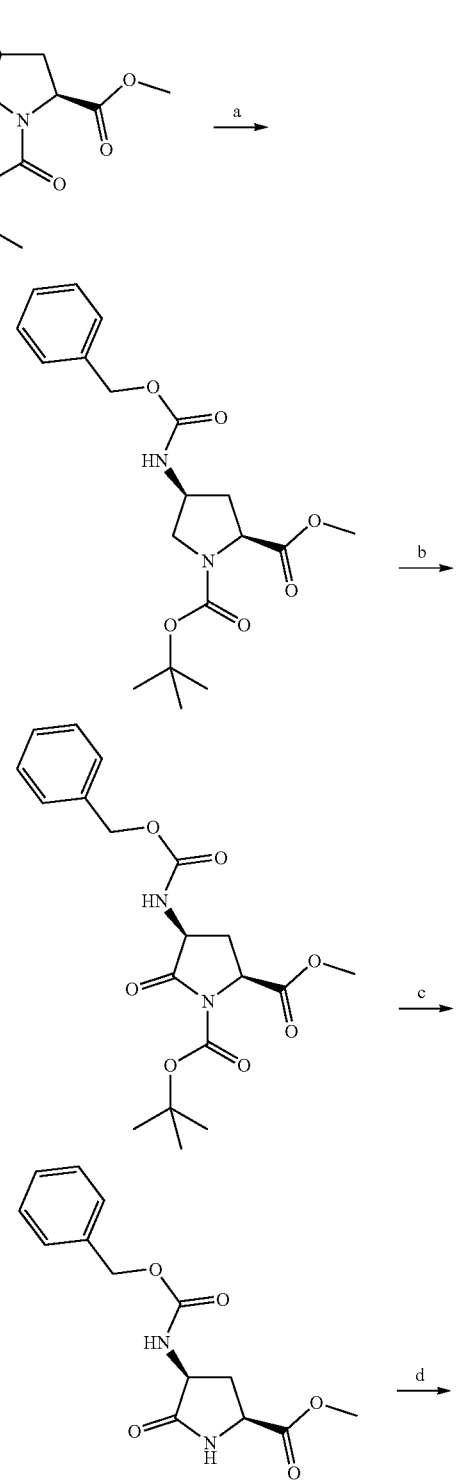

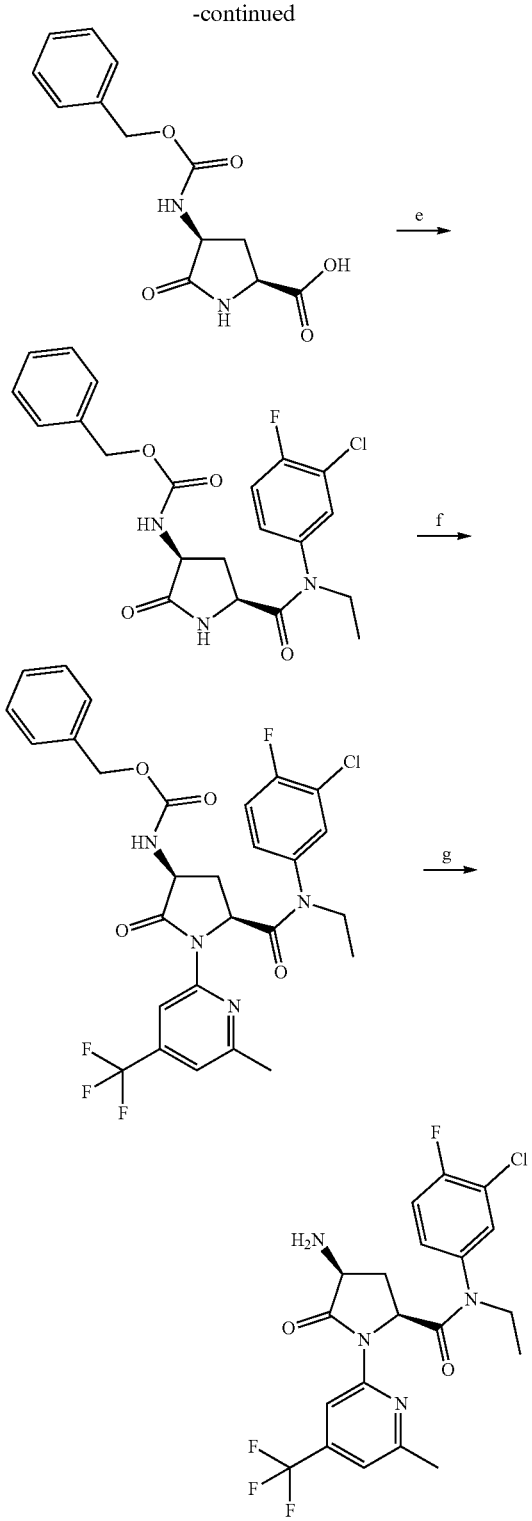

(200 mL). The organic layer was dried over sodium sulphate and evaporated. The residue was purified by column chromatography (25% EtOAc in PE) to give (2S,4S)-1-tert-butyl 2-methyl 4-(((benzyloxy)carbonyl)amino)pyrrolidine-1,2-dicarboxylate (10.0 g, 99% yield) as a colourless oil.

$^1$H NMR (400 MHz, CDCl$_3$) δ ppm 7.41-7.27 (m, 5H), 5.85-5.70 (m, 1H), 5.10 (s, 2H), 4.50-4.20 (m, 2H), 3.93-3.73 (m, 3H), 3.71-3.61 (m, 1H), 3.60-3.40 (m, 1H), 2.60-2.35 (m, 1H), 2.03-1.88 (m, 1H), 1.52-1.35 (m, 9H).

Step b. To a solution of NaIO$_4$ (17.0 g, 79.3 mmol) in water (100 mL) was added RuO$_2$—H$_2$O (2.0 g, 13.2 mmol). Then a solution of (2S,4S)-1-tert-butyl 2-methyl 4-(((benzyloxy)carbonyl)-amino)pyrrolidine-1,2-dicarboxylate (10.0 g, 26.4 mmol) in EtOAc (100 mL) was added. The reaction mixture was stirred at rt for 12 h under N$_2$ atmosphere. Upon completion, the reaction mixture was filtered. The filtrate was washed with sat. Na$_2$S$_2$O$_3$ (50 mL), dried and evaporated. The residue was purified by column chromatography (20% EtOAc in PE) to give (2S,4S)-1-tert-butyl 2-methyl 4-(((benzyloxy)carbonyl)amino)-5-oxopyrrolidine-1,2-dicarboxylate (850 mg, 8% yield) as a yellow solid.

$^1$H NMR (400 MHz, CDCl$_3$) δ ppm 7.41-7.30 (m, 5H), 5.13 (s, 2H), 4.53-4.37 (m, 2H), 3.81 (s, 3H), 3.01-2.84 (m, 1H), 1.89-1.77 (m, 1H), 1.51 (s, 9H).

Step c. A solution of (2S,4S)-1-tert-butyl 2-methyl 4-(((benzyloxy)carbonyl)amino)-5-oxo-pyrrolidine-1,2-dicarboxylate (0.8 g, 2.0 mmol) in HCl in 1,4-dioxane (4 M, 24 mL) was stirred at rt for 30 min. The reaction mixture was evaporated to give (2S,4S)-methyl 4-(((benzyloxy)-carbonyl)amino)-5-oxopyrrolidine-2-carboxylate (0.59 g, crude) as a yellow solid.

m/z ES+[M+H]$^+$ 293.0

Step d. A mixture of (2S,4S)-methyl 4-(((benzyloxy)carbonyl)amino)-5-oxopyrrolidine-2-carboxylate (0.59 g, 2.0 mmol) and LiOH monohydrate (254 mg, 6.1 mmol) in MeOH (10 mL) was stirred at rt for 1 h. Upon completion, the reaction mixture was adjusted to pH 4-5 by slow addition of 0.5 M aq. HCl. The resulting solid was collected by filtration. The filtrate was diluted with brine (30 mL) and extracted with EtOAc (30 mL). The organic layer was dried over Na$_2$SO$_4$ and evaporated. The resulting residue was combined with the filtered solid to give (2S,4S)-4-(((benzyloxy)carbonyl)amino)-5-oxopyrrolidine-2-carboxylic acid (0.5 g, 89% yield) as a brown solid.

m/z ES+[M+H]$^+$ 279.1; $^1$H NMR (400 MHz, DMSO-d6) δ ppm 12.85 (s, 1H), 8.14 (s, 1H), 7.52 (d, J=8.8 Hz, 1H), 7.39-7.31 (m, 5H), 5.03 (s, 2H), 4.26-4.14 (m, 1H), 4.12-4.00 (m, 1H), 2.63-2.54 (m, 1H), 1.87-1.74 (m, 1H).

Step e. To a solution of (2S,4S)-4-(((benzyloxy)carbonyl)amino)-5-oxopyrrolidine-2-carboxylic acid (490 mg, 1.8 mmol) and 3-chloro-N-ethyl-4-fluoroaniline (611 mg, 3.2 mmol) in pyridine (20 mL) was added T3P (3.36 g, 5.3 mmol, 50 wt. % in EtOAc). The reaction mixture was stirred at rt for 12 h. Upon completion, the reaction mixture was concentrated under vacuum. The resultant residue was diluted with water (50 mL), extracted with EtOAc (50 mL). The organic layer was dried and evaporated. The residue was purified by prep-HPLC to give benzyl ((3S,5S)-5-((3-chloro-4-fluorophenyl)(ethyl)carbamoyl)-2-oxopyrrolidin-3-yl)carbamate (200 mg, 26% yield) as a white solid.

m/z ES+[M+H]$^+$ 434.0; $^1$H NMR (400 MHz, CDCl$_3$) δ ppm 7.40-7.28 (m, 6H), 7.09 (d, J=8.0 Hz, 1H), 6.84 (s, 1H), 5.84 (d, J=6.8 Hz, 1H), 5.15-4.96 (m, 2H), 4.35-4.21 (m, 1H), 4.15-3.95 (m, 1H), 3.86-3.71 (m, 1H), 3.69-3.52 (m, 1H), 2.49-2.32 (m, 1H), 1.98-1.92 (m, 1H), 1.10 (t, J=7.2 Hz, 3H).

Step a. To a solution of (2S,4S)-1-tert-butyl 2-methyl 4-aminopyrrolidine-1,2-dicarboxylate (CAS Number 171110-72-8; 7.50 g, 26.7 mmol, HCl salt) and Na$_2$CO$_3$ (8.49 g, 80.1 mmol) in 1,4-dioxane (120 mL) and water (60 mL) was added benzyl chloroformate (5.01 g, 29.4 mmol) at 0° C. The reaction mixture was stirred at rt for 12 h. Upon completion, the reaction mixture was evaporated, the residue was diluted with water (80 mL) and extracted with EtOAc Step f. A mixture of benzyl ((3S,5S)-5-((3-chloro-4-fluorophenyl)(ethyl)carbamoyl)-2-oxopyrrolidin-3-yl)carbamate (200 mg, 0.46 mmol), 2-bromo-6-methyl-4-(trifluoromethyl)-pyridine (144 mg, 0.60 mmol), Pd$_2$(dba)$_3$ (42 mg, 0.046 mmol), XantPhos (40 mg, 0.069 mmol) and Cs$_2$CO$_3$ (300 mg, 0.92 mmol) in 1,4-dioxane (10 mL) was stirred at 120° C. for 2 h under N$_2$ atmosphere. Upon completion, the reaction mixture was evaporated and the residue was purified by column chromatography (50% EtOAc in PE) to give benzyl ((3S,5S)-5-((3-chloro-4-fluorophenyl)(ethyl)carbamoyl)-1-(6-methyl-4-(trifluoromethyl)pyridin-2-yl)-2-oxopyrrolidin-3-yl)carbamate (200 mg, 73% yield) as a yellow oil.

m/z ES+[M+H]$^+$ 593.1

Step g. A solution of benzyl ((3S,5S)-5-((3-chloro-4-fluorophenyl)(ethyl)carbamoyl)-1-(6-methyl-4-(trifluoromethyl)pyridin-2-yl)-2-oxopyrrolidin-3-yl)carbamate (200 mg, 0.34 mmol) in HBr (7.45 g, 30.4 mmol, 33 wt. % in acetic acid) was stirred at rt for 1 h. Upon completion, the reaction mixture was poured into sat. aq. NaHCO$_3$ (100 mL) and extracted with EtOAc (100 mL). The organic layer was dried and evaporated. The residue was purified by preparative HPLC to give the title compound (60 mg, 39% yield) as a yellow solid.

m/z ES+[M+H]$^+$ 458.9; $^1$H NMR (400 MHz, CD$_3$OD) δ ppm 8.55 (s, 1H), 7.85 (d, J=3.6 Hz, 1H), 7.58 (s, 1H), 7.51-7.43 (m, 1H), 7.29 (s, 1H), 4.94 (d, J=8.4 Hz, 1H), 3.97-3.80 (m, 2H), 3.67-3.56 (m, 1H), 2.67 (s, 3H), 2.54-2.43 (m, 1H), 1.87-1.72 (m, 1H), 1.15 (t, J=7.2 Hz, 3H).

Example 62

(2S,4S)-4-Acetamido-N-(3-chloro-4-fluorophenyl)-N-ethyl-1-(6-methyl-4-(trifluoromethyl)pyridin-2-yl)-5-oxopyrrolidine-2-carboxamide

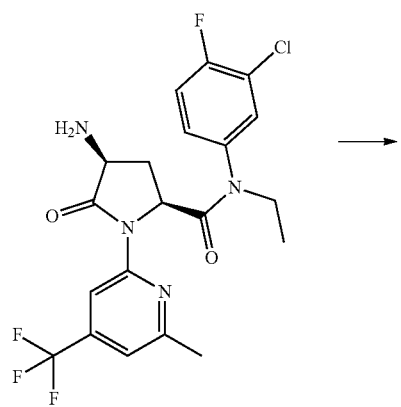

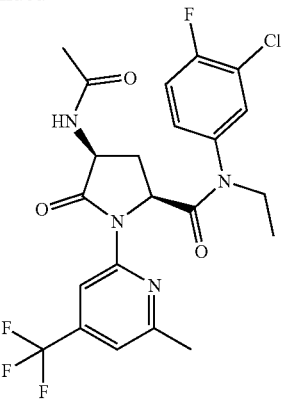

To a solution of Example 61 (10 mg, 0.022 mmol) and TEA (4 mg, 0.044 mmol) in DCM (1 mL) was added acetyl chloride (3 mg, 0.033 mmol). The reaction mixture was stirred at rt for 1 h. Upon completion, the reaction mixture was concentrated under vacuum. The resultant residue was purified by preparative HPLC and dried by lyophilization to give the title compound (6.6 mg, 56% yield) as a yellow solid.

m/z ES+[M+H]$^+$ 501.0; $^1$H NMR (400 MHz, CD$_3$OD) δ ppm 8.52 (s, 1H), 7.85 (d, J=4.8 Hz, 1H), 7.58 (s, 1H), 7.51-7.43 (m, 1H), 7.31 (s, 1H), 4.98 (d, J=8.8 Hz, 1H), 4.80-4.70 (m, 1H), 3.97-3.80 (m, 1H), 3.67-3.56 (m, 1H), 2.67 (s, 3H), 2.54-2.43 (m, 1H), 2.10-2.00 (m, 1H), 1.99 (s, 3H), 1.15 (t, J=7.2 Hz, 3H).

Example 63

(2S,4S)—N-(3-Chloro-4-fluorophenyl)-N-ethyl-1-(6-methyl-4-(trifluoro-methyl)pyridin-2-yl)-4-morpholino-5-oxopyrrolidine-2-carboxamide

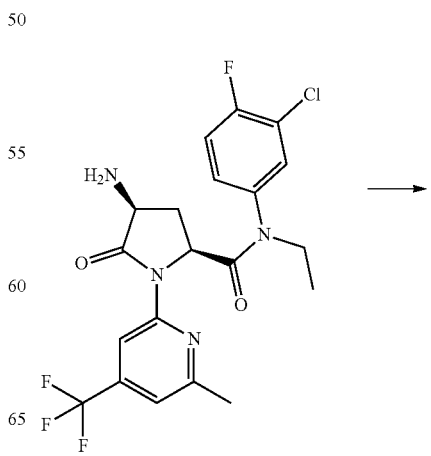

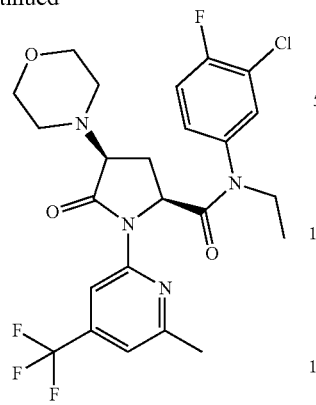

A solution of Example 61 (15 mg, 0.033 mmol), 1-bromo-2-(2-bromoethoxy)ethane (15 mg, 0.065 mmol), NaI (5 mg, 0.033 mmol) and K$_2$CO$_3$ (23 mg, 0.16 mmol) in MeCN (2 mL) was stirred at 80° C. for 3 h. Upon completion, the reaction mixture was filtered and concentrated under vacuum. The residue was purified by preparative HPLC and dried by lyophilization to give the title compound (7.4 mg, 43% yield) as a white solid.

m/z ES+[M+H]$^+$ 529.0; $^1$H NMR (400 MHz, CD$_3$OD) δ ppm 8.54 (s, 1H), 7.86 (d, J=4.4 Hz, 1H), 7.59 (s, 1H), 7.51-7.44 (m, 1H), 7.30 (s, 1H), 4.99-4.92 (m, 1H), 3.97-3.84 (m, 2H), 3.77-3.67 (m, 4H), 3.66-3.55 (m, 1H), 2.93-2.83 (m, 2H), 2.67 (s, 3H), 2.64-2.52 (m, 2H), 2.34-2.24 (m, 1H), 2.20-2.10 (m, 1H), 1.15 (t, J=7.2 Hz, 3H).

Example 64

(2S,4S)—N-(3-Chloro-4-fluorophenyl)-N-ethyl-4-hydroxy-1-(4-methyl-6-(trifluoromethyl)-pyrimidin-2-yl)pyrrolidine-2-carboxamide

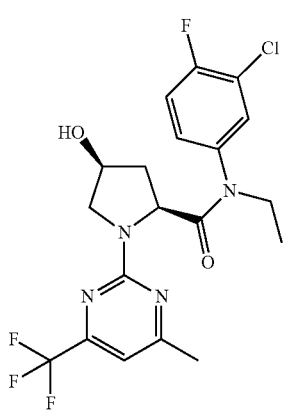 [SMILES: CCN(C(=O)[C@@H]1C[C@H](O)CN1c1nc(C)cc(C(F)(F)F)n1)c1ccc(F)c(Cl)c1]

The title compound was prepared in a similar manner to Example 2, using Intermediate 2 in step a and 2-chloro-4-methyl-6-trifluoromethylpyrimidine (CAS Number 241164-09-0) in step c.

m/z ES+[M+H]$^+$ 447.1; $^1$H NMR (400 MHz, DMSO-d6) δ ppm 7.58 (s, 1H), 7.45-7.38 (m, 1H), 7.36 (s, 1H), 6.92 (s, 1H), 4.29 (s, 1H), 4.20-4.10 (m, 1H), 3.80 (s, 1H), 3.71 (qd, J=7.2, 14.0 Hz, 1H), 3.53-3.42 (m, 2H), 3.35-3.30 (m, 1H), 2.36 (s, 3H), 2.28-2.09 (m, 1H), 1.84-1.75 (m, 1H), 0.98 (t, J=6.8 Hz, 3H).

Example 65

(2S,3S,4S)—N-(3-Chloro-4-fluorophenyl)-3,4-dihydroxy-N-methyl-1-(6-methyl-4-(trifluoromethyl)pyridin-2-yl)-5-oxopyrrolidine-2-carboxamide

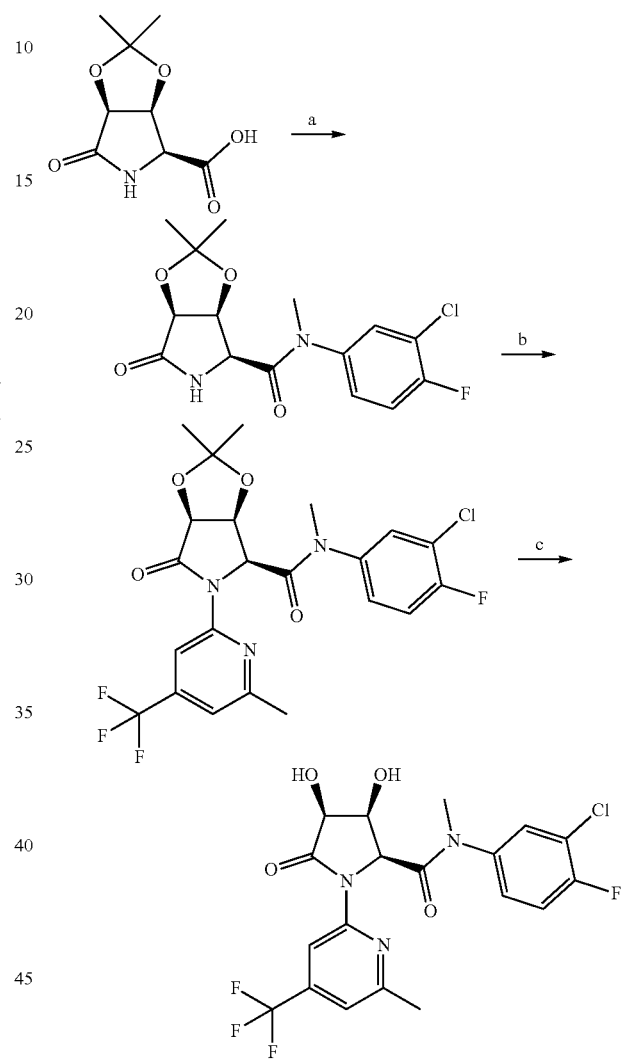

Step a. A mixture of Intermediate 5 (100 mg, 0.45 mmol), 3-chloro-4-fluoro-N-methyl-aniline (CAS Number 77898-24-9; 159 mg, 0.99 mmol), T3P (3.16 g, 4.97 mmol, 50% wt. % in DMF) in pyridine (5 mL) was degassed and purged 3 times with N$_2$, and then stirred at rt for 12 h. The reaction mixture was stirred at 60° C. for another 3 h. The reaction mixture was evaporated and the crude residue purified by reverse phase column chromatography to afford (3aS,4S,6aS)—N-(3-chloro-4-fluorophenyl)-N,2,2-trimethyl-6-oxo-tetrahydro-3aH-[1,3]dioxolo[4,5-c]pyrrole-4-carboxamide (100 mg, 59% yield) as a yellow solid.

$^1$H NMR (400 MHz, CD$_3$OD) δ ppm 7.65 (d, J=5.2 Hz, 1H), 7.43-7.38 (m, 2H), 4.48 (d, J=6.0 Hz, 1H), 4.41 (d, J=5.2 Hz, 1H), 4.06-4.04 (m, 1H), 3.66 (s, 3H), 1.40 (s, 3H), 1.32 (s, 3H).

Step b. A mixture of (3aS,4S,6aS)—N-(3-chloro-4-fluorophenyl)-N,2,2-trimethyl-6-oxo-tetrahydro-3aH-[1,3]dioxolo[4,5-c]pyrrole-4-carboxamide (80 mg, 0.23 mmol), 2-bromo-6-methyl-4-(trifluoromethyl)pyridine (84 mg, 0.35 mmol), XantPhos (27 mg, 0.047 mmol), Pd₂(dba)₃ (21 mg, 0.023 mmol) and Cs₂CO₃ (152 mg, 0.47 mmol) in 1,4-dioxane (4 mL) was degassed and purged 3 times with N₂ and then stirred at 120° C. for 2 h. The reaction mixture was evaporated and the crude residue purified by column chromatography (20% EtOAc in PE) to afford (3aS,4S,6aS)—N-(3-chloro-4-fluorophenyl)-N,2,2-trimethyl-5-(6-methyl-4-(trifluoromethyl)pyridin-2-yl)-6-oxotetrahydro-3aH-[1,3]dioxolo[4,5-c]pyrrole-4-carboxamide (60 mg, 46% yield) as a yellow oil.

$^1$H NMR (400 MHz, CD₃OD) δ ppm 8.47 (s, 1H), 7.77 (d, J=6.4 Hz, 1H), 7.60-7.58 (m, 1H), 7.52-7.47 (m, 1H), 7.32 (s, 1H), 5.20 (d, J=6.8 Hz, 1H), 4.80 (d, J=6.8 Hz, 1H), 4.54 (d, J=6.8 Hz, 1H), 3.25 (s, 3H), 2.64 (s, 3H), 1.47 (s, 3H), 1.41 (s, 3H).

Step c. A solution of (3aS,4S,6aS)—N-(3-chloro-4-fluorophenyl)-N,2,2-trimethyl-5-(6-methyl-4-(trifluoromethyl)pyridin-2-yl)-6-oxotetrahydro-3aH-[1,3]dioxolo[4,5-c]pyrrole-4-carboxamide (60 mg, 0.1 mmol) in HCl in 1,4-dioxane (4 M, 2 mL) was stirred at rt for 6 h, then at 60° C. for 2 h. The reaction mixture was evaporated and the crude residue purified by reverse phase column to afford the title compound (32 mg, 56% yield) as yellow solid.

m/z ES+[M+H]⁺ 462.0; $^1$H NMR (400 MHz, CD₃OD) δ ppm 8.41 (s, 1H), 7.83 (dd, J=6.4 Hz, 2.0 Hz, 1H), 7.64-7.61 (m, 1H), 7.49-7.44 (m, 1H), 7.29 (s, 1H), 5.12 (d, J=5.2 Hz, 1H), 4.26-4.19 (m, 2H), 3.27 (s, 3H), 2.64 (s, 3H).

Examples in Table 5 were prepared by a procedure similar to that described for the synthesis of Example 65.

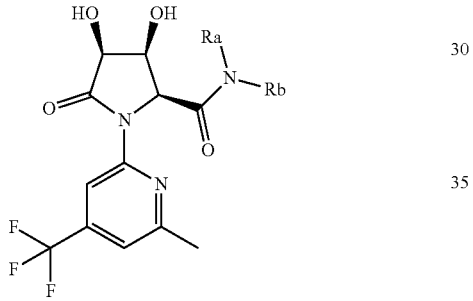

Example 69

(3aS,4S,6aS)—N-(3-Chloro-2,4-difluorophenyl)-N,2,2-trimethyl-5-(6-methyl-4-(trifluoromethyl)-pyridin-2-yl)-6-oxotetrahydro-4H-[1,3]dioxolo[4,5-c]pyrrole-4-carboxamide

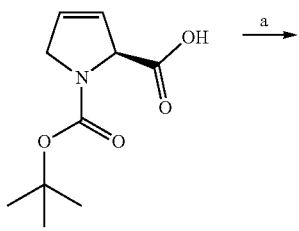

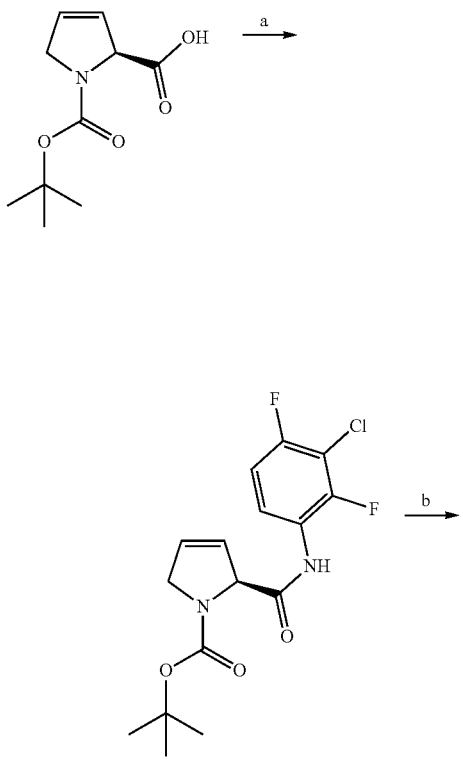

TABLE 5

| Example Number | Ra | Rb | Name | Amine CAS No. | $^1$H NMR (400 MHz) δ ppm | MI |
|---|---|---|---|---|---|---|
| 66 | CH₂CH₃ | ![Cl,F phenyl] | (2S,3S,4S)-N-(3-Chloro-4-fluorophenyl)-N-ethyl-3,4-dihydroxy-1-(6-methyl-4-(trifluoromethyl)pyridin-2-yl)-5-oxopyrrolidine-2-carboxamide | 106847-36-3 | (CD₃OD) 8.42 (s, 1H), 7.85-7.75 (m, 1H), 7.65-7.55 (m, 1H), 7.48 (t, J = 8.8 Hz, 1H), 7.30 (s, 1H), 5.07 (d, J = 5.6 Hz, 1H), 4.25 (d, J = 6.0 Hz, 1H), 4.17-4.14 (m, 1H), 3.95-3.88 (m, 1H), 3.59-3.48 (m, 1H), 2.63 (s, 3H), 1.15 (t, J = 7.2 Hz, 3H) | 476.0 |
| 67 | CH₃ | ![methyl,F phenyl] | (2S,3S,4S)-N-(4-Fluoro-3-methylphenyl)-3,4-dihydroxy-N-methyl-1-(6-methyl-4-(trifluoromethyl)pyridin-2-yl)-5-oxopyrrolidine-2-carboxamide | 77488-82-5 | (DMSO-d6) 8.24 (s, 1H), 7.46-7.31 (m, 4H), 5.52 (d, J = 8.8 Hz, 1H), 5.37 (d, J = 5.6 Hz, 1H), 4.90 (d, J = 5.6 Hz, 1H), 4.22-4.18 (m, 1H), 4.03-3.98 (m, 1H), 3.12 (s, 3H), 2.57 (s, 3H), 2.30 (s, 3H). | 441.9 |
| 68 | CH₃ | ![Cl,F phenyl] | (2S,3S,4S)-N-(3-Chloro-5-fluorophenyl)-3,4-dihydroxy-N-methyl-1-(6-methyl-4-(trifluoromethyl)pyridin-2-yl)-5-oxopyrrolidine-2-carboxamide | 1070892-68-0 | (CD₃OD) 8.42 (s, 1H), 7.60 (br s, 1H), 7.41 (br dd, J = 8.0, 18.4 Hz, 2H), 7.29 (s, 1H), 5.19 (br s, 1H), 4.27 (br s, 2H), 3.30-3.26 (m, 3H), 2.63 (s, 3H) | 462.0 |

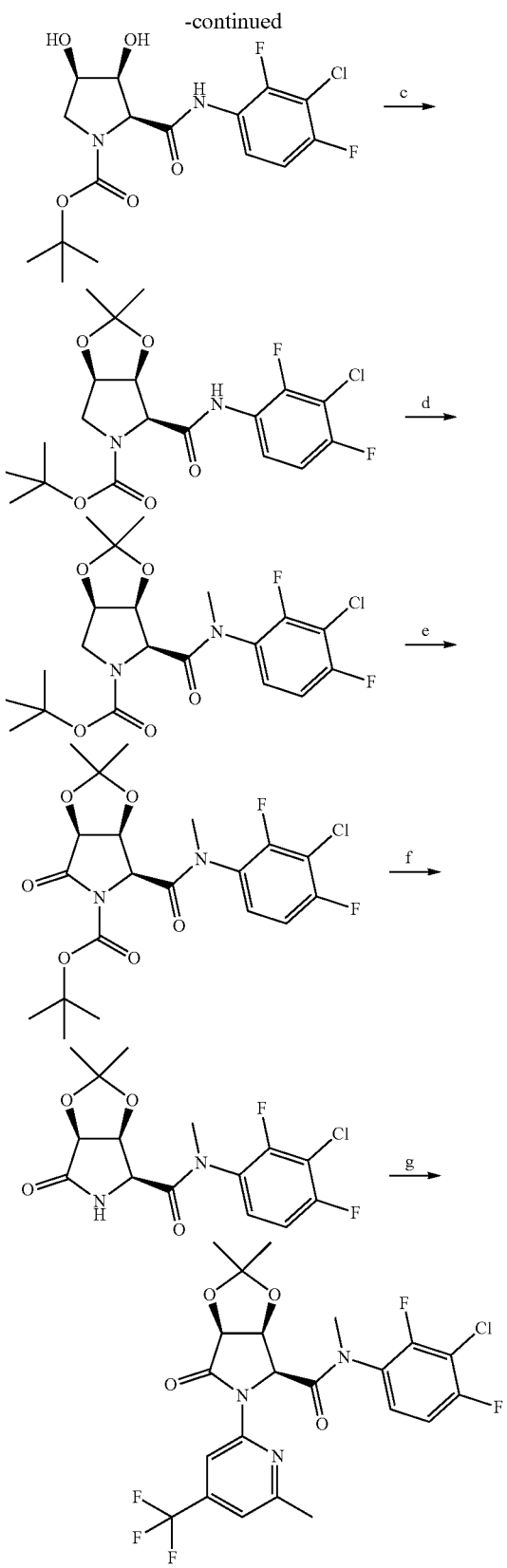

Step a. To a solution of (S)-1-(tert-butoxycarbonyl)-2,5-dihydro-1H-pyrrole-2-carboxylic acid (3 g, 14.1 mmol), 3-chloro-2,4-difluoro-aniline (2.99 g, 18.3 mmol) in pyridine (50 mL) was added T3P (44.8 g, 70.4 mmol, 50 wt. % in EtOAc) and the mixture was stirred at rt for 12 h. Upon completion, the reaction mixture was quenched with aq. NH₄Cl (60 mL), diluted with water (100 mL) and extracted with EtOAc (100 mL×3). The combined organic layers were washed with brine (30 mL×3), dried over Na₂SO₄ and evaporated. The residue was purified by column chromatography (20-30% EtOAc in PE) to give (S)-tert-butyl 2-((3-chloro-2,4-difluorophenyl)carbamoyl)-2,5-dihydro-1H-pyrrole-1-carboxylate (4.8 g, 91% yield) as a colorless solid.

m/z ES+[M+H-Boc]⁺259.0

Step b. To a solution of (S)-tert-butyl 2-((3-chloro-2,4-difluorophenyl)carbamoyl)-2,5-dihydro-1H-pyrrole-1-carboxylate (4.8 g, 13.4 mmol) in MeCN (5 mL), water (5 mL) and tert-butanol (5 mL) was added OsO₄ (340 mg, 1.34 mmol) and NMO (1.88 g, 16.05 mmol). The mixture was stirred at rt for 12 h. Upon completion, the reaction mixture was quenched with aq. Na₂S₂O₃ solution (20 mL), filtered and concentrated. The residue was purified by prep-HPLC to give the minor isomer (2S,3S,4R)-tert-butyl 2-((3-chloro-2,4-difluorophenyl)carbamoyl)-3,4-dihydroxy-pyrrolidine-1-carboxylate (720 mg, 13% yield) as a yellow solid, which was used in the next step.

m/z ES+[M+Na]⁺415.1

Step c. To a solution of (2S,3S,4R)-tert-butyl 2-((3-chloro-2,4-difluorophenyl)carbamoyl)-3,4-dihydroxypyrrolidine-1-carboxylate (720 mg, 1.83 mmol) and 2,2-dimethoxypropane (9.55 g, 91.7 mmol) in acetone (30 mL) was added pyridinium p-toluenesulfonate (553 mg, 2.20 mmol). The mixture was stirred at 60° C. for 3 h. Upon completion, the reaction mixture was filtered and concentrated. The residue was diluted with water (60 mL) and extracted with EtOAc (50 mL×3). The combined organic layers were washed with brine (30 mL×3), dried and evaporated. The residue was purified by column chromatography (20-30% EtOAc in PE) to give (3aS,4S,6aR)-tert-butyl 4-((3-chloro-2,4-difluorophenyl)carbamoyl)-2,2-dimethyl-dihydro-3aH-[1,3]dioxolo[4,5-c]pyrrole-5(4H)-carboxylate (630 mg, 79% yield) as a solid.

Step d. A solution of (3aS,4S,6aR)-tert-butyl 4-((3-chloro-2,4-difluorophenyl)carbamoyl)-2,2-dimethyldihydro-3aH-[1,3]dioxolo[4,5-c]pyrrole-5(4H)-carboxylate (620 mg, 1.43 mmol) in DMF (20 mL) was treated with NaH (86 mg, 2.15 mmol, 60% dispersion in mineral oil) and degassed with N₂ 3 times. The mixture was stirred at 0° C. for 30 min under N₂ atmosphere. Methyl iodide (610 mg, 4.30 mmol) was added slowly and the mixture was stirred at 0° C. for 1.5 h. Upon completion, the reaction mixture was quenched with aq. NH₄Cl (30 mL) and extracted with EtOAc (50 mL×3). The combined organic layers were washed with brine (20 mL×3), dried and evaporated. The residue was purified by column chromatography (0-50% EtOAc in PE) to give (3aS,4S,6aR)-tert-butyl 4-((3-chloro-2,4-difluorophenyl)(methyl)carbamoyl)-2,2-dimethyldihydro-3aH-[1,3]dioxolo[4,5-c]pyrrole-5(4H)-carboxylate (630 mg, 98% yield) as a white solid.

m/z ES+[M+H-Boc]⁺347.2

Step e. A mixture of ruthenium(IV) dioxide hydrate (20 mg, 0.14 mmol) and NaIO₄ (862 mg, 4.03 mmol) in water (20 mL) was degassed with N₂ 3 times and then stirred at rt for 15 min under N₂ atmosphere. A solution of (3aS,4S,6aR)-tert-butyl 4-((3-chloro-2,4-difluorophenyl)(methyl)carbamoyl)-2,2-dimethyldihydro-3aH-[1,3]dioxolo[4,5-c]pyrrole-5(4H)-carboxylate (600 mg, 1.34 mmol) in EtOAc (20 mL) was added and the mixture was stirred at rt for 12 h. On completion, the reaction mixture was quenched with water (30 mL) and extracted with EtOAc (50 mL×3). The organic layers were washed with brine (50 mL×3), dried and evaporated. The residue was purified by prep-HPLC to give (3aS,4S,6aS)-tert-butyl 4-((3-chloro-2,4-difluorophenyl)(methyl)carbamoyl)-2,2-dimethyl-6-oxodihydro-3aH-[1,3]dioxolo[4,5-c]pyrrole-5(4H)-carboxylate (100 mg, 16% yield) as a yellow solid.

Step f. To a solution of (3aS,4S,6aS)-tert-butyl 4-((3-chloro-2,4-difluorophenyl)(methyl)-carbamoyl)-2,2-dimethyl-6-oxodihydro-3aH-[1,3]dioxolo[4,5-c]pyrrole-5(4H)-carboxylate (100 mg, 0.22 mmol) in DCM (10 mL) was added ZnBr$_2$ (245 mg, 1.08 mmol) and the mixture was stirred at rt for 12 h. Upon completion, the reaction mixture was quenched with sat. aq. NaHCO$_3$ (20 mL) at rt, diluted with water (20 mL) and extracted with DCM (50 mL×3). The combined organic layers were washed with brine (20 mL×3), dried over Na$_2$SO$_4$ and evaporated to give (3aS,4S,6aS)—N-(3-chloro-2,4-difluorophenyl)-N,2,2-trimethyl-6-oxo-tetrahydro-3aH-[1,3]dioxolo[4,5-c]pyrrole-4-carboxamide (70 mg, 89% yield) as a yellow solid which was used directly in the next step.

Step g. A mixture of (3aS,4S,6aS)—N-(3-chloro-2,4-difluorophenyl)-N,2,2-trimethyl-6-oxo-tetrahydro-3aH-[1,3]dioxolo[4,5-c]pyrrole-4-carboxamide (70 mg, 0.20 mmol), 2-bromo-6-methyl-4-(trifluoromethyl)pyridine (60 mg, 0.25 mmol), Pd$_2$(dba)$_3$ (18 mg, 0.019 mmol), XantPhos (22 mg, 0.039 mmol) and Cs$_2$CO$_3$ (190 mg, 0.58 mmol) in dioxane (3 mL) was degassed with N$_2$ 3 times, and then stirred at 100° C. for 2 h. Upon completion, the reaction mixture was filtered and concentrated. The obtained residue was purified by prep-HPLC to give the title compound (60 mg, 60% yield) as a yellow solid.

m/z ES+[M+H]$^+$ 520.1; $^1$H NMR (400 MHz, DMSO-d6) δ ppm 8.40-8.25 (m, 1H), 7.85-7.54 (m, 2H), 7.51-7.44 (m, 1H), 5.13-4.97 (m, 1H), 4.84-4.74 (m, 1H), 4.51-4.40 (m, 1H), 3.12 (s, 3H), 2.63 (s, 3H), 1.40-1.35 (m, 3H) 1.34-1.22 (m, 3H).

Example 70

(2S,3S,4S)—N-(3-Chloro-2,4-difluorophenyl)-3,4-dihydroxy-N-methyl-1-(6-methyl-4-(trifluoromethyl)pyridin-2-yl)-5-oxopyrrolidine-2-carboxamide

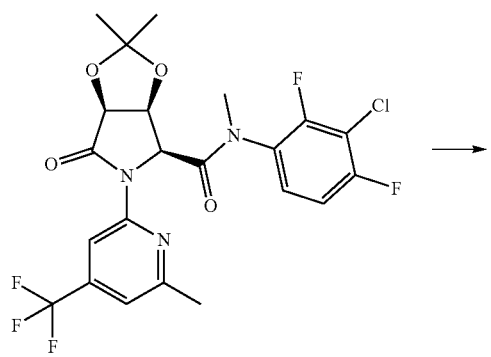

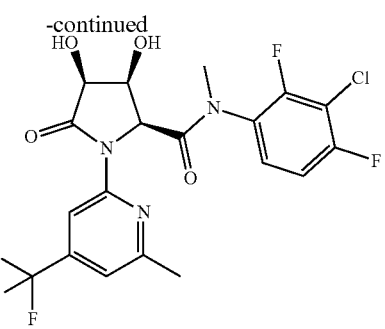

To a solution of (3aS,4S,6aS)—N-(3-chloro-2,4-difluorophenyl)-N,2,2-trimethyl-5-(6-methyl-4-(trifluoromethyl)pyridin-2-yl)-6-oxotetrahydro-3aH-[1,3]dioxolo[4,5-c]pyrrole-4-carboxamide (60 mg, 0.12 mmol) in MeCN (5 mL) was added Amberlyst®-15 (200 mg) and the mixture was stirred at 80° C. for 12 h. Upon completion, the reaction mixture was filtered and concentrated. The residue was purified by prep-HPLC to give the title compound (13 mg, 23% yield) as a white solid.

m/z ES+[M+H]$^+$ 480.0; $^1$H NMR (400 MHz, DMSO-d6) δ ppm 8.26-8.15 (m, 1H), 7.77-7.63 (m, 1H), 7.60-7.50 (m, 1H), 7.46-7.34 (m, 1H), 4.89-4.47 (m, 1H), 4.30-4.20 (m, 1H), 4.02-3.91 (m, 1H), 3.11 (s, 3H), 2.60 (s, 3H).

Example 71

(2S,3R,4R)—N-(3-Chloro-2,4-difluorophenyl)-3,4-dihydroxy-N-methyl-1-(6-methyl-4-(trifluoromethyl)pyridin-2-yl)-5-oxopyrrolidine-2-carboxamide

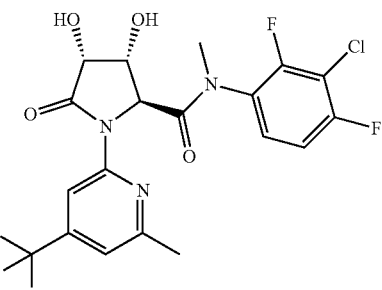

The title compound was prepared in a similar manner to Example 70, using (2S,3R,4S)-tert-butyl 2-((3-chloro-2,4-difluorophenyl)carbamoyl)-3,4-dihydroxy-pyrrolidine-1-carboxylate, the major isomer isolated in step b of the synthesis of Example 69.

m/z ES+[M+H]$^+$ 480.0; $^1$H NMR (400 MHz, CD$_3$OD) δ ppm 8.59-8.54 (m, 1H), 7.92-7.68 (m, 1H), 7.45-7.18 (m, 2H), 4.94 and 4.87 (s x2, 1H), 4.60-4.54 (m, 1H), 4.52 and 4.27 (d x2, J=5.2 Hz, 1H), 3.30 and 3.29 (s x2, 3H), 2.67 and 2.56 (s x2, 3H).

Example 72

(2S,3R,4R)—N-(3-Chloro-4-fluorophenyl)-3,4-dihydroxy-N-methyl-1-(6-methyl-4-(trifluoromethyl)pyridin-2-yl)-5-oxopyrrolidine-2-carboxamide

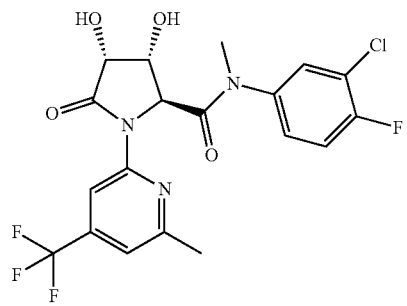 [SMILES: Cc1cc(C(F)(F)F)cc(N2C(=O)[C@H](O)[C@H](O)[C@H]2C(=O)N(C)c2ccc(F)c(Cl)c2)n1]

The title compound was prepared in a similar manner to Example 71, using 3-chloro-4-fluoroaniline (CAS Number 367-21-5).

m/z ES+[M+H]$^+$ 462.1; $^1$H NMR (400 MHz, CD$_3$OD) δ ppm 8.58 (s, 1H), 7.91 (dd, J=6.4, 2.4 Hz, 1H), 7.70-7.63 (m, 1H), 7.50 (t, J=8.8 Hz, 1H), 7.31 (s, 1H), 4.96 (s, 1H), 4.55 (d, J=5.2 Hz, 1H), 4.46 (d, J=5.2 Hz, 1H), 3.32 (s, 3H), 2.67 (s, 3H).

Example 73

(2S,3S,4S)—N-(5-Chloro-2,4-difluorophenyl)-3,4-dihydroxy-N-methyl-1-(6-methyl-4-(trifluoromethyl)pyridin-2-yl)-5-oxopyrrolidine-2-carboxamide

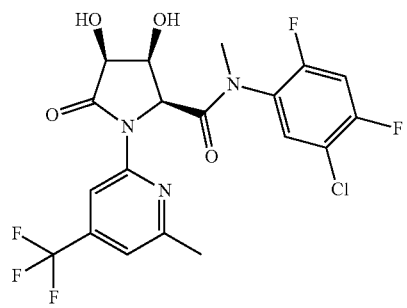 [SMILES: Cc1cc(C(F)(F)F)cc(N2C(=O)[C@@H](O)[C@@H](O)[C@H]2C(=O)N(C)c2cc(Cl)c(F)cc2F)n1]

The title compound was prepared in a similar manner to Example 70, using 5-chloro-2,4-difluoroaniline (CAS Number 348-65-2).

m/z ES+[M+H]$^+$ 480.2; $^1$H NMR (400 MHz, CD$_3$OD) δ ppm 8.44-8.35 (m, 1H), 8.11-7.84 (m, 1H), 7.57-7.45 (m, 1H), 7.35-7.17 (m, 1H), 5.19 and 5.03 (d x2, J=5.4 Hz, 1H), 4.28 (dd, J=6.8 Hz, 1H), 4.24-4.16 (m, 1H), 3.26-3.21 (m, 3H), 2.67 and 2.53 (s x2, 3H).

Example 74

(2S,4S)—N-(3-Chloro-4-fluorophenyl)-4-hydroxy-N-methyl-1-(6-methyl-4-(trifluoromethyl)-pyridin-2-yl)-5-oxopyrrolidine-2-carboxamide

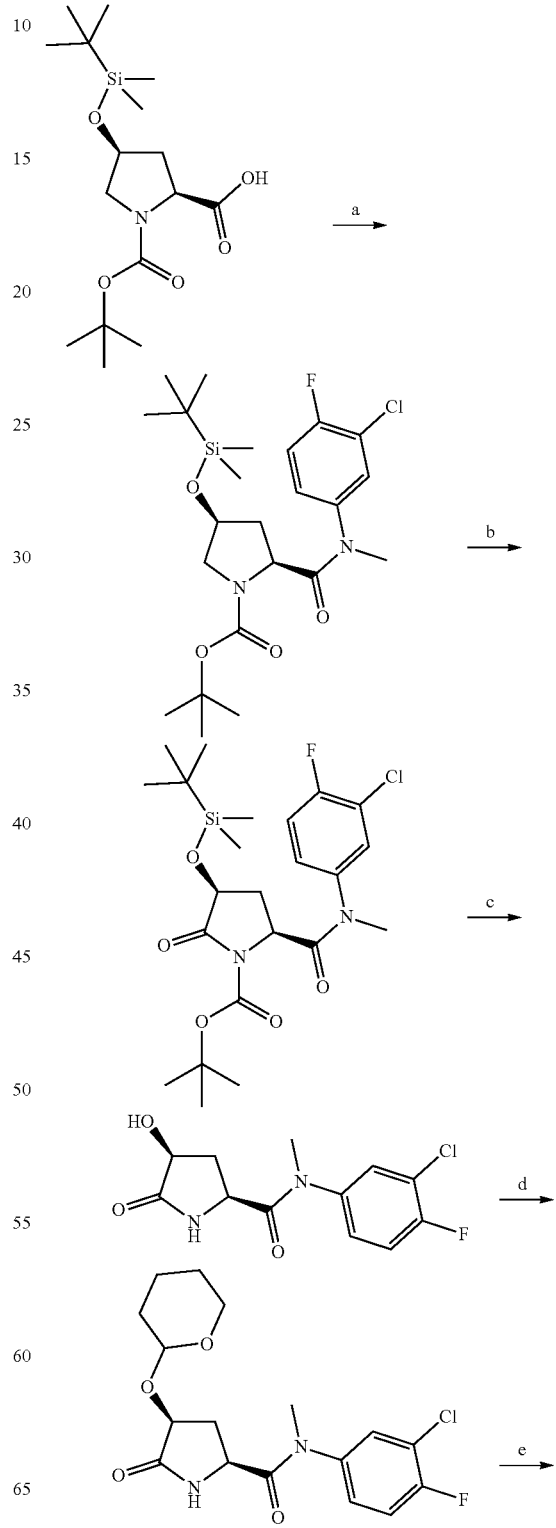

-continued

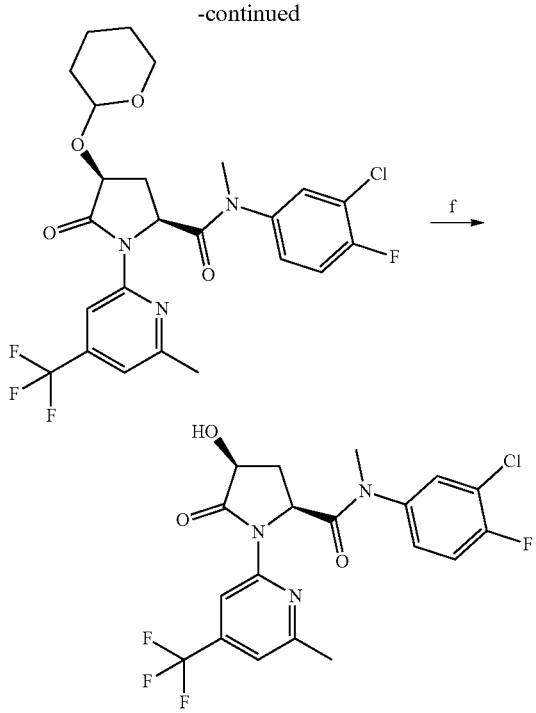

Step a. To a solution of (2S,4S)-1-(tert-butoxycarbonyl)-4-((tert-butyldimethylsilyl)oxy)-pyrrolidine-2-carboxylic acid (2.0 g, 5.79 mmol) and 3-chloro-4-fluoro-N-methylaniline (1.39 g, 8.68 mmol) in pyridine (21.8 g, 275 mmol) was added T3P (11.1 g, 17.4 mmol, 50 wt. % in EtOAc). The mixture was stirred at rt for 12 h. Upon completion, the mixture was quenched with water (10 mL) and extracted with EtOAc (10 mL×3). The combined organic layers were washed with brine (10 mL×3), dried over $Na_2SO_4$ and evaporated. The residue was purified by column chromatography (5-25% EtOAc in PE) to give (2S,4S)-tert-butyl 4-((tert-butyl-dimethylsilyl)oxy)-2-((3-chloro-4-fluorophenyl)(methyl)carbamoyl)-pyrrolidine-1-carboxylate (900 mg, 32% yield) as a colorless oil.

Step b. To a solution of $NaIO_4$ (1.19 g, 5.54 mmol) in water (10 mL) was added $RuCl_3$ (192 mg, 0.92 mmol) at rt under $N_2$ atmosphere. The mixture was stirred for 15 min and then treated with a solution of (2S,4S)-tert-butyl 4-((tert-butyldimethylsilyl)oxy)-2-((3-chloro-4-fluorophenyl)(methyl)carbamoyl)pyrrolidine-1-carboxylate (900 mg, 1.85 mmol) in EtOAc (10 mL) and the mixture was stirred for a further 3 h. Upon completion, the mixture was quenched with water (10 mL) and extracted with EtOAc (10 mL×3). The combined organic layers were washed with brine (10 mL×3), dried and evaporated. The residue was purified by column chromatography (20-30% EtOAc in PE) to give (3S,5S)-tert-butyl 3-((tert-butyl-dimethylsilyl)oxy)-5-((3-chloro-4-fluorophenyl)(methyl)carbamoyl)-2-oxopyrrolidine-1-carboxylate (250 mg, 26% yield) as a yellow solid.

Step c. A mixture of (3S,5S)-tert-butyl 3-((tert-butyldimethylsilyl)oxy)-5-((3-chloro-4-fluoro-phenyl)(methyl)carbamoyl)-2-oxopyrrolidine-1-carboxylate (200 mg, 0.40 mmol) in HCl/dioxane (4 M, 2.5 mL) was stirred at rt for 30 min. Upon completion, the mixture was concentrated to give (2S,4S)—N-(3-chloro-4-fluorophenyl)-4-hydroxy-N-methyl-5-oxo-pyrrolidine-2-carboxamide (120 mg, crude) as a yellow oil, which was used in the next step without further purification.

Step d. To a solution of (2S,4S)—N-(3-chloro-4-fluorophenyl)-4-hydroxy-N-methyl-5-oxo-pyrrolidine-2-carboxamide (100 mg, 0.35 mmol) in DCM (1 mL) was added dihydropyran (59 mg, 0.70 mmol) and p-toluenesulfonic acid (6 mg, 0.035 mmol). The mixture was stirred at rt for 1 h. Upon completion, the mixture was concentrated and purified by column chromatography (50% EtOAc in PE) to give (2S,4S)—N-(3-chloro-4-fluorophenyl)-N-methyl-5-oxo-4-((tetrahydro-2H-pyran-2-yl)oxy)pyrrolidine-2-carboxamide (60 mg, 46% yield over two steps) as a yellow solid.

Step e. To a solution of (2S,4S)—N-(3-chloro-4-fluorophenyl)-N-methyl-5-oxo-4-((tetrahydro-2H-pyran-2-yl)oxy)pyrrolidine-2-carboxamide (60 mg, 0.16 mmol) in dioxane (1 mL) was added 2-bromo-6-methyl-4-(trifluoromethyl)pyridine (58 mg, 0.24 mmol), $Pd(dba)_2$ (9.3 mg, 0.016 mmol), XantPhos (14 mg, 0.024 mmol) and $Cs_2CO_3$ (158 mg, 0.49 mmol). The mixture was degassed with $N_2$ three times, then stirred at 120° C. for 2 h. Upon completion, the mixture was cooled, quenched with water (2 mL) and extracted with EtOAc (2 mL×3). The combined organic layers were washed with brine (2 mL×3), dried and evaporated. The residue was purified by prep-TLC (25% EtOAc in PE) to give (2S,4S)—N-(3-chloro-4-fluoro-phenyl)-N-methyl-1-(6-methyl-4-(trifluoromethyl)pyridin-2-yl)-5-oxo-4-((tetrahydro-2H-pyran-2-yl)oxy)pyrrolidine-2-carboxamide (60 mg, 32% yield) as a yellow solid.

Step f. To a solution of (2S,4S)—N-(3-chloro-4-fluorophenyl)-N-methyl-1-(6-methyl-4-(trifluoromethyl)pyridin-2-yl)-5-oxo-4-((tetrahydro-2H-pyran-2-yl)oxy)pyrrolidine-2-carboxamide (60 mg, 0.11 mmol) in EtOH (1 mL) was added p-toluenesulfonic acid (19 mg, 0.11 mmol). The mixture was stirred at 50° C. for 1 h. Upon completion, the mixture was concentrated and purified by prep-HPLC to give the title compound (11 mg, 19% yield) as a yellow solid.

m/z ES+[M+H]$^+$ 446.0; $^1$H NMR (400 MHz, DMSO-d6) δ ppm 8.35 (s, 1H), 7.89 (d, J=7.2 Hz, 1H), 7.63 (d, J=7.2 Hz, 2H), 7.44 (s, 1H), 5.93 (s, 1H), 4.66 (t, J=8.0 Hz, 1H), 4.32 (t, J=9.2 Hz, 1H), 3.16 (s, 3H), 2.62 (s, 3H), 2.42-2.36 (m, 1H), 1.73-1.67 (m, 1H).

Example 75

(2S,4S)—N-(3-Chloro-4-fluorophenyl)-N-ethyl-4-hydroxy-1-(6-methyl-4-(trifluoromethyl)pyridin-2-yl)-5-oxopyrrolidine-2-carboxamide

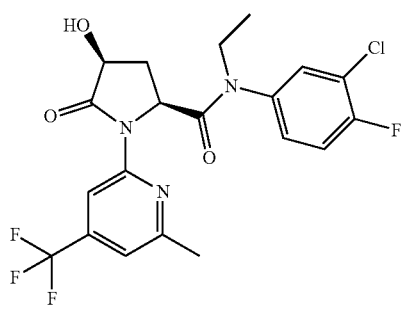 [SMILES: CCN(C(=O)[C@@H]1C[C@H](O)C(=O)N1c1cc(C(F)(F)F)cc(C)n1)c1ccc(F)c(Cl)c1]

The title compound was prepared in a similar manner to Example 74.

m/z ES+[M+H]$^+$ 460.1; $^1$H NMR (400 MHz, CD$_3$OD) δ ppm 8.49 (s, 1H), 7.84 (s, 1H), 7.65-7.60 (m, 1H), 7.50-7.45

(m, 1H), 7.31 (s, 1H), 4.79-4.75 (m, 1H), 4.36 (t, J=9.2 Hz, 1H), 3.97-3.85 (m, 1H), 3.60-3.52 (m, 1H), 2.67 (s, 3H), 2.55-2.49 (m, 1H), 1.88-1.78 (m, 1H), 1.15 (t, J=7.2 Hz, 3H).

Example 76

(2S,4R)-4-((Benzyloxy)methyl)-N-(3-chloro-4-fluorophenyl)-N-methyl-1-(6-methyl-4-(trifluoromethyl)pyridin-2-yl)-5-oxopyrrolidine-2-carboxamide

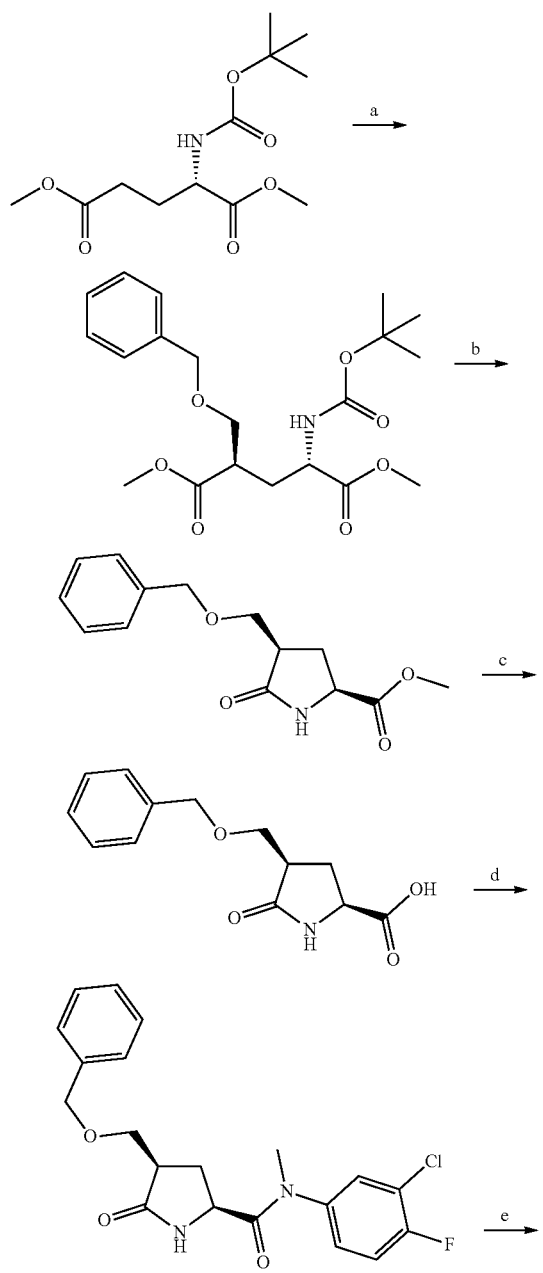

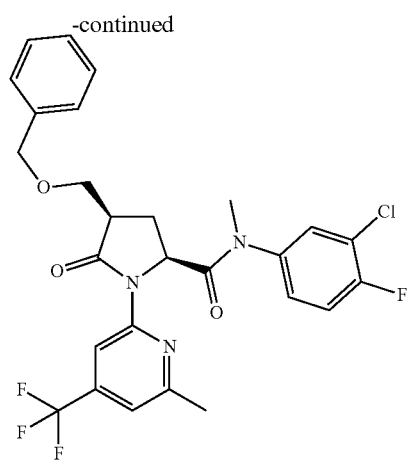

Step a. To a solution of dimethyl (2S)-2-(tert-butoxycarbonylamino)pentanedioate (5 g, 18.1 mmol) in THF (50 mL) was added LiHMDS (1 M, 36.3 mL) dropwise at −78° C. The mixture was stirred at −78° C. for 30 min under N₂ atmosphere. Chloromethoxymethylbenzene (5.69 g, 36.3 mmol) was added dropwise and the mixture was stirred at −78° C. for 3 h. Upon completion, the reaction mixture was quenched with sat. aq. NH₄Cl (50 mL) at −78° C., diluted with water (50 mL) and extracted with EtOAc (50 mL×3). The combined organic layers were washed with brine (50 mL×2), dried and evaporated. The residue was purified by column chromatography (5-30% EtOAc in PE) to give dimethyl (2R,4S)-2-(benzyloxy-methyl)-4-(tert-butoxycarbonylamino)pentanedioate (4.2 g, 58% yield) as a colorless oil.

Step b. A solution of dimethyl (2R,4S)-2-(benzyloxymethyl)-4-(tert-butoxycarbonylamino)-pentanedioate (2.20 g, 5.56 mmol) in TFA (20 mL) and DCM (20 mL) was stirred at rt for 1 h. On completion, the reaction was concentrated, diluted with sat. aq. NaHCO₃ (50 mL) and extracted with EtOAc (50 mL×3). The combined organic layers were washed with brine (50 mL×2), dried and evaporated. The residue was diluted in toluene (20 mL) and heated at 120° C. for 12 h. Upon completion, the reaction was concentrated and purified by column chromatography (0-25% EtOAc in PE) to give methyl (2S,4R)-4-(benzyloxymethyl)-5-oxopyrrolidine-2-carboxylate (400 mg, 37% yield) as a colorless oil.

m/z ES+[M+H]⁺ 264.0

Step c. To a solution of methyl (2S,4R)-4-(benzyloxymethyl)-5-oxo-pyrrolidine-2-carboxylate (400 mg, 1.52 mmol) in MeOH (4 mL) and water (0.5 mL) was added LiOH monohydrate (191 mg, 4.56 mmol). The mixture was stirred at rt for 5 h. On completion, the reaction mixture was concentrated. The residue was diluted with water (10 mL) and adjusted to pH 2 with 2 M HCl, then extracted with EtOAc (20 mL×3). The combined organic layers were washed with brine (20 mL×2), dried over Na₂SO₄ and evaporated to give (2S,4R)-4-(benzyloxymethyl)-5-oxopyrrolidine-2-carboxylic acid (300 mg, 98% yield) as a colorless oil.

m/z ES+[M+H]⁺ 250.1

Step d. To a solution of (2S,4R)-4-(benzyloxymethyl)-5-oxo-pyrrolidine-2-carboxylic acid (620 mg, 2.49 mmol) and 3-chloro-4-fluoro-N-methyl-aniline (476 mg, 2.98 mmol) in pyridine (10 mL) was added T3P (4.75 g, 7.46 mmol, 50 wt. % in EtOAc). The mixture was stirred at rt for 12 h. On completion, the reaction mixture was concentrated. The residue was diluted with sat. aq. NH₄Cl (20 mL) and extracted with EtOAc (20 mL×3). The combined organic layers were washed with brine (30 mL×2), dried and evaporated. The residue was purified by column chromatography (0-20% EtOAc in PE) to give (2S,4R)-4-(benzyloxymethyl)-N-(3-chloro-4-fluoro-phenyl)-N-methyl-5-oxo-pyrrolidine-2-carboxamide (680 mg, 70% yield) as a colorless oil.

m/z ES+[M+H]⁺ 391.0

Step e. A mixture of (2S,4R)-4-(benzyloxymethyl)-N-(3-chloro-4-fluoro-phenyl)-N-methyl-5-oxo-pyrrolidine-2-carboxamide (200 mg, 0.51 mmol), 2-bromo-6-methyl-4-(trifluoromethyl)-pyridine (147 mg, 0.61 mmol), Pd₂(dba)₃ (47 mg, 0.051 mmol), XantPhos (59 mg, 0.10 mmol) and Cs₂CO₃ (333 mg, 1.02 mmol) in dioxane (10 mL) was degassed with N₂ 3 times and then stirred at 80° C. for 1 h. On completion, the reaction was concentrated and purified by column chromatography (20-50% EtOAc in PE) to give the title compound (180 mg, 61% yield) as a colorless oil.

m/z ES+[M+H]⁺ 550.1; ¹H NMR (400 MHz, DMSO-d6) δ ppm 8.34 (s, 1H), 7.94-7.85 (m, 1H), 7.63 (d, J=7.2 Hz, 2H), 7.43 (s, 1H), 7.40-7.30 (m, 5H), 4.88-4.74 (m, 1H), 4.52 (s, 2H), 3.74-3.63 (m, 3H), 3.17 (s, 3H), 3.05-2.94 (m, 1H), 2.62 (s, 3H), 2.29-2.16 (m, 1H), 2.00-1.90 (m, 1H).

Example 77

(2S,4R)—N-(3-Chloro-4-fluorophenyl)-4-(hydroxymethyl)-N-methyl-1-(6-methyl-4-(trifluoromethyl)pyridin-2-yl)-5-oxopyrrolidine-2-carboxamide

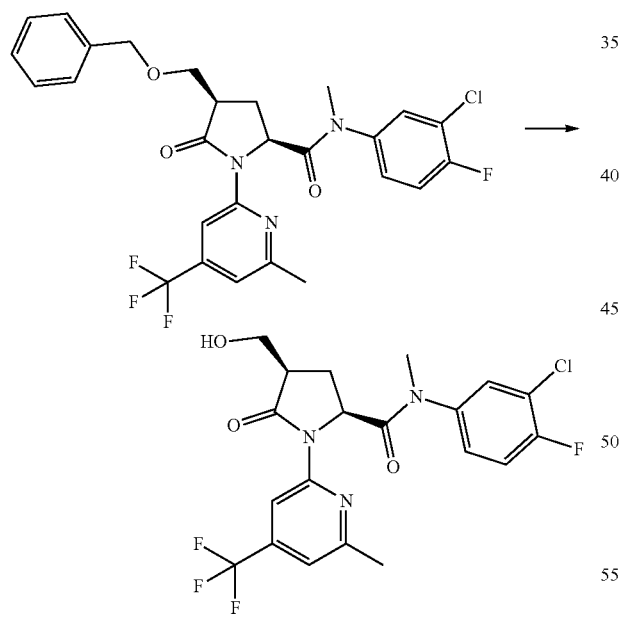

To a solution of Example 76 (160 mg, 0.28 mmol) in DCM (16 mL) was added BCl₃ (1 M, 5.59 mL) dropwise at 0° C. The mixture was stirred at 0° C. for 5 min. Upon completion, the reaction mixture was quenched with ice water (5 mL) at 0° C. and adjusted to pH 9 with 5% NaOH solution. The aqueous was extracted into DCM (10 mL×3), dried over Na₂SO₄ and evaporated. The residue was purified by prep-HPLC to give the title compound (80 mg, 61% yield) as a white solid.

m/z ES+[M+H]⁺ 460.0; ¹H NMR (400 MHz, DMSO-d6) δ ppm 8.35 (s, 1H), 7.87 (dd, J=2.0, 6.8 Hz, 1H), 7.67-7.54 (m, 2H), 7.41 (s, 1H), 4.89-4.74 (m, 2H), 3.64 (d, J=4.8 Hz, 2H), 3.17 (s, 3H), 2.86-2.73 (m, 1H), 2.61 (s, 3H), 2.20-2.10 (m, 1H), 2.05-1.90 (m, 1H).

Example 78

(2R,4S)—N-(3-Chloro-4-fluorophenyl)-4-((dimethylamino)methyl)-N-methyl-1-(6-methyl-4-(trifluoromethyl)pyridin-2-yl)-5-oxopyrrolidine-2-carboxamide

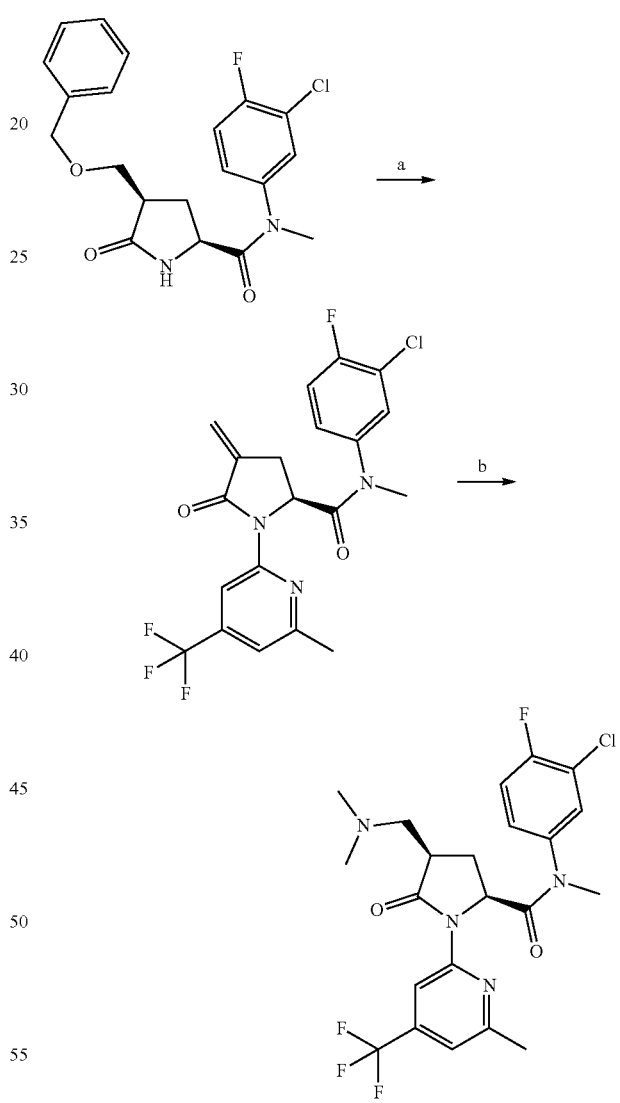

Step a. A solution of (2S,4R)-4-(benzyloxymethyl)-N-(3-chloro-4-fluoro-phenyl)-N-methyl-5-oxo-pyrrolidine-2-carboxamide (300 mg, 0.77 mmol), 2-bromo-6-methyl-4-(trifluoromethyl)-pyridine (184 mg, 0.77 mmol), Pd₂(dba)₃ (70 mg, 0.077 mmol), Cs₂CO₃ (750 mg, 2.30 mmol) and XantPhos (89 mg, 0.15 mmol) in dioxane (5 mL) was stirred at 100° C. for 1 h. Upon completion, the reaction mixture was quenched with water (10 mL) and extracted with EtOAc (10 mL×3). The combined organic layers were washed with brine (10 mL×3), dried and evaporated. The residue was purified by column chromatography (10-50% EtOAc in PE) to give (2S)—N-(3-chloro-4-fluoro-phenyl)-N-methyl-4-methylene-1-[6-methyl-4-(trifluoromethyl)-2-pyridyl]-5-oxopyrrolidine-2 carboxamide (70 mg, 17% yield) as a solid.

Step b. To a solution of (2S)—N-(3-chloro-4-fluoro-phenyl)-N-methyl-4-methylene-1-[6-methyl-4-(trifluoromethyl)-2-pyridyl]-5-oxo-pyrrolidine-2-carboxamide (50 mg, 0.11 mmol) in MeOH (10 mL) was added TEA (115 mg, 1.13 mmol) and dimethylamine (92 mg, 1.13 mmol, HCl salt). The mixture was stirred at 60° C. for 3 h. On completion, the reaction was concentrated. The residue was purified by prep-HPLC to give the title compound as the minor isomer (19 mg, 34% yield) as a white solid.

m/z ES+[M+H]$^+$ 487.1; $^1$H NMR (400 MHz, CD$_3$OD) δ ppm 8.48 (s, 1H), 7.89-7.82 (m, 1H), 7.64-7.56 (m, 1H), 7.50-7.42 (m, 1H), 7.29 (s, 1H), 5.00-4.93 (m, 1H), 3.27 (s, 3H), 2.98-2.88 (m, 1H), 2.76-2.69 (m, 2H), 2.66 (s, 3H), 2.38-2.32 (m, 1H), 2.29 (s, 6H), 2.00-1.89 (m, 1H).

Example 79

(2R,4R)—N-(3-Chloro-4-fluorophenyl)-4-((dimethylamino)methyl)-N-methyl-1-(6-methyl-4-(trifluoromethyl)pyridin-2-yl)-5-oxopyrrolidine-2-carboxamide

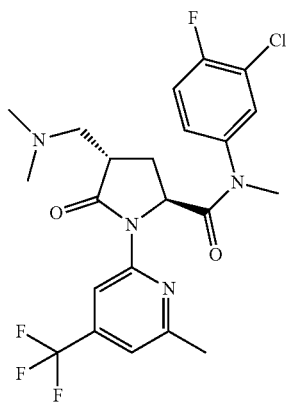

The title compound was prepared according to Example 78 and isolation of the major isomer in the final step.

m/z ES+[M+H]$^+$ 487.2; $^1$H NMR (400 MHz, CD$_3$OD) δ ppm 8.52 (s, 1H), 7.89-7.84 (m, 1H), 7.65-7.57 (m, 1H), 7.50-7.43 (m, 1H), 7.27 (s, 1H), 5.06-4.99 (m, 1H), 3.29 (s, 3H), 3.16-3.03 (m, 1H), 2.81 (dd, J=4.0, 12.4 Hz, 1H), 2.65 (s, 3H), 2.54-2.39 (m, 2H), 2.28 (s, 6H), 1.95 (td, J=10.4, 13.2 Hz, 1H).

Example 80

(2S,3R)—N-(3-Chloro-4-fluorophenyl)-3-hydroxy-N-methyl-1-(6-methyl-4-(trifluoromethyl)-pyridin-2-yl)-5-oxopyrrolidine-2-carboxamide

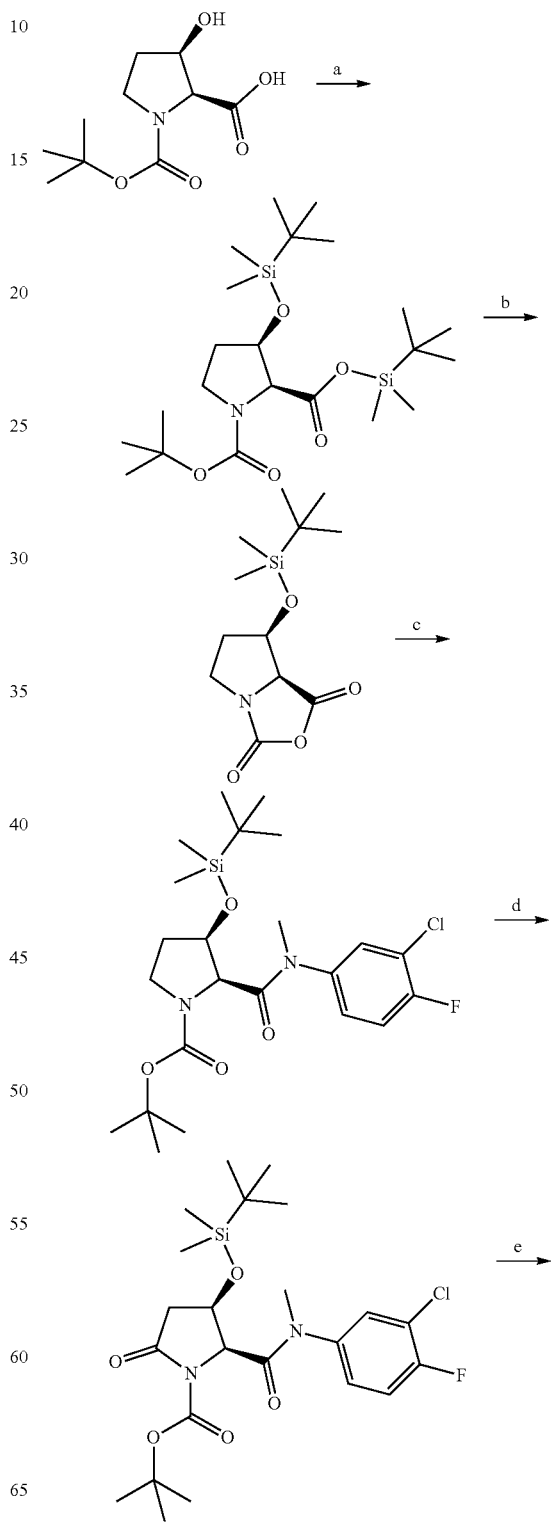

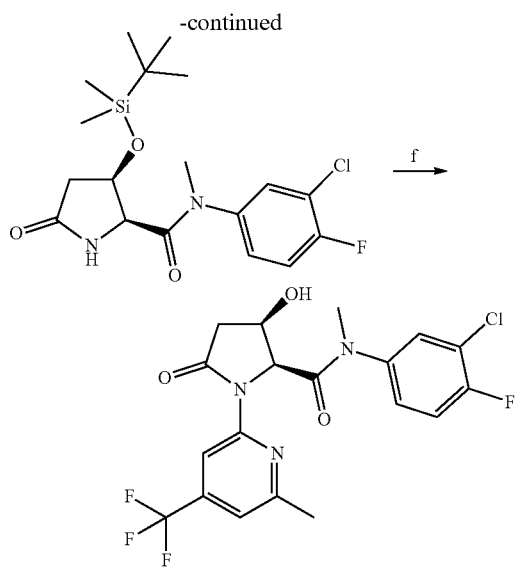

Step a. DMF (1.9 mL) was added to (2S,3R)-1-(tert-butoxycarbonyl)-3-hydroxypyrrolidine-2-carboxylic acid (1.85 g, 8.0 mmol), imidazole (2.23 g, 32.8 mmol) and tert-butyl-dimethylsilyl chloride (2.53 g, 16.8 mmol) and the mixture stirred for 18 h. The mixture was diluted with water and extracted with cyclohexane (×2) and the combined organics washed with sat. aq. NaHCO$_3$, dried and evaporated to give 1-(tert-butyl) 2-(tert-butyldimethylsilyl) (2S,3R)-3-((tert-butyldimethylsilyl)oxy)pyrrolidine-1,2-dicarboxylate, (3.55 g, 96%).

$^1$H NMR (400 MHz, CDCl$_3$) δ ppm 4.52-4.35 (m, 1H), 4.23-4.05 (m, 1H), 3.63-3.44 (m, 1H), 3.30-3.15 (m, 1H), 2.02-1.89 (m, 2H), 1.35-1.32 (m, 9H), 0.89-0.82 (m, 9H), 0.80-0.77 (m, 9H), 0.23-0.14 (m, 6H), 0.02--0.02 (m, 6H).

Step b. To 1-(tert-butyl) 2-(tert-butyldimethylsilyl) (2S,3R)-3-((tert-butyldimethylsilyl)oxy)-pyrrolidine-1,2-dicarboxylate (308 mg, 0.67 mmol) in DCM (3 mL) was added DMF (0.01 mL, 0.129 mmol) and the mixture cooled to 0° C. Oxalyl chloride (0.07 mL, 0.804 mmol) was added and the resultant effervescence subsided within 5 min. Further DMF (0.01 mL, 0.129 mmol) was added and the mixture warmed to rt and stirred for 10 min. The mixture was diluted with THF (5 mL) and then evaporated. The residue was dissolved in THF (5 mL) and evaporated a second time to give (7R,7aS)-7-((tert-butyldimethylsilyl)oxy)tetrahydro-1H,3H-pyrrolo[1,2-c]oxazole-1,3-dione (176 mg, 97%) as a colourless waxy solid.

$^1$H NMR (400 MHz, CDCl$_3$) δ ppm 4.47 (td, J=2.9, 1.2 Hz, 1H), 4.20 (d, J=2.8 Hz, 1H), 3.77 (td, J=10.4, 7.9 Hz, 1H), 3.35 (ddd, J=10.9, 8.4, 2.7 Hz, 1H), 2.10-1.99 (m, 2H), 0.76 (s, 9H), 0.01 (d, J=4.3 Hz, 6H). $^{13}$C NMR (101 MHz, CDCl$_3$) δ ppm 166.00, 156.30, 71.14, 70.76, 44.90, 36.44, 25.36, 17.69, -4.75, -5.34.

Step c. To 3-chloro-4-fluoro-N-methyl-aniline (770 mg, 4.82 mmol) in DMF (2 mL) was added 4M HCl in dioxane (0.6 mL, 2.40 mmol) and the mixture stirred for 5 min. This mixture was added to a solution of (7R,7aS)-7-((tert-butyldimethylsilyl)oxy)tetrahydro-1H,3H-pyrrolo[1,2-c]oxazole-1,3-dione (483 mg, 1.78 mmol) in DMF (2 mL) and stirred at 100° C. for 20 h. The mixture was evaporated to give a crude oil, which was suspended in DCM (10 mL) and treated with DIPEA (1.24 mL, 7.12 mmol). (Boc)$_2$O (1.55 g, 7.12 mmol) and DMAP (0.04 g, 0.356 mmol) were added and the mixture stirred for 18 h at rt. The mixture was partitioned between DCM and water. The aqueous layer was extracted into DCM and the combined organics were dried and evaporated. The mixture was purified by column chromatography (0-25% EtOAc in cyclohexane) to give tert-butyl (2S,3R)-3-[tert-butyl(dimethyl)silyl]oxy-2-[(3-chloro-4-fluoro-phenyl)-methyl-carbamoyl]pyrrolidine-1-carboxylate, (60 mg, 7%).

m/z ES+[M+H]$^+$ 487.2; $^1$H NMR (400 MHz, CDCl$_3$) δ ppm 7.49-7.03 (m, 3H), 4.48-4.37 (m, 1H), 4.34-4.15 (m, 1H), 3.63-3.51 (m, 1H), 3.41-3.23 (m, 1H), 3.20-3.16 (m, 3H), 2.29-2.03 (m, 1H), 1.94-1.79 (m, 1H), 1.36 (s, 9H), 0.84 (s, 9H), 0.07--0.02 (m, 6H)

Step d. Ruthenium(III) chloride hydrate (5.1 mg, 0.025 mmol) and sodium metaperiodate (32 mg, 0.148 mmol) were added to tert-butyl (2S,3R)-3-[tert-butyl(dimethyl)silyl]oxy-2-[(3-chloro-4-fluoro-phenyl)-methyl-carbamoyl]pyrrolidine-1-carboxylate (60 mg, 0.123 mmol) in EtOAc (4 mL) and water (4 mL) to give a dark brown/grey mixture. After 5 min the mixture had become light brown in colour and was stirred for 1 h before it returned to its original colour. Further sodium metaperiodate (0.07 g, 0.308 mmol) was added and the mixture stirred for 17 h. The mixture was evaporated and the residue partitioned between EtOAc and water. The layers were separated and the aqueous re-extracted with EtOAc. The combined organics were dried and evaporated to give a brown oil. The mixture was purified by column chromatography (0-30% EtOAc in cyclohexane) to give tert-butyl (2S,3R)-3-[tert-butyl-(dimethyl)silyl]oxy-2-[(3-chloro-4-fluoro-phenyl)-methyl-carbamoyl]-5-oxo-pyrrolidine-1-carboxylate (80 mg) as a brown oil, which was used directly in the next step.

m/z ES+[M+H]$^+$ 501.2; $^1$H NMR (400 MHz, CDCl$_3$) δ ppm 7.43 (dd, J=6.6, 2.6 Hz, 1H), 7.28 (dq, J=6.4, 2.1, 1.6 Hz, 1H), 7.05-7.00 (m, 1H), 4.64 (d, J=7.8 Hz, 1H), 4.29 (dt, J=9.6, 7.9 Hz, 1H), 3.17 (s, 3H), 2.84 (dd, J=16.3, 9.5 Hz, 1H), 2.45 (dd, J=16.4, 7.9 Hz, 1H), 1.38 (s, 9H), 0.81-0.79 (m, 9H), -0.00 (s, 3H), -0.04 (s, 3H).

Step e. 4M HCl in dioxane (2.0 mL, 8.0 mmol) was added to tert-butyl (2S,3R)-3-[tert-butyl(dimethyl)silyl]oxy-2-[(3-chloro-4-fluoro-phenyl)-methyl-carbamoyl]-5-oxo-pyrrolidine-1-carboxylate (80 mg, 0.16 mmol). The mixture was stirred for 30 min and evaporated to give (2S,3R)-3-[tert-butyl(dimethyl)silyl]oxy-N-(3-chloro-4-fluoro-phenyl)-N-methyl-5-oxo-pyrrolidine-2-carboxamide HCl salt, (62 mg, 89%), which was used directly in the next step.

m/z ES+[M+H]$^+$ 401.1; $^1$H NMR (400 MHz, CDCl$_3$) δ ppm 7.25 (s, 1H), 7.19 (t, J=7.8 Hz, 1H), 7.08 (d, J=7.5 Hz, 1H), 4.34-4.12 (m, 2H), 3.13 (s, 3H), 2.48 (dd, J=16.3, 5.6 Hz, 1H), 2.34-2.26 (m, 1H), 0.77 (d, J=4.5 Hz, 9H), 0.00 (s, 3H), -0.03 (s, 3H).

Step f. A mixture of Cs$_2$CO$_3$ (0.17 g, 0.512 mmol), Xantphos (0.01 g, 0.026 mmol) and (2S,3R)-3-[tert-butyl(dimethyl)silyl]oxy-N-(3-chloro-4-fluoro-phenyl)-N-methyl-5-oxo-pyrrolidine-2-carboxamide HCl salt (56 mg, 0.128 mmol) in 1,4-dioxane (2 mL) was evacuated and backfilled with N$_2$ 3 times. A mixture of Pd$_2$(dba)$_3$ (0.01 g, 0.013 mmol) and 2-bromo-6-methyl-4-(trifluoromethyl)pyridine (44 mg, 0.183 mmol) in 1,4-dioxane (2 mL) (degassed in the same way as above) was added and the mixture heated to reflux for 2 h. The mixture was evaporated and the crude residue purified by column chromatography (0-20% EtOAc in cyclohexane) to give the desired product with minor impurities. The other fractions from the column were evaporated and contained a small amount of desired product. Both fractions were treated individually with TBAF (1 M in THF; 1 mL) and stirred for 2 h. The two mixtures were combined and washed with sat. aq. NH$_4$HCO$_3$. The organic layer was dried, evaporated and the residue was purified by prep-HPLC to provide the title compound (1.2 mg, 2%).

m/z ES+[M+H]+ 446.1; $^1$H NMR (400 MHz, CDCl$_3$) δ ppm 8.52 (s, 1H), 7.81-7.74 (m, 1H), 7.53-7.50 (m, 1H), 7.34-7.29 (m, 1H), 7.13 (s, 1H), 5.22 (d, J=7.6 Hz, 1H), 4.47 (m, 1H), 3.35 (s, 3H), 2.94 (dd, J=7.3, 5.1 Hz, 1H), 2.62 (s, 3H), 2.41 (d, J=8.7 Hz, 1H). One aromatic peak obscured by CHCl$_3$.

Example 81

(2S,3R)—N-(3-Chloro-4-fluorophenyl)-1-(3-cyano-6-methyl-4-(trifluoromethyl)pyridin-2-yl)-3-hydroxy-N-methylpyrrolidine-2-carboxamide

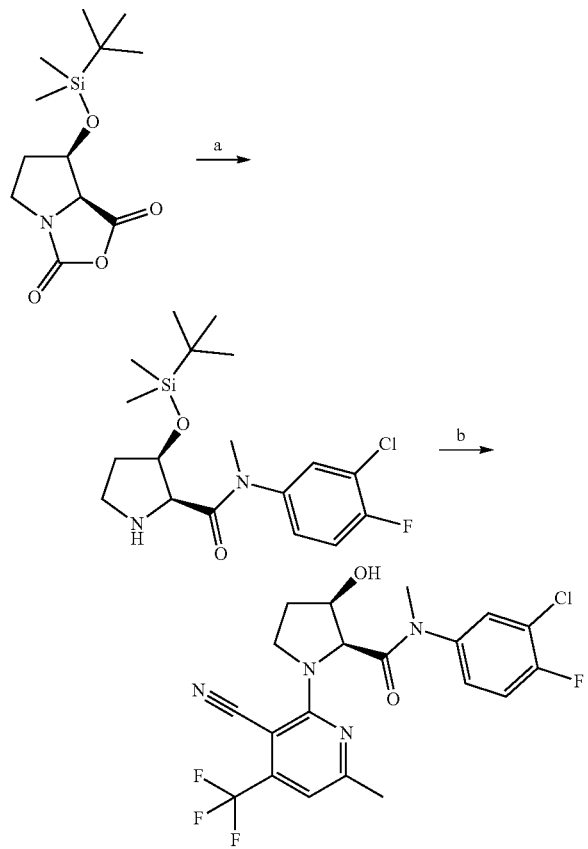

Step a. To 3-chloro-4-fluoro-N-methyl-aniline (237 mg, 1.483 mmol) in NMP (1.0 mL) was added 4M HCl in dioxane (0.19 mL, 0.742 mmol) and the mixture stirred for 5 min. The suspension was transferred to a flask containing (7R,7aS)-7-[tert-butyl(dimethyl)silyl]oxy-5,6,7,7a-tetrahydropyrrolo[1,2-c]oxazole-1,3-dione (161 mg, 0.593 mmol) in NMP (0.5 mL) and the mixture stirred at 80° C. for 20 h and then evaporated. The mixture was purified by column chromatography (0-7% MeOH in DCM). Product fractions were combined and solvent was removed under vacuum to give (2S,3R)-3-[tert-butyl(dimethyl)silyl]oxy-N-(3-chloro-4-fluoro-phenyl)-N-methyl-pyrrolidine-2-carboxamide, (21 mg, 9%).

m/z ES+[M+H]+ 387.1

Step b. A mixture of 2-chloro-6-methyl-4-(trifluoromethyl)nicotinonitrile (10 mg, 0.065 mmol), (2S,3R)-3-[tert-butyl(dimethyl)silyl]oxy-N-(3-chloro-4-fluoro-phenyl)-N-methyl-pyrrolidine-2-carboxamide (21 mg, 0.054 mmol) and DIPEA (0.04 mL, 0.217 mmol) in NMP (0.5 mL) was heated to 90° C. for 2.5 h. The mixture was treated with TBAF (0.22 mL, 0.217 mmol, 1 M in THF) and stirred for 3 h. The mixture was evaporated and purified by prep-HPLC to provide the title compound (15 mg, 60%).

m/z ES+[M+H]+ 456.8; $^1$H NMR (400 MHz, DMSO-d6) δ ppm 7.79 (d, J=6.7 Hz, 1H), 7.57 (d, J=6.6 Hz, 2H), 7.07 (s, 1H), 5.54 (d, J=5.2 Hz, 1H), 4.72 (d, J=6.2 Hz, 1H), 4.21-4.12 (m, 1H), 4.02-3.92 (m, 1H), 3.88-3.77 (m, 1H), 3.15 (s, 3H), 2.00 (d, J=6.5 Hz, 2H). One methyl signal hidden under DMSO peak Example 82

(2S,3R)—N-(3-Chloro-4-fluorophenyl)-1-(3-cyano-6-methyl-4-(trifluoromethyl)pyridin-2-yl)-N-ethyl-3-hydroxypyrrolidine-2-carboxamide

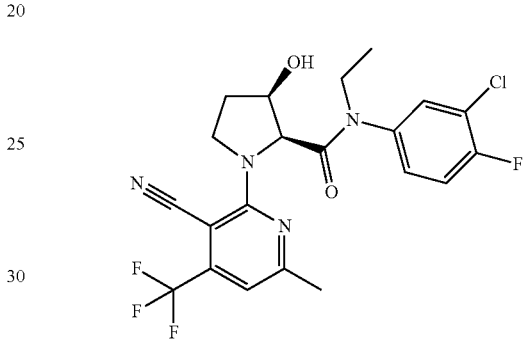

The title compound was prepared in a similar manner to Example 81.

m/z ES+[M+H]+ 471.3; $^1$H NMR (400 MHz, DMSO-d6) δ ppm 7.77-7.71 (m, 1H), 7.63-7.51 (m, 2H), 7.07 (s, 1H), 5.45 (d, J=5.5 Hz, 1H), 4.64 (d, J=5.9 Hz, 1H), 4.13-4.03 (m, 1H), 4.02-3.88 (m, 1H), 3.87-3.72 (m, 2H), 2.45-2.39 (m, 3H), 2.02-1.90 (m, 2H), 0.99 (t, J=7.1 Hz, 3H).

Example 83

(S)—N-(3-Chloro-4-fluorophenyl)-N-methyl-3-(6-methyl-4-(trifluoromethyl)pyridin-2-yl)-2-oxooxazolidine-4-carboxamide

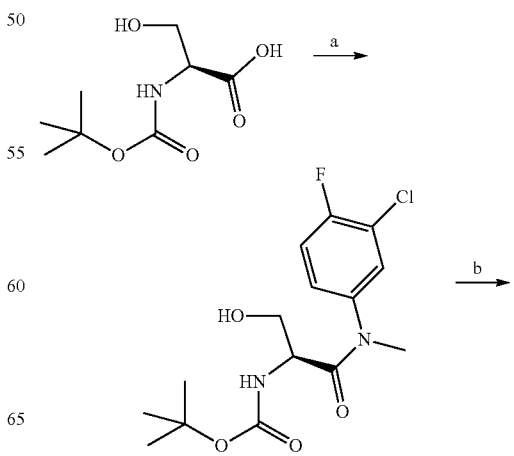

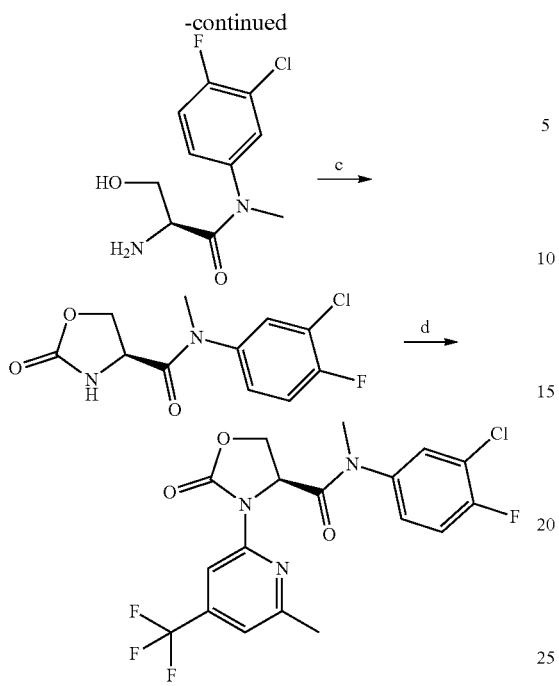

Step a. To a mixture of (S)-2-((tert-butoxycarbonyl)amino)-3-hydroxypropanoic acid (300 mg, 1.46 mmol) and 3-chloro-4-fluoro-N-methyl-aniline (303 mg, 1.90 mmol) in IPA (3 mL) was added DIPEA (378 mg, 2.92 mmol) and T3P (1.86 g, 2.92 mmol, 50 wt. % in EtOAc), the mixture was stirred at rt for 16 h. Upon completion, the mixture was concentrated and purified by column chromatography (25-100% EtOAc in PE) to give (S)-tert-butyl (1-((3-chloro-4-fluorophenyl)(methyl)amino)-3-hydroxy-1-oxopropan-2-yl)carbamate (220 mg, 43% yield) as a yellow oil.

Step b. A mixture of (S)-tert-butyl (1-((3-chloro-4-fluorophenyl)(methyl)amino)-3-hydroxy-1-oxopropan-2-yl)carbamate (220 mg, 0.63 mmol) in HCl/dioxane (4 M, 2 mL) was stirred at rt for 1 h. Upon completion, the mixture was evaporated to give (S)-2-amino-N-(3-chloro-4-fluorophenyl)-3-hydroxy-N-methylpropanamide (200 mg, crude) as a brown oil which was used in the next step without further purification.

Step c. To a solution of (S)-2-amino-N-(3-chloro-4-fluorophenyl)-3-hydroxy-N-methyl-propanamide (100 mg, 0.41 mmol) in water (1 mL) was added K$_2$CO$_3$ (62 mg, 0.45 mmol) and KHCO$_3$ (45 mg, 0.45 mmol). The mixture was stirred at rt for 30 min. A solution of triphosgene (60 mg, 0.20 mmol) in toluene (1 mL) was added at 0° C. and the mixture stirred at 0° C. for 2 h. Upon completion, the mixture was quenched with water (1 mL) and extracted with EtOAc (1 mL×3). The combined organic layers were washed with brine (2 mL×3), dried over Na$_2$SO$_4$ and evaporated. The residue was purified by prep-TLC (25% EtOAc in PE) to give (S)—N-(3-chloro-4-fluoro-phenyl)-N-methyl-2-oxooxazolidine-4-carboxamide (30 mg, 27% yield) as a white solid over two steps.

Step d. To a solution of (S)—N-(3-chloro-4-fluorophenyl)-N-methyl-2-oxooxazolidine-4-carboxamide (30 mg, 0.11 mmol) in dioxane (1 mL) was added 2-bromo-6-methyl-4-(trifluoromethyl)pyridine (32 mg, 0.13 mmol), Pd(dba)$_2$ (6.3 mg, 0.011 mmol), Xantphos (9.5 mg, 0.017 mmol) and Cs$_2$CO$_3$ (108 mg, 0.33 mmol). The mixture was stirred at 120° C. for 2 h under N$_2$ atmosphere. Upon completion, the mixture was quenched with water (1 mL) and extracted with EtOAc (1 mL×3). The combined organic layers were washed with brine (2 mL×3), dried and evaporated. The residue was purified by prep-HPLC to give the title compound (25 mg, 51% yield) as a yellow solid.

m/z ES+[M+H]$^+$ 432.0; $^1$H NMR (400 MHz, DMSO-d6) δ ppm 8.14 (s, 1H), 7.85 (dd, J=2.4, 6.4 Hz, 1H), 7.68-7.60 (m, 1H), 7.56 (m, 1H), 7.42 (s, 1H), 5.01 (dd, J=3.2, 8.8 Hz, 1H), 4.60 (dd, J=3.2, 8.8 Hz, 1H), 4.35 (t, J=8.8 Hz, 1H), 3.20 (s, 3H), 2.60 (s, 3H)

Example 84

(S)—N-(4-Chloro-3-methylphenyl)-N-methyl-3-(6-methyl-4-(trifluoromethyl)pyridin-2-yl)-2-oxooxazolidine-4-carboxamide

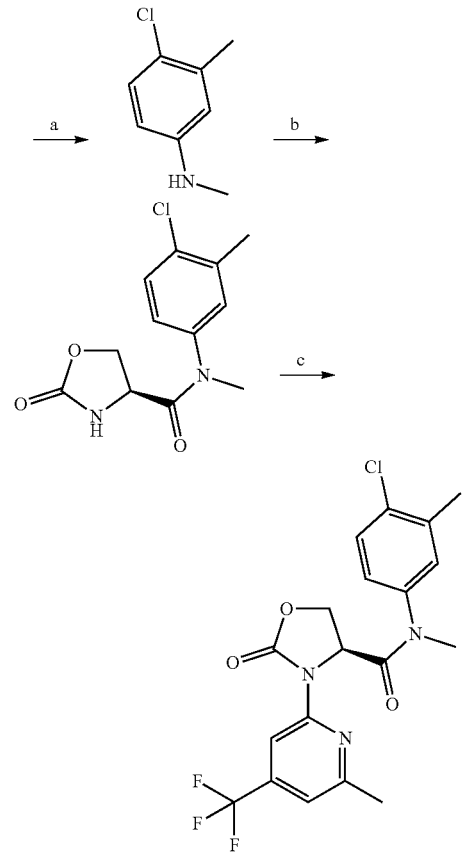

Step a. MeOH (250 mL) was added in portions to sodium methoxide (19.0 g, 353 mmol). When the temperature cooled to rt, 4-chloro-3-methyl-aniline (5.0 g, 35 mmol) and formaldehyde (1.27 g, 42 mmol) were added and the mixture was stirred at rt for 8 h. NaBH$_4$ (2.7 g, 71 mmol) was added and the mixture stirred at rt for 12 h. On completion, the reaction was diluted with water (15 mL) and extracted with EtOAc (30 mL×3). The combined organic layers were washed with brine (10 mL×3), dried over Na$_2$SO$_4$ and evaporated. The residue was purified by column chromatography (100% PE) to afford 4-chloro-N,3-dimethylaniline (3 g, 53% yield) as a yellow liquid.

m/z ES+[M+H]$^+$ 156.1; $^1$H NMR (400 MHz, CDCl$_3$) δ ppm 7.13 (d, J=8.4 Hz, 1H), 6.48 (d, J=2.8 Hz, 1H), 6.40 (dd, J=2.8, 8.4 Hz, 1H), 2.82 (s, 3H), 2.37-2.27 (m, 3H).

Step b. A solution of T3P (2.9 g, 4.6 mmol, 50 wt. % in DMF), 4-chloro-N,3-dimethylaniline (261 mg, 1.7 mmol) and (4S)-2-oxooxazolidine-4-carboxylic acid (200 mg, 1.5 mmol) in pyridine (2 mL) was stirred at rt for 20 h. On completion, the reaction mixture was concentrated under vacuum, diluted with water (15 mL) and extracted with EtOAc (30 mL×3). The combined organic layers were washed with brine (10 mL×3), dried and evaporated. The residue was purified by column chromatography (10-50% EtOAc in PE) to afford (4S)—N-(4-chloro-3-methyl-phenyl)-N-methyl-2-oxo-oxazolidine-4-carboxamide (200 mg, 49% yield) as an oil.

m/z ES+[M+H]$^+$ 269.0; $^1$H NMR (400 MHz, CDCl$_3$) δ ppm 7.37 (d, J=8.4 Hz, 1H), 7.05 (d, J=2.4 Hz, 1H), 6.93 (dd, J=2.4, 8.4 Hz, 1H), 6.13 (br s, 1H), 4.35 (dd, J=6.0, 9.2 Hz, 1H), 4.27 (dd, J=6.0, 8.4 Hz, 1H), 4.06-3.95 (m, 1H), 3.22 (s, 3H), 2.34 (s, 3H).

Step c. A mixture of (4S)—N-(4-chloro-3-methyl-phenyl)-N-methyl-2-oxo-oxazolidine-4-carboxamide (100 mg, 0.37 mmol), 2-bromo-6-methyl-4-(trifluoromethyl)pyridine (134 mg, 0.56 mmol), XantPhos (43 mg, 0.074 mmol), Pd$_2$(dba)$_3$ (34 mg, 0.037 mmol) and Cs$_2$CO$_3$ (243 mg, 0.74 mmol) in dioxane (2 mL) was degassed with N$_2$ 3 times and then stirred at 80° C. for 1 h. On completion, the reaction mixture was diluted with water (15 mL) and extracted with EtOAc (30 mL×3). The combined organic layers were washed with brine (10 mL×3), dried and evaporated. The residue was purified by prep-TLC (25% EtOAc in PE) to give the title compound (123 mg, 75% yield) as an off-white solid.

m/z ES+[M+H]$^+$ 428.1; $^1$H NMR (400 MHz, CD$_3$OD) δ ppm 8.26 (s, 1H), 7.57 (d, J=8.4 Hz, 1H), 7.49 (s, 1H), 7.35 (d, J=7.6 Hz, 1H), 7.27 (s, 1H), 5.18 (dd, J=4.4, 9.2 Hz, 1H), 4.53-4.44 (m, 1H), 4.43-4.36 (m, 1H), 3.31 (s, 3H), 2.64 (s, 3H), 2.47 (s, 3H).

Example 85

(S)—N-(3-Chloro-2,4-difluorophenyl)-N-methyl-3-(6-methyl-4-(trifluoromethyl)pyridin-2-yl)-2-oxooxazolidine-4-carboxamide

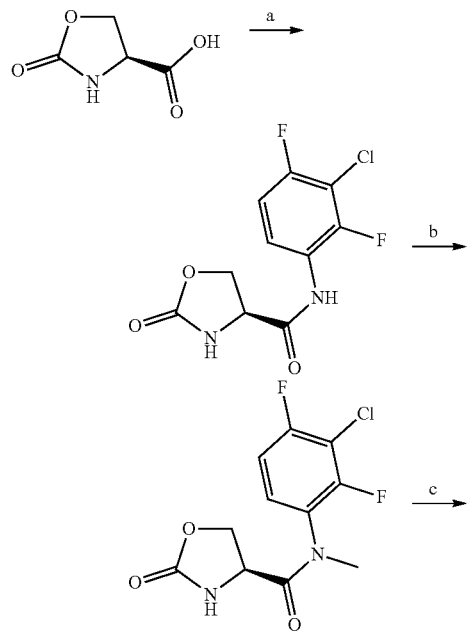

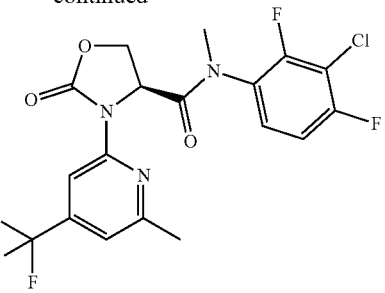

Step a. A solution of 3-chloro-2,4-difluoroaniline (623 mg, 3.81 mmol), (S)-2-oxooxazolidine-4-carboxylic acid (0.5 g, 3.81 mmol) and T3P (6.06 g, 11.43 mmol, 50 wt. % in EtOAc) in pyridine (10 mL) was stirred at 60° C. for 2 h. Upon completion, the mixture was evaporated. The obtained residue was purified by column chromatography (20-100% EtOAc in PE) to give (S)—N-(3-chloro-2,4-difluorophenyl)-2-oxooxazolidine-4-carboxamide (0.75 g, 71% yield) as a white solid.

Step b. To a solution of (S)—N-(3-chloro-2,4-difluorophenyl)-2-oxooxazolidine-4-carboxamide (0.2 g, 0.72 mmol) in DMF (5 mL) was added NaH (35 mg, 0.87 mmol, 60% dispersion in mineral oil) at 0° C. The mixture was stirred at 0° C. for 30 min. Methyl iodide (123 mg, 0.87 mmol) was added and the mixture was stirred at rt for 2 h. Upon completion, the reaction was quenched with water (10 mL) and extracted with EtOAc (20 mL×3). The combined organic layers were washed with brine (10 mL×3), dried and evaporated. The residue was purified by prep-HPLC to give (S)—N-(3-chloro-2,4-difluorophenyl)-N-methyl-2-oxo-oxazolidine-4-carboxamide (100 mg, 48% yield) as a colorless oil.

Step c. A solution of (S)—N-(3-chloro-2,4-difluorophenyl)-N-methyl-2-oxooxazolidine-4-carboxamide (100 mg, 0.34 mmol), 2-bromo-6-methyl-4-(trifluoromethyl)pyridine (83 mg, 0.34 mmol), XantPhos (40 mg, 0.069 mmol), Cs$_2$CO$_3$ (336 mg, 1.03 mmol) and Pd(dba)$_2$ (20 mg, 0.034 mmol) in dioxane (2 mL) was stirred at 100° C. for 1 h. Upon completion, the reaction mixture was evaporated and the residue purified by prep-TLC (35% EtOAc in PE) to give the title compound (35 mg, 62% yield) as a white solid.

m/z ES+[M+H]$^+$ 450.2; $^1$H NMR (400 MHz, DMSO-d6) δ=8.15 (s, 1H), 7.64-7.35 (m, 3H), 5.90-5.00 (m, 1H), 4.85-4.25 (m, 2H), 3.54-3.20 (m, 3H), 2.62-2.52 (m, 3H).

The Examples in Table 6 were prepared using methods similar to those described in the synthesis of Examples 83-85.

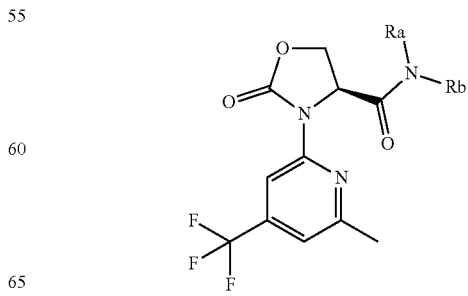

TABLE 6

| Example Number | Ra | Rb | Name | Amine CAS No. | ¹H NMR (400 MHz) δ ppm | MI |
|---|---|---|---|---|---|---|
| 86 | CH₃ | 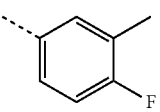 | (S)-N-(4-Fluoro-3-methyl-phenyl)-N-methyl-3-(6-methyl-4-(trifluoromethyl)pyridin-2-yl)-2-oxooxazolidine-4-carboxamide | 77488-82-5 | (DMSO-d6) 8.13 (s, 1H), 7.47-7.30 (m, 4H), 4.97 (dd, J = 3.2, 8.8 Hz, 1H), 4.56 (dd, J = 3.2, 8.8 Hz, 1H), 4.34 (t, J = 8.8 Hz, 1H), 3.18 (s, 3H), 2.58 (s, 3H), 2.29 (s, 3H) | 412.1 |
| 87 | CH₃ | 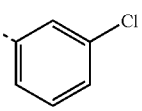 | (S)-N-(3-Chlorophenyl)-N-methyl-3-(6-methyl-4-(trifluoromethyl)pyridin-2-yl)-2-oxooxazolidine-4-carboxamide | 7006-52-2 | (DMSO-d6) 8.14 (s, 1H), 7.68 (s, 1H), 7.63-7.52 (m, 2H), 7.49 (d, J = 8.0 Hz, 1H), 7.41 (s, 1H), 4.99 (dd, J = 3.2, 8.8 Hz, 1H), 4.60 (dd, J = 3.2, 8.8 Hz, 1H), 4.35 (t, J = 8.8 Hz, 1H), 3.21 (s, 3H), 2.60 (s, 33H) | 414.0 |
| 88 | CH₃ | 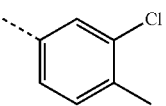 | (S)-N-(3-Chloro-4-methyl-phenyl)-N-methyl-3-(6-methyl-4-(trifluoromethyl)pyridin-2-yl)-2-oxooxazolidine-4-carboxamide | 41456-55-7 | ((DMSO-d6) 8.14 (s, 1H), 7.66 (d, J = 2.0 Hz, 1H), 7.54 (d, J = 8.0 Hz, 1H), 7.45-7.35 (m, 2H), 4.99 (dd, J = 3.2, 8.8 Hz, 1H), 4.59 (dd, J = 3.2, 8.8 Hz, 1H), 4.34 (t, J = 8.8 Hz, 1H), 3.19 (s, 3H), 2.60 (s, 3H), 2.38 (s, 3H) | 428.1 |
| 89 | CH₃ | 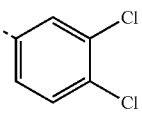 | (S)-N-(3,4-Dichlorophenyl)-N-methyl-3-(6-methyl-4-(trifluoromethyl)-pyridin-2-yl)-2-oxooxazolidine-4-carboxamide | 40750-59-2 | (DMSO-d6) 8.14 (s, 1H), 7.92-7.80 (m, 2H), 7.53 (d, J = 8.8 Hz, 1H), 7.42 (s, 1H), 5.03 (dd, J = 3.2, 8.8 Hz, 1H), 4.60 (dd, J = 3.2, 8.8 Hz, 1H), 4.41-4.33 (m, 1H), 3.21 (s, 3H), 2.59 (s, 3H). | 448.0 |
| 90 | CH₃ | 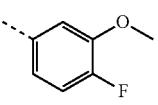 | (S)-N-(4-Fluoro-3-methoxy-phenyl)-N-methyl-3-(6-methyl-4-(trifluoromethyl)pyridin-2-yl)-2-oxooxazolidine-4-carboxamide | prepared from: 64465-53-8 | ¹H NMR (400 MHz, CD₃OD) δ = 8.25 (s, 1H), 7.33-7.21 (m, 3H), 7.12-7.00 (m, 1H), 5.19 (dd, J = 9.6, 4.4 Hz, 1H), 4.53-4.47 (m, 1H), 4.43-4.34 (m, 1H), 3.94 (s, 3H), 3.31 (s, 3H), 2.63 (s, 3H) | 428.0 |
| 91 | CH₃ | 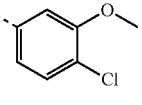 | (S)-N-(4-Chloro-3-methoxy-phenyl)-N-methyl-3-(6-methyl-4-(trifluoromethyl)pyridin-2-yl)-2-oxooxazolidine-4-carboxamide | prepared from: 13726-14-2 | (DMSO-d6) 8.14 (s, 1H), 7.62 (d, J = 8.4 Hz, 1H), 7.41 (s, 1H), 7.27 (d, J = 2.2 Hz, 1H), 7.11 (dd, J = 2.2, 8.4 Hz, 1H), 5.04 (dd, J = 3.4, 9.2 Hz, 1H), 4.66 (dd, J = 3.4, 9.2 Hz, 1H), 4.40 (t, J = 9.2 Hz, 1H), 3.92 (s, 3H), 3.23 (s, 3H), 2.59 (s, 3H) | 444.0 |
| 92 | CH₃ | 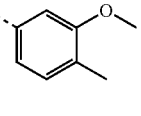 | (S)-N-(3-Methoxy-4-methyl-phenyl)-N-methyl-3-(6-methyl-4-(trifluoromethyl)pyridin-2-yl)-2-oxooxazolidine-4-carboxamide | prepared from: 16452-01-0 | (DMSO-d6) 8.14 (s, 1H), 7.40 (s, 1H), 7.30 (d, J = 8.0 Hz, 1H), 7.04 (d, J = 1.6 Hz, 1H), 6.97 (d, J = 7.6 Hz, 1H), 5.01 (dd, J = 3.2, 8.8 Hz, 1H), 4.64 (dd, J = 3.2, 8.8 Hz, 1H), 4.36 (t, J = 8.8 Hz, 1H), 3.84 (s, 3H), 3.20 (s, 3H), 2.58 (s, 3H), 2.17 (s, 3H) | 424.0 |
| 93 | CH₃ | 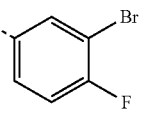 | (S)-N-(3-Bromo-4-fluorophenyl)-N-methyl-3-(6-methyl-4-(trifluoromethyl)pyridin-2-yl)-2-oxooxazolidine-4-carboxamide | prepared from: 656-64-4 | (CD₃OD) 8.27 (s, 1H), 8.00-7.95 (m, 1H), 7.60-7.55 (m, 1H), 7.50-7.37 (m, 1H), 7.28 (s, 1H), 5.18 (dd, J = 4.0, 9.2 Hz, 1H), 4.53-4.46 (m, 1H), 4.44-4.34 (m, 1H), 3.32 (s, 3H), 2.66 (s, 3H). | 475.0, 477.0 |
| 94 | CH₃ | 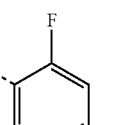 | (S)-N-(4-Bromo-2-fluorophenyl)-N-methyl-3-(6-methyl-4-(trifluoromethyl)pyridin-2-yl)-2-oxooxazolidine-4-carboxamide | 213190-12-6 | (DMSO-d6) 8.15 (s, 1H), 7.85-7.71 (m, 1H), 7.62-7.32 (m, 3H), 5.15-4.91 (m, 1H), 4.63-4.33 (m, 2H), 3.19 (s, 3H), 2.55 (s, 3H) | 475.8, 477.8 |
| 95 | CH₃ | 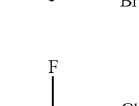 | (S)-N-(3-Chloro-2-fluorophenyl)-N-methyl-3-(6-methyl-4-(trifluoromethyl)pyridin-2-yl)-2-oxooxazolidine-4-carboxamide | 1040041-75-5 | (DMSO-d6) 8.15 (s, 1H), 7.76-7.70 (m, 1H), 7.60-7.25 (m, 3H), 5.10-5.05 (m, 0.3H), 5.00-4.95 (m, 0.5H), 4.85-4.75 (m, 0.2H), 4.72-4.67 (m, 0.5H), 4.58-4.45 (m, 0.5H), 4.40-4.25 (m, 1H), 3.57 (s, 0.3H), 3.25-3.15 (m, 2.7H), 2.60-2.53 (m, 3H). | 431.8 |

TABLE 6-continued

| Example Number | Ra | Rb | Name | Amine CAS No. | ¹H NMR (400 MHz) δ ppm | MI |
|---|---|---|---|---|---|---|
| 96 | $CH_3$ | 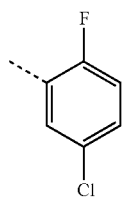 | (S)-N-(5-Chloro-2-fluorophenyl)-N-methyl-3-(6-methyl-4-(trifluoromethyl)pyridin-2-yl)-2-oxooxazolidine-4-carboxamide | 1156149-56-2 | (DMSO-d6) 8.23-8.18 (m, 1H), 7.93 (dd, J = 6.8, 2.4 Hz, 0.5H), 7.86 (dd, J = 6.8, 2.4 Hz, 0.5H), 7.73-7.65 (m, 1H), 7.63-7.57 (m, 1H), 7.50-7.40 (m, 1H), 5.15-5.10 (m, 0.5H), 5.07-5.00 (m, 0.5H), 4.85-4.75 (m, 0.5H), 4.58-4.52 (m, 0.5H), 4.45-4.30 (m, 1H), 3.33-3.15 (m, 3H), 2.68-2.58 (m, 3H). | 432.0 |
| 97 | $CH_3$ | 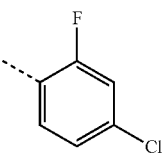 | (S)-N-(4-Chloro-2-fluorophenyl)-N-methyl-3-(6-methyl-4-(trifluoromethyl)pyridin-2-yl)-2-oxooxazolidine-4-carboxamide | 894099-96-8 | (CD₃OD) 8.30-8.20 (m, 1H), 7.81-7.71 (m, 1H), 7.57-7.30 (m, 2H), 7.25-7.15 (m, 1H), 5.22-5.07 (m, 1H), 4.55-4.53 (m, 1H), 4.50-4.39 (m, 1H), 3.28 (s, 3H), 2.64-2.51 (m, 3H) | 432.0 |
| 98 | $CH_3$ | 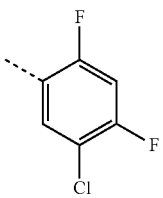 | (S)-N-(5-Chloro-2,4-difluorophenyl)-N-methyl-3-(6-methyl-4-(trifluoromethyl)pyridin-2-yl)-2-oxooxazolidine-4-carboxamide | prepared from: 348-65-2 | (DMSO-d6) 8.17-8.13 (m, 1H), 8.09-7.62 (m, 2H), 7.44-7.39 (m, 1H), 5.15-5.00 (m, 1H), 4.80-4.57 (m, 1H), 4.50-4.25 (m, 1H), 3.23-3.13 (m, 3H), 2.61-2.51 (m, 3H) | 450.0 |
| 99 | $CH_3$ | 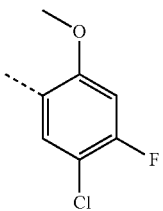 | (S)-N-(5-Chloro-4-fluoro-2-methoxyphenyl)-N-methyl-3-(6-methyl-4-(trifluoromethyl)pyridin-2-yl)-2-oxooxazolidine-4-carboxamide | 1394839-94-1 | (CDCl₃) 8.35 (s, 1H), 7.65 (d, J = 7.6 Hz, 1H), 7.10 (s, 1H), 6.88 (d, J = 10.4 Hz, 1H), 5.07 (dd, J = 4.8, 9.2 Hz, 1H), 4.34 (dd, J = 4.8, 9.2 Hz, 1H), 4.21-4.15 (m, 1H), 3.90 (s, 3H), 3.22 (s, 3H), 2.61 (s, 3H) | 462.1 |
| 100 | $CH_3$ | 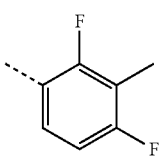 | (S)-N-(2,4-Difluoro-3-methylphenyl)-N-methyl-3-(6-methyl-4-(trifluoromethyl)pyridin-2-yl)-2-oxooxazolidine-4-carboxamide | prepared from: 76350-70-4 | (DMSO-d6) 8.15 (s, 1H), 7.60-7.13 (m, 3H), 5.10-4.90 (m, 1H), 4.61-4.19 (m, 2H), 3.18 (s, 3H), 2.58 (s, 3H), 2.25 (s, 3H) | 429.9 |
| 101 | $CH_3$ | 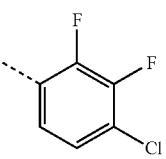 | (S)-N-(4-Chloro-2,3-difluorophenyl)-N-methyl-3-(6-methyl-4-(trifluoromethyl)pyridin-2-yl)-2-oxooxazolidine-4-carboxamide | prepared from: 878285-12-2 | (DMSO-d6) 8.13 (s, 1H), 7.75-7.55 (m, 1H), 7.55-7.45 (m, 0.7H), 7.35-7.28 (m, 0.3H), 7.43-7.35 (m, 1H), 5.90-5.85 (m, 0.2H), 5.14-5.02 (m, 0.8H), 4.72-4.47 (m, 1H), 4.36-4.23 (m, 1H), 3.57 (s, 0.5H), 3.25-3.10 (m, 2.5H), 2.62-2.44 (m, 3H). | 450.0 |
| 102 | $CH_3$ | 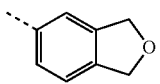 | (S)-N-(1,3-Dihydro-isobenzofuran-5-yl)-N-methyl-3-(6-methyl-4-(trifluoromethyl)-pyridin-2-yl)-2-oxooxazolidine-4-carboxamide | prepared from: 61964-08-7 | (CD₃OD) 8.25 (s, 1H), 7.50-7.46 (m, 1H), 7.46-7.39 (m, 2H), 7.25 (s, 1H), 5.19-5.15 (m, 1H), 5.15-5.10 (m, 4H), 4.47 (dd, J = 4.4, 8.8 Hz, 1H), 4.41-4.32 (m, 1H), 3.32 (s, 3H), 2.62 (s, 3H). | 422.1 |
| 103 | $CH_3CH_3$ | 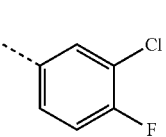 | (S)-N-(3-Chloro-4-fluorophenyl)-N-ethyl-3-(6-methyl-4-(trifluoromethyl)-pyridin-2-yl)-2-oxooxazolidine-4-carboxamide | 77898-24-9 | (DMSO-d6) 8.15 (s, 1H), 7.82 (dd, J = 2.4, 6.6 Hz, 1H), 7.71-7.60 (m, 1H), 7.60-7.50 (m, 1H), 7.43 (s, 1H), 4.95 (dd, J = 3.2, 9.2 Hz, 1H), 4.58 (dd, J = 3.2, 9.2 Hz, 1H), 4.32 (t, J = 9.2 Hz, 1H), 3.84-3.68 (m, 1H), 3.65-3.50 (m, 1H), 2.61 (s, 3H), 1.04 (t, J = 7.2 Hz, 3H) | 445.9 |

TABLE 6-continued

| Example Number | Ra | Rb | Name | Amine CAS No. | $^1$H NMR (400 MHz) δ ppm | MI |
|---|---|---|---|---|---|---|
| 104 | CH(CH$_3$)$_2$ | 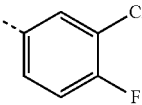 (3-Cl, 4-F phenyl) | (S)-N-(3-Chloro-4-fluorophenyl)-N-isopropyl-3-(6-methyl-4-(trifluoromethyl)pyridin-2-yl)-2-oxooxazolidine-4-carboxamide | 77898-24-9 | (CD$_3$OD) 8.27 (s, 1H), 7.81-7.74 (m, 0.5H), 7.63-7.57 (m, 1H), 7.54-7.42 (m, 1H), 7.36-7.30 (m, 0.5H), 7.28-7.23 (m, 1H), 4.97-4.91 (m, 1H), 4.85-4.78 (m, 1H), 4.52-4.45 (m, 0.5H), 4.43-4.38 (m, 0.5H), 4.35-4.25 (m, 1H), 2.70-2.60 (m, 3H), 1.18 (d, J = 6.8 Hz, 3H), 1.09 (d, J = 6.8 Hz, 3H) | 460.0 |
| 171 | CH$_3$ | 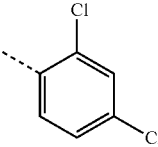 (2,4-diCl phenyl) | (S)-N-(2,4-Dichlorophenyl)-N-methyl-3-(6-methyl-4-(trifluoromethyl)pyridin-2-yl)-2-oxooxazolidine-4-carboxamide | 35113-88-3 | (DMSO-d6) 8.19-8.17 (m, 1H), 7.95 (dd, J = 2.4, 9.6 Hz, 1H), 7.84-7.80 (m, 0.6H), 7.77-7.73 (m, 1H), 7.65-7.60 (m, 0.4H), 7.46-7.38 (m, 1H), 4.98 (dd, J = 4.0, 9.6 Hz, 1H), 4.71-4.41 (m, 1H), 4.34-4.24 (m, 1H), 3.16-3.13 (m, 3H), 2.53 (s, 3H) | 448.0 |
| 172 | CH$_3$ | 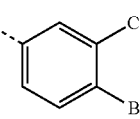 (3-Cl, 4-Br phenyl) | (S)-N-(4-Bromo-3-chlorophenyl)-N-methyl-3-(6-methyl-4-(trifluoromethyl)pyridin-2-yl)-2-oxooxazolidine-4-carboxamide | 1233505-99-1 | (CDCl$_3$) 8.14 (s, 1H), 7.98 (d, J = 8.4 Hz, 1H), 7.88 (d, J = 2.4 Hz, 1H), 7.48-7.35 (m, 2H), 5.03 (dd, J = 3.2, 9.2 Hz, 1H), 4.60 (dd, J = 3.2, 8.8 Hz, 1H), 4.37 (t, J = 8.8 Hz, 1H), 3.21 (s, 3H), 2.60 (s, 3H). | 494.2 |

Example 105

(S)—N-(3-Hydroxy-4-methylphenyl)-N-methyl-3-(6-methyl-4-(trifluoromethyl)pyridin-2-yl)-2-oxooxazolidine-4-carboxamide

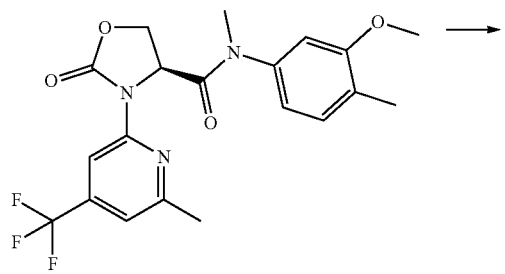

To a solution of Example 92 (100 mg, 0.24 mmol) in DCM (3 mL) was added BBr$_3$ (592 mg, 2.36 mmol) at −60° C. The reaction mixture was slowly warmed to 0° C. and stirred at 0° C. for 1 h. Upon completion, the mixture was quenched with ice water (3 mL) and extracted with DCM (10 mL×3). The combined organic layers were washed with brine (5 mL×3), dried over Na$_2$SO$_4$ and evaporated. The residue was purified by prep-HPLC to give the title compound (51 mg, 53% yield) as a white solid.

m/z ES+[M+H]$^+$ 410.0; $^1$H NMR (400 MHz, DMSO-d6) δ ppm 9.83 (s, 1H), 8.12 (s, 1H), 7.39 (s, 1H), 7.20 (d, J=8.0 Hz, 1H), 6.86-6.74 (m, 2H), 4.99 (dd, J=3.6, 8.8 Hz, 1H), 4.52 (dd, J=3.6, 8.8 Hz, 1H), 4.36 (t, J=8.8 Hz, 1H), 3.15 (s, 3H), 2.58 (s, 3H), 2.14 (s, 3H)

Example 106

(S)—N-(4-Fluoro-3-hydroxyphenyl)-N-methyl-3-(6-methyl-4-(trifluoromethyl)pyridin-2-yl)-2-oxooxazolidine-4-carboxamide

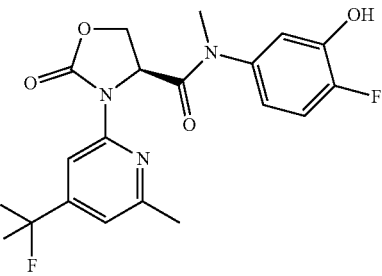

The title compound was prepared in a similar manner to Example 105, using Example 90 as the starting material.

m/z ES+[M+H]$^+$ 414.0; $^1$H NMR (400 MHz, CD$_3$OD) δ ppm 8.24 (s, 1H), 7.24 (s, 1H), 7.19 (dd, J=10.8, 8.4 Hz, 1H), 7.08-6.99 (m, 1H), 6.92-6.82 (m, 1H), 5.20 (dd, J=9.2, 4.4 Hz, 1H), 4.50-4.35 (m, 2H), 3.27 (s, 3H), 2.62 (s, 3H).

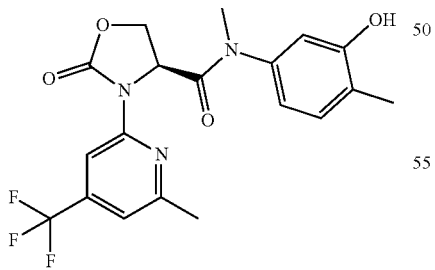

Example 107

(S)—N-(2,4-Difluoro-3-vinylphenyl)-N-methyl-3-(6-methyl-4-(trifluoromethyl)pyridin-2-yl)-2-oxooxazolidine-4-carboxamide

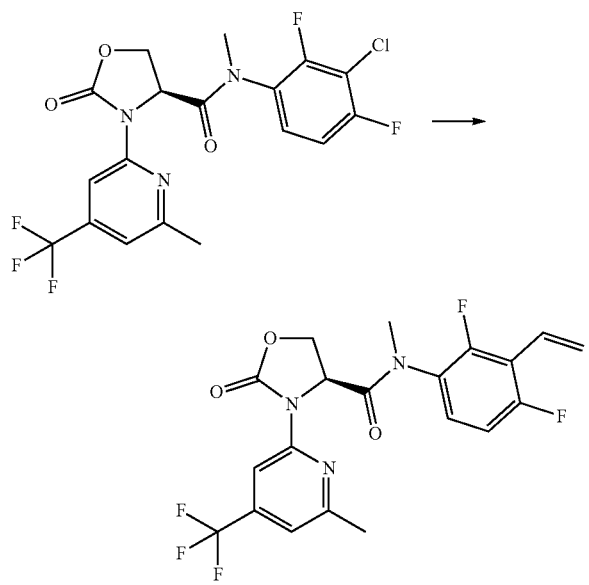

To a solution of Example 85 (30 mg, 0.067 mmol), potassium trifluoro(vinyl)borate (27 mg, 0.20 mmol) and $K_2CO_3$ (28 mg, 0.20 mmol) in dioxane (4 mL) and water (1 mL) was added XPhos-Pd-G2 (5.3 mg, 0.0067 mmol). The mixture was purged with $N_2$ three times and stirred at 80° C. for 2 h. On completion, the reaction mixture was quenched with water (10 mL) and extracted with EtOAc (10 mL×3). The combined organic layers were washed with brine (10 mL×3), dried and evaporated. The residue was purified by prep-TLC (25% EtOAc in PE) to give the title compound (6.9 mg, 23% yield) as a white solid.

m/z ES+[M+H]$^+$ 442.3; $^1$H NMR (400 MHz, CD$_3$OD) δ ppm 8.28-8.26 (m, 1H), 7.77-7.36 (m, 1H), 7.30-7.14 (m, 2H), 6.87-6.73 (m, 1H), 6.18-6.10 (m, 1H), 5.78-5.74 (m, 1H), 5.22-5.12 (m, 1H), 4.58-4.45 (m, 1H), 4.44-4.33 (m, 1H), 3.31-3.29 (m, 3H), 2.64-2.55 (m, 3H).

Example 108

(S)—N-(3-Ethyl-2,4-difluorophenyl)-N-methyl-3-(6-methyl-4-(trifluoromethyl)pyridin-2-yl)-2-oxooxazolidine-4-carboxamide

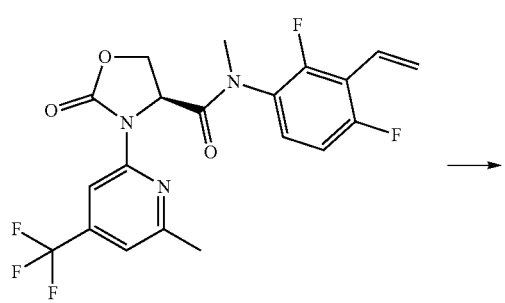

-continued

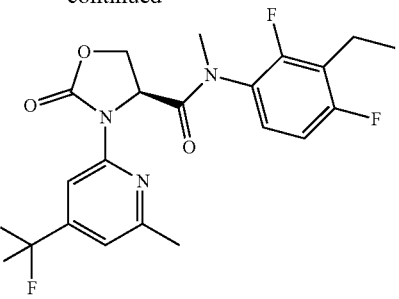

To a solution of Example 107 (20 mg, 0.045 mmol) in MeOH (2 mL) was added Pd/C (2 mg, 10% loading on activated carbon). The mixture was purged with $H_2$ three times and then stirred at rt for 30 min under $H_2$ atmosphere (15 psi). On completion, the mixture was filtered, evaporated and purified by prep-HPLC to give the title compound (3 mg, 14% yield) as an off-white solid.

m/z ES+[M+H]$^+$ 444.2; $^1$H NMR (400 MHz, CD$_3$OD) δ ppm 8.30-8.28 (m, 1H), 7.70-7.05 (m, 3H), 5.19-5.10 (m, 1H), 4.58-4.44 (m, 1H), 4.43-4.33 (m, 1H), 3.30-3.25 (m, 3H), 2.86-2.80 (m, 2H), 2.64-2.57 (m, 3H), 1.30-1.25 (m, 3H).

Example 109

(S)—N-(4-Fluoro-3-vinylphenyl)-N-methyl-3-(6-methyl-4-(trifluoromethyl)pyridin-2-yl)-2-oxooxazolidine-4-carboxamide

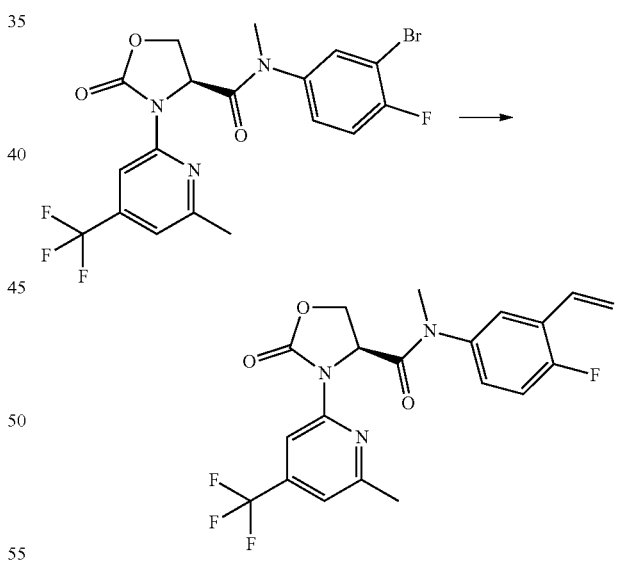

A mixture of Example 93 (70 mg, 0.15 mmol), potassium trifluoro(vinyl)-borate (30 mg, 0.2 mmol), Pd(dppf)Cl$_2$ (11 mg, 0.015 mmol) and Na$_2$CO$_3$ (47 mg, 0.44 mmol) in dioxane (0.4 mL) and water (0.1 mL) was degassed with N$_2$ 3 times and then stirred at 100° C. for 1 h. On completion, the reaction mixture was diluted with water (10 mL) and extracted with EtOAc (30 mL×3). The combined organic layers were washed with brine (8 mL×3), dried and evaporated. The residue was purified by prep-TLC (50% EtOAc in PE) followed by prep-HPLC to afford the title compound (57 mg, 92% yield) as a white solid.

m/z ES+[M+H]+ 424.1; $^1$H NMR (400 MHz, CD$_3$OD) δ ppm 8.25 (s, 1H), 7.94-7.71 (m, 1H), 7.55-7.39 (m, 1H), 7.33-7.24 (m, 2H), 6.91 (dd, J=11.2, 17.6 Hz, 1H), 5.97 (d, J=17.6 Hz, 1H), 5.52 (d, J=11.2 Hz, 1H), 5.16 (dd, J=4.0, 9.6 Hz, 1H), 4.54-4.46 (m, 1H), 4.42-4.33 (m, 1H), 3.30-3.29 (m, 3H), 2.62 (s, 3H).

Example 110

(S)—N-(3-Ethyl-4-fluorophenyl)-N-methyl-3-(6-methyl-4-(trifluoromethyl)pyridin-2-yl)-2-oxo-oxazolidine-4-carboxamide

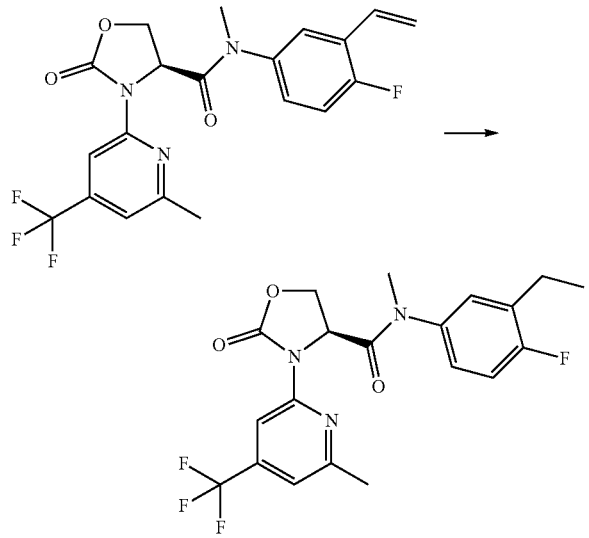

A solution of Example 109 (50 mg, 0.12 mmol) and Pd/C (5 mg, 10% loading on activated carbon) in MeOH (5 mL) was stirred at rt under H$_2$ atmosphere (15 psi) for 2 h. On completion, the reaction mixture was filtered and concentrated to give a residue, which was purified by prep-HPLC to afford the title compound (22 mg, 42% yield) as an off-white solid.

m/z ES+[M+H]+ 426.0; $^1$H NMR (400 MHz, CD$_3$OD) δ ppm 8.27 (s, 1H), 7.46 (br s, 1H), 7.37 (br s, 1H), 7.29-7.22 (m, 2H), 5.16 (dd, J=4.4, 9.2 Hz, 1H), 4.50 (dd, J=4.4, 9.2 Hz, 1H), 4.42-4.32 (m, 1H), 3.31 (s, 3H), 2.81-2.73 (m, 2H), 2.65 (s, 3H), 1.30 (t, J=7.6 Hz, 3H).

Example 111

(S)—N-(2-Fluoro-4-vinylphenyl)-N-methyl-3-(6-methyl-4-(trifluoromethyl)pyridin-2-yl)-2-oxooxazolidine-4-carboxamide

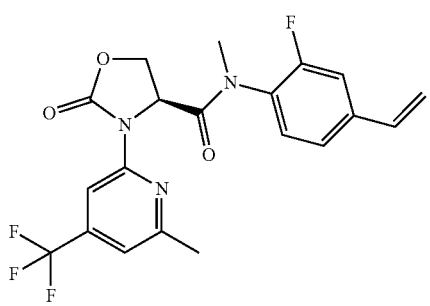 [SMILES: C=Cc1ccc(N(C)C(=O)[C@@H]2COC(=O)N2c2cc(C(F)(F)F)cc(C)n2)c(F)c1]

The title compound was prepared in a similar manner to Example 109, using Example 94 as the starting material.

m/z ES+[M+H]+ 424.0; $^1$H NMR (400 MHz, CD$_3$OD) δ ppm 8.29-8.19 (m, 1H), 7.75-7.45 (m, 2H), 7.41-7.17 (m, 2H), 6.84-6.73 (m, 1H), 5.96-5.86 (m, 1H), 5.45-5.39 (m, 1H), 5.23-5.09 (m, 1H), 4.57-4.48 (m, 1H), 4.47-4.38 (m, 1H), 3.30-3.24 (m, 3H), 2.65-2.51 (m, 3H).

Example 112

(S)—N-(4-Ethyl-2-fluorophenyl)-N-methyl-3-(6-methyl-4-(trifluoromethyl)pyridin-2-yl)-2-oxooxazolidine-4-carboxamide

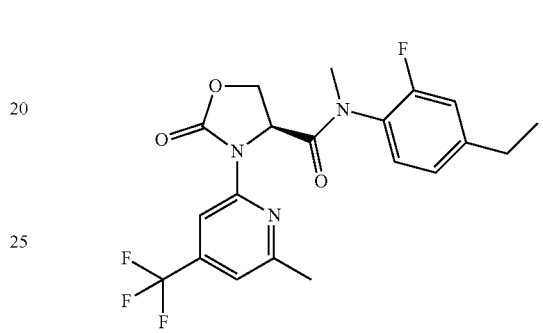

The title compound was prepared in a similar manner to Example 108, using Example 111 as the starting material.

m/z ES+[M+H]+ 426.1; $^1$H NMR (400 MHz, DMSO-d$_6$) δ ppm 8.14 (s, 1H), 7.69-7.15 (m, 4H), 5.14-4.95 (m, 1H), 4.70-4.45 (m, 1H), 4.38-4.20 (m, 1H), 3.18 and 3.14 (s x2, 3H), 2.75-2.65 (m, 2H), 1.28-1.20 (m, 3H). Additional 3H partially obscured by DMSO.

Example 113

(S)-3-(6-Chloro-4-(trifluoromethyl)pyridin-2-yl)-N-(3-chloro-4-fluorophenyl)-N-methyl-2-oxooxazolidine-4-carboxamide

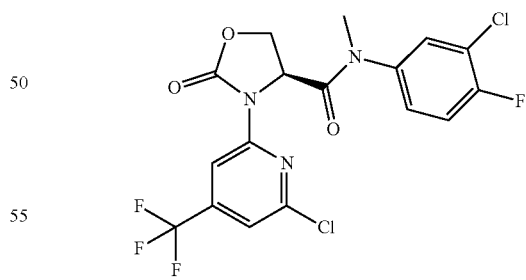

The title compound was prepared in a similar manner to Example 83, using 2,6-dichloro-4-(trifluoromethyl)pyridine (CAS Number 39890-98-7) in step d.

m/z ES+[M+H]+ 452.0; $^1$H NMR (400 MHz, DMSO-d$_6$) δ ppm 8.27 (s, 1H), 7.86 (dd, J=2.4, 6.4 Hz, 1H), 7.78 (s, 1H), 7.68-7.61 (m, 1H), 7.61-7.54 (m, 1H), 4.98 (dd, J=3.2, 8.8 Hz, 1H), 4.63 (dd, J=3.2, 8.8 Hz, 1H), 4.36 (t, J=8.8 Hz, 1H), 3.20 (s, 3H)

Example 114

(S)—N-(3-Chloro-4-fluorophenyl)-N-methyl-2-oxo-3-(4-(trifluoromethyl)-6-vinylpyridin-2-yl)oxazolidine-4-carboxamide

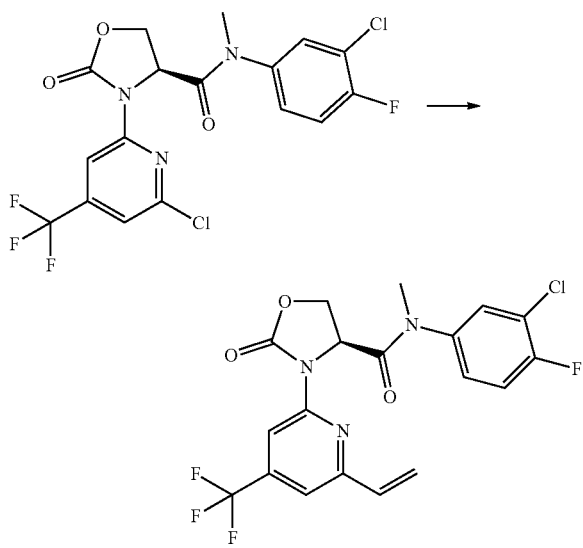

To a solution of Example 113 (90 mg, 0.20 mmol), potassium vinyltrifluoroborate (27 mg, 0.20 mmol) and Na₂CO₃ (63 mg, 0.60 mmol) in dioxane (0.8 mL) and water (0.2 mL) was added Pd(dppf)Cl₂·CH₂Cl₂ (16 mg, 0.020 mmol). The mixture was stirred at 60° C. for 2 h under N₂ atmosphere. Upon completion, the reaction mixture was quenched by NH₄Cl (10 mL) and extracted with EtOAc (10 mL×3). The combined organic layers were washed with brine (10 mL×2), dried over Na₂SO₄ and evaporated. The residue was purified by prep-TLC (35% EtOAc in PE) to give the title compound (50 mg, 50% yield) as a white solid.

m/z ES+[M+H]⁺ 444.1; ¹H NMR (400 MHz, CDCl₃) δ ppm 8.41 (s, 1H), 7.45 (d, J=4.8 Hz, 1H), 7.35-7.29 (m, 2H), 7.26-7.20 (m, 1H), 6.80 (dd, J=10.8, 17.2 Hz, 1H), 6.15 (d, J=17.2 Hz, 1H), 5.67 (d, J=10.8 Hz, 1H), 5.22 (dd, J=5.2, 9.2 Hz, 1H), 4.37-4.27 (m, 2H), 3.31 (s, 3H).

Example 115

(S)—N-(3-Chloro-4-fluorophenyl)-3-(6-ethyl-4-(trifluoromethyl)pyridin-2-yl)-N-methyl-2-oxooxazolidine-4-carboxamide

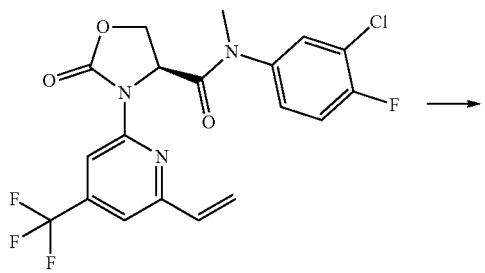

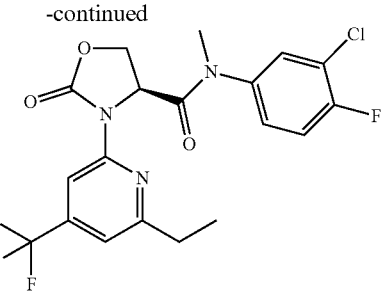

To a solution Example 114 (50 mg, 0.099 mmol) in MeOH (0.5 mL) was added PtO₂ (4.50 mg, 0.020 mmol) under N₂ atmosphere. The suspension was degassed under vacuum and purged with H₂ three times. The mixture was stirred under H₂ atmosphere (15 psi) at 30° C. for 15 min. Upon completion, the reaction mixture was filtered and evaporated, and the residue purified by prep-HPLC to give the title compound (8 mg, 17% yield) as a yellow solid.

m/z ES+[M+H]⁺ 446.1; ¹H NMR (400 MHz, CD₃OD) δ ppm 8.27 (s, 1H), 7.75-7.72 (m, 1H), 7.49-7.44 (m, 2H), 7.26 (s, 1H), 5.19 (dd, J=4.0, 9.6 Hz, 1H), 4.51-4.47 (m, 1H), 4.42-4.36 (m, 1H), 3.29 (s, 3H), 2.93-2.88 (m, 2H), 1.36-1.32 (m, 3H).

Example 116

(S)-3-(4-Bromo-6-methylpyridin-2-yl)-N-(3-chloro-4-fluorophenyl)-N-methyl-2-oxooxazolidine-4-carboxamide

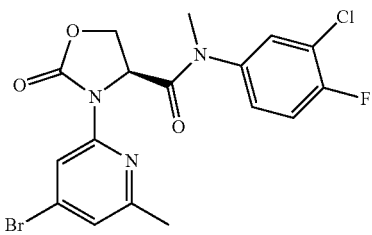 [SMILES: Cc1cc(Br)cc(N2C(=O)OC[C@H]2C(=O)N(C)c2ccc(F)c(Cl)c2)n1]

The title compound was prepared in a similar manner to Example 83, using 2,4-dibromo-6-methylpyridine (CAS Number 79055-52-0) in step d.

m/z ES+[M+H]⁺ 443.9; ¹H NMR (400 MHz, CDCl₃) δ ppm 8.28 (s, 1H), 7.60-7.55 (m, 1H), 7.32-7.26 (m, 2H), 7.08 (s, 1H), 5.15-5.08 (m, 1H), 4.31-4.25 (m, 2H), 3.30 (s, 3H), 2.49 (s, 3H)

Example 117

(S)—N-(3-Chloro-4-fluorophenyl)-N-methyl-3-(6-methyl-4-(prop-1-en-2-yl)pyridin-2-yl)-2-oxooxazolidine-4-carboxamide

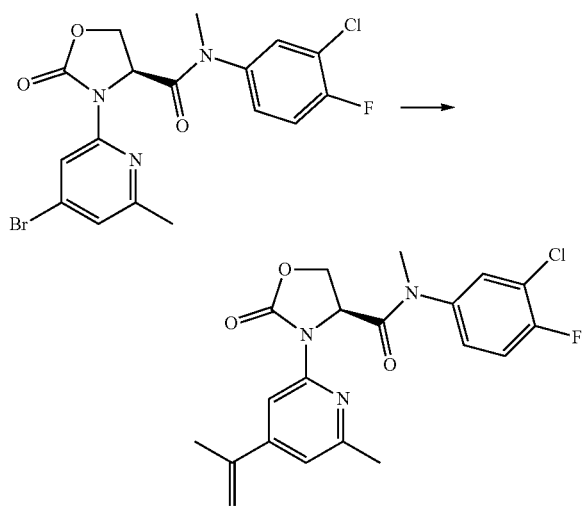

To a solution of Example 116 (20 mg, 0.045 mmol), potassium trifluoro(prop-1-en-2-yl)borate (13.4 mg, 0.090 mmol) and Na$_2$CO$_3$ (14.4 mg, 0.14 mmol) in dioxane (0.4 mL) and water (0.1 mL) was added Pd(dppf)Cl$_2$·CH$_2$Cl$_2$ (3.7 mg, 0.0045 mmol). The mixture was stirred at 60° C. for 45 min under N$_2$ atmosphere. Upon completion, the reaction mixture was diluted with water (5 mL) and extracted with EtOAc (5 mL×3). The combined organic layers were washed with brine (4 mL×2), dried over Na$_2$SO$_4$, evaporated and purified by prep-HPLC to give the title compound (11 mg, 61% yield) as a white solid.

m/z ES+[M+H]$^+$ 404.1; $^1$H NMR (400 MHz, CDCl$_3$) δ ppm 8.10 (s, 1H), 7.68-7.56 (m, 1H), 7.34-7.27 (m, 2H), 6.95 (s, 1H), 5.55 (s, 1H), 5.29-5.10 (m, 2H), 4.32-4.20 (m, 2H), 3.31 (s, 3H), 2.52 (s, 3H), 2.13 (s, 3H).

Example 118

(S)—N-(3-Chloro-4-fluorophenyl)-3-(4-isopropyl-6-methylpyridin-2-yl)-N-methyl-2-oxooxazolidine-4-carboxamide

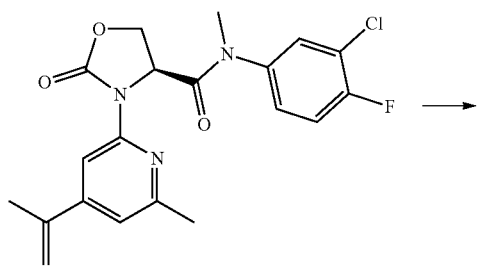

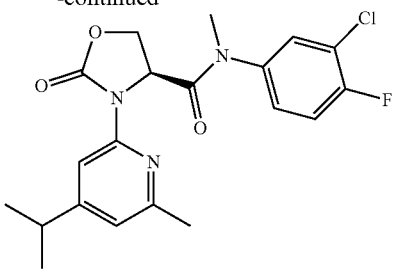

To a solution of Example 117 (100 mg, 0.25 mmol) in MeOH (2 mL) was added PtO$_2$ (5.6 mg, 0.025 mmol) under N$_2$ atmosphere. The suspension was degassed under vacuum and purged with H$_2$ for three times. The mixture was stirred under H$_2$ atmosphere (15 psi) at rt for 1 h. Upon completion, the reaction mixture was filtered and concentrated. The residue was purified by prep-HPLC to give the title compound (28 mg, 56% yield) as a white solid.

m/z ES+[M+H]$^+$ 406.1; $^1$H NMR (400 MHz, CDCl$_3$) δ ppm 7.91 (s, 1H), 7.72-7.58 (m, 1H), 7.35-7.28 (m, 2H), 6.76 (s, 1H), 5.18-5.10 (m, 1H), 4.36-4.16 (m, 2H), 3.31 (s, 3H), 2.95-2.80 (m, 1H), 2.50 (s, 3H), 1.24 (d, J=7.2 Hz, 6H).

Example 119

(S)—N-(3-Chloro-4-fluorophenyl)-3-(4-ethyl-6-methylpyridin-2-yl)-N-methyl-2-oxooxazolidine-4-carboxamide

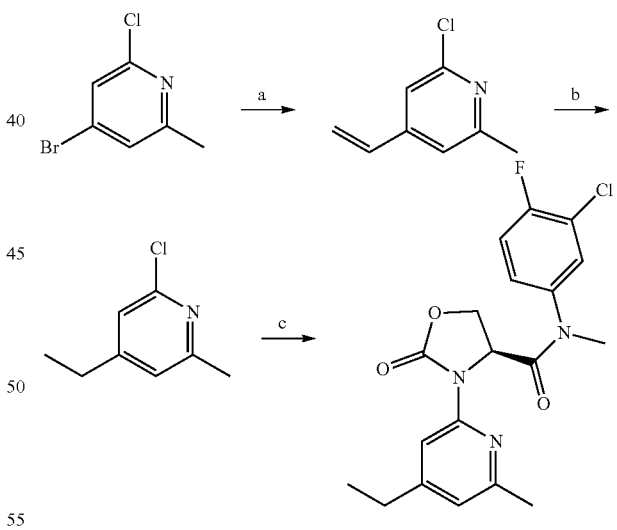

Step a. A mixture of 4-bromo-2-chloro-6-methylpyridine (500 mg, 2.42 mmol), potassium vinyltrifluoroborate (973 mg, 7.27 mmol), Pd(dppf)Cl$_2$·CH$_2$Cl$_2$ (198 mg, 0.24 mmol) and Na$_2$CO$_3$ (770 mg, 7.27 mmol) in dioxane (4 mL) and water (1 mL) was stirred at 60° C. for 1 h under N$_2$ atmosphere. Upon completion, the reaction mixture was quenched with water (20 mL) and extracted with EtOAc (30 mL×3). The combined organic layers were dried over Na$_2$SO$_4$ and evaporated. The residue was purified by prep-HPLC to give 2-chloro-6-methyl-4-vinylpyridine (200 mg, 51% yield) as a yellow oil.

m/z ES+[M+H]⁺ 154.1; ¹H NMR (400 MHz, CDCl₃) δ ppm 7.14 (s, 1H), 7.05 (s, 1H), 6.59 (dd, J=10.8, 17.6 Hz, 1H), 5.96 (d, J=17.6 Hz, 1H), 5.52 (d, J=10.8 Hz, 1H), 2.53 (s, 3H).

Step b. To a solution of 2-chloro-6-methyl-4-vinylpyridine (70 mg, 0.43 mmol) in MeOH (1 mL) was added PtO₂ (49 mg, 0.22 mmol) under N₂ atmosphere. The suspension was degassed under vacuum and purged with H₂ three times. The mixture was stirred under H₂ atmosphere (15 psi) at 30° C. for 15 min. Upon completion, the mixture was filtered and concentrated to give 2-chloro-4-ethyl-6-methylpyridine (50 mg, crude) as a colorless oil which was used in the next step without further purification.

m/z ES+[M+H]⁺ 156.1

Step c. To a solution of 2-chloro-4-ethyl-6-methyl-pyridine (40 mg, 0.18 mmol), (4S)—N-(3-chloro-4-fluoro-phenyl)-N-methyl-2-oxo-oxazolidine-4-carboxamide (72 mg, 0.26 mmol), Xantphos (22 mg, 0.039 mmol) and Cs₂CO₃ (251 mg, 0.77 mmol) in dioxane (1 mL) was added Pd(dba)₂ (15 mg, 0.026 mmol). The mixture was purged with N₂ three times and then stirred at 100° C. for 1 h. On completion, the reaction mixture was diluted with water (5 mL) and extracted with EtOAc (5 mL×3). The combined organic layers were washed with brine (4 mL×2), dried over Na₂SO₄ and evaporated. The residue was purified by prep-HPLC to give the title compound (HCl salt, 10.4 mg, 13% yield) as a yellow solid.

m/z ES+[M+H]⁺ 392.1; ¹H NMR (400 MHz, CDCl₃) δ ppm 7.91 (s, 1H), 7.65 (s, 1H), 7.50-7.30 (m, 2H), 6.81 (s, 1H), 5.55-5.45 (m, 1H), 4.30-4.20 (m, 2H), 3.31 (s, 3H), 2.70-2.60 (m, 2H), 2.56 (s, 3H), 1.26 (t, J=7.6 Hz, 3H).

Example 120

(S)-3-(6-Chloro-4-(difluoromethoxy)pyridin-2-yl)-N-(3-chloro-4-fluorophenyl)-N-methyl-2-oxooxazolidine-4-carboxamide

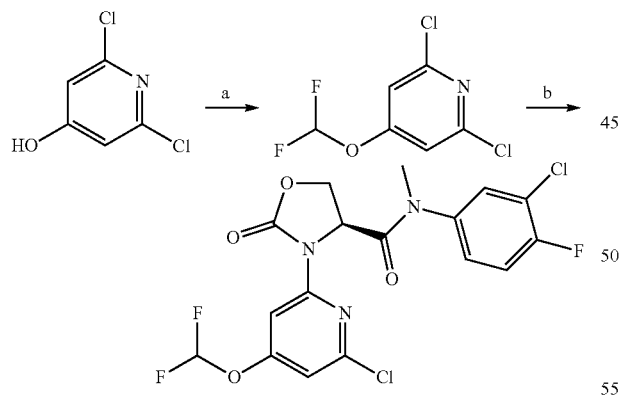

Step a. To a solution of 2,6-dichloropyridin-4-ol (1 g, 6.1 mmol) in dioxane (10 mL) was added water (5 mL) and NaOH (1.22 g, 30.5 mmol) at rt. Chlorodifluoromethane (1.05 g, 12.2 mmol) was bubbled into the mixture at 55° C. for 5 h. Upon completion, EtOAc (50 mL) and water (50 mL) were added to the cooled reaction mixture and separated. The aqueous phase was extracted with EtOAc (50 mL×2). The combined organic phase was dried and evaporated. The residue was purified by column chromatography (10-25% EtOAc in PE) to give 2,6-dichloro-4-(difluoromethoxy)pyridine (630 mg, 48% yield) as an oil.

m/z ES+[M+H]⁺ 214.0

Step b. A mixture of 2,6-dichloro-4-(difluoromethoxy)pyridine (118 mg, 0.55 mmol), (4S)—N-(3-chloro-4-fluorophenyl)-N-methyl-2-oxo-oxazolidine-4-carboxamide (100 mg, 0.37 mmol), Pd₂(dba)₃ (33 mg, 0.037 mmol), XantPhos (42 mg, 0.073 mmol) and Cs₂CO₃ (239 mg, 0.73 mmol) in dioxane (2.5 mL) was degassed and purged with N₂ three times and then stirred at 80° C. for 2 h. Upon completion, the reaction was concentrated. The residue was purified by column chromatography (10-35% EtOAc in PE) to give the title compound (120 mg, 73% yield) as a white solid.

m/z ES+[M+H]⁺ 449.7; ¹H NMR (400 MHz, DMSO-d₆) δ ppm 7.86 (dd, J=2.2, 6.4 Hz, 1H), 7.76 (d, J=1.6 Hz, 1H), 7.70-7.35 (m, 3H), 7.21 (d, J=1.6 Hz, 1H), 4.94 (dd, J=3.6, 9.2 Hz, 1H), 4.56 (dd, J=3.6, 9.2 Hz, 1H), 4.39-4.27 (m, 1H), 3.19 (s, 3H)

Example 121

(S)—N-(3-Chloro-4-fluorophenyl)-3-(4-(difluoromethoxy)-6-methylpyridin-2-yl)-N-methyl-2-oxooxazolidine-4-carboxamide

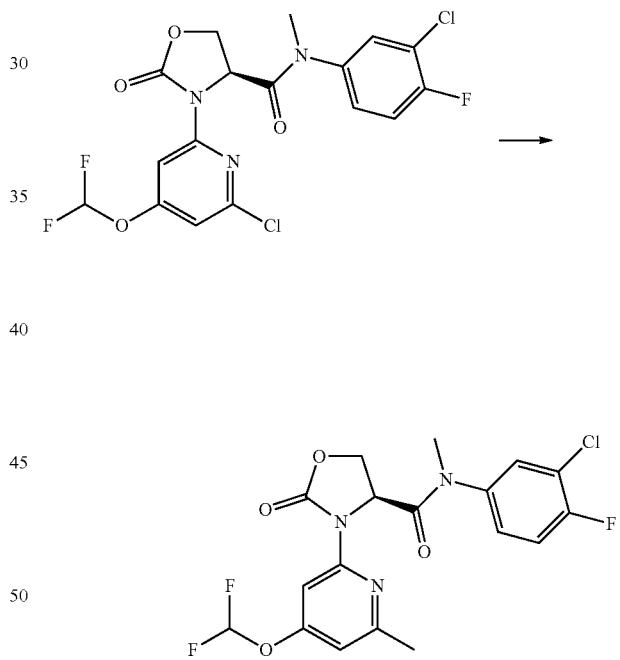

A mixture of Example 120 (50 mg, 0.11 mmol), MeB(OH)₂ (10 mg, 0.17 mmol), Pd(dppf)Cl₂·CH₂Cl₂ (9.1 mg, 0.011 mmol), K₂CO₃ (31 mg, 0.22 mmol) in water (0.25 mL) and dioxane (2 mL) was degassed and purged with N₂ 3 times, and then stirred at 80° C. for 12 h. Upon completion, the reaction was concentrated. The residue was purified by column chromatography (20-30% EtOAc in PE) and further purified by prep-HPLC to give the title compound (24 mg, 51% yield) as a white solid.

m/z ES+[M+H]⁺ 430.0; ¹H NMR (400 MHz, CD₃OD) δ ppm 7.80-7.70 (m, 2H), 7.55-7.40 (m, 2H), 7.25-6.85 (m, 1H), 6.76 (s, 1H), 5.17-5.08 (m, 1H), 4.47-4.40 (m, 1H), 4.39-4.32 (m, 1H), 3.29 (s, 3H), 2.53 (s, 3H).

Example 122

(S)-3-(4-(tert-Butyl)-6-chloropyridin-2-yl)-N-(3-chloro-4-fluorophenyl)-N-methyl-2-oxooxazolidine-4-carboxamide

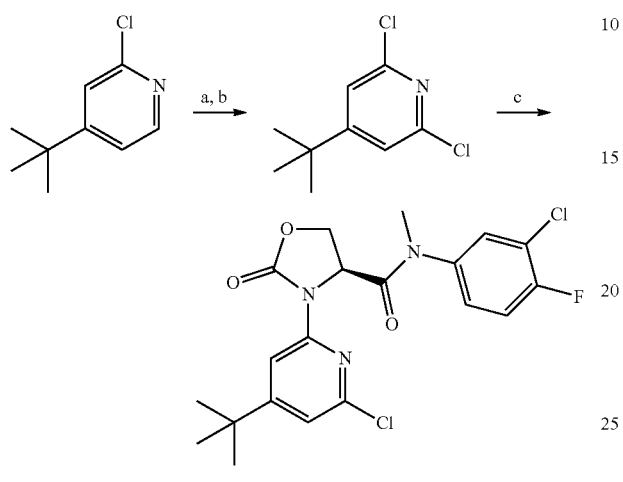

Step a. To a solution of 4-tert-butyl-2-chloro-pyridine (200 mg, 1.18 mmol) in DCM (10 mL) was added m-CPBA (1.02 g, 5.89 mmol) in portions. The mixture was stirred at rt for 12 h. Upon completion, EtOAc (100 mL) was added and the mixture was washed with sat. aq. NaHCO₃ solution (100 mL×3). The combined aqueous phase was extracted with EtOAc (50 mL×2). The combined organic phase was then dried over Na₂SO₄ and evaporated. The residue was purified by column chromatography (10-50% EtOAc in PE) to give 4-tert-butyl-2-chloro-1-oxido-pyridin-1-ium (150 mg, 69% yield) as a yellow solid.

m/z ES+[M+H]⁺ 186.1

Step b. A mixture of 4-tert-butyl-2-chloro-1-oxido-pyridin-1-ium (150 mg, 0.81 mmol) and POCl₃ (3.3 g, 21.5 mmol) was stirred at 110° C. for 5 h. Upon completion, the reaction mixture was quenched by slow addition of water (100 mL), and then extracted with EtOAc (100 mL×3). The combined organic layers were washed with brine (100 mL×3), dried and evaporated to give 4-tert-butyl-2,6-dichloro-pyridine (150 mg, 91% yield) as a brown solid.

Step c. A solution of (4S)—N-(3-chloro-4-fluoro-phenyl)-N-methyl-2-oxo-oxazolidine-4-carboxamide (60 mg, 0.22 mmol), 4-tert-butyl-2,6-dichloro-pyridine (67 mg, 0.33 mmol), Pd₂(dba)₃ (20 mg, 0.022 mmol), XantPhos (25 mg, 0.044 mmol) and Cs₂CO₃ (143 mg, 0.44 mmol) in dioxane (1 mL) was degassed and purged with N₂ three times and then stirred at 80° C. for 1 h. Upon completion, the reaction was concentrated. The obtained residue was purified by column chromatography (10-35% EtOAc in PE) and further purified by prep-HPLC to give the title compound (30 mg, 31% yield) as a white solid.

m/z ES+[M+H]⁺ 439.9; ¹H NMR (400 MHz, DMSO-d₆) δ ppm 8.06 (d, J=1.2 Hz, 1H), 7.89 (dd, J=2.4, 6.8 Hz, 1H), 7.67-7.57 (m, 2H), 7.30 (d, J=1.2 Hz, 1H), 4.93 (dd, J=3.2, 9.2 Hz, 1H), 4.52 (dd, J=3.2, 9.2 Hz, 1H), 4.35-4.28 (m, 1H), 3.19 (s, 3H), 1.28 (s, 9H).

Example 123

(S)-3-(4-(tert-Butyl)-6-methylpyridin-2-yl)-N-(3-chloro-4-fluorophenyl)-N-methyl-2-oxooxazolidine-4-carboxamide

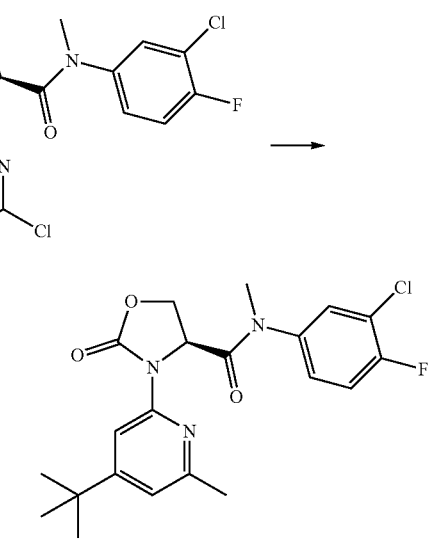

A mixture of (4S)-3-(4-tert-butyl-6-chloro-2-pyridyl)-N-(3-chloro-4-fluoro-phenyl)-N-methyl-2-oxo-oxazolidine-4-carboxamide (50 mg, 0.11 mmol), MeB(OH)₂ (10 mg, 0.17 mmol), Pd(dppf)Cl₂·CH₂Cl₂ (9.3 mg, 0.011 mmol), K₂CO₃ (31 mg, 0.23 mmol) in water (0.25 mL) and dioxane (2 mL) was degassed and purged with N₂ 3 times and then stirred at 80° C. for 12 h. Upon completion, the reaction was concentrated. The obtained residue was purified by column chromatography (20-30% EtOAc in PE) and further purified by prep-HPLC to give the title compound (8 mg, 16% yield) as a white solid.

m/z ES+[M+H]⁺ 420.2; ¹H NMR (400 MHz, CD₃OD) δ ppm 8.01 (s, 1H), 7.88-7.77 (m, 1H), 7.59-7.50 (m, 1H), 7.49-7.41 (m, 1H), 7.04 (s, 1H), 5.20-5.10 (m, 1H), 4.48-4.31 (m, 2H), 3.30 (s, 3H), 2.56-2.53 (m, 3H), 1.33 (s, 9H).

Example 124

(4S)—N-(3-Chloro-4-fluorophenyl)-N-methyl-3-(6-methyl-4-(1,1,1-trifluoropropan-2-yl)pyridin-2-yl)-2-oxooxazolidine-4-carboxamide

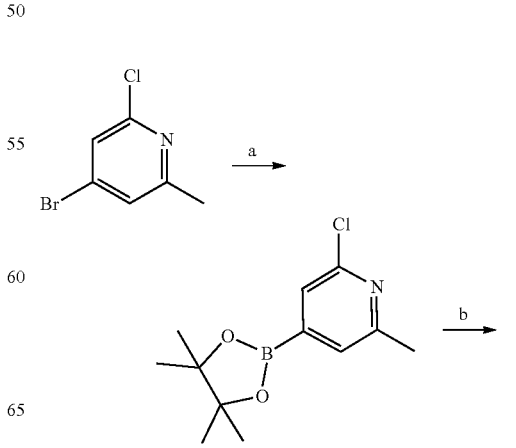

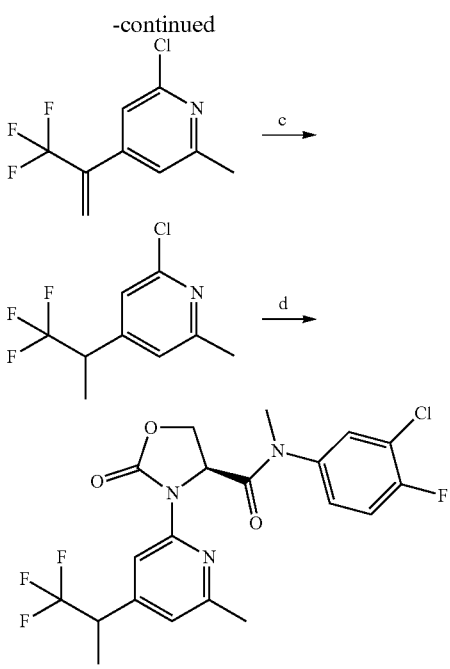

Step a. A mixture of 4-bromo-2-chloro-6-methyl-pyridine (1 g, 4.84 mmol), 4,4,5,5-tetramethyl-2-(4,4,5,5-tetramethyl-1,3,2-dioxaborolan-2-yl)-1,3,2-dioxaborolane (1.48 g, 5.81 mmol), Pd(dppf)Cl$_2$ (354 mg, 0.48 mmol) and potassium acetate (951 mg, 9.69 mmol) in dioxane (10 mL) was stirred at 60° C. for 2 h under N$_2$ atmosphere. Upon completion, the reaction mixture was concentrated under vacuum. The obtained residue was purified by column chromatography (10% EtOAc in PE) to give 2-chloro-6-methyl-4-(4,4,5,5-tetramethyl-1,3,2-dioxaborolan-2-yl)pyridine (1.1 g, 90% yield) as a white solid.

$^1$H NMR (400 MHz, CDCl$_3$) δ ppm 7.48 (s, 1H), 7.41 (s, 1H), 2.54 (s, 3H), 1.35 (s, 12H).

Step b. A mixture of 2-chloro-6-methyl-4-(4,4,5,5-tetramethyl-1,3,2-dioxaborolan-2-yl)pyridine (1.1 g, 4.34 mmol), 2-bromo-3,3,3-trifluoro-prop-1-ene (7.59 g, 43.4 mmol), Pd(dppf)Cl$_2$·CH$_2$Cl$_2$ (354 mg, 0.43 mmol) and Cs$_2$CO$_3$ (2.83 g, 8.68 mmol) in dioxane (15 mL) and water (3 mL) was stirred at 80° C. for 12 h under N$_2$ atmosphere. Upon completion, the reaction mixture was concentrated under vacuum. The residue was purified by column chromatography (1% EtOAc in PE) to give 2-chloro-6-methyl-4-[1-(trifluoromethyl)-vinyl]pyridine (0.8 g, 83% yield) as a yellow oil.

$^1$H-NMR (400 MHz, CDCl$_3$) δ ppm 7.22 (s, 1H), 7.14 (s, 1H), 6.14 (d, J=0.8 Hz, 1H), 5.97 (d, J=1.6 Hz, 1H), 2.58 (s, 3H).

Step c. A mixture of 2-chloro-6-methyl-4-[1-(trifluoromethyl)vinyl]pyridine (0.1 g, 0.45 mmol), PtO$_2$ (10.3 mg, 0.045 mmol) in MeOH (5 mL) was stirred at rt for 5 min under H$_2$ (15 Psi) atmosphere. Upon completion, the reaction mixture was filtered and concentrated under vacuum to give 2-chloro-6-methyl-4-(2,2,2-trifluoro-1-methyl-ethyl) pyridine (0.1 g, 99% yield) as a yellow oil which was used in the next step without further purification.

Step d. A mixture of (4S)—N-(3-chloro-4-fluoro-phenyl)-N-methyl-2-oxo-oxazolidine-4-carboxamide (0.1 g, 0.37 mmol), 2-chloro-6-methyl-4-(2,2,2-trifluoro-1-methyl-ethyl)pyridine (100 mg, 0.45 mmol), Xantphos (32 mg, 0.055 mmol), Pd$_2$(dba)$_3$ (33 mg, 0.037 mmol) and Cs$_2$CO$_3$ (239 mg, 0.73 mmol) in dioxane (1 mL) was stirred at 100° C. for 2 h under N$_2$ atmosphere. Upon completion, the reaction mixture was filtered and concentrated under vacuum. The residue was purified by prep-HPLC and further purified by prep-TLC (50% EtOAc in PE) to give the title compound (14 mg, 8% yield) as an off-white solid.

m/z ES+[M+H]$^+$ 460.1; $^1$H NMR (400 MHz, CD$_3$OD) δ ppm 8.01 (d, J=2.8 Hz, 1H), 7.80 (d, J=4.8 Hz, 1H), 7.55-7.48 (m, 1H), 7.44 (t, J=8.8 Hz, 1H), 7.00 (s, 1H), 5.19-5.06 (m, 1H), 4.45-4.39 (m, 1H), 4.39-4.32 (m, 1H), 3.69-3.56 (m, 1H), 3.28 (s, 3H), 2.55 (s, 3H), 1.48 (d, J=7.2 Hz, 3H).

Example 125

(S)—N-(3-Chloro-4-fluorophenyl)-3-(4-(1,1-difluoroethyl)-6-methylpyridin-2-yl)-N-ethyl-2-oxooxazolidine-4-carboxamide

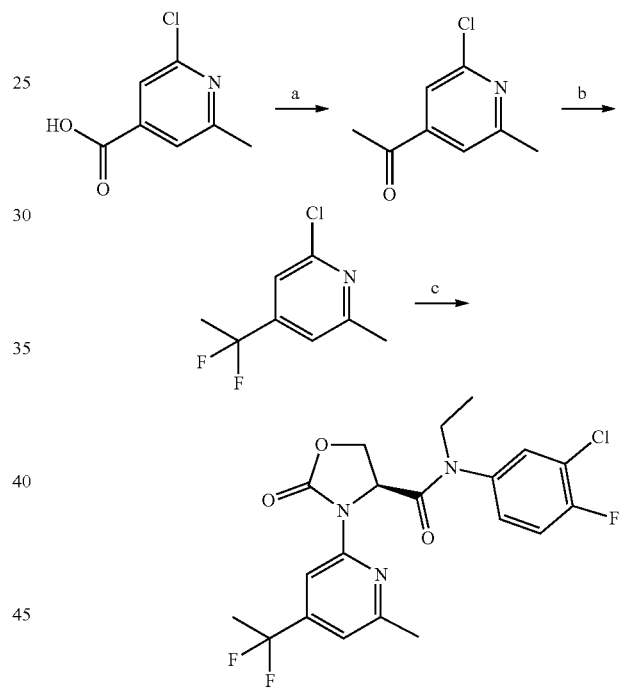

Step a. To a solution of 2-chloro-6-methyl-pyridine-4-carboxylic acid (2.5 g, 14.6 mmol) in THF (10 mL) was added methylmagnesium iodide (33.5 mmol, 3 M) dropwise at 0° C. under N$_2$ atmosphere and then stirred at 0° C. for 12 h. Upon completion, the reaction mixture was diluted with water (100 mL) and extracted with EtOAc (50 mL×3). The combined organic layers were washed with brine (50 mL), dried and evaporated. The residue was purified by column chromatography (5-20% EtOAc in PE) to give 1-(2-chloro-6-methyl-4-pyridyl)ethanone (2.0 g, 79% yield) as a red oil.

m/z ES+[M+H]$^+$ 169.9; $^1$H NMR (400 MHz, CDCl$_3$) δ ppm 7.49 (s, 1H), 7.43 (s, 1H), 2.55 (s, 3H), 2.53 (s, 3H).

Step b. A mixture of 1-(2-chloro-6-methyl-4-pyridyl)ethanone (300 mg, 1.8 mmol) and DAST (2.9 g, 17.7 mmol) in EtOH (0.05 mL) and DCM (2.34 mL) was degassed and purged with N$_2$ 3 times and then stirred at rt for 12 h. Upon completion, the reaction mixture was quenched with sat. aq. NaHCO$_3$ (100 mL) at 0° C. and then extracted with EtOAc (50 mL×3). The combined organic layers were washed with brine (50 mL), dried and evaporated. The residue was purified by prep-TLC (20% EtOAc in PE) to give 2-chloro-4-(1,1-difluoroethyl)-6-methyl-pyridine (200 mg, 59% yield) as a red oil.

$^1$H NMR (400 MHz, CDCl$_3$) δ ppm 7.26 (s, 1H), 7.18 (s, 1H), 2.60 (s, 3H), 1.89 (t, J=18.0 Hz, 3H).

Step c. To a solution of (4S)—N-(3-chloro-4-fluorophenyl)-N-ethyl-2-oxo-oxazolidine-4-carboxamide (60 mg, 0.21 mmol), 2-chloro-4-(1,1-difluoroethyl)-6-methyl-pyridine (60 mg, 0.31 mmol), Pd$_2$(dba)$_3$ (19 mg, 0.021 mmol), Cs$_2$CO$_3$ (136 mg, 0.42 mmol) in dioxane (5 mL) was added Xantphos (24 mg, 0.042 mmol). The mixture was degassed and purged with N$_2$ three times and then stirred at 120° C. for 2 h. On completion, the mixture was diluted with water (30 mL) and extracted with EtOAc (30 mL×2). The combined organic layers were washed with brine (30 mL), dried and evaporated. The obtained residue was purified by prep-HPLC to give the title compound (36 mg, 39% yield) as a yellow solid.

m/z ES+[M+H]$^+$ 442.0; $^1$H NMR (400 MHz, CDCl$_3$) δ ppm 8.19 (s, 1H), 7.83-7.46 (m, 1H), 7.39-7.23 (m, 2H), 7.04 (s, 1H), 5.08 (dd, J=5.6, 8.4 Hz, 1H), 4.33-4.22 (m, 2H), 4.00-3.90 (m, 1H), 3.65-3.55 (m, 1H), 2.59 (s, 3H), 1.91 (t, J=18.4 Hz, 3H), 1.18 (t, J=7.2 Hz, 3H)

Example 126

(S)—N-(1H-Indol-6-yl)-N-methyl-3-(6-methyl-4-(trifluoromethyl)pyridin-2-yl)-2-oxooxazolidine-4-carboxamide

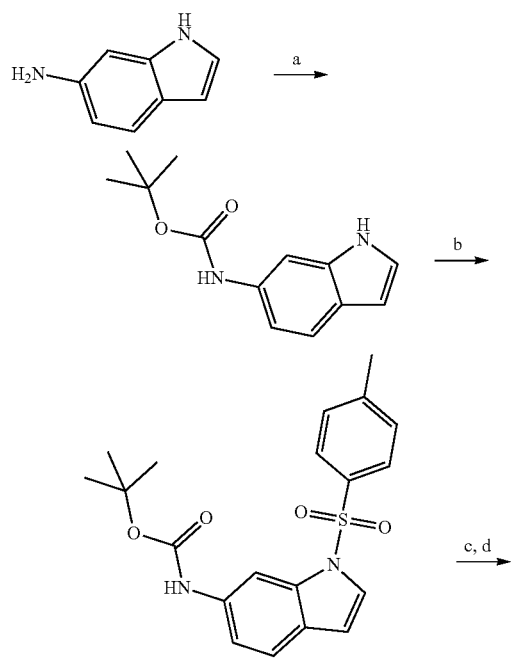

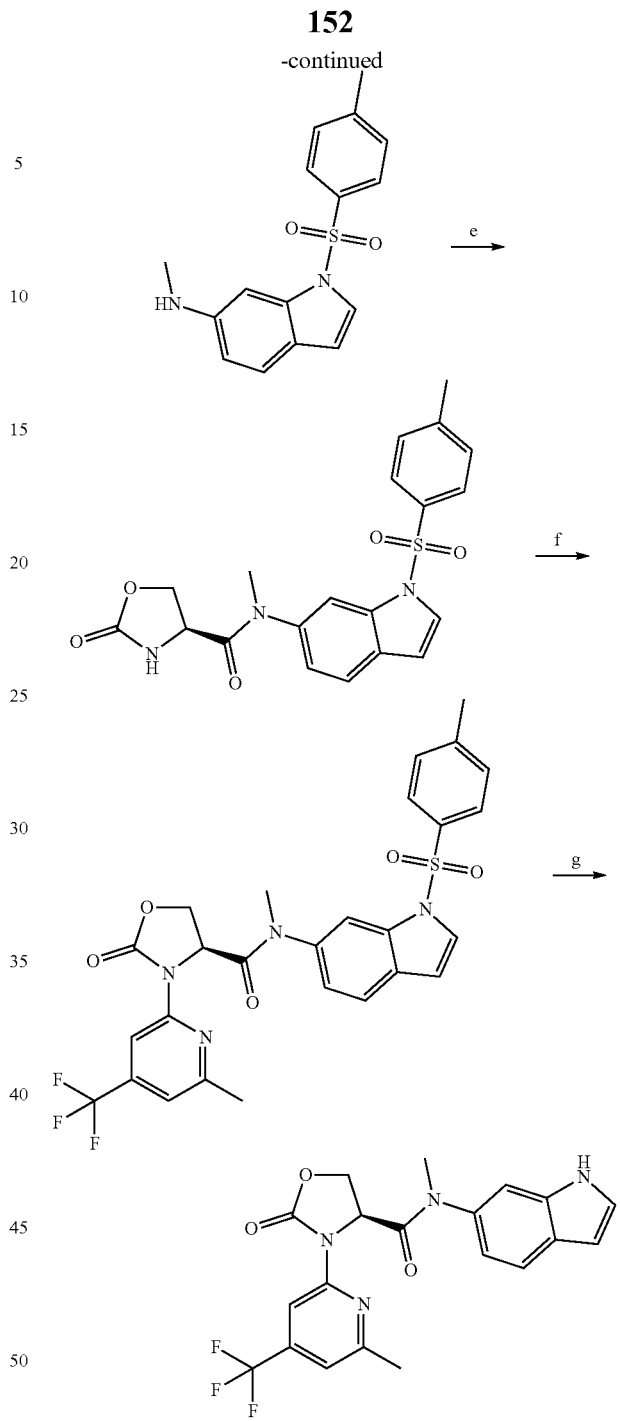

Step a. To a stirred solution of 1H-indol-6-amine (1.12 g, 8.47 mmol) in THF (6 mL) was added (Boc)$_2$O (1.94 g, 8.90 mmol) followed by sat. aq. NaHCO$_3$ (6 mL) and the reaction was stirred at 30° C. for 18 h. Upon completion, the mixture was quenched with water (30 mL) and extracted with EtOAc (30 mL×2). The combined organic layers were washed with brine (30 mL), dried over Na$_2$SO$_4$ and evaporated. The residue was purified by column chromatography (20% EtOAc in PE) to give tert-butyl 1H-indol-6-yl-carbamate (1.6 g, 77% yield) as a white solid.

m/z ES+[M+Na]$^+$255.0; $^1$H NMR (400 MHz, DMSO-d6) δ ppm 10.93 (s, 1H), 9.20 (s, 1H), 7.74 (s, 1H), 7.41 (d, J=8.4 Hz, 1H), 7.29-7.22 (m, 1H), 7.04 (dd, J=1.6, 8.4 Hz, 1H), 6.36 (t, J=2.0 Hz, 1H), 1.54 (s, 9H).

Step b. To a suspension of NaOH (1.21 g, 30 mmol) in dry DCM (7 mL) at −20° C. under N₂ atmosphere was added tert-butyl 1H-indol-6-ylcarbamate (700 mg, 3.01 mmol), TBAB (48 mg, 0.15 mmol) and p-toluenesulfonyl chloride (5.75 g, 30 mmol) sequentially. The resulting mixture was stirred under N₂ atmosphere at −20° C. for 3 h. Then the mixture was slowly warmed to rt and stirred for 9 h. Upon completion, the mixture was diluted with water (100 mL), extracted with EtOAc (100 mL×2). The combined organic layers were washed with brine (80 mL), dried and evaporated. The residue was purified by column chromatography (10% EtOAc in PE) to give tert-butyl (1-tosyl-1H-indol-6-yl)carbamate (0.9 g, 77% yield) as a white solid.

m/z ES+[M+Na]⁺409.1

Step c. To a solution of tert-butyl (1-tosyl-1H-indol-6-yl) carbamate (0.9 g, 2.33 mmol) in DMF (5 mL) was added NaH (112 mg, 2.8 mmol, 60% dispersion in mineral oil) at 0° C. The mixture was stirred at 0° C. for 30 min. Methyl iodide (496 mg, 3.5 mmol) was added to the mixture and the reaction stirred at 30° C. for 12 h. Upon completion, the mixture was quenched with water (50 mL) and extracted with EtOAc (50 mL×2). The combined organic layers were washed with brine (50 mL), dried over Na₂SO₄ and evaporated. The residue was purified by column chromatography (25% EtOAc in PE) to give tert-butyl methyl (1-tosyl-1H-indol-6-yl)carbamate (820 mg, 88% yield) as a white solid.

Step d. To a solution of tert-butyl methyl (1-tosyl-1H-indol-6-yl)carbamate (820 mg, 2 mmol) in dioxane (2 mL) was added HCl/dioxane (4 M, 2 mL). The mixture was stirred at rt for 1 h. Upon completion, the mixture was evaporated. The obtained residue was treated with sat. aq. Na₂CO₃ (20 mL) and extracted with EtOAc (20 mL×3). The combined organic layers were dried and evaporated to give N-methyl-1-tosyl-1H-indol-6-amine (600 mg, crude) as a yellow oil which was used in the next step without further purification.

Step e. (i) To a solution of (S)-2-oxooxazolidine-4-carboxylic acid (350 mg, 2.67 mmol) and DMF (2 mg, 0.027 mmol) in DCM (5 mL) was added oxalyl chloride (678 mg, 5.34 mmol) at 0° C. The mixture was stirred at 0° C. for 1 h. Upon completion, the mixture was concentrated to give (S)-2-oxooxazolidine-4-carbonyl chloride (399 mg, crude) as a yellow solid which was used in the next step without further purification.

(ii) To a solution of N-methyl-1-tosyl-1H-indol-6-amine (600 mg, 2.00 mmol) and TEA (404 mg, 4.00 mmol) in DCM (6 mL) was added a solution of (S)-2-oxooxazolidine-4-carbonyl chloride (358 mg, 2.40 mmol) in DCM (3 mL) dropwise at 0° C. The mixture was stirred at 0° C. for 1 h. Upon completion, the mixture was quenched with water (30 mL) and extracted with EtOAc (30 mL×2). The combined organic layers were washed with brine (30 mL), dried over Na₂SO₄ and evaporated. The residue was purified by column chromatography (25% EtOAc in PE) to give (S)—N-methyl-2-oxo-N-(1-tosyl-1H-indol-6-yl)oxazolidine-4-carboxamide (500 mg, 42% yield) as a white solid.

m/z ES+[M+H]⁺ 414.0

Step f. To a solution of (S)—N-methyl-2-oxo-N-(1-tosyl-1H-indol-6-yl)oxazolidine-4-carboxamide (200 mg, 0.48 mmol), 2-bromo-6-methyl-4-(trifluoromethyl)pyridine (151 mg, 0.63 mmol), Pd₂(dba)₃ (44 mg, 0.048 mmol), XantPhos (56 mg, 0.097 mmol) in dioxane (2 mL) was added Cs₂CO₃ (315 mg, 0.97 mmol). The mixture was degassed and purged with N₂ 3 times and then stirred at 100° C. for 1 h. Upon completion, the mixture was diluted with water (30 mL) and extracted with EtOAc (30 mL×2). The combined organic layers were washed with brine (30 mL), dried and evaporated. The residue was purified by column chromatography (35% EtOAc in PE) to give (S)—N-methyl-3-(6-methyl-4-(trifluoromethyl)-pyridin-2-yl)-2-oxo-N-(1-tosyl-1H-indol-6-yl) oxazolidine-4-carboxamide (160 mg, 56% yield) as a white solid.

m/z ES+[M+H]⁺ 573.1; ¹H NMR (400 MHz, CD₃OD) δ ppm 8.28 (s, 1H), 8.21-8.08 (m, 1H), 7.86-7.73 (m, 4H), 7.44-7.29 (m, 2H), 7.21 (br s, 2H), 6.85 (d, J=3.2 Hz, 1H), 5.04 (dd, J=4.4, 9.2 Hz, 1H), 4.44 (dd, J=4.4, 8.8 Hz, 1H), 4.09 (br t, J=8.8 Hz, 1H), 3.38 (s, 3H), 2.76 (br s, 3H), 2.32 (s, 3H).

Step g. To a solution of (S)—N-methyl-3-(6-methyl-4-(trifluoromethyl)pyridin-2-yl)-2-oxo-N-(1-tosyl-1H-indol-6-yl)oxazolidine-4-carboxamide (100 mg, 0.17 mmol) in DMF (1 mL) was added CsF (53 mg, 0.35 mmol). The mixture was stirred at 100° C. for 12 h. Upon completion, the mixture was diluted with water (30 mL) and then extracted with EtOAc (30 mL×2). The combined organic layers were washed with brine (30 mL), dried and evaporated. The residue was purified by prep-HPLC to give the title compound (20 mg, 27% yield) as a yellow solid.

m/z ES+[M+H]⁺ 419.3; ¹H NMR (400 MHz, CD₃OD) δ ppm 8.26 (s, 1H), 7.73 (d, J=8.4 Hz, 1H), 7.64-7.44 (m, 1H), 7.39 (d, J=3.2 Hz, 1H), 7.27 (s, 1H), 7.24-7.03 (m, 1H), 6.55 (d, J=3.2 Hz, 1H), 5.22 (dd, J=4.4, 9.2 Hz, 1H), 4.50 (dd, J=4.4, 9.2 Hz, 1H), 4.32 (t, J=9.2 Hz, 1H), 3.38 (s, 3H), 2.71 (s, 3H).

Example 127

(S)—N-Methyl-3-(6-methyl-4-(trifluoromethyl)pyridin-2-yl)-2-oxo-N-(1H-pyrrolo[2,3-b]pyridin-6-yl) oxazolidine-4-carboxamide

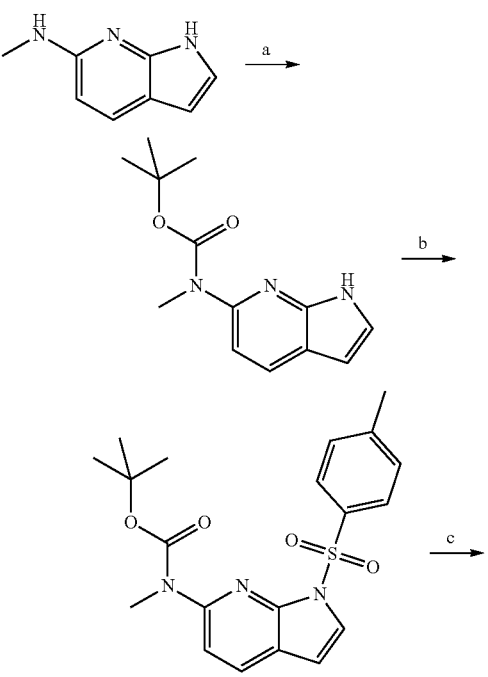

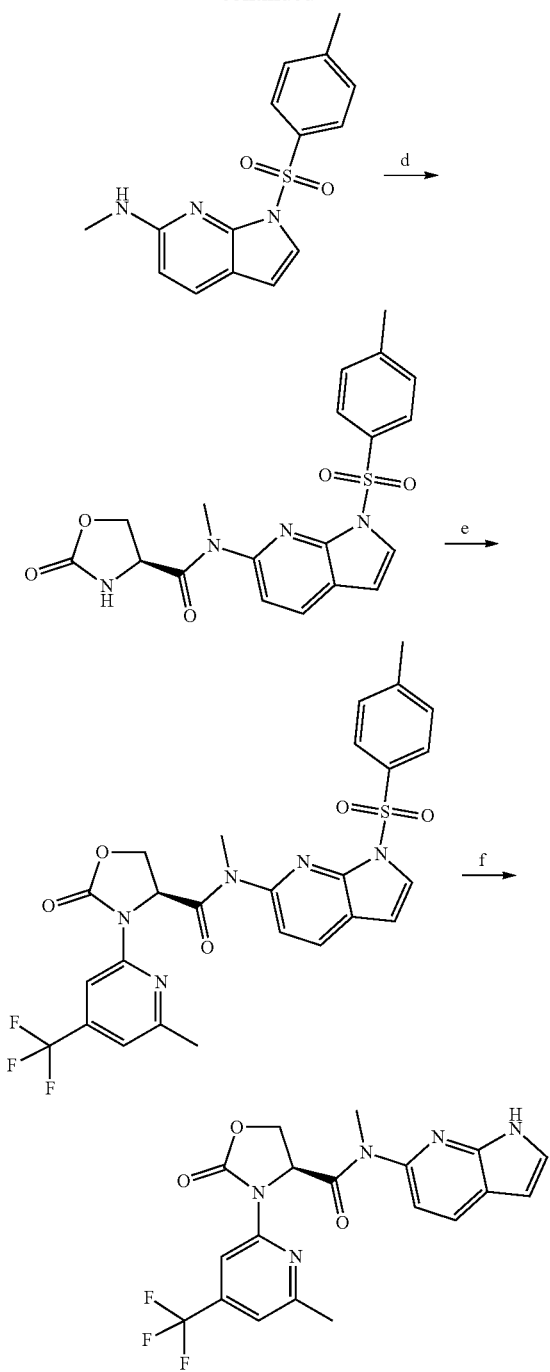

$^1$H NMR (400 MHz, DMSO-d6) δ ppm 11.57 (br s, 1H), 7.90 (d, J=8.4 Hz, 1H), 7.39 (t, J=2.8 Hz, 1H), 7.17 (d, J=8.4 Hz, 1H), 6.44-6.38 (m, 1H), 3.29 (s, 3H), 1.44 (s, 9H)

Step b. To a suspension of NaOH (712 mg, 17.79 mmol) in dry DCM (5 mL) at −20° C. under N$_2$ atmosphere was added tert-butyl methyl(1H-pyrrolo[2,3-b]pyridin-6-yl)carbamate (440 mg, 1.78 mmol), TBAB (28.7 mg, 0.089 mmol) and p-toluenesulfonyl chloride (3.39 g, 17.79 mmol) sequentially. The resulting mixture was stirred at −20° C. for 3 h and then rt for 9 h. Upon completion, the mixture was diluted with water (30 mL) and extracted with EtOAc (30 mL×2). The combined organic layers were washed with brine (30 mL), dried over Na$_2$SO$_4$ and evaporated. The residue was purified by column chromatography (15% EtOAc in PE) to give tert-butyl methyl(1-tosyl-1H-pyrrolo[2,3-b]pyridin-6-yl)carbamate (600 mg, 88% yield) as a white solid.

m/z ES+[M+Na]$^+$424.0

Step c. To a solution of tert-butyl methyl(1-tosyl-1H-pyrrolo[2,3-b]pyridin-6-yl)carbamate (600 mg, 1.49 mmol) in dioxane (5 mL) was added HCl/dioxane (4 M, 5 mL). The mixture was stirred at rt for 1 h. Upon completion, the mixture was evaporated. The obtained residue was treated with sat. aq. Na$_2$CO$_3$ (20 mL) and extracted with EtOAc (20 mL×3). The combined organic layers were dried over Na$_2$SO$_4$ and evaporated to give N-methyl-1-tosyl-1H-pyrrolo[2,3-b]pyridin-6-amine (420 mg, crude) as a yellow oil which was used in the next step without further purification.

m/z ES+[M+H]$^+$ 302.1

Step d. To a solution of (S)-2-oxooxazolidine-4-carboxylic acid (201 mg, 1.53 mmol) in MeCN (1 mL) was added Ghosez's reagent (CAS Number 26189-59-3; 372 mg, 2.79 mmol) in MeCN (1 mL) dropwise at 0° C. The mixture was stirred at 0° C. for 1 h. Then the mixture was added dropwise into a solution of N-methyl-1-tosyl-1H-pyrrolo[2,3-b]pyridin-6-amine (420 mg, 1.39 mmol), DIPEA (216 mg, 1.67 mmol) in MeCN (3 mL) at 0° C. The mixture was stirred at 0° C. for 30 min. Upon completion, the mixture was quenched with water (50 mL) and extracted with EtOAc (50 mL×2). The combined organic layers were washed with brine (50 mL), dried and evaporated. The residue was purified by column chromatography (10-50% EtOAc in PE) to give (S)—N-methyl-2-oxo-N-(1-tosyl-1H-pyrrolo[2,3-b]pyridin-6-yl)oxazolidine-4-carboxamide (70 mg, 12% yield) as a white solid.

m/z ES+[M+H]$^+$ 415.2

Step e. To a solution of 2-bromo-6-methyl-4-(trifluoromethyl)-pyridine (42 mg, 0.17 mmol), (S)—N-methyl-2-oxo-N-(1-tosyl-1H-pyrrolo[2,3-b]pyridin-6-yl)-oxazolidine-4-carboxamide (60 mg, 0.14 mmol), Pd$_2$(dba)$_3$ (13 mg, 0.014 mmol) and XantPhos (17 mg, 0.029 mmol) in dioxane (2 mL) was added Cs$_2$CO$_3$ (94 mg, 0.29 mmol). The mixture was degassed and purged with N$_2$ 3 times, and then stirred at 80° C. for 1 h. Upon completion, the mixture was quenched with water (30 mL) and extracted with EtOAc (30 mL×2). The combined organic layers were washed with brine (30 mL), dried over Na$_2$SO$_4$ and evaporated. The residue was purified by prep-TLC (50% EtOAc in PE) to give (S)—N-methyl-3-(6-methyl-4-(trifluoromethyl)pyridin-2-yl)-2-oxo-N-(1-tosyl-1H-pyrrolo[2,3-b]pyridin-6-yl) oxazolidine-4-carboxamide (40 mg, 43% yield) as a white solid.

m/z ES+[M+H]$^+$ 574.0

Step a. To a stirred solution of N-methyl-1H-pyrrolo[2,3-b]pyridin-6-amine (400 mg, 2.72 mmol) in THF (5 mL) was added (Boc)$_2$O (623 mg, 2.85 mmol) followed by sat. Na$_2$CO$_3$ (3.46 g, 0.45 mL, 10% aq. solution) and the reaction was stirred at 1500 for 18 h and at 40° C. for 78 h. On completion, the mixture was diluted with water (30 mL) and extracted with EtOAc (30 mL×3). The combined organic layers were washed with brine (30 mL), dried and evaporated. The residue was purified by column chromatography (25% EtOAc in PE) to give tert-butyl methyl(1H-pyrrolo[2,3-b]pyridin-6-yl)carbamate (440 mg, 77% yield) as a white solid.

Step f. To a solution of (S)—N-methyl-3-(6-methyl-4-(trifluoromethyl)pyridin-2-yl)-2-oxo-N-(1-tosyl-1H-pyrrolo[2,3-b]pyridin-6-yl)oxazolidine-4-carboxamide (30 mg, 0.047 mmol) in THF (2 mL) was added TBAF (1 M in THF, 0.24 mL). The mixture was stirred at 10° C. for 1 h. Upon completion, the mixture was diluted with water (30 mL) and extracted with EtOAc (30 mL×2). The combined organic layers were washed with brine (30 mL), dried over Na₂SO₄ and evaporated. The residue was purified by prep-HPLC to give the title compound (4.4 mg, 22% yield) as a white solid.

m/z ES+[M+H]⁺ 420.0; ¹H NMR (400 MHz, CD₃OD) δ ppm 8.23 (s, 1H), 8.16 (d, J=8.4 Hz, 1H), 7.46 (d, J=3.2 Hz, 1H), 7.27 (d, J=8.4 Hz, 1H), 7.21 (s, 1H), 6.56 (d, J=3.2 Hz, 1H), 5.18 (dd, J=5.2, 8.4 Hz, 1H), 4.80-4.73 (m, 2H), 3.46 (s, 3H), 2.54 (s, 3H)

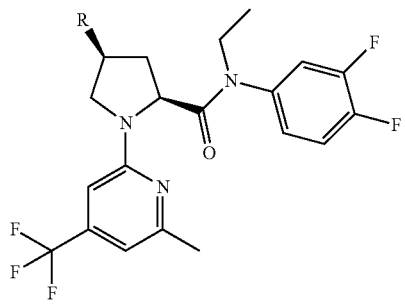

The Examples in Table 7 were prepared by a procedure similar to that described for the synthesis of Example 42.

TABLE 7

| Example Number | R | Name | Amine CAS No. | ¹H NMR (400 MHz) δ ppm | MI |
|---|---|---|---|---|---|
| 128 | (morpholine with CH₂OH) | (2S,4S)-N-(3,4-Difluorophenyl)-N-ethyl-4-(2-(hydroxymethyl)-morpholino)-1-(6-methyl-4-(trifluoromethyl)pyridin-2-yl)pyrrolidine-2-carboxamide | 103003-01-6 | (DMSO-d6) 7.72-7.53 (m, 2H), 7.50-7.36 (m, 1H), 6.73 (s, 1H), 6.68-6.53 (m, 1H), 4.73-4.63 (m, 1H), 4.34-4.24 (m, 1H), 3.87-3.72 (m, 3H), 3.54-3.41 (m, 4H), 3.24-3.16 (m, 1H), 2.88-2.79 (m, 1H), 2.74-2.66 (m, 2H), 2.44 (s, 3H), 2.43-2.38 (m, 1H), 2.28-2.16 (m, 1H), 2.13-1.97 (m, 1H), 1.89-1.63 (m, 2H), 1.02 (t, J = 7.2 Hz, 3H) | 529.0 |
| 129 | (3-hydroxypyrrolidine) | (3S,5S)-N-(3,4-Difluorophenyl)-N-ethyl-3-hydroxy-1'-(6-methyl-4-(trifluoromethyl)pyridin-2-yl)-[1,3'-bipyrrolidine]-5'-carboxamide | 40499-83-0 | (DMSO-d6) 7.73-7.54 (m, 2H), 7.43 (br s, 1H), 6.72 (s, 1H), 6.56 (br s, 1H), 4.72 (d, J = 4.5 Hz, 1H), 4.29 (br t, J = 8.3 Hz, 1H), 4.19 (br s, 1H), 3.79 (td, J = 7.2, 14.3 Hz, 2H), 3.53-3.45 (m, 1H), 3.24-3.15 (m, 1H), 2.77-2.66 (m, 2H), 2.63-2.57 (m, 1H), 2.44 (s, 4H), 2.38-2.29 (m, 1H), 2.22-2.09 (m, 1H), 2.04-1.91 (m, 1H), 1.79-1.65 (m, 1H), 1.53 (br d, J = 3.4 Hz, 1H), 1.02 (br t, J = 7.1 Hz, 3H) | 499.2 |
| 130 | (3-hydroxyazetidine) | (2S,4S)-N-(3,4-Difluorophenyl)-N-ethyl-4-(3-hydroxyazetidin-1-yl)-1-(6-methyl-4-(trifluoromethyl)-pyridin-2-yl)pyrrolidine-2-carboxamide | 45347-82-8 | (DMSO-d6) 7.70-7.54 (m, 2H), 7.45-7.35 (m, 1H), 6.72 (s, 1H), 6.56-6.44 (m, 1H), 5.30 (d, J = 6.4 Hz, 1H), 4.40-4 10 (m, 4H), 3.88-3.73 (m, 3H), 3.32-3.27 (m, 3H), 2.93-2.74 (m, 2H), 2.47-2.39 (m, 4H), 1.06-0.97 (m, 3H) | 485.2 |
| 131 | ((3S,4R)-3-hydroxytetrahydropyran-4-yl)amino | (2S,4S)-N-(3,4-Difluorophenyl)-N-ethyl-4-(((3S,4R)-3-hydroxytetrahydro-2H-pyran-4-yl)amino)-1-(6-methyl-4-(trifluoromethyl)pyridin-2-yl)pyrrolidine-2-carboxamide | 1309081-53-5 | (DMSO-d6 + D₂O) 7.70-7.58 (m, 2H), 7.41 (br s, 1H), 6.84 (s, 1H), 6.57 (s, 1H), 4.35 (dd, J = 3.2, 8.8 Hz, 1H), 4.20 (s, 1H), 3.95-3.81 (m, 5H), 3.81-3.77 (m, 2H), 3.61-3.50 (m, 2H), 3.34-3.24 (m, 2H), 3.04 (t, J = 10.4 Hz, 1H), 2.46 (s, 3H), 2.45-2.35 (m, 2H), 2.15-2.05 (m, 1H), 1.65-1.55 (m, 1H), 1.06 (t, J = 7.2 Hz, 3H) | 529.0 |
| 132 | ((3R,4R)-4-hydroxytetrahydropyran-3-yl)amino | (2S,4S)-N-(3,4-Difluorophenyl)-N-ethyl-4-(((3R,4R)-4-hydroxytetrahydro-2H-pyran-3-yl)amino)-1-(6-methyl-4-(trifluoromethyl)pyridin-2-yl)pyrrolidine-2-carboxamide | 1350734-61-0 | (DMSO-d6) 7.72-7.56 (m, 2H), 7.47-7.35 (m, 1H), 6.72 (s, 1H), 6.50 (s, 1H), 4.78 (d, J = 5.2 Hz, 1H), 4.25 (t, J = 7.6 Hz, 1H), 3.90-3.72 (m, 4H), 3.44 (dd, J = 6.8, 13.2 Hz, 1H), 3.30-3.16 (m, 3H), 2.84 (t, J = 10.4 Hz, 1H), 2.44 (s, 3H), 2.41-2.32 (m, 1H), 2.27-2.10 (m, 2H), 1.82-1.62 (m, 2H), 1.49-1.37 (m, 1H), 1.03 (t, J = 7.2 Hz, 3H) | 529.2 |
| 133 | (((1R,2R)-2-hydroxycyclopentyl)amino) | (2S,4S)-N-(3,4-Difluorophenyl)-N-ethyl-4-(((1R,2R)-2-hydroxy-cyclopentyl)amino)-1-(6-methyl-4-(trifluoromethyl)pyridin-2-yl)-pyrrolidine-2-carboxamide | 68327-03-7 | (DMSO-d6) 7.76-7.58 (m, 2H), 7.50-7.36 (m, 1H), 6.72 (s, 1H), 6.50 (s, 1H), 4.51 (d, J = 4.0 Hz, 1H), 4.26 (t, J = 7.6 Hz, 1H), 3.80 (dd, J = 7.2, 13.6 Hz, 1H), 3.70-3.63 (m, 2H), 3.50-3.40 (m, 1H), 3.26-3.16 (m, 2H), 2.84-2.77 (m, 1H), 2.44 (s, 4H), 2.23-2.14 (m, 1H), 1.90-1.66 (m, 3H), 1.63-1.48 (m, 2H), 1.45-1.33 (m, 1H), 1.27-1.14 (m, 1H), 1.03 (t, J = 7.2 Hz, 3H). | 513.3 |
| 134 | (((1S,2R)-2-hydroxycyclopentyl)amino) | (2S,4S)-N-(3,4-Difluorophenyl)-N-ethyl-4-(((1S,2R)-2-hydroxy-cyclopentyl)amino)-1-(6-methyl-4-(trifluoromethyl)pyridin-2-yl)-pyrrolidine-2-carboxamide | 137254-03-6 | (DMSO-d6 + D₂O) 7.66-7.52 (m, 2H), 7.41-7.35 (m, 1H), 6.71 (s, 1H), 6.48 (s, 1H), 4.24 (t, J = 7.6 Hz, 1H), 4.00-3.90 (m, 2H), 3.75-3.65 (m, 1H), 3.42 (dd, J = 7.2, 13.2 Hz, 1H), 3.37-3.15 (m, 2H), 2.96-2.84 (m, 1H), 2.42 (s, 3H), 2.27-2.17 (m, 1H), 1.80-1.53 (m, 6H), 1.48-1.30 (m, 2H), 1.01 (t, J = 7.2 Hz, 3H) | 513.1 |

TABLE 7-continued

| Example Number | R | Name | Amine CAS No. | $^1$H NMR (400 MHz) δ ppm | MI |
|---|---|---|---|---|---|
| 135 | (structure: rac-tert-butyl carbamate with 3-hydroxy-pyrrolidine, N-methylamino linker) | rac-tert-Butyl (3R,4R)-3-(((3S,5S)-5-((3,4-difluorophenyl)-(ethyl)carbamoyl)-1-(6-methyl-4-(trifluoromethyl)pyridin-2-yl)-pyrrolidin-3-yl)amino)-4-hydroxy-pyrrolidine-1-carboxylate | 148214-90-8 | (DMSO-d6 + D$_2$O) 7.66-7.55 (m, 2H), 7.44-7.35 (m, 1H), 6.71 (s, 1H), 6.48 (s, 1H), 4.23 (t, J = 7.2 Hz, 1H), 3.92-3.74 (m, 4H), 3.44-3.36 (m, 3H), 3.33-3.19 (m, 2H), 3.08-3.00 (m, 3H), 2.42 (s, 3H), 2.23-2.13 (m, 1H), 1.77-1.65 (m, 1H), 1.37 (s, 9H), 1.02 (t, J = 7.2 Hz, 3H) | 614.2 |
| 136 | (structure: tert-butyl carbamate with 3-hydroxy-pyrrolidine, N-methylamino linker) | tert-Butyl (3S,4R)-3-(((3S,5S)-5-((3,4-difluorophenyl)(ethyl)-carbamoyl)-1-(6-methyl-4-(trifluoromethyl)pyridin-2-yl)-pyrrolidin-3-yl)amino)-4-hydroxy-pyrrolidine-1-carboxylate | 190792-75-7 | (DMSO-d6 + D$_2$O) 7.68-7.52 (m, 2H), 7.39 (s, 1H), 6.71 (s, 1H), 6.47 (s, 1H), 4.25 (t, J = 7.6 Hz, 1H), 4.04 (s, 1H), 3.85-3.70 (m, 2H), 3.68-3.60 (m, 1H), 3.47-3.10 (m, 8H), 2.91-2.82 (m, 1H), 2.43 (s, 3H), 2.26-2.16 (m, 1H), 1.76-1.64 (m, 1H), 1.37 (s, 9H), 1.01 (t, J = 7.2 Hz, 3H) | 614.1 |
| 137 | (structure: 5-oxopyrrolidin-3-ylamino) | (2S,4S)-N-(3,4-Difluorophenyl)-N-ethyl-1-(6-methyl-4-(trifluoromethyl)pyridin-2-yl)-4-((5-oxopyrrolidin-3-yl)amino)-pyrrolidine-2-carboxamide | 88016-17-5 | (DMSO-d6) 7.69-7.57 (m, 2H), 7.50-7.37 (m, 2H), 6.71 (s, 1H), 6.53 (s, 1H), 4.30-4.20 (m, 1H), 3.82-3.65 (m, 2H), 3.49-3.37 (m, 4H), 3.26-3.15 (m, 2H), 2.92-2.86 (m, 1H), 2.46-2.40 (m, 4H), 2.24-2.12 (m, 1H), 1.92-1.84 (m, 1H), 1.75-1.63 (m, 1H), 1.02 (t, J = 7.2 Hz, 3H) | 512.0 |
| 138 | (structure: oxetan-3-ylamino) | (2S,4S)-N-(3,4-Difluorophenyl)-N-ethyl-1-(6-methyl-4-(trifluoromethyl)pyridin-2-yl)-4-(oxetan-3-ylamino)pyrrolidine-2-carboxamide | 21635-88-1 | (CD$_3$OD) 7.61 (br s, 1H), 7.54-7.34 (m, 2H), 6.71 (s, 1H), 6.49 (s, 1H), 4.85-4.80 (m, 3H), 4.58 (s, 1H), 4.51 (t, J = 6.4 Hz, 2H), 4.42 (t, J = 7.6 Hz, 1H), 4.15-4.05 (m, 1H), 4.00-3.90 (m, 1H), 3.71-3.52 (m, 2H), 2.53-2.50 (m, 3H), 2.31-2.19 (m, 1H), 1.84-1.72 (m, 1H), 1.18 (t, J = 7.2 Hz, 3H) | 485.0 |

Example 139

(2S,4S)—N-(3,4-Difluorophenyl)-N-ethyl-4-(((3S,4R)-3-hydroxytetrahydro-2H-pyran-4-yl)(methyl)amino)-1-(6-methyl-4-(trifluoromethyl)pyridin-2-yl)pyrrolidine-2-carboxamide

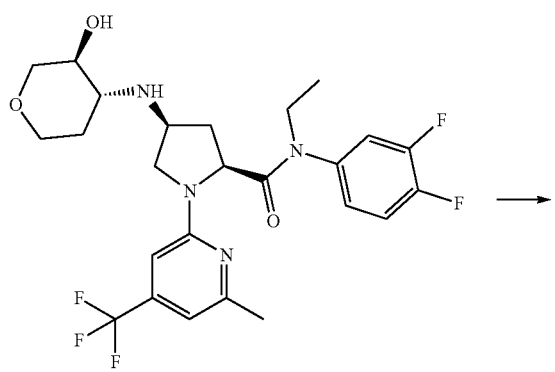

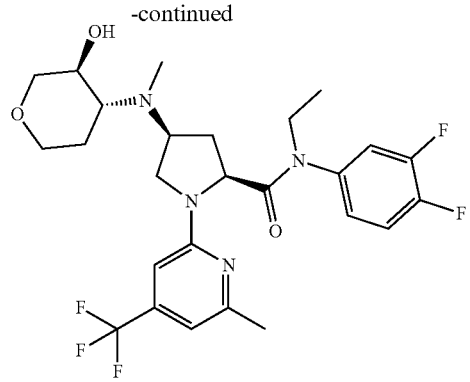

A mixture of Example 131 (30 mg, 0.057 mmol), formaldehyde (17 mg, 0.57 mmol), acetic acid (0.3 mg, 0.0057 mmol) and NaBH(OAc)$_3$ (24 mg, 0.11 mmol) in THF (2 mL) was stirred at rt for 12 h. Upon completion, the reaction mixture was diluted with water (20 mL) and extracted with EtOAc (20 mL). The organic layer was concentrated. The residue was purified by prep-HPLC to give the title compound (20 mg, 62% yield) as a white solid.

m/z ES+[M+H]$^+$ 543.2; $^1$H NMR (400 MHz, CD$_3$OD) δ ppm 7.62 (s, 1H), 7.51-7.35 (m, 2H), 6.67 (s, 1H), 6.52 (s, 1H), 4.41 (dd, J=7.2, 9.6 Hz, 1H), 3.98-3.84 (m, 3H), 3.79-3.69 (m, 1H), 3.64-3.49 (m, 2H), 3.44-3.33 (m, 3H), 3.07 (t, J=10.4 Hz, 1H), 2.65-2.54 (m, 1H), 2.50 (s, 3H), 2.31 (s, 3H), 2.29-2.22 (m, 1H), 2.06-2.01 (m, 1H), 1.72-1.54 (m, 2H), 1.16 (t, J=7.2 Hz, 3H).

The Examples in Table 8 were prepared using methods similar to those described in the synthesis of Example 139.

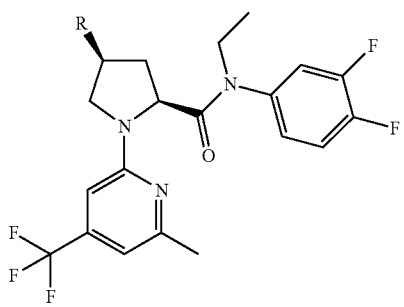

5

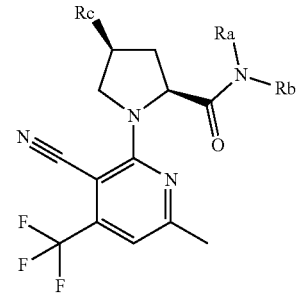

The Examples in Table 9 were prepared by a procedure similar to that described for the synthesis of Example 42.

10

TABLE 8

| Example Number | R | Name | Starting Material | ¹H NMR (400 MHz) δ ppm | MI |
|---|---|---|---|---|---|
| 140 | OH (tetrahydropyran) | (2S,4S)-N-(3,4-Difluorophenyl)-N-ethyl-4-(((3R,4R)-4-hydroxytetrahydro-2H-pyran-3-yl)(methyl)amino)-1-(6-methyl-4-(trifluoromethyl)pyridin-2-yl)pyrrolidine-2-carboxamide | Example 132 | (CD$_3$OD) 7.61 (s, 1H), 7.51-7.35 (m, 2H), 6.67 (s, 1H), 6.50 (s, 1H), 4.56 (s, 1H), 4.41 (dd, J = 7.2, 9.6 Hz, 1H), 3.99-3.75 (m, 4H), 3.73-3.65 (m, 1H), 3.64-3.42 (m, 2H), 3.41-3.32 (m, 2H), 2.59-2.42 (m, 4H), 2.38 (s, 3H), 2.32-2.22 (m, 1H), 1.99-1.83 (m, 2H), 1.65-1.50 (m, 1H), 1.15 (t, J = 7.2 Hz, 3H). | 543.2 |
| 141 | HO (cyclopentyl) | (2S,4S)-N-(3,4-Difluorophenyl)-N-ethyl-4-(((1R,2R)-2-hydroxycyclopentyl)(methyl)amino)-1-(6-methyl-4-(trifluoromethyl)pyridin-2-yl)pyrrolidine-2-carboxamide | Example 133 | (DMSO-d6) 7.73-7.56 (m, 2H), 7.44 (br s, 1H), 6.72 (s, 1H), 6.58 (brs, 1H), 4.59-4.45 (m, 1H), 4.27 (t, J = 8.4 Hz, 1H), 3.95-3.71 (m, 3H), 3.48-3.38 (m, 1H), 3.27-3.18 (m, 2H), 2.91-2.82 (m, 1H), 2.44 (s, 3H), 2.23-2.07 (m, 4H), 1.77-1.64 (m, 3H), 1.55-1.39 (m, 4H), 1.02 (t, J = 7.2 Hz, 3H) | 527.0 |
| 142 | HO (cyclopentyl) | (2S,4S)-N-(3,4-Difluorophenyl)-N-ethyl-4-(((1S,2R)-2-hydroxycyclopentyl)(methyl)amino)-1-(6-methyl-4-(trifluoromethyl)pyridin-2-yl)pyrrolidine-2-carboxamide | Example 134 | (CD$_3$OD) 7.67-7.40 (m, 3H), 6.87 (s, 1H), 6.71-6.61 (m, 1H), 4.52 (t, J = 8.0 Hz, 1H), 4.46-4.24 (m, 2H), 4.01-3.82 (m, 3H), 3.69-3.56 (m, 2H), 3.12-2.96 (m, 3H), 2.60-2.47 (m, 4H), 2.40-2.27 (m, 1H), 2.24-2.12 (m, 1H), 2.09-1.91 (m, 3H), 1.90-1.67 (m, 2H), 1.20 (t, J = 7.2 Hz, 3H) | 527.3 |
| 143 | HO, N-Boc pyrrolidine | rac-tert-Butyl (3R,4R)-3-(((3S,5S)-5-((3,4-difluorophenyl)(ethyl)carbamoyl)-1-(6-methyl-4-(trifluoromethyl)pyridin-2-yl)pyrrolidin-3-yl)(methyl)amino)-4-hydroxypyrrolidine-1-carboxylate | Example 135 | (CD$_3$OD) 7.71-7.58 (m, 1H), 7.55-7.44 (m, 2H), 6.85 (s, 1H), 6.72-6.60 (m, 1H), 4.68-4.62 (m, 1H), 4.53 (q, J = 7.2 Hz, 1H), 4.35-4.25 (m, 1H), 4.08-4.00 (m, 2H), 3.94-3.80 (m, 4H), 3.71-3.48 (m, 2H), 3.25-3.18 (m, 1H), 3.02 (s, 3H), 2.72-2.62 (m, 1H), 2.59-2.55 (m, 3H), 2.45-2.21 (m, 1H), 1.49 (s, 9H), 1.20 (dt, J = 2.4, 7.2 Hz, 3H) | 628.3 |
| 144 | HO, N-Boc pyrrolidine | tert-Butyl (3S,4R)-3-(((3S,5S)-5-((3,4-difluorophenyl)(ethyl)carbamoyl)-1-(6-methyl-4-(trifluoromethyl)pyridin-2-yl)pyrrolidin-3-yl)(methyl)amino)-4-hydroxypyrrolidine-1-carboxylate | Example 136 | (CD$_3$OD) 7.67-7.40 (m, 3H), 6.86 (s, 1H), 6.70-6.60 (m, 1H), 4.58 (br s, 1H), 4.54-4.48 (m, 1H), 4.07-3.84 (m, 6H), 3.65-3.51 (m, 4H), 3.06 (br s, 3H), 2.60-2.51 (m, 4H), 2.40-2.27 (m, 1H), 1.50 (s, 9H), 1.20 (t, J = 7.2 Hz, 3H) | 628.3 |
| 145 | oxopyrrolidinyl | (2S,4S)-N-(3,4-Difluorophenyl)-N-ethyl-4-(methyl(5-oxopyrrolidin-3-yl)amino)-1-(6-methyl-4-(trifluoromethyl)pyridin-2-yl)pyrrolidine-2-carboxamide | Example 137 | (DMSO-d6) 7.72-7.52 (m, 3H), 7.43 (br s, 1H), 6.71 (s, 1H), 6.59 (s, 1H), 4.26 (t, J = 8.4 Hz, 1H), 3.88-3.68 (m, 2H), 3.64-3.42 (m, 4H), 3.30-3.16 (m, 2H), 2.43 (s, 3H), 2.27-2.07 (m, 6H), 1.78-1.66 (m, 1H), 1.01 (t, J = 7.2 Hz, 3H) | 526.1 |
| 146 | oxetanyl | (2S,4S)-N-(3,4-Difluorophenyl)-N-ethyl-4-(methyl(oxetan-3-yl)amino)-1-(6-methyl-4-(trifluoromethyl)pyridin-2-yl)pyrrolidine-2-carboxamide | Example 138 | (DMSO-d6) 7.73-7.56 (m, 2H), 7.42 (br s, 1H), 6.72 (s, 1H), 6.57 (s, 1H), 4.54-4.45 (m, 4H), 4.25 (t, J = 8.4 Hz, 1H), 3.88-3.71 (m, 2H), 3.64 (t, J = 7.6 Hz, 1H), 3.47-3.36 (m, 1H), 3.19 (t, J = 9.6 Hz, 1H), 2.94-2.82 (m, 1H), 2.44 (s, 3H), 2.14 (s, 3H), 2.08-1.91 (m, 1H), 1.78-1.59 (m, 1H), 1.02 (t, J = 7.2 Hz, 3H) | 499.0 |

TABLE 9

| Example Number | Ra | Rb | Rc | Name | Amine CAS No. | $^1$H NMR (400 MHz) δ ppm | MI |
|---|---|---|---|---|---|---|---|
| 147 | CH$_2$CH$_3$ |  | 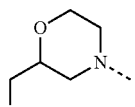 | (2S,4S)-N-(3-Chlorophenyl)-1-(3-cyano-6-methyl-4-(trifluoromethyl)pyridin-2-yl)-N-ethyl-4-(2-(hydroxymethyl)-morpholino)pyrrolidine-2-carboxamide | 103003-01-6 | (CD$_3$OD) 7.66 (br s, 1H), 7.58-7.43 (m, 3H), 6.99 (s, 1H), 4.63 (dd, J = 7.2, 10.4 Hz, 1H), 4.26-4.14 (m, 1H), 3.97-3.79 (m, 3H), 3.70-3.62 (m, 1H), 3.61-3.47 (m, 4H), 2.89 (d, J = 11.2 Hz, 0.5H), 2.83-2.71 (m, 2H), 2.66 (d, J = 12.0 Hz, 0.5H), 2.60 (s, 3H), 2.31-2.13 (m, 2H), 2.08-1.90 (m, 1H), 1.82 (dq, J = 2.4, 11.2 Hz, 1H), 1.13 (t, J = 7.2 Hz, 3H) | 552.2 |
| 148 | CH$_2$CH$_3$ |  | 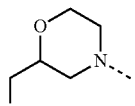 | (2S,4S)-1-(3-Cyano-6-methyl-4-(trifluoromethyl)-pyridin-2-yl)-N-(3,4-dichlorophenyl)-N-ethyl-4-(2-(hydroxymethyl)-morpholino)-pyrrolidine-2-carboxamide | 103003-01-6 | (CD$_3$OD) 7.81 (s, 1H), 7.75-7.63 (m, 1H), 7.58-7.45 (m, 1H), 7.00 (s, 1H), 4.64 (dd, J = 10.8, 6.8 Hz, 1H), 4.30-4.16 (m, 1H), 4.00-3.85 (m, 3H), 3.76-3.67 (m, 1H), 3.66-3.51 (m, 4H), 2.89 (d, J = 10.8 Hz, 0.5H), 2.87-2.74 (m, 2H), 2.66 (d, J = 11.6 Hz, 0.5H), 2.60 (s, 3H), 2.33-2.16 (m, 2H), 2.11-2.03 (m, 1H), 2.01-1.92 (m, 1H), 1.13 (t, J = 7.2 Hz, 3H) | 586.1 |
| 149 | CH$_2$CH$_3$ |  | 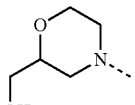 | (2S,4S)-N-(3-Chloro-4-methylphenyl)-1-(3-cyano-6-methyl-4-(trifluoromethyl)-pyridin-2-yl)-N-ethyl-4-(2-(hydroxymethyl)morpholino)pyrrolidine-2-carboxamide | 103003-01-6 | (CD$_3$OD) 7.69-7.53 (m, 1H), 7.47 (d, J = 8.0 Hz, 1H), 7.44-7.30 (m, 1H), 6.99 (s, 1H), 4.64 (dd, J = 6.8, 10.8 Hz, 1H), 4.24-4.15 (m, 1H), 3.94-3.82 (m, 3H), 3.71-3.62 (m, 1H), 3.61-3.46 (m, 4H), 2.93-2.63 (m, 3H), 2.60 (s, 3H), 2.43 (s, 3H), 2.31-2.14 (m, 2H), 2.09-1.91 (m, 1H), 1.82 (dq, J = 2.4, 11.2 Hz, 1H), 1.13 (t, J = 7.2 Hz, 3H) | 566.2 |
| 150 | CH$_2$CH$_3$ |  | 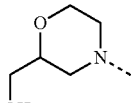 | (2S,4S)-1-(3-Cyano-6-methyl-4-(trifluoromethyl)-pyridin-2-yl)-N-ethyl-N-(4-fluoro-3-methylphenyl)-4-(2-(hydroxymethyl)morpholino)pyrrolidine-2-carboxamide | 103003-01-6 | (CD$_3$OD) 7.41 (m, 2H), 7.24 (t, J = 8.8 Hz, 1H), 7.14 (s, 1H), 4.79-4.71 (m, 1H), 4.51-4.43 (m, 1H), 4.34 (dd, J = 7.6, 10.2 Hz, 1H), 4.26-4.15 (m, 1H), 3.97-3.82 (m, 4H), 3.73-3.61 (m, 4H), 3.55-3.45 (m, 1H), 3.28-3.04 (m, 2H), 2.65 (s, 3H), 2.59-2.51 (m, 1H), 2.36 (s, 3H), 2.32-2.23 (m, 1H), 1.17 (t, J = 7.2 Hz, 3H) | 550.1 |
| 151 | CH$_3$ |  | 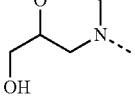 | (2S,4S)-N-(3-Chloro-4-fluorophenyl)-1-(3-cyano-6-methyl-4-(trifluoromethyl)-pyridin-2-yl)-4-(2-(hydroxy-methyl)morpholino)-N-methylpyrrolidine-2-carboxamide | 103003-01-6 | (CDCl$_3$) 7.61 (s, 1H), 7.35-7.20 (m, 2H), 6.81 (s, 1H), 4.80-4.60 (m, 1H), 4.31-4.13 (m, 1H), 3.99-3.86 (m, 2H), 3.78-3.63 (m, 3H), 3.60-3.50 (m, 1H), 3.25 (s, 3H), 2.80-2.64 (m, 3H), 2.54 (s, 3H), 2.29-2.19 (m, 1H), 2.16-2.01 (m, 3H), 1.92-1.78 (m, 1H) | 556.2 |
| 152 | CH$_2$CH$_3$ |  | 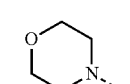 | (2S,4S)-N-(3-Chloro-4-fluorophenyl)-1-(3-cyano-6-methyl-4-(trifluoromethyl)-pyridin-2-yl)-N-ethyl-4-((S)-3-(hydroxymethyl)morpholino)pyrrolidine-2-carboxamide | 211053-50-8 | (CD$_3$OD) 7.79 (br s, 1H), 7.59-7.41 (m, 2H), 7.01 (s, 1H), 4.62 (dd, J = 7.2, 10.4 Hz, 1H), 4.16 (dd, J = 7.6, 9.2 Hz, 1H), 3.95-3.84 (m, 2H), 3.78-3.65 (m, 6H), 3.58 (dd, J = 7.2, 13.6 Hz, 1H), 3.52-3.43 (m, 1H), 2.85 (ddd, J = 4.0, 8.4, 12.0 Hz, 1H), 2.76-2.70 (m, 1H), 2.61 (s, 3H), 2.51-2.44 (m, 1H), 2.34-2.26 (m, 1H), 1.87 (q, J = 11.2 Hz, 1H), 1.15 (t, J = 7.2 Hz, 3H) | 570.0 |
| 153 | CH$_2$CH$_3$ |  | 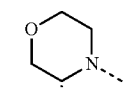 | (2S,4S)-N-(3-Chloro-4-fluorophenyl)-1-(3-cyano-6-methyl-4-(trifluoromethyl)-pyridin-2-yl)-N-ethyl-4-((R)-3-(hydroxymethyl)morpholino)pyrrolidine-2-carboxamide | 211053-49-5 | (CD$_3$OD) 7.78 (br s, 1H), 7.53 (br s, 1H), 7.49-7.42 (m, 1H), 7.01 (s, 1H), 4.67-4.54 (m, 1H), 4.19 (dd, J = 7.2, 9.2 Hz, 1H), 3.98-3.88 (m, 2H), 3.84-3.65 (m, 6H), 3.62-3.45 (m, 2H), 2.83 (ddd, J = 4.4, 7.6, 12.0 Hz, 1H), 2.69-2.63 (m, 1H), 2.61 (s, 3H), 2.58-2.53 (m, 1H), 2.22-2.13 (m, 1H), 1.87 (q, J = 11.2 Hz, 1H), 1.15 (t, J = 7.2 Hz, 3H) | 570.0 |
| 154 | CH$_2$CH$_3$ |  | 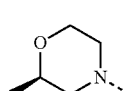 | (2S,4S)-N-(3-Chloro-4-fluorophenyl)-1-(3-cyano-6-methyl-4-(trifluoromethyl)-pyridin-2-yl)-N-ethyl-4-((S)-2-(hydroxymethyl)morpholino)pyrrolidine-2-carboxamide | 132073-83-7 | (CD$_3$OD) 7.78 (br s, 1H), 7.53 (br s, 1H), 7.49-7.40 (m, 1H), 7.02 (s, 1H), 4.64 (dd, J = 7.2, 10.4 Hz, 1H), 4.21 (dd, J = 7.6, 9.2 Hz, 1H), 3.96-3.84 (m, 3H), 3.72-3.52 (m, 5H), 2.85-2.75 (m, 3H), 2.61 (s, 3H), 2.29-2.16 (m, 2H), 2.07 (t, J = 10.8 Hz, 1H), 1.84 (q, J = 11.2 Hz, 1H), 1.15 (t, J = 7.2 Hz, 3H) | 570.0 |

TABLE 9-continued

| Example Number | Ra | Rb | Rc | Name | Amine CAS No. | 1H NMR (400 MHz) δ ppm | MI |
|---|---|---|---|---|---|---|---|
| 155 | CH₂CH₃ | 3-chloro-4-fluorophenyl | (R)-(hydroxymethyl)morpholino | (2S,4S)-N-(3-Chloro-4-fluorophenyl)-1-(3-cyano-6-methyl-4-(trifluoromethyl)-pyridin-2-yl)-N-ethyl-4-((R)-2-(hydroxymethyl)morpholino)pyrrolidine-2-carboxamide | 156925-22-3 | (CD₃OD) 7.81 (br s, 1H), 7.59 (br s, 1H), 7.53-7.45 (m, 1H), 7.15 (s, 1H), 4.79-4.73 (m, 2H), 4.50 (dd, J = 7.2, 10.4 Hz, 1H), 4.38-4.31 (m, 1H), 4.19 (dd, J = 2.8, 13.2 Hz, 1H), 3.95-3.80 (m, 4H), 3.72-3.60 (m, 4H), 3.48 (d, J = 12.0 Hz, 1H), 3.30-3.20 (m, 1H), 3.12-3.02 (m, 1H), 2.65 (s, 3H), 2.63-2.54 (m, 1H), 2.36-2.24 (m, 1H), 1.17 (t, J = 7.2 Hz, 3H) | 570.2 |

Example 156

(S)—N-(3-Chloro-4-fluorophenyl)-N-methyl-3-(6-methyl-4-(trifluoromethyl)pyridin-2-yl)-2-oxoimidazolidine-4-carboxamide

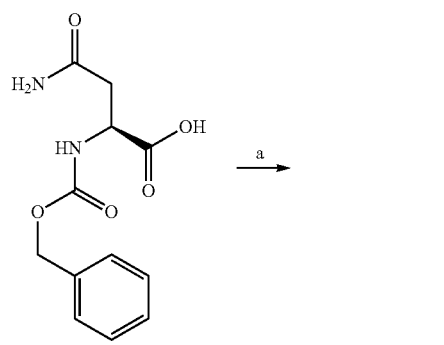

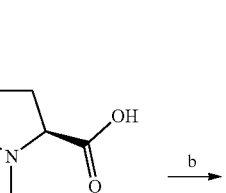

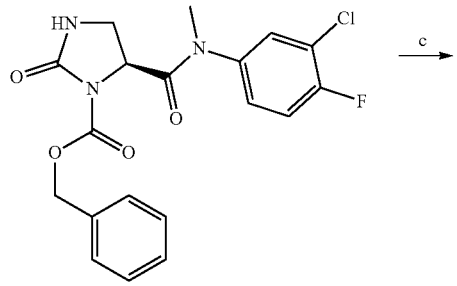

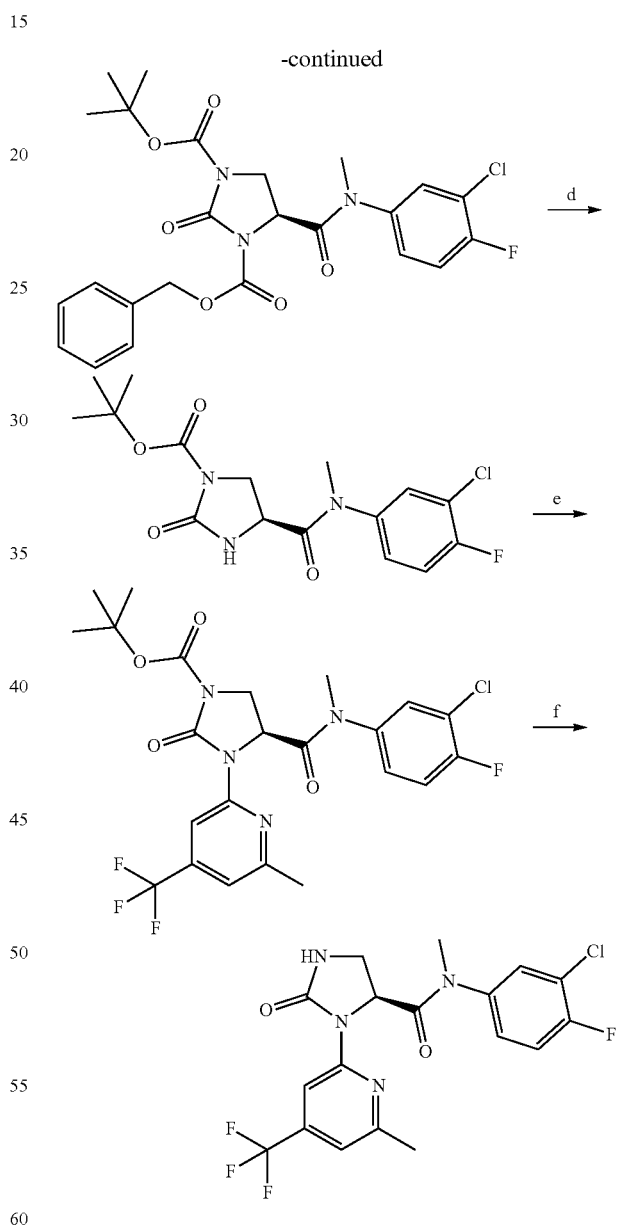

Step a. A solution of NaOH (2.98 g, 74.51 mmol) in water (60 mL) was cooled to 0° C. and slowly treated with bromine (3.60 g, 22.54 mmol) over 30 min, resulting in a clear yellow solution. Dry (S)-4-amino-2-(((benzyloxy)carbonyl) amino)-4-oxobutanoic acid (CAS Number 2304-96-3; 6 g, 22.5 mmol) was added in portions over 2 min. The resulting clear, colorless solution was heated at 55° C. for 3 h. Upon completion, the mixture was washed with methyl tert-butyl ether (50 mL×2). The aqueous phase was collected and adjusted to pH 1-2 with 6 M HCl solution and then stirred at 0° C. for 12 h. The mixture was filtered and the filter cake collected and dried to give (S)-3-((benzyloxy) carbonyl)-2-oxoimidazolidine-4-carboxylic acid (4.3 g, 72% yield) as a white solid.

m/z ES+[M+H]+ 265.0

Step b. A solution of (S)-3-((benzyloxy) carbonyl)-2-oxoimidazolidine-4-carboxylic acid (500 mg, 1.89 mmol), 3-chloro-4-fluoro-N-methylaniline (362 mg, 2.27 mmol) and T3P (4.82 g, 7.57 mmol, 50 wt. % in EtOAc) in pyridine (12 mL) was stirred at 100° C. for 16 h. Upon completion, the reaction mixture was evaporated and purified by prep-HPLC to give (S)-benzyl 5-((3-chloro-4-fluorophenyl)(methyl)carbamoyl)-2-oxoimidazolidine-1-carboxylate (400 mg, 77% yield) as a white solid.

m/z ES+[M+H]+ 406.0

Step c. A mixture of (S)-benzyl 5-((3-chloro-4-fluorophenyl)(methyl)carbamoyl)-2-oxo-imidazolidine-1-carboxylate (100 mg, 0.25 mmol) and (Boc)₂O (2 mL) was stirred at 60° C. for 2 h. DMAP (3 mg, 0.025 mmol) was added and the mixture was stirred at 60° C. for 4 h. Upon completion, the mixture was evaporated and the crude residue was purified by column chromatography (50% EtOAc in PE) to give (S)-3-benzyl 1-tert-butyl 4-((3-chloro-4-fluoro-phenyl)(methyl)carbamoyl)-2-oxoimidazolidine-1,3-dicarboxylate (150 mg, crude) as a colorless oil which was used in the next step without further purification.

m/z ES+[M+H]+ 506.2

Step d. To a solution of (S)-3-benzyl 1-tert-butyl 4-((3-chloro-4-fluorophenyl)(methyl)-carbamoyl)-2-oxoimidazolidine-1,3-dicarboxylate (140 mg, 0.17 mmol) in MeOH (5 mL) was added PtO₂ (3.8 mg, 0.017 mmol). The mixture was purged with H₂ 3 times and stirred at 30° C. for 2 h. Upon completion, the mixture was filtered, washed with MeOH (20 mL) and the filtrate evaporated to give (S)-tert-butyl 4-((3-chloro-4-fluorophenyl) (methyl) carbamoyl)-2-oxoimidazolidine-1-carboxylate (90 mg, crude) as a light-yellow oil which was used in the next step without further purification.

m/z ES+[M+H]+ 371.9

Step e. To a solution of (S)-tert-butyl 4-((3-chloro-4-fluorophenyl) (methyl) carbamoyl)-2-oxoimidazolidine-1-carboxylate (90 mg, 0.24 mmol), 2-bromo-6-methyl-4-(trifluoromethyl)-pyridine (64 mg, 0.27 mmol), Pd₂(dba)₃ (22 mg, 0.024 mmol), XantPhos (21 mg, 0.036 mmol) in dioxane (1 mL) was added Cs₂CO₃ (158 mg, 0.48 mmol). The mixture was purged with N₂ 3 times and then stirred at 100° C. for 2 h. Upon completion, the mixture was quenched with water (30 mL) and extracted with EtOAc (30 mL×2). The combined organic layers were washed with brine (30 mL), dried over Na₂SO₄ and evaporated. The residue was purified by prep-HPLC to give (S)-tert-butyl 4-((3-chloro-4-fluorophenyl)(methyl)carbamoyl)-3-(6-methyl-4-(trifluoromethyl)pyridin-2-yl)-2-oxoimidazolidine-1-carboxylate (40 mg, 31% yield) as a white solid.

m/z ES+[M+H]+ 531.1; ¹H NMR (400 MHz, CD₃OD) δ ppm 8.40 (s, 1H), 7.86 (dd, J=2.4, 6.4 Hz, 1H), 7.62-7.55 (m, 1H), 7.53-7.45 (m, 1H), 7.26 (s, 1H), 5.01 (dd, J=4.0, 10.0 Hz, 1H), 3.94-3.86 (m, 1H), 3.85-3.77 (m, 1H), 3.31 (s, 3H), 2.66 (s, 3H), 1.57 (s, 9H).

Step f. To a solution of (S)-tert-butyl 4-((3-chloro-4-fluorophenyl)(methyl)carbamoyl)-3-(6-methyl-4-(trifluoromethyl)pyridin-2-yl)-2-oxoimidazolidine-1-carboxylate (30 mg, 0.057 mmol) in dioxane (1 mL) was added HCl/dioxane (4 M, 0.5 mL). The mixture was stirred at 30° C. for 2 h. Upon completion, the reaction mixture was evaporated. The residue was purified by prep-HPLC to give the title compound (6.1 mg, 25% yield) as an off-white solid.

m/z ES+[M+H]+ 430.8; ¹H NMR (400 MHz, CD₃OD) δ ppm 8.35 (s, 1H), 7.80 (dd, J=2.0, 6.4 Hz, 1H), 7.57-7.50 (m, 1H), 7.49-7.42 (m, 1H), 7.12 (s, 1H), 5.05 (dd, J=5.2, 9.6 Hz, 1H), 3.55-3.45 (m, 2H), 3.30 (s, 3H), 2.62 (s, 3H)

Example 157

(S)—N-(3-Chloro-4-fluorophenyl)-N-ethyl-3-(6-methyl-4-(trifluoromethyl)pyridin-2-yl)-2-oxoimidazolidine-4-carboxamide

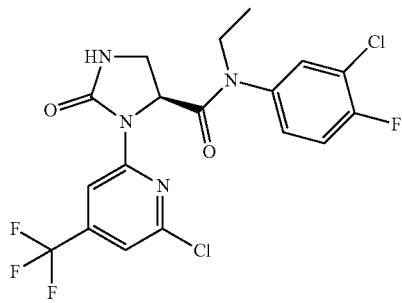 [SMILES: CCN(C(=O)[C@@H]1CNC(=O)N1c1cc(C(F)(F)F)cc(Cl)n1)c1ccc(F)c(Cl)c1]

The title compound was prepared in a similar manner to Example 156.

m/z ES+[M+H]+ 445.1; ¹H NMR (400 MHz, CD₃OD) δ ppm 8.40-8.24 (m, 1H), 7.84-7.62 (m, 1H), 7.51-7.35 (m, 2H), 7.11 (d, J=10.0 Hz, 1H), 5.03-4.98 (m, 1H), 4.35-4.10 (m, 1H), 3.93-3.61 (m, 2H), 3.53-3.40 (m, 1H), 2.65-2.52 (m, 3H), 1.17 (dt, J=4.8, 7.2 Hz, 3H).

Example 158

(S)—N-(3-Chloro-2,4-difluorophenyl)-N-methyl-3-(6-methyl-4-(trifluoromethyl)pyridin-2-yl)-2-oxoimidazolidine-4-carboxamide

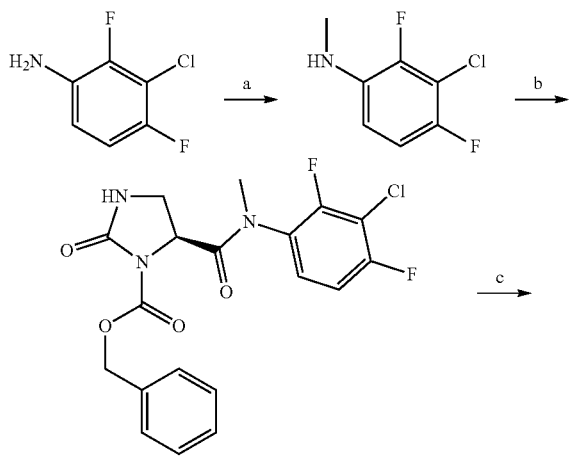

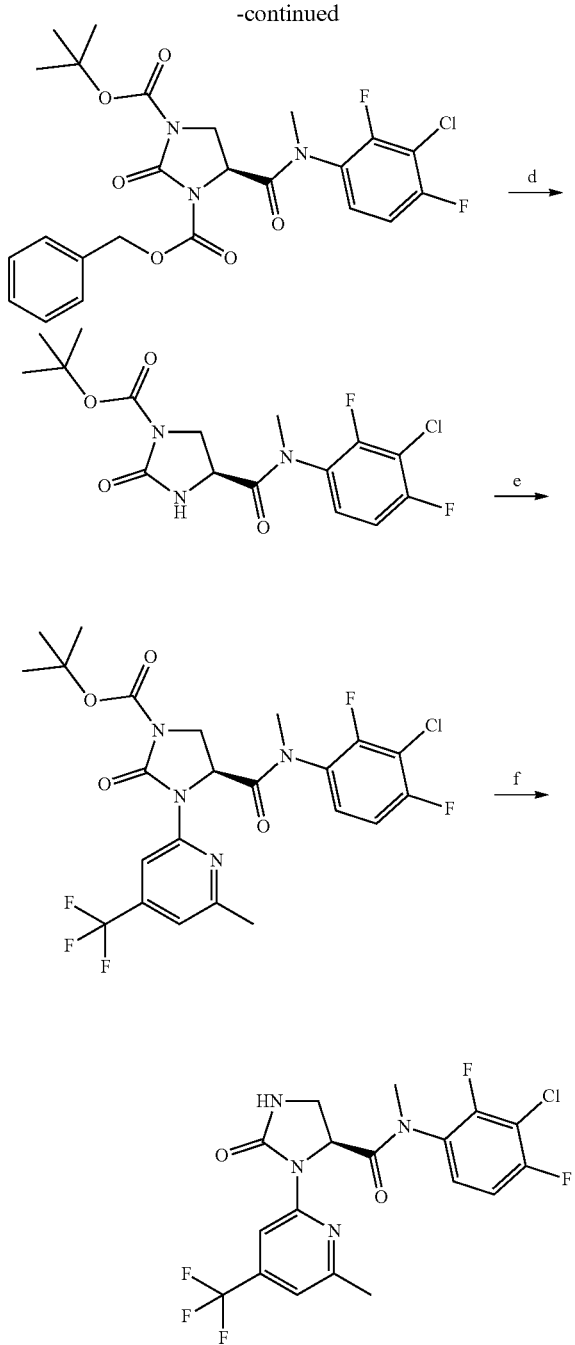

-continued

MeCN (5 mL) was added Ghosez's reagent (CAS Number 26189-59-3; 307 mg, 4.54 mmol) in MeCN (5 mL) dropwise at 0° C. The mixture was stirred at 0° C. for 1 h to obtain a clear solution. The resulting solution was added dropwise into a solution of 3-chloro-2,4-difluoro-N-methylaniline (484 mg, 2.72 mmol) and DIPEA (352 mg, 2.72 mmol) in MeCN (5 mL) at 0° C. and the mixture was stirred at 0° C. for 30 min. Upon completion, the mixture was evaporated and purified by column chromatography (25% EtOAc in PE) to give (S)-benzyl 5-((3-chloro-2,4-difluorophenyl)(methyl) carbamoyl)-2-oxoimidazolidine-1-carboxylate (500 mg, 52% yield) as a yellow solid.

Step c. A mixture of (S)-benzyl 5-((3-chloro-2,4-difluorophenyl)(methyl)carbamoyl)-2-oxoimidazolidine-1-carboxylate (500 mg, 1.18 mmol), (Boc)$_2$O (4.75 g, 21.76 mmol) and DMAP (14 mg, 0.12 mmol) was heated to 60° C. and stirred for 2 h. Upon completion, the mixture was concentrated and purified by column chromatography (25% EtOAc in PE) to give (S)-3-benzyl 1-tert-butyl 4-((3-chloro-2,4-difluorophenyl)(methyl)-carbamoyl)-2-oxo-imidazolidine-1,3-dicarboxylate (500 mg, 81% yield) as a yellow solid.

Step d. To a solution of (S)-3-benzyl 1-tert-butyl 4-((3-chloro-2,4-difluorophenyl)(methyl)-carbamoyl)-2-oxoimidazolidine-1,3-dicarboxylate (400 mg, 0.76 mmol) in THF (4 mL) was added PtO$_2$ (40 mg, 0.18 mmol). The mixture was stirred at rt for 1 h under H$_2$ atmosphere (15 psi). Upon completion, the mixture was filtered, washed with MeOH (10 mL) and evaporated. The residue was purified by prep-HPLC to give (S)-tert-butyl 4-((3-chloro-2,4-difluorophenyl)(methyl)carbamoyl)-2-oxo-imidazolidine-1-carboxylate (250 mg, 84% yield) as a white solid.

Step e. To a solution of (S)-tert-butyl 4-((3-chloro-2,4-difluorophenyl)(methyl)carbamoyl)-2-oxoimidazolidine-1-carboxylate (300 mg, 0.77 mmol) in dioxane (5 mL) was added 2-bromo-6-methyl-4-(trifluoromethyl)pyridine (222 mg, 0.92 mmol), Pd$_2$(dba)$_3$ (70 mg, 0.077 mmol), XantPhos (44 mg, 0.077 mmol) and Cs$_2$CO$_3$ (752 mg, 2.31 mmol). The mixture was stirred at 80° C. for 2 h under N$_2$ atmosphere. Upon completion, the mixture was quenched with water (10 mL) and extracted with EtOAc (10 mL×3). The combined organic layers were washed with brine (10 mL×3), dried over Na$_2$SO$_4$ and evaporated. The residue was purified by column chromatography (20-30% EtOAc in PE) to give (S)-tert-butyl 4-((3-chloro-2,4-difluorophenyl)(methyl)carbamoyl)-3-(6-methyl-4-(trifluoromethyl)pyridin-2-yl)-2-oxo-imidazolidine-1-carboxylate (200 mg, 47% yield) as a white solid.

Step a. To a solution of sodium methoxide (33.0 g, 611 mmol) in MeOH (300 mL) was added 3-chloro-2,4-difluoroaniline (10.0 g, 61 mmol), followed by formaldehyde (2.75 g, 92 mmol) and the mixture was stirred at rt for 12 h. NaBH$_4$ (4.63 g, 122 mmol) was added and the mixture was stirred at rt for 2 h. The reaction mixture was evaporated, treated with water (200 mL) and extracted into EtOAc (200 mL×3). The combined organic layers were washed with brine (200 mL×3), dried and evaporated. The residue was purified by column chromatography (0-1% EtOAc in PE) to give 3-chloro-2,4-difluoro-N-methylaniline (7.30 g, 65% yield) as a colorless oil.

Step b. To a solution of (S)-3-((benzyloxy)carbonyl)-2-oxoimidazolidine-4-carboxylic acid (600 mg, 2.27 mmol) in Step f. To a solution of (S)-tert-butyl 4-((3-chloro-2,4-difluorophenyl)(methyl)carbamoyl)-3-(6-methyl-4-(trifluoromethyl)pyridin-2-yl)-2-oxoimidazolidine-1-carboxylate (180 mg, 0.33 mmol) in DCM (5 mL) was added TFA (0.5 mL). The mixture was stirred at rt for 1 h. Upon completion, the mixture was concentrated and purified by prep-HPLC to give the title compound (61 mg, 41% yield) as a yellow solid.

m/z ES+[M+H]$^+$ 449.0; $^1$H NMR (400 MHz, DMSO-d6) δ ppm 8.31 (s, 1H), 7.80-7.35 (m, 3H), 7.25-7.15 (m, 1H), 5.75-4.75 (m, 1H), 3.58-3.35 (m, 2H), 3.19-3.09 (m, 3H), 2.57-2.42 (m, 3H)

Example 159

(S)—N-(3-Chloro-4-fluorophenyl)-N-methyl-3-(6-methyl-4-(trifluoromethyl)pyridin-2-yl)-1-(methylsulfonyl)-2-oxoimidazolidine-4-carboxamide

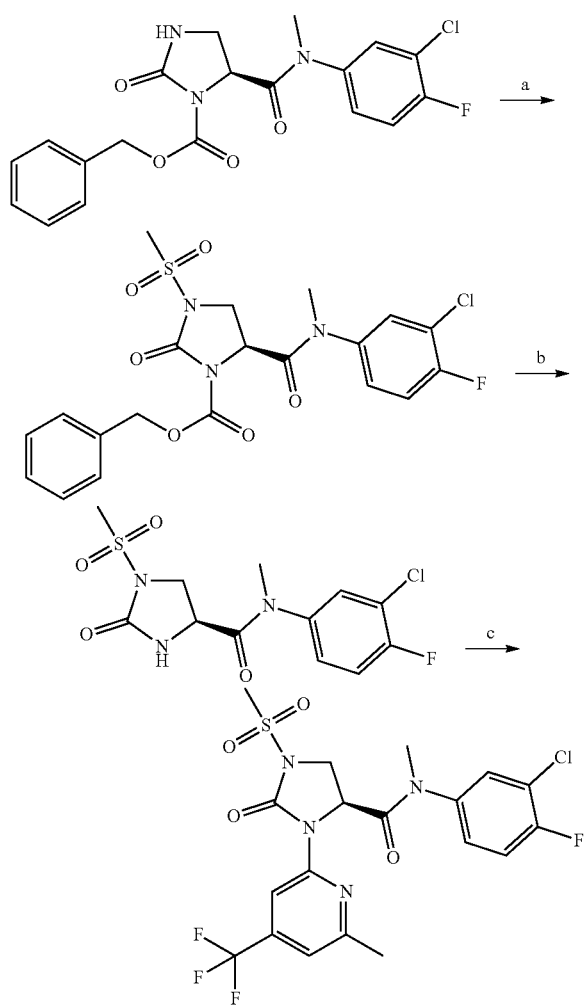

Step a. To a solution of benzyl (5S)-5-[(3-chloro-4-fluorophenyl)-methyl-carbamoyl]-2-oxo-imidazolidine-1-carboxylate (180 mg, 0.44 mmol) in THF (2 mL) was added NaH (20 mg, 0.49 mmol, 60% dispersion in mineral oil) at 0° C. and then stirred for 30 min under N₂ atmosphere. Methanesulphonyl chloride (56 mg, 0.49 mmol) was added and the mixture was stirred at 0° C. for 1.5 h. On completion, the reaction mixture was quenched with water (15 mL) and extracted with EtOAc (20 mL×3). The combined organic layers were washed with brine (5 mL×3), dried over Na₂SO₄ and evaporated. The residue was purified by column chromatography (0-100% EtOAc in PE) to afford benzyl (5S)-5-[(3-chloro-4-fluoro-phenyl)-methyl-carbamoyl]-3-methylsulfonyl-2-oxo-imidazolidine-1-carboxylate (140 mg, 65% yield) as a white solid.

m/z ES+[M-43]⁺440.0; ¹H NMR (400 MHz, CDCl₃) δ ppm 7.47-7.35 (m, 5H), 7.18 (t, J=8.4 Hz, 1H), 7.15-7.07 (m, 1H), 7.03-6.89 (m, 1H), 5.40-5.28 (m, 1H), 5.24-5.12 (m, 1H), 4.64-4.52 (m, 1H), 3.82-3.65 (m, 2H), 3.37-3.29 (m, 3H), 3.26-3.19 (m, 3H).

Step b. A solution of benzyl (5S)-5-[(3-chloro-4-fluorophenyl)-methyl-carbamoyl]-3-methyl-sulfonyl-2-oxo-imidazolidine-1-carboxylate (120 mg, 0.25 mmol) in TFA (1.2 mL) was stirred at 40° C. for 30 min. The reaction mixture was then concentrated. The residue was purified by prep-HPLC to afford (4S)—N-(3-chloro-4-fluoro-phenyl)-N-methyl-1-methylsulfonyl-2-oxo-imidazolidine-4-carboxamide (25 mg, 29% yield) as a white solid.

m/z ES+[M+H]⁺ 350.1; ¹H NMR (400 MHz, CD₃OD) δ ppm 7.64 (d, J=4.0 Hz, 1H), 7.47-7.32 (m, 2H), 4.31 (dd, J=4.8, 9.6 Hz, 1H), 3.92 (dd, J=4.8, 9.6 Hz, 1H), 3.85-3.74 (m, 1H), 3.29 (s, 3H), 3.23 (s, 3H).

Step c. A mixture of (4S)—N-(3-chloro-4-fluoro-phenyl)-N-methyl-1-methylsulfonyl-2-oxo-imidazolidine-4-carboxamide (23 mg, 0.066 mmol), 2-bromo-6-methyl-4-(trifluoromethyl)-pyridine (19 mg, 0.079 mmol), Pd₂(dba)₃ (6 mg, 0.007 mmol), Xantphos (6 mg, 0.010 mmol) and Cs₂CO₃ (64 mg, 0.2 mmol) in dioxane (2 mL) was degassed and purged with N₂ 3 times, and then stirred at 80° C. for 1 h. The reaction mixture was filtered and concentrated. The residue was purified by prep-HPLC to afford the title compound (36 mg, quantitative yield) as a white solid.

m/z ES+[M+H]⁺ 509.1; ¹H NMR (400 MHz, CD₃OD) δ ppm 8.31 (s, 1H), 7.84 (d, J=4.0 Hz, 1H), 7.60-7.55 (m, 1H), 7.52-7.45 (m, 1H), 7.28 (s, 1H), 5.09 (dd, J=3.2, 9.6 Hz, 1H), 4.01 (dd, J=3.2, 9.6 Hz, 1H), 3.95-3.86 (m, 1H), 3.33 (s, 3H), 3.31 (s, 3H), 2.66 (s, 3H).

Example 160

(4S)—N-(3-Chloro-4-fluorophenyl)-1-(2-hydroxypropyl)-N-methyl-3-(6-methyl-4-(trifluoromethyl)pyridin-2-yl)-2-oxoimidazolidine-4-carboxamide

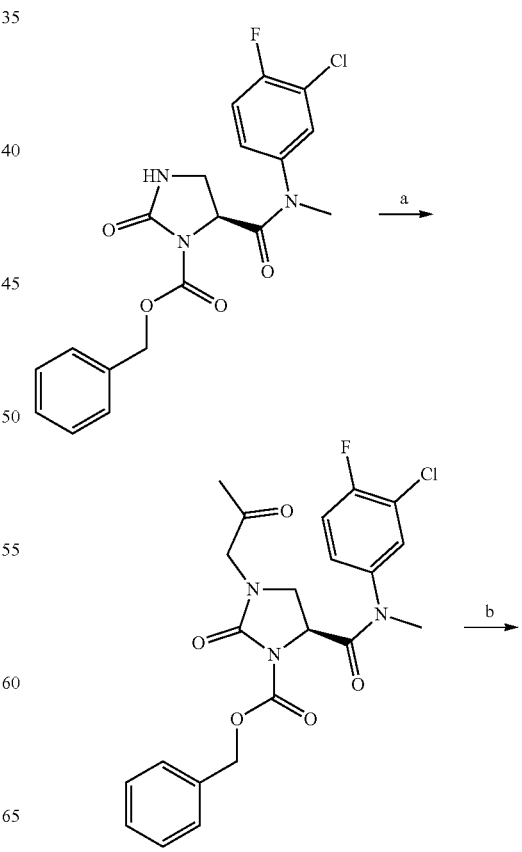

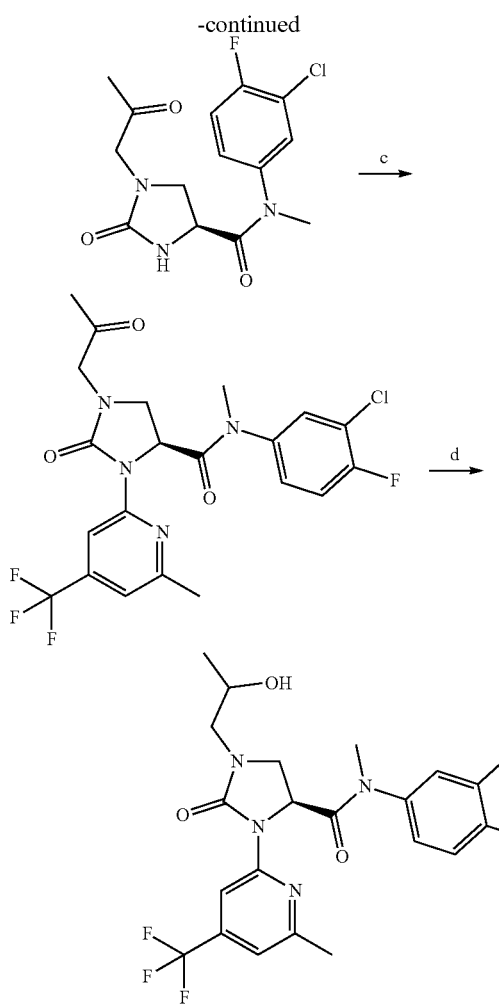

Step a. To a solution of benzyl (5S)-5-[(3-chloro-4-fluoro-phenyl)-methyl-carbamoyl]-2-oxo-imidazolidine-1-carboxylate (300 mg, 0.74 mmol) in acetone (5 mL) was added Cs$_2$CO$_3$ (482 mg, 1.48 mmol) and 1-chloropropan-2-one (2.44 g, 26.37 mmol). Then the mixture was stirred at 60° C. for 15 h. On completion, the reaction mixture was concentrated. The residue was purified by prep-HPLC to give benzyl (5S)-3-acetonyl-5-[(3-chloro-4-fluoro-phenyl)-methyl-carbamoyl]-2-oxo-imidazolidine-1-carboxylate (120 mg, 32% yield) as a yellow oil.

m/z ES+[M+H]$^+$ 462.0

Step b. A mixture of benzyl (5S)-3-acetonyl-5-[(3-chloro-4-fluoro-phenyl)-methyl-carbamoyl]-2-oxo-imidazolidine-1-carboxylate (100 mg, 0.22 mmol) in TFA (0.5 mL) and DCM (0.5 mL) was stirred at 30° C. for 12 h. On completion, the reaction mixture was concentrated, diluted with sat. aq. NaHCO$_3$ (100 mL) and extracted with EtOAc (30 mL×3). The combined organic layers were washed with brine (30 mL), dried and evaporated. The residue was purified by prep-TLC (50% EtOAc in PE) to give (4S)-1-acetonyl-N-(3-chloro-4-fluoro-phenyl)-N-methyl-2-oxo-imidazolidine-4-carboxamide (50 mg, 68% yield) as a colorless oil.

m/z ES+[M+H]$^+$ 328.0

Step c. A mixture of (4S)-1-acetonyl-N-(3-chloro-4-fluoro-phenyl)-N-methyl-2-oxo-imidazolidine-4-carboxamide (40 mg, 0.12 mmol), 2-chloro-6-methyl-4-(trifluoromethyl)-pyridine (28 mg, 0.15 mmol), Pd$_2$(dba)$_3$ (11 mg, 0.012 mmol), XantPhos (14 mg, 0.024 mmol) and Cs$_2$CO$_3$ (79 mg, 0.24 mmol) in dioxane (1 mL) was degassed and purged with N$_2$ 3 times, and then stirred at 100° C. for 2 h. On completion, the reaction mixture was filtered, concentrated and the residue was purified by prep-TLC (35% EtOAc in PE) to give (4S)-1-acetonyl-N-(3-chloro-4-fluoro-phenyl)-N-methyl-3-[6-methyl-4-(trifluoromethyl)-2-pyridyl]-2-oxo-imidazolidine-4-carboxamide (42 mg, 68% yield) as a brown solid.

m/z ES+[M+H]$^+$ 487.0

Step d. A mixture of (4S)-1-acetonyl-N-(3-chloro-4-fluoro-phenyl)-N-methyl-3-[6-methyl-4-(trifluoromethyl)-2-pyridyl]-2-oxo-imidazolidine-4-carboxamide (42 mg, 0.086 mmol) and NaBH$_4$ (9.8 mg, 0.26 mmol) in MeOH (1 mL) was stirred at rt for 4 h. On completion, the reaction mixture was concentrated. The residue was purified by prep-HPLC to give the title compound (19 mg, 45% yield) as a yellow solid.

m/z ES+[M+H]$^+$ 489.1; $^1$H NMR (400 MHz, CD$_3$OD) δ ppm 8.37 (s, 1H), 7.81 (d, J=5.6 Hz, 1H), 7.60-7.50 (m, 1H), 7.50-7.44 (m, 1H), 7.12 (s, 1H), 5.03-4.94 (m, 1H), 4.00 (dd, J=6.4, 10.8 Hz, 1H), 3.73-3.57 (m, 2H), 3.30 (s, 3H), 3.29-3.17 (m, 2H), 2.62 (s, 3H), 1.19 (d, J=6.4 Hz, 3H).

Example 161

(S)—N-(3-Chloro-2,4-difluorophenyl)-N-cyclopropyl-3-(6-methyl-4-(trifluoromethyl)-pyridin-2-yl)-2-oxoimidazolidine-4-carboxamide

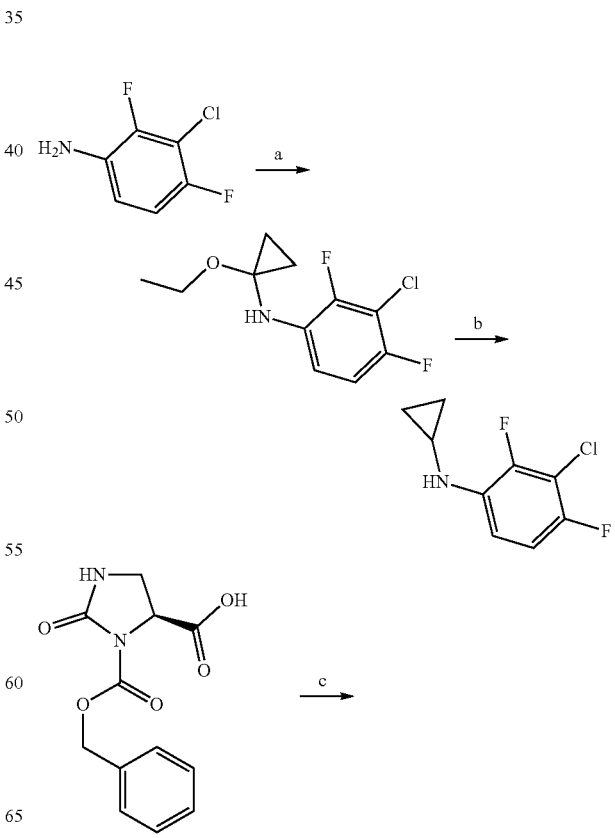

-continued

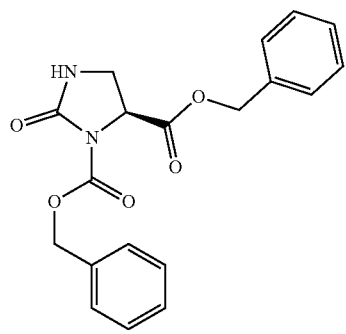

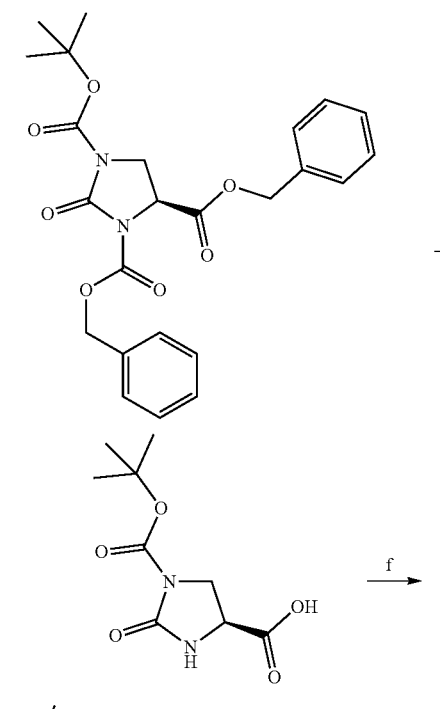

-continued

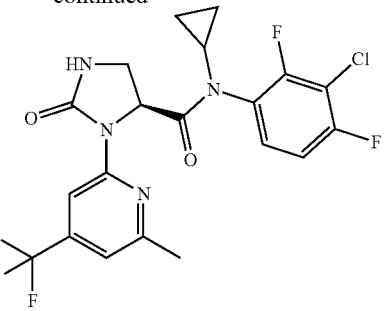

Step a. To a solution of 3-chloro-2,4-difluoroaniline (500 mg, 3.06 mmol) and acetic acid (734 mg, 12.2 mmol) in MeOH (10 mL) was added (1-ethoxycyclopropoxy)-trimethyl-silane (799 mg, 4.59 mmol). The mixture was stirred under reflux for 3 h. Then (1-ethoxy-cyclopropoxy)-trimethyl-silane (266 mg, 1.53 mmol) and acetic acid (734 mg, 12.2 mmol) was added, and the mixture was stirred under reflux conditions for a further 16 h. Upon completion, the mixture was evaporated to give compound 3-chloro-N-(1-ethoxycyclopropyl)-2,4-difluoroaniline (0.9 g, crude) as a yellow solid.

Step b. To a solution of NaBH$_4$ (107 mg, 2.83 mmol) in THF (10 mL) at 5° C. was added BF$_3$·Et$_2$O (401 mg, 2.83 mmol). The mixture was stirred at 5° C. for 45 min. 3-Chloro-N-(1-ethoxycyclopropyl)-2,4-difluoroaniline (350 mg, 1.41 mmol) was added and the mixture was stirred for a further 1 h at 5° C. The reaction was warmed to rt and stirred for 16 h. Upon completion, the reaction mixture was quenched with water (10 mL) and extracted with EtOAc (30 mL×3). The combined organic layers were washed with brine (10 mL×3), dried over Na$_2$SO$_4$ and evaporated. The residue was purified by column chromatography (10-100% EtOAc in PE) to give 3-chloro-N-cyclopropyl-2,4-difluoroaniline (0.2 g, 29% yield over two steps) as a yellow oil.

m/z ES+[M+H]$^+$ 204.6

Step c. To a solution of (S)-3-((benzyloxy)carbonyl)-2-oxoimidazolidine-4-carboxylic acid (2 g, 7.57 mmol) in DMF (20 mL) was added (bromomethyl)benzene (1.42 g, 8.33 mmol) and DIPEA (2.93 g, 22.7 mmol) in one portion. The resulting mixture was stirred at rt for 12 h. Upon completion, the reaction mixture was diluted with water (50 mL) and extracted with EtOAc (50 mL×2). The combined organic layers were washed with brine (20 mL×2), dried over Na$_2$SO$_4$ and evaporated to give (S)-dibenzyl 2-oxoimidazolidine-1,5-dicarboxylate (3.0 g, crude) as a yellow solid.

m/z ES+[M+H]$^+$ 355.1; $^1$H NMR (400 MHz, CDCl$_3$) δ ppm 7.37-7.30 (m, 6H), 7.26-7.17 (m, 4H), 6.66 (s, 1H), 5.18-5.12 (m, 2H), 5.08 (d, J=5.6 Hz, 2H), 4.71 (dd, J=3.6, 10.0 Hz, 1H), 3.64 (t, J=10.0 Hz, 1H), 3.32 (dd, J=3.6, 9.6 Hz, 1H).

Step d. To a solution of (S)-dibenzyl 2-oxoimidazolidine-1,5-dicarboxylate (3.0 g, 8.47 mmol) in (Boc)$_2$O (36.95 g, 169.3 mmol) was added DMAP (1.03 g, 8.47 mmol) in one portion. The resulting mixture was stirred at 60° C. for 2 h. Upon completion, the reaction mixture was diluted with water (50 mL) and extracted with EtOAc (50 mL×2). The combined organic layers were washed with brine (20 mL×2), dried over Na$_2$SO$_4$ and evaporated. The residue was purified by column chromatography (2-25% EtOAc in PE) to give (S)-3,4-dibenzyl 1-tert-butyl 2-oxoimidazolidine-1,3,4-tricarboxylate (2.0 g, 52% yield) as a yellow oil.

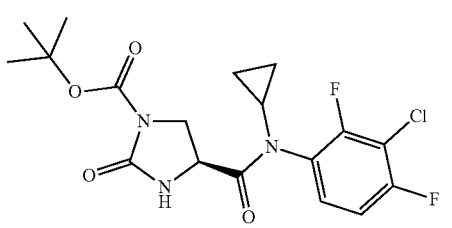

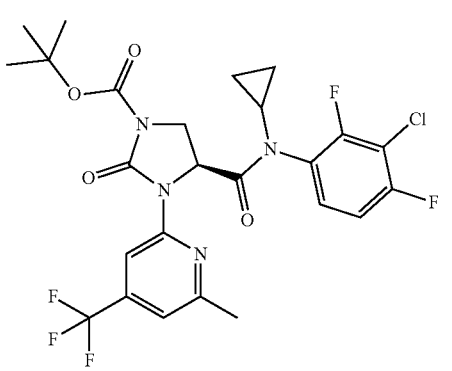

m/z ES+[M+H]+ 455.2; ¹H NMR (400 MHz, CDCl₃) δ ppm 7.41-7.29 (m, 10H), 5.25 (s, 2H), 5.17 (d, J=2.8 Hz, 2H), 4.71-4.65 (m, 1H), 3.95 (d, J=0.8 Hz, 1H), 3.75 (dd, J=3.2, 11.2 Hz, 1H), 1.53 (s, 9H).

Step e. To a solution of (S)-3,4-dibenzyl 1-tert-butyl 2-oxoimidazolidine-1,3,4-tricarboxylate (2.0 g, 4.40 mmol) in MeOH (30 mL) was added Pd/C (0.2 g, 10% loading on activated carbon). The resulting mixture was purged with H₂ three times and then stirred for 12 h under H₂ atmosphere (15 psi) at 30° C. Upon completion, the mixture was filtered and the filtratate was evaporated to give (S)-1-(tert-butoxycarbonyl)-2-oxoimidazolidine-4-carboxylic acid (0.75 g, 74% yield) as a white solid.

m/z ES+[M+H]+ 230.2; ¹H NMR (400 MHz, DMSO-d6) δ ppm 13.73-12.82 (m, 1H), 7.79 (s, 1H), 4.11 (dd, J=4.0, 10.0 Hz, 1H), 3.95 (t, J=10.0 Hz, 1H), 3.70 (dd, J=4.0, 10.4 Hz, 1H), 1.43 (s, 9H).

Step f. To a solution of (S)-1-(tert-butoxycarbonyl)-2-oxoimidazolidine-4-carboxylic acid (376 mg, 1.64 mmol) in MeCN (2 mL) was added Ghosez's reagent (CAS Number 26189-59-3; 437 mg, 3.27 mmol) dropwise at 0° C. The mixture was stirred at 0° C. for 1 h. Then 3-chloro-N-cyclopropyl-2,4-difluoroaniline (300 mg, 1.47 mmol) and N,N-dimethylpyridin-2-amine (240 mg, 1.96 mmol) were added. The mixture was stirred at 0° C. for 30 min. Upon completion, the reaction mixture was quenched with water (10 mL) and extracted with EtOAc (10 mL×3). The combined organic layers were washed with brine (10 mL×3), dried over Na₂SO₄ and evaporated. The residue was purified by prep-TLC (50% EtOAc in PE) to give (S)-tert-butyl 4-((3-chloro-2,4-difluorophenyl)(cyclopropyl)carbamoyl)-2-oxoimidazolidine-1-carboxylate (100 mg, 7% yield) as a yellow oil.

Step g. A solution of (S)-tert-butyl 4-((3-chloro-2,4-difluorophenyl)(cyclopropyl)carbamoyl)-2-oxoimidazolidine-1-carboxylate (80 mg, 0.19 mmol), 2-bromo-6-methyl-4-(trifluoromethyl)-pyridine (46 mg, 0.19 mmol), Pd₂(dba)₃ (17 mg, 0.019 mmol), Cs₂CO₃ (188 mg, 0.58 mmol) and XantPhos (11 mg, 0.019 mmol) in dioxane (2 mL) was degassed and purged with N₂ three times and then stirred at 80° C. for 1 h. Upon completion, the reaction mixture was quenched with water (10 mL) and extracted with EtOAc (10 mL×3). The combined organic layers were washed with brine (10 mL×3), dried and evaporated. The residue was purified by prep-TLC (50% EtOAc in PE) to give (S)-tert-butyl 4-((3-chloro-2,4-difluorophenyl)-(cyclopropyl)carbamoyl)-3-(6-methyl-4-(trifluoromethyl)pyridin-2-yl)-2-oxoimidazolidine-1-carboxylate (100 mg, 72% yield) as a yellow oil.

Step h. A solution of (S)-tert-butyl 4-((3-chloro-2,4-difluorophenyl)(cyclopropyl)carbamoyl)-3-(6-methyl-4-(trifluoromethyl)pyridin-2-yl)-2-oxoimidazolidine-1-carboxylate (100 mg, 0.17 mmol) in TFA (308 mg, 2.70 mmol) and DCM (2 mL) was stirred at rt for 1 h. Upon completion, the mixture was evaporated. The residue was dissolved in water (2 mL), adjusted to pH 8-9 by sat. Na₂CO₃ solution and further extracted with EtOAc (10 mL×3). The combined organic layers were washed with brine (10 mL×3), dried over Na₂SO₄ and evaporated. The residue was purified by column chromatography (10-50% EtOAc in PE) to give the title compound (12.4 mg, 15% yield) as a yellow solid.

m/z ES+[M+H]+ 475.2; ¹H NMR (400 MHz, CD₃OD) δ ppm 8.39-8.29 (m, 1H), 7.38-7.14 (m, 2H), 7.10-7.07 (m, 1H), 6.19-6.15 (m, 1H), 4.05-4.00 (m, 1H), 3.57-3.44 (m, 2H), 2.57-2.51 (m, 3H), 1.10-0.46 (m, 4H).

Example 162

(2S,3S,4S)—N-(3-Chloro-2,4-difluorophenyl)-3,4-dihydroxy-N-(methyl-d3)-1-(6-methyl-4-(trifluoromethyl)pyridin-2-yl)-5-oxopyrrolidine-2-carboxamide

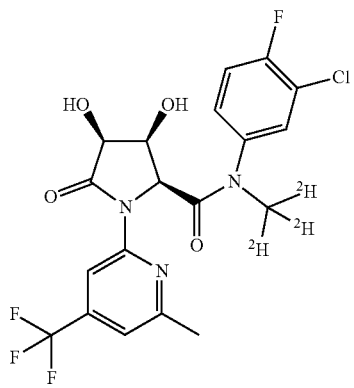 [SMILES: [2H]C([2H])([2H])N(C(=O)[C@@H]1[C@H](O)[C@H](O)C(=O)N1c1cc(C(F)(F)F)cc(C)n1)c1ccc(F)c(Cl)c1]

The title compound was prepared in a similar manner to Example 70, using (3aS,4S,6aS)—N-(3-chloro-2,4-difluorophenyl)-2,2-dimethyl-N-(methyl-d3)-5-(6-methyl-4-(trifluoromethyl)-pyridin-2-yl)-6-oxotetrahydro-4H-[1,3]dioxolo[4,5-c]pyrrole-4-carboxamide, which was prepared in a similar manner to Example 69, using methyl-d3 iodide in step d.

m/z ES+[M+H]+ 483.0; ¹H NMR (400 MHz, CD₃OD) δ ppm 8.40-8.35 (m, 1H), 7.87-7.65 (m, 1H), 7.34-7.15 (m, 2H), 5.16-5.01 (m, 1H), 4.26-4.15 (m, 2H), 2.63-2.55 (m, 3H).

Example 163

(2S,3S,4S)—N-(3-Chloro-4-fluorophenyl)-3,4-dihydroxy-N-(methyl-d3)-1-(6-methyl-4-(trifluoromethyl)pyridin-2-yl)-5-oxopyrrolidine-2-carboxamide

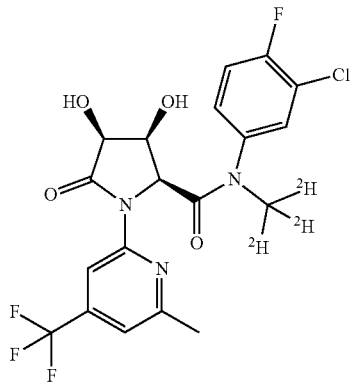 [SMILES: [2H]C([2H])([2H])N(C(=O)[C@@H]1[C@H](O)[C@H](O)C(=O)N1c1cc(C(F)(F)F)cc(C)n1)c1ccc(F)c(Cl)c1]

The title compound was prepared in a similar manner to Example 70, using (3aS,4S,6aS)—N-(3-chloro-4-fluorophenyl)-2,2-dimethyl-N-(methyl-d3)-5-(6-methyl-4-(trifluoromethyl)-pyridin-2-yl)-6-oxotetrahydro-4H-[1,3]dioxolo[4,5-c]pyrrole-4-carboxamide, which was prepared in a similar manner to Example 69, using 3-chloro-4-fluoroaniline in step a and methyl-d3 iodide in step d.

m/z ES+[M+H]+ 465.1; $^1$H NMR (400 MHz, CD$_3$OD) δ ppm 8.43 (s, 1H), 7.85-7.84 (m, 1H), 7.65-7.63 (m, 1H), 7.50-7.46 (m, 1H), 7.31 (s, 1H), 5.15-5.13 (m, 1H), 4.27-4.26 (m, 1H), 4.23-4.20 (m, 1H), 2.65 (s, 3H).

Example 164

(2S,3S,4S)—N-(5-Chloro-2,4-difluorophenyl)-3,4-dihydroxy-N-(methyl-d3)-1-(6-methyl-4-(trifluoromethyl)pyridin-2-yl)-5-oxopyrrolidine-2-carboxamide

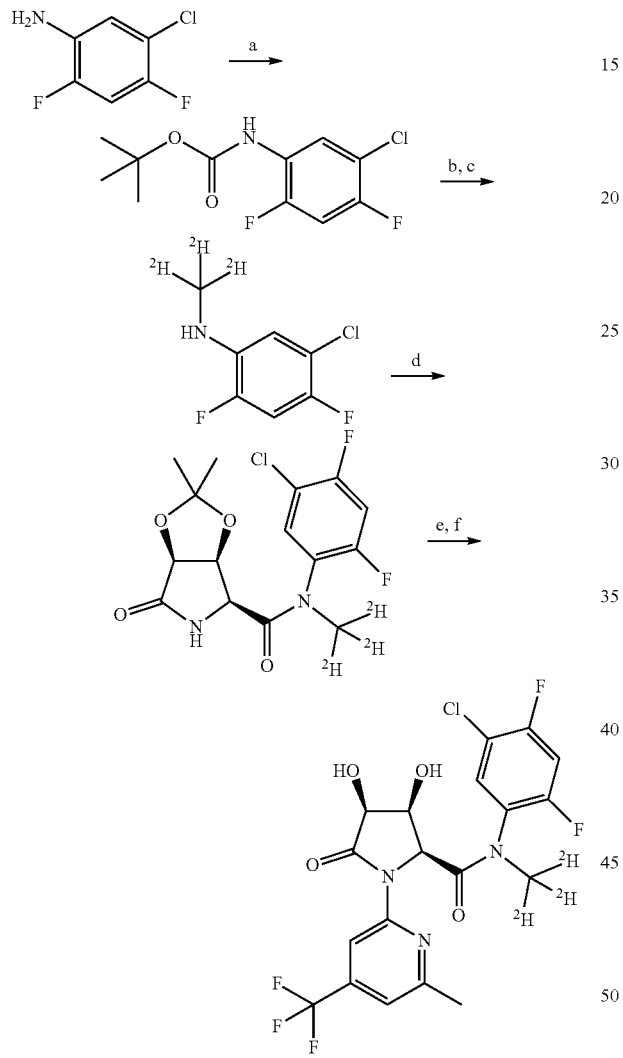

Step a. To a solution of 5-chloro-2,4-difluoroaniline (2.00 g, 12.2 mmol) in dioxane (10 mL) and water (10 mL) was added (Boc)$_2$O (5.34 g, 24.5 mmol) and NaHCO$_3$ (4.11 g, 48.9 mmol). The mixture was stirred at 40° C. for 12 h. On completion, the reaction mixture was concentrated under vacuum, then diluted with water (20 mL) and extracted with EtOAc (20 mL×3). The combined organic layers were washed with brine (60 mL×2), dried over Na$_2$SO$_4$ and evaporated. The residue was purified by column chromatography (3-5% EtOAc in PE) to afford tert-butyl (5-chloro-2,4-difluorophenyl)carbamate (1.00 g, 31% yield) as a white solid.

$^1$H NMR (400 MHz, DMSO-d6) δ ppm 9.21 (s, 1H), 7.82 (t, J=8.0 Hz, 1H), 7.55 (dd, J=9.6, 10.8 Hz, 1H), 1.45 (s, 9H).

Step b. To a solution of tert-butyl (5-chloro-2,4-difluorophenyl)carbamate (900 mg, 3.41 mmol) in DMF (9 mL) was added NaH (205 mg, 5.12 mmol, 60% dispersion in mineral oil) portionwise under N$_2$ at 0° C. and the mixture was stirred at 0° C. for 30 min. Then methyl-d3 iodide (594 mg, 4.10 mmol) was added dropwise and the mixture was stirred at 0° C. for 1 h. On completion, the reaction mixture was diluted with water (10 mL) and extracted with EtOAc (10 mL×3). The combined organic layers were washed with brine (30 mL×3), dried and evaporated to afford tert-butyl (5-chloro-2,4-difluorophenyl)(methyl-d3)carbamate (990 mg, crude) as a colorless oil.

m/z ES+[M-55]+225.0

Step c. A solution of tert-butyl (5-chloro-2,4-difluorophenyl)(methyl-d3)carbamate (990 mg, 3.53 mmol) and TFA (3.08 g, 27.0 mmol) in DCM (10 mL) was stirred at rt for 30 min. On completion, the reaction mixture was diluted with water (15 mL) and extracted with DCM (15 mL×3). The combined organic layers were washed with brine (40 mL×2), dried and evaporated. The residue was purified by column chromatography (3-5% EtOAc in PE) to afford 5-chloro-2,4-difluoro-N-(methyl-d3)aniline (490 mg, 77% yield) as a colorless oil.

m/z ES+[M+H]+ 181.1

Steps d-f. The title compound was prepared in a similar manner to Example 65, using 5-chloro-2,4-difluoro-N-(methyl-d3)aniline. m/z ES+[M+H]+ 483.1; $^1$H NMR (400 MHz, DMSO-d6) δ ppm 8.25-8.18 (m, 1H), 7.97-7.55 (m, 2H), 7.44-7.38 (m, 1H), 5.67-5.54 (m, 2H), 5.18-4.83 (m, 1H), 4.47-4.23 (m, 1H), 4.00-3.96 (m, 1H), 2.62-2.48 (m, 3H).

Example 165

(2S,3S,4S)—N-(4-Chloro-2-fluorophenyl)-3,4-dihydroxy-N-methyl-1-(6-methyl-4-(trifluoromethyl)pyridin-2-yl)-5-oxopyrrolidine-2-carboxamide

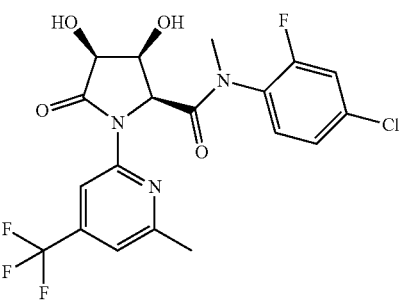 [SMILES: Cc1cc(C(F)(F)F)cc(N2C(=O)[C@@H](O)[C@@H](O)[C@H]2C(=O)N(C)c2ccc(Cl)cc2F)n1]

The title compound was prepared in a similar manner to Example 70, using 4-chloro-2-fluoroaniline (CAS Number 57946-56-2).

m/z ES+[M+H]+ 462.0; $^1$H NMR (400 MHz, CD$_3$OD) δ ppm 8.43-8.37 (m, 1H), 7.90-7.65 (m, 1H), 7.55 (dd, J=2.0, 9.6 Hz, 1H), 7.47-7.41 (m, 1H), 7.35-7.25 (m, 1H), 5.88-5.03 (m, 1H), 4.30-4.17 (m, 2H), 3.68-3.24 (m, 3H), 2.67-2.55 (m, 3H).

Example 166

(2S,3S,4S)-3,4-Dihydroxy-N-methyl-1-(6-methyl-4-(trifluoromethyl)pyridin-2-yl)-5-oxo-N-(1H-pyrrolo[2,3-b]pyridin-6-yl)pyrrolidine-2-carboxamide

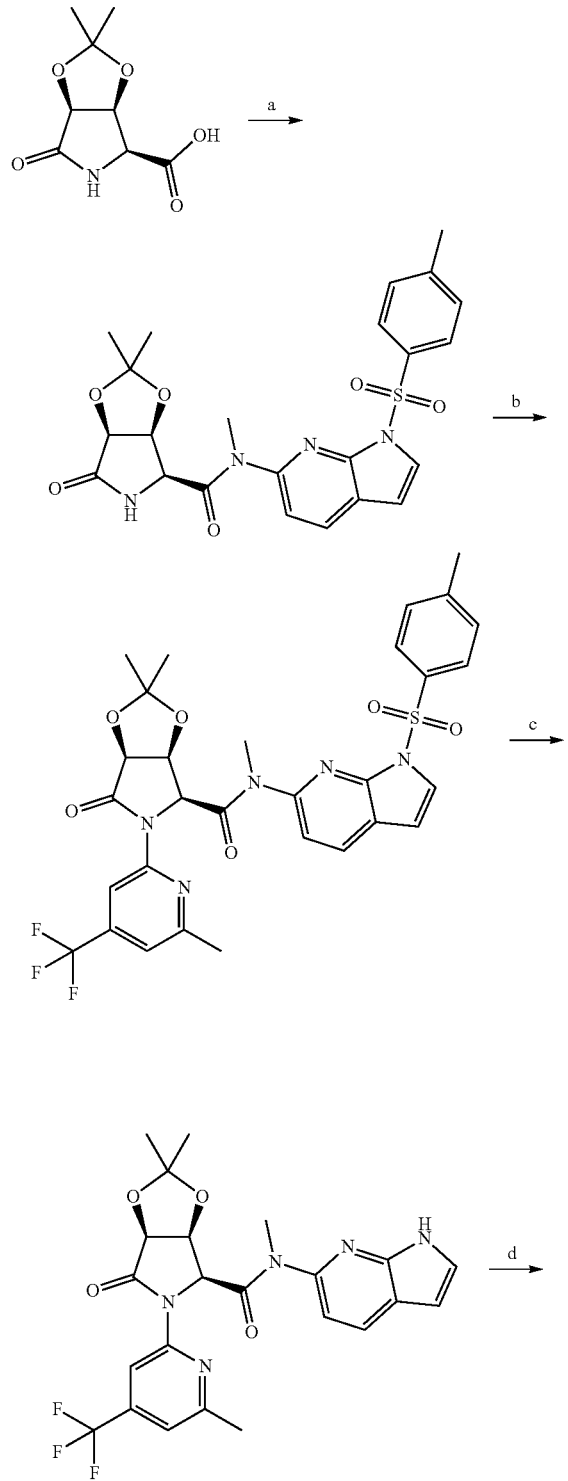

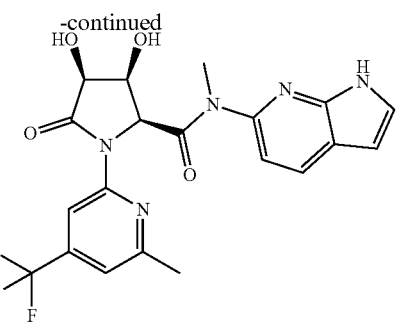

Step a. To a solution of Intermediate 5 (200 mg, 0.99 mmol) in MeCN (0.5 mL) was added Ghosez's reagent (CAS Number 26189-59-3; 120 mg, 0.89 mmol) dropwise at 0° C. under $N_2$ atmosphere. The mixture was stirred at 0° C. for 30 min. Then the mixture was added into a solution of N-methyl-1-tosyl-1H-pyrrolo[2,3-b]pyridin-6-amine (Example 127, steps a-c; 240 mg, 0.8 mmol) and N,N-dimethylpyridin-2-amine (146 mg, 1.19 mmol) in MeCN (0.5 mL) at 0° C. The resulting mixture was stirred at 0° C. for 1 h under $N_2$ atmosphere. On completion, the mixture was evaporated. The residue was purified by reverse-phase HPLC to afford (3aS,4S,6aS)—N,2,2-trimethyl-6-oxo-N-(1-tosyl-1H-pyrrolo[2,3-b]pyridin-6-yl)tetrahydro-3aH-[1,3]dioxolo[4,5-c]pyrrole-4-carboxamide (435 mg, 90% yield) as a white solid.

m/z ES+[M+H]+ 485.1; $^1$H NMR (400 MHz, CDCl$_3$) δ ppm 8.04-7.95 (m, 3H), 7.83 (d, J=4.0 Hz, 1H), 7.31 (d, J=8.4 Hz, 2H), 7.17 (d, J=8.4 Hz, 1H), 6.66 (d, J=4.0 Hz, 1H), 6.10 (s, 1H), 4.89 (d, J=4.8 Hz, 1H), 4.26 (d, J=5.2 Hz, 1H), 3.70-3.60 (m, 1H), 3.43 (s, 3H), 2.41 (s, 3H), 1.38 (s, 3H), 1.15 (s, 3H).

Step b. A mixture of (3aS,4S,6aS)—N,2,2-trimethyl-6-oxo-N-(1-tosyl-1H-pyrrolo[2,3-b]pyridin-6-yl)tetrahydro-3aH-[1,3]dioxolo[4,5-c]pyrrole-4-carboxamide (200 mg, 0.41 mmol), 2-bromo-6-methyl-4-(trifluoromethyl)pyridine (139 mg, 0.58 mmol), Pd$_2$(dba)$_3$ (38 mg, 0.041 mmol), XantPhos (48 mg, 0.083 mmol) and K$_2$CO$_3$ (114 mg, 0.83 mmol) in dioxane (0.5 mL) was degassed and purged with N$_2$ 3 times, and then the mixture was stirred at 100° C. for 12 h under N$_2$ atmosphere. On completion, the reaction mixture was diluted with water (10 mL) and extracted with EtOAc (20 mL×3). The combined organic layers were washed with brine (6 mL×3), dried over Na$_2$SO$_4$ and evaporated. The residue was purified by column chromatography (10-50% EtOAc in PE) to afford (3aS,4S,6aS)—N,2,2-trimethyl-5-(6-methyl-4-(trifluoromethyl)pyridin-2-yl)-6-oxo-N-(1-tosyl-1H-pyrrolo[2,3-b]pyridin-6-yl)tetrahydro-3aH-[1,3]dioxolo[4,5-c]pyrrole-4-carboxamide (230 mg, 87% yield) as a yellow solid.

m/z ES+[M+H]+ 644.2

Step c. To a solution of (3aS,4S,6aS)—N,2,2-trimethyl-5-(6-methyl-4-(trifluoromethyl)pyridin-2-yl)-6-oxo-N-(1-tosyl-1H-pyrrolo[2,3-b]pyridin-6-yl)tetrahydro-3aH-[1,3]dioxolo[4,5-c]pyrrole-4-carboxamide (0.16 g, 0.25 mmol) in THF (1 mL) was added TBAF (1 M in THF, 1.24 mmol). The resulting mixture was stirred at rt for 3 h. On completion, the reaction mixture was diluted with EtOAc (20 mL) and washed with water (5 mL×3). The organic layer was dried over Na$_2$SO$_4$ and evaporated. The residue was purified by prep-HPLC to afford (3aS,4S,6aS)—N,2,2-trimethyl-5-(6-methyl-4-(trifluoromethyl)pyridin-2-yl)-6-oxo-N-(1H- pyrrolo[2,3-b]pyridin-6-yl)tetrahydro-3aH-[1,3]dioxolo[4,5-c]pyrrole-4-carboxamide (50 mg, 41% yield) as a white solid.

m/z ES+[M+H]⁺ 490.1; ¹H NMR (400 MHz, CD₃OD) δ ppm 8.33 (s, 1H), 8.06 (d, J=8.0 Hz, 1H), 7.37 (d, J=3.6 Hz, 1H), 7.27-7.17 (m, 2H), 6.47 (d, J=3.2 Hz, 1H), 5.14 (d, J=6.4 Hz, 1H), 4.88 (t, J=6.4 Hz, 1H), 4.69 (d, J=6.4 Hz, 1H), 3.29 (s, 3H), 2.52 (s, 3H), 1.41 (s, 3H), 1.36 (s, 3H).

Step d. To a solution of (3aS,4S,6aS)—N,2,2-trimethyl-5-(6-methyl-4-(trifluoromethyl)pyridin-2-yl)-6-oxo-N-(1H-pyrrolo[2,3-b]pyridin-6-yl)tetrahydro-3aH-[1,3]dioxolo[4,5-c]pyrrole-4-carboxamide (25 mg, 0.051 mmol) in DCM (0.5 mL) was added BCl₃ (1 M in toluene, 0.1 mmol) at 0° C. The mixture was slowly warmed to rt and stirred at rt for 5 h. On completion, the reaction mixture was quenched with sat. aq. NaHCO₃ (10 mL) and extracted with EtOAc (20 mL×3). The combined organic layers were dried over Na₂SO₄ and evaporated. The residue was purified by prep-HPLC to give the title compound (10 mg, 46% yield) as a yellow solid.

m/z ES+[M+H]⁺ 450.1; ¹H NMR (400 MHz, CD₃OD) δ ppm 8.33 (s, 1H), 8.14 (d, J=8.4 Hz, 1H), 7.48 (d, J=3.6 Hz, 1H), 7.33 (d, J=7.6 Hz, 1H), 7.25 (s, 1H), 6.57 (d, J=3.6 Hz, 1H), 5.18-5.09 (m, 1H), 4.60-4.53 (m, 1H), 4.27 (d, J=6.4 Hz, 1H), 3.42 (s, 3H), 2.60 (s, 3H).

Example 167

(2S,3S,4S)-3,4-Dihydroxy-N-methyl-N-(1-methyl-1H-pyrrolo[2,3-b]pyridin-6-yl)-1-(6-methyl-4-(trifluoromethyl)pyridin-2-yl)-5-oxopyrrolidine-2-carboxamide

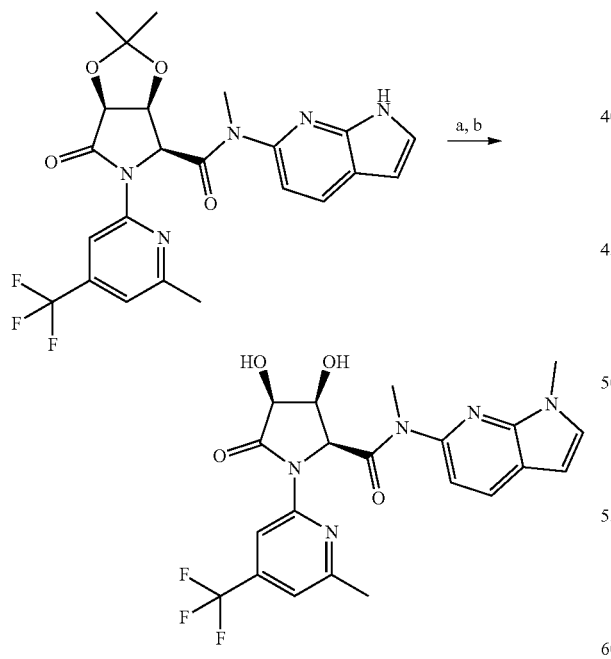

Step a. To a solution of (3aS,6S,6aS)—N,2,2-trimethyl-5-[6-methyl-4-(trifluoromethyl)-2-pyridyl]-4-oxo-N-(1H-pyrrolo[2,3-b]pyridin-6-yl)-6,6a-dihydro-3aH-[1,3]dioxolo[4,5-c]pyrrole-6-carboxamide (Example 166, steps a-c; 100 mg, 0.20 mmol) and Cs₂CO₃ (200 mg, 0.61 mmol) in DMF (2 mL) was added methyl iodide (35 mg, 0.25 mmol). The mixture was stirred at 60° C. for 1 h. On completion, the reaction mixture was diluted with water (10 mL) and extracted with EtOAc (50 mL×3). The combined organic layers were washed with brine (10 mL×3), dried over Na₂SO₄ and evaporated. The residue was purified by prep-TLC (35% EtOAc in PE) to afford (3aS,6S,6aS)—N,2,2-trimethyl-N-(1-methylpyrrolo[2,3-b]pyridin-6-yl)-5-[6-methyl-4-(trifluoromethyl)-2-pyridyl]-4-oxo-6,6a-dihydro-3aH-[1,3]dioxolo[4,5-c]pyrrole-6-carboxamide (15 mg, 15% yield) as a white solid.

m/z ES+[M+H]⁺ 504.4

Step b. To a solution of (3aS,6S,6aS)—N,2,2-trimethyl-N-(1-methylpyrrolo[2,3-b]pyridin-6-yl)-5-[6-methyl-4-(trifluoromethyl)-2-pyridyl]-4-oxo-6,6a-dihydro-3aH-[1,3]dioxolo[4,5-c]pyrrole-6-carboxamide (15 mg, 0.03 mmol) in DCM (2 mL) was added BCl₃ (1 M, 0.06 mmol) at 0° C. The mixture was stirred at rt for 5 h. On completion, the reaction mixture was quenched with sat. aq. NaHCO₃ (10 mL) and extracted with EtOAc (20 mL×3). The combined organic layers were dried over Na₂SO₄ and concentrated under vacuum. The residue was purified by prep-HPLC to give the title compound (1.2 mg, 8% yield) as a yellow solid.

m/z ES+[M+H]⁺ 464.3; ¹H NMR (400 MHz, CD₃OD) δ ppm 8.36 (s, 1H), 8.15 (d, J=7.6 Hz, 1H), 7.50-7.45 (m, 1H), 7.40-7.33 (m, 1H), 7.27 (s, 1H), 6.58 (d, J=2.0 Hz, 1H), 5.14 (s, 1H), 4.64 (s, 1H), 4.30 (d, J=6.4 Hz, 1H), 3.95 (s, 3H), 3.44 (s, 3H), 2.63 (s, 3H).

Example 168

(2S,3S,4S)-3,4-Dihydroxy-N-methyl-N-(1-methyl-1H-indazol-6-yl)-1-(6-methyl-4-(trifluoromethyl)pyridin-2-yl)-5-oxopyrrolidine-2-carboxamide

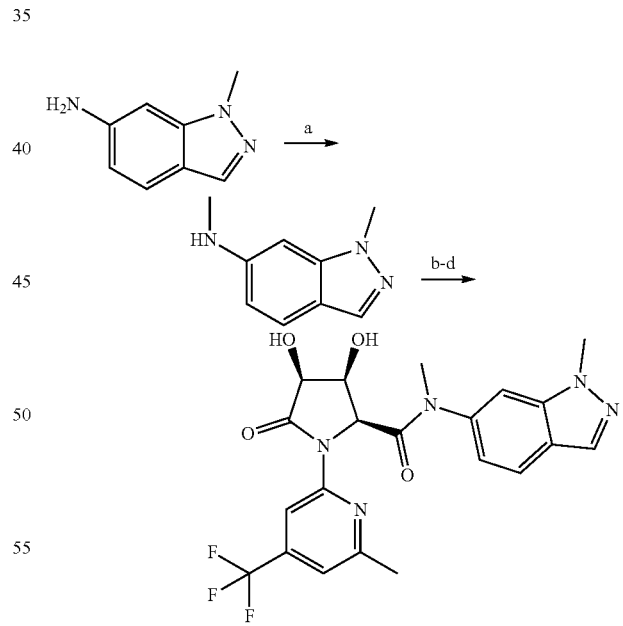

Step a. To a mixture of 1-methyl-1H-indazol-6-amine (0.3 g, 2.04 mmol) and sodium methoxide (1.10 g, 20.4 mmol) in MeOH (5 mL) was added formaldehyde (104 mg, 3.06 mmol) at rt. The mixture was stirred at rt for 16 h. Then NaBH₄ (154 mg, 4.08 mmol) was added and the mixture was stirred for 4 h. On completion, the reaction mixture was quenched with sat. aq. NH₄Cl (10 mL), and then extracted with DCM (20 mL×3). The combined organic layers were washed with water (20 mL×2), dried over $Na_2SO_4$ and evaporated to give N,1-dimethyl-1H-indazol-6-amine (0.3 g, 74% yield) as a yellow solid which was directly used in the next step.

$^1$H NMR (400 MHz, $CDCl_3$) δ ppm 7.76-7.68 (m, 1H), 7.38 (d, J=8.4 Hz, 1H), 6.43 (dd, J=8.8, 2.0 Hz, 1H), 6.31 (s, 1H), 3.90 (s, 3H), 2.86 (d, J=5.2 Hz, 3H).

Steps b-d. The title compound was prepared in a similar manner to Example 65, using N,1-dimethyl-1H-indazol-6-amine.

m/z ES+[M+H]$^+$ 464.2; $^1$H NMR (400 MHz, $CD_3OD$) δ ppm 8.41 (s, 1H), 8.11 (s, 1H), 7.97 (d, J=8.4 Hz, 1H), 7.85 (s, 1H), 7.46 (d, J=8.0 Hz, 1H), 7.32 (s, 1H), 5.18 (d, J=3.6 Hz, 1H), 4.25-4.18 (m, 2H), 4.14 (s, 3H), 3.39 (s, 3H), 2.71 (s, 3H).

Example 169

(2S,3S,4S)-3,4-Dihydroxy-N-methyl-N-(4-methyl-3,4-dihydro-2H-pyrido[3,2-b][1,4]oxazin-6-yl)-1-(6-methyl-4-(trifluoromethyl)pyridin-2-yl)-5-oxopyrrolidine-2-carboxamide

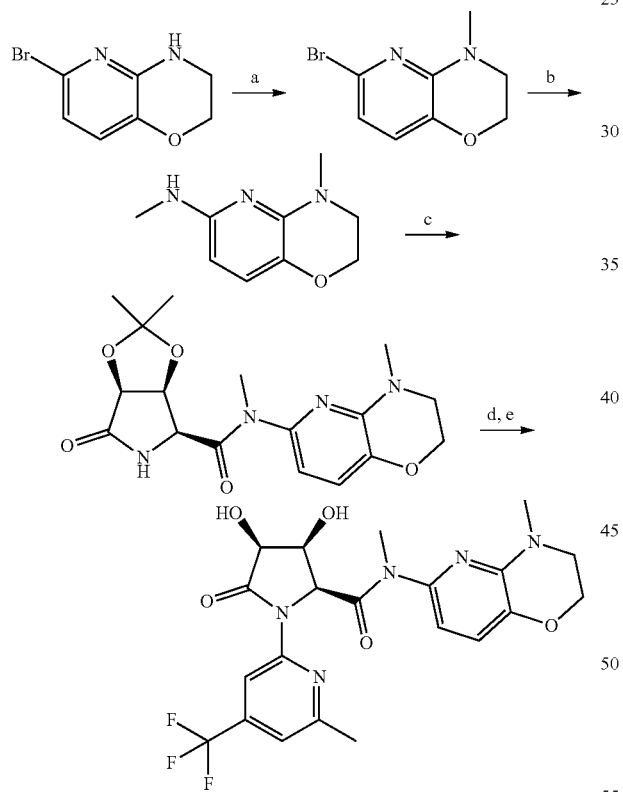

Step a. To a solution of 6-bromo-3,4-dihydro-2H-pyrido[3,2-b][1,4]oxazine (CAS Number 959992-62-2; 2.0 g, 9.3 mmol) in DMF (20 mL) was added NaH (409 mg, 10 mmol, 60% dispersion in mineral oil) portionwise at 0° C. The mixture was then stirred at 0° C. for 30 min. Methyl iodide (1.58 g, 11.2 mmol) was added and the mixture was stirred 0° C. for 1.5 h. Upon completion, the reaction mixture was concentrated. The residue was purified by column chromatography (10-25% EtOAc in PE) to afford 6-bromo-4-methyl-3,4-dihydro-2H-pyrido[3,2-b][1,4]oxazine (1.5 g, 70% yield) as a yellow solid.

$^1$H NMR (400 MHz, $CDCl_3$) δ ppm 8.04 (s, 1H), 6.77 (d, J=8.0 Hz, 1H), 6.62 (d, J=8.0 Hz, 1H), 4.31-4.14 (m, 2H), 3.48-3.39 (m, 2H), 3.19-3.06 (m, 3H).

Step b. A mixture of 6-bromo-4-methyl-3,4-dihydro-2H-pyrido[3,2-b][1,4]oxazine (1.0 g, 4.37 mmol), $MeNH_2$ (2 M, 43.7 mmol), BrettPhos (466 mg, 0.87 mmol), BrettPhos-Pd-G2 (234 mg, 0.44 mmol) and LiHMDS (1 M, 13.1 mmol) in THF (1 mL) was degassed and purged with $N_2$ 3 times, and then the mixture was stirred at 60° C. for 2 h under $N_2$ atmosphere. Upon completion, the reaction mixture was concentrated. The residue was purified by column chromatography (10-50% EtOAc in PE) to afford N,4-dimethyl-3,4-dihydro-2H-pyrido[3,2-b][1,4]oxazin-6-amine (550 mg, 70% yield) as a brown oil.

m/z ES+[M+H]$^+$ 180.0

Steps c-e. The title compound was prepared in a similar manner to Example 65, using N,4-dimethyl-3,4-dihydro-2H-pyrido[3,2-b][1,4]oxazin-6-amine.

m/z ES+[M+H]$^+$ 482.1; $^1$H NMR (400 MHz, DMSO-d6) δ ppm 8.22 (s, 1H), 7.37 (s, 1H), 7.09 (d, J=7.6 Hz, 1H), 6.66 (d, J=7.6 Hz, 1H), 5.05-5.00 (m, 1H), 4.34-4.30 (m, 1H), 4.29-4.26 (m, 1H), 4.25-4.20 (m, 2H), 3.50-3.45 (m, 2H), 3.13 (s, 3H), 3.08 (s, 3H), 2.52 (s, 3H).

Example 170

(2S,3S,4S)—N-(5-Fluoro-6-methylpyridin-2-yl)-3,4-dihydroxy-N-methyl-1-(6-methyl-4-(trifluoromethyl)pyridin-2-yl)-5-oxopyrrolidine-2-carboxamide

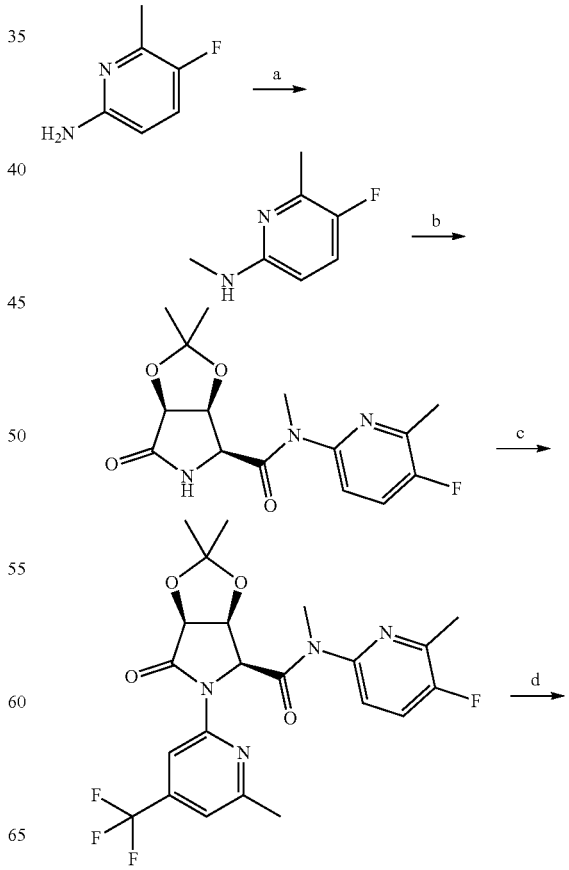

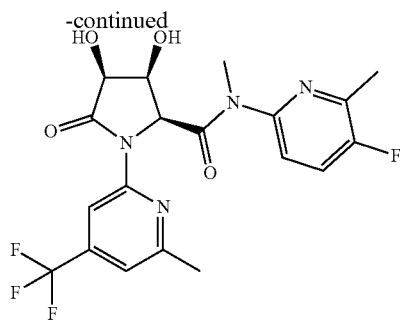

Step a. To a solution of 5-fluoro-6-methylpyridin-2-amine (1 g, 7.93 mmol) in MeOH (10 mL) was added sodium methoxide (4.28 g, 79.3 mmol) and formaldehyde (476 mg, 16.0 mmol). The mixture was stirred at 40° C. for 16 h. Then NaBH$_4$ (900 mg, 23.8 mmol) was added and the mixture was stirred at rt for 1 h. On completion, the reaction mixture was quenched with water (50 mL) and then extracted with EtOAc (50 mL×3). The combined organic layers were washed with brine (40 mL×3), dried over Na$_2$SO$_4$ and evaporated. The residue was purified by column chromatography (10-15% EtOAc in PE) to give 5-fluoro-N,6-dimethylpyridin-2-amine (950 mg, 74% yield) as a yellow oil. 1H NMR (400 MHz, DMSO-d6) δ ppm 7.23 (t, J=9.2 Hz, 1H), 6.28 (d, J=4.8 Hz, 1H), 6.24 (dd, J=2.8, 8.8 Hz, 1H), 2.71 (d, J=4.8 Hz, 3H), 2.24 (d, J=3.2 Hz, 3H).

Step b. To a solution of Intermediate 5 (120 mg, 0.60 mmol) in MeCN (2 mL) was added Ghosez's reagent (CAS Number 26189-59-3; 87 mg, 0.65 mmol) in MeCN (2 mL) dropwise at 0° C. The mixture was stirred at 0° C. for 30 min. Then the mixture was added dropwise into a solution of 5-fluoro-N,6-dimethylpyridin-2-amine (100 mg, 0.71 mmol) and N, N-dimethylpyridin-2-amine (87.2 mg, 0.71 mmol) in MeCN (2 mL) at 0° C. The mixture was stirred at 0° C. for 30 min. Upon completion, the reaction was concentrated under vacuum. The residue was purified by prep-HPLC followed by prep-TLC (10% MeOH in EtOAc) to give (3aS,4S,6aS)—N-(5-fluoro-6-methylpyridin-2-yl)-N,2,2-trimethyl-6-oxotetrahydro-3aH-[1,3]dioxolo[4,5-c]pyrrole-4-carboxamide (100 mg, 48% yield) as a white solid.

m/z ES+[M+H]$^+$ 324.0

Step c. To a solution of (3aS,4S,6aS)—N-(5-fluoro-6-methylpyridin-2-yl)-N,2,2-trimethyl-6-oxotetrahydro-3aH-[1,3]dioxolo[4,5-c]pyrrole-4-carboxamide (80 mg, 0.24 mmol) and 2-bromo-6-methyl-4-(trifluoromethyl)pyridine (77 mg, 0.32 mmol) in dioxane (2 mL) was added Pd$_2$(dba)$_3$ (23 mg, 0.025 mmol), XantPhos (29 mg, 0.050 mmol) and K$_2$CO$_3$ (68 mg, 0.50 mmol). The mixture was degassed and purged with N$_2$ 3 times, and then stirred at 100° C. for 2 h under N$_2$ atmosphere. Upon completion, the reaction mixture was filtered and concentrated under vacuum. The residue was purified by prep-TLC (10% MeOH in EtOAc) to give (3aS,4S,6aS)—N-(5-fluoro-6-methylpyridin-2-yl)-N,2,2-trimethyl-5-(6-methyl-4-(trifluoromethyl)pyridin-2-yl)-6-oxotetrahydro-3aH-[1,3]dioxolo[4,5-c]pyrrole-4-carboxamide (100 mg, 81% yield) as a yellow oil.

m/z ES+[M+H]$^+$ 483.1

Step d. A solution of (3aS,4S,6aS)—N-(5-fluoro-6-methylpyridin-2-yl)-N,2,2-trimethyl-5-(6-methyl-4-(trifluoromethyl)pyridin-2-yl)-6-oxotetrahydro-3aH-[1,3]dioxolo[4,5-c]pyrrole-4-carboxamide (50 mg, 0.085 mmol) in HCl/MeOH (4 M, 0.5 mL) was stirred at rt for 30 min. Upon completion, the reaction mixture was concentrated under vacuum. The residue was purified twice by prep-HPLC to give the title compound (10.7 mg, 28% yield) as a yellow solid.

m/z ES+[M+H]$^+$ 443.1; $^1$H NMR (400 MHz, CDCl$_3$) δ ppm 8.47 (s, 1H), 7.57 (t, J=8.0 Hz, 1H), 7.35 (dd, J=3.2, 8.8 Hz, 1H), 7.06 (s, 1H), 5.40-5.27 (m, 1H), 5.25 (d, J=7.2 Hz, 1H), 4.51 (t, J=6.4 Hz, 1H), 4.42-4.23 (m, 2H), 3.45 (s, 3H), 2.58 (d, J=2.8 Hz, 3H), 2.45 (s, 3H).

Examples 171 and 172 may be found in Table 6.

Example 173

(S)—N-(3-Chloro-4-cyclopropylphenyl)-N-methyl-3-(6-methyl-4-(trifluoromethyl)pyridin-2-yl)-2-oxooxazolidine-4-carboxamide

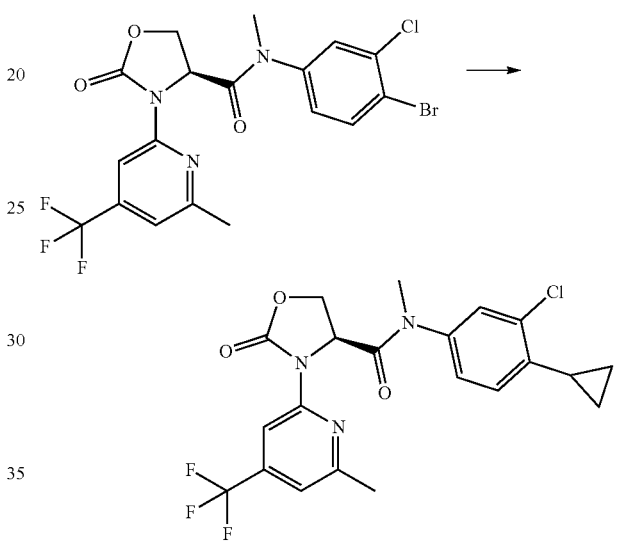

A mixture of Example 172 (150 mg, 0.30 mmol), cyclopropylboronic acid (34 mg, 0.40 mmol), Pd(dppf)Cl$_2$·CH$_2$Cl$_2$ (25 mg, 0.030 mmol) and K$_2$CO$_3$ (84 mg, 0.61 mmol) in dioxane (1.0 mL) and water (0.2 mL) was stirred at 100° C. for 2 h under N$_2$ atmosphere. Upon completion, the reaction mixture was filtered and concentrated under vacuum. The residue was purified by prep-TLC (25% EtOAc in PE) to give the title compound (53 mg, 38% yield) as a white solid.

m/z ES+[M+H]$^+$ 454.0; $^1$H NMR (400 MHz, DMSO-d6) δ ppm 8.14 (s, 1H), 7.65 (d, J=2.0 Hz, 1H), 7.42 (s, 1H), 7.38 (dd, J=2.0, 8.4 Hz, 1H), 7.19 (d, J=8.0 Hz, 1H), 4.98 (dd, J=3.2, 9.2 Hz, 1H), 4.59 (dd, J=3.2, 9.2 Hz, 1H), 4.34 (t, J=8.8 Hz, 1H), 3.18 (s, 3H), 2.60 (s, 3H), 2.23-2.13 (m, 1H), 1.09-1.01 (m, 2H), 0.80-0.72 (m, 2H)

Example 174

(S)—N-(1H-Indazol-6-yl)-N-methyl-3-(6-methyl-4-(trifluoromethyl)pyridin-2-yl)-2-oxooxazolidine-4-carboxamide

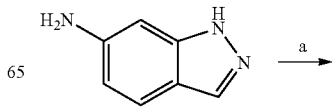

-continued

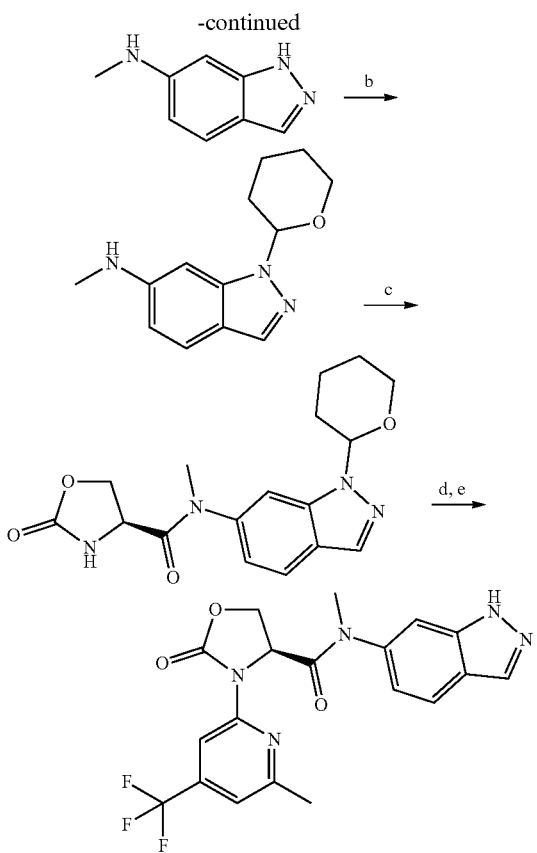

Step a. To a mixture of 1H-indazol-6-amine (1 g, 7.51 mmol) and formaldehyde (338 mg, 11.3 mmol) in MeOH (25 mL) was added sodium methoxide (4.06 g, 75.10 mmol). The mixture was stirred at rt for 16 h. Then NaBH₄ (568 mg, 15.0 mmol) was added, and the mixture was stirred at rt for 4 h. On completion, the reaction mixture was quenched with sat. aq. NH₄Cl (20 mL) and extracted with DCM (50 mL×3). The combined organic layers were washed with water (20 mL×2), dried over Na₂SO₄ and evaporated. The residue was purified by prep-HPLC to give N-methyl-1H-indazol-6-amine (0.3 g, 18% yield) as a yellow solid.

m/z ES+[M+H]⁺ 148.2

Step b. To a mixture of N-methyl-1H-indazol-6-amine (0.1 g, 0.68 mmol) and 3,4-dihydro-2H-pyran (86 mg, 1.02 mmol) in THF (2 mL) was added p-toluenesulfonic acid (23 mg, 0.14 mmol). The mixture was then stirred at 40° C. for 16 h. On completion, the reaction mixture was concentrated under vacuum. The residue was purified by prep-HPLC to give N-methyl-1-(tetrahydro-2H-pyran-2-yl)-1H-indazol-6-amine (20 mg, 11% yield) as a yellow solid.

m/z ES+[M+H]⁺ 232.0

Step c. To a mixture of N-methyl-1-(tetrahydro-2H-pyran-2-yl)-1H-indazol-6-amine (20 mg, 0.086 mmol) and (4S)-2-oxooxazolidine-4-carboxylic acid (17 mg, 0.13 mmol) in pyridine (0.5 mL) was added T3P (165 mg, 0.26 mmol, 50 wt. % in EtOAc). The mixture was stirred at rt for 5 h. On completion, the reaction mixture was quenched with water (3 mL) and extracted with EtOAc (5 mL×3). The combined organic layers were washed with water (5 mL×2), dried over Na₂SO₄ and evaporated. The residue was purified by reverse-phase HPLC to give (4S)—N-methyl-2-oxo-N-(1-(tetrahydro-2H-pyran-2-yl)-1H-indazol-6-yl)oxazolidine-4-carboxamide (20 mg, 62% yield) as a yellow solid.

m/z ES+[M+H]⁺ 345.1

Step d. To a mixture of (4S)—N-methyl-2-oxo-N-(1-(tetrahydro-2H-pyran-2-yl)-1H-indazol-6-yl)oxazolidine-4-carboxamide (20 mg, 0.058 mmol) and 2-bromo-6-methyl-4-(trifluoromethyl)pyridine (21 mg, 0.087 mmol) in dioxane (0.5 mL) was added Pd₂(dba)₃ (5.3 mg, 0.0058 mmol), XantPhos (6.7 mg, 0.012 mmol) and K₂CO₃ (16 mg, 0.12 mmol) under N₂ atmosphere. The mixture was then stirred at 100° C. for 4 h. On completion, the reaction mixture was quenched with water (2 mL) and extracted with EtOAc (5 mL×3). The combined organic layers were washed with water (2 mL×2), dried over Na₂SO₄ and evaporated. The residue was purified by column chromatography (10-50% EtOAc in PE) to give (4S)—N-methyl-3-(6-methyl-4-(trifluoromethyl)pyridin-2-yl)-2-oxo-N-(1-(tetrahydro-2H-pyran-2-yl)-1H-indazol-6-yl)oxazolidine-4-carboxamide (20 mg, 55% yield) as a yellow solid.

m/z ES+[M+H]⁺ 504.3

Step e. A mixture of (4S)—N-methyl-3-(6-methyl-4-(trifluoromethyl)pyridin-2-yl)-2-oxo-N-(1-(tetrahydro-2H-pyran-2-yl)-1H-indazol-6-yl)oxazolidine-4-carboxamide (20 mg, 0.040 mmol) in HCl/MeOH (1 mL) was stirred at rt for 5 h. On completion, the reaction mixture was concentrated under vacuum. The residue was purified by prep-HPLC to give the title compound (4.0 mg, 24% yield) as an off-white solid.

m/z ES+[M+H]⁺ 420.1; ¹H NMR (400 MHz, CD₃OD) δ ppm 8.28 (s, 1H), 8.21 (s, 1H), 8.05-8.00 (m, 1H), 7.75 (s, 1H), 7.37-7.27 (m, 2H), 5.25-5.17 (m, 1H), 4.61-4.52 (m, 1H), 4.42-4.33 (m, 1H), 3.40 (s, 3H), 2.71 (s, 3H).

Example 175

(S)—N-(6-Aminopyridin-2-yl)-N-methyl-3-(6-methyl-4-(trifluoromethyl)pyridin-2-yl)-2-oxooxazolidine-4-carboxamide

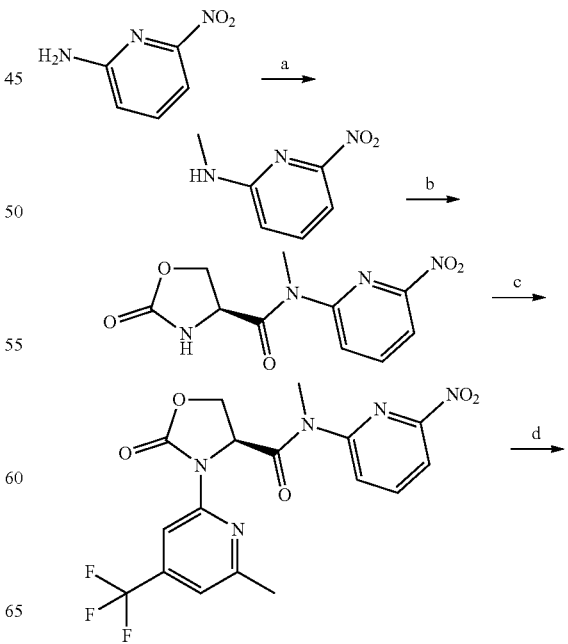

-continued

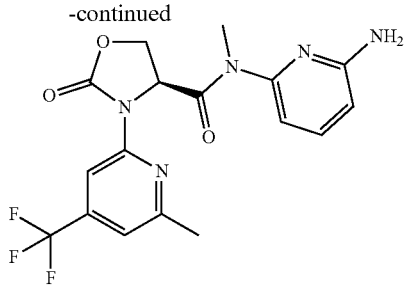

Step a. To a mixture of sodium methoxide (3.88 g, 71.9 mmol) in MeOH (60 mL) was added 6-nitropyridin-2-amine (1 g, 7.19 mmol) and formaldehyde (324 mg, 10.8 mmol). The mixture was stirred at 50° C. for 16 h. Then NaBH$_4$ (544 mg, 14.4 mmol) was added, and the mixture was stirred at 50° C. for 16 h. Upon completion, the mixture was concentrated, diluted with water (50 mL) and extracted with EtOAc (50 mL×3). The combined organic layers were washed with brine (60 mL×3), dried over Na$_2$SO$_4$ and evaporated. The residue was purified by column chromatography (25-50% EtOAc in PE) to give N-methyl-6-nitropyridin-2-amine (500 mg, 45% yield) as a yellow solid.

Step b. To a solution of (S)-2-oxooxazolidine-4-carboxylic acid (100 mg, 0.76 mmol) in MeCN (1 mL) was added Ghosez's reagent (CAS Number 26189-59-3; 204 mg, 1.53 mmol) dropwise at 0° C. The reaction mixture was stirred at 0° C. for 30 min. Then the mixture was added into a solution of N-methyl-6-nitropyridin-2-amine (129 mg, 0.84 mmol) and N,N-dimethylpyridin-2-amine (112 mg, 0.92 mmol) in MeCN (1 mL) at 0° C. and the mixture was stirred at 0° C. for 1 h under N$_2$ atmosphere. Upon completion, the mixture was concentrated and purified by prep-TLC (100% EtOAc) to give (S)—N-methyl-N-(6-nitropyridin-2-yl)-2-oxooxazolidine-4-carboxamide (100 mg, 49% yield) as a yellow solid.

m/z ES+[M+H]$^+$ 267.1

Step c. To a solution of (S)—N-methyl-N-(6-nitropyridin-2-yl)-2-oxooxazolidine-4-carboxamide (80 mg, 0.30 mmol) and 2-bromo-6-methyl-4-(trifluoromethyl)pyridine (79 mg, 0.33 mmol) in dioxane (2 mL) was added K$_2$CO$_3$ (124 mg, 0.90 mmol), Pd(dba)$_2$ (17 mg, 0.030 mmol) and XantPhos (17.4 mg, 0.030 mmol). The mixture was stirred at 80° C. for 1 h under N$_2$ atmosphere. Upon completion, the mixture was quenched with water (2 mL) and extracted with EtOAc (2 mL×3). The combined organic layers were washed with brine (3 mL×3), dried over Na$_2$SO$_4$ and evaporated. The residue was purified by prep-TLC (50% EtOAc in PE) to give (S)—N-methyl-3-(6-methyl-4-(trifluoromethyl)pyridin-2-yl)-N-(6-nitropyridin-2-yl)-2-oxooxazolidine-4-carboxamide (100 mg, 78% yield) as a yellow solid.

m/z ES+[M+H]$^+$ 426.1

Step d. To a solution of (S)—N-methyl-3-(6-methyl-4-(trifluoromethyl)pyridin-2-yl)-N-(6-nitropyridin-2-yl)-2-oxooxazolidine-4-carboxamide (80 mg, 0.19 mmol) in EtOH (1 mL) was added Pd on activated carbon (8 mg, 10 wt %). The mixture was stirred at rt for 16 h under hydrogen atmosphere (15 psi). Upon completion, the reaction mixture was filtered. The filtrate was concentrated under vacuum and further purified by prep-HPLC to give the title compound (11.6 mg, 14% yield) as an off-white solid.

m/z ES+[M+H]$^+$ 396.1; $^1$H NMR (400 MHz, DMSO-d6) δ ppm 8.12 (s, 1H), 7.54 (t, J=7.6 Hz, 1H), 7.34 (s, 1H), 6.56 (d, J=7.6 Hz, 1H), 6.37 (d, J=8.4 Hz, 1H), 5.25-5.20 (m, 1H), 4.80 (t, J=9.6 Hz, 1H), 4.55-4.46 (m, 1H), 3.22 (s, 3H), 2.43 (s, 3H).

Example 176

(S)—N-Methyl-3-(6-methyl-4-(trifluoromethyl)pyridin-2-yl)-N-(6-(methylamino)pyridin-2-yl)-2-oxooxazolidine-4-carboxamide

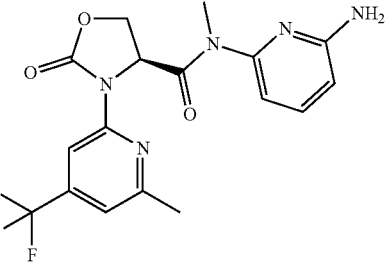

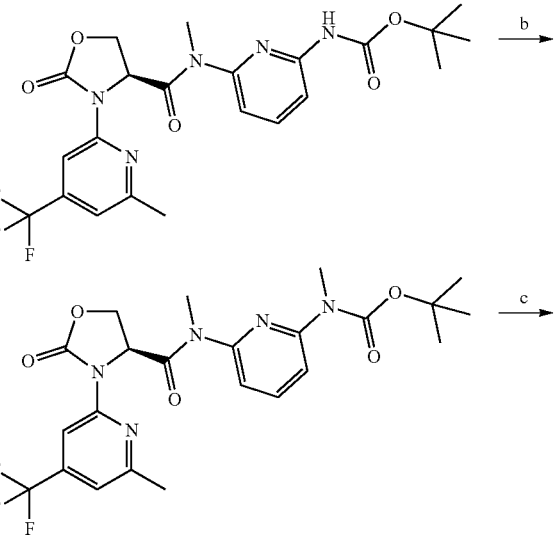

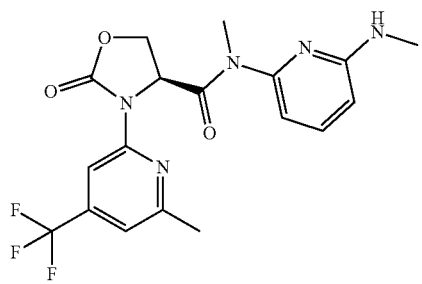

Step a. To a solution of Example 175 (40 mg, 0.10 mmol) in DCM (1 mL) was added TEA (31 mg, 0.30 mmol) and (Boc)$_2$O (33 mg, 0.15 mmol) at 0° C. The mixture was stirred at rt for 16 h. Upon completion, the mixture was concentrated and purified by prep-TLC (50% EtOAc in PE) to give (S)-tert-butyl (6-(N-methyl-3-(6-methyl-4-(trifluoromethyl)pyridin-2-yl)-2-oxooxazolidine-4-carboxamido)pyridin-2-yl)carbamate (20 mg, 40% yield) as a yellow oil.

m/z ES+[M+H]$^+$ 496.3

Step b. To a solution of (S)-tert-butyl (6-(N-methyl-3-(6-methyl-4-(trifluoromethyl)pyridin-2-yl)-2-oxooxazolidine-4-carboxamido)pyridin-2-yl)carbamate (20 mg, 0.040 mmol) in THF (1 mL) was added NaH (2.4 mg, 0.061 mmol, 60% dispersion in mineral oil) at 0° C. under N$_2$ atmosphere. The mixture was stirred at 0° C. for 30 min. Then methyl iodide (8.6 mg, 0.061 mmol) was added and the mixture was stirred at rt for 1 h under N$_2$ atmosphere. Upon completion, the mixture was quenched with water (2 mL) and extracted with EtOAc (2 mL×3). The combined organic layers were washed with brine (3 mL×3), dried over Na₂SO₄ and evaporated. The residue was purified by prep-TLC (25% EtOAc in PE) to give (S)-tert-butyl methyl(6-(N-methyl-3-(6-methyl-4-(trifluoromethyl)pyridin-2-yl)-2-oxooxazolidine-4-carboxamido)pyridin-2-yl)carbamate (20 mg, 97% yield) as a yellow solid.

m/z ES+[M+H]⁺ 510.2

Step c. To a solution of (S)-tert-butyl methyl(6-(N-methyl-3-(6-methyl-4-(trifluoromethyl)pyridin-2-yl)-2-oxooxazolidine-4-carboxamido)pyridin-2-yl)carbamate (20 mg, 0.039 mmol) in DCM (1 mL) was added TFA (0.1 mL). The mixture was stirred at rt for 1 h. Upon completion, the mixture was concentrated and purified twice by prep-HPLC to give the title compound (2 mg, 11% yield) as a yellow solid.

m/z ES+[M+H]⁺ 410.3; ¹H NMR (400 MHz, DMSO-d6) δ ppm 8.11 (s, 1H), 7.56 (t, J=8.0 Hz, 1H), 7.35 (s, 1H), 6.87-6.61 (m, 1H), 6.56 (d, J=7.2 Hz, 1H), 6.38 (d, J=8.4 Hz, 1H), 5.23 (dd, J=4.0, 9.2 Hz, 1H), 4.72 (t, J=9.2 Hz, 1H), 4.55 (dd, J=4.0, 8.8 Hz, 1H), 3.23 (s, 3H), 2.77 (s, 3H), 2.44 (s, 3H).

Example 177

(S)—N-(6-(Dimethylamino)pyridin-2-yl)-N-methyl-3-(6-methyl-4-(trifluoromethyl)pyridin-2-yl)-2-oxooxazolidine-4-carboxamide

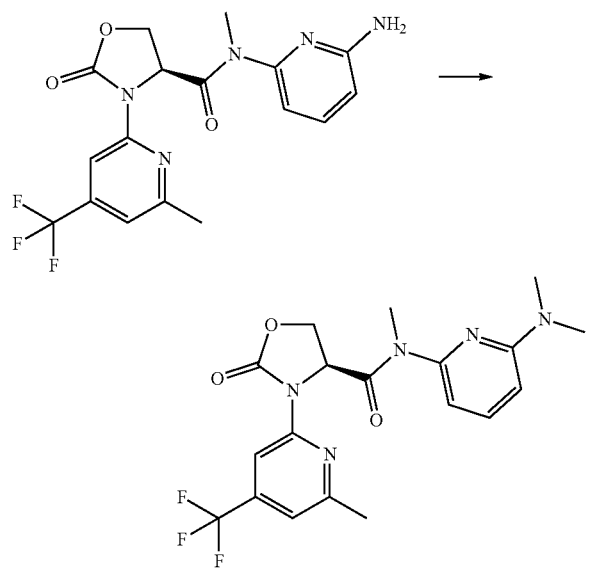

To a solution of Example 175 (80 mg, 0.20 mmol), formaldehyde (30 mg, 1.01 mmol) and NaBH₃CN (38 mg, 0.61 mmol) in THF (1 mL) was added acetic acid (1.05 g, 17.5 mmol). The mixture was stirred at rt for 16 h. Upon completion, the mixture was concentrated under vacuum. The residue was purified by prep-HPLC to give the title compound (32 mg, 37% yield) as a yellow solid.

m/z ES+[M+H]⁺ 424.1; ¹H NMR (400 MHz, DMSO-d6) δ ppm 8.10 (s, 1H), 7.68 (t, J=8.0 Hz, 1H), 7.36 (s, 1H), 6.65 (d, J=7.2 Hz, 1H), 6.59 (d, J=8.4 Hz, 1H), 5.25-5.15 (m, 1H), 4.67-4.53 (m, 2H), 3.24 (s, 3H), 3.04 (s, 6H), 2.46 (s, 3H).

Example 178

(S)—N-Methyl-3-(6-methyl-4-(trifluoromethyl)pyridin-2-yl)-2-oxo-N-(quinolin-7-yl)oxazolidine-4-carboxamide

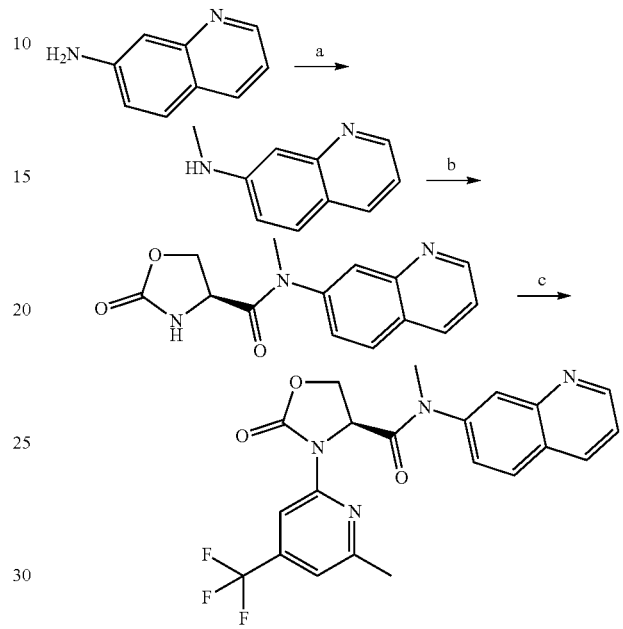

Step a. To a solution of sodium methoxide (3.75 g, 69.4 mmol) in MeOH (40 mL) was added quinolin-7-amine (1 g, 6.94 mmol). Then formaldehyde (312 mg, 10.4 mmol) was added. The mixture was stirred at rt for 12 h. Then NaBH₄ (525 mg, 13.9 mmol) was added and the mixture was stirred at rt for 5 h. Upon completion, the reaction mixture was adjusted to pH 8 by aq. HCl solution, then filtered and concentrated. The residue was purified by column chromatography (10% MeOH in DCM) and further purified by prep-HPLC to give N-methylquinolin-7-amine (800 mg, 73% yield) as a yellow solid.

¹H NMR (400 MHz, DMSO-d6) δ ppm 8.62 (dd, J=4.4, 1.6 Hz, 1H), 8.02 (dd, J=8.0, 1.2 Hz, 1H), 7.61 (d, J=8.8 Hz, 1H), 7.12-7.06 (m, 1H), 7.01 (dd, J=8.8, 2.4 Hz, 1H), 6.74 (d, J=2.0 Hz, 1H), 6.36 (q, J=5.2 Hz, 1H), 2.80 (d, J=5.2 Hz, 3H).

Step b. To a stirred solution of (4S)-2-oxooxazolidine-4-carboxylic acid (110 mg, 0.84 mmol) in MeCN (1 mL) was added Ghosez's reagent (CAS Number 26189-59-3; 112 mg, 0.84 mmol) in MeCN (0.5 mL) dropwise at 0° C. The suspension was stirred at 0° C. for 30 min to obtain a clear solution. The resulting solution was added dropwise into a solution of N-methylquinolin-7-amine (159 mg, 1.01 mmol), N,N-dimethylpyridin-2-amine (123 mg, 1.01 mmol) in MeCN (0.5 mL) at 0° C. The mixture was stirred at 0° C. for 1 h. Upon completion, the reaction mixture was concentrated. The residue was purified by prep-TLC (5% EtOH in EtOAc) to give (S)—N-methyl-2-oxo-N-(quinolin-7-yl)oxazolidine-4-carboxamide (120 mg, 53% yield) as a yellow oil.

m/z ES+[M+H]⁺ 272.1

Step c. A mixture of (4S)—N-methyl-2-oxo-N-(7-quinolyl)oxazolidine-4-carboxamide (110 mg, 0.40 mmol), 2-bromo-6-methyl-4-(trifluoromethyl)pyridine (146.0 mg, 0.60 mmol), K$_2$CO$_3$ (112 mg, 0.80 mmol), Pd$_2$(dba)$_3$ (37 mg, 0.040 mmol) and XantPhos (47 mg, 0.080 mmol) in dioxane (2 mL) was degassed and purged with N$_2$ 3 times, and then the mixture was stirred at 100° C. for 2 h under N$_2$ atmosphere. Upon completion, the reaction mixture was filtered and concentrated. The residue was purified by column chromatography (25-50% EtOAc in PE) and further purified by prep-HPLC to give the title compound (61 mg, 35% yield) as a yellow solid.

m/z ES+[M+H]$^+$ 431.0; $^1$H NMR (400 MHz, DMSO-d6) δ ppm 9.08 (d, J=3.2 Hz, 1H), 8.63 (d, J=6.8 Hz, 1H), 8.30-8.20 (m, 2H), 8.13 (s, 1H), 7.85-7.70 (m, 2H), 7.42 (s, 1H), 5.10-5.00 (m, 1H), 4.71 (dd, J=8.8, 3.6 Hz, 1H), 4.42-4.30 (m, 1H), 3.35 (s, 3H), 2.65 (s, 3H).

Example 179

(S)—N-(3-Chloro-4-fluorophenyl)-N-isopropyl-3-(6-methyl-4-(trifluoromethyl)pyridin-2-yl)-2-oxo-imidazolidine-4-carboxamide

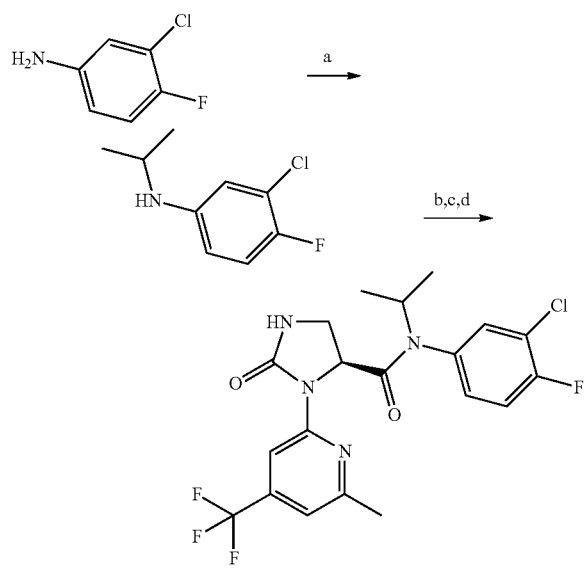

Step a. A mixture of 3-chloro-4-fluoroaniline (500 mg, 3.43 mmol), 2-iodopropane (2.92 g, 17.1 mmol) and K$_2$CO$_3$ (1.42 g, 10.3 mmol) in DMF (2 mL) was stirred at 60° C. for 12 h. Upon completion, the reaction mixture was diluted with water (15 mL) and extracted with EtOAc (20 mL×3). The combined organic layers were washed with brine (30 mL×2), dried and evaporated. The residue was purified by column chromatography (0-95% EtOAc in PE) to give 3-chloro-4-fluoro-N-isopropylaniline (470 mg, 73% yield) as a yellow oil.

m/z ES+[M+H]$^+$ 188.6

Steps b-d. Following the procedure described for Example 161, steps f-h.

m/z ES+[M+H]$^+$ 459.1; $^1$H NMR (400 MHz, CD$_3$OD) δ ppm 8.48 (d, J=6.8 Hz, 1H), 7.81 (dd, J=2.4, 6.4 Hz, 0.5H), 7.66-7.60 (m, 0.5H), 7.57-7.45 (m, 1H), 7.45-7.40 (m, 0.5H), 7.35-7.27 (m, 0.5H), 7.10 (d, J=6.8 Hz, 1H), 4.82-4.75 (m, 2H), 3.50-3.37 (m, 2H), 2.65-2.55 (d, J=14.8 Hz, 3H), 1.16 (d, J=6.8 Hz, 3H), 1.08 (d, J=6.8 Hz, 3H).

Example 180

(S)—N-(3-Chloro-4-fluorophenyl)-N-methyl-3-(6-methyl-4-(trifluoromethyl)pyridin-2-yl)-1-(2-(methylsulfonyl)ethyl)-2-oxoimidazolidine-4-carboxamide

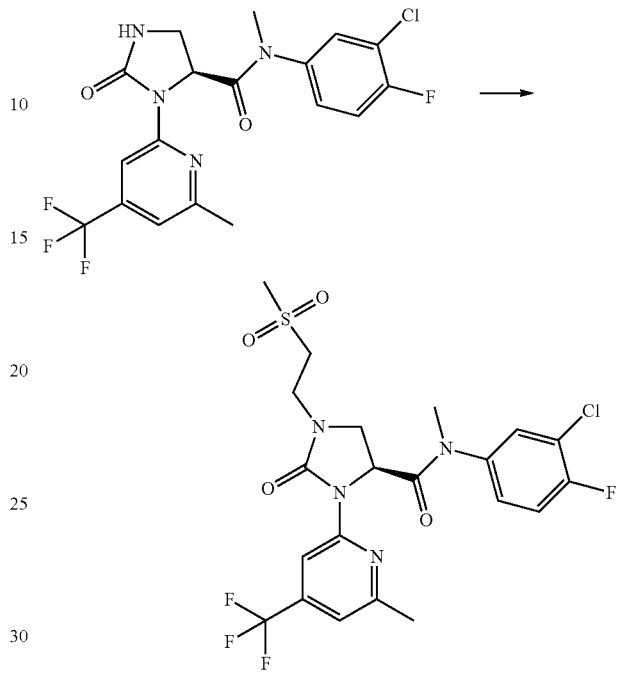

To a solution of Example 156 (100 mg, 0.23 mmol) in DMF (1 mL) was added NaH (27 mg, 0.69 mmol, 60% dispersion in mineral oil) portionwise. The reaction mixture was stirred at 15° C. for 30 min and then 1-bromo-2-methylsulfonyl-ethane (86 mg, 0.46 mmol) was added. The mixture was stirred at rt for 10.5 h. Upon completion, the reaction mixture was quenched with water (0.2 mL). The residue was purified by prep-HPLC to give the title compound (47 mg, 38% yield) as a white solid.

m/z ES+[M+H]$^+$ 537.1; $^1$H NMR (400 MHz, CDCl$_3$) δ ppm 8.39 (s, 1H), 7.63 (s, 1H), 7.29 (t, J=7.6 Hz, 2H), 7.00 (s, 1H), 4.98 (dd, J=4.8, 9.2 Hz, 1H), 3.85-3.67 (m, 2H), 3.59-3.43 (m, 3H), 3.36-3.26 (m, 4H), 3.03 (s, 3H), 2.58 (s, 3H).

Example 181

(S)—N-(3-Chloro-4-fluorophenyl)-1-(2-(N,N-dimethylsulfamoyl)ethyl)-N-methyl-3-(6-methyl-4-(trifluoromethyl)pyridin-2-yl)-2-oxoimidazolidine-4-carboxamide

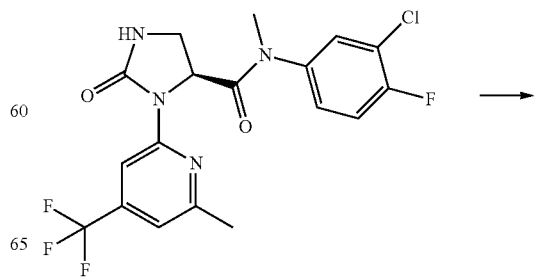

-continued

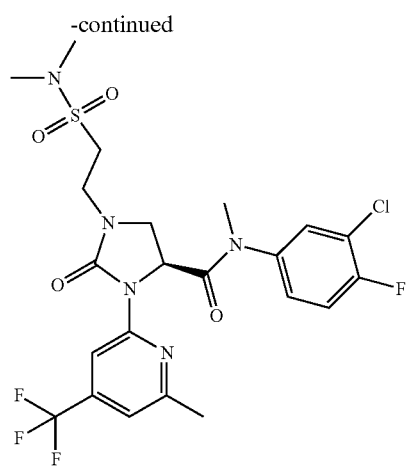

To a solution of Example 156 (100 mg, 0.23 mmol) in DMF (1 mL) was added NaH (28 mg, 0.70 mmol, 60% dispersion in mineral oil) at 0° C. The mixture was stirred at 0° C. for 30 min. N,N-Dimethylethenesulfonamide (CAS Number 7700-07-4; 38 mg, 0.28 mmol) was added, and the mixture was stirred at rt for 1 h. Upon completion, EtOAc (10 mL) and water (10 mL) were added to the reaction mixture and separated. The aqueous phase was extracted with EtOAc (10 mL×2). The combined organic layers were dried over $Na_2SO_4$ and evaporated. The residue was purified by prep-HPLC to give the title compound (21 mg, 15% yield) as a white solid.

m/z ES+[M+H]$^+$ 566.1; $^1$H NMR (400 MHz, $CD_3OD$) δ ppm 8.33 (s, 1H), 7.83-7.72 (m, 1H), 7.56-7.49 (m, 1H), 7.45 (t, J=8.8 Hz, 1H), 7.12 (s, 1H), 4.97 (t, J=7.2 Hz, 1H), 4.85-4.80 (m, 2H), 3.77-3.67 (m, 2H), 3.64-3.56 (m, 2H), 3.28 (s, 3H), 2.88 (s, 6H), 2.60 (s, 3H).

The examples in Table 10 were prepared by a procedure similar to that described for the synthesis of Example 180, using either Example 156 or Example 158.

TABLE 10

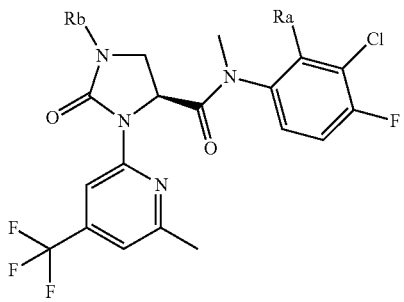

| Example Number | Ra | Rb | Name | Alkyl bromide CAS No. | $^1$H NMR (400 MHz) δ ppm | MI |
|---|---|---|---|---|---|---|
| 182 | H | (CH$_3$)$_2$N-CH$_2$CH$_2$- | (S)-N-(3-Chloro-4-fluorophenyl)-1-(2-(dimethylamino)ethyl)-N-methyl-3-(6-methyl-4-(trifluoromethyl)pyridin-2-yl)-2-oxoimidazolidine-4-carboxamide | 5459-68-7 | (CDCl$_3$) 8.44 (s, 1H), 7.65-7.58 (m, 1H), 7.35-7.25 (m, 2H), 6.96 (s, 1H), 4.95 (dd, J = 5.6, 10.0 Hz, 1H), 3.61-3.49 (m, 2H), 3.44-3.38 (m, 1H), 3.32-3.24 (m, 4H), 2.59-2.43 (m, 5H), 2.27 (s, 6H). | 502.2 |
| 183 | H | (CH$_3$)$_2$N-CH$_2$CH$_2$CH$_2$- | (S)-N-(3-Chloro-4-fluorophenyl)-1-(3-(dimethylamino)propyl)-N-methyl-3-(6-methyl-4-(trifluoromethyl)pyridin-2-yl)-2-oxoimidazolidine-4-carboxamide | 53929-74-1 | (CD$_3$OD) 8.33 (s, 1H), 7.85 (dd, J = 2.4, 6.4 Hz, 1H), 7.63-7.57 (m, 1H), 7.48 (t, J = 8.8 Hz, 1H), 7.14 (s, 1H), 5.00 (dd, J = 3.6, 10.0 Hz, 1H), 3.72-3.65 (m, 1H), 3.58-3.53 (m, 1H), 3.33-3.31 (m, 5H), 3.26-3.17 (m, 2H), 2.91 (s, 6H), 2.62 (s, 3H), 2.12-2.01 (m, 2H). | 516.1 |
| 184 | H | H$_2$N-C(O)-CH$_2$- | (S)-1-(2-Amino-2-oxoethyl)-N-(3-chloro-4-fluorophenyl)-N-methyl-3-(6-methyl-4-(trifluoromethyl)-pyridin-2-yl)-2-oxoimidazolidine-4-carboxamide | 683-57-8 | (DMSO-d6) 8.27 (s, 1H), 7.87-7.80 (m, 1H), 7.62 (t, J = 8.8 Hz, 1H), 7.58-7.52 (m, 1H), 7.37 (s, 1H), 7.23 (s, 1H), 7.17 (s, 1H), 4.82 (dd, J = 4.4, 9.6 Hz, 1H), 3.90 (d, J = 17.2 Hz, 1H), 3.66 (d, J = 17.2 Hz, 1H), 3.56-3.48 (m, 2H), 3.18 (s, 3H), 2.56 (s, 3H) | 488.0 |
| 185 | H | (CH$_3$)$_2$N-C(O)-CH$_2$- | (S)-N-(3-Chloro-4-fluorophenyl)-1-(2-(dimethylamino)-2-oxoethyl)-N-methyl-3-(6-methyl-4-(trifluoromethyl)pyridin-2-yl)-2-oxoimidazolidine-4-carboxamide | 5468-77-9 | (CD$_3$OD) 8.35 (s, 1H), 7.78 (d, J = 4.4 Hz, 1H), 7.57-7.49 (m, 1H), 7.46 (t, J = 8.8 Hz, 1H), 7.13 (s, 1H), 5.03 (dd, J = 4.4, 10.4 Hz, 1H), 4.36 (d, J = 16.8 Hz, 1H), 4.04 (d, J = 16.8 Hz, 1H), 3.65-3.59 (m, 1H), 3.56-3.50 (m, 1H), 3.30 (s, 3H), 3.08 (s, 3H), 2.95 (s, 3H), 2.63 (s, 3H) | 516.1 |
| 186 | F | HO-CH$_2$-(oxetan-3-yl)-CH$_2$- | (S)-N-(3-Chloro-2,4-difluorophenyl)-1-((3-(hydroxymethyl)oxetan-3-yl)methyl)-N-methyl-3-(6-methyl-4-(trifluoromethyl)-pyridin-2-yl)-2-oxoimidazolidine-4-carboxamide | 22633-44-9 | (CD$_3$OD) 8.37-8.305 (m, 1H), 7.90-7.44 (m, 1H), 7.43-7.17 (m, 1H), 7.16-7.07 (m, 1H), 5.80-4.90 (m, 1H), 4.73-4.55 (m, 2H), 4.54-4.36 (m, 4H), 3.86-3.69 (m, 4H), 3.68-3.59 (m, 2H), 3.58-3.43 (m, 1H), 2.65-2.48 (m, 3H). | 549.1 |

Example 187

(S)—N-(3-Chloro-4-fluorophenyl)-N-methyl-3-(6-methyl-4-(trifluoromethyl)pyridin-2-yl)-1-(2-(methylsulfonamido)ethyl)-2-oxoimidazolidine-4-carboxamide

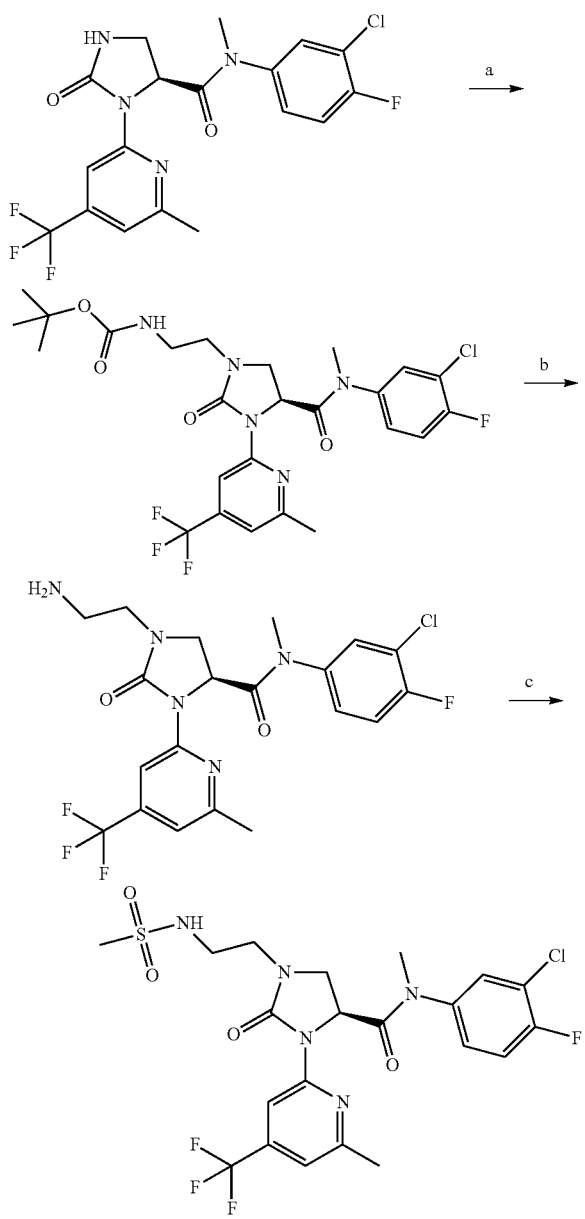

Step a. To a solution of Example 156 (30 mg, 0.070 mmol) and tert-butyl N-(2-bromoethyl)carbamate (23 mg, 0.10 mmol) in DMF (0.7 mL) was added Cs$_2$CO$_3$ (68 mg, 0.21 mmol). The mixture was stirred at 80° C. for 3 h. Upon completion, the reaction mixture was diluted with water (5 mL) and then extracted with EtOAc (5 mL×3). The combined organic layers were washed with water (6 mL) and brine (6 mL), dried over Na$_2$SO$_4$ and evaporated. The residue was purified by prep-TLC (EtOAc) to give (S)-tert-butyl (2-(4-((3-chloro-4-fluorophenyl)(methyl)carbamoyl)-3-(6-methyl-4-(trifluoromethyl)pyridin-2-yl)-2-oxoimidazolidin-1-yl)ethyl)carbamate (33 mg, 72% yield) as a yellow oil.

m/z ES+[M+H]$^+$ 574.3

Step b. To a solution of (S)-tert-butyl (2-(4-((3-chloro-4-fluorophenyl)(methyl)carbamoyl)-3-(6-methyl-4-(trifluoromethyl)pyridin-2-yl)-2-oxoimidazolidin-1-yl)ethyl)carbamate (31 mg, 0.047 mmol) in DCM (0.5 mL) was added TFA (0.05 mL). The mixture was stirred at rt for 30 min. Upon completion, the reaction mixture was diluted with sat. aq. Na$_2$CO$_3$ (5 mL) and then extracted with EtOAc (5 mL×3). The combined organic layers were washed with brine (8 mL), dried over Na$_2$SO$_4$ and evaporated to give (S)-1-(2-aminoethyl)-N-(3-chloro-4-fluorophenyl)-N-methyl-3-(6-methyl-4-(trifluoromethyl)pyridin-2-yl)-2-oxoimidazolidine-4-carboxamide (24 mg, crude) as a yellow oil.

m/z ES+[M+H]$^+$ 474.3

Step c. To a solution of (S)-1-(2-aminoethyl)-N-(3-chloro-4-fluorophenyl)-N-methyl-3-(6-methyl-4-(trifluoromethyl)pyridin-2-yl)-2-oxoimidazolidine-4-carboxamide (24 mg, 0.051 mmol) in DCM (1 mL) was added TEA (15 mg, 0.15 mmol) and methanesulfonyl chloride (9 mg, 0.076 mmol) in DCM (0.5 mL) dropwise at 0° C. The mixture was stirred at 0° C. for 1 h. Upon completion, the reaction mixture was concentrated under vacuum to give a residue. The residue was purified by prep-HPLC to give the title compound (11 mg, 39% yield) as a white solid.

m/z ES+[M+H]$^+$ 552.1; $^1$H NMR (400 MHz, CD$_3$OD) δ ppm 8.36 (s, 1H), 7.82 (dd, J=1.6, 6.4 Hz, 1H), 7.58-7.54 (m, 1H), 7.47 (t, J=8.8 Hz, 1H), 7.12 (s, 1H), 5.00 (dd, J=6.0, 8.8 Hz, 1H), 3.65-3.60 (m, 2H), 3.45-3.37 (m, 2H), 3.31 (s, 3H), 3.30-3.25 (m, 2H), 2.98 (s, 3H), 2.62 (s, 3H).

Example 188

(S)-1-(Azetidin-3-ylmethyl)-N-(3-chloro-2,4-difluorophenyl)-N-methyl-3-(6-methyl-4-(trifluoromethyl)pyridin-2-yl)-2-oxoimidazolidine-4-carboxamide

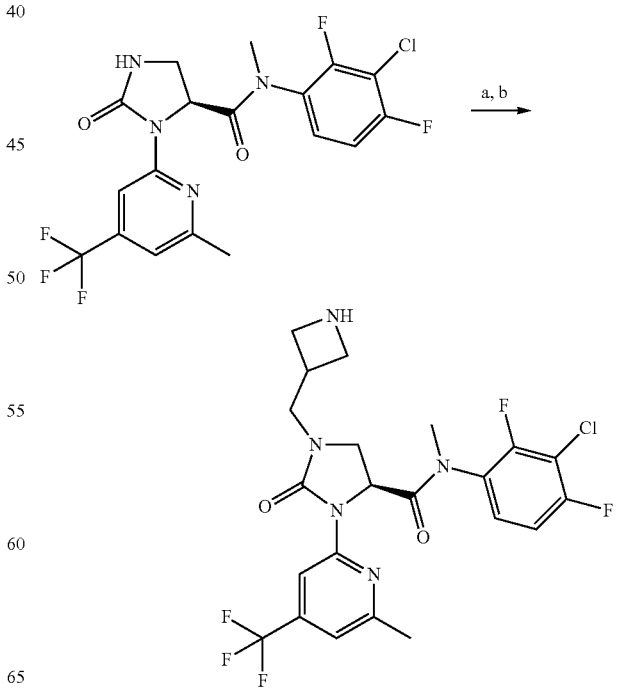

Step a. A mixture of Example 158 (70 mg, 0.16 mmol), tert-butyl 3-(bromomethyl)azetidine-1-carboxylate (47 mg, 0.19 mmol) and Cs₂CO₃ (152 mg, 0.47 mmol) in DMF (5 mL) was stirred at 80° C. for 2 h. Upon completion, EtOAc (20 mL) and water (20 mL) were added to the crude reaction mixture and separated. The aqueous phase was extracted with EtOAc (20 mL×2). The combined organic layers were dried over Na₂SO₄ and evaporated. The residue was purified by prep-TLC (25% EtOAc in PE) to give (S)-tert-butyl 3-((4-((3-chloro-2,4-difluoro-phenyl)(methyl)carbamoyl)-3-(6-methyl-4-(trifluoromethyl)pyridin-2-yl)-2-oxoimidazolidin-1-yl)methyl)azetidine-1-carboxylate (90 mg, 93% yield) as a white solid.

m/z ES+[M+H]⁺ 618.2

Step b. To a solution of (S)-tert-butyl 3-((4-((3-chloro-2,4-difluorophenyl)(methyl)carbamoyl)-3-(6-methyl-4-(trifluoromethyl)pyridin-2-yl)-2-oxoimidazolidin-1-yl)methyl)azetidine-1-carboxylate (80 mg, 0.13 mmol) in DCM (4 mL) was added TFA (1.54 g, 13.51 mmol). The mixture was stirred at rt for 1 h. Upon completion, the reaction mixture was concentrated under vacuum. The residue was diluted with sat. aq. NaHCO₃ (10 mL) and extracted with EtOAc (10 mL×3). The combined organic layers were washed with brine (10 mL×2), dried over Na₂SO₄ and evaporated. The residue was purified by prep-HPLC to give the title compound (19 mg, 72% yield, HCl salt) as a yellow oil.

m/z ES+[M+H]⁺ 518.2; ¹H NMR (400 MHz, DMSO-d6) δ ppm 8.95-8.53 (m, 2H), 8.28 (s, 1H), 7.86-7.57 (m, 1H), 7.55-7.34 (m, 1H), 7.30-7.16 (m, 1H), 5.69-4.70 (m, 1H), 4.00-3.90 (m, 2H), 3.79-3.72 (m, 2H), 3.61-3.55 (m, 2H), 3.48-3.45 (m, 2H), 3.26-3.11 (m, 3H), 3.09-2.94 (m, 1H), 2.58-2.54 (m, 1.5H), 2.47-2.43 (m, 1.5H)

Example 189

(S)—N-(3-Chloro-2,4-difluorophenyl)-N-methyl-3-(6-methyl-4-(trifluoromethyl)pyridin-2-yl)-1-((1-methylazetidin-3-yl)methyl)-2-oxoimidazolidine-4-carboxamide

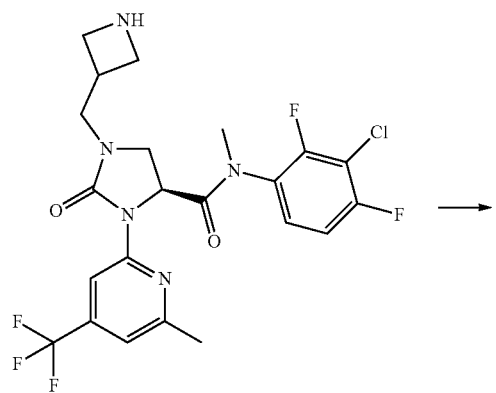

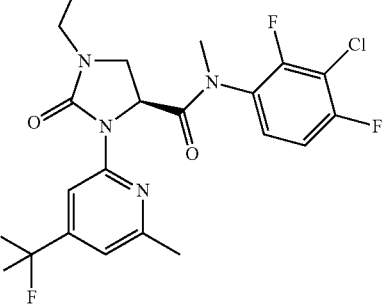

To a solution of Example 188 (60 mg, 0.12 mmol) in MeOH (1 mL) was added a solution of formaldehyde (14 mg, 0.17 mmol, 37% in water) and NaBH(OAc)₃ (32 mg, 0.15 mmol). The mixture was stirred at rt for 1 h. Upon completion, the reaction was concentrated under vacuum to give a residue. The residue was purified by prep-HPLC to give the title compound (35 mg, 51% yield, HCl salt) as an oil.

m/z ES+[M+H]⁺ 532.2; ¹H NMR (400 MHz, DMSO-d6) δ ppm 10.61-8.71 (m, 1H), 8.29 (s, 1H), 7.86-7.55 (m, 1H), 7.54-7.34 (m, 1H), 7.30-7.12 (m, 1H), 5.73-4.65 (m, 1H), 4.24-4.12 (m, 1H), 4.03-3.94 (m, 3H), 3.81-3.73 (m, 1H), 3.65-3.37 (m, 4H), 3.30-3.12 (m, 3H), 3.10-2.93 (m, 1H), 2.87-2.74 (m, 2H), 2.61-2.53 (m, 1.5H), 2.49-2.41 (m, 1.5H).

Example 190

(S)—N-(3-Chloro-4-fluorophenyl)-1-(3-(dimethylamino)-3-oxopropyl)-N-methyl-3-(6-methyl-4-(trifluoromethyl)pyridin-2-yl)-2-oxoimidazolidine-4-carboxamide

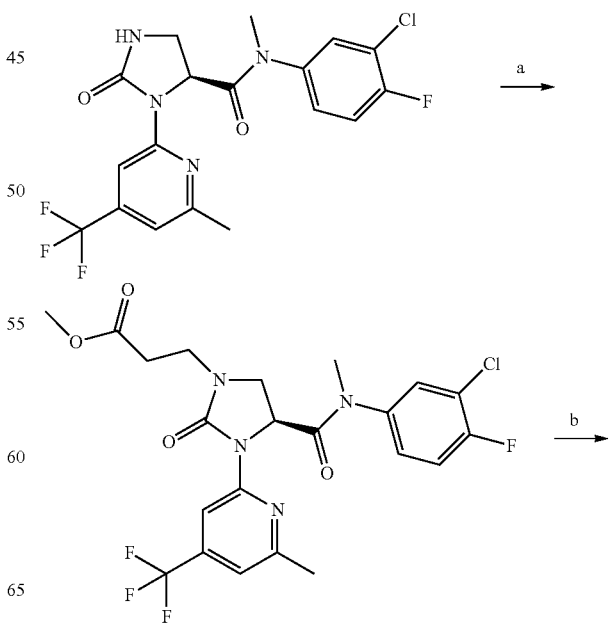

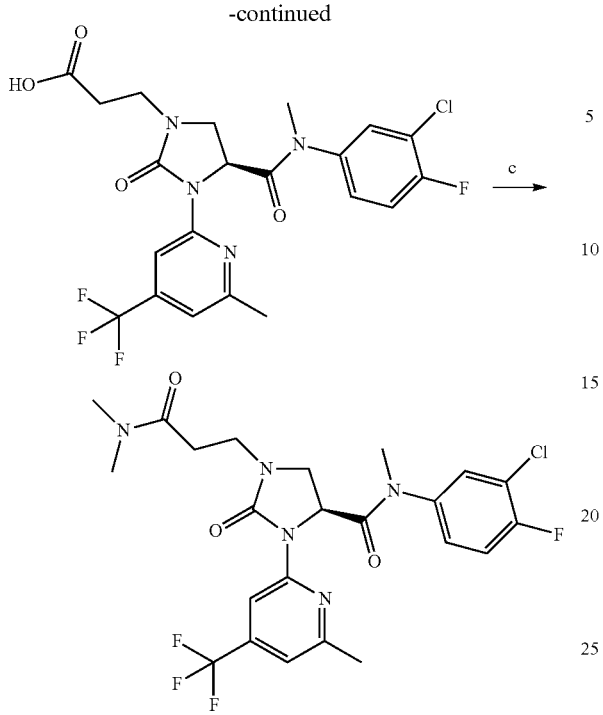

Step a. To a solution of Example 156 (151 mg, 0.35 mmol) and methyl 3-bromopropanoate (87 mg, 0.52 mmol) in DMF (2 mL) was added Cs$_2$CO$_3$ (340 mg, 1.04 mmol). The mixture was stirred at 80° C. for 4 h. Upon completion, the reaction mixture was diluted with water (100 mL) and then extracted with EtOAc (50 mL×3). The combined organic layers were washed with brine (30 mL), dried over Na$_2$SO$_4$ and evaporated. The residue was purified by prep-TLC (50% EtOAc in PE) to give (S)-methyl 3-(4-((3-chloro-4-fluorophenyl)(methyl)carbamoyl)-3-(6-methyl-4-(trifluoromethyl)pyridin-2-yl)-2-oxoimidazolidin-1-yl)propanoate (100 mg, 56% yield) as a white solid.

m/z ES+[M+H]$^+$ 517.3

Step b. To a solution of (S)-methyl 3-(4-((3-chloro-4-fluorophenyl)(methyl)carbamoyl)-3-(6-methyl-4-(trifluoromethyl)pyridin-2-yl)-2-oxoimidazolidin-1-yl)propanoate (80 mg, 0.15 mmol) in THF (3 mL) was added LiOH monohydrate (19.5 mg, 0.46 mmol) in water (1 mL). The mixture was stirred at rt for 1 h. Upon completion, the reaction mixture was concentrated under vacuum. The residue was acidified with aq. HCl (2 M) to pH 5 and extracted with EtOAc (50 mL×3). The combined organic layers were washed with brine (50 mL), dried and evaporated to give (S)-3-(4-((3-chloro-4-fluorophenyl)(methyl)carbamoyl)-3-(6-methyl-4-(trifluoromethyl)pyridin-2-yl)-2-oxoimidazolidin-1-yl)propanoic acid (140 mg, crude) as an oil.

m/z ES+[M+H]$^+$ 503.1

Step c. To a solution of (S)-3-(4-((3-chloro-4-fluorophenyl)(methyl)carbamoyl)-3-(6-methyl-4-(trifluoromethyl)pyridin-2-yl)-2-oxoimidazolidin-1-yl)propanoic acid (60 mg, 0.12 mmol) and dimethylamine hydrochloride (15 mg, 0.18 mmol) in DCM (1 mL) was added DIPEA (46 mg, 0.36 mmol) and HATU (54 mg, 0.14 mmol). The mixture was stirred at rt for 1 h. Upon completion, the reaction mixture was diluted with water (30 mL) and then extracted with EtOAc (30 mL×3). The combined organic layers were washed with brine (30 mL), dried over Na$_2$SO$_4$ and evaporated. The residue was purified by prep-HPLC to give the title compound (30 mg, 47% yield) as a white solid.

m/z ES+[M+H]$^+$ 530.2; $^1$H NMR (400 MHz, DMSO-d6) δ ppm 8.30 (s, 1H), 7.83 (d, J=6.0 Hz, 1H), 7.64 (t, J=8.8 Hz, 1H), 7.56 (s, 1H), 7.21 (s, 1H), 4.80 (d, J=9.2 Hz, 1H), 3.56-3.47 (m, 2H), 3.40 (t, J=6.8 Hz, 4H), 3.18 (s, 3H), 2.95 (s, 3H), 2.81 (s, 3H), 2.56 (s, 3H).

Example 191

(S)—N-(3-Chloro-4-fluorophenyl)-N-methyl-3-(6-methyl-4-(trifluoromethyl)pyridin-2-yl)-1-(3-(methylamino)-3-oxopropyl)-2-oxoimidazolidine-4-carboxamide

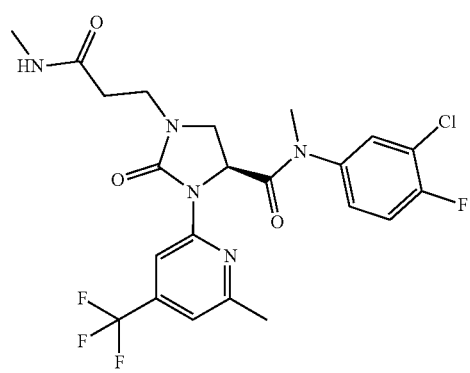 [SMILES: CNC(=O)CCN1C[C@@H](C(=O)N(C)c2ccc(F)c(Cl)c2)N(c2cc(C(F)(F)F)cc(C)n2)C1=O]

The title compound was prepared in a similar manner to Example 190, using methylamine in step c.

m/z ES+[M+H]$^+$ 516.1; $^1$H NMR (400 MHz, DMSO-d6) δ=8.29 (s, 1H), 7.90-7.77 (m, 2H), 7.67-7.59 (m, 1H), 7.58-7.49 (m, 1H), 7.20 (s, 1H), 4.82-4.73 (m, 1H), 3.55-3.45 (m, 2H), 3.43-3.38 (m, 2H), 3.17 (s, 3H), 2.55 (s, 6H), 2.32-2.25 (m, 2H).

Example 192

(S)—N-(3-Chloro-2,4-difluorophenyl)-N-methyl-3-(6-methyl-4-(trifluoromethyl)pyridin-2-yl)-2-oxo-1-(2-(piperazin-1-yl)ethyl)imidazolidine-4-carboxamide

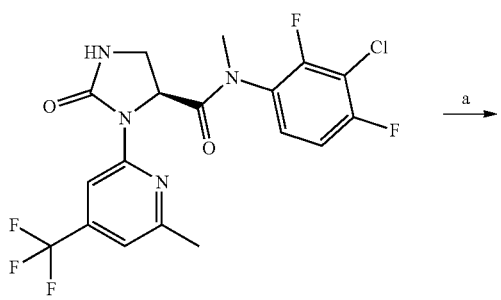

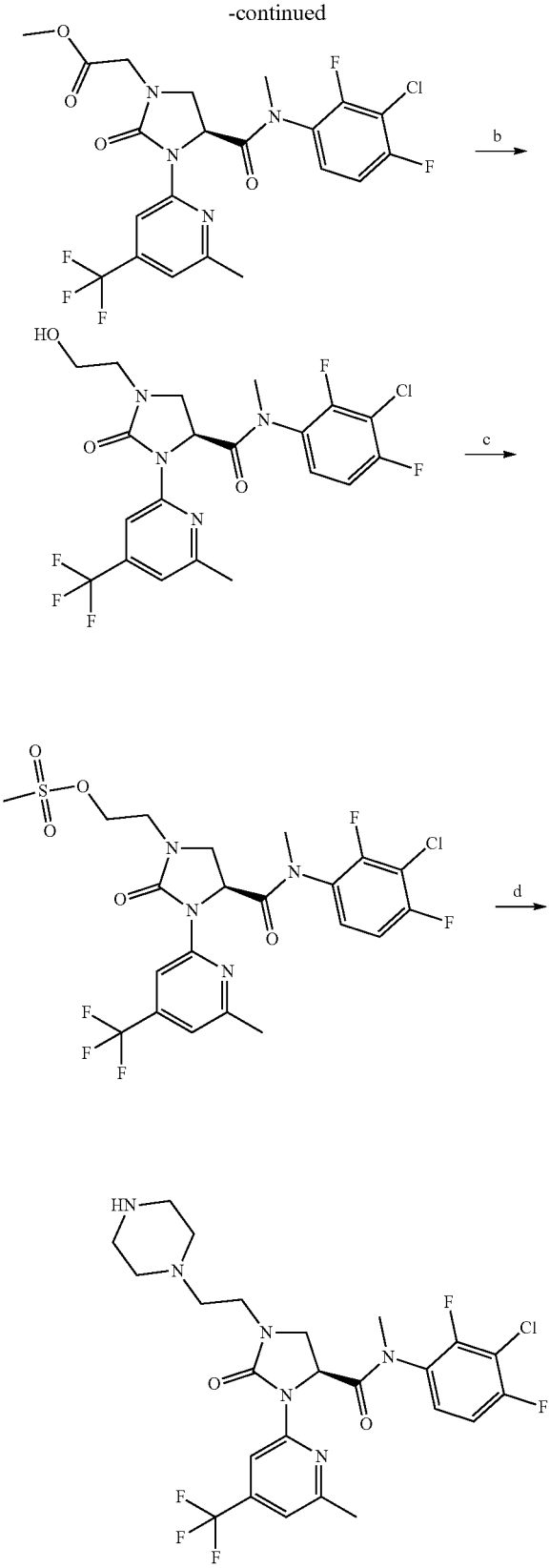

Step a. To a solution of Example 158 (1 g, 2.23 mmol) and ethyl 2-bromoacetate (558 mg, 3.34 mmol) in DMF (8 mL) was added Cs$_2$CO$_3$ (2.18 g, 6.68 mmol). The mixture was stirred at 80° C. for 2 h. Upon completion, the mixture was diluted with water (30 mL) and extracted with EtOAc (60 mL×2). The combined organic layers were washed with brine (80 mL), dried over Na$_2$SO$_4$ and evaporated. The residue was purified by column chromatography (50% EtOAc in PE) to give (S)-methyl 2-(4-((3-chloro-2,4-difluorophenyl)(methyl)-carbamoyl)-3-(6-methyl-4-(trifluoromethyl)pyridin-2-yl)-2-oxoimidazolidin-1-yl)acetate (1.0 g, 84% yield) as a white solid.

m/z ES+[M+H]$^+$ 535.2

Step b. To a solution of (S)-methyl 2-(4-((3-chloro-2,4-difluorophenyl)(methyl)carbamoyl)-3-(6-methyl-4-(trifluoromethyl)pyridin-2-yl)-2-oxoimidazolidin-1-yl)acetate (1.0 g, 1.87 mmol) in DME (10 mL) was added LiBH$_4$ (244 mg, 11.2 mmol) portionwise at 0° C. The mixture was stirred at 0° C. for 30 min and then at 15° C. for 5 h. Upon completion, the mixture was carefully quenched with water (50 mL) and then extracted with EtOAc (50 mL×3). The combined organic layers were washed with brine (50 mL), dried over Na$_2$SO$_4$ and evaporated. The residue was purified by column chromatography (50% EtOAc in PE) to give (S)—N-(3-chloro-2,4-difluorophenyl)-1-(2-hydroxyethyl)-N-methyl-3-(6-methyl-4-(trifluoromethyl)pyridin-2-yl)-2-oxoimidazolidine-4-carboxamide (0.6 g, 88% yield) as a light yellow solid.

m/z ES+[M+H]$^+$ 493.1

Step c. To a solution of (S)—N-(3-chloro-2,4-difluorophenyl)-1-(2-hydroxyethyl)-N-methyl-3-(6-methyl-4-(trifluoromethyl)pyridin-2-yl)-2-oxoimidazolidine-4-carboxamide (600 mg, 1.22 mmol) and TEA (370 mg, 3.65 mmol) in DCM (10 mL) was added methanesulfonyl chloride (209 mg, 1.83 mmol) dropwise at 0° C. The reaction mixture was stirred at 0° C. for 2 h. Upon completion, the mixture was quenched with water (50 mL) and then extracted with DCM (50 mL×2). The organic layers were washed with brine (50 mL), dried over Na$_2$SO$_4$ and evaporated. The residue was purified by column chromatography (50% EtOAc in PE) to give (S)-2-(4-((3-chloro-2,4-difluorophenyl)(methyl)carbamoyl)-3-(6-methyl-4-(trifluoromethyl)-pyridin-2-yl)-2-oxoimidazolidin-1-yl)ethyl methanesulfonate (430 mg, 62% yield) as an oil.

m/z ES+[M+H]$^+$ 571.1

Step d. A mixture of (S)-2-(4-((3-chloro-2,4-difluorophenyl)(methyl)carbamoyl)-3-(6-methyl-4-(trifluoromethyl)pyridin-2-yl)-2-oxoimidazolidin-1-yl)ethyl methanesulfonate (60 mg, 0.11 mmol), K$_2$CO$_3$ (44 mg, 0.32 mmol) and piperazine (90 mg, 1.05 mmol) in MeCN (1 mL) was stirred at 60° C. for 2 h. Upon completion, the mixture was diluted with water (30 mL) and then extracted with EtOAc (30 mL×2). The combined organic layers were washed with brine (30 mL), dried over Na$_2$SO$_4$ and evaporated. The residue was purified by prep-HPLC to give the title compound (19 mg, 30% yield) as a white solid.

m/z ES+[M+H]$^+$ 561.1; $^1$H NMR (400 MHz, CD$_3$OD) δ ppm 8.35-8.26 (m, 1H), 7.81-7.48 (m, 1H), 7.45-7.16 (m, 1H), 7.15-7.07 (m, 1H), 5.69-4.95 (m, 1H), 3.70-3.60 (m, 2H), 3.55-3.40 (m, 2H), 3.31-3.26 (m, 3H), 2.93-2.82 (m, 4H), 2.65-2.43 (m, 9H).

Example 193

(S)—N-(3-Chloro-4-fluorophenyl)-1-(2-hydroxyethyl)-N-methyl-3-(6-methyl-4-(trifluoromethyl)pyridin-2-yl)-2-oxoimidazolidine-4-carboxamide

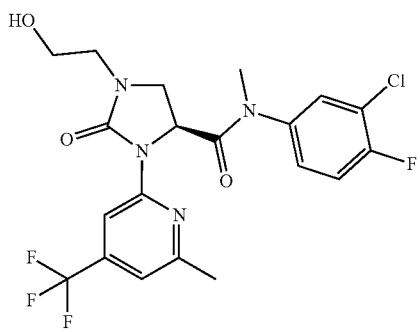 [SMILES: Cc1cc(C(F)(F)F)cc(N2C(=O)N(CCO)C[C@H]2C(=O)N(C)c2ccc(F)c(Cl)c2)n1]

The title compound was prepared according to Example 192 steps a and b, using Example 156 in step a.

m/z ES+[M+H]+ 475.1; $^1$H NMR (400 MHz, DMSO-d6) δ ppm 8.30 (s, 1H), 7.83 (dd, J=2.4, 6.4 Hz, 1H), 7.63 (t, J=8.8 Hz, 1H), 7.60-7.50 (m, 1H), 7.20 (s, 1H), 4.79 (dd, J=4.8, 9.6 Hz, 1H), 4.73 (t, J=5.6 Hz, 1H), 3.60-3.45 (m, 4H), 3.28-3.20 (m, 2H), 3.18 (s, 3H), 2.55 (s, 3H).

The examples in Table 11 were prepared by a procedure similar to that described for the synthesis of Example 192.

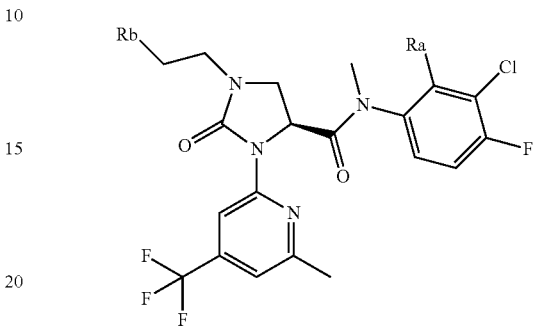

TABLE 11

| Example Number | Ra | Rb | Name | Amine CAS No. | $^1$H NMR (400 MHz, CD$_3$OD) δ ppm | MI |
|---|---|---|---|---|---|---|
| 194 | H | ![morpholinoethyl] | (S)-N-(3-Chloro-4-fluorophenyl)-N-methyl-3-(6-methyl-4-(trifluoromethyl)pyridin-2-yl)-1-(2-morpholinoethyl)-2-oxoimidazolidine-4-carboxamide | 110-91-8 | 8.34 (s, 1H), 7.86-7.79 (m, 1H), 7.61-7.53 (m, 1H), 7.48 (t, J = 8.8 Hz, 1H), 7.17 (s, 1H), 5.06-4.98 (m, 1H), 4.16-4.02 (m, 2H), 3.97-3.86 (m, 1H), 3.85-3.63 (m, 5H), 3.62-3.52 (m, 2H), 3.51-3.40 (m, 2H), 3.32 (s, 3H), 3.27-3.16 (m, 2H), 2.63 (s, 3H) | 544.3 |
| 195 | F | ![morpholinoethyl] | (S)-N-(3-Chloro-2,4difluorophenyl)-N-methyl-3-(6-methyl-4-(trifluoromethyl)pyridin-2-yl)-1-(2-morpholinoethyl)-2-oxoimidazolidine-4-carboxamide | 110-91-8 | 8.36 (d, J = 10.8 Hz, 1H), 7.92-7.54 (m, 1H), 7.47-7.32 (m, 1H), 7.27-7.12 (m, 1H), 5.82-4.95 (m, 1H), 4.23-3.91 (m, 3H), 3.90-3.52 (m, 9H), 3.52-3.42 (m, 2H), 3.31 (s, 1H), 3.30-3.17 (m, 2H), 2.66-2.52 (m, 3H) | 562.2 |
| 196 | H | (S)-3-hydroxypyrrolidinyl | (S)-N-(3-Chloro-4-fluorophenyl)-1-(2-((S)-3-hydroxypyrrolidin-1-yl)ethyl)-N-methyl-3-(6-methyl-4-(trifluoromethyl)pyridin-2-yl)-2-oxoimidazolidine-4-carboxamide | 100243-39-8 | 8.39 (s, 1H), 7.84-7.78 (m, 1H), 7.60-7.52 (m, 1H), 7.48 (t, J = 8.8 Hz, 1H), 7.16 (s, 1H), 5.05-4.97 (m, 1H), 4.65-4.53 (m, 1H), 4.02-3.78 (m, 3H), 3.72-3.66 (m, 1H), 3.55-3.43 (m, 3H), 3.41-3.34 (m, 1H), 3.32 (s, 3H), 3.27-3.18 (m, 1H), 2.62 (s, 3H), 2.40-2.33 (m, 1H), 2.17-2.10 (m, 1H), 2.08-2.00 (m, 1H) | 544.1 |
| 197 | H | (R)-3-hydroxypyrrolidinyl | (S)-N-(3-Chloro-4-fluorophenyl)-1-(2-((R)-3-hydroxypyrrolidin-1-yl)ethyl)-N-methyl-3-(6-methyl-4-(trifluoromethyl)pyridin-2-yl)-2-oxoimidazolidine-4-carboxamide | 2799-21-5 | 8.38 (s, 1H), 7.86-7.75 (m, 1H), 7.59-7.51 (m, 1H), 7.48 (t, J = 8.8 Hz, 1H), 7.16 (s, 1H), 5.06-4.94 (m, 1H), 4.63-4.53 (m, 1H), 4.01-3.77 (m, 3H), 3.76-3.60 (m, 1H), 3.60-3.49 (m, 3H), 3.44-3.37 (m, 1H), 3.31 (s, 3H), 3.26-3.16 (m, 1H), 2.62 (s, 3H), 2.42-2.29 (m, 1H), 2.17-1.99 (m, 2H) | 544.3 |
| 198 | H | 2-(hydroxymethyl)pyrrolidinyl | (S)-N-(3-Chloro-4-fluorophenyl)-1-(2-((R/S)-2-(hydroxymethyl)-pyrrolidin-1-yl)ethyl)-N-methyl-3-(6-methyl-4-(trifluoromethyl)-pyridin-2-yl)-2-oxoimidazolidine-4-carboxamide isomer 1 | 498-63-5 | 8.36 (s, 1H), 7.85-7.78 (m, 1H), 7.61-7.53 (m, 1H), 7.48 (t, J = 8.8 Hz, 1H), 7.15 (s, 1H), 5.06-4.95 (m, 1H), 3.95-3.88 (m, 1H), 3.87-3.75 (m, 2H), 3.75-3.67 (m, 4H), 3.66-3.55 (m, 2H), 3.39-3.33 (m, 1H), 3.30 (s, 3H), 3.29-3.22 (m, 1H), 2.62 (s, 3H), 2.28-2.07 (m, 2H), 2.07-1.94 (m, 1H), 1.91-1.80 (m, 1H) | 558.3 |
| 199 | H | 2-(hydroxymethyl)pyrrolidinyl | (S)-N-(3-Chloro-4-fluorophenyl)-1-(2-((S/R)-2-(hydroxymethyl)-pyrrolidin-1-yl)ethyl)-N-methyl-3-(6-methyl-4-(trifluoromethyl)-pyridin-2-yl)-2-oxoimidazolidine-4-carboxamide isomer 2 | 498-63-5 | 8.36 (s, 1H), 7.85-7.77 (m, 1H), 7.59-7.51 (m, 1H), 7.48 (t, J = 8.8 Hz, 1H), 7.16 (s, 1H), 5.09-4.95 (m, 1H), 4.11-3.99 (m, 1H), 3.98-3.88 (m, 1H), 3.88-3.56 (m, 5H), 3.55-3.47 (m, 1H), 3.39-3.34 (m, 1H), 3.32 (s, 3H), 3.30-3.24 (m, 1H), 2.62 (s, 3H), 2.30-2.11 (m, 2H), 2.10-1.98 (m, 1H), 1.95-1.81 (m, 1H) | 558.3 |

TABLE 11-continued

| Example Number | Ra | Rb | Name | Amine CAS No. | ¹H NMR (400 MHz, CD₃OD) δ ppm | MI |
|---|---|---|---|---|---|---|
| 200 | H | azetidine | (S)-1-(2-(Azetidin-1-yl)ethyl)-N-(3-chloro-4-fluorophenyl)-N-methyl-3-(6-methyl-4-(trifluoromethyl)pyridin-2-yl)-2-oxoimidazolidine-4-carboxamide | 503-29-7 | 8.39 (s, 1H), 7.88-7.75 (m, 1H), 7.60-7.54 (m, 1H), 7.53-7.46 (m, 1H), 7.17 (s, 1H), 5.06-5.00 (m, 1H), 3.91-3.80 (m, 1H), 3.71-3.64 (m, 1H), 3.59-3.51 (m, 1H), 3.50-3.44 (m, 1H), 3.40-3.35 (m, 3H), 3.33 (s, 3H), 2.93-2.84 (m, 1H), 2.64 (s, 3H), 0.99-0.90 (m, 4H) | 514.1 |
| 201 | F | azetidine | (S)-1-(2-(Azetidin-1-yl)ethyl)-N-(3-chloro-2,4-difluorophenyl)-N-methyl-3-(6-methyl-4-(trifluoromethyl)-pyridin-2-yl)-2-oxoimidazolidine-4-carboxamide | 503-29-7 | 8.36 (d, J = 4.0 Hz, 1H), 7.88-7.48 (m, 1H), 7.44-7.18 (m, 1H), 7.15-7.06 (m, 1H), 5.76-4.89 (m, 1H), 3.69-3.53 (m, 2H), 3.53-3.34 (m, 4H), 3.28 (d, J = 4.8 Hz, 4H), 3.25-3.15 (m, 1H), 2.82-2.65 (m, 1H), 2.62-2.51 (m, 4H), 2.17-2.08 (m, 2H) | 532.0 |
| 202 | F | 3-hydroxyazetidine | (S)-N-(3-Chloro-2,4-difluorophenyl)-1-(2-(3-hydroxyazetidin-1-yl)ethyl)-N-methyl-3-(6-methyl-4-(trifluoromethyl)pyridin-2-yl)-2-oxoimidazolidine-4-carboxamide | 45347-82-8 | 8.36 (d, J = 3.6 Hz, 1H), 7.88-7.47 (m, 1H), 7.44-7.18 (m, 1H), 7.14-7.06 (m, 1H), 5.73-4.91 (m, 1H), 4.40-4.31 (m, 1H), 3.71-3.56 (m, 3H), 3.50-3.35 (m, 2H), 3.32-3.10 (m, 4H), 3.02-2.91 (m, 2H), 2.82-2.70 (m, 1H), 2.64-2.50 (m, 4H) | 548.1 |
| 203 | F | 2-(hydroxymethyl)azetidine | (4S)-N-(3-Chloro-2,4-difluoro-phenyl)-1-(2-(2-(hydroxymethyl)-azetidin-1-yl)-ethyl)-N-methyl-3-(6-methyl-4-(trifluoromethyl)pyridin-2-yl)-2-oxoimidazolidine-4-carboxamide | 250274-91-0 | 8.36 (d, J = 3.6 Hz, 1H), 7.87-7.46 (m, 1H), 7.43-7.17 (m, 1H), 7.14-7.06 (m, 1H), 5.73-4.87 (m, 1H), 3.70-3.53 (m, 4H), 3.50-3.35 (m, 3H), 3.28 (d, J = 4.4 Hz, 4H), 3.00-2.75 (m, 2H), 2.65-2.50 (m, 4H), 2.10-1.90 (m, 2H) | 562.1 |
| 204 | F | 4-acetylpiperazine | (S)-1-(2-(4-Acetylpiperazin-1-yl)ethyl)-N-(3-chloro-2,4-difluoro-phenyl)-N-methyl-3-(6-methyl-4-(trifluoromethyl)pyridin-2-yl)-2-oxoimidazolidine-4-carboxamide | 13889-98-0 | 8.35 (d, J = 4.8 Hz, 1H), 7.91-7.47 (m, 1H), 7.44-7.20 (m, 1H), 7.15-7.05 (m, 1H), 5.78-4.97 (m, 1H), 3.71-3.62 (m, 2H), 3.61-3.43 (m, 7H), 3.29 (d, J = 4.4 Hz, 3H), 2.64-2.48 (m, 8H), 2.10 (s, 3H) | 603.1 |
| 205 | F | (S)-3-fluoropyrrolidine | (S)-N-(3-Chloro-2,4-difluorophenyl)-1-(2-((S)-3-fluoropyrrolidin-1-yl)ethyl)-N-methyl-3-(6-methyl-4-(trifluoromethyl)pyridin-2-yl)-2-oxoimidazolidine-4-carboxamide | 136725-54-7 | 8.40 (d, J = 10.0 Hz, 1H), 7.92-7.22 (m, 2H), 7.22-7.11 (m, 1H), 5.90-4.93 (m, 2H), 4.35-3.75 (m, 4H), 3.75-3.34 (m, 8H), 3.32-3.29 (m, 1H), 2.70-2.13 (m, 5H) | 564.2 |
| 206 | F | 3,3-difluoropyrrolidine | (S)-N-(3-Chloro-2,4-difluorophenyl)-1-(2-(3,3-difluoropyrrolidin-1-yl)ethyl)-N-methyl-3-(6-methyl-4-(trifluoromethyl)pyridin-2-yl)-2-oxoimidazolidine-4-carboxamide | 316131-01-8 | 8.40 (d, J = 10.0 Hz, 1H), 8.17-7.31 (m, 2H), 7.28-7.08 (m, 1H), 5.87-4.95 (m, 1H), 4.16-3.97 (m, 2H), 3.94-3.41 (m, 9H), 3.32-3.27 (m, 2H), 2.78-2.50 (m, 5H) | 582.1 |
| 207 | F | 3-(N-methylacetamido)pyrrolidine | (4S)-N-(3-Chloro-2,4-difluoro-phenyl)-N-methyl-3-(6-methyl-4-(trifluoromethyl)pyridin-2-yl)-1-(2-(3-(N-methylacetamido)-pyrrolidin-1-yl)ethyl)-2-oxoimidazolidine-4-carboxamide | 79286-87-6 | 8.35 (s, 1H), 7.93-7.48 (m, 1H), 7.47-7.22 (m, 1H), 7.21-7.09 (m, 1H), 5.84-4.92 (m, 1H), 4.58-4.18 (m, 1H), 4.14-3.78 (m, 3H), 3.78-3.40 (m, 6H), 3.31 (s, 2H), 3.21-2.83 (m, 4H), 2.70-2.41 (m, 4H), 2.40-1.73 (m, 5H) | 617.1 |
| 208 | F | 1,1-dioxidothiomorpholine | (S)-N-(3-Chloro-2,4-difluorophenyl)-1-(2-(1,1-dioxidothiomorpholino)-ethyl)-N-methyl-3-(6-methyl-4-(trifluoromethyl)pyridin-2-yl)-2-oxoimidazolidine-4-carboxamide | 39093-93-1 | 8.96-7.77 (m, 1.5H), 7.60-7.29 (m, 1.5H), 7.27-7.08 (m, 1H), 5.85-4.94 (m, 1H), 3.82-3.37 (m, 12H), 3.34 (s, 2H), 3.31 (s, 1H), 2.70-2.45 (m, 3H), 2.14-1.73 (m, 2H) | 610.1 |
| 209 | F | 4-(2-hydroxyethyl)piperazine | (S)-N-(3-Chloro-2,4-difluorophenyl)-1-(2-(4-(2-hydroxyethyl)piperazin-1-yl)ethyl)-N-methyl-3-(6-methyl-4-(trifluoromethyl)pyridin-2-yl)-2-oxoimidazolidine-4-carboxamide | 103-76-4 | 8.34 (d, J = 9.2 Hz, 1H), 7.90-7.55 (m, 1H), 7.47-7.29 (m, 1H), 7.25-7.10 (m, 1H), 5.88-4.99 (m, 1H), 4.18-3.34 (m, 19H), 3.31 (s, 2H), 2.68-2.49 (m, 3H) | 605.2 |

TABLE 11-continued

| Example Number | Ra | Rb | Name | Amine CAS No. | 1H NMR (400 MHz, CD3OD) δ ppm | MI |
|---|---|---|---|---|---|---|
| 210 | F | (methyl-oxopiperazinyl group) | (S)-N-(3-Chloro-2,4-difluorophenyl)-N-methyl-1-(2-(4-methyl-3-oxopiperazin-1-yl)ethyl)-3-(6-methyl-4-(trifluoromethyl)pyridin-2-yl)-2-oxoimidazolidine-4-carboxamide | 59702-07-7 | 8.42-8.34 (m, 1H), 7.91-7.23 (m, 2H), 7.22-7.11 (m, 1H), 5.85-4.96 (m, 1H), 4.40-3.90 (m, 4H), 3.88-3.39 (m, 10H), 3.32-3.31 (m, 1H), 3.08-2.99 (m, 3H), 2.68-2.51 (m, 3H) | 589.2 |
| 211 | F | (4-cyanopiperidinyl group) | (S)-N-(3-Chloro-2,4-difluorophenyl)-1-(2-(4-cyanopiperidin-1-yl)ethyl)-N-methyl-3-(6-methyl-4-(trifluoromethyl)pyridin-2-yl)-2-oxoimidazolidine-4-carboxamide | 4395-98-6 | 8.36 (d, J = 10.0 Hz, 1H), 7.92-7.47 (m, 1H), 7.47-7.23 (m, 1H), 7.23-7.12 (m, 1H), 5.87-4.94 (m, 1H), 4.10-3.34 (m, 10H), 3.31 (s, 2H), 3.25-2.92 (m, 2H), 2.67-2.52 (m, 3H), 2.47-1.94 (m, 4H) | 585.2 |

Example 212

(4S)—N-(3-Chloro-2,4-difluorophenyl)-N-methyl-3-(6-methyl-4-(trifluoromethyl)pyridin-2-yl)-1-(2-(S-methylsulfonimidoyl)ethyl)-2-oxoimidazolidine-4-carboxamide

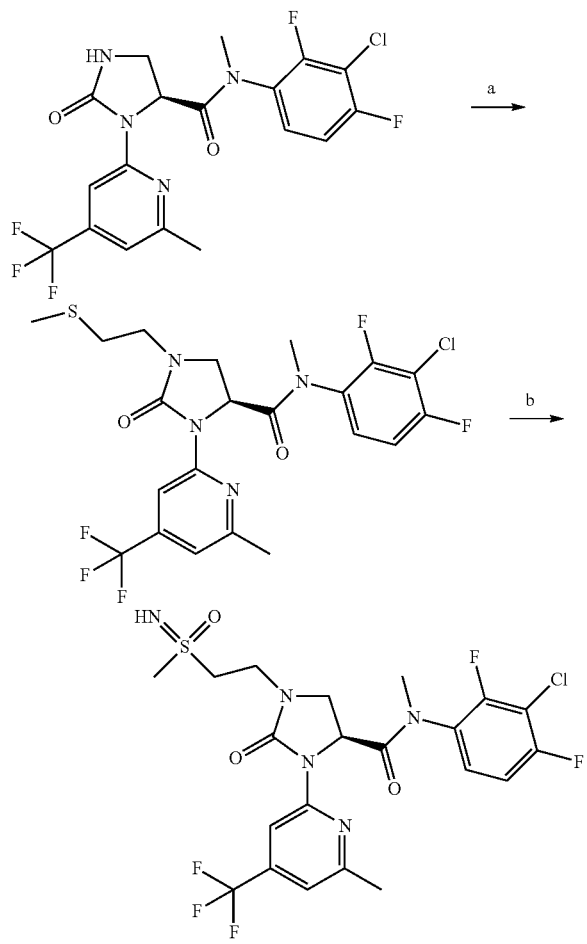

Step a. A mixture of Example 158 (100 mg, 0.22 mmol) and (2-chloroethyl)(methyl)sulfane (34 mg, 0.33 mmol) in DMF (0.5 mL) was added Cs$_2$CO$_3$ (145 mg, 0.45 mmol). The mixture was stirred at 60° C. for 2 h. Upon completion, the reaction mixture was evaporated and the residue was purified by prep-TLC (50% EtOAc in PE) to give (S)—N-(3-chloro-2,4-difluoro-phenyl)-N-methyl-3-(6-methyl-4-(trifluoromethyl)pyridin-2-yl)-1-(2-(methylthio)ethyl)-2-oxoimidazolidine-4-carboxamide (30 mg, 26% yield) as a colourless oil.

m/z ES+[M+H]$^+$ 523.0

Step b. A mixture of (S)—N-(3-chloro-2,4-difluorophenyl)-N-methyl-3-(6-methyl-4-(trifluoromethyl)pyridin-2-yl)-1-(2-(methylthio)ethyl)-2-oxoimidazolidine-4-carboxamide (50 mg, 0.095 mmol), PhI(OAc)$_2$ (77 mg, 0.24 mmol) and NH$_2$COONH$_4$ (19 mg, 0.24 mmol) in MeOH (0.1 mL) was degassed and purged with N$_2$ 3 times, and then the mixture was stirred at −10° C. for 20 min under N$_2$ atmosphere. Upon completion, the reaction mixture was concentrated under vacuum. The residue was purified by prep-HPLC to give the title compound (13 mg, 22% yield, HCl salt) as a yellow solid.

m/z ES+[M+H]$^+$ 554.0; $^1$H NMR (400 MHz, CD$_3$OD) δ ppm 8.41-8.32 (m, 1H), 7.93-7.49 (m, 1H), 7.46-7.30 (m, 1H), 7.24-7.14 (m, 1H), 5.85-5.00 (m, 1H), 4.42-4.03 (m, 3H), 3.90-3.69 (m, 5H), 3.67-3.56 (m, 1H), 3.30 (d, J=6.8 Hz, 3H), 2.66-2.50 (m, 3H).

Example 213

(4S)—N-(3-Chloro-4-fluorophenyl)-N-methyl-3-(6-methyl-4-(trifluoromethyl)pyridin-2-yl)-1-(2-(S-methylsulfonimidoyl)ethyl)-2-oxoimidazolidine-4-carboxamide

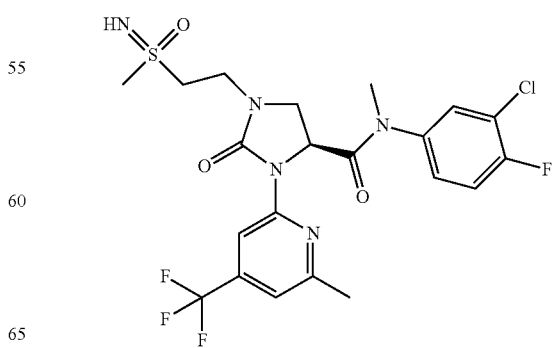

The title compound was prepared in a similar manner to Example 212, using Example 156 in the first step.

m/z ES+[M+H]+ 536.0; ¹H NMR (400 MHz, CD₃OD) δ ppm 8.35 (s, 1H), 7.80 (d, J=5.6 Hz, 1H), 7.57-7.51 (m, 1H), 7.50-7.43 (m, 1H), 7.15 (s, 1H), 5.01 (dd, J=10.0, 3.6 Hz, 1H), 4.16-4.07 (m, 1H), 4.07-3.95 (m, 2H), 3.81-3.71 (m, 1H), 3.66 (td, J=9.2, 3.2 Hz, 1H), 3.61 (d, J=2.4 Hz, 3H), 3.59-3.52 (m, 1H), 3.29 (s, 3H), 2.61 (s, 3H).

Example 214

(4S)—N-(3-Chloro-2,4-difluorophenyl)-1-(3-(dimethylamino)-2-hydroxypropyl)-N-methyl-3-(6-methyl-4-(trifluoromethyl)pyridin-2-yl)-2-oxoimidazolidine-4-carboxamide

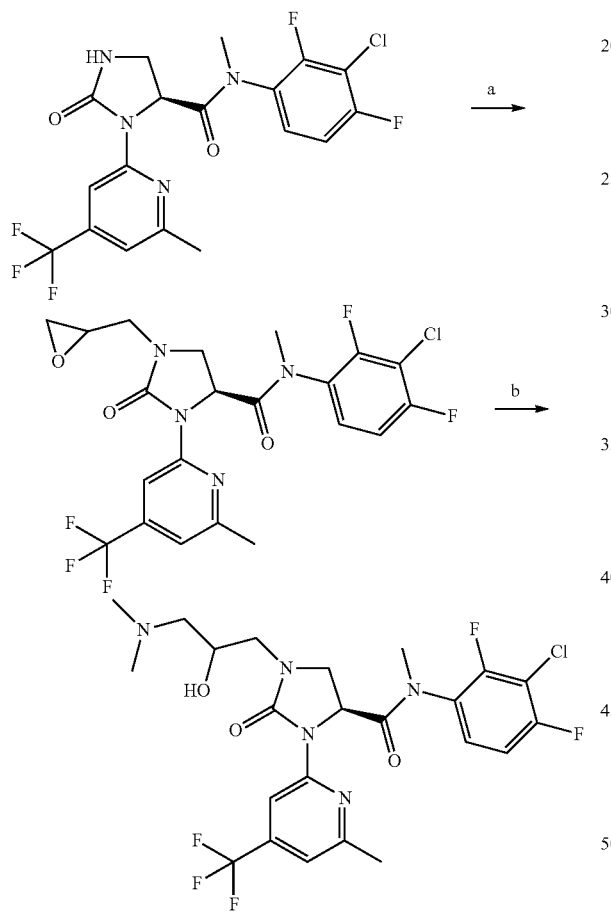

Step a. A mixture of Example 158 (40 mg, 0.089 mmol), 2-(bromomethyl)oxirane (18 mg, 0.13 mmol) and Cs₂CO₃ (87 mg, 0.27 mmol) in DMF (1 mL) was degassed and purged with N₂ 3 times, and then the mixture was stirred at 80° C. for 30 min under N₂ atmosphere. Upon completion, EtOAc (10 mL) and water (10 mL) were added to the crude reaction mixture and separated. The aqueous phase was extracted with EtOAc (10 mL×2). The combined organic layers were dried over Na₂SO₄ and evaporated. The residue was purified by prep-TLC (50% EtOAc in PE) to give (4S)—N-(3-chloro-2,4-difluorophenyl)-N-methyl-3-(6-methyl-4-(trifluoromethyl)pyridin-2-yl)-1-(oxiran-2-ylmethyl)-2-oxoimidazolidine-4-carboxamide (40 mg, 89% yield) as a colorless oil.

m/z ES+[M+H]+ 505.1

Step b. To a solution of (4S)—N-(3-chloro-2,4-difluorophenyl)-N-methyl-3-(6-methyl-4-(trifluoromethyl)pyridin-2-yl)-1-(oxiran-2-ylmethyl)-2-oxoimidazolidine-4-carboxamide (40 mg, 0.079 mmol) in MeOH (2 mL) was added a solution of dimethylamine (2 M in THF, 2.67 mL). The mixture was stirred at rt for 12 h. Upon completion, the reaction was concentrated under vacuum. The residue was purified by prep-HPLC to give the title compound (28 mg, 61% yield) as a yellow solid.

m/z ES+[M+H]+ 550.2; ¹H NMR (400 MHz, DMSO-d6) δ ppm 8.30 (s, 1H), 7.82-7.35 (m, 2H), 7.24-7.15 (m, 1H), 5.66-4.65 (m, 2H), 3.82-3.69 (m, 1H), 3.69-3.49 (m, 2H), 3.46-3.36 (m, 1H), 3.16 (d, J=8.4 Hz, 3H), 3.12-2.96 (m, 1H), 2.56 (s, 1.5H), 2.45 (s, 1.5H), 2.23-2.17 (m, 2H), 2.15 (d, J=3.2 Hz, 6H).

Example 215

(4S)—N-(3-Chloro-2,4-difluorophenyl)-1-(3-((R)-3-fluoropyrrolidin-1-yl)-2-hydroxy-propyl)-N-methyl-3-(6-methyl-4-(trifluoromethyl)pyridin-2-yl)-2-oxoimidazolidine-4-carboxamide

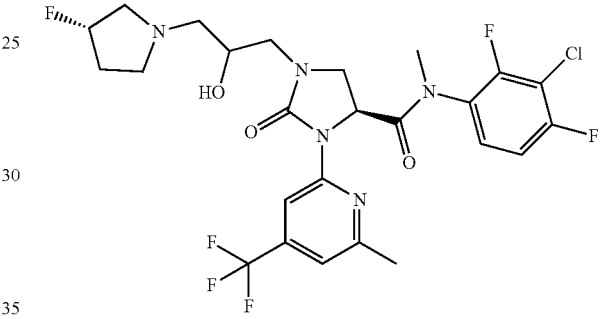

The title compound was prepared in a similar manner to Example 214.

m/z ES+[M+H]+ 594.2; ¹H NMR (400 MHz, CD₃OD) δ ppm 8.39-8.32 (m, 1H), 7.91-7.20 (m, 2H), 7.20-7.11 (m, 1H), 5.83-5.30 (m, 1H), 5.06-4.94 (m, 1H), 4.33-4.14 (m, 1H), 4.13-3.34 (m, 1OH), 3.32-3.28 (m, 3H), 2.67-2.15 (m, 5H)

Example 216

(4S)—N-(3-Chloro-2,4-difluorophenyl)-1-(3-(3,3-difluoropyrrolidin-1-yl)-2-hydroxy-propyl)-N-methyl-3-(6-methyl-4-(trifluoromethyl)pyridin-2-yl)-2-oxoimidazolidine-4-carboxamide

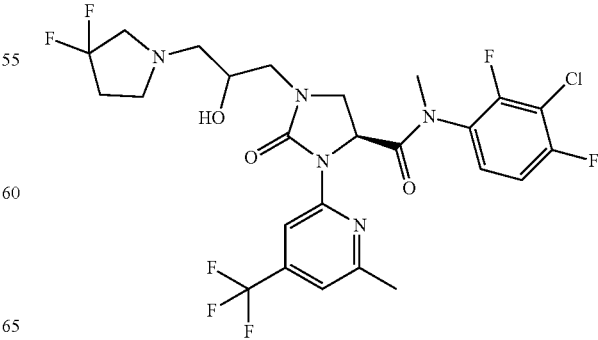

The title compound was prepared in a similar manner to Example 214.

m/z ES+[M+H]+ 612.2; ¹H NMR (400 MHz, CD₃OD) δ ppm 8.40-8.31 (m, 1H), 7.91-7.20 (m, 2H), 7.19-7.09 (m, 1H), 5.81-4.92 (m, 1H), 4.30-4.15 (m, 1H), 4.13-3.69 (m, 6H), 3.67-3.35 (m, 4H), 3.32-3.18 (m, 3H), 2.75-2.50 (m, 5H)

Example 217

(4S)—N-(3-Chloro-2,4-difluorophenyl)-1-(2-hydroxy-3-morpholinopropyl)-N-methyl-3-(6-methyl-4-(trifluoromethyl)pyridin-2-yl)-2-oxoimidazolidine-4-carboxamide

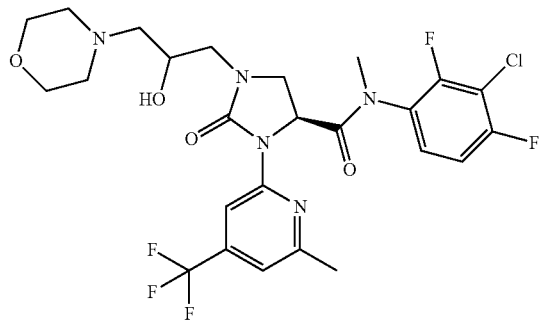 [SMILES: Cc1cc(C(F)(F)F)cc(N2C(=O)N(CC(O)CN3CCOCC3)C[C@H]2C(=O)N(C)c2ccc(F)c(Cl)c2F)n1]

The title compound was prepared in a similar manner to Example 214.

m/z ES+[M+H]+ 592.2; ¹H NMR (400 MHz, CD₃OD) δ ppm 8.38-8.31 (m, 1H), 7.90-7.20 (m, 2H), 7.19-7.09 (m, 1H), 5.82-4.95 (m, 1H), 4.44-4.26 (m, 1H), 4.16-3.97 (m, 2H), 3.93-3.42 (m, 8H), 3.32-3.13 (m, 7H), 2.67-2.50 (m, 3H)

Example 218

(4S)—N-(3-Chloro-2,4-difluorophenyl)-N-methyl-3-(6-methyl-4-(trifluoromethyl)pyridin-2-yl)-1-(morpholin-2-ylmethyl)-2-oxoimidazolidine-4-carboxamide

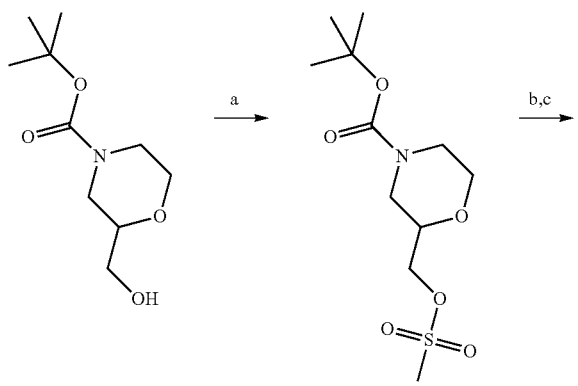

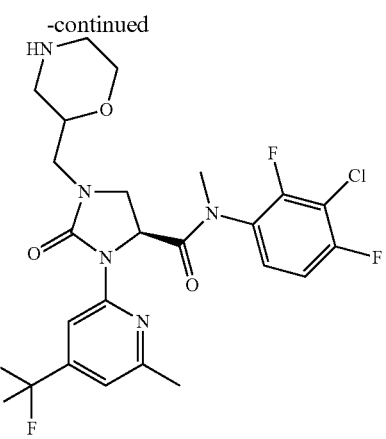

Step a. To a solution of tert-butyl 2-(hydroxymethyl)morpholine-4-carboxylate (500 mg, 2.30 mmol) and TEA (349 mg, 3.45 mmol) in DCM (5 mL) was added methanesulfonyl chloride (290 mg, 2.53 mmol) dropwise at 0° C. The mixture was stirred at 0° C. for 2 h. Upon completion, DCM (20 mL) and water (20 mL) were added to the crude reaction mixture and separated. The aqueous phase was extracted with EtOAc (20 mL×2). The combined organic layers were dried and evaporated to give tert-butyl 2-(((methylsulfonyl)oxy)methyl)-morpholine-4-carboxylate (500 mg, 74% yield) as a yellow oil.

Step b. A mixture of Example 158 (100 mg, 0.22 mmol), tert-butyl 2-(((methylsulfonyl)oxy)-methyl)morpholine-4-carboxylate (79 mg, 0.27 mmol) and Cs₂CO₃ (218 mg, 0.67 mmol) in DMF (2 mL) was degassed and purged with N₂ 3 times, and then the mixture was stirred at 80° C. for 2 h under N₂ atmosphere. Upon completion, EtOAc (10 mL) and water (10 mL) were added to the crude reaction mixture and separated. The aqueous phase was extracted with EtOAc (10 mL×2). The combined organic layers were dried over Na₂SO₄ and evaporated. The residue was purified by prep-TLC (25% EtOAc in PE) to give tert-butyl 2-(((S)-4-((3-chloro-2,4-difluorophenyl)(methyl)carbamoyl)-3-(6-methyl-4-(trifluoromethyl)pyridin-2-yl)-2-oxoimidazolidin-1-yl)methyl)morpholine-4-carboxylate (80 mg, 55% yield) as an oil.

m/z ES+[M+H]+ 648.2

Step c. To a solution of tert-butyl 2-(((S)-4-((3-chloro-2,4-difluorophenyl)(methyl)carbamoyl)-3-(6-methyl-4-(trifluoromethyl)pyridin-2-yl)-2-oxoimidazolidin-1-yl)methyl)morpholine-4-carboxylate (80 mg, 0.12 mmol) in DCM (4 mL) was added TFA (1.54 g, 13.5 mmol). The mixture was stirred at rt for 1 h. Upon completion, the reaction was concentrated under vacuum. The residue was purified by prep-HPLC to give the title compound (19 mg, 28% yield) as a yellow solid.

m/z ES+[M+H]+ 548.1; ¹H NMR (400 MHz, DMSO-d6) δ ppm 9.08 (br s, 2H), 8.28 (s, 1H), 7.84-7.59 (m, 1H), 7.56-7.36 (m, 1H), 7.24 (d, J=15.2 Hz, 1H), 5.73-4.75 (m, 1H), 4.02-3.94 (m, 1H), 3.93-3.84 (m, 1H), 3.74-3.60 (m, 2H), 3.59-3.53 (m, 1H), 3.52-3.50 (m, 1H), 3.37-3.27 (m, 2H), 3.22-3.14 (m, 4H), 3.04-2.88 (m, 1H), 2.85-2.73 (m, 1H), 2.57 (s, 1.5H), 2.47 (s, 1.5H).

Example 219

5 (4S)—N-(3-Chloro-2,4-difluorophenyl)-N-methyl-3-(6-methyl-4-(trifluoromethyl)pyridin-2-yl)-1-((4-methylmorpholin-2-yl)methyl)-2-oxoimidazolidine-4-carboxamide

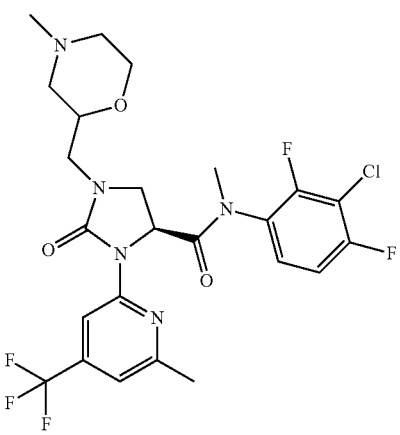 [SMILES: Cc1cc(C(F)(F)F)cc(N2C(=O)N(CC3CN(C)CCO3)C[C@H]2C(=O)N(C)c2ccc(F)c(Cl)c2F)n1]

The title compound was prepared in a similar manner to Example 218, using (4-methyl-morpholin-2-yl)methanol (CAS Number 40987-46-0).

m/z ES+[M+H]$^+$ 562.1; $^1$H NMR (400 MHz, CD$_3$OD) δ ppm 8.35 (s, 1H), 7.90-7.43 (m, 1H), 7.41-7.31 (m, 1H), 7.15-7.05 (m, 1H), 5.07-4.97 (m, 1H), 4.18-3.86 (m, 1H), 3.78-3.58 (m, 4H), 3.53-3.36 (m, 2H), 3.28 (t, J=3.6 Hz, 3H), 2.86-2.74 (m, 1H), 2.72-2.65 (m, 1H), 2.63-2.51 (m, 3H), 2.31 (d, J=2.4 Hz, 3H), 2.20-2.11 (m, 1H), 2.03-1.85 (m, 1H).

Example 220

(S)—N-(3-Chloro-2,4-difluorophenyl)-N-methyl-3-(6-methyl-4-(trifluoromethyl)pyridin-2-yl)-2-oxo-1-(3-(piperazin-1-yl)propyl)imidazolidine-4-carboxamide

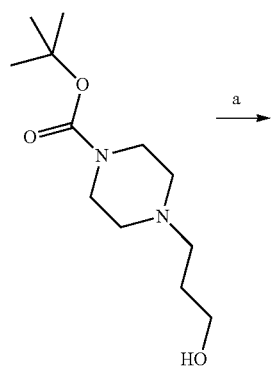

-continued

Step a. To a solution of tert-butyl 4-(3-hydroxypropyl)piperazine-1-carboxylate (500 mg, 2.05 mmol) and TEA (518 mg, 5.12 mmol) in DCM (5 mL) was added methanesulfonyl chloride (352 mg, 3.07 mmol) at 0° C. dropwise, and the mixture was stirred at 0° C. for 2 h. Upon completion, the mixture was quenched with water (30 mL) and extracted with DCM (30 mL×2). The combined organic layers were dried over Na$_2$SO$_4$ and evaporated to give tert-butyl 4-(3-((methylsulfonyl)oxy)propyl)piperazine-1-carboxylate (1 g, 84% yield) as a white solid.

$^1$H NMR (400 MHz, CD$_3$OD) δ ppm 3.67-3.51 (m, 1H), 3.41-3.32 (m, 4H), 3.07 (s, 1H), 2.95 (s, 3H), 2.42 (t, J=6.8 Hz, 2H), 2.33 (t, J=4.8 Hz, 4H), 1.87 (t, J=6.8 Hz, 2H), 1.39 (s, 9H).

Step b. To a solution of Example 158 (200 mg, 0.45 mmol) and tert-butyl 4-(3-((methylsulfonyl)oxy)propyl)piperazine-1-carboxylate (187 mg, 0.58 mmol) in DMF (0.5 mL) was added Cs$_2$CO$_3$ (290 mg, 0.89 mmol). The mixture was stirred at 60° C. for 2 h. Upon completion, the mixture was quenched with water (50 mL) and extracted with EtOAc (50 mL×2). The combined organic layers were dried over Na$_2$SO$_4$ and evaporated. The residue was purified by column chromatography (30% EtOAc in PE) to give (S)-tert-butyl 4-(3-(4-((3-chloro-2-fluorophenyl)(methyl)carbamoyl)-3-(6-methyl-4-(trifluoromethyl)pyridin-2-yl)-2-oxoimidazolidin-1-yl)propyl)piperazine-1-carboxylate (250 mg, 83% yield) as a yellow oil.

m/z ES+[M+H]$^+$ 675.1

Step c. A mixture of (S)-tert-butyl 4-(3-(4-((3-chloro-2-fluorophenyl)(methyl)carbamoyl)-3-(6-methyl-4-(trifluoromethyl)pyridin-2-yl)-2-oxoimidazolidin-1-yl)propyl)piperazine-1-carboxylate (230 mg, 0.34 mmol) and HCl/dioxane (4 M, 1.84 mL) in dioxane (2 mL) was stirred at 10° C. for 1 h. Upon completion, the mixture was concentrated under vacuum to give a residue. The residue was purified by prep-HPLC to give the title compound (70 mg, 62% yield, HCl salt) as a white solid.

m/z ES+[M+H]$^+$ 575.1; $^1$H NMR (400 MHz, CD$_3$OD) δ ppm 8.33 (d, J=8.0 Hz, 1H), 7.91-7.49 (m, 1H), 7.46-7.20 (m, 1H), 7.19-7.09 (m, 1H), 5.84-4.92 (m, 1H), 4.08-3.45 (m, 11H), 3.44-3.34 (m, 3H), 3.31 (s, 3H), 2.64-2.52 (m, 3H), 2.33-2.07 (m, 2H).

Example 221

(S)-1-(3-(4-Acetylpiperazin-1-yl)propyl)-N-(3-chloro-2,4-difluorophenyl)-N-methyl-3-(6-methyl-4-(trifluoromethyl)pyridin-2-yl)-2-oxoimidazolidine-4-carboxamide

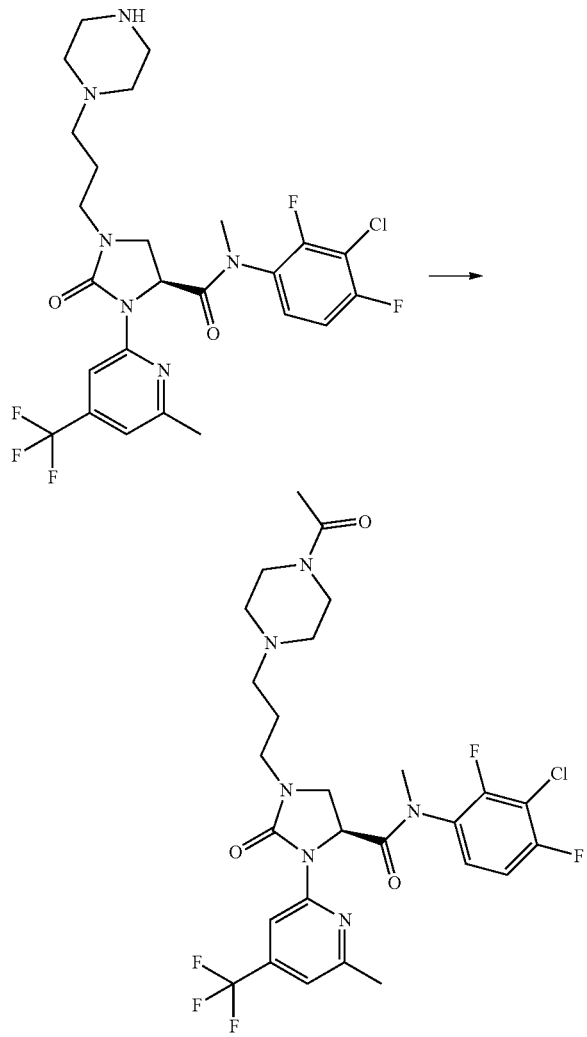

To a solution of Example 220 (20 mg, 0.035 mmol) in DCM (0.5 mL) was added acetic anhydride (7 mg, 0.070 mmol). Then the mixture was stirred at 10° C. for 1 h. Upon completion, the mixture was diluted with water (30 mL) and extracted with EtOAc (30 mL×2). The combined organic layers were dried over Na$_2$SO$_4$ and evaporated. The residue was purified by prep-HPLC to give the title compound (9 mg, 42% yield) as a yellow solid.

m/z ES+[M+H]$^+$ 617.1; $^1$H NMR (400 MHz, CD$_3$OD) δ ppm 8.38-8.33 (m, 1H), 7.89-7.48 (m, 1H), 7.45-7.28 (m, 1H), 7.15-7.07 (m, 1H), 5.79-4.91 (m, 1H), 3.68-3.54 (m, 6H), 3.52-3.36 (m, 2H), 3.28 (d, J=4.4 Hz, 3H), 2.64-2.56 (m, 2H), 2.55-2.42 (m, 7H), 2.13-2.08 (m, 3H), 1.88-1.76 (m, 2H).

Example 222

(4S)—N-(3-Chloro-2,4-difluorophenyl)-1-((3-hydroxypyrrolidin-3-yl)methyl)-N-methyl-3-(6-methyl-4-(trifluoromethyl) pyridin-2-yl)-2-oxoimidazolidine-4-carboxamide

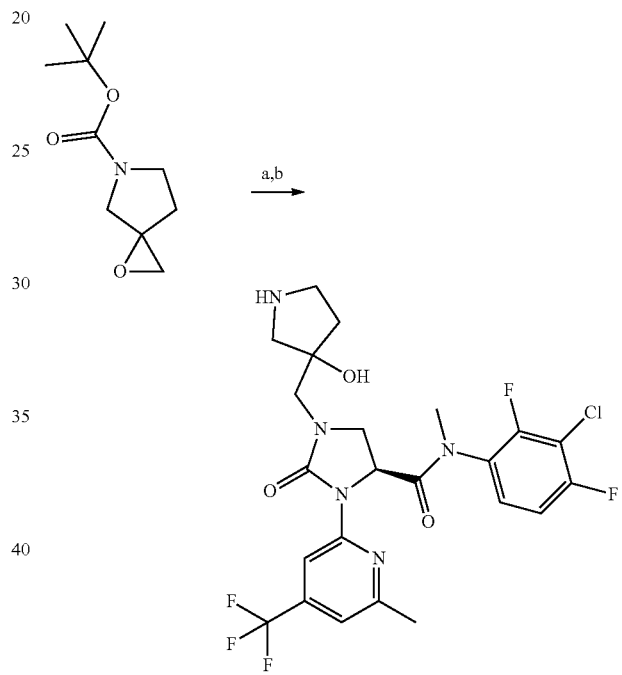

Step a. To a solution of Example 158 (150 mg, 0.33 mmol) and tert-butyl 1-oxa-5-azaspiro[2.4]heptane-5-carboxylate (80 mg, 0.40 mmol) in DMF (1 mL) was added Cs$_2$CO$_3$ (218 mg, 0.67 mmol). The mixture was stirred at 10° C. for 4 h. Upon completion, the mixture was quenched with water (1 mL), adjusted to pH 6-7 by aq. HCl solution (1 M) and extracted with EtOAc (30 mL×2). The combined organic layers were dried over Na$_2$SO$_4$ and evaporated. The residue was purified by prep-HPLC to give tert-butyl 3-(((S)-4-((3-chloro-2,4-difluorophenyl)(methyl)carbamoyl)-3-(6-methyl-4-(trifluoromethyl)pyridin-2-yl)-2-oxoimidazolidin-1-yl)methyl)-3-hydroxypyrrolidine-1-carboxylate (80 mg, 37% yield) as a yellow solid.

m/z ES+[M+H]$^+$ 648.4

Step b. To a solution of tert-butyl 3-(((S)-4-((3-chloro-2,4-difluorophenyl)(methyl)carbamoyl)-3-(6-methyl-4-(trifluoromethyl)pyridin-2-yl)-2-oxoimidazolidin-1-yl)methyl)-3-hydroxypyrrolidine-1-carboxylate (75 mg, 0.12 mmol) in dioxane (1 mL) was added HCl/dioxane (4 M, 0.95 mL). The mixture was stirred at rt for 1 h. Upon completion, the mixture was concentrated under vacuum to give a residue.

The residue was purified by prep-HPLC to give the title compound (39 mg, 62% yield) as a yellow oil.

m/z ES+[M+H]+ 548.1; $^1$H NMR (400 MHz, CD$_3$OD) δ ppm 8.40-8.33 (m, 1H), 7.84 (dt, J=5.6, 8.8 Hz, 0.5H), 7.54-7.28 (m, 1.5H), 7.17-7.05 (m, 1H), 5.75-4.89 (m, 1H), 4.23-3.66 (m, 2H), 3.65-3.36 (m, 3H), 3.29 (d, J=4.8 Hz, 3H), 3.27-2.87 (m, 3H), 2.64-2.50 (m, 3H), 2.07-1.84 (m, 2H).

Example 223

(4S)—N-(3-Chloro-2,4-difluorophenyl)-1-((3-hydroxy-1-methylpyrrolidin-3-yl)methyl)-N-methyl-3-(6-methyl-4-(trifluoromethyl)pyridin-2-yl)-2-oxo-imidazolidine-4-carboxamide

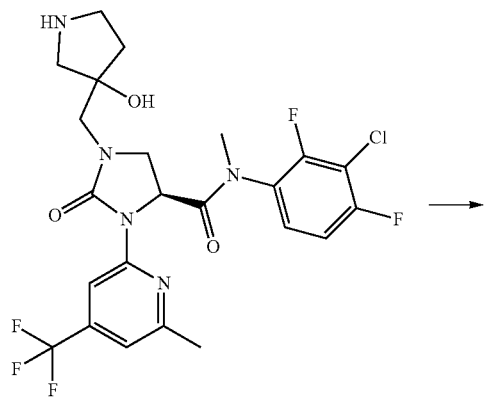

A mixture of Example 222 (50 mg, 0.091 mmol) and formaldehyde (1.09 g, 14.52 mmol, 40% in water) in formic acid (1 mL) was stirred at 100° C. for 1 h. Upon completion, the mixture was concentrated under vacuum to give a residue, which was purified by prep-HPLC to give the title compound (15 mg, 28% yield) as a brown solid.

m/z ES+[M+H]+ 562.1; $^1$H NMR (400 MHz, CD$_3$OD) δ ppm 8.37 (d, J=5.6 Hz, 1H), 7.83 (dt, J=5.6, 8.8 Hz, 0.5H), 7.53-7.28 (m, 1.51H), 7.25-7.06 (m, 1H), 5.78-4.88 (m, 1H), 3.85-3.65 (m, 2H), 3.64-3.39 (m, 2H), 3.37-3.26 (m, 3H), 2.85-2.70 (m, 2H), 2.66-2.51 (m, 5H), 2.36 (dd, J=2.4, 6.0 Hz, 3H), 2.13-1.74 (m, 2H).

Example 224

(S)—N-(3-Chloro-2,4-difluorophenyl)-1-((3-hydroxyazetidin-3-yl)methyl)-N-methyl-3-(6-methyl-4-(trifluoromethyl)pyridin-2-yl)-2-oxoimidazolidine-4-carboxamide

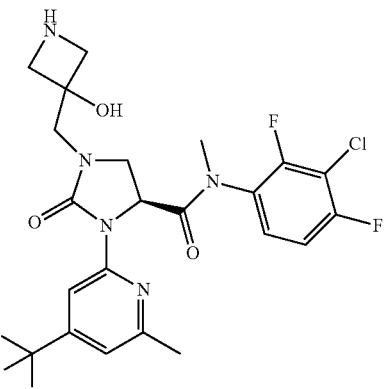

The title compound was prepared in a similar manner to Example 222, using tert-butyl 1-oxa-5-azaspiro[2.3]hexane-5-carboxylate (CAS Number 934664-42-3).

m/z ES+[M+H]+ 534.1; $^1$H NMR (400 MHz, CD$_3$OD) δ ppm 8.40-8.35 (m, 1H), 7.84-7.11 (m, 3H), 5.77-4.92 (m, 1H), 4.27-4.13 (m, 2H), 4.03-3.91 (m, 2H), 3.80-3.69 (m, 2H), 3.69-3.44 (m, 2H), 3.31-3.27 (m, 3H), 2.65-2.51 (m, 3H).

Example 225

(S)—N-(3-Chloro-4-fluorophenyl)-1-((3-hydroxyazetidin-3-yl)methyl)-N-methyl-3-(6-methyl-4-(trifluoromethyl)pyridin-2-yl)-2-oxoimidazolidine-4-carboxamide

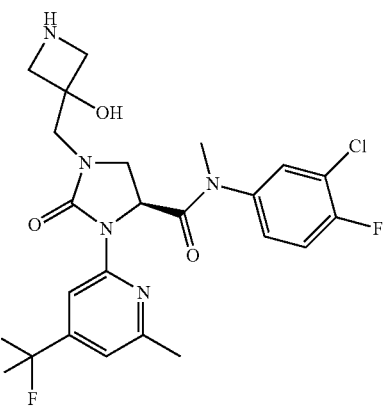

The title compound was prepared in a similar manner to Example 224, using Example 156 in the first step.

m/z ES+[M+H]+ 516.1; $^1$H NMR (400 MHz, CD$_3$OD) δ ppm 8.38 (s, 1H), 7.82 (d, J=4.8 Hz, 1H), 7.56 (d, J=7.6 Hz, 1H), 7.51-7.45 (m, 1H), 7.16 (s, 1H), 5.00 (dd, J=4.4, 10.0

Hz, 1H), 4.21 (d, J=11.2 Hz, 2H), 4.02-3.93 (m, 2H), 3.76-3.64 (m, 3H), 3.50 (d, J=14.8 Hz, 1H), 3.32 (s, 3H), 2.64 (s, 3H).

Example 226

(4S)—N-(3-Chloro-2,4-difluorophenyl)-1-(2,3-dihydroxypropyl)-N-methyl-3-(6-methyl-4-(trifluoromethyl)pyridin-2-yl)-2-oxoimidazolidine-4-carboxamide

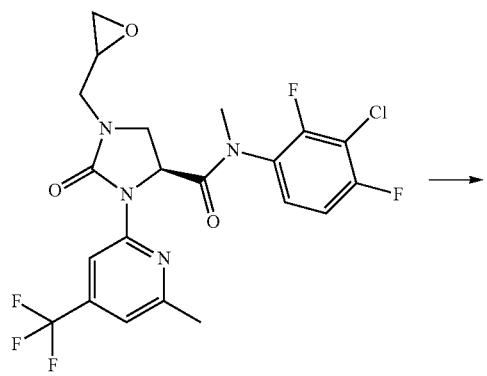

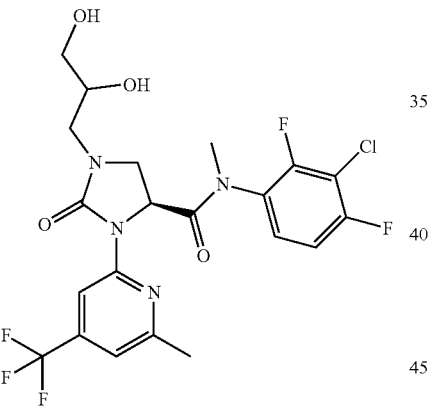

To a solution of (4S)—N-(3-chloro-2,4-difluorophenyl)-N-methyl-3-(6-methyl-4-(trifluoromethyl)pyridin-2-yl)-1-(oxiran-2-ylmethyl)-2-oxoimidazolidine-4-carboxamide (Example 214, step a; 70 mg, 0.14 mmol) in 1,4-dioxane (1 mL) was added $H_2SO_4$ (0.2 M, 0.69 mL). The mixture was stirred at 15° C. for 1 h. Upon completion, the mixture was concentrated under vacuum. The residue was purified by prep-HPLC to give the title compound (10 mg, 14% yield) as a white solid.

m/z ES+[M+H]$^+$ 523.1; $^1$H NMR (400 MHz, CD$_3$OD) δ ppm 8.40-8.33 (m, 1H), 7.87-7.46 (m, 1H), 7.44-7.16 (m, 1H), 7.16-7.03 (m, 1H), 5.80-4.89 (m, 1H), 4.14-3.81 (m, 1H), 3.75-3.63 (m, 2H), 3.61-3.35 (m, 4H), 3.29 (d, J=4.4 Hz, 3H), 2.63-2.50 (m, 3H).

Example 227

(S)-2-(4-((3-Chloro-2,4-difluorophenyl)(methyl)carbamoyl)-3-(6-methyl-4-(trifluoromethyl)pyridin-2-yl)-2-oxoimidazolidin-1-yl 1 sulfamate

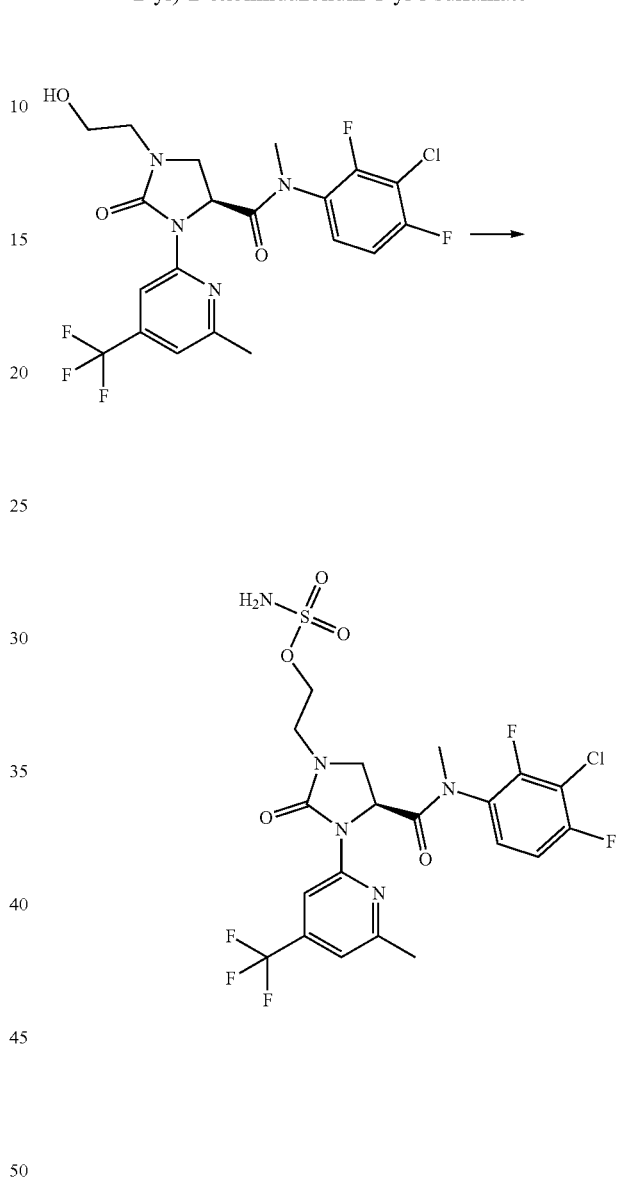

To a solution of (4S)—N-(3-chloro-2,4-difluoro-phenyl)-1-(2-hydroxyethyl)-N-methyl-3-[6-methyl-4-(trifluoromethyl)-2-pyridyl]-2-oxo-imidazolidine-4-carboxamide (Example 192 steps a,b; 50 mg, 0.10 mmol) in THF (0.5 mL) and DMF (0.5 mL) was added TEA (41 mg, 0.41 mmol) and sulfamoyl chloride (47 mg, 0.41 mmol) at 0° C. The mixture was stirred at 0° C. for 15 min. Upon completion, the mixture was concentrated under vacuum. The residue was purified by prep-HPLC to give the title compound (12 mg, 19% yield) as an off-white solid.

m/z ES+[M+H]$^+$ 572.1; $^1$H NMR (400 MHz, CD$_3$OD) δ ppm 8.25-8.18 (m, 1H), 7.75-7.35 (m, 1H), 7.30-7.16 (m, 1H), 7.10-6.95 (m, 1H), 5.70-4.78 (m, 1H), 4.25-4.12 (m, 2H), 3.65-3.40 (m, 4H), 3.20-3.15 (m, 3H), 2.52-2.38 (m, 3H).

225

Example 228

(S)—N-(3-Chloro-4-fluorophenyl)-1-(2-((dimethyl(oxo)-16-sulfaneylidene)amino)ethyl)-N-methyl-3-(6-methyl-4-(trifluoromethyl)pyridin-2-yl)-2-oxo-imidazolidine-4-carboxamide

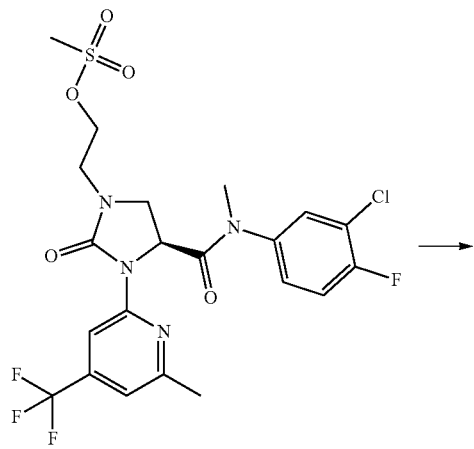

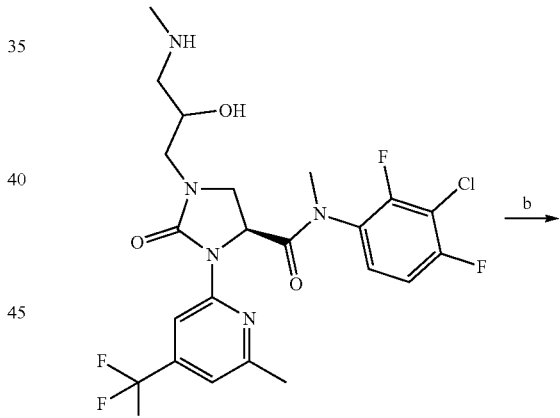

To a solution of (S)-2-(4-((3-chloro-4-fluorophenyl)(methyl)carbamoyl)-3-(6-methyl-4-(trifluoromethyl)pyridin-2-yl)-2-oxoimidazolidin-1-yl)ethyl methanesulfonate (Example 192 steps a-c; 60 mg, 0.11 mmol) and (S-methylsulfonimidoyl)methane (15 mg, 0.16 mmol) in MeCN (2 mL) was added NaHCO$_3$ (14 mg, 0.16 mmol). The mixture was stirred at 80° C. for 4 h. Upon completion, the reaction mixture was filtered and concentrated. The residue was purified by prep-HPLC to give the title compound (5.6 mg, 8.6% yield) as a brown oil.

m/z ES+[M+H]$^+$ 550.1; $^1$H NMR (400 MHz, CD$_3$OD) δ ppm 8.36 (s, 1H), 7.85-7.72 (m, 1H), 7.60-7.53 (m, 1H), 7.52-7.41 (m, 1H), 7.15 (s, 1H), 5.00 (dd, J=10.0, 4.0 Hz, 1H), 3.73 (s, 6H), 3.70-3.63 (m, 2H), 3.63-3.57 (m, 2H), 3.57-3.52 (m, 1H), 3.45-3.35 (m, 1H), 3.32 (s, 3H), 2.62 (s, 3H).

226

Example 229

(S)—N-(3-Chloro-2,4-difluorophenyl)-N-methyl-1-(((S/R)-3-methyl-2-oxooxazolidin-5-yl)methyl)-3-(6-methyl-4-(trifluoromethyl)pyridin-2-yl)-2-oxo-imidazolidine-4-carboxamide isomer 1

Example 230

(S)—N-(3-Chloro-2,4-difluorophenyl)-N-methyl-1-(((R/S)-3-methyl-2-oxooxazolidin-5-yl)methyl)-3-(6-methyl-4-(trifluoromethyl)pyridin-2-yl)-2-oxo-imidazolidine-4-carboxamide isomer 2

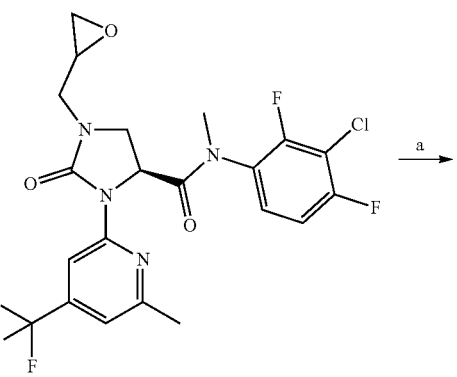

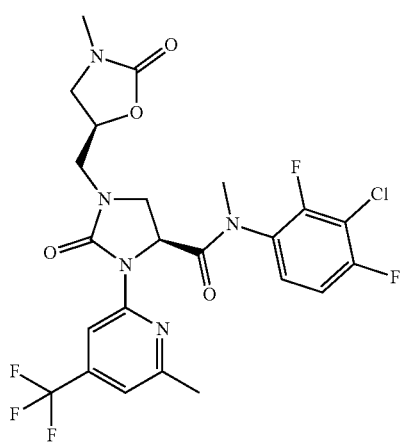

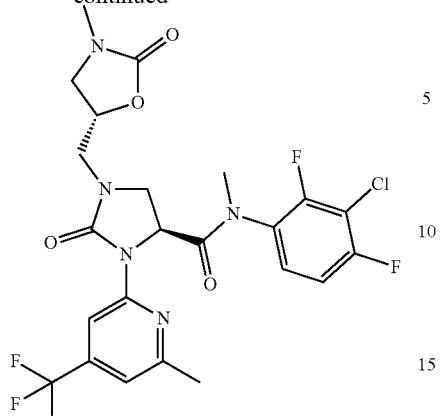

Step a. (4S)—N-(3-chloro-2,4-difluorophenyl)-N-methyl-3-(6-methyl-4-(trifluoromethyl)pyridin-2-yl)-1-(oxiran-2-ylmethyl)-2-oxoimidazolidine-4-carboxamide (80 mg, 0.16 mmol) in MeNH$_2$ (1.60 g, 15.5 mmol, 30% in THF) was stirred at 15° C. for 12 h. Upon completion, the mixture was concentrated under vacuum to give (4S)—N-(3-chloro-2,4-difluorophenyl)-1-(2-hydroxy-3-(methylamino)propyl)-N-methyl-3-(6-methyl-4-(trifluoromethyl)pyridin-2-yl)-2-oxoimidazolidine-4-carboxamide (30 mg, 35% yield) as a colorless oil which was directly used in the next step.

m/z ES+[M+H]$^+$ 536.1

Step b. To a mixture of (4S)—N-(3-chloro-2,4-difluorophenyl)-1-(2-hydroxy-3-(methylamino)propyl)-N-methyl-3-(6-methyl-4-(trifluoromethyl)pyridin-2-yl)-2-oxoimidazolidine-4-carboxamide (25 mg, 0.047 mmol) and CDI (9.1 mg, 0.056 mmol) in toluene (0.5 mL) was added DMAP (0.6 mg, 0.0047 mmol). The mixture was stirred at 110° C. for 4 h. Upon completion, the mixture was concentrated under vacuum. The residue was purified by prep-HPLC to give (S)—N-(3-chloro-2,4-difluorophenyl)-N-methyl-1-(((S/R)-3-methyl-2-oxooxazolidin-5-yl)methyl)-3-(6-methyl-4-(trifluoromethyl)pyridin-2-yl)-2-oxoimidazolidine-4-carboxamide isomer 1 (4.4 mg, 15% yield) as an off-white solid and (S)—N-(3-chloro-2,4-difluorophenyl)-N-methyl-1-(((R/S)-3-methyl-2-oxooxazolidin-5-yl)methyl)-3-(6-methyl-4-(trifluoromethyl)pyridin-2-yl)-2-oxoimidazolidine-4-carboxamide isomer 2 (4.3 mg, 14% yield) as an off-white solid.

Example 229 m/z ES+[M+H]$^+$ 562.2; $^1$H NMR (400 MHz, CD$_3$OD) δ ppm 8.35 (d, J=5.2 Hz, 1H), 7.90-7.48 (m, 1H), 7.44-7.28 (m, 1H), 7.23-7.09 (m, 1H), 5.82-4.93 (m, 1H), 4.82-4.65 (m, 1H), 3.77-3.69 (m, 2H), 3.69-3.58 (m, 2H), 3.57-3.44 (m, 2H), 3.44-3.38 (m, 1H), 3.29 (d, J=3.6 Hz, 2H), 2.94-2.82 (m, 3H), 2.64-2.50 (m, 3H).

Example 230 m/z ES+[M+H]$^+$ 562.2; $^1$H NMR (400 MHz, CD$_3$OD) δ ppm 8.35 (d, J=4.4 Hz, 1H), 7.87-7.52 (m, 1H), 7.49-7.30 (m, 1H), 7.25-7.09 (m, 1H), 5.80-4.95 (m, 1H), 4.80-4.75 (m, 1H), 3.77-3.67 (m, 2H), 3.66-3.55 (m, 2H), 3.50-3.37 (m, 2H), 3.27 (d, J=4.4 Hz, 3H), 2.87 (s, 2.5H), 2.69 (s, 0.5H), 2.63-2.51 (m, 3H).

Example 231

(4S)—N-(3-Chloro-4-fluorophenyl)-N-cyclopropyl-1-(2,3-dihydroxypropyl)-3-(6-methyl-4-(trifluoromethyl)pyridin-2-yl)-2-oxoimidazolidine-4-carboxamide The title compound was prepared in two steps from (S)—N-(3-chloro-4-fluorophenyl)-N-cyclopropyl-3-(6-methyl-4-(trifluoromethyl)-pyridin-2-yl)-2-oxoimidazolidine-4-carboxamide (prepared in a similar manner to Example 161) using a similar procedure as described for Example 226.

m/z ES+[M+H]$^+$ 531.1; $^1$H NMR (400 MHz, DMSO-d6) δ ppm 8.37-8.26 (m, 1H), 7.72-7.21 (m, 4H), 5.91-4.55 (m, 3H), 4.15-2.95 (m, 6H), 2.57-2.52 (m, 3H), 1.10-1.00 (m, 1H), 0.86-0.62 (m, 2H), 0.57-0.31 (m, 1H).

Example 232

(4S)—N-(3-Chloro-4-fluorophenyl)-1-(3,4-dihydroxybutyl)-N-methyl-3-(6-methyl-4-(trifluoromethyl)pyridin-2-yl)-2-oxoimidazolidine-4-carboxamide

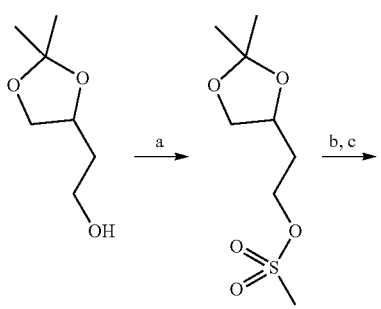

-continued

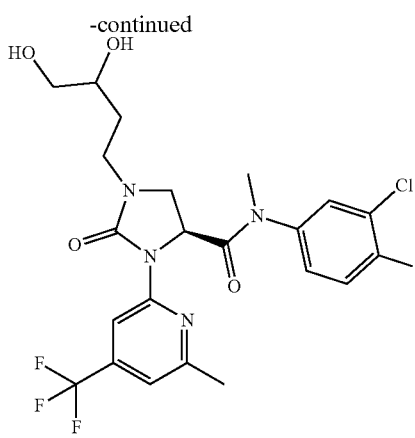

Step a. To a solution of 2-(2,2-dimethyl-1,3-dioxolan-4-yl)ethanol (0.5 g, 3 mmol) in DCM (5 mL) was added TEA (692 mg, 7 mmol). Then methanesulphonyl chloride (588 mg, 5 mmol) was added dropwise at 0° C. The mixture was stirred at 0° C. for 30 min. Upon completion, the reaction mixture was concentrated under vacuum. The residue was diluted with water (10 mL) and extracted with EtOAc (10 mL×3). The combined organic layers were dried over Na$_2$SO$_4$ and evaporated to give 2-(2,2-dimethyl-1,3-dioxolan-4-yl)ethyl methanesulfonate (750 mg, crude) as a yellow oil.

$^1$H NMR (400 MHz, DMSO-d6) δ=4.33-4.21 (m, 2H), 4.17-4.10 (m, 1H), 3.57-3.51 (m, 2H), 3.18 (s, 3H), 1.98-1.85 (m, 2H), 1.33 (s, 3H), 1.27 (s, 3H).

Step b. To a solution of Example 156 (100 mg, 0.23 mmol) and 2-(2,2-dimethyl-1,3-dioxolan-4-yl)ethyl methanesulfonate (104 mg, 0.46 mmol) in DMF (1.5 mL) was added Cs$_2$CO$_3$ (227 mg, 0.70 mmol). The mixture was stirred at 80° C. for 2 h. Upon completion, the reaction mixture was diluted with water (8 mL) and extracted with EtOAc (8 mL×3). The combined organic layers were washed with brine (10 mL), dried over Na$_2$SO$_4$ and evaporated. The residue was purified by prep-TLC (EtOAc) to give (4S)—N-(3-chloro-4-fluorophenyl)-1-(2-(2,2-dimethyl-1,3-dioxolan-4-yl)ethyl)-N-methyl-3-(6-methyl-4-(trifluoromethyl)pyridin-2-yl)-2-oxoimidazolidine-4-carboxamide (90 mg, 66% yield) as a white solid.

m/z ES+[M+H]$^+$ 559.1

Step c. A solution of (4S)—N-(3-chloro-4-fluorophenyl)-1-(2-(2,2-dimethyl-1,3-dioxolan-4-yl)ethyl)-N-methyl-3-(6-methyl-4-(trifluoromethyl)pyridin-2-yl)-2-oxoimidazolidine-4-carboxamide (80 mg, 0.14 mmol) in HCl/dioxane (4 M, 1.5 mL) was stirred at rt for 30 min. Upon completion, the reaction mixture was concentrated under vacuum. The residue was purified by prep-HPLC to give the title compound (26 mg, 34% yield) as a white solid.

m/z ES+[M+H]$^+$ 519.1; $^1$H NMR (400 MHz, DMSO-d6) δ=8.32 (s, 1H), 7.85 (dd, J=2.0, 6.4 Hz, 1H), 7.65-7.60 (m, 1H), 7.59-7.55 (m, 1H), 7.19 (s, 1H), 4.80 (dd, J=3.2, 10.4 Hz, 1H), 4.53 (d, J=4.4 Hz, 2H), 3.57-3.48 (m, 2H), 3.47-3.40 (m, 2H), 3.37-3.33 (m, 1H), 3.29-3.24 (m, 2H), 3.19 (s, 3H), 2.56 (s, 3H), 1.73-1.66 (m, 1H), 1.44-1.37 (m, 1H).

Example 233

(S)—N-Methyl-3-(6-methyl-4-(trifluoromethyl)pyridin-2-yl)-2-oxo-N-(1H-pyrrolo[2,3-b]pyridin-6-yl)imidazolidine-4-carboxamide

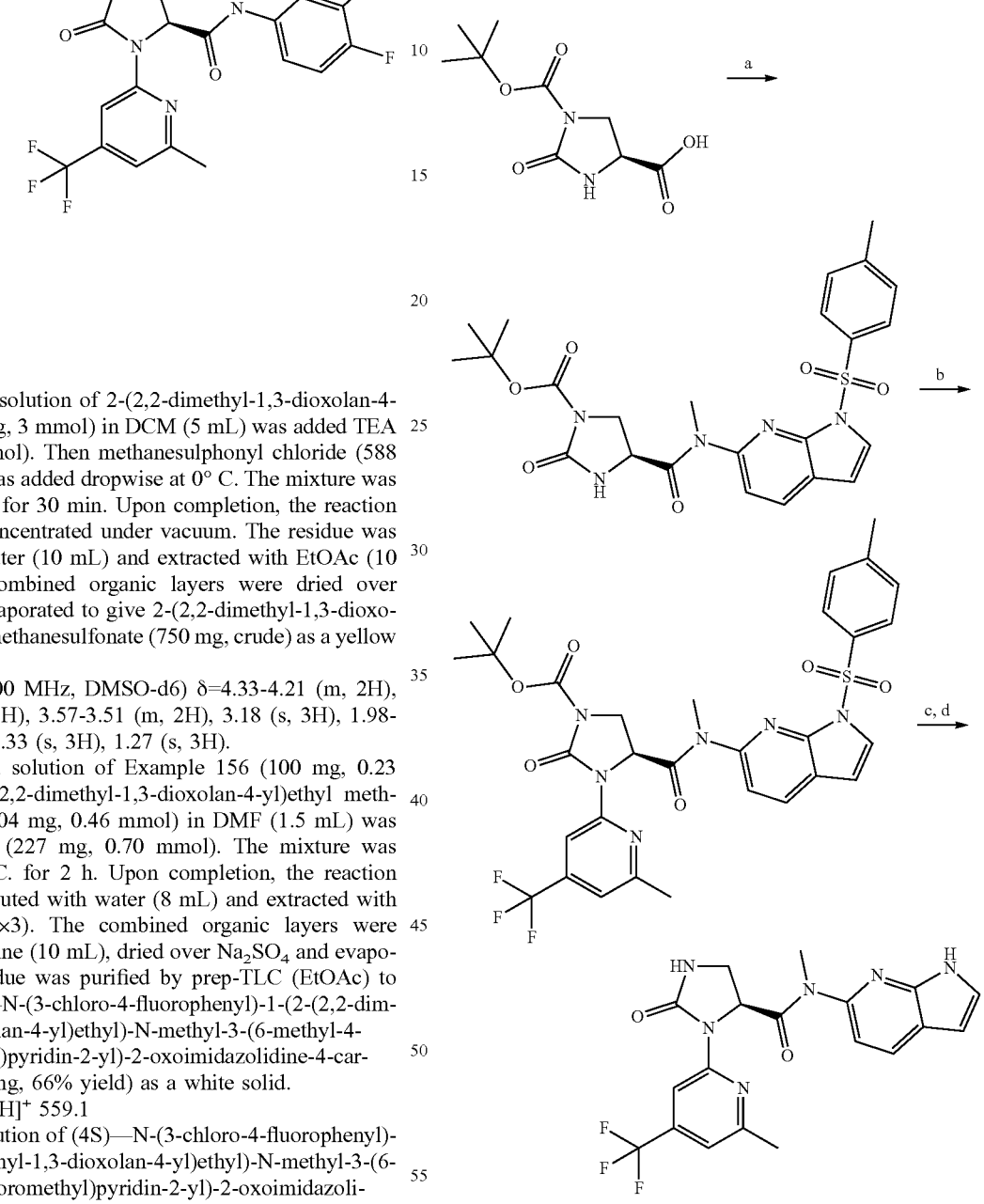

Step a. To a solution of (S)-1-(tert-butoxycarbonyl)-2-oxoimidazolidine-4-carboxylic acid (Example 61, steps c-e; 252 mg, 1.10 mmol) in MeCN (1 mL) was added 1-chloro-N,N,2-trimethylpropenylamine (146 mg, 1.10 mmol) in MeCN (1 mL) dropwise at 0° C. The mixture was stirred at 0° C. for 1 h. Then the mixture was added dropwise into a solution of N-methyl-1-tosyl-1H-pyrrolo[2,3-b]pyridin-6-amine (Example 127, steps a-c; 0.3 g, 1.00 mmol), DIPEA (154 mg, 1.20 mmol) in MeCN (1 mL) at 0° C. The mixture was stirred at 0° C. for 30 min. Upon completion, the reaction mixture was quenched with water (30 mL) and then extracted with EtOAc (30 mL×3). The combined organic layers were washed with brine (50 mL×3), dried over Na$_2$SO$_4$ and evaporated. The residue was purified by column chromatography (10-50% EtOAc in PE) to give (S)-tert-butyl 4-(methyl(1-tosyl-1H-pyrrolo[2,3-b]pyridin-6-yl)carbamoyl)-2-oxoimidazolidine-1-carboxylate (0.31 g, 58% yield) as a white solid.

$^1$H NMR (400 MHz, CDCl$_3$) δ ppm 7.98 (d, J=8.4 Hz, 1H), 7.94 (d, J=8.4 Hz, 2H), 7.81 (d, J=4.0 Hz, 1H), 7.30 (d, J=8.0 Hz, 2H), 7.11 (d, J=8.4 Hz, 1H), 6.65 (d, J=4.0 Hz, 1H), 5.94 (s, 1H), 4.38-4.33 (m, 1H), 4.04 (dd, J=5.2, 10.8 Hz, 1H), 3.61 (t, J=10.4 Hz, 1H), 3.39 (s, 3H), 2.40 (s, 3H), 1.50 (s, 9H).

Step b. To a solution of (S)-tert-butyl 4-(methyl-1H-pyrrolo[2,3-b]pyridin-6-yl)carbamoyl)-2-oxoimidazolidine-1-carboxylate (300 mg, 0.58 mmol) and 2-bromo-6-methyl-4-(trifluoromethyl)pyridine (196 mg, 0.82 mmol) in dioxane (3 mL) was added Pd$_2$(dba)$_3$ (53.5 mg, 0.059 mmol), XantPhos (68 mg, 0.12 mmol) and K$_2$CO$_3$ (161 mg, 1.20 mmol). The mixture was degassed and purged with N$_2$ 3 times, then it was stirred at 100° C. for 3 h under N$_2$ atmosphere. Upon completion, the reaction mixture was diluted with water (10 mL) and extracted with EtOAc (10 mL×3). The combined organic layers were washed with brine (20 mL), dried over Na$_2$SO$_4$ and evaporated. The residue was purified by column chromatography (10-50% EtOAc in PE) to give (S)-tert-butyl 4-(methyl(1-tosyl-1H-pyrrolo[2,3-b]pyridin-6-yl)carbamoyl)-3-(6-methyl-4-(trifluoromethyl)pyridin-2-yl)-2-oxoimidazolidine-1-carboxylate (300 mg, 76% yield) as a yellow solid.

$^1$H NMR (400 MHz, CDCl$_3$) δ ppm 8.49 (s, 1H), 8.03-7.98 (m, 3H), 7.82 (d, J=4.0 Hz, 1H), 7.29 (d, J=8.0 Hz, 3H), 6.99 (s, 1H), 6.66 (d, J=4.0 Hz, 1H), 5.12-5.05 (m, 1H), 4.43 (t, J=10.8 Hz, 1H), 4.18-4.14 (m, 1H), 2.44 (s, 3H), 2.39 (s, 3H), 1.59 (s, 9H), 1.57 (s, 3H).

Step c. A solution of (S)-tert-butyl 4-(methyl(1-tosyl-1H-pyrrolo[2,3-b]pyridin-6-yl)carbamoyl)-3-(6-methyl-4-(trifluoromethyl)pyridin-2-yl)-2-oxoimidazolidine-1-carboxylate (0.27 g, 0.40 mmol) in HCl/dioxane (4 M, 4 mL) was stirred at rt for 30 min. Upon completion, the reaction mixture was quenched with sat. aq. NaHCO$_3$ (30 mL), and then extracted with EtOAc (20 mL×3). The combined organic layers were washed with brine (50 mL), dried over Na$_2$SO$_4$ and evaporated to give (S)—N-methyl-3-(6-methyl-4-(trifluoromethyl)pyridin-2-yl)-2-oxo-N-(1-tosyl-1H-pyrrolo[2,3-b]pyridin-6-yl)imidazolidine-4-carboxamide (220 mg, crude) as a yellow solid.

m/z ES+[M+H]$^+$ 573.3

Step d. To a solution of (S)—N-methyl-3-(6-methyl-4-(trifluoromethyl)pyridin-2-yl)-2-oxo-N-(1-tosyl-1H-pyrrolo[2,3-b]pyridin-6-yl)imidazolidine-4-carboxamide (100 mg, 0.18 mmol) in THF (5 mL) was added TBAF (1 M in THF, 0.87 mmol). The mixture was stirred at rt for 12 h. Upon completion, the reaction mixture was diluted with water (10 mL) and extracted with EtOAc (10 mL×3). The combined organic layers were washed with brine (20 mL×2), dried over Na$_2$SO$_4$ and evaporated. The residue was purified by prep-HPLC to give the title compound (13 mg, 18% yield) as a white solid.

m/z ES+[M+H]$^+$ 419.2; $^1$H NMR (400 MHz, CD$_3$OD) δ ppm 8.29 (s, 1H), 8.14 (d, J=8.4 Hz, 1H), 7.44 (d, J=3.6 Hz, 1H), 7.27 (d, J=8.4 Hz, 1H), 7.04 (s, 1H), 6.54 (d, J=3.6 Hz, 1H), 5.00 (dd, J=5.2, 10.0 Hz, 1H), 3.83-3.77 (m, 1H), 3.75-3.70 (m, 1H), 3.41 (s, 3H), 2.52 (s, 3H).

Example 234

(S)—N-Methyl-N-(1-methyl-1H-pyrrolo[2,3-b]pyridin-6-yl)-3-(6-methyl-4-(trifluoromethyl)pyridin-2-yl)-2-oxoimidazolidine-4-carboxamide

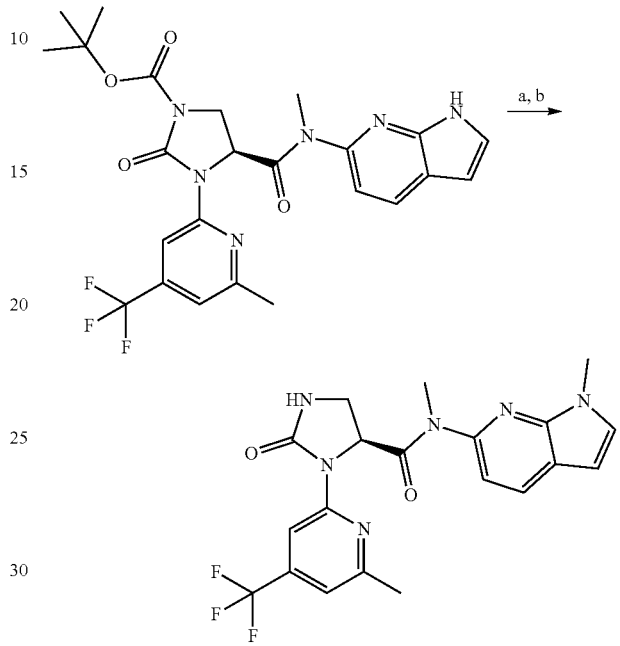

Step a. To a solution of (S)-tert-butyl 4-(methyl(1H-pyrrolo[2,3-b]pyridin-6-yl)carbamoyl)-3-(6-methyl-4-(trifluoromethyl)pyridin-2-yl)-2-oxoimidazolidine-1-carboxylate (Example 233, steps a-f; 100 mg, 0.19 mmol) in THF (3 mL) was added NaH (9.3 mg, 0.23 mmol, 60% dispersion in mineral oil) at 0° C. Then methyl iodide (33 mg, 0.23 mmol) was added. The reaction mixture was stirred at rt for 1 h. Upon completion, the reaction mixture was poured into sat. aq. NH$_4$Cl (10 mL) and extracted with EtOAc (10 mL×3). The combined organic layers were dried over Na$_2$SO$_4$ and evaporated. The residue was purified by prep-TLC (25% EtOAc in PE) to give (S)-tert-butyl 4-(methyl(1-methyl-1H-pyrrolo[2,3-b]pyridin-6-yl)carbamoyl)-3-(6-methyl-4-(trifluoromethyl)pyridin-2-yl)-2-oxoimidazolidine-1-carboxylate (50 mg, 49% yield) as a yellow solid.

Step b. To a solution of (S)-tert-butyl 4-(methyl-1H-pyrrolo[2,3-b]pyridin-6-yl)carbamoyl)-3-(6-methyl-4-(trifluoromethyl)pyridin-2-yl)-2-oxoimidazolidine-1-carboxylate (50 mg, 0.094 mmol) in DCM (5 mL) was added TFA (770 mg, 6.75 mmol). The reaction mixture was stirred at rt for 30 min. Upon completion, the reaction mixture was concentrated under vacuum. The residue was diluted with sat. aq. NaHCO$_3$ (10 mL) and extracted with EtOAc (10 mL×3). The combined organic layers were concentrated under vacuum. The residue was purified by prep-HPLC to give the title compound (15 mg, 37% yield) as an off-white solid.

m/z ES+[M+H]$^+$ 433.0; $^1$H NMR (400 MHz, DMSO-d6) δ ppm 8.25 (s, 1H), 8.15 (d, J=8.0 Hz, 1H), 7.57 (d, J=2.8 Hz, 2H), 7.22 (d, J=8.0 Hz, 1H), 7.12 (s, 1H), 6.52 (d, J=3.6 Hz, 1H), 4.97-4.86 (m, 1H), 3.82 (s, 3H), 3.76 (t, J=10.0 Hz, 1H), 3.66-3.58 (m, 1H), 3.32 (s, 3H), 2.44 (s, 3H).

Example 235

(S)—N-Methyl-N-(1-methyl-1H-indazol-6-yl)-3-(6-methyl-4-(trifluoromethyl)pyridin-2-yl)-2-oxoimidazolidine-4-carboxamide

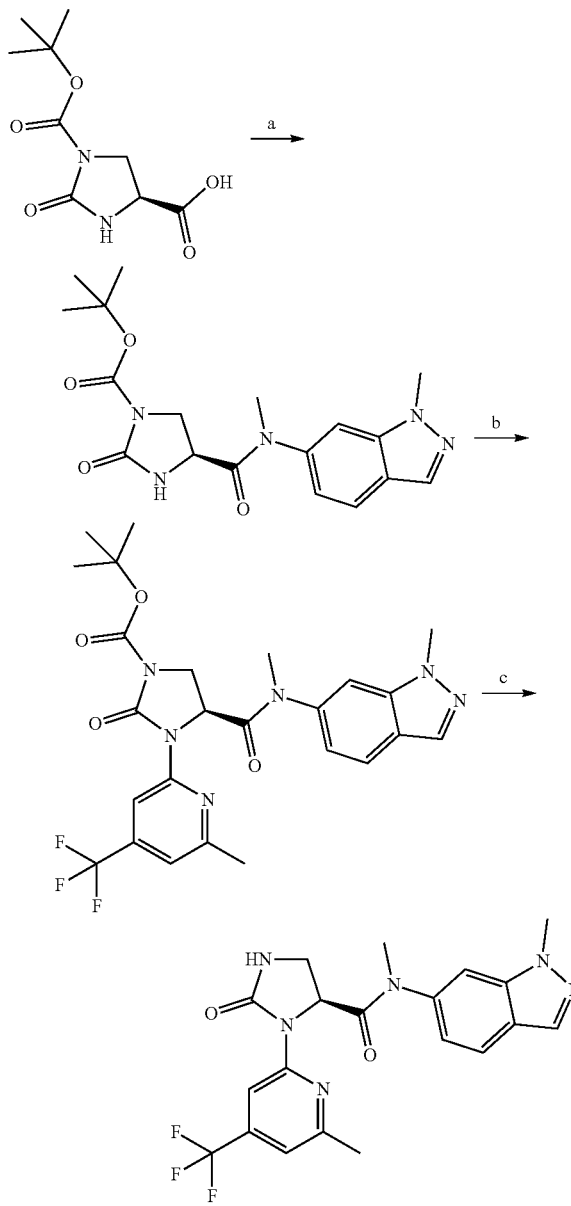

Step a. To a mixture of N,1-dimethyl-1H-indazol-6-amine (Example 168, step a; 250 mg, 1.55 mmol) and (S)-1-(tert-butoxycarbonyl)-2-oxoimidazolidine-4-carboxylic acid (Example 61, steps c-e; 535 mg, 2.33 mmol) in pyridine (5 mL) was added T3P (2.96 g, 4.65 mmol, 50 wt. % in EtOAc). The mixture was stirred at rt for 5 h. On completion, the reaction mixture was quenched with water (10 mL) and extracted with EtOAc (10 mL×3). The combined organic layers were washed with water (10 mL×2), dried over $Na_2SO_4$ and evaporated. The residue was purified by reverse-phase column chromatography to give (S)-tert-butyl 4-(methyl(1-methyl-1H-indazol-6-yl)carbamoyl)-2-oxoimidazolidine-1-carboxylate (0.5 g, 78% yield) as a yellow solid.

m/z ES+[M-55]$^+$ 318.2

Step b. To a mixture of (S)-tert-butyl 4-(methyl(1-methyl-1H-indazol-6-yl)carbamoyl)-2-oxoimidazolidine-1-carboxylate (200 mg, 0.54 mmol) and 2-bromo-6-methyl-4-(trifluoromethyl)pyridine (167 mg, 0.70 mmol) in dioxane (5 mL) was added $Pd_2(dba)_3$ (49 mg, 0.054 mmol), XantPhos (62 mg, 0.11 mmol) and $K_2CO_3$ (148 mg, 1.07 mmol) under $N_2$ atmosphere. The mixture was then stirred at 100° C. for 2 h. On completion, the reaction mixture was quenched with water (10 mL) and extracted with EtOAc (20 mL×3). The combined organic layers were washed with water (10 mL×2), dried and evaporated. The residue was purified by column chromatography (5-50% EtOAc in PE) to give (S)-tert-butyl 4-(methyl(1-methyl-1H-indazol-6-yl)carbamoyl)-3-(6-methyl-4-(trifluoromethyl)pyridin-2-yl)-2-oxoimidazolidine-1-carboxylate (250 mg, 71% yield) as a yellow solid.

m/z ES+[M+H]$^+$ 533.2

Step c. To a mixture of (S)-tert-butyl 4-(methyl(1-methyl-1H-indazol-6-yl)carbamoyl)-3-(6-methyl-4-(trifluoromethyl)pyridin-2-yl)-2-oxoimidazolidine-1-carboxylate (0.1 g, 0.19 mmol) in DCM (5 mL) was added TFA (770 mg, 6.75 mmol). The mixture was stirred at rt for 2 h. On completion, the reaction mixture was quenched with sat. aq. $NaHCO_3$ (5 mL) and extracted with DCM (10 mL×3). The combined organic layers were washed with water (5 mL×2), dried over $Na_2SO_4$ and evaporated. The residue was purified by prep-HPLC to give the title compound (53 mg, 65% yield) as a white solid.

m/z ES+[M+H]$^+$ 433.1; $^1$H NMR (400 MHz, $CD_3OD$) δ ppm 8.32 (s, 1H), 8.10 (s, 1H), 7.93 (d, J=8.4 Hz, 1H), 7.73 (s, 1H), 7.42-7.30 (m, 1H), 7.10 (s, 1H), 5.12-5.06 (m, 1H), 4.10 (s, 3H), 3.60-3.54 (m, 1H), 3.51-3.44 (m, 1H), 3.37 (s, 3H), 2.60 (s, 3H).

Example 236

(S)—N-Methyl-3-(6-methyl-4-(trifluoromethyl)pyridin-2-yl)-N-(3-methylfuro[3,2-b]pyridin-5-yl)-2-oxoimidazolidine-4-carboxamide

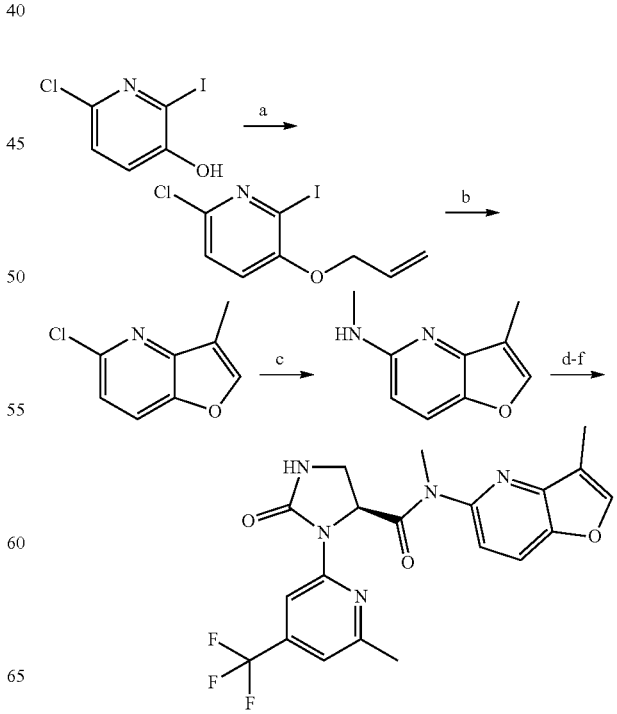

Step a. To a solution of 6-chloro-2-iodopyridin-3-ol (5 g, 19.6 mmol) and 3-bromoprop-1-ene (2.6 g, 21.5 mmol) in DMF (50 mL) was added $K_2CO_3$ (5.41 g, 39 mmol). The mixture was stirred at 60° C. for 2 h. Upon completion, the reaction mixture was quenched with sat. aq. $NH_4Cl$ (50 mL), and then extracted with EtOAc (150 mL×3). The combined organic layers were washed with brine (50 mL×3), dried over $Na_2SO_4$ and evaporated. The residue was purified by column chromatography (5-10% EtOAc in PE) to give 3-(allyloxy)-6-chloro-2-iodopyridine (5.35 g, 93% yield) as a yellow solid.

m/z ES+[M+H]$^+$ 295.9

Step b. To a solution of 3-(allyloxy)-6-chloro-2-iodopyridine (5.1 g, 17.3 mmol) in DMF (50 mL) was added $Cs_2CO_3$ (8.43 g, 26 mmol) and $Pd(dppf)Cl_2$ (1.26 g, 1.73 mmol). The mixture was stirred at 150° C. for 2 h under microwave irradiation under $N_2$ atmosphere. Upon completion, the reaction mixture was quenched with sat. aq. $NH_4Cl$ (50 mL) and then extracted with EtOAc (150 mL×3). The combined organic layers were washed with brine (50 mL×3), dried over $Na_2SO_4$ and evaporated. The residue was purified by column chromatography (5-10% EtOAc in PE) to give 5-chloro-3-methylfuro[3,2-b]pyridine (1.12 g, 39% yield) as a yellow solid.

m/z ES+[M+H]$^+$ 168.0

Step c. A mixture of 5-chloro-3-methyl-furo[3,2-b]pyridine (0.6 g, 3.58 mmol), $MeNH_2$/THF (2 M, 35.8 mmol), BrettPhos (96 mg, 0.18 mmol), BrettPhos-Pd-G2 (163 mg, 0.18 mmol) and LiHMDS (2 M, 10.7 mmol) in THF (10 mL) was degassed and purged with $N_2$ 3 times, and then the mixture was stirred at 60° C. for 12 h under $N_2$ atmosphere. Upon completion, the reaction mixture was quenched with sat. aq. $NH_4Cl$ (20 mL) and then extracted with EtOAc (50 mL×3). The combined organic layers were washed with brine (20 mL×3), dried and evaporated. The residue was purified by column chromatography (5-10% EtOAc in PE) to give N,3-dimethylfuro[3,2-b]pyridin-5-amine (0.48 g, 83% yield) as a yellow solid.

m/z ES+[M+H]$^+$ 163.2

Steps d-f. The title compound was prepared in a similar manner to Example 235, steps b-d, using N,3-dimethylfuro[3,2-b]pyridin-5-amine.

m/z ES+[M+H]$^+$ 434.1; $^1$H NMR (400 MHz, $CD_3OD$) δ ppm 8.27 (s, 1H), 8.02 (d, J=8.4 Hz, 1H), 7.93 (s, 1H), 7.47 (d, J=8.4 Hz, 1H), 7.02 (s, 1H), 5.00-4.90 (m, 1H), 3.88-3.70 (m, 2H), 3.42 (s, 3H), 2.49 (s, 3H), 2.29 (s, 3H).

Example 237

(S)—N-Methyl-3-(6-methyl-4-(trifluoromethyl)pyridin-2-yl)-2-oxo-N-(thieno[3,2-b]pyridin-5-yl)imidazolidine-4-carboxamide

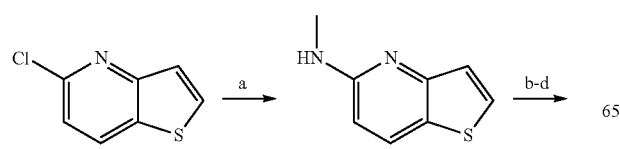

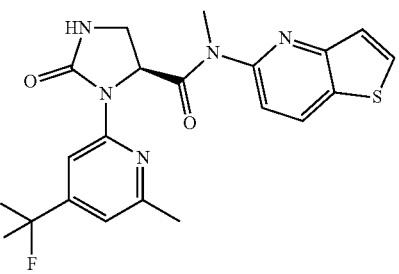

Step a. A mixture of 5-chlorothieno[3,2-b]pyridine (0.2 g, 1.18 mmol), BrettPhos (32 mg, 0.059 mmol), BrettPhos-Pd-G$_2$ (53 mg, 0.059 mmol), LiHMDS (1 M, 3.54 mmol) and $MeNH_2$/THF (2 M, 11.8 mmol) in THF (6 mL) was degassed and purged with $N_2$ 3 times, and then the mixture was stirred at 60° C. for 2 h under $N_2$ atmosphere. Upon completion, the reaction mixture was quenched with sat. aq. $NH_4Cl$ (5 mL), and then extracted with EtOAc (10 mL×3). The combined organic layers were washed with brine (30 mL), dried over $Na_2SO_4$ and evaporated. The residue was purified by column chromatography (0-100% EtOAc in PE) to give N-methylthieno[3,2-b]pyridin-5-amine (140 mg, 69% yield) as a dark brown solid.

$^1$H NMR (400 MHz, $CDCl_3$) δ ppm 7.87 (dd, J=0.8, 8.8 Hz, 1H), 7.59 (d, J=5.2 Hz, 1H), 7.29 (dd, J=0.8, 5.2 Hz, 1H), 6.47 (d, J=8.8 Hz, 1H), 4.59 (s, 1H), 3.02 (d, J=5.2 Hz, 3H).

Steps b-d. The title compound was prepared in a similar manner to Example 235, steps b-d, using N-methylthieno[3,2-b]pyridin-5-amine.

m/z ES+[M+H]$^+$ 436.0; $^1$H NMR (400 MHz, DMSO-d6) δ ppm 8.65 (d, J=8.8 Hz, 1H), 8.26 (s, 1H), 8.23 (d, J=5.6 Hz, 1H), 7.61 (s, 1H), 7.58-7.51 (m, 2H), 7.13 (s, 1H), 5.05-4.95 (m, 1H), 3.80 (t, J=10.0 Hz, 1H), 3.57 (dd, J=4.4, 10.0 Hz, 1H), 3.37 (s, 3H), 2.42 (s, 3H).

Example 238

(S)—N-Methyl-N-(3-methyl-1H-indazol-6-yl)-3-(6-methyl-4-(trifluoromethyl)pyridin-2-yl)-2-oxoimidazolidine-4-carboxamide

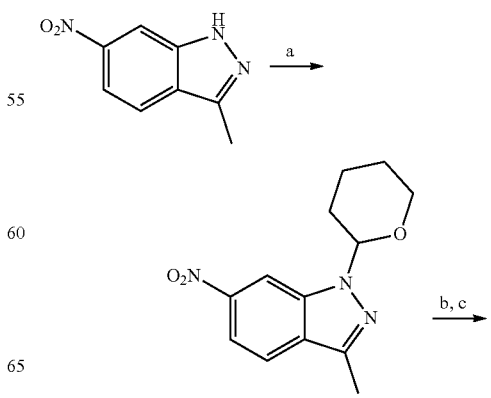

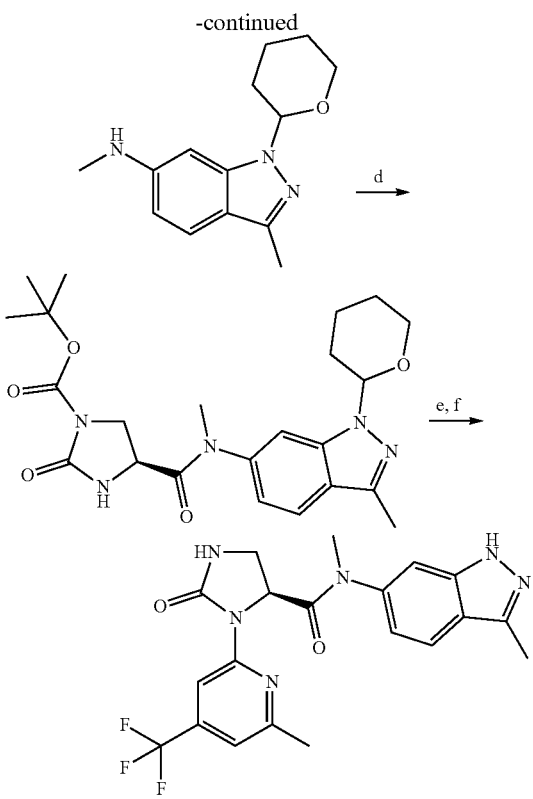

Step a. A mixture of 3-methyl-6-nitro-1H-indazole (2 g, 11.3 mmol), 3,4-dihydro-2H-pyran (2.85 g, 33.9 mmol) and p-toluenesulfonic acid (194 mg, 1.13 mmol) in DCM (60 mL) was stirred at rt for 12 h. On completion, the reaction mixture was quenched with sat. aq. NaHCO₃ (50 mL) and extracted with DCM (50 mL×3). The combined organic layers were washed with water (40 mL), dried over Na₂SO₄ and evaporated. The residue was purified by column chromatography (0-100% EtOAc in PE) to afford 3-methyl-6-nitro-1-(tetrahydro-2H-pyran-2-yl)-1H-indazole (2.9 g, 98% yield) as a yellow solid.

¹H NMR (400 MHz, CDCl₃) δ ppm 8.50 (d, J=1.6 Hz, 1H), 8.03 (dd, J=2.0, 8.8 Hz, 1H), 7.76 (d, J=8.8 Hz, 1H), 5.74 (dd, J=2.4, 10.0 Hz, 1H), 4.15-4.05 (m, 1H), 3.86-3.76 (m, 1H), 2.64 (s, 3H), 2.23-2.02 (m, 2H), 1.86-1.76 (m, 3H), 1.73-1.66 (m, 1H).

Step b. A mixture of 3-methyl-6-nitro-1-(tetrahydro-2H-pyran-2-yl)-1H-indazole (1.89 g, 7.23 mmol), Fe (2.02 g, 36.2 mmol) and NH₄Cl (3.87 g, 72 mmol) in EtOH (20 mL) and water (4 mL) was stirred at 60° C. for 2 h. On completion, the reaction mixture was filtered through celite and washed with MeOH (30 mL). The filtrate was concentrated under vacuum. The residue was diluted with water (80 mL) and extracted with DCM (100 mL×3). The combined organic layers were washed with brine (20 mL×3), dried over Na₂SO₄ and evaporated. The residue was purified by column chromatography (0-100% EtOAc in PE) to afford 3-methyl-1-(tetrahydro-2H-pyran-2-yl)-1H-indazol-6-amine (1.6 g, 96% yield) as a yellow oil.

¹H NMR (400 MHz, CDCl₃) δ ppm 7.39 (d, J=8.4 Hz, 1H), 6.68 (d, J=1.6 Hz, 1H), 6.56 (dd, J=1.6, 8.8 Hz, 1H), 5.48 (dd, J=2.4, 10.0 Hz, 1H), 4.17-4.04 (m, 2H), 3.76-3.66 (m, 1H), 2.49 (s, 3H), 2.13 (d, J=5.6 Hz, 1H), 2.04-1.95 (m, 2H), 1.77-1.71 (m, 2H).

Step c. A mixture of 3-methyl-1-(tetrahydro-2H-pyran-2-yl)-1H-indazol-6-amine (1 g, 4.32 mmol), sodium methoxide (2.34 g, 43 mmol) and formaldehyde (195 mg, 6.5 mmol) in MeOH (15 mL) was stirred at rt for 16 h. NaBH₄ (327 mg, 8.65 mmol) was added to the mixture and it was stirred for 4 h. On completion, the reaction mixture was diluted with water (10 mL) and extracted with EtOAc (50 mL×3). The combined extracts were washed with brine (10 mL×3), dried over Na₂SO₄ and evaporated. The residue was purified by column chromatography (0-100% EtOAc in PE) to afford N,3-dimethyl-1-(tetrahydro-2H-pyran-2-yl)-1H-indazol-6-amine (0.42 g, 40% yield) as a white solid.

m/z ES+[M+H]⁺ 246.3

Step d. To a solution of (S)-1-(tert-butoxycarbonyl)-2-oxoimidazolidine-4-carboxylic acid (Example 61, steps c-e; 0.33 g, 1.43 mmol) and N,3-dimethyl-1-tetrahydropyran-2-yl-indazol-6-amine (422 mg, 1.72 mmol) in pyridine (1 mL) was added T3P (2.74 g, 4.30 mmol, 50 wt. % in EtOAc). The resulting mixture was stirred at rt for 1 h. On completion, the crude product was purified by prep-HPLC to give (4S)-tert-butyl 4-(methyl(3-methyl-1-(tetrahydro-2H-pyran-2-yl)-1H-indazol-6-yl)carbamoyl)-2-oxoimidazolidine-1-carboxylate (350 mg, 53% yield) as a white solid.

m/z ES+[M+H]⁺ 458.2

Step e. A mixture of (4S)-tert-butyl 4-(methyl(3-methyl-1-(tetrahydro-2H-pyran-2-yl)-1H-indazol-6-yl)carbamoyl)-2-oxoimidazolidine-1-carboxylate (200 mg, 0.44 mmol), 2-bromo-6-methyl-4-(trifluoromethyl)pyridine (126 mg, 0.52 mmol), Pd₂(dba)₃ (40 mg, 0.044 mmol), XantPhos (51 mg, 0.087 mmol) and K₂CO₃ (181 mg, 1.31 mmol) in dioxane (2 mL) was degassed and purged with N₂ 3 times, and then the mixture was stirred at 100° C. for 2 h under N₂ atmosphere. On completion, the reaction mixture was diluted with water (10 mL) and extracted with EtOAc (20 mL×3). The combined organic layers were washed with brine (10 mL×3), dried over Na₂SO₄ and evaporated. The residue was purified by column chromatography (0-100% EtOAc in PE) to give (4S)-tert-butyl 4-(methyl(3-methyl-1-(tetrahydro-2H-pyran-2-yl)-1H-indazol-6-yl)carbamoyl)-3-(6-methyl-4-(trifluoromethyl)pyridin-2-yl)-2-oxoimidazolidine-1-carboxylate (160 mg, 59% yield) as a yellow solid.

m/z ES+[M+H]⁺ 617.5

Step f. A solution of (4S)-tert-butyl 4-(methyl(3-methyl-1-(tetrahydro-2H-pyran-2-yl)-1H-indazol-6-yl)carbamoyl)-3-(6-methyl-4-(trifluoromethyl)pyridin-2-yl)-2-oxoimidazolidine-1-carboxylate (80 mg, 0.13 mmol) in 4 M HCl/MeOH (2 mL) was stirred at rt for 12 h. On completion, the reaction mixture was concentrated under vacuum. The residue was purified by prep-HPLC to give the title compound (19 mg, 31% yield, HCl) as a white solid.

m/z ES+[M+H]⁺ 433.1; ¹H NMR (400 MHz, CD₃OD) δ ppm 8.35 (s, 1H), 7.99-7.88 (m, 1H), 7.70-7.65 (m, 1H), 7.35-7.27 (m, 1H), 7.12 (s, 1H), 5.09 (dd, J=5.2, 10.4 Hz, 1H), 3.56-3.45 (m, 2H), 3.38 (s, 3H), 2.67 (s, 3H), 2.65-2.61 (m, 3H).

Example 239

(S)—N-(3-Fluoro-1H-pyrrolo[2,3-b]pyridin-6-yl)-N-methyl-3-(6-methyl-4-(trifluoromethyl)pyridin-2-yl)-2-oxoimidazolidine-4-carboxamide

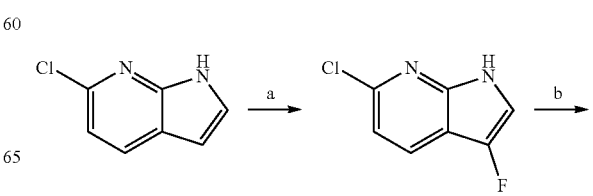

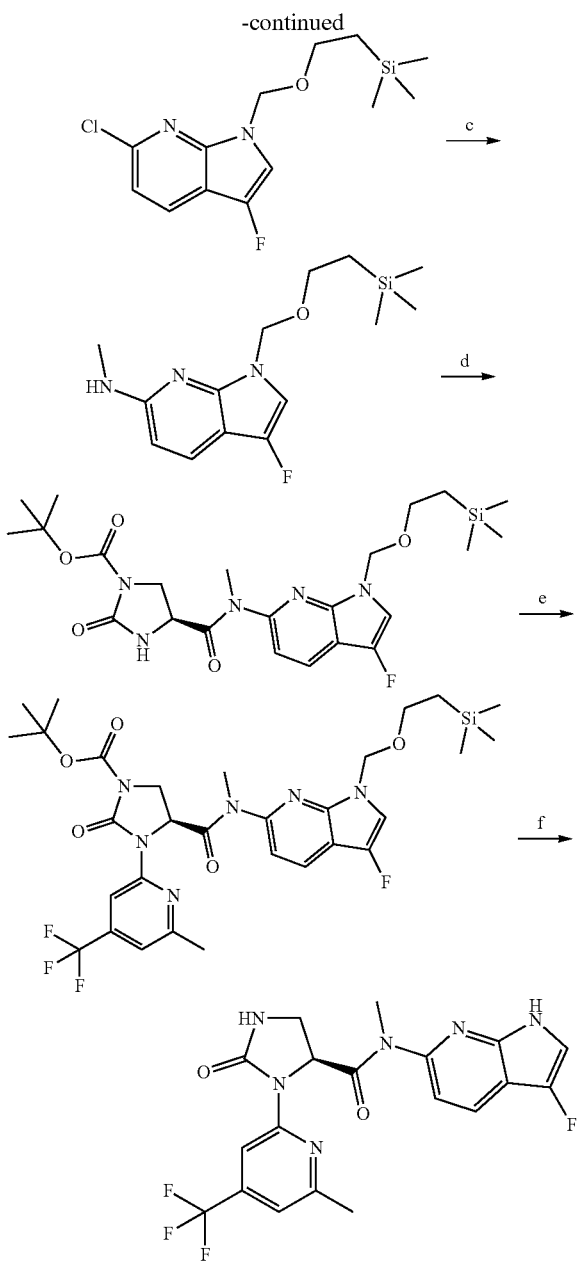

Step a. To a mixture of 6-chloro-1H-pyrrolo[2,3-b]pyridine (3.78 g, 24.8 mmol) in MeCN (38 mL) and pyridine (11.4 mL) was added Selectfluor (7.90 g, 22.3 mmol). The mixture was stirred at rt for 16 h. Upon completion, the reaction mixture was diluted with water (70 mL) and extracted with EtOAc (70 mL×3). The combined organic layers were washed with brine (100 mL×2), dried over Na$_2$SO$_4$ and evaporated. The residue was purified by prep-HPLC to give 6-chloro-3-fluoro-1H-pyrrolo[2,3-b]pyridine (0.9 g, 21% yield) as a dark brown solid.

m/z ES+[M+H]$^+$ 171.1

Step b. To a solution of 6-chloro-3-fluoro-1H-pyrrolo[2,3-b]pyridine (0.7 g, 4.10 mmol) in THF (13 mL) was added NaH (328 mg, 8.00 mmol, 60% dispersion in mineral oil) portionwise at 0° C. The mixture was then stirred at 0° C. for 1 h before addition of 2-(trimethylsilyl)-ethoxymethyl chloride (821 mg, 4.92 mmol). The mixture was stirred at 0° C. for 1 h. Upon completion, the reaction mixture was quenched with sat. aq. NH$_4$Cl (40 mL), and then extracted with EtOAc (50 mL×3). The combined organic layers were washed with brine (90 mL), dried over Na$_2$SO$_4$ and evaporated. The residue was purified by reverse-phase column chromatography to give 6-chloro-3-fluoro-1-((2-(trimethylsilyl)ethoxy)methyl)-1H-pyrrolo[2,3-b]pyridine (0.8 g, 65% yield) as a yellow oil.

$^1$H NMR (400 MHz, DMSO-d6) δ ppm 8.14 (d, J=8.4 Hz, 1H), 7.75 (d, J=2.0 Hz, 1H), 7.29 (d, J=8.4 Hz, 1H), 5.54 (s, 2H), 3.53-3.48 (m, 2H), 0.86-0.81 (m, 2H),−0.10 (s, 9H).

Step c. A mixture of 6-chloro-3-fluoro-1-((2-(trimethylsilyl)ethoxy)methyl)-1H-pyrrolo[2,3-b]pyridine (0.32 g, 1.06 mmol), MeNH$_2$/THF (2 M, 10.6 mmol), BrettPhos (29 mg, 0.053 mmol), BrettPhos-Pd-G2 (48 mg, 0.053 mmol) and LiHMDS (1 M, 3.19 mmol) in THF (3 mL) was degassed and purged with N$_2$ 3 times, and then the mixture was stirred at 60° C. for 4 h under N$_2$ atmosphere. Upon completion, the reaction mixture was quenched with sat. NH$_4$Cl solution (10 mL) and then extracted with EtOAc (15 mL×3). The combined organic layers were washed with brine (30 mL), dried over Na$_2$SO$_4$ and evaporated. The residue was purified by column chromatography (0-100% EtOAc in PE) to give 3-fluoro-N-methyl-1-((2-(trimethylsilyl)ethoxy)methyl)-1H-pyrrolo[2,3-b]pyridin-6-amine (0.29 g, 74% yield) as a dark brown oil.

m/z ES+[M+H]$^+$ 296.0

Step d. To a solution of (S)-1-(tert-butoxycarbonyl)-2-oxoimidazolidine-4-carboxylic acid (Example 61, steps c-e; 240 mg, 1.00 mmol) in MeCN (0.5 mL) was added Ghosez's reagent (CAS Number 26189-59-3; 152 mg, 1.14 mmol) in MeCN (0.5 mL) dropwise at 0° C. The mixture was stirred at 0° C. for 1 h and then added dropwise to a solution of 3-fluoro-N-methyl-1-((2-(trimethylsilyl)ethoxy)methyl)-1H-pyrrolo[2,3-b]pyridin-6-amine (0.28 g, 0.95 mmol) and DIPEA (147 mg, 1.14 mmol) in MeCN (1 mL). The mixture was stirred at 0° C. for 30 min. Upon completion, the reaction mixture was quenched with water (20 mL) and extracted with EtOAc (25 mL×3). The combined organic layers were washed with brine (70 mL), dried over Na$_2$SO$_4$ and evaporated. The residue was purified by column chromatography (0-100% EtOAc in PE) to give (S)-tert-butyl 4-((3-fluoro-1-((2-(trimethylsilyl)ethoxy)methyl)-1H-pyrrolo[2,3-b]pyridin-6-yl)(methyl)carbamoyl)-2-oxoimidazolidine-1-carboxylate (0.19 g, 38% yield) as a yellow solid.

$^1$H NMR (400 MHz, DMSO-d6) δ ppm 8.20 (d, J=8.4 Hz, 1H), 7.74 (d, J=2.0 Hz, 1H), 7.50 (s, 1H), 7.30 (d, J=8.4 Hz, 1H), 5.55-5.45 (m, 2H), 4.25-4.19 (m, 1H), 3.91-3.81 (m, 2H), 3.52 (t, J=8.0 Hz, 2H), 1.43 (s, 9H), 0.89-0.76 (m, 2H),−0.11 (s, 9H).

Step e. A mixture of (S)-tert-butyl 4-((3-fluoro-1-((2-(trimethylsilyl)ethoxy)methyl)-1H-pyrrolo[2,3-b]pyridin-6-yl)(methyl)carbamoyl)-2-oxoimidazolidine-1-carboxylate (170 mg, 0.34 mmol), 2-bromo-6-methyl-4-(trifluoromethyl)pyridine (113 mg, 0.47 mmol), Pd$_2$(dba)$_3$ (31 mg, 0.034 mmol), XantPhos (39 mg, 0.067 mmol) and K$_2$CO$_3$ (93 mg, 0.67 mmol) in dioxane (2 mL) was degassed and purged with N$_2$ 3 times. Then the mixture was stirred at 100° C. for 2 h under N$_2$ atmosphere. Upon completion, the reaction mixture was diluted with water (20 mL) and extracted with EtOAc (25 mL×3). The combined organic layers were washed with brine (80 mL), dried over Na$_2$SO$_4$ and evaporated. The residue was purified by column chromatography (0-100% EtOAc in PE) to give (S)-tert-butyl 4-((3-fluoro-1-((2-(trimethylsilyl)ethoxy)methyl)-1H-pyrrolo[2,3-b]pyridin-6-yl)(methyl)carbamoyl)-3-(6-methyl-4-(trifluoromethyl)pyridin-2-yl)-2-oxoimidazolidine-1-carboxylate (170 mg, 69% yield) as a yellow solid.

m/z ES+[M+H]$^+$ 667.3

Step f. To a solution of (S)-tert-butyl 4-((3-fluoro-1-((2-(trimethylsilyl)ethoxy)methyl)-1H-pyrrolo[2,3-b]pyridin-6-yl)(methyl)carbamoyl)-3-(6-methyl-4-(trifluoromethyl)pyridin-2-yl)-2-oxoimidazolidine-1-carboxylate (100 mg, 0.15 mmol) in DCM (1 mL) was added TFA (4.62 g, 40.5 mmol). The mixture was stirred at rt for 2 h. On completion, the mixture was concentrated under vacuum to give a residue. The residue was dissolved in THF (3 mL), treated with aq. ammonia (210 mg, 1.50 mmol, 25 wt %) and stirred at rt for 4 h. Upon completion, the reaction mixture was concentrated under vacuum. The residue was purified by prep-HPLC to give the title compound (27 mg, 41% yield) as a yellow solid.

m/z ES+[M+H]$^+$ 437.0; $^1$H NMR (400 MHz, CD$_3$OD) δ ppm 8.30 (s, 1H), 8.17 (d, J=8.4 Hz, 1H), 7.33 (d, J=8.4 Hz, 1H), 7.27 (d, J=2.4 Hz, 1H), 7.05 (s, 1H), 5.07-5.00 (m, 1H), 3.90-3.83 (m, 1H), 3.74 (dd, J=5.2, 10.0 Hz, 1H), 3.43 (s, 3H), 2.52 (s, 3H).

Example 240

(S)—N-(3-Chloro-1H-pyrrolo[2,3-b]pyridin-6-yl)-N-methyl-3-(6-methyl-4-(trifluoromethyl)pyridin-2-yl)-2-oxoimidazolidine-4-carboxamide

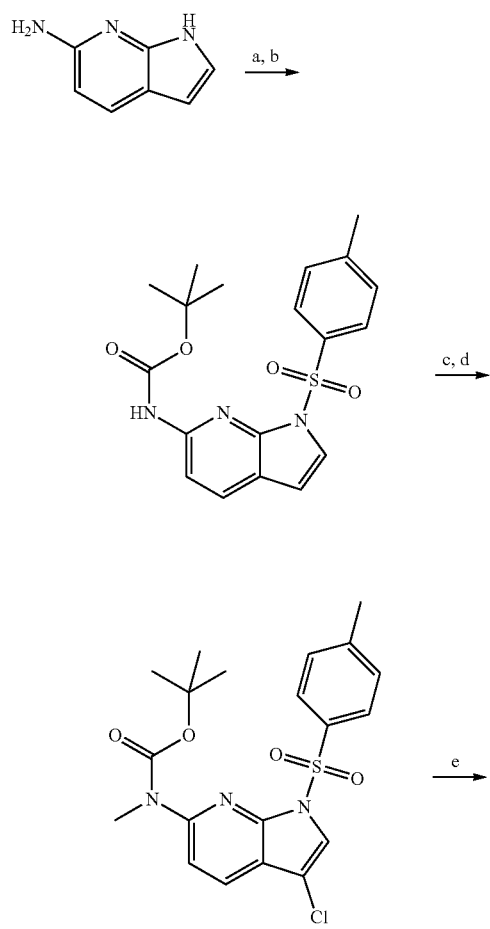

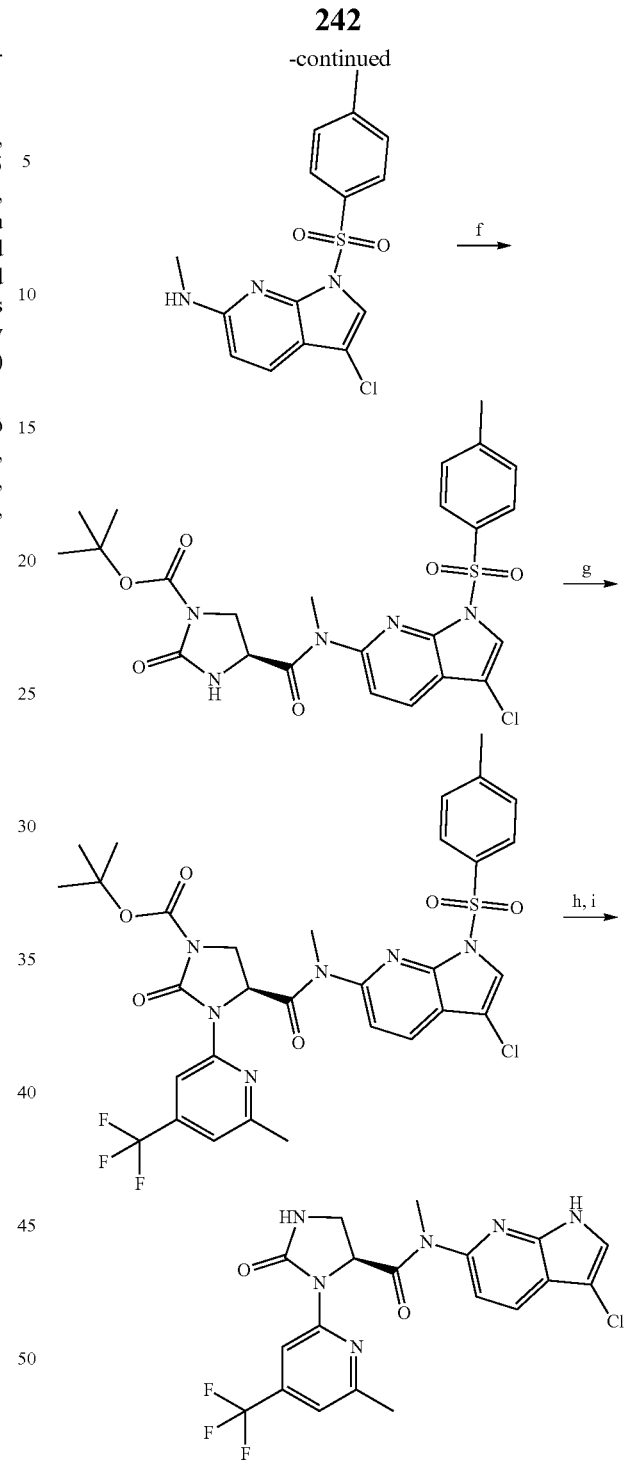

Step a. To a mixture of 1H-pyrrolo[2,3-b]pyridin-6-amine (2 g, 15.02 mmol) in THF (20 mL) and water (4 mL) was added Na$_2$CO$_3$ (3.98 g, 37.6 mmol) and (Boc)$_2$O (3.44 g, 15.8 mmol). The mixture was stirred at 40° C. for 12 h. Upon completion, the reaction mixture was diluted with water (30 mL) and extracted with EtOAc (40 mL×3). The combined organic layers were washed with brine (80 mL×2), dried over Na$_2$SO$_4$ and evaporated. The residue was purified by column chromatography (0-100% EtOAc in PE) to give tert-butyl 1H-pyrrolo[2,3-b]pyridin-6-ylcarbamate (0.9 g, 24% yield) as a white solid.

m/z ES+[M-55]$^+$ 178.1

Step b. To a solution of tert-butyl 1H-pyrrolo[2,3-b]pyridin-6-ylcarbamate (0.9 g, 3.86 mmol) in DCM (15 mL) was added NaOH (1.54 g, 38.6 mmol), TBAB (62 mg, 0.19 mmol) and p-toluenesulfonyl chloride (7.36 g, 38.6 mmol). The mixture was stirred at −20° C. for 3 h. Then the mixture was stirred at rt for 9 h. Upon completion, the reaction mixture was diluted with water (20 mL) and extracted with DCM (20 mL×3). The combined organic layers were washed with brine (50 mL), dried over Na$_2$SO$_4$ and evaporated. The residue was purified by column chromatography (0-100% EtOAc in PE) to give tert-butyl (1-tosyl-1H-pyrrolo[2,3-b]pyridin-6-yl)carbamate (1.15 g, 69% yield) as a white solid.

m/z ES+[M+H]$^+$ 388.2

Step c. To a mixture of tert-butyl (1-tosyl-1H-pyrrolo[2,3-b]pyridin-6-yl)carbamate (1.12 g, 2.89 mmol) in DMF (15 mL) was added NaH (139 mg, 3.47 mmol, 60% dispersion in mineral oil) at 0° C. The mixture was stirred at 0° C. for 30 min, and then methyl iodide (492 mg, 3.47 mmol) was added at 0° C. The mixture was stirred at 0° C. for 30 min. Upon completion, the reaction mixture was diluted with water (30 mL) and extracted with EtOAc (30 mL×3). The combined organic layers were washed with brine (80 mL), dried over Na$_2$SO$_4$ and evaporated. The residue was purified by column chromatography (0-100% EtOAc in PE) to give tert-butyl methyl(1-tosyl-1H-pyrrolo[2,3-b]pyridin-6-yl)carbamate (0.86 g, 73% yield) as a white solid.

m/z ES+[M+H]$^+$ 402.1

Step d. To a solution of tert-butyl methyl(1-tosyl-1H-pyrrolo[2,3-b]pyridin-6-yl)carbamate (0.86 g, 2.14 mmol) in dioxane (7 mL) was added 1, 3-dichloro-5, 5-dimethyl-imidazolidine-2, 4-dione (232 mg, 1.18 mmol). The mixture was stirred at 80° C. for 12 h. Upon completion, the reaction mixture was concentrated under vacuum to give tert-butyl (3-chloro-1-tosyl-1H-pyrrolo[2,3-b]pyridin-6-yl)(methyl)carbamate (0.9 g, crude) as a black solid.

m/z ES+[M-55]$^+$380.1

Step e. To a solution of tert-butyl (3-chloro-1-tosyl-1H-pyrrolo[2,3-b]pyridin-6-yl)(methyl)carbamate (0.9 g, 1.03 mmol) in DCM (3 mL) was added TFA (13.9 g, 122 mmol). The mixture was stirred at rt for 30 min. Upon completion, the reaction mixture was evaporated and the residue was purified by column chromatography (0-100% EtOAc in PE) to give 3-chloro-N-methyl-1-tosyl-1H-pyrrolo[2,3-b]pyridin-6-amine (270 mg, 74% yield) as a white solid.

m/z ES+[M+H]$^+$ 335.9

Step f. To a solution of (S)-1-(tert-butoxycarbonyl)-2-oxoimidazolidine-4-carboxylic acid (Example 61, steps c-e; 98 mg, 0.43 mmol) in MeCN (0.8 mL) was added Ghosez's reagent (CAS Number 26189-59-3; 62 mg, 0.46 mmol) in MeCN (0.8 mL) dropwise at 0° C. The mixture was stirred at 0° C. for 1 h. Then the mixture was added dropwise into a solution of 3-chloro-N-methyl-1-tosyl-1H-pyrrolo[2,3-b]pyridin-6-amine (130 mg, 0.39 mmol) and N, N-dimethylpyridin-2-amine (57 mg, 0.47 mmol) in MeCN (1.4 mL). The mixture was stirred at 0° C. for 30 min. Upon completion, the reaction mixture was diluted with water (10 mL) and extracted with EtOAc (10 mL×3). The combined organic layers were washed with brine (30 mL), dried over Na$_2$SO$_4$ and evaporated. The residue was purified by column chromatography (0-100% EtOAc in PE) to give (S)-tert-butyl 4-((3-chloro-1-tosyl-1H-pyrrolo[2,3-b]pyridin-6-yl)(methyl)carbamoyl)-2-oxoimidazolidine-1-carboxylate (200 mg, 57% yield) as a yellow solid.

m/z ES+[M-55]$^+$492.2

Step g. A solution of (S)-tert-butyl 4-((3-chloro-1-tosyl-1H-pyrrolo[2,3-b]pyridin-6-yl)(methyl)carbamoyl)-2-oxo-imidazolidine-1-carboxylate (170 mg, 0.19 mmol), 2-bromo-6-methyl-4-(trifluoromethyl)pyridine (63 mg, 0.26 mmol), Pd$_2$(dba)$_3$ (17 mg, 0.019 mmol), Xantphos (22 mg, 0.037 mmol) and K$_2$CO$_3$ (52 mg, 0.37 mmol) in dioxane (3 mL) was degassed and purged with N$_2$ 3 times, and then the mixture was stirred at 100° C. for 2 h under N$_2$ atmosphere. Upon completion, the reaction mixture was diluted with water (10 mL) and extracted with EtOAc (10 mL×3). The combined organic layers were washed with brine (30 mL), dried over Na$_2$SO$_4$ and evaporated. The residue was purified by column chromatography (0-100% EtOAc in PE) to give (S)-tert-butyl 4-((3-chloro-1-tosyl-1H-pyrrolo[2,3-b]pyridin-6-yl)(methyl)carbamoyl)-3-(6-methyl-4-(trifluoromethyl)pyridin-2-yl)-2-oxoimidazolidine-1-carboxylate (60 mg, 41% yield) as a yellow solid.

m/z ES+[M+H]$^+$ 707.0

Step h. A solution of (S)-tert-butyl 4-((3-chloro-1-tosyl-1H-pyrrolo[2,3-b]pyridin-6-yl)(methyl)carbamoyl)-3-(6-methyl-4-(trifluoromethyl)pyridin-2-yl)-2-oxoimidazolidine-1-carboxylate (50 mg, 0.071 mmol) in TBAF/THF (1 M, 1 mmol) was stirred at rt for 3 h. Upon completion, the reaction mixture was diluted with water (1 mL) and extracted with EtOAc (2 mL×3). The combined organic layers were washed with water (0.5 mL×4) and brine (1 mL×2), dried over Na$_2$SO$_4$ and evaporated to give (S)-tert-butyl 4-((3-chloro-1H-pyrrolo[2,3-b]pyridin-6-yl)(methyl)carbamoyl)-3-(6-methyl-4-(trifluoromethyl)pyridin-2-yl)-2-oxoimidazolidine-1-carboxylate (40 mg, crude) as a yellow solid.

m/z ES+[M+H]$^+$ 553.3

Step i. To a solution of (S)-tert-butyl 4-((3-chloro-1H-pyrrolo[2,3-b]pyridin-6-yl)(methyl)carbamoyl)-3-(6-methyl-4-(trifluoromethyl)pyridin-2-yl)-2-oxoimidazolidine-1-carboxylate (40 mg, 0.072 mmol) in DCM (0.4 mL) was added TFA (616 mg, 5.40 mmol). The mixture was stirred at rt for 30 min. Upon completion, the reaction mixture was concentrated under vacuum to give a residue. The residue was purified by prep-HPLC to give the title compound (15 mg, 42% yield, HCl) as a white solid.

m/z ES+[M+H]$^+$ 453.1; $^1$H NMR (400 MHz, CD$_3$OD) δ ppm 8.27 (s, 1H), 8.12 (d, J=8.4 Hz, 1H), 7.47 (s, 1H), 7.35 (d, J=8.4 Hz, 1H), 7.04 (s, 1H), 5.07-4.98 (m, 1H), 3.88-3.81 (m, 1H), 3.72 (dd, J=5.2, 10.0 Hz, 1H), 3.42 (s, 3H), 2.51 (s, 3H).

Example 241

(2S,5R)—N-(3-Chloro-4-fluorophenyl)-1-(3-cyano-6-methyl-4-(trifluoromethyl)pyridin-2-yl)-N,5-dimethylpyrrolidine-2-carboxamide

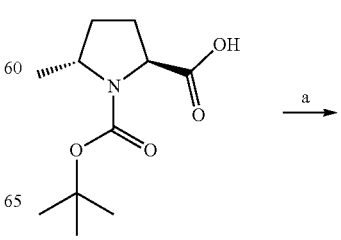

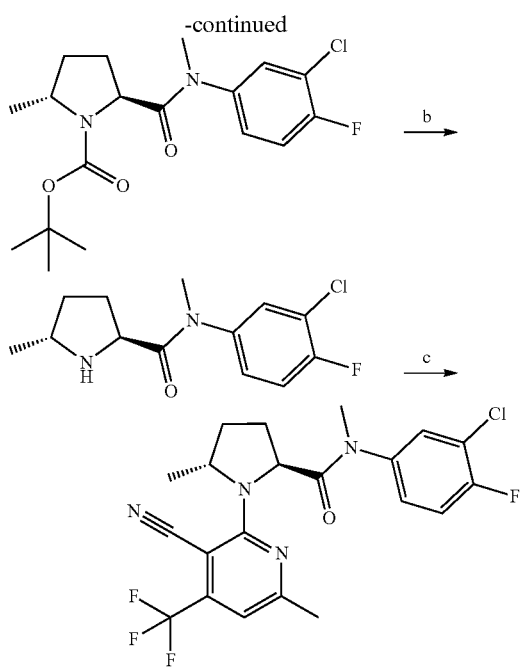

Step a. A mixture of (2S,5R)-1-(tert-butoxycarbonyl)-5-methylpyrrolidine-2-carboxylic acid (200 mg, 0.87 mmol), 3-chloro-4-fluoro-N-methyl-aniline (167 mg, 1.05 mmol) and T3P (1.67 g, 2.62 mmol, 50 wt. % in EtOAc) in pyridine (1 mL) was stirred at 10° C. for 12 h. Upon completion, the mixture was diluted with water (30 mL) and extracted with EtOAc (30 mL×2). The combined organic layers were dried over Na$_2$SO$_4$ and evaporated. The residue was purified by column chromatography (25% EtOAc in PE) to give (2S, 5R)-tert-butyl 2-((3-chloro-4-fluorophenyl)(methyl)carbamoyl)-5-methylpyrrolidine-1-carboxylate (200 mg, 61% yield) as a yellow oil.

m/z ES+[M+H]$^+$ 371.1

Step b. To a solution of (2S,5R)-tert-butyl 2-((3-chloro-4-fluorophenyl)(methyl)carbamoyl)-5-methylpyrrolidine-1-carboxylate (200 mg, 0.54 mmol) in DCM (3 mL) was added TFA (0.6 mL). The mixture was stirred at 10° C. for 1 h. Upon completion, the mixture was adjusted to pH 8-9 by sat. aq. NaHCO$_3$, diluted with water (30 mL) and extracted with DCM (30 mL×2). The combined organic layers were washed with brine (30 mL), dried over Na$_2$SO$_4$ and evaporated to give (2S,5R)—N-(3-chloro-4-fluorophenyl)-N,5-dimethylpyrrolidine-2-carboxamide (100 mg, 68% yield) as a yellow oil.

m/z ES+[M+H]$^+$ 271.0

Step c. To a solution of (2S,5R)—N-(3-chloro-4-fluorophenyl)-N,5-dimethylpyrrolidine-2-carboxamide (90 mg, 0.33 mmol) and 2-chloro-6-methyl-4-(trifluoromethyl)nicotinonitrile (110 mg, 0.50 mmol) in NMP (1 mL) was added DIPEA (129 mg, 1.00 mmol). The mixture was stirred at 60° C. for 5 h. Upon completion, the mixture was quenched with water (30 mL) and extracted with EtOAc (30 mL×2). The combined organic layers were washed with brine (30 mL), dried over Na$_2$SO$_4$ and evaporated. The residue was purified by prep-HPLC to give the title compound (6.4 mg, 4% yield) as a white solid.

m/z ES+[M+H]$^+$ 455.1; $^1$H NMR (400 MHz, CD$_3$OD) δ ppm 7.83-7.46 (m, 2H), 7.39 (s, 1H), 6.91 (s, 1H), 4.96-4.83 (m, 1H), 3.70-3.41 (m, 1H), 3.28 (s, 3H), 2.56 (s, 3H), 2.17-1.80 (m, 4H), 1.46 (d, J=6.4 Hz, 3H).

Example 242

(2S,5S)—N-(3-Chloro-4-fluorophenyl)-1-(3-cyano-6-methyl-4-(trifluoromethyl)pyridin-2-yl)-N,5-dimethylpyrrolidine-2-carboxamide

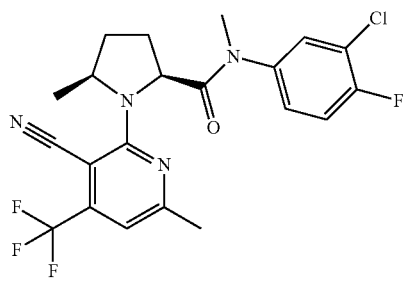 [SMILES: Cc1cc(C(F)(F)F)c(C#N)c(N2[C@@H](C)CC[C@H]2C(=O)N(C)c2ccc(F)c(Cl)c2)n1]

The title compound was prepared in a similar manner to Example 241, using (2S,5S)-1-(tert-butoxycarbonyl)-5-methylpyrrolidine-2-carboxylic acid (CAS Number 334769-80-1).

m/z ES+[M+H]$^+$ 455.1; $^1$H NMR (400 MHz, DMSO-d6) δ ppm 7.69 (s, 1H), 7.49 (d, J=6.4 Hz, 2H), 6.99 (s, 1H), 4.88-4.68 (m, 2H), 3.05 (s, 3H), 2.52 (s, 3H), 2.15-1.95 (m, 3H), 1.83-1.74 (m, 1H), 1.39 (d, J=6.4 Hz, 3H).

Example 243

(S)-1-(3-Cyano-6-methyl-4-(trifluoromethyl)pyridin-2-yl)-N-methyl-N-(1-methyl-1H-pyrrolo[2,3-b]pyridin-6-yl)pyrrolidine-2-carboxamide

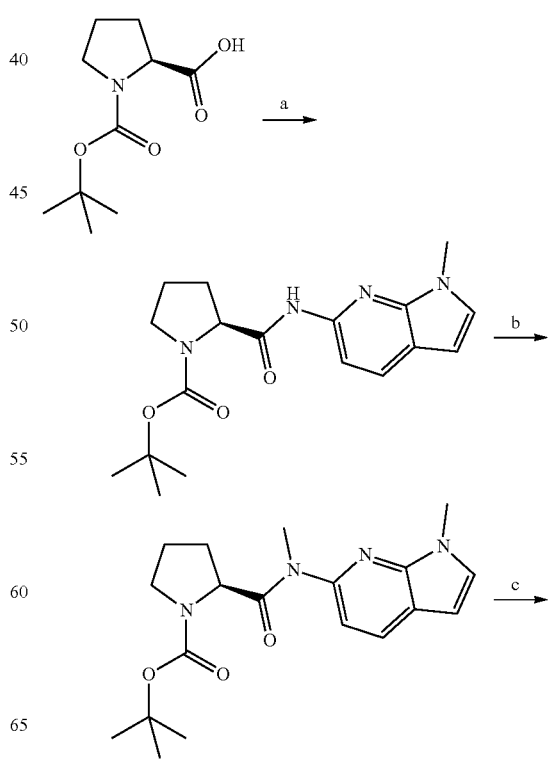

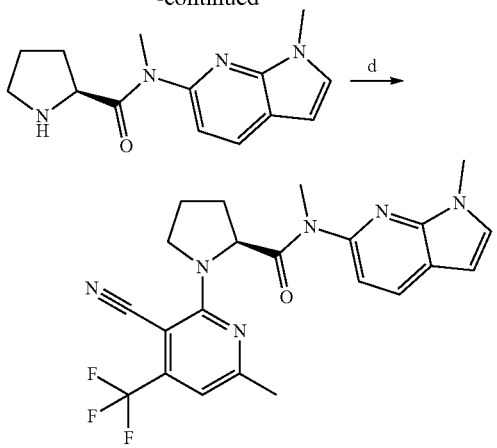

Step a. DIPEA (0.24 mL, 1.359 mmol) was added to a suspension of 1-methyl-1h-pyrrolo[2,3-b]pyridin-6-amine (0.1 g, 0.679 mmol), (S)-1-(tert-butoxycarbonyl)pyrrolidine-2-carboxylic acid (0.15 g, 0.679 mmol) and HATU (0.31 g, 0.815 mmol) in DCM (5 mL). The reaction mixture was stirred at rt for 2 h. The reaction mixture was quenched with brine and extracted with DCM (×2). The combined organics were dried and evaporated to give a brown gum. The crude product was purified by column chromatography (0-6% MeOH in DCM) to give tert-butyl (2S)-2-[(1-methylpyrrolo[2,3-b]pyridin-6-yl)carbamoyl]pyrrolidine-1-carboxylate (394 mg) as a crude brown oil, which crystallised on standing.

m/z ES+[M+H]+ 345.2

Step b. Methyl iodide (0.04 mL, 0.679 mmol) was added to tert-butyl (2S)-2-[(1-methylpyrrolo[2,3-b]pyridin-6-yl)carbamoyl]pyrrolidine-1-carboxylate (0.23 g, 0.679 mmol, assuming quantitative yield from step a) and Cs₂CO₃ (0.31 g, 0.951 mmol) in DMF (1.5 mL). The reaction mixture was stirred at rt for 2.5 h. An additional 0.2 equivalents of methyl iodide (0.01 mL, 0.136 mmol) were added and the reaction mixture was stirred at rt for a further 1 h. An additional 0.3 equivalents of methyl iodide (0.01 mL, 0.204 mmol) and 0.7 equivalents of Cs₂CO₃ (0.15 g, 0.476 mmol) were added and the reaction mixture was stirred at rt overnight. The reaction mixture was quenched with water and extracted with EtOAc (×2). The combined organics were washed with brine, dried and concentrated under vacuum. The crude product was purified by column chromatography (0-6% MeOH in DCM) to give tert-butyl (2S)-2-[methyl-(1-methylpyrrolo[2,3-b]pyridin-6-yl)carbamoyl]pyrrolidine-1-carboxylate (204 mg, 84%) as a brown gum.

m/z ES+[M+H]+ 359.2; ¹H NMR (400 MHz, CDCl₃) δ ppm 7.95 (dd, J=8.2, 4.6 Hz, 1H), 7.25-7.18 (m, 1H), 6.96 (d, J=8.2 Hz, 1H), 6.48 (dd, J=5.2, 3.4 Hz, 1H), 4.30 (d, J=78.5 Hz, 1H), 3.86 (d, J=10.1 Hz, 3H), 3.70-3.53 (m, 1H), 3.41 (s, 3H), 2.31 (dt, J=11.4, 6.2 Hz, 1H), 2.23-1.89 (m, 2H), 1.88-1.65 (m, 2H), 1.44 (d, J=2.6 Hz, 9H).

Step c. To a solution of tert-butyl (2S)-2-[methyl-(1-methylpyrrolo[2,3-b]pyridin-6-yl)carbamoyl]pyrrolidine-1-carboxylate (0.2 g, 0.569 mmol) in dioxane (2 mL) was added HCl (4M in dioxane, 2.13 mL, 8.537 mmol). The reaction mixture was stirred at rt overnight and concentrated under vacuum to give (2S)—N-methyl-N-(1-methylpyrrolo[2,3-b]pyridin-6-yl)pyrrolidine-2-carboxamide hydrochloride (197 mg, quant.) as an orange foam.

m/z ES+[M+H]+ 259.2; ¹H NMR (400 MHz, DMSO-d6) δ ppm 9.85-9.67 (m, 1H), 8.70-8.51 (m, 1H), 8.16 (d, J=8.2 Hz, 1H), 7.63 (d, J=3.5 Hz, 1H), 7.21 (d, J=8.1 Hz, 1H), 6.56 (d, J=3.4 Hz, 1H), 4.46-4.28 (m, 1H), 3.82 (s, 3H), 3.37 (s, 3H), 3.29-3.04 (m, 2H), 1.97-1.70 (m, 4H).

Step d. To a solution of (2S)—N-methyl-N-(1-methylpyrrolo[2,3-b]pyridin-6-yl)pyrrolidine-2-carboxamide hydrochloride (168 mg, 0.57 mmol, assuming quantitative yield from step c) and 2-chloro-6-methyl-4-(trifluoromethyl)nicotinonitrile (0.15 g, 0.684 mmol) in DMF (5 mL) was added DIPEA (0.4 mL, 2.28 mmol). The reaction mixture was heated to 100° C. for 75 min. Upon completion, the reaction mixture was quenched with sat. aq. NaHCO₃ and extracted with EtOAc (×3). The combined organics were washed with brine, dried over Na₂SO₄ and concentrated under vacuum to a dark red gum. The crude product was purified by column chromatography (0-6% MeOH in DCM) and further purified by column chromatography (0-80% EtOAc in cyclohexane) to provide the title compound (120 mg, 47%) as a pink foam.

m/z ES+[M+H]+ 443.2; ¹H NMR (400 MHz, CD₃OD) δ ppm 8.08 (d, J=8.1 Hz, 1H), 7.43 (d, J=3.5 Hz, 1H), 7.27 (d, J=8.1 Hz, 1H), 6.90 (s, 1H), 6.53 (d, J=3.5 Hz, 1H), 4.70-4.56 (m, 1H), 4.15-4.04 (m, 1H), 4.04-3.93 (m, 1H), 3.88 (s, 3H), 3.38 (s, 3H), 2.54 (s, 3H), 2.35-2.16 (m, 3H), 2.00-1.87 (m, 1H).

Example 244

(S)—N-(4-Chloro-1-methyl-pyrrolo[2,3-b]pyridin-6-yl)-1-[3-cyano-6-methyl-4-(trifluoromethyl)-2-pyridyl]-N-methyl-pyrrolidine-2-carboxamide

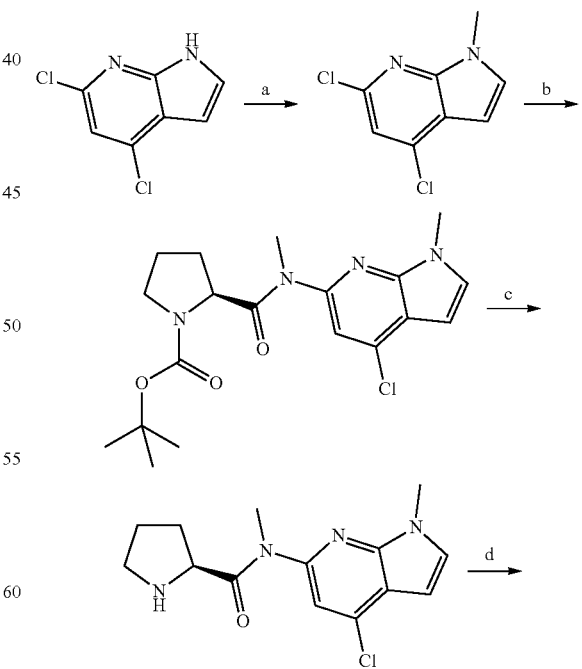

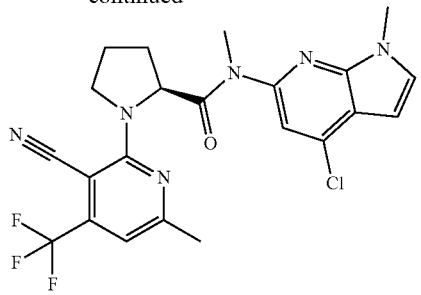

Step a. To a mixture of 4,6-dichloro-1 h-pyrrolo[2,3-b]pyridine (250 mg, 1.34 mmol) and Cs$_2$CO$_3$ (460 mg, 1.40 mmol) in DMF (3 mL) was added dimethyl sulfate (0.15 mL, 1.60 mmol) and the reaction was stirred at rt for 18 h. Water was added to the mixture and the precipitated solid was collected by filtration, washing with water to give 4,6-dichloro-1-methyl-pyrrolo[2,3-b]pyridine (178 mg, 66%).

m/z ES+[M+H]$^+$ 200.95; $^1$H NMR (400 MHz, CDCl$_3$) δ ppm 7.21 (s, 1H), 7.15 (s, 1H), 6.56 (s, 1H), 3.89 (s, 3H).

Step b. Conducted under strictly anhydrous conditions, the reaction flask was evacuated and then backfilled with N$_2$ 3 times after each addition of catalyst and ligand. A mixture of 4,6-dichloro-1-methyl-pyrrolo[2,3-b]pyridine (175 mg, 0.87 mmol), tert-butyl (2S)-2-(methylcarbamoyl)pyrrolidine-1-carboxylate (198 mg, 0.87 mmol), dppf (43 mg, 0.08 mmol) and potassium phosphate tribasic (370 mg, 1.74 mmol) in 1,4-dioxane (1.75 mL) was treated with palladium acetate (6 mg, 0.03 mmol) and heated to 90° C. for 18 h. The mixture was cooled to rt and further dppf (43 mg, 0.08 mmol) and palladium acetate (6 mg, 0.03 mmol) were added and then heating was continued at 90° C. After 36 h the mixture was cooled to rt and further dppf (43 mg, 0.08 mmol), palladium acetate (6 mg, 0.03 mmol), potassium phosphate tribasic (370 mg, 1.74 mmol), tert-butyl (2S)-2-(methylcarbamoyl)pyrrolidine-1-carboxylate (100 mg, 0.44 mmol) and 1,4-dioxane (1.5 mL) was added and the mixture was heated to reflux for 6 h. The mixture was filtered through celite and purified by column chromatography (25-75% EtOAc in cyclohexane) to give tert-butyl (2S)-2-[(4-chloro-1-methyl-pyrrolo[2,3-b]pyridin-6-yl)-methyl-carbamoyl]pyrrolidine-1-carboxylate (121 mg, 35%).

m/z ES+[M+H]$^+$ 393.14; $^1$H NMR (400 MHz, DMSO-d6) δ ppm 7.73-7.65 (m, 1H), 7.42-7.20 (m, 1H), 6.62-6.52 (m, 1H), 4.34-4.02 (m, 1H), 3.82 (s, 3H), 3.42-3.37 (m, 1H), 3.33-3.23 (m, 4H), 2.24-2.02 (m, 2H), 1.96-1.80 (m, 1H), 1.80-1.65 (m, 1H), 1.38-1.32 (m, 9H).

Step c. 4M HCl in dioxane (3.0 mL, 12.0 mmol) was added to tert-butyl (2S)-2-[(4-chloro-1-methyl-pyrrolo[2,3-b]pyridin-6-yl)-methyl-carbamoyl]pyrrolidine-1-carboxylate (121 mg, 0.31 mmol) and the mixture was stirred for 1 h then evaporated to give (2S)—N-(4-chloro-1-methyl-pyrrolo[2,3-b]pyridin-6-yl)-N-methyl-pyrrolidine-2-carboxamide as an oil (107 mg, crude). m/z m/z ES+[M+H]$^+$ 293.10

Step d. A solution of (2S)—N-(4-chloro-1-methyl-pyrrolo[2,3-b]pyridin-6-yl)-N-methyl-pyrrolidine-2-carboxamide (107 mg, crude) in NMP (0.6 mL) was treated with 2-chloro-6-methyl-4-(trifluoromethyl)nicotinonitrile (90 mg, 0.37 mmol) and DIPEA (0.3 mL, 1.85 mmol). The mixture was heated to 100° C. for 2 h and then cooled to rt. The mixture was partitioned between EtOAc and sat. aq. NaHCO$_3$ and the layers were separated. The aqueous was reextracted with EtOAc and the combined organics were washed with brine, dried over Na$_2$SO$_4$ and the mixture was evaporated under vacuum to give a crude residue (230 mg). The mixture was purified by column chromatography (10-50% EtOAc in cyclohexane) to give the title compound (101 mg, 69%).

m/z ES+[M+H]$^+$ 477.11; $^1$H NMR (400 MHz, CDCl$_3$) δ ppm 7.31-7.29 (m, 1H), 7.27 (s, 1H), 6.73 (s, 1H), 6.61 (d, J=3.5 Hz, 1H), 4.84-4.63 (m, 1H), 4.28-4.15 (m, 1H), 4.12-4.03 (m, 1H), 3.90 (s, 3H), 3.43 (s, 3H), 2.50 (s, 3H), 2.41-2.28 (m, 2H), 2.24-2.11 (m, 1H), 2.03-1.94 (m, 1H).

Example 245

(S)-1-(3-Cyano-6-methyl-4-(trifluoromethyl)pyridin-2-yl)-N-methyl-N-(4-methyl-3,4-dihydro-2H-pyrido[3,2-b][1,4]oxazin-6-yl)pyrrolidine-2-carboxamide

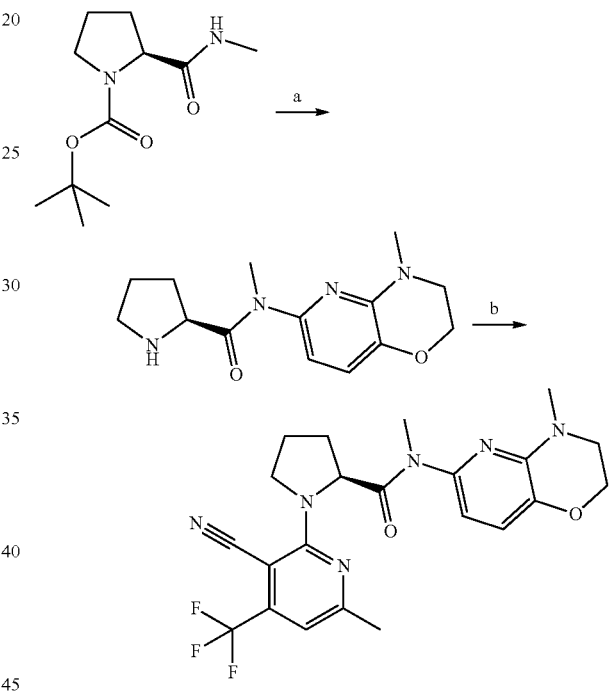

Step a. To a degassed solution of 6-bromo-4-methyl-2,3-dihydropyrido[3,2-b][1,4]oxazine (100 mg, 0.44 mmol), (S)-tert-butyl 2-(methylcarbamoyl)pyrrolidine-1-carboxylate (100 mg, 0.44 mmol) and Cs$_2$CO$_3$ (284 mg, 0.87 mmol) in 1,4-dioxane (2 mL) was added Pd$_2$(dba)$_3$ (40 mg, 0.044 mmol) and xantphos (38 mg, 0.065 mmol). The vessel was sealed under N$_2$ and heated to 85° C. for 18 h. The reaction mixture was filtered through a plug of celite before the filtrate was diluted with water (30 mL). The mixture was extracted with EtOAc (3×30 mL), the combined organics were dried over Na$_2$SO$_4$ and concentrated under vacuum and purified by column chromatography (0-100% EtOAc in PE) to give tert-butyl (2S)-2-[methyl-(4-methyl-2,3-dihydropyrido[3,2-b][1,4]oxazin-6-yl)-carbamoyl]pyrrolidine-1-carboxylate (68 mg, 41%) as a colourless film.

m/z ES+[M+H]$^+$ 377.24; $^1$H NMR (400 MHz, CDCl$_3$) δ ppm 6.94 (d, J=7.9 Hz, 1H), 6.70-6.23 (m, 1H), 4.58-4.20 (m, 3H), 3.70-3.32 (m, 3H), 3.28 (s, 3H), 3.09 (s, 3H), 2.23-1.66 (m, 4H), 1.46-1.43 (m, 9H).

Step b. tert-Butyl (2S)-2-[methyl-(4-methyl-2,3-dihydropyrido[3,2-b][1,4]oxazin-6-yl)-carbamoyl]pyrrolidine-1- carboxylate (68 mg, 0.18 mmol) was dissolved in 4 M HCl in 1,4-dioxane (2 mL, 219 mmol) and stirred at rt for 2 h. The reaction mixture was concentrated under vacuum affording (2S)—N-methyl-N-(4-methyl-2,3-dihydropyrido[3,2-b][1,4]oxazin-6-yl)pyrrolidine-2-carboxamide hydrochloride (56 mg, 100%) as a yellow film.

m/z ES+[M+H]$^+$ 277.17; $^1$H NMR (400 MHz, DMSO-d6) δ ppm 9.51 (s, 1H), 8.54 (s, 1H), 7.07 (d, J=7.9 Hz, 1H), 6.56 (d, J=8.0 Hz, 1H), 4.39 (s, 1H), 4.24 (t, J=4.5 Hz, 2H), 3.48 (t, J=4.6 Hz, 2H), 3.30-3.07 (m, 5H), 3.01 (s, 3H), 1.81 (s, 4H).

Step c. To a stirred solution of 2-chloro-6-methyl-4-(trifluoromethyl)nicotinonitrile (44 mg, 0.2 mmol) in DMF (2 mL) was added DIPEA (0.09 mL, 0.54 mmol) and (2S)—N-methyl-N-(4-methyl-2,3-dihydropyrido[3,2-b][1,4]oxazin-6-yl)pyrrolidine-2-carboxamide hydrochloride (56 mg, 0.18 mmol). The reaction mixture was heated to 65° C. for 18 h. Upon completion, the reaction mixture was cooled to rt and diluted with water (30 mL). The mixture was extracted with EtOAc (3×40 mL) and the combined organics were dried over Na$_2$SO$_4$ and evaporated. The obtained residue was purified by prep-HPLC to give the title compound (51 mg, 61%) as a tan powder.

m/z ES+[M+H]$^+$ 461.19; $^1$H NMR (400 MHz, DMSO-d6) δ ppm 7.09-6.96 (m, 2H), 6.57 (d, J=7.9 Hz, 1H), 4.68 (s, 1H), 4.29-4.15 (m, 2H), 3.97-3.84 (m, 2H), 3.46 (t, J=4.5 Hz, 2H), 3.13 (s, 3H), 3.03 (s, 3H), 2.44 (s, 3H), 2.22-1.85 (m, 4H).

Biological Data

Polθ Full Length Enzyme Potency Assay

PicoGreen assay was used to measure the ability of compounds to inhibit the activity of Polθ in vitro. N-His, C-term FLAG tagged Polθ protein (amino acids 2-2590) expressed in baculovirus was purified and stored at −80° C. in aliquots. Assay measurements were performed with 1× buffer comprising 25 mM Tris HCl pH 7.5, 12.5 mM NaCl, 0.5 mM MgCl2, 5% glycerol, 0.01% Triton X-100, 0.01% BGG and 1 mM DTT. Test compounds were prepared by dilution in 100% DMSO to give the correct dose range for 12 point concentration response and appropriate volume (60 nL) dispensed into 384 well micro assay plates (Perkin Elmer low volume black ProxiPlates™ product code 6008269) using a Labcyte Echo 550 acoustic liquid dispenser. DMSO concentration was maintained at 1% by back filling with DMSO solution. 3 μL purified recombinant Polθ and primer (5'-GCG GCT GTC ATA AG-3' (SEQ ID NO: 1)): template (5'-GCT ACA TTG ACA ATG GCA TCA AAT CTC AGA TTG CGT CTT ATG ACA GCC GCG-3' (SEQ ID NO: 2)) duplex (1:1.1) was diluted in assay buffer to a 2× working concentration (4 nM Polθ and 100 nM PTD). This was dispensed into each well of the compound plate using a VIAFLO 16 channel manual pipette (Integra) and pre-incubated at rt for 30 min. 3 μL of 2× working solution of dNTPs (40 μM) (dATP, dCTP, dGTP, dTTP; Sigma D6500, D4635, D4010, T0251) diluted in assay buffer was then added and the reaction incubated for 60 min at rt. The reaction was stopped by addition of 10 mM EDTA, 25 mM Tris pH 7.5 and 1:200 dilution of PicoGreen dye (Invitrogen P7581). After 90 minutes at rt in the dark, fluorescence was read on a BMG Pherastar FS plate reader using 485/520 nm module and raw data analysed using IDBS Activity Base to generate IC$_{50}$ values. The compounds of Examples 1 to 245 were tested in the above mentioned enzyme potency assay and the results are shown in the following table:

| Example Number | Polθ IC$_{50}$ (nM) |
| --- | --- |
| 1 | 72 |
| 2 | 9 |
| 3 | 16 |
| 4 | 288 |
| 5 | 16 |
| 6 | 11 |
| 7 | 438 |
| 8 | 180 |
| 9 | 87 |
| 10 | 316 |
| 11 | 452 |
| 12 | 710 |
| 13 | 180 |
| 14 | 415 |
| 15 | 57 |
| 16 | 274 |
| 17 | 97 |
| 18 | 33 |
| 19 | 524 |
| 20 | 67 |
| 21 | 77 |
| 22 | 27 |
| 23 | 137 |
| 24 | 9 |
| 25 | 32 |
| 26 | 61 |
| 27 | 12 |
| 28 | 48 |
| 29 | 172 |
| 30 | 514 |
| 31 | 395 |
| 32 | 209 |
| 33 | 30 |
| 34 | 969 |
| 35 | 620 |
| 36 | 48 |
| 37 | 248 |
| 38 | 273 |
| 39 | 27 |
| 40 | 1758 |
| 41 | 263 |
| 42 | 25 |
| 43 | 221 |
| 44 | 88 |
| 45 | 85 |
| 46 | 227 |
| 47 | 329 |
| 48 | 573 |
| 49 | 573 |
| 50 | 232 |
| 51 | 1560 |
| 52 | 588 |
| 53 | 121 |
| 54 | 13 |
| 55 | 118 |
| 56 | 42 |
| 57 | 10 |
| 58 | 7 |
| 59 | 7 |
| 60 | 76 |
| 61 | 136 |
| 62 | 208 |
| 63 | 410 |
| 64 | 166 |
| 65 | 8 |
| 66 | 20 |
| 67 | 6 |
| 68 | 31 |
| 69 | 69 |
| 70 | 4 |
| 71 | 10 |
| 72 | 32 |
| 73 | 7 |
| 74 | 25 |
| 75 | 95 |
| 76 | 24 |
| 77 | 11 |
| 78 | 48 |

| Example Number | Polθ IC$_{50}$ (nM) |
|---|---|
| 79 | 90 |
| 80 | 6 |
| 81 | 8 |
| 82 | 8 |
| 83 | 16 |
| 84 | 6 |
| 85 | 5 |
| 86 | 9 |
| 87 | 15 |
| 88 | 6 |
| 89 | 16 |
| 90 | 226 |
| 91 | 81 |
| 92 | 18 |
| 93 | 16 |
| 94 | 12 |
| 95 | 15 |
| 96 | 24 |
| 97 | 11 |
| 98 | 32 |
| 99 | 437 |
| 100 | 4 |
| 101 | 23 |
| 102 | 86 |
| 103 | 54 |
| 104 | 35 |
| 105 | 19 |
| 106 | 324 |
| 107 | 18 |
| 108 | 12 |
| 109 | 49 |
| 110 | 21 |
| 111 | 18 |
| 112 | 11 |
| 113 | 21 |
| 114 | 46 |
| 115 | 54 |
| 116 | 71 |
| 117 | 61 |
| 118 | 25 |
| 119 | 39 |
| 120 | 94 |
| 121 | 167 |
| 122 | 41 |
| 123 | 36 |
| 124 | 304 |
| 125 | 261 |
| 126 | 11 |
| 127 | 15 |
| 128 | 42 |
| 129 | 78 |
| 130 | 100 |
| 131 | 248 |
| 132 | 156 |
| 133 | 122 |
| 134 | 124 |
| 135 | 223 |
| 136 | 45 |
| 137 | 300 |
| 138 | 165 |
| 139 | 164 |
| 140 | 60 |
| 141 | 56 |
| 142 | 160 |
| 143 | 409 |
| 144 | 1312 |
| 145 | 708 |
| 146 | 163 |
| 147 | 28 |
| 148 | 6 |
| 149 | 5 |
| 150 | 11 |
| 151 | 23 |
| 152 | 26 |
| 153 | 104 |
| 154 | 15 |
| 155 | 15 |
| 156 | 4 |
| 157 | 32 |
| 158 | 2 |
| 159 | 178 |
| 160 | 6 |
| 161 | 12 |
| 162 | 3 |
| 163 | 11 |
| 164 | 21 |
| 165 | 20 |
| 166 | 7 |
| 167 | 56 |
| 168 | 71 |
| 169 | 106 |
| 170 | 193 |
| 171 | 68 |
| 172 | 20 |
| 173 | 13 |
| 174 | 158 |
| 175 | 519 |
| 176 | 94 |
| 177 | 109 |
| 178 | 833 |
| 179 | 15 |
| 180 | 9 |
| 181 | 45 |
| 182 | 61 |
| 183 | 24 |
| 184 | 13 |
| 185 | 10 |
| 186 | 9 |
| 187 | 22 |
| 188 | 18 |
| 189 | 32 |
| 190 | 13 |
| 191 | 12 |
| 192 | 9 |
| 193 | 6 |
| 194 | 7 |
| 195 | 4 |
| 196 | 24 |
| 197 | 19 |
| 198 | 28 |
| 199 | 32 |
| 200 | 12 |
| 201 | 26 |
| 202 | 7 |
| 203 | 10 |
| 204 | 3 |
| 205 | 6 |
| 206 | 15 |
| 207 | 7 |
| 208 | 9 |
| 209 | 8 |
| 210 | 7 |
| 211 | 5 |
| 212 | 6 |
| 213 | 26 |
| 214 | 11 |
| 215 | 8 |
| 216 | 4 |
| 217 | 7 |
| 218 | 16 |
| 219 | 11 |
| 220 | 11 |
| 221 | 11 |
| 222 | 9 |
| 223 | 8 |
| 224 | 6 |
| 225 | 17 |
| 226 | 19 |
| 227 | 6 |
| 228 | 62 |
| 229 | 15 |
| 230 | 16 |

-continued

| Example Number | Pol⊖ IC$_{50}$ (nM) |
|---|---|
| 231 | 94 |
| 232 | 15 |
| 233 | 3 |
| 234 | 5 |
| 235 | 27 |
| 236 | 14 |
| 237 | 37 |
| 238 | 28 |
| 239 | 6 |
| 240 | 7 |
| 241 | 240 |
| 242 | 311 |
| 243 | 39 |
| 244 | 130 |
| 245 | 74 |

The invention claimed is:

1. A compound of formula (I):

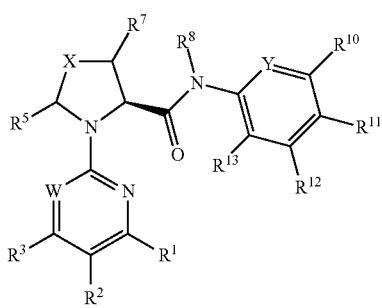

(I)

or a tautomeric or a stereochemically isomeric form, a pharmaceutically acceptable salt or a solvate thereof, wherein:

W represents =C(R$^4$)— or =N—;

R$^1$, R$^2$, R$^3$ and R$^4$ independently represent hydrogen, C$_{1-6}$ alkyl, C$_{2-6}$ alkenyl, C$_{1-6}$ alkoxy, halogen, haloC$_{1-6}$ alkyl, haloC$_{1-6}$ alkoxy, C$_{3-8}$ cycloalkyl, cyano or —NR$^x$R$^y$;

X represents —C(H)(R$^6$)—, —N(R$^{14}$)— or —O—;

R$^5$ represents hydrogen, —CH$_2$—R$^z$ or oxo, such that when X represents —N(R$^{14}$)— or —O—, R$^5$ represents oxo;

R$^6$ represents hydrogen, —OR$^{15a}$, cyano, C$_{1-6}$ alkyl, haloC$_{1-6}$ alkyl, C$_{1-6}$ alkoxy, C$_{1-6}$ alkanol, C$_{3-8}$ cycloalkyl, halogen, —NR$^v$R$^w$, —CH$_2$—NR$^v$R$^w$, —Z-aryl or heterocyclyl, wherein said aryl or heterocyclyl groups may be optionally substituted by one or more oxo, hydroxy, C$_{1-6}$ alkanol, —COC$_{1-6}$ alkyl or —COOC$_{1-6}$ alkyl groups;

Z represents a bond or C$_{1-6}$ alkylenyl optionally substituted with an oxygen atom;

R$^7$ represents hydrogen, —CH$_2$—R$^z$ or —OR$^{15b}$, such that when X represents —N(H)— or —O—, R$^7$ represents hydrogen;

R$^8$ represents C$_{1-6}$ alkyl, haloC$_{1-6}$ alkyl or C$_{3-8}$ cycloalkyl;

Y represents —C(R$^9$)= or —N=;

R$^9$, R$^{10}$, R$^{11}$, R$^{12}$ and R$^{13}$ independently represent hydrogen, C$_{1-6}$ alkyl, C$_{2-6}$ alkenyl, hydroxy, C$_{1-6}$ alkoxy, C$_{3-8}$ cycloalkyl, halogen or haloC$_{1-6}$ alkyl or two adjacent groups of said R$^9$, R$^{10}$, R$^{11}$, R$^{12}$ and R$^{13}$ groups may join to form a 5 to 7 membered saturated or unsaturated ring optionally containing one or more heteroatoms selected from O, N or S;

R$^{14}$ represents hydrogen, C$_{1-6}$ alkyl, C$_{1-6}$ alkanol or —SO$_2$—C$_{1-6}$ alkyl;

R$^{15a}$ and R$^{15b}$ independently represent hydrogen or R$^{15a}$ and R$^{15b}$ join together to form a 5 to 7 membered saturated ring system which may be optionally substituted by one or more C$_{1-6}$ alkyl groups;

R$^v$, R$^w$, R$^x$ and R$^y$ independently represent hydrogen, C$_{1-6}$ alkyl, haloC$_{1-6}$ alkyl, C$_{3-8}$ cycloalkyl, —COC$_{1-6}$ alkyl or heterocyclyl, wherein said alkyl groups may be optionally substituted with one or more hydroxy, amino or sulfone groups and said heterocyclyl ring may be optionally substituted by one or more oxo, hydroxy, $C_{1-6}$ alkanol or —$COC_{1-6}$ alkyl groups; and $R^z$ represents $C_{1-6}$ alkyl, hydroxy, $C_{1-6}$ alkoxy or $C_{1-6}$ alkanol.

2. The compound as defined in claim 1, which is a compound of formula $(I)^a$

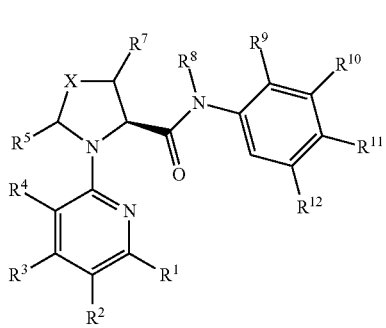

wherein $R^1$, $R^2$, $R^3$, $R^4$, $R^5$, X, $R^7$, $R^8$, $R^9$, $R^{10}$, $R^{11}$ and $R^{12}$ are as defined in claim 1; or a compound of formula $(I)^b$:

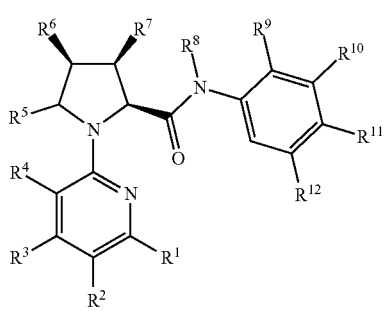

wherein $R^1$, $R^2$, $R^3$, $R^4$, $R^5$, $R^6$, $R^7$, $R^8$, $R^9$, $R^{10}$, $R^{11}$ and $R^{12}$ are as defined in claim 1.

3. The compound as defined in claim 1, wherein:
$R^x$ and $R^y$ represent $C_{1-6}$ alkyl; or
$R^x$ and $R^y$ both represent $C_{1-6}$ alkyl; or
$R^x$ and $R^y$ both represent methyl or one represents methyl and the other represents ethyl.

4. The compound as defined in claim 1, wherein W represents =$C(R^4)$— and:
$R^1$ represents $C_{1-6}$ alkyl, $R^2$ represents hydrogen, $R^3$ represents halo$C_{1-6}$ alkyl and $R^4$ represents cyano; or
$R^1$ represents $C_{1-6}$ alkyl, $R^2$ represents hydrogen, $R^3$ represents $C_{1-6}$ alkyl and $R^4$ represents cyano; or
$R^1$ represents $C_{1-6}$ alkyl, $R^2$ represents hydrogen, $R^3$ represents halo$C_{1-6}$ alkyl and $R^4$ represents hydrogen; or
$R^1$ represents $C_{1-6}$ alkyl, $R^2$ represents hydrogen, $R^3$ represents $C_{1-6}$ alkyl and $R^4$ represents hydrogen; or
$R^1$ represents $C_{1-6}$ alkyl, $R^2$ represents halogen, $R^3$ represents $C_{1-6}$ alkyl and $R^4$ represents hydrogen; or
$R^1$ represents $C_{1-6}$ alkoxy, $R^2$ represents hydrogen, $R^3$ represents halo$C_{1-6}$ alkyl and $R^4$ represents cyano; or
$R^1$ represents —$NR^xR^y$, $R^2$ represents hydrogen, $R^3$ represents halo$C_{1-6}$ alkyl and $R^4$ represents cyano; or
$R^1$ represents hydrogen, $R^2$ represents hydrogen, $R^3$ represents halo$C_{1-6}$ alkyl and $R^4$ represents cyano; or
$R^1$ represents hydrogen, $R^2$ represents $C_{1-6}$ alkyl, $R^3$ represents $C_{1-6}$ alkyl and $R^4$ represents hydrogen; or
$R^1$ represents halogen, $R^2$ represents hydrogen, $R^3$ represents halo$C_{1-6}$ alkyl and $R^4$ represents hydrogen; or
$R^1$ represents halogen, $R^2$ represents hydrogen, $R^3$ represents halo$C_{1-6}$ alkoxy and $R^4$ represents hydrogen; or
$R^1$ represents $C_{2-6}$ alkenyl, $R^2$ represents hydrogen, $R^3$ represents halo$C_{1-6}$ alkyl and $R^4$ represents hydrogen; or
$R^1$ represents $C_{1-6}$ alkyl, $R^2$ represents hydrogen, $R^3$ represents halo$C_{1-6}$ alkoxy and $R^4$ represents hydrogen; or
$R^1$ represents $C_{1-6}$ alkyl, $R^2$ represents hydrogen, $R^3$ represents $C_{2-6}$ alkenyl and $R^4$ represents hydrogen; or
$R^1$ represents $C_{1-6}$ alkyl, $R^2$ represents hydrogen, $R^3$ represents halogen and $R^4$ represents hydrogen.

5. The compound as defined in claim 1, wherein W represents =N— and:
$R^1$ represents $C_{1-6}$ alkyl, $R^2$ represents hydrogen and $R^3$ represents halo$C_{1-6}$ alkyl.

6. The compound as defined in claim 1, wherein X represents —$C(H)(R^6)$— and:
$R^5$, $R^6$ and $R^7$ each represent hydrogen; or
$R^5$ and $R^7$ both represent hydrogen and $R^6$ represents —$OR^{15a}$; or
$R^5$ and $R^6$ both represent hydrogen and $R^7$ represents —$OR^{15b}$; or
$R^5$ and $R^7$ both represent hydrogen and $R^6$ represents halogen; or
$R^5$ and $R^7$ both represent hydrogen and $R^6$ represents $C_{1-6}$ alkoxy; or
$R^5$ and $R^7$ both represent hydrogen and $R^6$ represents —$NR^vR^w$; or
$R^5$ and $R^7$ both represent hydrogen and $R^6$ represents heterocyclyl; or
$R^5$ represents hydrogen, $R^6$ represents —$OR^{15a}$ and $R^7$ represents —$OR^{15b}$; or
$R^5$ represents oxo and $R^6$ and $R^7$ both represent hydrogen; or
$R^5$ represents oxo, $R^6$ represents —$NR^vR^w$ and $R^7$ represents hydrogen; or
$R^5$ represents oxo, $R^6$ represents heterocyclyl and $R^7$ represents hydrogen; or
$R^5$ represents oxo, $R^6$ represents —$OR^{15a}$ and $R^7$ represents —$OR^{15b}$; or
$R^5$ represents oxo, $R^6$ represents —$OR^{15a}$ and $R^7$ represents hydrogen; or
$R^5$ represents oxo, $R^6$ represents —Z-aryl and $R^7$ represents hydrogen; or
$R^5$ represents oxo, $R^6$ represents $C_{1-6}$ alkanol and $R^7$ represents hydrogen; or
$R^5$ represents oxo, $R^6$ represents hydrogen and $R^7$ represents —$OR^{15b}$; or
$R^5$ represents oxo, $R^6$ represents —$CH_2$—$NR^vR^w$ and $R^7$ represents hydrogen; or
$R^5$ represents oxo, $R^6$ represents —$OR^{15a}$ and $R^7$ represents —$OR^{15b}$ wherein $R^{15a}$ and $R^{15b}$ join together to form a 5 to 7 membered saturated ring system which may be optionally substituted by one or more $C_{1-6}$ alkyl groups.

7. The compound as defined in claim 1, wherein X represents —O— and:
$R^5$ represents oxo and $R^7$ represent hydrogen.

8. The compound as defined in claim 1, wherein X represents —$N(R^{14})$— and:
$R^5$ represents oxo and $R^7$ and $R^{14}$ both represent hydrogen; or $R^5$ represents oxo, $R^7$ represents hydrogen and $R^{14}$ represents $C_{1-6}$ alkanol; or $R^5$ represents oxo, $R^7$ represents hydrogen and $R^{14}$ represents —$SO_2$—$C_{1-6}$ alkyl.

9. The compound as defined in claim 1, wherein:

$R^v$ and $R^w$ represent hydrogen, $C_{1-6}$ alkyl, —$COC_{1-6}$ alkyl, $C_{3-8}$ cycloalkyl or heterocyclyl, wherein said alkyl groups may be optionally substituted with one or more hydroxy, amino or sulfone groups and said heterocyclyl ring may be optionally substituted by one or more oxo or —$COC_{1-6}$ alkyl groups; or $R^v$ and $R^w$ both represent hydrogen or $C_{1-6}$ alkyl or one represents hydrogen and the other represents $C_{1-6}$ alkyl or one represents hydrogen or $C_{1-6}$ alkyl and the other represents —$COC_{1-6}$ alkyl, $C_{3-8}$ cycloalkyl or heterocyclyl, wherein said alkyl groups may be optionally substituted with one or more hydroxy, amino or sulfone groups and said heterocyclyl ring may be optionally substituted by one or more oxo or —$COC_{1-6}$ alkyl groups.

10. The compound as defined in claim 1, wherein $R^8$ represents $C_{1-6}$ alkyl or $C_{3-8}$ cycloalkyl.

11. The compound as defined in claim 1, wherein Y represents —$C(R^9)$= and:

each of $R^9$, $R^{10}$, $R^{11}$, $R^{12}$ and $R^{13}$ represent hydrogen; or each of $R^9$, $R^{10}$, $R^{11}$ and $R^{13}$ represent hydrogen and $R^{12}$ represents $C_{1-6}$ alkyl; or each of $R^9$, $R^{10}$ and $R^{13}$ represent hydrogen and $R^{11}$ and $R^{12}$ both represent halogen; or each of $R^9$, $R^{10}$ and $R^{13}$ represent hydrogen, $R^{11}$ represents halogen and $R^{12}$ represents $C_{1-6}$ alkyl; or each of $R^9$, $R^{10}$ and $R^{13}$ represent hydrogen, $R^{11}$ represents halogen and $R^{12}$ represents $haloC_{1-6}$ alkyl; or each of $R^9$, $R^{10}$, $R^{11}$ and $R^{13}$ represent hydrogen and $R^{12}$ represents $haloC_{1-6}$ alkyl; or each of $R^9$, $R^{10}$, $R^{11}$ and $R^{13}$ represent hydrogen and $R^{12}$ represents halogen; or each of $R^9$, $R^{10}$ and $R^{13}$ represent hydrogen, $R^{11}$ represents halogen and $R^{12}$ represents $C_{1-6}$ alkoxy; or each of $R^9$, $R^{11}$ and $R^{13}$ represent hydrogen and $R^{10}$ and $R^{12}$ both represent halogen; or each of $R^9$, $R^{10}$ and $R^{13}$ represent hydrogen, $R^{11}$ represents $haloC_{1-6}$ alkyl and $R^{12}$ represents halogen; or each of $R^9$, $R^{11}$, $R^{12}$ and $R^{13}$ represent hydrogen and $R^{10}$ represents $C_{1-6}$ alkyl; or each of $R^9$, $R^{11}$, $R^{12}$ and $R^{13}$ represent hydrogen and $R^{10}$ represents halogen; or each of $R^9$, $R^{12}$ and $R^{13}$ represent hydrogen and $R^{10}$ and $R^{11}$ both represent halogen; or each of $R^9$, $R^{10}$ and $R^{13}$ represent hydrogen, $R^{11}$ represents $C_{1-6}$ alkyl and $R^{12}$ represents halogen; or each of $R^9$, $R^{12}$ and $R^{13}$ represent hydrogen, $R^{10}$ represents $C_{1-6}$ alkyl and $R^1$ represents halogen; or each of $R^9$, $R^{12}$ and $R^{13}$ represent hydrogen, $R^{10}$ represents $C_{1-6}$ alkoxy and $R^{11}$ represents halogen; or each of $R^9$, $R^{12}$ and $R^{13}$ represent hydrogen, $R^{10}$ represents $C_{1-6}$ alkoxy and $R^{11}$ represents $C_{1-6}$ alkyl; or each of $R^9$, $R^{12}$ and $R^{13}$ represent hydrogen, $R^{10}$ represents halogen and $R^1$ represents $C_{1-6}$ alkyl; or both of $R^{12}$ and $R^{13}$ represent hydrogen, both of $R^9$ and $R^{11}$ represent halogen and $R^{10}$ represents $C_{1-6}$ alkyl; or each of $R^{10}$, $R^{12}$ and $R^{13}$ represent hydrogen and both of $R^9$ and $R^{11}$ represent halogen; or both of $R^9$ and $R^{12}$ represent hydrogen and each of $R^{10}$, $R^1$ and $R^{13}$ represent halogen; or each of $R^{11}$, $R^{12}$ and $R^{13}$ represent hydrogen and both of $R^9$ and $R^{10}$ represent halogen; or each of $R^9$, $R^{12}$ and $R^{13}$ represent hydrogen, $R^{10}$ represents hydroxy and $R^{11}$ represents halogen; or each of $R^9$, $R^{12}$ and $R^{13}$ represent hydrogen, $R^{10}$ represents $C_{2-6}$ alkenyl and $R^{11}$ represents halogen; or each of $R^9$, $R^{12}$ and $R^{13}$ represent hydrogen, $R^{10}$ represents hydroxy and $R^{11}$ represents $C_{1-6}$ alkyl; or each of $R^{10}$, $R^{11}$ and $R^{13}$ represent hydrogen and both of $R^9$ and $R^{12}$ represent halogen; or both of $R^{10}$ and $R^{13}$ represent hydrogen, both of $R^{11}$ and $R^{12}$ represent halogen and $R^9$ represents $C_{1-6}$ alkoxy; or both of $R^{12}$ and $R^{13}$ represent hydrogen and each of $R^9$, $R^{10}$ and $R^1$ represent halogen; or both of $R^{12}$ and $R^{13}$ represent hydrogen, both of $R^9$ and $R^{11}$ represent halogen and $R^{10}$ represents $C_{2-6}$ alkenyl; or each of $R^9$, $R^{12}$ and $R^{13}$ represent hydrogen and $R^{10}$ and $R^{11}$ join to form a pyrrolinyl or tetrahydropyranyl ring; or both of $R^{10}$ and $R^{13}$ represent hydrogen and each of $R^9$, $R^{11}$ and $R^{12}$ represent halogen.

12. The compound as defined in claim 1, wherein Y represents —N= and:

$R^{11}$ and $R^{13}$ both represent hydrogen, $R^{10}$ represents $C_{1-6}$ alkyl and $R^{12}$ represents $haloC_{1-6}$ alkyl; or $R^{10}$ and $R^{11}$ join to form a pyrrolinyl ring and $R^{12}$ and $R^{13}$ both represent hydrogen.

13. A pharmaceutical composition comprising a compound of formula (I) as defined in claim 1.

14. A pharmaceutical composition comprising a compound of formula (I) as defined in claim 1, in combination with one or more therapeutic agents.

15. A method for the treatment of cancer mediated by Polθ, the method comprising administering a compound as defined in claim 1 to an animal.

16. A process for preparing a compound of formula (I) as herein defined in claim 1 which comprises:

(a) reacting a compound of formula (II):

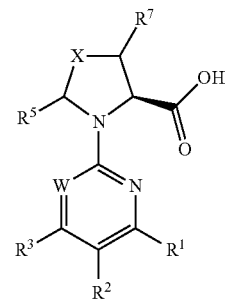

(II)

wherein $R^1$, $R^2$, $R^3$, W, $R_5$, X and $R^7$ are as defined in claim 1, with a compound of formula (III):

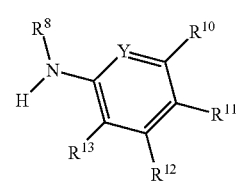

(III)

wherein $R^8$, Y, $R^{10}$, $R^{11}$, $R^{12}$ and $R^{13}$ are as defined in claim 1; or (b) reacting a compound of formula (IV):

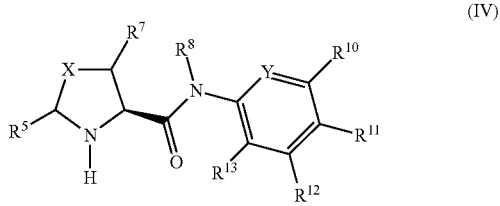

(IV)

wherein R⁵, X, R⁷, R⁸, Y, R¹⁰, R¹¹, R¹² and R¹³ are as defined in claim 1, with a compound of formula (V):

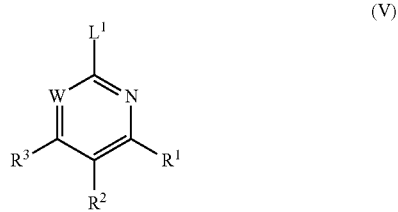

(V)

wherein R¹, R², R³ and W are as defined in claim 1 and L¹ represents a suitable leaving group;
(c) deprotection of a protected derivative of a compound of formula (I);
(d) interconversion of a compound of formula (I) or protected derivative thereof to a further compound of formula (I) or protected derivative thereof; and
(e) optional formation of a pharmaceutically acceptable salt of a compound of formula (I).

17. A compound selected from
(S)-1-(3-Cyano-6-methyl-4-(trifluoromethyl)pyridin-2-yl)-N-methyl-N-phenylpyrrolidine-2-carboxamide;
(S)-1-(3-Cyano-6-methyl-4-(trifluoromethyl)pyridin-2-yl)-N-isopropyl-N-(m-tolyl)pyrrolidine-2-carboxamide;
(2S,4S)-1-(3-Cyano-6-methyl-4-(trifluoromethyl)pyridin-2-yl)-4-hydroxy-N-methyl-N-(m-tolyl)pyrrolidine-2-carboxamide;
(2S,4S)-1-(3-Cyano-4,6-dimethylpyridin-2-yl)-N-(3,4-difluorophenyl)-4-hydroxy-N-methylpyrrolidine-2-carboxamide;
(2S,4S)—N-(3-Chloro-4-fluorophenyl)-1-(3-cyano-6-methyl-4-(trifluoro-methyl)pyridin-2-yl)-4-hydroxy-N-methylpyrrolidine-2-carboxamide;
(2S,4S)-1-(3-Cyano-6-methyl-4-(trifluoromethyl)pyridin-2-yl)-N-(4-fluoro-3-methylphenyl)-4-hydroxy-N-methylpyrrolidine-2-carboxamide;
(2S,4S)-1-(3-Cyano-4,6-dimethylpyridin-2-yl)-4-hydroxy-N-methyl-N-phenylpyrrolidine-2-carboxamide;
(2S,4S)-1-(3-Cyano-6-methyl-4-(trifluoromethyl)pyridin-2-yl)-4-hydroxy-N-methyl-N-phenylpyrrolidine-2-carboxamide;
(2S,4S)-1-(3-Cyano-4,6-dimethylpyridin-2-yl)-4-hydroxy-N-methyl-N-(m-tolyl)pyrrolidine-2-carboxamide;
(2S,4S)-1-(3-Cyano-4,6-dimethylpyridin-2-yl)-N-(4-fluoro-3-(trifluoromethyl)phenyl)-4-hydroxy-N-methylpyrrolidine-2-carboxamide;
(2S,4S)-1-(3-Cyano-4,6-dimethylpyridin-2-yl)-N-(3-(fluoromethyl)phenyl)-4-hydroxy-N-methylpyrrolidine-2-carboxamide;
(2S,4S)-1-(3-Cyano-4,6-dimethylpyridin-2-yl)-N-(3-(difluoromethyl)phenyl)-4-hydroxy-N-methylpyrrolidine-2-carboxamide;
(2S,4S)—N-(3-Chlorophenyl)-1-(3-cyano-4,6-dimethylpyridin-2-yl)-4-hydroxy-N-methylpyrrolidine-2-carboxamide;
(2S,4S)-1-(3-Cyano-4,6-dimethylpyridin-2-yl)-N-(4-fluoro-3-(fluoromethyl)phenyl)-4-hydroxy-N-methylpyrrolidine-2-carboxamide;
(2S,4S)-1-(3-Cyano-6-methyl-4-(trifluoromethyl)pyridin-2-yl)-N-(4-fluoro-3-(fluoromethyl)-phenyl)-4-hydroxy-N-methyl-pyrrolidine-2-carboxamide;
(2S,4S)-1-(3-Cyano-6-methyl-4-(trifluoromethyl)pyridin-2-yl)-N-(4-fluoro-3-methoxyphenyl)-4-hydroxy-N-methylpyrrolidine-2-carboxamide;
(2S,4S)-1-(3-Cyano-6-methyl-4-(trifluoromethyl)pyridin-2-yl)-N-(3,5-difluorophenyl)-4-hydroxy-N-methylpyrrolidine-2-carboxamide;
(2S,4S)—N-(4-Chloro-3-fluorophenyl)-1-(3-cyano-6-methyl-4-(trifluoromethyl)pyridin-2-yl)-4-hydroxy-N-methyl-pyrrolidine-2-carboxamide;
(2S,4S)-1-(3-Cyano-6-methyl-4-(trifluoromethyl)pyridin-2-yl)-N-(3-fluoro-4-(trifluoromethyl)-phenyl)-4-hydroxy-N-methyl-pyrrolidine-2-carboxamide;
(2S,4S)-1-(3-Cyano-6-methyl-4-(trifluoromethyl)pyridin-2-yl)-4-hydroxy-N-methyl-N-(2,4,5-trifluorophenyl)pyrrolidine-2-carboxamide;
(2S,4S)-1-(3-Cyano-4,6-dimethylpyridin-2-yl)-N-ethyl-4-hydroxy-N-(m-tolyl)pyrrolidine-2-carboxamide;
(2S,4S)-1-(3-Cyano-6-methyl-4-(trifluoromethyl)pyridin-2-yl)-N-ethyl-4-hydroxy-N-(m-tolyl)-pyrrolidine-2-carboxamide;
(2S,4R)-1-(3-Cyano-6-methyl-4-(trifluoromethyl)pyridin-2-yl)-4-hydroxy-N-methyl-N-(m-tolyl)pyrrolidine-2-carboxamide;
(2S,3R)-1-(3-Cyano-6-methyl-4-(trifluoromethyl)pyridin-2-yl)-3-hydroxy-N-methyl-N-(m-tolyl)pyrrolidine-2-carboxamide;
(2S,3R)-1-(3-Cyano-4,6-dimethylpyridin-2-yl)-3-hydroxy-N-methyl-N-(m-tolyl)pyrrolidine-2-carboxamide;
(2S,3S)-1-(3-Cyano-6-methyl-4-(trifluoromethyl)pyridin-2-yl)-3-hydroxy-N-methyl-N-(m-tolyl)pyrrolidine-2-carboxamide;
(2S,4S)-4-Hydroxy-N-methyl-1-(6-methyl-4-(trifluoromethyl)pyridin-2-yl)-N-(m-tolyl)pyrrolidine-2-carboxamide;
(2S,4S)-4-Hydroxy-1-(4-isopropyl-6-methylpyridin-2-yl)-N-methyl-N-(m-tolyl)pyrrolidine-2-carboxamide;
(2S,4S)-1-(5-Chloro-4,6-dimethylpyridin-2-yl)-4-hydroxy-N-methyl-N-(m-tolyl)pyrrolidine-2-carboxamide;
(2S,4S)-1-(3-Cyano-6-methoxy-4-(trifluoromethyl)pyridin-2-yl)-4-hydroxy-N-methyl-N-(m-tolyl)pyrrolidine-2-carboxamide;
(2S,4S)-1-(3-Cyano-6-(ethyl(methyl)amino)-4-(trifluoromethyl)pyridin-2-yl)-4-hydroxy-N-methyl-N-(m-tolyl)pyrrolidine-2-carboxamide;
(2S,4S)-1-(3-Cyano-6-(dimethylamino)-4-(trifluoromethyl)pyridin-2-yl)-4-hydroxy-N-methyl-N-(m-tolyl)pyrrolidine-2-carboxamide;
(2S,4S)-1-(3-Cyano-4-isopropyl-6-methylpyridin-2-yl)-4-hydroxy-N-methyl-N-(m-tolyl)pyrrolidine-2-carboxamide;
(2S,4S)-1-(3-Cyano-4-(trifluoromethyl)pyridin-2-yl)-4-hydroxy-N-methyl-N-(m-tolyl)pyrrolidine-2-carboxamide;

(2S,4S)-1-(4-Ethyl-5-methylpyridin-2-yl)-4-hydroxy-N-methyl-N-(m-tolyl)pyrrolidine-2-carboxamide;

(2S,4S)-1-(3-Cyano-6-methyl-4-(trifluoromethyl)pyridin-2-yl)-4-methoxy-N-methyl-N-(m-tolyl)pyrrolidine-2-carboxamide;

(2S,4S)-1-(3-Cyano-4,6-dimethylpyridin-2-yl)-N-(3,4-difluorophenyl)-N-ethyl-4-fluoropyrrolidine-2-carboxamide;

(2S,4S)-4-Amino-1-(3-cyano-4,6-dimethylpyridin-2-yl)-N-ethyl-N-(m-tolyl)pyrrolidine-2-carboxamide;

(2R,4R)-1-(3-Cyano-4,6-dimethylpyridin-2-yl)-4-(dimethylamino)-N-ethyl-N-(m-tolyl)pyrrolidine-2-carboxamide;

(2S,4R)-4-Amino-1-(3-cyano-4,6-dimethylpyridin-2-yl)-N-ethyl-N-(m-tolyl)pyrrolidine-2-carboxamide;

(2S,4R)-1-(3-Cyano-4,6-dimethylpyridin-2-yl)-4-(dimethylamino)-N-ethyl-N-(m-tolyl)pyrrolidine-2-carboxamide;

(2S,4S)-1-(3-Cyano-4,6-dimethylpyridin-2-yl)-N-ethyl-4-morpholino-N-(m-tolyl)pyrrolidine-2-carboxamide;

(2R,4R)-1-(3-Cyano-4,6-dimethylpyridin-2-yl)-N-ethyl-4-(methylamino)-N-(m-tolyl)-pyrrolidine-2-carboxamide;

(2R,4R)-1-(3-Cyano-4,6-dimethylpyridin-2-yl)-N-ethyl-4-((2-hydroxyethyl)amino)-N-(m-tolyl)pyrrolidine-2-carboxamide;

(2R,4R)-1-(3-Cyano-4,6-dimethylpyridin-2-yl)-N-ethyl-4-((2-(methylsulfonyl)ethyl)-amino)-N-(m-tolyl)pyrrolidine-2-carboxamide;

(2S,4S)-1-(3-Cyano-4,6-dimethylpyridin-2-yl)-N-ethyl-4-(methyl(2-(methylsulfonyl)-ethyl)amino)-N-(m-tolyl)-pyrrolidine-2-carboxamide;

(2R,4R)-1-(3-Cyano-4,6-dimethylpyridin-2-yl)-N-ethyl-4-((2-oxopyrrolidin-3-yl)amino)-N-(m-tolyl)pyrrolidine-2-carboxamide;

(2R,4R)-1-(3-Cyano-4,6-dimethylpyridin-2-yl)-N-ethyl-4-(methyl(pyrrolidin-3-yl)amino)-N-(m-tolyl)pyrrolidine-2-carboxamide;

(2R,4R)-4-((2-Aminoethyl)amino)-1-(3-cyano-4,6-dimethylpyridin-2-yl)-N-ethyl-N-(m-tolyl)pyrrolidine-2-carboxamide;

(2R,4R)-1-(3-Cyano-4,6-dimethylpyridin-2-yl)-N-ethyl-4-(piperazin-1-yl)-N-(m-tolyl)-pyrrolidine-2-carboxamide;

(2S,4S)-4-(Azetidin-3-ylamino)-1-(3-cyano-4,6-dimethylpyridin-2-yl)-N-ethyl-N-(m-tolyl)pyrrolidine-2-carboxamide;

(2R,4R)-4-((1-Acetylpyrrolidin-3-yl)(methyl)amino)-1-(3-cyano-4,6-dimethylpyridin-2-yl)-N-ethyl-N-(m-tolyl)pyrrolidine-2-carboxamide;

(2S,3R,4S)-1-(3-Cyano-6-methyl-4-(trifluoromethyl)pyridin-2-yl)-3,4-dihydroxy-N-methyl-N-(m-tolyl)pyrrolidine-2-carboxamide;

(2S,3S,4R)-1-(3-Cyano-6-methyl-4-(trifluoromethyl)pyridin-2-yl)-3,4-dihydroxy-N-methyl-N-(m-tolyl)pyrrolidine-2-carboxamide;

(2S,3S,4R)-1-(3-Cyano-4,6-dimethyl-pyridin-2-yl)-3,4-dihydroxy-N-methyl-N-(m-tolyl)-pyrrolidine-2-carboxamide;

(2S,3S,4R)-1-(3-Cyano-6-methyl-4-(trifluoromethyl)pyridin-2-yl)-N-(3,4-difluorophenyl)-N-ethyl-3,4-dihydroxypyrrolidine-2-carboxamide;

(2S,3S,4R)—N-(3-Chloro-4-fluoro-phenyl)-1-(3-cyano-6-methyl-4-(trifluoromethyl)pyridin-2-yl)-N-ethyl-3,4-dihydroxypyrrolidine-2-carboxamide;

(S)—N-Methyl-3-(6-methyl-4-(trifluoromethyl)pyridin-2-yl)-2-oxo-N-(m-tolyl)oxazolidine-4-carboxamide;

(S)—N-Methyl-1-(6-methyl-4-(trifluoromethyl)pyridin-2-yl)-5-oxo-N-(m-tolyl)pyrrolidine-2-carboxamide;

(S)—N-(5-Fluoro-6-methylpyridin-2-yl)-N-methyl-1-(6-methyl-4-(trifluoromethyl)pyridin-2-yl)-5-oxopyrrolidine-2-carboxamide;

(2S,4S)-4-Amino-N-(3-chloro-4-fluorophenyl)-N-ethyl-1-(6-methyl-4-(trifluoromethyl)pyridin-2-yl)-5-oxopyrrolidine-2-carboxamide;

(2S,4S)-4-Acetamido-N-(3-chloro-4-fluorophenyl)-N-ethyl-1-(6-methyl-4-(trifluoromethyl)pyridin-2-yl)-5-oxopyrrolidine-2-carboxamide;

(2S,4S)—N-(3-Chloro-4-fluorophenyl)-N-ethyl-1-(6-methyl-4-(trifluoro-methyl)pyridin-2-yl)-4-morpholino-5-oxopyrrolidine-2-carboxamide;

(2S,4S)—N-(3-Chloro-4-fluorophenyl)-N-ethyl-4-hydroxy-1-(4-methyl-6-(trifluoromethyl)-pyrimidin-2-yl)pyrrolidine-2-carboxamide;

(2S,3S,4S)—N-(3-Chloro-4-fluorophenyl)-3,4-dihydroxy-N-methyl-1-(6-methyl-4-(trifluoromethyl)pyridin-2-yl)-5-oxopyrrolidine-2-carboxamide;

(2S,3S,4S)—N-(3-Chloro-4-fluoro-phenyl)-N-ethyl-3,4-dihydroxy-1-(6-methyl-4-(trifluoromethyl)pyridin-2-yl)-5-oxopyrrolidine-2-carboxamide;

(2S,3S,4S)—N-(4-Fluoro-3-methyl-phenyl)-3,4-dihydroxy-N-methyl-1-(6-methyl-4-(trifluoromethyl)pyridin-2-yl)-5-oxopyrrolidine-2-carboxamide;

(2S,3S,4S)—N-(3-Chloro-5-fluoro-phenyl)-3,4-dihydroxy-N-methyl-1-(6-methyl-4-(trifluoromethyl)pyridin-2-yl)-5-oxopyrrolidine-2-carboxamide;

(3aS,4S,6aS)—N-(3-Chloro-2,4-difluorophenyl)-N,2,2-trimethyl-5-(6-methyl-4-(trifluoromethyl)-pyridin-2-yl)-6-oxotetrahydro-4H-[1,3]dioxolo[4,5-c]pyrrole-4-carboxamide;

(2S,3S,4S)—N-(3-Chloro-2,4-difluorophenyl)-3,4-dihydroxy-N-methyl-1-(6-methyl-4-(trifluoromethyl)pyridin-2-yl)-5-oxopyrrolidine-2-carboxamide;

(2S,3R,4R)—N-(3-Chloro-2,4-difluorophenyl)-3,4-dihydroxy-N-methyl-1-(6-methyl-4-(trifluoromethyl)pyridin-2-yl)-5-oxopyrrolidine-2-carboxamide;

(2S,3R,4R)—N-(3-Chloro-4-fluorophenyl)-3,4-dihydroxy-N-methyl-1-(6-methyl-4-(trifluoromethyl)pyridin-2-yl)-5-oxopyrrolidine-2-carboxamide;

(2S,3S,4S)—N-(5-Chloro-2,4-difluorophenyl)-3,4-dihydroxy-N-methyl-1-(6-methyl-4-(trifluoromethyl)pyridin-2-yl)-5-oxopyrrolidine-2-carboxamide;

(2S,4S)—N-(3-Chloro-4-fluorophenyl)-4-hydroxy-N-methyl-1-(6-methyl-4-(trifluoromethyl)-pyridin-2-yl)-5-oxopyrrolidine-2-carboxamide;

(2S,4S)—N-(3-Chloro-4-fluorophenyl)-N-ethyl-4-hydroxy-1-(6-methyl-4-(trifluoromethyl)pyridin-2-yl)-5-oxopyrrolidine-2-carboxamide;

(2S,4R)-4-((Benzyloxy)methyl)-N-(3-chloro-4-fluorophenyl)-N-methyl-1-(6-methyl-4-(trifluoromethyl)pyridin-2-yl)-5-oxopyrrolidine-2-carboxamide;

(2S,4R)—N-(3-Chloro-4-fluorophenyl)-4-(hydroxymethyl)-N-methyl-1-(6-methyl-4-(trifluoromethyl)pyridin-2-yl)-5-oxopyrrolidine-2-carboxamide;

(2R,4S)—N-(3-Chloro-4-fluorophenyl)-4-((dimethylamino)methyl)-N-methyl-1-(6-methyl-4-(trifluoromethyl)pyridin-2-yl)-5-oxopyrrolidine-2-carboxamide;

(2R,4R)—N-(3-Chloro-4-fluorophenyl)-4-((dimethylamino)methyl)-N-methyl-1-(6-methyl-4-(trifluoromethyl)pyridin-2-yl)-5-oxopyrrolidine-2-carboxamide;

(2S,3R)—N-(3-Chloro-4-fluorophenyl)-3-hydroxy-N-methyl-1-(6-methyl-4-(trifluoromethyl)-pyridin-2-yl)-5-oxopyrrolidine-2-carboxamide;

(2S,3R)—N-(3-Chloro-4-fluorophenyl)-1-(3-cyano-6-methyl-4-(trifluoromethyl)pyridin-2-yl)-3-hydroxy-N-methylpyrrolidine-2-carboxamide;

(2S,3R)—N-(3-Chloro-4-fluorophenyl)-1-(3-cyano-6-methyl-4-(trifluoromethyl)pyridin-2-yl)-N-ethyl-3-hydroxypyrrolidine-2-carboxamide;

(S)—N-(3-Chloro-4-fluorophenyl)-N-methyl-3-(6-methyl-4-(trifluoromethyl)pyridin-2-yl)-2-oxooxazolidine-4-carboxamide;

(S)—N-(4-Chloro-3-methylphenyl)-N-methyl-3-(6-methyl-4-(trifluoromethyl)pyridin-2-yl)-2-oxooxazolidine-4-carboxamide;

(S)—N-(3-Chloro-2,4-difluorophenyl)-N-methyl-3-(6-methyl-4-(trifluoromethyl)pyridin-2-yl)-2-oxooxazolidine-4-carboxamide;

(S)—N-(4-Fluoro-3-methyl-phenyl)-N-methyl-3-(6-methyl-4-(trifluoromethyl)pyridin-2-yl)-2-oxooxazolidine-4-carboxamide;

(S)—N-(3-Chlorophenyl)-N-methyl-3-(6-methyl-4-(trifluoromethyl)pyridin-2-yl)-2-oxooxazolidine-4-carboxamide;

(S)—N-(3-Chloro-4-methyl-phenyl)-N-methyl-3-(6-methyl-4-(trifluoromethyl)pyridin-2-yl)-2-oxooxazolidine-4-carboxamide;

(S)—N-(3,4-Dichlorophenyl)-N-methyl-3-(6-methyl-4-(trifluoromethyl)-pyridin-2-yl)-2-oxooxazolidine-4-carboxamide;

(S)—N-(4-Fluoro-3-methoxy-phenyl)-N-methyl-3-(6-methyl-4-(trifluoromethyl)pyridin-2-yl)-2-oxooxazolidine-4-carboxamide;

(S)—N-(4-Chloro-3-methoxy-phenyl)-N-methyl-3-(6-methyl-4-(trifluoromethyl)pyridin-2-yl)-2-oxooxazolidine-4-carboxamide;

(S)—N-(3-Methoxy-4-methyl-phenyl)-N-methyl-3-(6-methyl-4-(trifluoromethyl)pyridin-2-yl)-2-oxooxazolidine-4-carboxamide;

(S)—N-(3-Bromo-4-fluorophenyl)-N-methyl-3-(6-methyl-4-(trifluoromethyl)pyridin-2-yl)-2-oxooxazolidine-4-carboxamide;

(S)—N-(4-Bromo-2-fluorophenyl)-N-methyl-3-(6-methyl-4-(trifluoromethyl)pyridin-2-yl)-2-oxooxazolidine-4-carboxamide;

(S)—N-(3-Chloro-2-fluorophenyl)-N-methyl-3-(6-methyl-4-(trifluoromethyl)pyridin-2-yl)-2-oxooxazolidine-4-carboxamide;

(S)—N-(5-Chloro-2-fluorophenyl)-N-methyl-3-(6-methyl-4-(trifluoromethyl)pyridin-2-yl)-2-oxooxazolidine-4-carboxamide;

(S)—N-(4-Chloro-2-fluorophenyl)-N-methyl-3-(6-methyl-4-(trifluoromethyl)pyridin-2-yl)-2-oxooxazolidine-4-carboxamide;

(S)—N-(5-Chloro-2,4-difluoro-phenyl)-N-methyl-3-(6-methyl-4-(trifluoromethyl)pyridin-2-yl)-2-oxooxazolidine-4-carboxamide;

(S)—N-(5-Chloro-4-fluoro-2-methoxyphenyl)-N-methyl-3-(6-methyl-4-(trifluoromethyl)pyridin-2-yl)-2-oxooxazolidine-4-carboxamide;

(S)—N-(2,4-Difluoro-3-methyl-phenyl)-N-methyl-3-(6-methyl-4-(trifluoromethyl)pyridin-2-yl)-2-oxooxazolidine-4-carboxamide;

(S)—N-(4-Chloro-2,3-difluoro-phenyl)-N-methyl-3-(6-methyl-4-(trifluoromethyl)pyridin-2-yl)-2-oxooxazolidine-4-carboxamide;

(S)—N-(1,3-Dihydro-isobenzofuran-5-yl)-N-methyl-3-(6-methyl-4-(trifluoromethyl)-pyridin-2-yl)-2-oxooxazolidine-4-carboxamide;

(S)—N-(3-Chloro-4-fluorophenyl)-N-ethyl-3-(6-methyl-4-(trifluoromethyl)-pyridin-2-yl)-2-oxooxazolidine-4-carboxamide;

(S)—N-(3-Chloro-4-fluorophenyl)-N-isopropyl-3-(6-methyl-4-(trifluoromethyl)pyridin-2-yl)-2-oxooxazolidine-4-carboxamide;

(S)—N-(2,4-Dichlorophenyl)-N-methyl-3-(6-methyl-4-(trifluoromethyl)pyridin-2-yl)-2-oxooxazolidine-4-carboxamide;

(S)—N-(4-Bromo-3-chlorophenyl)-N-methyl-3-(6-methyl-4-(trifluoromethyl)pyridin-2-yl)-2-oxooxazolidine-4-carboxamide;

(S)—N-(3-Hydroxy-4-methylphenyl)-N-methyl-3-(6-methyl-4-(trifluoromethyl)pyridin-2-yl)-2-oxooxazolidine-4-carboxamide;

(S)—N-(4-Fluoro-3-hydroxyphenyl)-N-methyl-3-(6-methyl-4-(trifluoromethyl)pyridin-2-yl)-2-oxooxazolidine-4-carboxamide;

(S)—N-(2,4-Difluoro-3-vinylphenyl)-N-methyl-3-(6-methyl-4-(trifluoromethyl)pyridin-2-yl)-2-oxooxazolidine-4-carboxamide;

(S)—N-(3-Ethyl-2,4-difluorophenyl)-N-methyl-3-(6-methyl-4-(trifluoromethyl)pyridin-2-yl)-2-oxooxazolidine-4-carboxamide;

(S)—N-(4-Fluoro-3-vinylphenyl)-N-methyl-3-(6-methyl-4-(trifluoromethyl)pyridin-2-yl)-2-oxooxazolidine-4-carboxamide;

(S)—N-(3-Ethyl-4-fluorophenyl)-N-methyl-3-(6-methyl-4-(trifluoromethyl)pyridin-2-yl)-2-oxo-oxazolidine-4-carboxamide;

(S)—N-(2-Fluoro-4-vinylphenyl)-N-methyl-3-(6-methyl-4-(trifluoromethyl)pyridin-2-yl)-2-oxooxazolidine-4-carboxamide;

(S)—N-(4-Ethyl-2-fluorophenyl)-N-methyl-3-(6-methyl-4-(trifluoromethyl)pyridin-2-yl)-2-oxooxazolidine-4-carboxamide;

(S)-3-(6-Chloro-4-(trifluoromethyl)pyridin-2-yl)-N-(3-chloro-4-fluorophenyl)-N-methyl-2-oxooxazolidine-4-carboxamide;

(S)—N-(3-Chloro-4-fluorophenyl)-N-methyl-2-oxo-3-(4-(trifluoromethyl)-6-vinylpyridin-2-yl)oxazolidine-4-carboxamide;

(S)—N-(3-Chloro-4-fluorophenyl)-3-(6-ethyl-4-(trifluoromethyl)pyridin-2-yl)-N-methyl-2-oxooxazolidine-4-carboxamide;

(S)-3-(4-Bromo-6-methylpyridin-2-yl)-N-(3-chloro-4-fluorophenyl)-N-methyl-2-oxooxazolidine-4-carboxamide;

(S)—N-(3-Chloro-4-fluorophenyl)-N-methyl-3-(6-methyl-4-(prop-1-en-2-yl)pyridin-2-yl)-2-oxooxazolidine-4-carboxamide;

(S)—N-(3-Chloro-4-fluorophenyl)-3-(4-isopropyl-6-methylpyridin-2-yl)-N-methyl-2-oxooxazolidine-4-carboxamide;

(S)—N-(3-Chloro-4-fluorophenyl)-3-(4-ethyl-6-methylpyridin-2-yl)-N-methyl-2-oxooxazolidine-4-carboxamide;

(S)-3-(6-Chloro-4-(difluoromethoxy)pyridin-2-yl)-N-(3-chloro-4-fluorophenyl)-N-methyl-2-oxooxazolidine-4-carboxamide;

(S)—N-(3-Chloro-4-fluorophenyl)-3-(4-(difluoromethoxy)-6-methylpyridin-2-yl)-N-methyl-2-oxooxazolidine-4-carboxamide;

(S)-3-(4-(tert-Butyl)-6-chloropyridin-2-yl)-N-(3-chloro-4-fluorophenyl)-N-methyl-2-oxooxazolidine-4-carboxamide;

(S)-3-(4-(tert-Butyl)-6-methylpyridin-2-yl)-N-(3-chloro-4-fluorophenyl)-N-methyl-2-oxooxazolidine-4-carboxamide;

(4S)—N-(3-Chloro-4-fluorophenyl)-N-methyl-3-(6-methyl-4-(1,1,1-trifluoropropan-2-yl)pyridin-2-yl)-2-oxooxazolidine-4-carboxamide;

(S)—N-(3-Chloro-4-fluorophenyl)-3-(4-(1,1-difluoroethyl)-6-methylpyridin-2-yl)-N-ethyl-2-oxooxazolidine-4-carboxamide;

(S)—N-(1H-Indol-6-yl)-N-methyl-3-(6-methyl-4-(trifluoromethyl)pyridin-2-yl)-2-oxooxazolidine-4-carboxamide;

(S)—N-Methyl-3-(6-methyl-4-(trifluoromethyl)pyridin-2-yl)-2-oxo-N-(1H-pyrrolo[2,3-b]pyridin-6-yl)oxazolidine-4-carboxamide;

(2S,4S)—N-(3,4-Difluorophenyl)-N-ethyl-4-(2-(hydroxymethyl)-morpholino)-1-(6-methyl-4-(trifluoromethyl)pyridin-2-yl)pyrrolidine-2-carboxamide;

(3S,5S)—N-(3,4-Difluorophenyl)-N-ethyl-3-hydroxy-1'-(6-methyl-4-(trifluoromethyl)pyridin-2-yl)-[1,3'-bipyrrolidine]-5'-carboxamide;

(2S,4S)—N-(3,4-Difluorophenyl)-N-ethyl-4-(3-hydroxyazetidin-1-yl)-1-(6-methyl-4-(trifluoromethyl)pyridin-2-yl)pyrrolidine-2-carboxamide;

(2S,4S)—N-(3,4-Difluorophenyl)-N-ethyl-4-(((3S,4R)-3-hydroxytetrahydro-2H-pyran-4-yl)amino)-1-(6-methyl-4-(trifluoromethyl)pyridin-2-yl)pyrrolidine-2-carboxamide;

(2S,4S)—N-(3,4-Difluorophenyl)-N-ethyl-4-(((3R,4R)-4-hydroxytetrahydro-2H-pyran-3-yl)amino)-1-(6-methyl-4-(trifluoromethyl)pyridin-2-yl)pyrrolidine-2-carboxamide;

(2S,4S)—N-(3,4-Difluorophenyl)-N-ethyl-4-(((1R,2R)-2-hydroxy-cyclopentyl)amino)-1-(6-methyl-4-(trifluoromethyl)pyridin-2-yl)-pyrrolidine-2-carboxamide;

(2S,4S)—N-(3,4-Difluorophenyl)-N-ethyl-4-(((1S,2R)-2-hydroxy-cyclopentyl)amino)-1-(6-methyl-4-(trifluoromethyl)pyridin-2-yl)-pyrrolidine-2-carboxamide;

rac-tert-Butyl (3R,4R)-3-(((3S,5S)-5-((3,4-difluorophenyl)-(ethyl)carbamoyl)-1-(6-methyl-4-(trifluoromethyl)-pyridin-2-yl)-pyrrolidin-3-yl)amino)-4-hydroxy-pyrrolidine-1-carboxylate;

tert-Butyl (3S,4R)-3-(((3S,5S)-5-((3,4-difluorophenyl)(ethyl)-carbamoyl)-1-(6-methyl-4-(trifluoromethyl)pyridin-2-yl-pyrrolidin-3-yl)amino)-4-hydroxy-pyrrolidine-1-carboxylate;

(2S,4S)—N-(3,4-Difluorophenyl)-N-ethyl-1-(6-methyl-4-(trifluoromethyl)pyridin-2-yl)-4-((5-oxopyrrolidin-3-yl)amino)-pyrrolidine-2-carboxamide;

(2S,4S)—N-(3,4-Difluorophenyl)-N-ethyl-1-(6-methyl-4-(trifluoromethyl)pyridin-2-yl)-4-(oxetan-3-ylamino)pyrrolidine-2-carboxamide;

(2S,4S)—N-(3,4-Difluorophenyl)-N-ethyl-4-(((3S,4R)-3-hydroxytetrahydro-2H-pyran-4-yl)(methyl)amino)-1-(6-methyl-4-(trifluoromethyl)pyridin-2-yl)pyrrolidine-2-carboxamide;

(2S,4S)—N-(3,4-Difluorophenyl)-N-ethyl-4-(((3R,4R)-4-hydroxytetrahydro-2H-pyran-3-yl)(methyl)amino)-1-(6-methyl-4-(trifluoromethyl)pyridin-2-yl)pyrrolidine-2-carboxamide;

(2S,4S)—N-(3,4-Difluorophenyl)-N-ethyl-4-(((1R,2R)-2-hydroxycyclopentyl)-(methyl)amino)-1-(6-methyl-4-(trifluoromethyl)pyridin-2-yl)pyrrolidine-2-carboxamide;

(2S,4S)—N-(3,4-Difluorophenyl)-N-ethyl-4-(((1S,2R)-2-hydroxycyclopentyl)-(methyl)amino)-1-(6-methyl-4-(trifluoromethyl)pyridin-2-yl)pyrrolidine-2-carboxamide;

rac-tert-Butyl (3R,4R)-3-(((3S,5S)-5-((3,4-difluorophenyl)(ethyl)carbamoyl)-1-(6-methyl-4-(trifluoromethyl)pyridin-2-yl)pyrrolidin-3-yl)(methyl)amino)-4-hydroxypyrrolidine-1-carboxylate;

tert-Butyl (3S,4R)-3-(((3S,5S)-5-((3,4-difluorophenyl)(ethyl)carbamoyl)-1-(6-methyl-4-(trifluoromethyl)pyridin-2-yl)pyrrolidin-3-yl)(methyl)amino)-4-hydroxypyrrolidine-1-carboxylate;

(2S,4S)—N-(3,4-Difluorophenyl)-N-ethyl-4-(methyl(5-oxopyrrolidin-3-yl)amino)-1-(6-methyl-4-(trifluoromethyl)pyridin-2-yl)pyrrolidine-2-carboxamide;

(2S,4S)—N-(3,4-Difluorophenyl)-N-ethyl-4-(methyl(oxetan-3-yl)amino)-1-(6-methyl-4-(trifluoromethyl)pyridin-2-yl)pyrrolidine-2-carboxamide;

(2S,4S)—N-(3-Chlorophenyl)-1-(3-cyano-6-methyl-4-(trifluoromethyl)pyridin-2-yl)-N-ethyl-4-(2-(hydroxymethyl)-morpholino)pyrrolidine-2-carboxamide;

(2S,4S)-1-(3-Cyano-6-methyl-4-(trifluoromethyl)-pyridin-2-yl)-N-(3,4-dichlorophenyl)-N-ethyl-4-(2-(hydroxymethyl)-morpholino)-pyrrolidine-2-carboxamide;

(2S,4S)—N-(3-Chloro-4-methylphenyl)-1-(3-cyano-6-methyl-4-(trifluoromethyl)-pyridin-2-yl)-N-ethyl-4-(2-(hydroxymethyl)morpholino)pyrrolidine-2-carboxamide;

(2S,4S)-1-(3-Cyano-6-methyl-4-(trifluoromethyl)-pyridin-2-yl)-N-ethyl-N-(4-fluoro-3-methylphenyl)-4-(2-(hydroxymethyl)morpholino)pyrrolidine-2-carboxamide;

(2S,4S)—N-(3-Chloro-4-fluorophenyl)-1-(3-cyano-6-methyl-4-(trifluoromethyl)-pyridin-2-yl)-4-(2-(hydroxy-methyl)morpholino)-N-methylpyrrolidine-2-carboxamide;

(2S,4S)—N-(3-Chloro-4-fluorophenyl)-1-(3-cyano-6-methyl-4-(trifluoromethyl)-pyridin-2-yl)-N-ethyl-4-((S)-3-(hydroxymethyl)morpholino)pyrrolidine-2-carboxamide;

(2S,4S)—N-(3-Chloro-4-fluorophenyl)-1-(3-cyano-6-methyl-4-(trifluoromethyl)-pyridin-2-yl)-N-ethyl-4-((R)-3-(hydroxymethyl)morpholino)pyrrolidine-2-carboxamide;

(2S,4S)—N-(3-Chloro-4-fluorophenyl)-1-(3-cyano-6-methyl-4-(trifluoromethyl)-pyridin-2-yl)-N-ethyl-4-((S)-2-(hydroxymethyl)morpholino)pyrrolidine-2-carboxamide;

(2S,4S)—N-(3-Chloro-4-fluorophenyl)-1-(3-cyano-6-methyl-4-(trifluoromethyl)-pyridin-2-yl)-N-ethyl-4-((R)-2-(hydroxymethyl)morpholino)pyrrolidine-2-carboxamide;

(S)—N-(3-Chloro-4-fluorophenyl)-N-methyl-3-(6-methyl-4-(trifluoromethyl)pyridin-2-yl)-2-oxoimidazolidine-4-carboxamide;

(S)—N-(3-Chloro-4-fluorophenyl)-N-ethyl-3-(6-methyl-4-(trifluoromethyl)pyridin-2-yl)-2-oxoimidazolidine-4-carboxamide;

(S)—N-(3-Chloro-2,4-difluorophenyl)-N-methyl-3-(6-methyl-4-(trifluoromethyl)pyridin-2-yl)-2-oxoimidazolidine-4-carboxamide;

(S)—N-(3-Chloro-4-fluorophenyl)-N-methyl-3-(6-methyl-4-(trifluoromethyl)pyridin-2-yl)-1-(methylsulfonyl)-2-oxoimidazolidine-4-carboxamide;

(4S)—N-(3-Chloro-4-fluorophenyl)-1-(2-hydroxypropyl)-N-methyl-3-(6-methyl-4-(trifluoromethyl)pyridin-2-yl)-2-oxoimidazolidine-4-carboxamide;
(S)—N-(3-Chloro-2,4-difluorophenyl)-N-cyclopropyl-3-(6-methyl-4-(trifluoromethyl)-pyridin-2-yl)-2-oxoimidazolidine-4-carboxamide;
(2S,3S,4S)—N-(3-Chloro-2,4-difluorophenyl)-3,4-dihydroxy-N-(methyl-d3)-1-(6-methyl-4-(trifluoromethyl)pyridin-2-yl)-5-oxopyrrolidine-2-carboxamide;
(2S,3S,4S)—N-(3-Chloro-4-fluorophenyl)-3,4-dihydroxy-N-(methyl-d3)-1-(6-methyl-4-(trifluoromethyl)pyridin-2-yl)-5-oxopyrrolidine-2-carboxamide;
(2S,3S,4S)—N-(5-Chloro-2,4-difluorophenyl)-3,4-dihydroxy-N-(methyl-d3)-1-(6-methyl-4-(trifluoromethyl)pyridin-2-yl)-5-oxopyrrolidine-2-carboxamide;
(2S,3S,4S)—N-(4-Chloro-2-fluorophenyl)-3,4-dihydroxy-N-methyl-1-(6-methyl-4-(trifluoromethyl)pyridin-2-yl)-5-oxopyrrolidine-2-carboxamide;
(2S,3S,4S)-3,4-Dihydroxy-N-methyl-1-(6-methyl-4-(trifluoromethyl)pyridin-2-yl)-5-oxo-N-(1H-pyrrolo[2,3-b]pyridin-6-yl)pyrrolidine-2-carboxamide;
(2S,3S,4S)-3,4-Dihydroxy-N-methyl-N-(1-methyl-1H-pyrrolo[2,3-b]pyridin-6-yl)-1-(6-methyl-4-(trifluoromethyl)pyridin-2-yl)-5-oxopyrrolidine-2-carboxamide;
(2S,3S,4S)-3,4-Dihydroxy-N-methyl-N-(1-methyl-1H-indazol-6-yl)-1-(6-methyl-4-(trifluoromethyl)pyridin-2-yl)-5-oxopyrrolidine-2-carboxamide;
(2S,3S,4S)-3,4-Dihydroxy-N-methyl-N-(4-methyl-3,4-dihydro-2H-pyrido[3,2-b][1,4]oxazin-6-yl)-1-(6-methyl-4-(trifluoromethyl)pyridin-2-yl)-5-oxopyrrolidine-2-carboxamide;
(2S,3S,4S)—N-(5-Fluoro-6-methylpyridin-2-yl)-3,4-dihydroxy-N-methyl-1-(6-methyl-4-(trifluoromethyl)pyridin-2-yl)-5-oxopyrrolidine-2-carboxamide;
(S)—N-(3-Chloro-4-cyclopropylphenyl)-N-methyl-3-(6-methyl-4-(trifluoromethyl)pyridin-2-yl)-2-oxooxazolidine-4-carboxamide;
(S)—N-(1H-Indazol-6-yl)-N-methyl-3-(6-methyl-4-(trifluoromethyl)pyridin-2-yl)-2-oxooxazolidine-4-carboxamide;
(S)—N-(6-Aminopyridin-2-yl)-N-methyl-3-(6-methyl-4-(trifluoromethyl)pyridin-2-yl)-2-oxooxazolidine-4-carboxamide;
(S)—N-Methyl-3-(6-methyl-4-(trifluoromethyl)pyridin-2-yl)-N-(6-(methylamino)pyridin-2-yl)-2-oxooxazolidine-4-carboxamide;
(S)—N-(6-(Dimethylamino)pyridin-2-yl)-N-methyl-3-(6-methyl-4-(trifluoromethyl)pyridin-2-yl)-2-oxooxazolidine-4-carboxamide;
(S)—N-Methyl-3-(6-methyl-4-(trifluoromethyl)pyridin-2-yl)-2-oxo-N-(quinolin-7-yl)oxazolidine-4-carboxamide;
(S)—N-(3-Chloro-4-fluorophenyl)-N-isopropyl-3-(6-methyl-4-(trifluoromethyl)pyridin-2-yl)-2-oxoimidazolidine-4-carboxamide;
(S)—N-(3-Chloro-4-fluorophenyl)-N-methyl-3-(6-methyl-4-(trifluoromethyl)pyridin-2-yl)-1-(2-(methylsulfonyl)ethyl)-2-oxoimidazolidine-4-carboxamide;
(S)—N-(3-Chloro-4-fluorophenyl)-1-(2-(N,N-dimethylsulfamoyl)ethyl)-N-methyl-3-(6-methyl-4-(trifluoromethyl)pyridin-2-yl)-2-oxoimidazolidine-4-carboxamide;
(S)—N-(3-Chloro-4-fluorophenyl)-1-(2-(dimethylamino)ethyl)-N-methyl-3-(6-methyl-4-(trifluoromethyl)pyridin-2-yl)-2-oxoimidazolidine-4-carboxamide;
(S)—N-(3-Chloro-4-fluorophenyl)-1-(3-(dimethylamino)propyl)-N-methyl-3-(6-methyl-4-(trifluoromethyl)pyridin-2-yl)-2-oxoimidazolidine-4-carboxamide;
(S)-1-(2-Amino-2-oxoethyl)-N-(3-chloro-4-fluorophenyl)-N-methyl-3-(6-methyl-4-(trifluoromethyl)-pyridin-2-yl)-2-oxoimidazolidine-4-carboxamide;
(S)—N-(3-Chloro-4-fluorophenyl)-1-(2-(dimethylamino)-2-oxoethyl)-N-methyl-3-(6-methyl-4-(trifluoromethyl)pyridin-2-yl)-2-oxoimidazolidine-4-carboxamide;
(S)—N-(3-Chloro-2,4-difluoro-phenyl)-1-((3-(hydroxymethyl)-oxetan-3-yl)methyl)-N-methyl-3-(6-methyl-4-(trifluoromethyl)-pyridin-2-yl)-2-oxoimidazolidine-4-carboxamide;
(S)—N-(3-Chloro-4-fluorophenyl)-N-methyl-3-(6-methyl-4-(trifluoromethyl)pyridin-2-yl)-1-(2-(methylsulfonamido)ethyl)-2-oxoimidazolidine-4-carboxamide;
(S)-1-(Azetidin-3-ylmethyl)-N-(3-chloro-2,4-difluorophenyl)-N-methyl-3-(6-methyl-4-(trifluoromethyl)pyridin-2-yl)-2-oxoimidazolidine-4-carboxamide;
(S)—N-(3-Chloro-2,4-difluorophenyl)-N-methyl-3-(6-methyl-4-(trifluoromethyl)pyridin-2-yl)-1-((1-methylazetidin-3-yl)methyl)-2-oxoimidazolidine-4-carboxamide;
(S)—N-(3-Chloro-4-fluorophenyl)-1-(3-(dimethylamino)-3-oxopropyl)-N-methyl-3-(6-methyl-4-(trifluoromethyl)pyridin-2-yl)-2-oxoimidazolidine-4-carboxamide;
(S)—N-(3-Chloro-4-fluorophenyl)-N-methyl-3-(6-methyl-4-(trifluoromethyl)pyridin-2-yl)-1-(3-(methylamino)-3-oxopropyl)-2-oxoimidazolidine-4-carboxamide;
(S)—N-(3-Chloro-2,4-difluorophenyl)-N-methyl-3-(6-methyl-4-(trifluoromethyl)pyridin-2-yl)-2-oxo-1-(2-(piperazin-1-yl)ethyl)imidazolidine-4-carboxamide;
(S)—N-(3-Chloro-4-fluorophenyl)-1-(2-hydroxyethyl)-N-methyl-3-(6-methyl-4-(trifluoromethyl)pyridin-2-yl)-2-oxoimidazolidine-4-carboxamide;
(S)—N-(3-Chloro-4-fluorophenyl)-N-methyl-3-(6-methyl-4-(trifluoromethyl)pyridin-2-yl)-1-(2-morpholinoethyl)-2-oxoimidazolidine-4-carboxamide;
(S)—N-(3-Chloro-2,4-difluorophenyl)-N-methyl-3-(6-methyl-4-(trifluoromethyl)pyridin-2-yl)-1-(2-morpholinoethyl)-2-oxoimidazolidine-4-carboxamide;
(S)—N-(3-Chloro-4-fluorophenyl)-1-(2-((S)-3-hydroxypyrrolidin-1-yl)ethyl)-N-methyl-3-(6-methyl-4-(trifluoromethyl)pyridin-2-yl)-2-oxoimidazolidine-4-carboxamide;
(S)—N-(3-Chloro-4-fluorophenyl)-1-(2-((R)-3-hydroxypyrrolidin-1-yl)ethyl)-N-methyl-3-(6-methyl-4-(trifluoromethyl)pyridin-2-yl)-2-oxoimidazolidine-4-carboxamide;
(S)—N-(3-Chloro-4-fluorophenyl)-1-(2-((R/S)-2-(hydroxymethyl)-pyrrolidin-1-yl)ethyl)-N-methyl-3-(6-methyl-4-(trifluoromethyl)-pyridin-2-yl)-2-oxoimidazolidine-4-carboxamide isomer 1;
(S)—N-(3-Chloro-4-fluorophenyl)-1-(2-((S/R)-2-(hydroxymethyl)-pyrrolidin-1-yl)ethyl)-N-methyl-3-(6-methyl-4-(trifluoromethyl)-pyridin-2-yl)-2-oxoimidazolidine-4-carboxamide isomer 2;
(S)-1-(2-(Azetidin-1-yl)ethyl)-N-(3-chloro-4-fluorophenyl)-N-methyl-3-(6-methyl-4-(trifluoromethyl)pyridin-2-yl)-2-oxoimidazolidine-4-carboxamide;
(S)-1-(2-(Azetidin-1-yl)ethyl)-N-(3-chloro-2,4-difluorophenyl)-N-methyl-3-(6-methyl-4-(trifluoromethyl)-pyridin-2-yl)-2-oxoimidazolidine-4-carboxamide;

(S)—N-(3-Chloro-2,4-difluorophenyl)-1-(2-(3-hydroxyazetidin-1-yl)ethyl)-N-methyl-3-(6-methyl-4-(trifluoromethyl)pyridin-2-yl)-2-oxoimidazolidine-4-carboxamide;

(4S)—N-(3-Chloro-2,4-difluoro-phenyl)-1-(2-(2-(hydroxymethyl)-azetidin-1-yl)-ethyl)-N-methyl-3-(6-methyl-4-(trifluoromethyl)pyridin-2-yl)-2-oxoimidazolidine-4-carboxamide;

(S)-1-(2-(4-Acetylpiperazin-1-yl)ethyl)-N-(3-chloro-2,4-difluoro-phenyl)-N-methyl-3-(6-methyl-4-(trifluoromethyl)pyridin-2-yl)-2-oxoimidazolidine-4-carboxamide;

(S)—N-(3-Chloro-2,4-difluorophenyl)-1-(2-((S)-3-fluoropyrrolidin-1-yl)ethyl)-N-methyl-3-(6-methyl-4-(trifluoromethyl)pyridin-2-yl)-2-oxoimidazolidine-4-carboxamide;

(S)—N-(3-Chloro-2,4-difluorophenyl)-1-(2-(3,3-difluoropyrrolidin-1-yl)ethyl)-N-methyl-3-(6-methyl-4-(trifluoromethyl)pyridin-2-yl)-2-oxoimidazolidine-4-carboxamide;

(4S)—N-(3-Chloro-2,4-difluoro-phenyl)-N-methyl-3-(6-methyl-4-(trifluoromethyl)pyridin-2-yl)-1-(2-(3-(N-methylacetamido)-pyrrolidin-1-yl)ethyl)-2-oxoimidazolidine-4-carboxamide;

(S)—N-(3-Chloro-2,4-difluorophenyl)-1-(2-(1,1-dioxidothiomorpholino)-ethyl)-N-methyl-3-(6-methyl-4-(trifluoromethyl)pyridin-2-yl)-2-oxoimidazolidine-4-carboxamide;

(S)—N-(3-Chloro-2,4-difluorophenyl)-1-(2-(4-(2-hydroxyethyl)piperazin-1-yl)ethyl)-N-methyl-3-(6-methyl-4-(trifluoromethyl)pyridin-2-yl)-2-oxoimidazolidine-4-carboxamide;

(S)—N-(3-Chloro-2,4-difluorophenyl)-N-methyl-1-(2-(4-methyl-3-oxopiperazin-1-yl)ethyl)-3-(6-methyl-4-(trifluoromethyl)pyridin-2-yl)-2-oxoimidazolidine-4-carboxamide;

(S)—N-(3-Chloro-2,4-difluorophenyl)-1-(2-(4-cyanopiperidin-1-yl)ethyl)-N-methyl-3-(6-methyl-4-(trifluoromethyl)pyridin-2-yl)-2-oxoimidazolidine-4-carboxamide;

(4S)—N-(3-Chloro-2,4-difluorophenyl)-N-methyl-3-(6-methyl-4-(trifluoromethyl)pyridin-2-yl)-1-(2-(S-methylsulfonimidoyl)ethyl)-2-oxoimidazolidine-4-carboxamide;

(4S)—N-(3-Chloro-4-fluorophenyl)-N-methyl-3-(6-methyl-4-(trifluoromethyl)pyridin-2-yl)-1-(2-(S-methylsulfonimidoyl)ethyl)-2-oxoimidazolidine-4-carboxamide;

(4S)—N-(3-Chloro-2,4-difluorophenyl)-1-(3-(dimethylamino)-2-hydroxypropyl)-N-methyl-3-(6-methyl-4-(trifluoromethyl)pyridin-2-yl)-2-oxoimidazolidine-4-carboxamide;

(4S)—N-(3-Chloro-2,4-difluorophenyl)-1-(3-((R)-3-fluoropyrrolidin-1-yl)-2-hydroxy-propyl)-N-methyl-3-(6-methyl-4-(trifluoromethyl)pyridin-2-yl)-2-oxoimidazolidine-4-carboxamide;

(4S)—N-(3-Chloro-2,4-difluorophenyl)-1-(3-(3,3-difluoropyrrolidin-1-yl)-2-hydroxy-propyl)-N-methyl-3-(6-methyl-4-(trifluoromethyl)pyridin-2-yl)-2-oxoimidazolidine-4-carboxamide;

(4S)—N-(3-Chloro-2,4-difluorophenyl)-1-(2-hydroxy-3-morpholinopropyl)-N-methyl-3-(6-methyl-4-(trifluoromethyl)pyridin-2-yl)-2-oxoimidazolidine-4-carboxamide;

(4S)—N-(3-Chloro-2,4-difluorophenyl)-N-methyl-3-(6-methyl-4-(trifluoromethyl)pyridin-2-yl)-1-(morpholin-2-ylmethyl)-2-oxoimidazolidine-4-carboxamide;

(4S)—N-(3-Chloro-2,4-difluorophenyl)-N-methyl-3-(6-methyl-4-(trifluoromethyl)pyridin-2-yl)-1-((4-methylmorpholin-2-yl)methyl)-2-oxoimidazolidine-4-carboxamide;

(S)—N-(3-Chloro-2,4-difluorophenyl)-N-methyl-3-(6-methyl-4-(trifluoromethyl)pyridin-2-yl)-2-oxo-1-(3-(piperazin-1-yl)propyl)imidazolidine-4-carboxamide;

(S)-1-(3-(4-Acetylpiperazin-1-yl)propyl)-N-(3-chloro-2,4-difluorophenyl)-N-methyl-3-(6-methyl-4-(trifluoromethyl)pyridin-2-yl)-2-oxoimidazolidine-4-carboxamide;

(4S)—N-(3-Chloro-2,4-difluorophenyl)-1-((3-hydroxypyrrolidin-3-yl)methyl)-N-methyl-3-(6-methyl-4-(trifluoromethyl)pyridin-2-yl)-2-oxoimidazolidine-4-carboxamide;

(4S)—N-(3-Chloro-2,4-difluorophenyl)-1-((3-hydroxy-1-methylpyrrolidin-3-yl)methyl)-N-methyl-3-(6-methyl-4-(trifluoromethyl)pyridin-2-yl)-2-oxoimidazolidine-4-carboxamide;

(S)—N-(3-Chloro-2,4-difluorophenyl)-1-((3-hydroxyazetidin-3-yl)methyl)-N-methyl-3-(6-methyl-4-(trifluoromethyl)pyridin-2-yl)-2-oxoimidazolidine-4-carboxamide;

(S)—N-(3-Chloro-4-fluorophenyl)-1-((3-hydroxyazetidin-3-yl)methyl)-N-methyl-3-(6-methyl-4-(trifluoromethyl)pyridin-2-yl)-2-oxoimidazolidine-4-carboxamide;

(4S)—N-(3-Chloro-2,4-difluorophenyl)-1-(2,3-dihydroxypropyl)-N-methyl-3-(6-methyl-4-(trifluoromethyl)pyridin-2-yl)-2-oxoimidazolidine-4-carboxamide;

(S)-2-(4-(((3-Chloro-2,4-difluorophenyl)(methyl)carbamoyl)-3-(6-methyl-4-(trifluoromethyl)pyridin-2-yl)-2-oxoimidazolidin-1-yl)ethyl sulfamate;

(S)—N-(3-Chloro-4-fluorophenyl)-1-(2-((dimethyl(oxo)-16-sulfaneylidene)amino)ethyl)-N-methyl-3-(6-methyl-4-(trifluoromethyl)pyridin-2-yl)-2-oxoimidazolidine-4-carboxamide;

(S)—N-(3-Chloro-2,4-difluorophenyl)-N-methyl-1-(((S/R)-3-methyl-2-oxooxazolidin-5-yl)methyl)-3-(6-methyl-4-(trifluoromethyl)pyridin-2-yl)-2-oxoimidazolidine-4-carboxamide isomer 1;

(S)—N-(3-Chloro-2,4-difluorophenyl)-N-methyl-1-(((R/S)-3-methyl-2-oxooxazolidin-5-yl)methyl)-3-(6-methyl-4-(trifluoromethyl)pyridin-2-yl)-2-oxoimidazolidine-4-carboxamide isomer 2;

(4S)—N-(3-Chloro-4-fluorophenyl)-N-cyclopropyl-1-(2,3-dihydroxypropyl)-3-(6-methyl-4-(trifluoromethyl)pyridin-2-yl)-2-oxoimidazolidine-4-carboxamide;

(4S)—N-(3-Chloro-4-fluorophenyl)-1-(3,4-dihydroxybutyl)-N-methyl-3-(6-methyl-4-(trifluoromethyl)pyridin-2-yl)-2-oxoimidazolidine-4-carboxamide;

(S)—N-Methyl-3-(6-methyl-4-(trifluoromethyl)pyridin-2-yl)-2-oxo-N-(1H-pyrrolo[2,3-b]pyridin-6-yl)imidazolidine-4-carboxamide;

(S)—N-Methyl-N-(1-methyl-1H-pyrrolo[2,3-b]pyridin-6-yl)-3-(6-methyl-4-(trifluoromethyl)pyridin-2-yl)-2-oxoimidazolidine-4-carboxamide;

(S)—N-Methyl-N-(1-methyl-1H-indazol-6-yl)-3-(6-methyl-4-(trifluoromethyl)pyridin-2-yl)-2-oxoimidazolidine-4-carboxamide;

(S)—N-Methyl-3-(6-methyl-4-(trifluoromethyl)pyridin-2-yl)-N-(3-methylfuro[3,2-b]pyridin-5-yl)-2-oxoimidazolidine-4-carboxamide;

(S)—N-Methyl-3-(6-methyl-4-(trifluoromethyl)pyridin-2-yl)-2-oxo-N-(thieno[3,2-b]pyridin-5-yl)imidazolidine-4-carboxamide;

- (S)—N-Methyl-N-(3-methyl-1H-indazol-6-yl)-3-(6-methyl-4-(trifluoromethyl)pyridin-2-yl)-2-oxoimidazolidine-4-carboxamide;
- (S)—N-(3-Fluoro-1H-pyrrolo[2,3-b]pyridin-6-yl)-N-methyl-3-(6-methyl-4-(trifluoromethyl)pyridin-2-yl)-2-oxoimidazolidine-4-carboxamide;
- (S)—N-(3-Chloro-1H-pyrrolo[2,3-b]pyridin-6-yl)-N-methyl-3-(6-methyl-4-(trifluoromethyl)pyridin-2-yl)-2-oxoimidazolidine-4-carboxamide;
- (2S,5R)—N-(3-Chloro-4-fluorophenyl)-1-(3-cyano-6-methyl-4-(trifluoromethyl)pyridin-2-yl)-N,5-dimethylpyrrolidine-2-carboxamide;
- (2S,5S)—N-(3-Chloro-4-fluorophenyl)-1-(3-cyano-6-methyl-4-(trifluoromethyl)pyridin-2-yl)-N,5-dimethylpyrrolidine-2-carboxamide;
- (S)-1-(3-Cyano-6-methyl-4-(trifluoromethyl)pyridin-2-yl)-N-methyl-N-(1-methyl-1H-pyrrolo[2,3-b]pyridin-6-yl)pyrrolidine-2-carboxamide;
- (S)—N-(4-Chloro-1-methyl-pyrrolo[2,3-b]pyridin-6-yl)-1-[3-cyano-6-methyl-4-(trifluoromethyl)-2-pyridyl]-N-methyl-pyrrolidine-2-carboxamide; or
- (S)-1-(3-Cyano-6-methyl-4-(trifluoromethyl)pyridin-2-yl)-N-methyl-N-(4-methyl-3,4-dihydro-2H-pyrido[3,2-b][1,4]oxazin-6-yl)pyrrolidine-2-carboxamide;

or a pharmaceutically acceptable salt or solvate thereof.

* * * * *